United States Patent
Andrews, III et al.

(10) Patent No.: US 7,273,863 B1
(45) Date of Patent: Sep. 25, 2007

(54) BENZOPHENONES AS INHIBITORS OF REVERSE TRANSCRIPTASE

(75) Inventors: Clarence Webster Andrews, III, Durham, NC (US); Joseph Howing Chan, Durham, NC (US); George Andrew Freeman, Durham, NC (US); Karen Rene Romines, Durham, NC (US); Jeffrey H. Tidwell, Durham, NC (US); Pascal Maurice Charles Pianetti, Les Ulis (FR)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/070,084

(22) PCT Filed: Aug. 31, 2000

(86) PCT No.: PCT/EP00/08487

§ 371 (c)(1),
(2), (4) Date: Mar. 7, 2002

(87) PCT Pub. No.: WO01/17982

PCT Pub. Date: Mar. 15, 2001

(30) Foreign Application Priority Data

Sep. 4, 1999 (GB) ................... 9920872.0

(51) Int. Cl.
*C07D 277/24* (2006.01)
*A61K 31/16* (2006.01)

(52) U.S. Cl. ............... 514/227.5; 514/249; 514/365; 514/469; 514/621; 544/59; 544/356; 548/200; 549/468; 564/169

(58) Field of Classification Search ............... 564/169; 514/621

See application file for complete search history.

(56) References Cited

U.S. PATENT DOCUMENTS

| | | | | |
|---|---|---|---|---|
| 4,207,234 A | | 6/1980 | Masashi et al. | 260/239 |
| 4,797,415 A | * | 1/1989 | Tomiyama et al. | 514/469 |
| 4,883,815 A | | 11/1989 | Aschwenden et al. | 514/541 |
| 5,719,143 A | | 2/1998 | Badorc et al. | 514/221 |
| 5,945,450 A | | 8/1999 | Takenouchi et al. | 514/535 |

FOREIGN PATENT DOCUMENTS

| | | |
|---|---|---|
| EP | 0667344 A1 | 2/1995 |
| FR | 1 552 793 A | 1/1969 |
| HU | 198676 | 1/1989 |
| JP | 59 181246 | 10/1984 |
| WO | WO93/15043 | 5/1993 |
| WO | WO99 55682 A | 11/1999 |

OTHER PUBLICATIONS

Suarez et al., PubMed Abstract (Medicina (B Aries) 59(4):385:92), 1999.*
Van Heeswijk, PubMed Abstract (Ther Drug Monit. 24(3):323-37), Jun. 2002.*
Douglas Jr., Introductions to Viral Diseases, Cecil Textbook of Medicine, 20th Edtition, vol. 2, pp. 1739-1747, 1996.*
Perron et al., CAOLD Abstract 55:5407f, 1960.*
Brndl, CAPLUS Abstract 76:158266, 1972.*
De Clercq, "Perspectives of non-nucleoside reverse transcriptase inhibitors (NNRTIs) in the therapy of HIV-1 infection," I1 Farmco, 1999, vol. 54, pp. 26-45.
Balzarini, "Suppression of Resistance to Drugs Targeted to Human Immunodeficiency Virus Reverse Transcriptase by Combination Therapy;" Biochemical-Pharmacology, 1999, vol. 58, p. 1.
Inaba, et al., "Benzodiazepines. V. A Novel Synthesis of a 7-Nitro-1,4-benzodiazepine Derivative," Chem. Pharm. Bull., 1971, vol. 19, p. 722.
Wyatt, PG., et al: Journal of Medicinal Chemistry, US, American Chemical Society. Washington, Journal Of Medicinal Chemistry, US, American Chemistry Society. Washington, vol. 38, No. 10, 1995, pp 1657-1665 XPOO2084134.
Sugasawa, T., et al: "1-Azacycloalkyl-1,4-benzodiazepin-2-ones with anxiety-antidepressant actions," J. Med. Chem. (1985), 28(6), 699-707 XP002159556.
Capuano, L., et al: "Darstelling von alpha-'2-alkoxycarbonyl-anilino!-und alpha-'2-Acylanilino!-carbonsaureämiden" Justus Liebigs Ann. Chem. (1968), 712, 73-8 XP002159557.
Brandel, E.: "Penicillin reactions. 1. Behavior towards penicillinase" Sci. Pharm. (1971), 39(4), 267-92 XP000979965.
http://www.hivguidelines.org/public_html/center/clinical-education/q-and-a/hiv-2.htm, 2004.
http://www.aegis.com/aidsline/1992/nov/M92B0027.html, 1992.
European Search Report for 06075956.0 dated Aug. 11, 2006.

* cited by examiner

*Primary Examiner*—Deepak Rao
(74) *Attorney, Agent, or Firm*—Kimberly H. Parker

(57) ABSTRACT

The present invention includes benzophenone compounds (I)

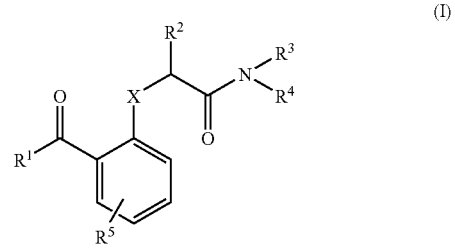

which are useful in the treatment of HIV infections.

35 Claims, No Drawings

BENZOPHENONES AS INHIBITORS OF REVERSE TRANSCRIPTASE

This application is filed pursuant to 35 U.S.C. § 371 as a United States National Phase Application of International Application No. PCT/EP00/08487 filed Aug. 31, 2000, which claims priority from GB 9920872.0 filed Sep. 4, 1999

BACKGROUND OF THE INVENTION

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss. HIV is a retrovirus; the conversion of its RNA to DNA is accomplished through the action of the enzyme reverse transcriptase. Compounds that inhibit the function of reverse transcriptase inhibit replication of HIV in infected cells. Such compounds are useful in the prevention or treatment of HIV infection in humans.

Non-nucleoside reverse transcriptase inhibitors (NNRTIs), in addition to the nucleoside reverse transcriptase inhibitors gained a definitive place in the treatment of HIV-1 infections. The NNRTIs interact with a specific site of HIV-1 reverse transcriptase that is closely associated with, but distinct from, the NRTI binding site. NNRTIs, however, are notorious for rapidly eliciting resistance due to mutations of the amino acids surrounding the NNRTI-binding site (E. De Clercq, Il Famaco 54, 26-45, 1999). Failure of long-term efficacy of NNRTIs is often associated with the emergence of drug-resistant virus strains (J. Balzarini, *Biochemical Pharmacology*, Vol 58, 1-27, 1999). Moreover, the mutations that appear in the reverse transcriptase enzyme frequently result in a decreased sensitivity to other reverse transcriptase inhibitors, which results in cross-resistance.

JP 59181246 disclosed certain benzophenones useful as anticancer agents. Certain benzophenone derivatives as inhibitors of HIV-1 reverse transriptase were disclosed in Wyatt et al. (J. Med. Chem. 38:1657-1665, 1995). However, these compounds were primarily active against wild-type HIV-1 reverse transcriptase, rapidly induced resistant virus, and were inactive against a common resistant strain.

We have now discovered that the compounds of the present invention are useful as inhibitors of both wild type and mutant variants of HIV reverse transcriptase.

BRIEF DESCRIPTION OF THE INVENTION

A first aspect of the invention features compounds of formula I, IA, IB, IC, ID, II, III, and IV. These compounds are useful in the inhibition of HIV reverse transcriptase, particularly its resistant varieties, the prevention of infection by HIV, the treatment of infection by HIV and in the treatment of AIDS and/or ARC, either as compounds, pharmaceutically acceptable salts or pharmaceutical composition ingredients. A second aspect of the invention features methods of treating AIDS, methods of preventing infection by HIV, and methods of treating infection by HIV as monotherapy or in combination with other antivirals, anti-infectives, immunomodulators, antibiotics or vaccines. A third aspect of the invention features pharmaceutical compositions comprising the above-mentioned compounds and which are suitable for the prevention or treatment of HIV infection. A fourth aspect of the invention features processes for making the above-mentioned compounds.

DETAILED DESCRIPTION OF THE INVENTION

The present invention relates to compounds of formula I, IA, IB, IC, ID, II, III, IV and combinations thereof, or pharmaceutically acceptable salts thereof, in the inhibition of HIV reverse transcriptase and its resistant varieties, the prevention or treatment of infection by HIV and in the treatment of the resulting acquired immune deficiency syndrome (AIDS).

The present invention features compounds of formula (I)

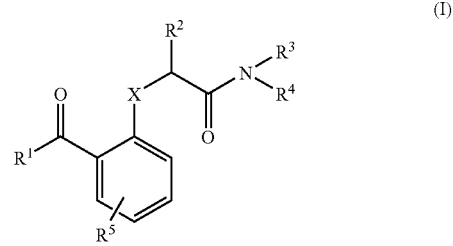

wherein:

X is C, O, or N;

$R^1$ is $C_{1-8}$alkyl; $C_{3-6}$cycloalkyl; $C_{6-14}$aryl which may be optionally substituted with one or more substituents selected from the group consisting of halogen, —$CF_3$, $C_{1-8}$alkyl, $C_{1-8}$alkylamino, alkoxy, $C_{3-6}$cycloalkyl$C_{2-6}$alkenyl, $C_{6-14}$aryl$C_{2-6}$alkenyl, —CN, —$NO_2$, —$NH_2$, —$SR^6$, —$S(O)_2R^6$, —$S(O)R^7$, —$S(O)_2R^7$, —$C(O)R^7$, $C_{2-6}$alkenyl which may be optionally substituted with a substituent selected from the group consisting of hydroxy, halogen, aryl, and heterocycle, and $C_{2-6}$alkynyl which may be optionally substituted with a substituent selected from the group consisting of hydroxy, halogen, aryl, $C_{3-6}$cycloalkyl, and heterocycle; or heterocycle, optionally substituted with one or more substituents selected from the group consisting of halogen, $C_{1-8}$alkyl, —CN, $C_{6-4}$aryl$C_{1-8}$alkyl and heterocycle;

$R^6$ is $C_{1-8}$alkyl, optionally substituted with one or more substituents selected from the group consisting of hydroxy, halogen, —$CF_3$, aryl, and heterocycle;

$R^7$ is $C_{1-8}$ alkyl, optionally substituted with one or more substituents selected from the group consisting of hydroxy, halogen, aryl, $C_{3-6}$cycloalkyl and heterocycle; —$NH_2$; or heterocycle;

$R^2$ is hydrogen, halogen, or $C_{1-8}$alkyl;

$R^3$ and $R^4$ are independently hydrogen; hydroxy; heterocycle optionally substituted with one or more substituents selected from the group consisting of oxo, hydroxy, hydroxy$C_{1-8}$alkyl, halogen, $C_{1-8}$alkyl, —$OR^{11}$, —$S(O)_2NR^8R^9$, and —$SR^{10}N(R^{10})_2$; or $C_{6-14}$aryl substituted with one or more substituents selected from the group consisting of hydroxy, halogen, —$CF_3$, $C_{1-8}$alkyl, hydroxy$C_{1-8}$alkyl, —CN, —$NO_2$, $C_{1-8}$alkylamino, heterocycle$C_{1-8}$alkyl, —$C(O)NH_2$, —$S(O)R^7$, —$S(O)_2R^7$, —$C(O)R^7$, —$NS(O)_2R^7$, —$S(O)_2NR^8R^9$, —$S(O)_2$ $NHR^{11}$, —$S(O)_2R^{11}$, —$S(O)_2NR^7COR^{11}$, —$S(O)_2NHCOR^{11}$, —$S(O)[COR^{11}]_n$ wherein n is 1, 2, or 3, —$OR^{11}$, —$OR^{11}OR^{11}$, —$C(O)R^{11}$, —$C(O)NR^{11}$, —$C(O)OR^{11}$, —$NR^{11}$, —NC(O)$R^{11}$, heterocycle$C_{2-6}$alkenyl, heterocycle which may be optionally substituted with one or more substituents selected from the group consisting of oxo, $C_{1-8}$alkyl, and $C(O)OR^{11}$, and $C_{1-8}$alkyl which may be optionally substituted with one or more substituents selected from the group consisting of —CN and heterocycle, optionally substituted with —$C(O)R^{11}$; provided that $R^3$ and $R^4$ cannot both be hydrogen or hydroxy;

$R^8$ and $R^9$ are independently selected from the group consisting of hydrogen, $C_{3-6}$cycloalkyl, $C_{1-8}$alkyl optionally substituted with one or more substituents selected from the group consisting of oxo, heterocycle, CN and $C_{6-14}$aryl optionally substituted with alkoxy, $C_{1-8}$alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloalkyl;

$R^{10}$ is $C_{1-8}$alkyl;

$R^{11}$ is $C_{1-8}$alkyl, optionally substituted with one or more substituents selected from the group consisting of hydrogen, hydroxy, halogen, $C_{1-8}$alkyl, $C_{3-6}$cycloalkyl, alkoxy, —$S(O)_2NR^8R^9$, $NCONH_2$, and heterocycle optionally substituted with one or more substituents selected from the group consisting of oxo, hydroxy, and $C_{1-8}$alkyl; heterocycle optionally substituted with heterocycle$C_{1-8}$alkyl; or $C_{6-14}$aryl optionally substituted with alkoxy;

$R^5$ is hydrogen, halogen, $C_{1-8}$alkyl, —$NO_2$, —$NH_2$, $C_{1-8}$alkylamino, $CF_3$, or alkoxy;

or a pharmaceutically acceptable derivative thereof, provided that (a) when X is N; $R^1$ is $C_{6-14}$aryl substituted with halogen; $R^2$ and $R^3$ are hydrogen; $R^5$ is halogen; $R^4$ cannot be heterocycle substituted with $C_{1-8}$alkyl;

(b) when X is C; $R^2$ is hydrogen, halogen or $C_{1-8}$alkyl; $R^3$ is hydrogen; $R^4$ is $C_{6-14}$aryl substituted with halogen, hydroxy, or $C_{1-8}$alkyl; $R^5$ is hydrogen, halogen, $C_{1-8}$alkyl, or alkoxy; then $R^1$ cannot be $C_{1-8}$alkyl, $C_{3-6}$cylcoalkyl, or $C_{6-14}$aryl substituted with halogen, $C_{1-8}$alkyl, alkoxy, or $C_{6-14}$aryl$C_{2-6}$alkenyl; and (c) when X is C; $R^2$ is hydrogen or alkyl, $R^3$ is hydrogen, $R^4$ is $C_{6-14}$aryl substituted with halogen, CN, $C_{1-8}$alkyl, or —$NO_2$; $R^5$ is hydrogen, —$NO_2$ or $NH_2$, then $R^1$ cannot be $C_{10-14}$aryl substituted with alkoxy.

Preferred compounds of formula (I) are those wherein X is O.

More preferred compounds of formula (I) are those wherein X is O; $R^1$ is $C_{6-14}$aryl substituted with one or more substituents selected from the group consisting of halogen, —$CF_3$, $C_{1-8}$alkyl, —CN, —$SR^6$, —$S(O)_2R^6$; or heterocycle, optionally substituted with one or more substituents selected from the group consisting of $C_{1-8}$alkyl, —CN, and $C_{6-14}$aryl$C_{1-8}$alkyl; $R^6$ is $C_{1-8}$alkyl, optionally substituted with halogen; $R^7$ is $C_{1-8}$ alkyl optionally substituted with one or more substituents selected from the group consisting of hydroxy; —$NH_2$, or heterocycle; $R^2$ is hydrogen; $R^3$ is hydrogen or $C_{1-8}$ alkyl; $R^4$ is heterocycle, optionally substituted with one or more substituents selected from the group consisting of oxo, halogen, $C_{1-8}$alkyl, —$OR^{11}$ and —$SR^{10}N(R^{10})_2$, $S(O)_2NR^8R^9$; or $C_{6-14}$aryl substituted with one or more substituents selected from the group consisting of hydroxy, halogen, —$CF_3$, $C_{1-8}$alkyl, hydroxy$C_{1-8}$alkyl, —CN, —$NO_2$, —$C(O)NH_2$, —$S(O)R^7$, —$S(O)_2R^7$, —$S(O)_2$ $NR^8R^9$, —$OR^{11}$, —$C(O)NR^{11}$, —$C(O)OR^{11}$, —$NR^{11}$, —$NC(O)R^{11}$, and heterocycle which may be optionally substituted with one or more substituents selected from the group consisting of oxo, $C_{1-8}$alkyl and heterocycle$C_{1-8}$alkyl; $R^8$ and $R^9$ are the same or different and are selected from the group consisting of hydrogen, $C_{1-8}$alkyl, $C_{1-8}$alkylheterocycle, heterocycle, and $C_{3-6}$cycloalkyl; $R^{10}$ is $C_{1-8}$alkyl; $R^{11}$ is $C_{1-8}$alkyl, optionally substituted with —$SO_2NR^8R^9$; and $R^5$ is halogen or —$NO_2$; or a pharmaceutically acceptable derivative thereof.

More preferred compounds of formula (I) are those wherein X is O; $R^1$ is $C_{6-14}$aryl substituted with one or more substituents selected from the group consisting of halogen, —$CF_3$, $C_{1-8}$alkyl, and —CN; $R^2$ and $R^3$ are hydrogen; $R^4$ is $C_{6-14}$aryl substituted with one or more substituents selected from the group consisting of halogen, $C_{1-8}$alkyl, —CN, —$NO_2$, —$S(O)R^7$, —$S(O)_2R^7$, —$NS(O)_2R^7$, wherein $R^7$ is —$NH_2$; and $R^5$ is halogen; or a pharmaceutically acceptable derivative thereof.

More preferred compounds of formula (I) are those wherein X is O; $R^1$ is $C_{6-14}$aryl which may be optionally substituted with one or more substituents selected from the group consisting of halogen, $C_{1-8}$alkyl, $CF_3$, —CN; $R^2$ and $R^3$ are hydrogen; $R^4$ is $C_{6-14}$aryl substituted with one or more substituents selected from the group consisting of $C_{1-8}$alkyl and $S(O)_2NR^8R^9$, wherein $R^8$ and $R^9$ are independently selected from the group consisting of hydrogen, $C_{3-6}$cycloalkyl, $C_{1-8}$alkyl optionally substituted with one or more substituents selected from the group consisting of oxo, heterocycle, CN and $C_{6-14}$aryl optionally substituted with alkoxy, $C_{1-8}$ alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloalkyl.

Other preferred compounds of formula (I) are those wherein $R^1$ is $C_{6-14}$aryl substituted with one or more substituents selected from the group consisting of halogen, —$CF_3$, $C_{1-8}$alkyl, and —CN; $R^2$ and $R^3$ are hydrogen; $R^4$ is $C_{6-14}$aryl substituted with one or more substituents selected from the group consisting of halogen, $C_{1-8}$alkyl, —CN, —$NO_2$, —$S(O)R^7$, —$S(O)_2R^7$, —$NS(O)_2R^7$, wherein $R^7$ is —$NH_2$; and $R^5$ is halogen; or a pharmaceutically acceptable derivative thereof provided that when X is C; $R^2$ and $R^3$ are hydrogen; $R^4$ is $C_{6-14}$aryl substituted with halogen, CN, $C_{1-8}$alkyl, —$NO_2$; and $R^5$ is halogen, then $R^1$ cannot be $C_{6-10}$ aryl substituted with alkoxy.

In another aspect of the present invention compounds of formula (IA) are disclosed:

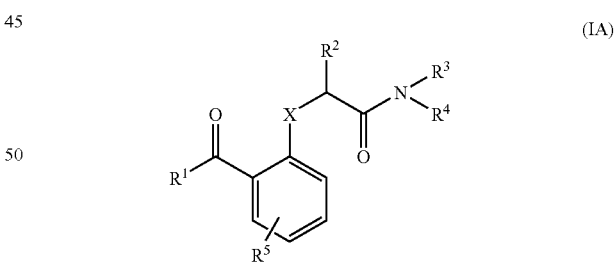

wherein:

X is C, O, or N;

$R^1$ is $C_{6-14}$aryl which may be optionally substituted with one or more substituents selected from the group consisting of halogen, —$CF_3$, $C_{1-8}$alkyl, $C_{1-8}$alkylamino, alkoxy, $C_{3-6}$cycloalkyl$C_{2-6}$alkenyl, $C_{6-14}$aryl$C_{2-6}$alkenyl, —CN, —$NO_2$, —$NH_2$, —$SR^6$, —$S(O)_2R^6$, —$S(O)R^7$, —$S(O)_2R^7$, —$C(O)R^7$, $C_{2-6}$alkenyl which may be optionally substituted with a substituent selected from the group consisting of hydroxy, halogen, aryl, and heterocycle and $C_{2-6}$alkynyl which may be optionally substituted with a substituent selected from the group consisting of hydroxy, halogen, aryl, $C_{3-6}$cycloalkyl, and heterocycle;

$R^6$ is $C_{1-8}$alkyl optionally substituted with one or more substituents selected from the group consisting of hydroxyl, halogen, —$CF_3$, aryl, and heterocycle;

$R^7$ is $C_{1-8}$ alkyl, optionally substituted with one or more substituents selected from the group consisting of hydroxy, halogen, aryl, $C_{3-6}$cycloalkyl and heterocycle; —$NH_2$; or heterocycle;

$R^2$ is hydrogen, halogen, or $C_{1-8}$alkyl;

$R^3$ is hydrogen;

$R^4$ is $C_{6-14}$aryl substituted with one or more substituents selected from the group consisting of hydroxy, halogen, —$CF_3$, $C_{1-8}$alkyl, hydroxy$C_{1-8}$alkyl, —CN, —$NO_2$, $C_{1-8}$alkylamino, heterocycle$C_{1-8}$alkyl, —$C(O)NH_2$, —$S(O)R^7$, —$S(O)_2R^7$, —$C(O)R^7$, —$NS(O)_2R^7$, —$S(O)_2NR^8R^9$, —$S(O)_2NHR^{11}$, —$S(O)_2R^{11}$, —$S(O)_2NR^7COR^{11}$, —$S(O)_2NHCOR^{11}$, —$S(O)_2[COR^{11}]_n$ wherein n is 1, 2, or 3, —$OR^{11}$, —$OR^{11}OR^{11}$, —$C(O)R^{11}$, —$C(O)NR^{11}$, —$C(O)OR^{11}$, —$NR^1$, —$NC(O)R^{11}$, heterocycle$C_{2-6}$alkenyl, heterocycle which may be optionally substituted with one or more substituents selected from the group consisting of oxo, $C_{1-8}$alkyl, and $C(O)OR^{11}$, and $C_{1-8}$alkyl which may be optionally substituted with one or more substituents selected from the group consisting of —CN and heterocycle, optionally substituted with —$C(O)R^{11}$;

$R^8$ and $R^9$ are independently selected from the group consisting of hydrogen, $C_{3-6}$cycloalkyl, $C_{1-8}$alkyl optionally substituted with one or more substituents selected from the group consisting of oxo, heterocycle, CN and $C_{6-4}$aryl optionally substituted with alkoxy, $C_{1-8}$ alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloalkyl;

$R^{11}$ is $C_{1-8}$alkyl, optionally substituted with one or more substituents selected from the group consisting of hydrogen, hydroxy, halogen, $C_{1-8}$alkyl, $C_{3-6}$cycloalkyl, alkoxy, —$S(O)_2NR^8R^9$, $NCONH_2$, and heterocycle optionally substituted with one or more substituents selected from the group consisting of oxo, hydroxy, and $C_{1-8}$alkyl; heterocycle optionally substituted with heterocycle$C_{1-8}$alkyl; or $C_{6-14}$aryl optionally substituted with alkoxy;

$R^5$ is hydrogen, halogen, $C_{1-8}$alkyl, —$NO_2$, —$NH_2$, $C_{1-8}$alkylamino, $CF_3$, or alkoxy;

or a pharmaceutically acceptable derivative thereof provided that
a) when X is C; $R^2$ is hydrogen, halogen or $C_{1-8}$alkyl; $R^3$ is hydrogen; $R^4$ is $C_{6-14}$aryl substituted with halogen, hydroxy, or $C_{1-8}$alkyl; $R^5$ is hydrogen, halogen, $C_{1-8}$alkyl, or alkoxy; then $R^1$ cannot be $C_{1-8}$alkyl, $C_{3-6}$cycloalkyl, or $C_{6-14}$aryl substituted with halogen, $C_{1-8}$alkyl, or $C_{6-14}$aryl$C_{2-6}$alkenyl; and
b) when X is C; $R^2$ is hydrogen or alkyl; $R^3$ is hydrogen; $R^4$ is $C_{6-14}$aryl substituted with halogen, CN, alkyl, or —$NO_2$; $R^5$ is hydrogen, —$NO_2$, or $NH_2$, then $R^1$ cannot be $C_{10-14}$ aryl substituted with alkoxy.

Preferred compounds of formula (IA) are compounds wherein X is O.

More preferred compounds of formula (IA) are compounds wherein X is O; $R^1$ is $C_{6-14}$aryl substituted with one or more substituents selected from the group consisting of halogen, —$CF_3$, $C_{1-8}$alkyl, —CN, $C_{2-6}$alkenyl which may be optionally substituted with a substituent selected from the group consisting of hydroxy, halogen, aryl, and heterocycle and $C_{2-6}$alkynyl which may be optionally substituted with a substituent selected from the group consisting of hydroxy, halogen, aryl, $C_{3-6}$cycloalkyl, and heterocycle; $R^2$ and $R^3$ are hydrogen; $R^4$ is $C_{6-14}$aryl substituted with one or more substituents selected from the group consisting of $C_{1-8}$alkyl, —$S(O)_2R^7$, —$S(O)_2NR^8R^9$, —$OR^{11}$, heterocycle$C_{2-6}$alkenyl, and heterocycle which may be optionally substituted with oxo; and $R^5$ is halogen; or a pharmaceutically acceptable derivative thereof.

In a further aspect of the present invention there is provided compounds of formula (IB):

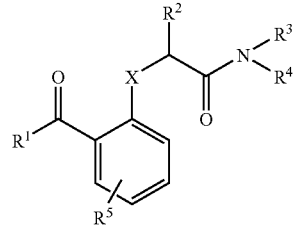

(IB)

wherein:

X is C, O, or N;

$R^1$ is $C_{6-14}$aryl substituted with one or more substituents selected from the group consisting of halogen, —$CF_3$, $C_{1-8}$alkyl, $C_{1-8}$alkylamino, alkoxy, $C_{3-6}$cycloalkyl$C_{2-6}$ alkenyl, $C_{6-14}$aryl$C_{2-6}$alkenyl, —CN, —$NO_2$, —$NH_2$, —$SR^6$, —$S(O)_2R^6$, —$S(O)R^7$, —$S(O)_2R^7$, —$C(O)R^7$, $C_{2-6}$alkenyl which may be optionally substituted with a substituent selected from the group consisting of hydroxy, halogen, aryl, and heterocycle, and $C_{2-6}$alkynyl which may be optionally substituted with a substituent selected from the group consisting of hydroxy, halogen, aryl, $C_{3-6}$cycloalkyl, and heterocycle;

$R^6$ is $C_{1-8}$alkyl, optionally substituted with one or more substituents selected from the group consisting of hydroxyl, halogen, —$CF_3$, aryl, and heterocycle;

$R^7$ is $C_{1-8}$ alkyl, optionally substituted with one or more substituents selected from the group consisting of hydroxyl, halogen, aryl, $C_{3-6}$cycloalkyl and heterocycle; —$NH_2$; or heterocycle;

$R^2$ is hydrogen, halogen, or $C_{1-8}$alkyl;

$R^3$ is hydrogen;

$R^4$ is heterocycle, optionally substituted with one or more substituents selected from the group consisting of oxo, hydroxy, hydroxy$C_{1-8}$alkyl, halogen, $C_{1-8}$alkyl, —$OR^{11}$, —$SR^{10}N(R^{10})_2$, and —$S(O)_2NR^8R^9$;

$R^8$ and $R^9$ are independently selected from the group consisting of hydrogen, $C_{3-6}$cycloalkyl, $C_{1-8}$alkyl optionally substituted with one or more substituents selected from the group consisting of oxo, heterocycle, CN and $C_{6-14}$aryl optionally substituted with alkoxy, $C_{1-8}$ alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloalkyl;

$R^{10}$ is $C_{1-8}$alkyl;

$R^{11}$ is $C_{1-8}$alkyl, optionally substituted with one or more substituents selected from the group consisting of hydrogen, hydroxy, halogen, $C_{1-8}$alkyl, $C_{3-6}$cycloalkyl, alkoxy, —$S(O)_2NR^8R^9$, $NCONH_2$, and heterocycle optionally substituted with one or more substituents selected from the group consisting of oxo, hydroxy, and $C_{1-8}$alkyl; heterocycle optionally substituted with heterocycle$C_{1-8}$alkyl; or $C_{6-14}$aryl optionally substituted with alkoxy;

$R^5$ is hydrogen, halogen, $C_{1-8}$alkyl, —$NO_2$, —$NH_2$, $C_{1-8}$alkylamino, $CF_3$, or alkoxy;

or a pharmaceutically acceptable derivative thereof provided that when X is N; $R^1$ is $C_{6-14}$aryl substituted with halogen; $R^2$ and $R^3$ are hydrogen; $R^5$ is halogen; $R^4$ cannot be heterocycle substituted with $C_{1-8}$alkyl.

Preferred compounds of formula (IB) are those wherein X is O.

More preferred compounds of formula (IB) are those wherein X is O; $R^1$ is $C_{6-14}$aryl substituted with one or more substituents selected from the group consisting of halogen, —$CF_3$, and —CN; $R^2$ is hydrogen; $R^3$ is hydrogen; $R^4$ is heterocycle; and $R^5$ is halogen; or a pharmaceutically acceptable derivative thereof.

In another aspect of the present invention there is provided compounds of formula (IC)

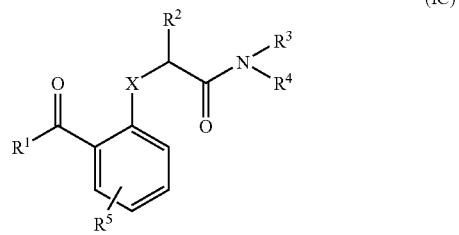

(IC)

wherein:

X is C, O, or N;

$R^1$ is heterocycle, optionally substituted with one or more substituents selected from the group consisting of $C_{1-8}$alkyl, halogen, —CN, $C_{6-14}$aryl$C_{1-8}$alkyl and heterocycle;

$R^2$ is hydrogen, halogen, or $C_{1-8}$alkyl;

$R^3$ is hydrogen;

$R^4$ is $C_{6-14}$aryl substituted with one or more substituents selected from the group consisting of hydroxy, halogen, —$CF_3$, $C_{1-8}$alkyl, hydroxy$C_{1-8}$alkyl, —CN, —$NO_2$, $C_{1-8}$alkylamino, heterocycle$C_{1-8}$alkyl, —$C(O)NH_2$, —$S(O)R^7$, —$S(O)_2R^7$, —$C(O)R^7$, —$NS(O)_2R^7$, —$S(O)_2NR^8R^9$, —$S(O)_2NHR^{11}$, —$S(O)_2R^{11}$, —$S(O)_2NR^7COR^{11}$, —$S(O)_2NHCOR^{11}$, —$S(O)_2[COR^{11}]_n$ wherein n is 1, 2, or 3, —$OR^{11}$, —$OR^{11}OR^{11}$, —$C(O)R^{11}$, —$C(O)NR^{11}$, —$C(O)OR^{11}$, —$NR^{11}$, —$NC(O)R^{11}$, heterocycle$C_{2-6}$alkenyl, heterocycle which may be optionally substituted with one or more substituents selected from the group consisting of oxo, $C_{1-8}$alkyl, and $C(O)OR^{11}$, and $C_{1-8}$alkyl which may be optionally substituted with one or more substituents selected from the group consisting of —CN and heterocycle, optionally substituted with —$C(O)R^{11}$;

$R^7$ is $C_{1-8}$ alkyl, optionally substituted with one or more substituents selected from the group consisting of hydroxy, halogen, aryl, $C_{3-6}$cycloalkyl and heterocycle; —$NH_2$; or heterocycle;

$R^8$ and $R^9$ are independently selected from the group consisting of hydrogen, $C_{3-6}$cycloalkyl, $C_{1-8}$alkyl optionally substituted with one or more substituents selected from the group consisting of oxo, heterocycle, CN and $C_{6-14}$aryl optionally substituted with alkoxy, $C_{1-8}$ alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloalkyl;

$R^{11}$ is $C_{1-8}$alkyl, optionally substituted with one or more substituents selected from the group consisting of hydrogen, $C_{1-8}$alkyl, alkoxy, —$S(O)_2NR^8R^9$, —$NR^8R^9$, and heterocycle, optionally substituted with one or more substituents selected from the group consisting of oxo and $C_{1-8}$alkyl;

$R^5$ is hydrogen, halogen, $C_{1-8}$alkyl, —$NO_2$, —$NH_2$, $C_{1-8}$alkylamino, $CF_3$, or alkoxy;

or a pharmaceutically acceptable derivative thereof.

Preferred compounds of formula (IC) are those wherein X is O.

More preferred compounds of formula (IC) are those wherein X is O; $R^1$ is heterocycle, optionally substituted with —CN; $R^2$ and $R^3$ are hydrogen; $R^4$ is $C_{6-14}$aryl substituted with one or more substituents selected from the group consisting of $C_{1-8}$alkyl, —$S(O)_2NR^8R^9$, —$OR^{11}$, and heterocycle which may be optionally substituted with one or more substituents selected from the group consisting of oxo; and $R^5$ is halogen; or a pharmaceutically acceptable derivative thereof.

The present invention also features compounds of formula (ID):

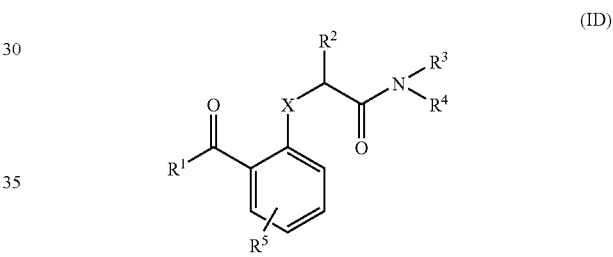

(ID)

wherein:

X is C, O, or N;

$R^1$ is heterocycle, optionally substituted with one or more substituents selected from the group consisting of $C_{1-8}$alkyl, halogen, —CN, $C_{6-14}$aryl$C_{1-8}$alkyl and heterocycle;

$R^2$ is hydrogen, halogen, or $C_{1-8}$alkyl;

$R^3$ and $R^4$ are independently hydrogen; hydroxy; heterocycle optionally substituted with one or more substituents selected from the group consisting of oxo, hydroxy, hydroxy$C_{1-8}$alkyl, halogen, $C_{1-8}$alkyl, —$OR^{11}$, —$S(O)_2NR^8R^9$, and —$SR^{10}N(R^{10})_2$; or $R^3$ and $R^4$ together with the nitrogen atom to which they are attached form a heterocycle which may be optionally substituted with $C_{6-14}$aryl, which may be optionally substituted with one or more substituents selected from the group consisting of $C_{1-8}$alkyl and —$NO_2$; provided that $R^3$ and $R^4$ cannot both be hydrogen or hydroxy;

$R^8$ and $R^9$ are independently selected from the group consisting of hydrogen, $C_{3-6}$cycloalkyl, $C_{1-8}$alkyl optionally substituted with one or more substituents selected from the group consisting of oxo, heterocycle, CN and $C_{6-14}$aryl optionally substituted with alkoxy, $C_{1-8}$ alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloalkyl;

$R^{10}$ is $C_{1-8}$alkyl;

R[11] is $C_{1-8}$alkyl, optionally substituted with one or more substituents selected from the group consisting of hydrogen, $C_{1-8}$alkyl, —S(O)$_2$NR[8]R[9], and heterocycle optionally substituted with one or more substituents selected from the group consisting of oxo, and $C_{1-8}$alkyl;

R[5] is hydrogen, halogen, $C_{1-8}$alkyl, —NO$_2$, —NH$_2$, $C_{1-8}$alkylamino, CF$_3$, or alkoxy;

or a pharmaceutically acceptable derivative thereof.

Preferred compounds of formula (ID) are those wherein X is O.

More preferred compounds of formula (ID) are those wherein X is O; R[1] is heterocycle; R[2] and R[3] are hydrogen; R[4] is heterocycle; and R[5] is halogen; or a pharmaceutically acceptable derivative thereof.

In a further aspect of the present invention there is provided compounds of formula (II):

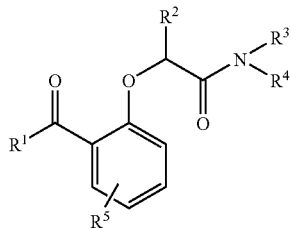

(II)

wherein:
R[1] is $C_{6-14}$aryl which may be optionally substituted with one or more substituents selected from the group consisting of halogen, —CF$_3$, $C_{1-8}$alkyl, $C_{1-8}$alkylamino, alkoxy, $C_{3-6}$cycloalkyl$C_{2-6}$alkenyl, $C_{6-14}$aryl$C_{2-6}$alkenyl, —CN, —NO$_2$, —NH$_2$, —SR[6], —S(O)$_2$R[6], —S(O)R[7], —S(O)$_2$R[7], —C(O)R[7], $C_{2-6}$alkenyl which may be optionally substituted with a substituent selected from the group consisting of hydroxy, halogen, aryl, and heterocycle, and $C_{2-6}$alkynyl which may be optionally substituted with a substituent selected from the group consisting of hydroxy, halogen, aryl, $C_{3-6}$cycloalkyl, and heterocycle;

R[6] is $C_{1-8}$alkyl, optionally substituted with one or more substituents selected from the group consisting of hydroxy, halogen, —CF$_3$, aryl, and heterocycle;

R[7] is $C_{1-8}$ alkyl, optionally substituted with one or more substituents selected from the group consisting of hydroxy, halogen, aryl, $C_{3-6}$cycloalkyl and heterocycle; —NH$_2$; or heterocycle;

R[2] is hydrogen, halogen, or $C_{1-8}$alkyl;

R[3] and R[4] form a heterocycle which may be optionally substituted with $C_{6-14}$aryl, which may be optionally substituted with one or more substituents selected from the group consisting of $C_{1-8}$alkyl and —NO$_2$;

provided that when R[1] is unsubstituted $C_{6-14}$aryl, then R[3]R[4] is substituted.

R[5] is hydrogen, halogen, $C_{1-8}$alkyl, —NO$_2$, —NH$_2$, $C_{1-8}$alkylamino, CF$_3$, or alkoxy;

or a pharmaceutically acceptable derivative thereof.

Preferred compounds of formula (II) are those wherein R[1] is $C_{6-14}$aryl which is substituted with halogen; R[2] is hydrogen; R[3] and R[4] form a heterocycle which may be optionally substituted with $C_{6-14}$aryl, which may be optionally substituted with one or more substituents selected from the group consisting of $C_{1-8}$alkyl and —NO$_2$; and R[5] is halogen; or a pharmaceutically acceptable derivative thereof.

A further aspect of the present invention features compounds of formula (III):

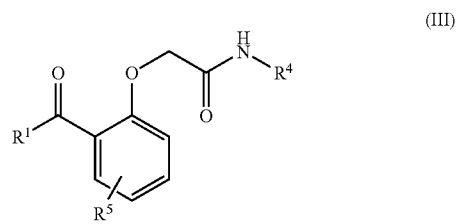

(III)

wherein:
R[1] is $C_{6-14}$aryl which may be optionally substituted with one or more substituents selected from the group consisting of halogen, —CF$_3$, $C_{1-8}$alkyl, $C_{1-8}$alkylamino, alkoxy, $C_{3-6}$cycloalkyl$C_{2-6}$alkenyl, $C_{6-14}$aryl$C_{2-6}$alkenyl, —CN, —NO$_2$, —NH$_2$, —SR[6], —S(O)$_2$R[6], —S(O)R[7], —S(O)$_2$R[7], —C(O)R$_1$, $C_{2-6}$alkenyl which may be optionally substituted with a substituent selected from the group consisting of hydroxy, halogen, aryl, and heterocycle, and $C_{2-6}$alkynyl which may be optionally substituted with a substituent selected from the group consisting of hydroxy, halogen, aryl, $C_{3-6}$cycloalkyl, and heterocycle; or heterocycle, optionally substituted with one or more substituents selected from the group consisting of $C_{1-8}$alkyl, —CN, $C_{6-14}$aryl$C_{1-8}$alkyl and heterocycle;

R[6] is $C_{1-8}$alkyl, optionally substituted with one or more substituents selected from the group consisting of hydroxy, halogen, —CF$_3$, aryl, and heterocycle;

R[7] is $C_{1-8}$ alkyl, optionally substituted with one or more substituents selected from the group consisting of hydroxy, halogen, aryl, $C_{3-6}$cycloalkyl and heterocycle; —NH$_2$; or heterocycle;

R[4] is heterocycle, optionally substituted with one or more substituents selected from the group consisting of oxo, hydroxy, hydroxy$C_{1-8}$alkyl, halogen, $C_{1-8}$alkyl, —OR[11] and —SR[10]N(R[10])$_2$; or $C_{6-14}$aryl substituted with one or more substituents selected from the group consisting of hydroxy, halogen, —CF$_3$, $C_{1-8}$alkyl, hydroxy$C_{1-8}$alkyl, —CN, —NO$_2$, $C_{1-8}$alkylamino, heterocycle$C_{1-8}$alkyl, —C(O)NH$_2$, —S(O)R[7], —S(O)$_2$R[7], —C(O)R[7], —NS(O)$_2$ R[7], —S(O)$_2$NR[8]R[9], —OR[11], —S(O)$_2$NHR[11], S(O)$_2$ R[11], OR[11]OR[11], —C(O)R[11], —C(O)NR[11], —C(O)OR[11], —NR[11], —NC(O)R[11], heterocycle$C_{2-6}$alkenyl, heterocycle which may be optionally substituted with one or more substituents selected from the group consisting of oxo, $C_{1-8}$alkyl, and —C(O)OR[11], and $C_{1-8}$alkyl which may be optionally substituted with one or more substituents selected from the group consisting of —CN and heterocycle, optionally substituted with —C(O)R[11];

R[8] and R[9] are independently selected from the group consisting of hydrogen; $C_{3-6}$cycloalkyl; $C_{1-8}$alkyl optionally substituted with one or more substituents selected from the group consisting of oxo, heterocycle, CN and $C_{6-14}$aryl optionally substituted with alkoxy, $C_{1-8}$alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloalkyl; or —C(O)NH$_2$;

R[10] is $C_{1-8}$alkyl;

R[11] is $C_{1-8}$alkyl, optionally substituted with one or more substituents selected from the group consisting of hydrogen, $C_{1-8}$alkyl, alkoxy, —S(O)$_2$NR$^8$R$^9$, —NR$^8$R$^9$ and heterocycle, optionally substituted with one or more substituents selected from the group consisting of oxo and $C_{1-8}$alkyl;

$R^5$ is hydrogen; halogen; $C_{1-8}$alkyl; —NO$_2$; —NH$_2$; $C_{1-8}$alkylamino; CF$_3$, or alkoxy;

or a pharmaceutically acceptable derivative thereof, provided that:
(a) when $R^4$ is $C_{6-14}$aryl substituted with OR$^{11}$ wherein $R^{11}$ is NR$^8$R$^9$ wherein $R^8$ and $R^9$ are $C_{1-8}$alkyl, and $R^1$ is $C_{6-14}$aryl, then $R^1$ cannot be substituted in the para position, and
(b) $R^1$ and $R^4$ cannot both be unsubstituted.

Preferred compounds of formula (III) are those wherein $R^1$ is $C_{6-14}$aryl substituted with one or more substituents selected from the group consisting of halogen, —CF$_3$, $C_{1-8}$alkyl, —CN, —SR$^6$, —S(O)$_2$R$^6$; or heterocycle, optionally substituted with one or more substituents selected from the group consisting of $C_{1-8}$alkyl, —CN, and $C_{6-14}$aryl$C_{1-8}$alkyl; $R^6$ is $C_{1-8}$alkyl, optionally substituted with halogen; $R^7$ is $C_{1-8}$ alkyl, optionally substituted with one or more substituents selected from the group consisting of hydroxy, —NH$_2$, or heterocycle; $R^4$ is heterocycle, optionally substituted with one or more substituents selected from the group consisting of oxo, halogen, $C_{1-8}$alkyl, —OR$^{11}$ and —SR$^{10}$N(R$^{10}$)$_2$; or $C_{6-14}$aryl substituted with one or more substituents selected from the group consisting of hydroxy, —CF$_3$, $C_{1-8}$alkyl, hydroxy$C_{1-8}$alkyl, —CN, —NO$_2$, —C(O)NH$_2$, —S(O)$_2$R$^7$, —S(O)$_2$NR$^8$R$^9$, —OR$^{11}$, —C(O)NR$^{11}$, —C(O)OR$^{11}$, —NR$^{11}$, —NC(O)R$^{11}$, heterocycle which may be optionally substituted with one or more substituents selected from the group consisting of oxo and $C_{1-8}$-alkyl; $R^8$ and $R^9$ are the same or different and are selected from the group consisting of hydrogen, $C_{1-8}$alkyl, $C_{1-8}$alkylheterocycle, heterocycle, and $C_{3-6}$cycloalkyl; $R^{10}$ is $C_{1-8}$alkyl; $R^{11}$ is $C_{1-8}$alkyl, optionally substituted with —S(O)$_2$NR$^8$R$^9$; and $R^5$ is halogen or —NO$_2$; or a pharmaceutically acceptable derivative thereof.

More preferred compounds of formula (III) are those wherein $R^1$ is $C_{6-14}$aryl substituted with one or more substituents selected from the group consisting of halogen, —CF$_3$, $C_{1-8}$alkyl, and —CN; $R^4$ is $C_{6-14}$aryl substituted with one or more substituents selected from the group consisting of halogen, $C_{1-8}$alkyl, —CN, —NO$_2$, —S(O)R$^7$, —S(O)$_2$R$^7$, —NS(O)$_2$R$^7$, wherein $R^7$ is —NH$_2$; and $R^5$ is halogen; or a pharmaceutically acceptable derivative thereof.

The present invention further features compounds of formula (I), wherein
$R^1$ is phenyl which is substituted in the meta position with one or more substituents selected from the group consisting of halogen, —CF$_3$, $C_{1-8}$alkyl, $C_{1-8}$alkylamino, alkoxy, $C_{3-6}$cycloalkyl$C_{2-6}$alkenyl, $C_{6-14}$aryl$C_{2-6}$alkenyl, —CN, —NO$_2$, —NH$_2$, —SR$^6$, —S(O)$_2$R$^6$, —S(O)R$^7$, —S(O)$_2$R$^7$, —C(O)R$^7$, $C_{2-6}$alkenyl which may be optionally substituted with a substituent selected from the group consisting of hydroxy, halogen, aryl, and heterocycle, and $C_{2-6}$alkynyl which may be optionally substituted with a substituent selected from the group consisting of hydroxy, halogen, aryl, $C_{3-6}$cycloalkyl, and heterocycle;
$R^2$ is hydrogen;
$R^3$ is hydrogen;
$R^4$ is phenyl substituted in the ortho position with a substituent selected from the group consisting of hydroxy, halogen, —CF$_3$, or $C_{1-8}$alkyl and substituted at the para position with a substituent selected from the group consisting of hydroxy, halogen, —CF$_3$, $C_{1-8}$alkyl, hydroxy$C_{1-8}$alkyl, —CN, —NO$_2$, $C_{1-8}$alkylamino, heterocycle$C_{1-8}$alkyl, —C(O)NH$_2$, —S(O)R$^7$, —S(O)$_2$R$^7$, —C(O)R$^7$, —NS(O)$_2$R$^7$, —S(O)$_2$NR$^8$R$^9$, —S(O)$_2$NHR$^{11}$, —SO$_2$R$^{11}$, —OR$^{11}$, —C(O)R$^{11}$, —C(O)NR$^{11}$, —C(O)OR$^{11}$, —NR$^{11}$, —NC(O)R$^1$, heterocycle$C_{2-6}$alkenyl, heterocycle which may be optionally substituted with one or more substituents selected from the group consisting of oxo, $C_{1-8}$alkyl, and C(O)OR$^{11}$, and $C_{1-8}$alkyl which may be optionally substituted with one or more substituents selected from the group consisting of —CN and heterocycle, optionally substituted with —C(O)R$^{11}$;
$R^5$ is a substituent in the para position relative to X and is selected from the group consisting of halogen, $C_{1-8}$alkyl, —NO$_2$, —NH$_2$, $C_{1-8}$alkylamino, CF$_3$, or alkoxy;
$R^{11}$ is $C_{1-8}$alkyl, optionally substituted with one or more substituents selected from the group consisting of hydrogen, $C_{1-8}$alkyl, —S(O)$_2$NR$^8$R$^9$, —NR$^8$R$^9$, and heterocycle, optionally substituted with one or more substituents selected from the group consisting of oxo and $C_{1-8}$alkyl;

or a pharmaceutically acceptable derivative thereof.

The present invention also features compounds of formula (IV)

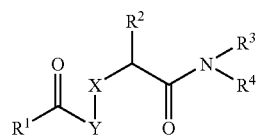

(IV)

wherein:
X is C, O, or N;
Y is heterocycle optionally substituted with one or more substituents selected from the group consisting of halogen, $C_{1-8}$alkyl, —NO$_2$, —NH$_2$, $C_{1-8}$alkylamino, —CF$_3$, or alkoxy;
$R^1$ is $C_{1-8}$alkyl; $C_{3-6}$cycloalkyl; $C_{6-14}$aryl which may be optionally substituted with one or more substituents selected from the group consisting of halogen, —CF$_3$, $C_{1-8}$alkyl, $C_{1-8}$alkylamino, $C_{3-6}$cycloalkyl$C_{2-6}$alkenyl, $C_{6-14}$aryl$C_{2-6}$alkenyl, —CN, —NO$_2$, —NH$_2$, —SR$^6$, —S(O)$_2$R$^6$, —S(O)R$^7$, —S(O)$_2$R$^7$, —C(O)R$^7$, $C_{2-6}$alkenyl which may be optionally substituted with a substituent selected from the group consisting of hydroxy, halogen, aryl, and heterocycle, and $C_{2-6}$alkynyl which may be optionally substituted with a substituent selected from the group consisting of hydroxy, halogen, aryl, $C_{3-6}$cycloalkyl, and heterocycle; or heterocycle, optionally substituted with one or more substituents selected from the group consisting of $C_{1-8}$alkyl, —CN, $C_{6-14}$aryl$C_{1-8}$alkyl and heterocycle;
$R^6$ is $C_{1-8}$alkyl, optionally substituted with one or more substituents selected from the group consisting of hydroxy, halogen, —CF$_3$, aryl, and heterocycle;
$R^7$ is $C_{1-8}$ alkyl, optionally substituted with one or more substituents selected from the group consisting of hydroxy, halogen, aryl, $C_{3-6}$cycloalkyl and heterocycle; —NH$_2$; or heterocycle;
$R^2$ is hydrogen, halogen, or $C_{1-8}$alkyl;
$R^3$ and $R^4$ are independently hydrogen; hydroxy; heterocycle, optionally substituted with one or more substituents selected from the group consisting of oxo, hydroxy, hydroxy$C_{1-8}$alkyl, halogen, $C_{1-8}$alkyl, OR$^{11}$ and —SR$^{10}$N(R$^{10}$)$_2$; or $C_{6-14}$aryl substituted with one or more substituents selected from the group consisting of hydroxy, halogen, —CF$_3$, C$_{1-8}$alkyl, hydroxyC$_{1-8}$alkyl, —CN, —NO$_2$, C$_{1-8}$alkylamino, heterocycleC$_{1-8}$alkyl, —C(O)NH$_2$, —S(O)R$^7$, —S(O)$_2$R$^7$, —C(O)R$^7$, —NSO$_2$R$^7$, —S(O)$_2$NR$^8$R$^9$, —OR$^{11}$, —C(O)R$^{11}$, —C(O)NR$^{11}$, —C(O)OR$^{11}$, —NR$^{11}$, —NC(O)R$^{11}$, heterocycleC$_{2-6}$alkenyl, heterocycle which may be optionally substituted with one or more substituents selected from the group consisting of oxo, C$_{1-8}$alkyl, and C(O)OR$^{11}$, and C$_{1-8}$alkyl which may be optionally substituted with one or more substituents selected from the group consisting of —CN and heterocycle, optionally substituted with —C(O)R$^{11}$; provided that R$^3$ and R$^4$ cannot both be hydrogen or hydroxy;

R$^8$ and R$^9$ are independently selected from the group consisting of hydrogen, C$_{1-8}$alkyl, C$_{1-8}$ alkylamino, C$_{1-8}$alkylheterocycle, heterocycle, and C$_{3-6}$cycloalkyl;

R$^{10}$ is C$_{1-8}$alkyl;

R$^{11}$ is C$_{1-8}$alkyl, optionally substituted with one or more substituents selected from the group consisting of hydrogen, C$_{1-8}$alkyl, —SO$_2$NR$^8$R$^9$, and heterocycle, optionally substituted with one or more substituents selected from the group consisting of oxo and C$_{1-8}$alkyl;

R$^5$ is hydrogen, halogen, C$_{1-8}$alkyl, —NO$_2$, —NH$_2$, C$_{1-8}$alkylamino, CF$_3$, or alkoxy;

or a pharmaceutically acceptable derivative thereof.

Preferred compounds of formula (IV) are compounds wherein Y is a heterocycle substituted with one or more substituents selected from the group consisting of halogen, C$_{1-8}$alkyl, —NO$_2$, —NH$_2$, C$_{1-8}$alkylamino, —CF$_3$, or alkoxy; or a pharmaceutically acceptable derivative thereof. More preferred compounds of formula (IV) are compounds wherein X is O. Most preferred compounds of formula (IV) are those wherein X is O and Y is a heterocycle substituted with one or more substituents selected from the group consisting of halogen, C$_{1-8}$alkyl, —NO$_2$, —NH$_2$, C$_{1-8}$alkylamino, —CF$_3$, or alkoxy; or a pharmaceutically acceptable derivative thereof.

Preferred compounds of the present invention include:

2-[2-(1-benzothiophen-2-ylcarbonyl)-4-chlorophenoxy]-N-phenylacetamide;
2-(2-benzoyl-4-chlorophenoxy)-N-[4-(1H-imidazol-1-yl) phenyl]acetamide;
2-[4-chloro-2-(2-thienylcarbonyl)phenoxy]-N-[2-methyl-4-(1-oxo-1lambda~4~,4-thiazinan-4-yl)phenyl]acetamide;
2-(2-benzoyl-4-chlorophenoxy)-N-[4-(1H-1,2,4-triazol-1-yl)phenyl]acetamide;
2-(2-benzoyl-4-chlorophenoxy)-N-[4-(4-morpholinyl)phenyl]acetamide;
N-[4-(aminosulfonyl)phenyl]-2-(2-benzoyl-4-chlorophenoxy)acetamide;
2-(2-benzoyl-4-chlorophenoxy)-N-{4-[(1,3-thiazol-2-ylamino)sulfonyl]phenyl}acetamide;
2-(2-benzoyl-4-chlorophenoxy)-N-[4-(4-methyl-1-piperazinyl)phenyl]acetamide;
2-(2-benzoyl-4-chlorophenoxy)-N-[4-(hydroxymethyl)phenyl]acetamide;
2-(2-benzoyl-4-chlorophenoxy)-N-{4-[(methylamino)sulfonyl]phenyl}acetamide;
2-(2-benzoyl-4-chlorophenoxy)-N-[4-(1-oxo-1lambda~4~,4-thiazinan-4-yl)phenyl]acetamide;
2-(2-benzoyl-4-chlorophenoxy)-N-[4-(1,1-dioxo-1lambda~6~,4-thiazinan-4-yl)phenyl]acetamide;
2-(2-benzoyl-4-chlorophenoxy)-N-[2-methyl-4-(4-morpholinyl)phenyl]acetamide;
2-(2-benzoyl-4-chlorophenoxy)-N-{4-[3-(dimethylamino)propoxy]-2-methylphenyl}acetamide;
2-(2-benzoyl-4-chlorophenoxy)-N-[4-(1-hydroxyethyl)phenyl]acetamide;
2-(2-benzoyl-4-chlorophenoxy)-N-[4-(1-hydroxyethyl)phenyl]acetamide;
2-(2-benzoyl-4-chlorophenoxy)-N-[2-methyl-4-(1-oxo-1lambda~4~,4-thiazinan-4-yl)phenyl]acetamide;
2-(2-benzoyl-4-chlorophenoxy)-N-{2-methyl-4-[3-(1-pyrrolidinyl)propoxy]phenyl}acetamide;
2-(2-benzoyl-4-chlorophenoxy)-N-(1H-indazol-5-yl)acetamide;
2-(2-benzoyl-4-chlorophenoxy)-N-{2-methyl-4-[3-(4-morpholinyl)propoxy]phenyl}acetamide;
2-(2-benzoyl-4-chlorophenoxy)-N-{4-[3-(1H-imidazol-1-yl)propoxy]-2-methylphenyl}acetamide;
2-(2-benzoyl-4-chlorophenoxy)-N-(1H-indazol-6-yl)acetamide;
2-[4-chloro-2-(2-thienylcarbonyl)phenoxy]-N-(1H-indazol-5-yl)acetamide;
2-[4-chloro-2-(2-furoyl)phenoxy]-N-(1H-indazol-5-yl)acetamide;
2-[4-chloro-2-(3-thienylcarbonyl)phenoxy]-N-(1H-indazol-5-yl)acetamide;
2-[4-chloro-2-(2-thienylcarbonyl)phenoxy]-N-{2-methyl-4-[3-(4-morpholinyl)propoxy]phenyl}acetamide;
2-[4-chloro-2-(2-thienylcarbonyl)phenoxy]-N-[4-(1-oxo-1lambda~4~,4-thiazinan-4-yl)phenyl]acetamide;
2-(2-benzoyl-4-chlorophenoxy)-N-{2-methyl-4-[3-(1-oxo-1lambda~4~,4-thiazinan-4-yl)propoxy]phenyl}acetamide;
2-[4-chloro-2-(2-furoyl)phenoxy]-N-[2-methyl-4-(1-oxo-1lambda~4~,4-thiazinan-4-yl)phenyl]acetamide;
N-[4-(aminosulfonyl)-2-methylphenyl]-2-(2-benzoyl-4-chlorophenoxy)acetamide;
N-[4-(aminosulfonyl)-2-methylphenyl]-2-[4-chloro-2-(2-thienylcarbonyl)phenoxy]acetamide;
2-[2-(1-benzofuran-2-ylcarbonyl)-4-chlorophenoxy]-N-phenylacetamide
2-[4-chloro-2-(1,3-thiazol-2-ylcarbonyl)phenoxy]-N-phenylacetamide;
N-[4-(aminosulfonyl)-2-methylphenyl]-2-[4-chloro-2-(2-furoyl)phenoxy]acetamide;
2-[4-chloro-2-(2-furoyl)phenoxy]-N-(1H-indazol-6-yl)acetamide;
2-[4-chloro-2-(3-furoyl)phenoxy]-N-[2-methyl-4-(1-oxo-1lambda~4~,4-thiazinan-4-yl)phenyl]acetamide;
2-[4-chloro-2-(3-thienylcarbonyl)phenoxy]-N-[4-(1-oxo-1lambda~4~,4-thiazinan-4-yl)phenyl]acetamide;
2-[4-chloro-2-(3-thienylcarbonyl)phenoxy]-N-[2-methyl-4-(1-oxo-1lambda~4~,4-thiazinan-4-yl)phenyl]acetamide;
2-{4-chloro-2-[(1-methyl-1H-pyrrol-2-yl)carbonyl]phenoxy}-N-phenylacetamide;
2-(4-chloro-2-{[5-(2-pyridinyl)-2-thienyl]carbonyl}phenoxy)-N-phenylacetamide;
2-[4-chloro-2-(1,3-thiazol-2-ylcarbonyl)phenoxy]-N-(1H-indazol-5-yl)acetamide;
2-[4-chloro-2-(1,3-thiazol-2-ylcarbonyl)phenoxy]-N-[2-methyl-4-(1-oxo-1lambda~4~,4-thiazinan-4-yl)phenyl] acetamide;
2-[4-chloro-2-(3-cyanobenzoyl)phenoxy]-N-[2-methyl-4-(1-oxo-1lambda~4~,4-thiazinan-4-yl)phenyl]acetamide;
2-[4-chloro-2-(3-pyridinylcarbonyl)phenoxy]-N-[2-methyl-4-(1-oxo-1lambda~4~,4-thiazinan-4-yl)phenyl]acetamide;
2-[2-(2-bromobenzoyl)-4-chlorophenoxy]-N-[2-methyl-4-(1-oxo-1lambda~4~, 4-thiazinan-4-yl)phenyl]acetamide;

2-[2-(4-bromobenzoyl)-4-chlorophenoxy]-N-[2-methyl-4-(1-oxo-1lambda~4~,4-thiazinan-4-yl)phenyl]acetamide;

N-[4-(aminosulfonyl)-2-methylphenyl]-2-[2-(2-bromobenzoyl)-4-chlorophenoxy]acetamide;

2-{4-chloro-2-[(5-methyl-3-isoxazolyl)carbonyl]phenoxy}-N-[2-methyl-4-(1-oxo-1 lambda~4~,4-thiazinan-4-yl)phenyl]acetamide;

2-[4-chloro-2-(3-fluorobenzoyl)phenoxy]-N-[2-methyl-4-(1-oxo-1lambda~4~,4-thiazinan-4-yl)phenyl]acetamide;

2-[4-chloro-2-(3-chlorobenzoyl)phenoxy]-N-[2-methyl-4-(1-oxo-1lambda~4~,4-thiazinan-4-yl)phenyl]acetamide;

N-[4-(aminosulfonyl)-2-methylphenyl]-2-[4-chloro-2-(3-cyanobenzoyl)phenoxy]acetamide;

N-[4-(aminosulfonyl)-2-methylphenyl]-2-[4-chloro-2-(3-fluorobenzoyl)phenoxy]acetamide;

N-[4-(aminosulfonyl)-2-methylphenyl]-2-[4-chloro-2-(3-chlorobenzoyl)phenoxy]acetamide;

2-{4-chloro-2-[(4-cyano-2-thienyl)carbonyl]phenoxy}-N-[2-methyl-4-(1-oxo-1lambda~4~,4-thiazinan-4-yl)phenyl]acetamide;

N-[4-(aminosulfonyl)-2-methylphenyl]-2-{4-chloro-2-[(4-cyano-2-thienyl)carbonyl]phenoxy}acetamide;

2-{4-chloro-2-[3-(trifluoromethyl)benzoyl]phenoxy}-N-[2-methyl-4-(1-oxo-1 lambda~4~,4-thiazinan-4-yl)phenyl]acetamide;

2-[2-(3-bromobenzoyl)-4-chlorophenoxy]-N-[2-methyl-4-(1-oxo-1lambda~4~,4-thiazinan-4-yl)phenyl]acetamide;

2-[4-chloro-2-(3,5-difluorobenzoyl)phenoxy]-N-[2-methyl-4-(1-oxo-1lambda~4~,4-thiazinan-4-yl)phenyl]acetamide;

N-[4-(aminosulfonyl)-2-methylphenyl]-2-[2-(3-bromobenzoyl)-4-chlorophenoxy]acetamide;

2-[4-chloro-2-(3-methylbenzoyl)phenoxy]-N-[2-methyl-4-(1-oxo-1lambda~4~,4-thiazinan-4-yl)phenyl]acetamide;

2-[4-chloro-2-(3-cyanobenzoyl)phenoxy]-N-(5-methyl-1H-indazol-6-yl)acetamide;

N-[4-(aminosulfonyl)-2-methylphenyl]-2-[4-chloro-2-(3-pyridinylcarbonyl)phenoxy]acetamide;

2-[4-chloro-2-(3-cyanobenzoyl)phenoxy]-N-{2-methyl-4-[3-(1-pyrrolidinyl)propoxy]phenyl}acetamide;

N-[4-(aminosulfonyl)-2-methylphenyl]-2-{4-chloro-2-[(1-methyl-1H-imidazol-2-yl)carbonyl]phenoxy}acetamide;

N-[4-(aminosulfonyl)-2-methylphenyl]-2-[4-chloro-2-(1,3-thiazol-2-ylcarbonyl)phenoxy]acetamide;

2-[4-chloro-2-(3,5-difluorobenzoyl)phenoxy]-N-{2-methyl-4-[3-(1-pyrrolidinyl)propoxy]phenyl}acetamide;

N-[4-(aminosulfonyl)-2-methylphenyl]-2-[4-chloro-2-(3,5-difluorobenzoyl)phenoxy]acetamide;

2-{4-chloro-2-[3-fluoro-5-(trifluoromethyl)benzoyl]phenoxy}-N-[2-methyl-4-(1-oxo-1 lambda~4~,4-thiazinan-4-yl)phenyl]acetamide N-(1,3-benzothiazol-6-yl)-2-(2-benzoyl-4-chlorophenoxy)acetamide 2-(4-chloro-2-{3-[(trifluoromethyl)sulfanyl]benzoyl}phenoxy)-N-[2-methyl-4-(1-oxo-1 lambda~4~,4-thiazinan-4-yl)phenyl]acetamide 2-[4-chloro-2-(3-ethynylbenzoyl)phenoxy]-N-[2-methyl-4-(1-oxo-1lambda~4~,4-thiazinan-4-yl)phenyl]acetamide;

2-[4-chloro-2-(3,5-dichlorobenzoyl)phenoxy]-N-[2-methyl-4-(1-oxo-1lambda~4~,4-thiazinan-4-yl)phenyl]acetamide;

N-[4-(aminosulfonyl)-2-methylphenyl]-2-[4-chloro-2-(3,5-dichlorobenzoyl)phenoxy]acetamide;

N-[4-(aminosulfonyl)-2-methylphenyl]-2-{4-chloro-2-[3-fluoro-5-(trifluoromethyl)benzoyl]phenoxy}acetamide;

N-(1,3-benzothiazol-6-yl)-2-[4-chloro-2-(3,5-difluorobenzoyl)phenoxy]acetamide

2-[4-chloro-2-(3-cyanobenzoyl)phenoxy]-N-(2-methyl-1,3-benzothiazol-5-yl)acetamide N-[4-(aminosulfonyl)-2-methylphenyl]-2-(4-chloro-2-{3-[(trifluoromethyl)sulfanyl]benzoyl}phenoxy)acetamide;

N-[4-(aminosulfonyl)-2-methylphenyl]-2-[4-chloro-2-(3-ethynylbenzoyl)phenoxy]acetamide;

2-(2-benzoyl-4-chlorophenoxy)-N-[4-(methylsulfonyl)phenyl]acetamide;

N-[4-(aminosulfonyl)-2-methylphenyl]-2-{4-chloro-2-[3-(2-cyclopentylethynyl)benzoyl]phenoxy}acetamide;

2-{4-chloro-2-[3-fluoro-5-(trifluoromethyl)benzoyl]phenoxy}-N-(5-methyl-1H-indazol-6-yl)acetamide;

2-[4-chloro-2-(3,5-dichlorobenzoyl)phenoxy]-N-(5-methyl-1H-indazol-6-yl)acetamide;

N-[4-(aminosulfonyl)-2-methylphenyl]-2-{4-chloro-2-[3-(2-phenylethynyl)benzoyl]phenoxy}acetamide;

2-[4-chloro-2-(3,5-difluorobenzoyl)phenoxy]-N-(5-methyl-H-indazol-6-yl)acetamide;

2-[4-chloro-2-(3,5-difluorobenzoyl)phenoxy]-N-[2-methyl-4-(methylsulfonyl)phenyl]acetamide;

N-(1,2-benzisothiazol-5-yl)-2-[4-chloro-2-(3-cyanobenzoyl)phenoxy]acetamide;

2-[4-chloro-2-(3,5-dichlorobenzoyl)phenoxy]-N-(5-methyl-1H-benzimidazol-6-yl)acetamide;

2-[4-chloro-2-(3,5-difluorobenzoyl)phenoxy]-N-(5-methyl-1H-benzimidazol-6-yl)acetamide;

2-{4-chloro-2-[3-fluoro-5-(trifluoromethyl)benzoyl]phenoxy}-N-(5-methyl-1H-benzimidazol-6-yl)acetamide 2-[4-chloro-2-(3,5-difluorobenzoyl)phenoxy]-1-(2,3-dihydro-1H-indol-1-yl)-1-ethanone;

2-[4-chloro-2-(3-cyanobenzoyl)phenoxy]-N-[2-methyl-4-(methylsulfonyl)phenyl]acetamide;

2-[4-chloro-2-(3-ethynylbenzoyl)phenoxy]-N-[2-methyl-4-(methylsulfonyl)phenyl]acetamide;

N-{4-[3-(aminosulfonyl)propoxy]-2-methylphenyl}-2-[4-chloro-2-(3,5-difluorobenzoyl)phenoxy]acetamide;

2-{2-[3,5-bis(trifluoromethyl)benzoyl]-4-chlorophenoxy}-N-(5-methyl-1H-benzimidazol-6-yl)acetamide;

2-{2-[(5-bromo-3-pyridinyl)carbonyl]-4-chlorophenoxy}-N-(5-methyl-1H-benzimidazol-6-yl)acetamide;

2-{4-chloro-2-[3-fluoro-5-(trifluoromethyl)benzoyl]phenoxy}-N-(6-methyl-1,3-benzothiazol-5-yl)acetamide;

N-{4-[3-(aminosulfonyl)propoxy]-2-methylphenyl}-2-{4-chloro-2-[3-fluoro-5-(trifluoromethyl)benzoyl]phenoxy}acetamide;

N-[4-(aminosulfonyl)-2-methylphenyl]-2-(4-chloro-2-{3-[(trifluoromethyl)sulfonyl]benzoyl}phenoxy)acetamide;

2-[4-chloro-2-(3,5-difluorobenzoyl)phenoxy]-N-[4-(1,3-thiazol-2-yl)phenyl]acetamide 2-[4-chloro-2-(3,5-difluorobenzoyl)phenoxy]-N-[4-(1,3-oxazol-2-yl)phenyl]acetamide 2-[4-chloro-2-(3,5-difluorobenzoyl)phenoxy]-N-{4-[(3-hydroxypropyl)sulfonyl]-2-methylphenyl}acetamide;

2-{4-chloro-2-[3-fluoro-5-(trifluoromethyl)benzoyl]phenoxy}-N-(2-methyl-4-{3-[(methylamino)sulfonyl]propoxy}phenyl)acetamide;

2-{4-chloro-2-[3-fluoro-5-(trifluoromethyl)benzoyl]phenoxy}-N-(4-{3-[(dimethylamino)sulfonyl]propoxy}-2-methylphenyl)acetamide;

N-[4-(aminosulfonyl)-2-methylphenyl]-2- {2-[(5-bromo-3-pyridinyl)carbonyl]-4-chlorophenoxy}acetamide;

2- {4-chloro-2-[3-fluoro-5-(trifluoromethyl)benzoyl]phenoxy}-N-{4-[3-(1H-imidazol-1-yl)propoxy]-2-methylphenyl}acetamide;

2-{4-chloro-2-[3-fluoro-5-(trifluoromethyl)benzoyl]phenoxy}-N-{2-methyl-4-[(E)-4-(1-pyrrolidinyl)-1-butenyl]phenyl}acetamide;

N-[4-(aminosulfonyl)-2-methylphenyl]-2-[4-chloro-2-(3-cyano-5-fluorobenzoyl)phenoxy]acetamide;
N-[4-(aminosulfonyl)-2-methylphenyl]-2-[4-chloro-2-(3-cyano-5-methylbenzoyl)phenoxy]acetamide;
N-[6-(aminosulfonyl)-4-methyl-3-pyridinyl]-2-[4-chloro-2-(3-cyano-5-methylbenzoyl)phenoxy]acetamide;
N-[4-(aminosulfonyl)-2-methylphenyl]-2-[4-chloro-2-(3-chloro-5-cyanobenzoyl)phenoxy]acetamide;
N-[4-(aminosulfonyl)-2-methylphenyl]-2-[4-chloro-2-(3,5-dimethylbenzoyl)phenoxy]acetamide;
N-[4-(aminosulfonyl)-2-methylphenyl]-2-[4-chloro-2-(3-cyano-5-ethylbenzoyl)phenoxy]acetamide;
2-[4-chloro-2-(3-cyano-5-methylbenzoyl)phenoxy]-N-{4-[3-(2,5-dihydro-1H-pyrrol-1-yl)propoxy]-2-methylphenyl}acetamide hydrochloride;
N-[4-(aminosulfonyl)-2-methylphenyl]-2-[4-chloro-2-(3-chloro-5-methylbenzoyl)phenoxy]acetamide;
N-[4-(aminosulfonyl)-2-methylphenyl]-2-[4-chloro-2-(3,5-dichlorobenzoyl)phenoxy]acetamide;
N-[4-(aminosulfonyl)-2-methylphenyl]-2-{4-chloro-2-[(6-cyano-2-pyridinyl)carbonyl]phenoxy}acetamide;
N-[6-(aminosulfonyl)-4-methyl-3-pyridinyl]-2-[4-chloro-2-(3-cyano-5-methylbenzoyl)phenoxy]acetamide;
N-[4-(aminosulfonyl)-2-methylphenyl]-2-[4-chloro-2-(3,5-dicyanobenzoyl)phenoxy]acetamide;
N-[4-(aminosulfonyl)-2-methylphenyl]-2-{4-chloro-2-[3-cyano-5-(trifluoromethyl)benzoyl]phenoxy}acetamide;

and pharmaceutically acceptable derivatives thereof.

Preferred compounds of the present invention include compound number 7, 32, 33, 36, 38, 44, 45, 49, 51, 52, 61, 65, 66, 71, 75, 76, 111, 112, 115, 118, 119, 128, 129, 171, 172, 191, 192, 199, 200, 206, 207, 224, 225, 232, 233, 235, 236, 246, 247, 253, 254, 255, 256, 259, 260, 261, 262, 264, 265, 267, 268, 288, 289, 290, 409, 412, 428, 430, 431, 433, 491, 564, 587, 475, 478, 498, 593, 483, 637, 503, 601, 658 and pharmaceutically acceptable derivatives thereof.

More preferred compounds of the present invention are selected from the group consisting of N-[4-(aminosulfonyl)-2-methylphenyl]-2-[4-chloro-2-(3-cyanobenzoyl)phenoxy]acetamide, N-[4-(aminosulfonyl)-2-methylphenyl]-2-[4-chloro-2-(3-fluoro-5-(trifluoromethyl)benzoyl]acetamide; N-{4-[3-(aminosulfonyl)propoxy]-2-methylphenyl}-2-{4-chloro-2-[3-fluoro-5-(trifluoromethyl)benzoyl]phenoxy}acetamide, N-[4-(aminosulfonyl)-2-methylphenyl]-2-[4-chloro-2-(3-cyano-5-fluorobenzoyl)phenoxy]acetamide, N-[4-(aminosulfonyl)-2-methylphenyl]-2-[4-chloro-2-(3-cyano-5-methylbenzoyl)phenoxy]acetamide, N-[6-(aminosulfonyl)-4-methyl-3-pyridinyl]-2-[4-chloro-2-(3-cyano-5-methylbenzoyl)phenoxy]acetamide, N-[4-(aminosulfonyl)-2-methylphenyl]-2-[4-chloro-2-(3-chloro-5-cyanobenzoyl)phenoxy]acetamide, N-[4-(aminosulfonyl)-2-methylphenyl]-2-[4-chloro-2-(3,5-dimethylbenzoyl)phenoxy]acetamide, N-[4-(aminosulfonyl)-2-methylphenyl]-2-[4-chloro-2-(3-cyano-5-ethylbenzoyl)phenoxy]acetamide, 2-[4-chloro-2-(3-cyano-5-methylbenzoyl)phenoxy]-N-{4-[3-(2,5-dihydro-1H-pyrrol-1-yl)propoxy]-2-methylphenyl}acetamide hydrochloride, N-[4-(aminosulfonyl)-2-methylphenyl]-2-[4-chloro-2-(3-chloro-5-methylbenzoyl)phenoxy]acetamide, N-[4-(aminosulfonyl)-2-methylphenyl]-2-[4-chloro-2-(3,5-dichlorobenzoyl)phenoxy]acetamide, N-[4-(aminosulfonyl)-2-methylphenyl]-2-{4-chloro-2-[(6-cyano-2-pyridinyl)carbonyl]phenoxy}acetamide, N-[6-(aminosulfonyl)-2-methyl-3-pyridinyl]-2-[4-chloro-2-(3-cyano-5-methylbenzoyl)phenoxy]acetamide, N-[4-(aminosulfonyl)-2-methylphenyl]-2-[4-chloro-2-(3,5-dicyanobenzoyl)phenoxy]acetamide and pharmaceutically acceptable derivatives thereof.

Compounds of the present invention that are advantageous are those wherein $R^1$ is $C_{6-14}$ aryl substituted in the meta position, particularly with halogen and wherein $R^3$ is hydrogen and $R^4$ is $C_{6-14}$aryl substituted with $C_{1-8}$alkyl, in particular methyl, in addition to one or more other substituents as defined above.

The term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl," alone or in combination with any other term, refers to a straight-chain or branched-chain alkyl group with at least one carbon-carbon double bond. Examples of alkenyl radicals include, but are not limited to, ethenyl, propenyl, isopropenyl, butenyl, isobutenyl, pentenyl, hexenyl, hexadienyl and the like.

The term "alkynyl" refers to hydrocarbon groups of either a straight or branched configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl," alone or in combination with any other term, refers to a carbocyclic aromatic radical (such as phenyl or naphthyl) containing the specified number of carbon atoms, preferably from 6-14 carbon atoms, and more preferably from 6-10 carbon atoms. Examples of aryl radicals include, but are not limited to phenyl, naphthyl, indenyl, indanyl, azulenyl, fluorenyl, anthracenyl and the like.

The term "heterocycle" or "heterocyclic" as used herein, refers to a 3- to 7- membered monocyclic heterocyclic ring or 8- to 11- membered bicyclic heterocyclic ring which is either saturated, partially saturated or unsaturated, and which may be optionally benzofused if monocyclic. Each heterocycle consists of one or more carbon atoms and from one to four heteroatoms selected from the group consisting of N, O and S, and wherein the nitrogen and sulfur heteroatoms may optionally be oxidized, and including any bicyclic group in which any of the above-defined heterocyclic rings is fused to a benzene ring. The heterocyclic ring may be attached at any carbon or heteroatom which results in the creation of a stable structure. Preferred heterocycles include 5-7 membered monocyclic heterocycles and 8-10 membered bicyclic heterocycles. Examples of such groups include imidazolyl, imidazolinoyl, imidazolidinyl, quinolyl, isoqinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyrano furanyl.

Preferred heterocycles include imidazolidinyl, indazolyl, pyrrolidinyl, thiamorpholinyl, thiophenyl, furyl, benzofuranyl, thiazolyl, oxazolyl, pyrrolyl, indolinolyl, benzthiazolyl, pyridinolyl, quinolinoyl, and benzothiophenyl.

The term "halogen" refers to a radical of fluorine, chlorine, bromine or iodine.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient, or the improvement of an ascertainable measurement associated with a particular disorder, and may include the suppression of symptom recurrance in an asymptomatic patient such as a patient in whom a viral infection has become latent. The term "prophylactically effective amount" refers to an amount effective in preventing a virus infection, for example an HIV infection, or preventing the occurrence of symptoms of such an infection, in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiviral agent.

As used herein, the compounds according to the invention are defined to include pharmaceutically acceptable derivatives thereof. A "pharmaceutically acceptable derivative" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium and NW+4 (wherein W is $C_{1-4}$ alkyl). Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$alkyl group).

Esters of the compounds according to the invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

Any reference to any of the above compounds also includes a reference to a pharmaceutically acceptable salts thereof.

In a further aspect of the invention there are provided the compounds according to the invention for use in medical therapy particularly for the treatment or prophylaxis of viral infections such as an HIV infection. Compounds according to the invention have been shown to be active against HIV infections, although these compounds may be active against HBV infections as well.

The compounds according to the invention are particularly suited to the treatment or prophylaxis of HIV infections and associated conditions. Reference herein to treatment extends to prophylaxis as well as the treatment of established infections, symptoms, and associated clinical conditions such as AIDS related complex (ARC), Kaposi's sarcoma, and AIDS dementia.

According to a particular embodiment of the present invention, there is provided a method of treatment of HIV mutant viruses that exhibit NNRTI drug resistance by administering a therapeutically effective amount of a compound of the present invention or a pharmaceutically acceptable derivative thereof to a mammal, in particular a human. In particular, the compounds of the present invention may be used to treat wild-type HIV-1 as well as several resistance mutations, for example, K103N, L1001, or Y181C.

According to another aspect, the present invention provides a method for the treatment or prevention of the symptoms or effects of a viral infection in an infected animal, for example, a mammal including a human, which comprises treating said animal with a therapeutically effective amount of a compound according to the invention. According to a particular embodiment of this aspect of the invention, the viral infection is a retorviral infection, in particular an HIV infection. A further aspect of the invention includes a method for the treatment or prevention of the symptoms or effects of an HBV infection.

The compounds according to the invention may also be used in adjuvant therapy in the treatment of HIV infections or HIV-associated symptoms or effects, for example Kaposi's sarcoma.

The present invention further provides a method for the treatment of a clinical condition in an animal, for example, a mammal including a human which clinical condition includes those which have been discussed in the introduction hereinbefore, which comprises treating said animal with a therapeutically effective amount of a compound according to the invention. The present invention also includes a method for the treatment or prophylaxis of any of the aforementioned infections or conditions.

In yet a further aspect, the present invention provides the use of a compound according to the invention in the manufacture of a medicament for the treatment or prophylaxis of any of the above mentioned viral infections or conditions.

The above compounds according to the invention and their pharmaceutically acceptable derivatives may be employed in combination with other therapeutic agents for the treatment of the above infections or conditions. Combination therapies according to the present invention comprise the administration of at least one compound of the present invention or a pharmaceutically acceptable derivative thereof and at least one other pharmaceutically active ingredient. The active ingredient(s) and pharmaceutically active agents may be administered simultaneously in either the same or different pharmaceutical formulations or sequentially in any order. The amounts of the active ingredient(s) and pharmaceutically active agent(s) and the relative timings of administration will be selected in order to achieve the desired combined therapeutic effect. Preferably the combination therapy involves the administration of one compound according to the invention and one of the agents mentioned herein below.

Examples of such further therapeutic agents include agents that are effective for the treatment of viral infections or associated conditions such as (1 alpha, 2 beta, 3 alpha)-9-[2,3-bis(hydroxymethyl)cyclobutyl]guanine [(−)BHCG, SQ-34514], oxetanocin-G (3,4-bis-(hydroxymethyl)-2-oxetanosyl]guanine), acyclic nucleosides (e.g. acyclovir, valaciclovir, famciclovir, ganciclovir, penciclovir), acyclic nucleoside phosphonates (e.g. (S)-1-(3-hydroxy-2-phosphonylmethoxypropyl)cytosine (HPMPC), PMEA, ribonucleotide reductase inhibitors such as 2-acetylpyridine 5-[(2-chloroanilino)thiocarbonyl)thiocarbonohydrazone, 3'-azido-3'-deoxythymidine, other 2',3'-dideoxynucleosides such as 2',3'-dideoxycytidine, 2',3'-dideoxyadenosine, 2',3'-dideoxyinosine, 2',3'-didehydrothymidine, protease inhibitors such as indinavir, ritonavir, nelfinavir, amprenavir, oxathiolane nucleoside analogues such as (−)-cis-1-(2-hydroxymethyl)-1,3-oxathiolane 5-yl)-cytosine (lamivudine) or cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9H-purin-9-yl]-2-cyclopentene-1-methanol (abacavir), ribavirin, 9-[4-hydroxy-2-(hydroxymethyl)but-1-yl]-guanine (H2G), tat inhibitors such as 7-chloro-5-(2-pyrryl)-3H-1,4-benzodiazepin-2-(H)one (Ro5-3335), 7-chloro-1,3-dihydro-5-(1H-pyrrol-2yl)-3H-1,4-benzodiazepin-2-amine (Ro24-7429), interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, or other non-nucleoside reverse transcriptase inhibitors (NNRTIs) such as nevirapine (BI-RG-587), loviride (α-APA) and delavuridine (BHAP), and phosphonoformic acid, and 1,4-dihydro-2H-3,1-benzoxazin-2-ones NNRTIs such as (−)-6chloro-4-cyclopropylethynyl-4-trifluoromethyl-1,4-dihydro-2H-3,1-benzoxazin-2-one (L-743,726 or DMP-266), and quinoxaline NNRTIs such as isopropyl (2S)-7-fluoro-3,4-dihydro-2-ethyl-3-oxo-1(2H)-quinoxalinecarboxylate (HBY1293).

The carrier(s) must be pharmaceutically acceptable in the sense of being compatible with the other ingredients of the formulation and not deleterious to the recipient thereof.

More preferably the combination therapy involves the administration of one of the above mentioned agents and a compound within one of the preferred or particularly preferred sub-groups within formulae (I)-(IV) (including IA, IB, IC and ID) as described above. Most preferably the combination therapy involves the joint use of one of the above named agents together with one of the compounds of the present invention specifically named herein.

The present invention further includes the use of a compound according to the invention in the manufacture of a medicament for simultaneous or sequential administration with at least one other therapeutic agent, such as those defined hereinbefore.

The compounds of the present invention may be synthesized by the following methods or by any method known in the art.

The compounds of the present invention may be prepared according to representative Schemes I-XXXIV, which are presented below. The compounds, which may be prepared according to these schemes, are not limited by the compounds contained in the schemes or by any particular substituents used in the schemes for illustrative purposes.

Compounds of formula (I) wherein $R_1$ is hereinbefore defined, can be readily prepared from compounds of formula IV and V wherein $R_1$, $R_2$, $R_3$, $R_4$, and $R_5$ are as hereinbefore defined and $R_6$ is hydrogen, using suitable coupling conditions known in the art.

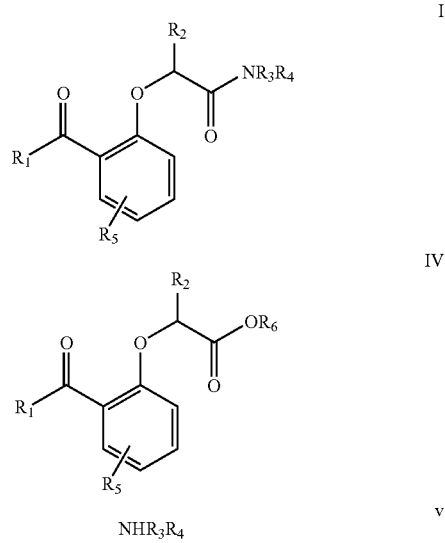

For example, compounds of formula IV can be allowed to react with compounds of formula V in the presence of a suitable dehydrating agent, such as a carbodiimide, dicyclohexylcarbodiimide (DCC) for example, or more preferably 1-(3-dimethylaminopropyl)-3-ethylcarbodiimide hydrochloride (EDAC). In addition, the presence of a suitable activating agent, such as 1-hydroxybenztriazole (HOBt), is usually required to promote efficient coupling of the carboxylic acid to the appropriate amine. These reactions are typically carried out in an aprotic solvent such as acetonitrile, tetrahydrofuran or more preferably N,N-dimethylformamide (DMF), at temperatures from 0° C. to 150° C., most preferably at ambient temperatures. For example, carboxylic acid 49 (Scheme I) is allowed to react with amine 399 in DMF and in the presence of EDAC and HOBt at ambient temperature to provide compound 46.

Scheme I

Alternatively, compounds of formula IV, wherein $R_1$, $R_2$, and $R_5$ are as hereinbefore defined, can first be converted to the corresponding acid chloride which is then allowed to react with compounds of formula V, wherein $R_3$ and $R_4$ are as hereinbefore defined, to afford compounds of (I). The preparation of the desired acid chloride can be accomplished by methods well-known in the art. The carboxylic acids can be allowed to react with a suitable dehydrating agent such as thionyl chloride or more preferably oxalyl chloride. These reactions are typically performed in an aprotic solvent such as acetonitrile or pyridine or a chlorinated solvent such as chloroform or more preferably dichloromethane. The corresponding acid chlorides are not typically isolated in pure form, but instead are allowed to react directly with compounds of formula V. Most often, reactions of the acid chlorides are performed in an aprotic solvent such as acetonitrile or chloroform, or more preferably in acetone. In addition, the presence of a compound capable of acting as a base such as triethylamine or pyridine, or more preferably sodium bicarbonate, is required in order to obtain sufficient yields of the coupling products. When inorganic bases such as sodium bicarbonate are used, the addition of a small amount of water to the reaction mixture promotes an efficient coupling reaction. For example, carboxylic acid 71 (Scheme II) is allowed to react with oxalyl chloride in dichloromethane and in the presence of a catalytic amount of DMF to afford the corresponding acid chloride. The acid chloride is then allowed to react with amine 466 in a mixture of acetone and water and in the presence of an excess of sodium bicarbonate to provide compound 78

Scheme II

Lastly, compounds of formula I in which $R_1$-$R_5$ are as hereinbefore defined, can be readily prepared by reaction of compounds of formula VI, wherein $R_7$ is hydrogen with compounds of formula VII wherein $R_2$, $R_3$ and $R_4$ are as hereinbefore defined, and $R_8$ is a suitable leaving group such as a halogen, preferably chlorine or bromine, or a methanesulfonate or para-toluenesulfonate ester.

The alkylation of compounds of formula VI by compounds of formula VII are typically performed in an aprotic solvent such as acetonitrile, DMF or more preferably in acetone. In addition, the presence of a compound capable of acting as a base such as triethyl amine, pyridine, or more preferably sodium carbonate, is usually required to promote efficient reaction. Furthermore, the reactions are typically carried out at elevated temperatures in the range of 40-100° C. For example, phenol 4 (Scheme III) is allowed to react with 2'-chloroacetanilide in the presence of sodium carbonate in refluxing acetone to provide compound 1.

Scheme III

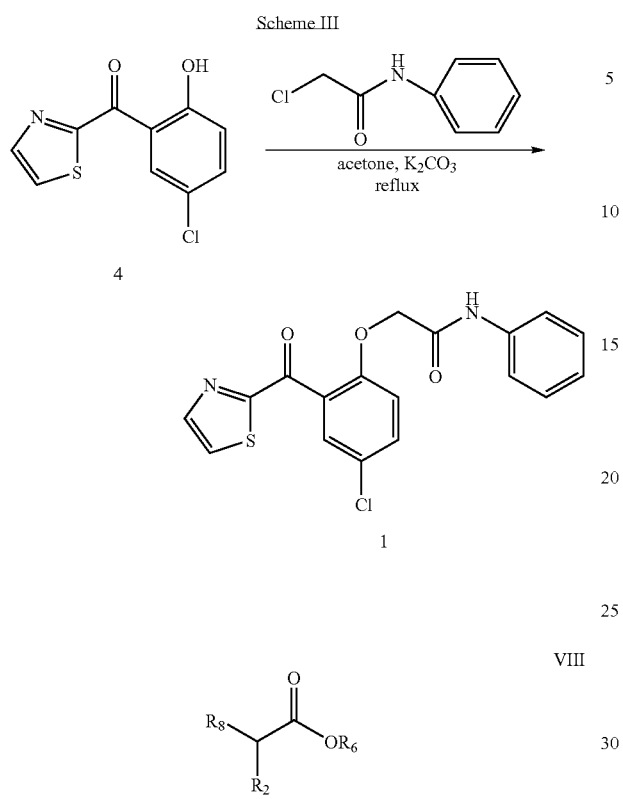

Compounds of formula IV, wherein $R_1$, $R_2$ and $R_5$ are as hereinbefore defined and $R_6$ is $C_{1-6}$alkyl, can be prepared by reaction of compounds of formula VI, wherein $R_1$ and $R_5$ are as hereinbefore defined, and $R_7$ is hydrogen, with those of formula VII, wherein $R_6$ is $C_{1-6}$alkyl, $R_2$ is as hereinbefore defined, and $R_8$ is a suitable leaving group such as a halogen, preferably chlorine or bromine, or a methanesulfonate or para-toluenesulfonate ester. Typically, the reactions are performed in an aprotic solvent such as acetonitrile, DMF, or more preferably acetone, and temperatures ranging from 40° C. to 100° C. In addition, the presence of an excess of a base such as triethylamine, pyridine, or more preferably potassium carbonate, is usually required for efficient reaction. For example, phenol 47 (Scheme IV) is allowed to react with ethyl bromoacetate in refluxing acetone and in the presence of potassium carbonate to afford ester 48.

Compounds of formula VIII are either commercially available or can be prepared using literature methods that are known in the art.

Scheme IV

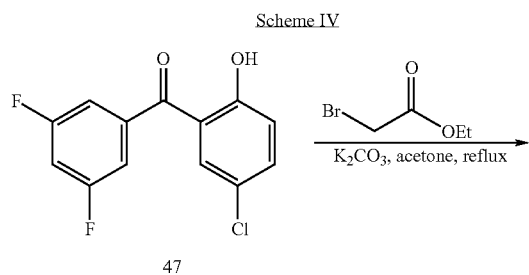

Compounds of formula IV, in which $R_1$, $R_2$ and $R_5$ are as hereinbefore defined and $R_6$ is hydrogen can be prepared from compounds of formula IV in which $R_1$, $R_2$ and $R_5$ are as hereinbefore defined and $R_6$ is $C_{1-6}$alkyl, by reaction with aqueous base or other suitable methods known in the art. A variety of inorganic bases can be used to affect the saponification of the esters of formula IV, such as sodium carbonate, sodium hydroxide or more preferably lithium hydroxide. Typically, these reactions are performed in water in addition to a solvent that is miscible with water and is capable of dissolving the compounds of formula IV such as tetrahydrofuran, methyl alcohol or ethyl alcohol.

For example, ester 48 (Scheme V) is allowed to react with lithium hydroxide in a mixture of THF, water, and ethanol to afford carboxylic acid 49.

Scheme V

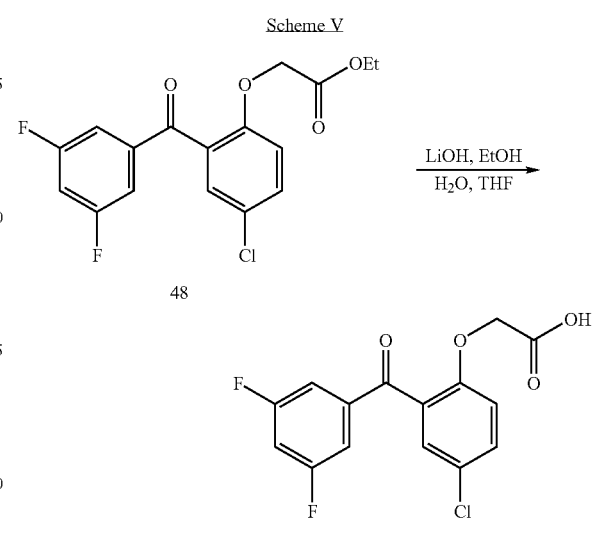

Below are schemes showing the preparation of compounds of formula VI, in which $R_1$ and $R_5$ are as hereinbefore defined, and $R_7$ is either hydrogen or methyl. Compounds of formula VI, in which $R_1$ and $R_5$ are as hereinbefore defined and $R_7$ is methyl, can be prepared by reaction of compounds of formula IX, wherein $R_5$ is as hereinbefore defined, and $R_7$ is methyl with those of formula X, wherein $R_1$ and $R_{10}$ are as hereinbefore defined, with the further stipulation that these groups are chemically compatible with the reaction conditions, $R_7$ is methyl, $R_9$ is a halogen, preferably bromine or iodine, and $R_{10}$ is N,O-dimethylhydroxylamino.

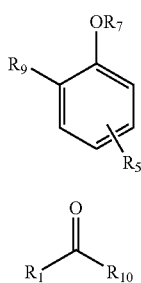

Typically, compounds of formula IX are treated with an agent capable of effecting a halogen-metal exchange reaction, such as sec-butyl lithium, methyl lithium, tert-butyl lithium, or more preferably n-butyl lithium. The halogen-metal exchange can be performed in an ethereal solvent such as THF, dioxane or more preferably diethyl ether, and at low temperatures ranging from −100° C. to 0° C., most preferably −78° C. When the halogen-metal exchange reaction is complete, the resulting compounds of formula IX, in which $R_9$ is lithium, are allowed to react with compounds of formula X, again in an ethereal solvent and at low temperatures. For example, 2-bromo-4-chloroanisole (Scheme VI) in diethyl ether is treated with n-butyl lithium at −78° C. After 15 minutes at −78° C., the resulting lithium species is allowed to react with amide 68 to afford the desired ketone 69.

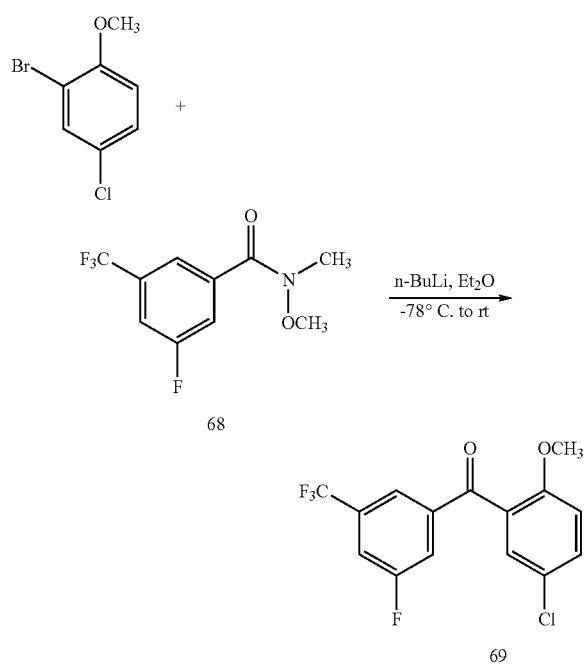

Compounds of formula IX, in which $R_5$ is as hereinbefore defined, $R_7$ is methyl and $R_9$ is either bromine or iodine are either commercially available or can be prepared using literature methods known in the art.

Compounds of formula X, in which $R_1$ is as hereinbefore defined and $R_{10}$ is N,O-dimethylhydroxylamino, can be prepared from compounds of formula X in which $R_{10}$ is a suitable leaving group, preferably chlorine, by reaction with N,O-dimethylhydroxylamine in an aprotic solvent, preferably acetonitrile, chloroform or dichloromethane, and in the presence of a base, preferably triethylamine. Compounds of formula X in which $R_{10}$ is chlorine can be prepared from compounds of formula X, in which $R_{10}$ is hydroxy, using literature methods known in the art, such as reaction with oxalyl chloride in an aprotic solvent, preferably dichloromethane or chloroform and in the presence of a catalytic amount of DMF. For example, 1-methyl-2-pyrrolecarboxylic acid (Scheme VII) in dichloromethane is allowed to react with excess oxalyl chloride in the presence of a catalytic amount of DMF. The resulting acid chloride is not isolated in pure form, but instead is allowed to react with N,O-dimethylhydroxylamine in chloroform and in the presence of triethylamine, to afford amide 14.

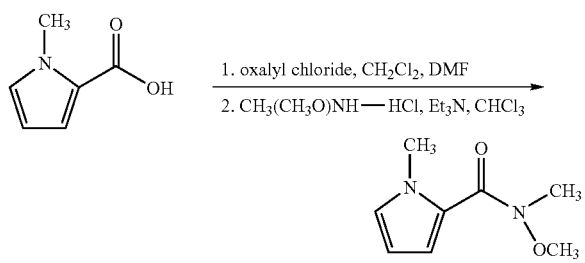

Alternatively, compounds of formula VI, in which $R_1$ and $R_5$ are as hereinbefore defined and $R_7$ is methyl can be prepared by reaction of compounds of formula IX with those of formula X, wherein $R_1$ and $R_5$ are as hereinbefore defined with the further stipulation that these groups are chemically compatible with the reaction conditions, $R_7$ is methyl, $R_9$ is a halogen, preferably bromine or iodine, and $R_{10}$ is N,O-dimethylhydroxylamino. Compounds of formula IX can be converted to a species in which $R_9$ is a magnesium halide, such as magnesium bromide or magnesium iodide, so-called Grignard reagents. The species containing the magnesium halide is then allowed to react with compounds of formula X, in which $R_{10}$ is N,O-dimethylhydroxylamino. These reactions are typically performed in ethereal solvents such as THF, dioxane or diethyl ether and at temperatures from 0° C. to 100° C., preferably ambient temperature. The preparation of compounds of formula IX in which $R_9$ is a magnesium halide can be accomplished by literature methods known in the art. Typically, a compound of formula IX, in which $R_9$ is either bromine or iodine, is allowed to react with elemental magnesium in an aprotic, ethereal solvent.

Alternatively, compounds of formula VI, in which $R_1$ and $R_5$ are as hereinbefore defined and $R_7$ is methyl, can be prepared from compounds of formula IX, in which $R_5$ is as hereinbefore defined, $R_7$ is methyl and $R_9$ is a halogen, preferably bromine or iodine, by reaction with compounds of formula X, in which $R_1$ is as hereinbefore defined and $R_{10}$ is hydrogen, with the further stipulation that $R_1$ is chemically compatible with subsequent reaction conditions. Compounds of formula X, in which $R_1$ is as hereinbefore defined and $R_{10}$ is hydrogen, are either commercially available or can be prepared using literature methods known in the art. Compounds of formula IX, in which $R_9$ is either bromine or iodine, are first treated with an agent capable of effecting a halogen-metal exchange reaction, preferably n-butyl lithium, in an ethereal solvent, preferably diethyl ether, and at low temperatures, preferably −78° C. After the compound of formula IX, in which $R_9$ is lithium, has formed, it is allowed to react with compounds of formula X, in which $R_{10}$ is hydrogen, to afford an intermediate alcohol species. Subsequently, the intermediate alcohol can be treated with an agent capable of oxidizing the alcohol to a compound of formula VI, the preferred oxidizing agent being manganese (IV) oxide. Typically, the oxidation reactions are performed in an aprotic solvent, preferably chloroform or dichloromethane, and at ambient temperatures. For example, 2-bromo-4-chloroanisole was treated with n-butyl lithium in ether and at −78° C. The resulting lithio species is then allowed to react with 2-thiazolecarboxaldehyde to afford intermediate alcohol 2. Alcohol 2 is then allowed to react with an excess of manganese dioxide in dichloromethane at room temperature to afford ketone 3

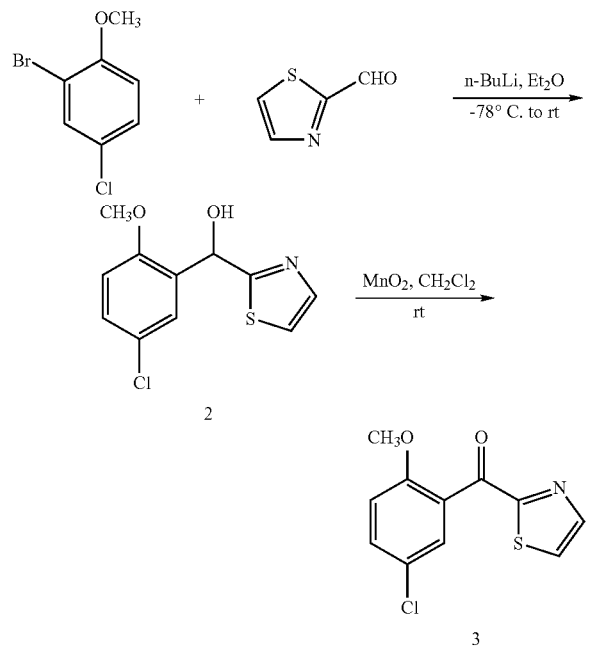

Alternatively, compounds of formula VI, in which $R_1$ and $R_5$ are as hereinbefore defined and $R_7$ is methyl, can be prepared by reaction of compounds of formula IX with those of formula X, wherein $R_1$ and $R_5$ are as hereinbefore defined, with the further stipulation that these groups are chemically compatible with the reaction conditions, $R_7$ is methyl, $R_9$ is a halogen, preferably bromine or iodine, and $R_{10}$ is hydrogen. Compounds of formula IX can be converted to a species in which $R_9$ is a magnesium halide, such as magnesium bromide or magnesium iodide, so-called Grignard reagents. The species containing the magnesium halide is then allowed to react with compounds of formula X, in which $R_{10}$ is hydrogen, to afford an intermediate alcohol. These reactions are typically performed in ethereal solvents such as THF, dioxane or diethyl ether and at temperatures from 0° C. to 100° C., preferably ambient temperature. The preparation of compounds of formula IX, in which $R_9$ is a magnesium halide, can be accomplished by literature methods known in the art. Typically, a compound of formula IX, in which $R_9$ is either bromine or iodine, is allowed to react with elemental magnesium, in an aprotic, ethereal solvent. The intermediate alcohol is then allowed to react with an agent capable of oxidizing it to the desired ketone, preferably manganese (IV) oxide, in an aprotic solvent, preferably dichloromethane or chloroform, and at ambient temperature.

Lastly, compounds of formula VI, in which $R_1$ and $R_5$ are as hereinbefore defined and $R_7$ is methyl, can be prepared by reaction of compounds of formula XII, in which $R_5$ is as hereinbefore defined, with compounds of formula XIII, in which $R_1$ is as hereinbefore defined, and $R_{11}$ is a halogen, preferably bromine or iodine, with the further stipulation that $R_1$ and $R_5$ are chemically compatible with subsequent chemical steps.

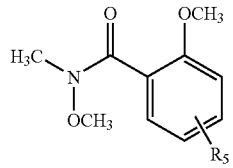

$R_1$—$R_{11}$ XIII

Typically, compounds of formula XIII, in which $R_{11}$ is a halogen, preferably iodine or bromine, are treated with an agent capable of effecting a halogen-metal exchange reaction, preferably n-butyl lithium, in an ethereal solvent, preferably diethyl ether and at low temperature, preferably −78° C.

Alternatively, compounds of formula VI, in which $R_1$ and $R_5$ are as hereinbefore defined and $R_7$ is methyl, can be prepared by reaction of compounds of formula XII with those of formula XIII, wherein $R_1$ and $R_5$ are as hereinbefore defined, with the further stipulation that these groups are chemically compatible with the reaction conditions, and $R_{11}$ is a halogen, preferably bromine or iodine. Compounds of formula XIII can be converted to a species in which $R_{11}$ is a magnesium halide, such as magnesium bromide or magnesium iodide, so-called Grignard reagents. The species containing the magnesium halide is then allowed to react with compounds of formula XII to afford the desired ketone. These reactions are typically performed in ethereal solvents such as THF, dioxane or diethyl ether and at temperatures from 0° C. to 100° C., preferably ambient temperature. The preparation of compounds of formula XIII, in which $R_{11}$ is a magnesium halide, can be accomplished by literature methods known in the art. Typically, a compound of formula XIII in which $R_{11}$ is either bromine or iodine is allowed to react with elemental magnesium, in an aprotic, ethereal solvent.

Compounds of formula XIII, in which $R_{11}$ is a halogen, preferably bromine or iodine, are either commercially available or can be prepared by literature methods.

Compounds of formula VI, in which $R_1$ and $R_5$ are as hereinbefore defined and $R_7$ is hydrogen, can be prepared from compounds of formula VI, in which $R_7$ is methyl, by reaction with agents capable of demethylating aryl methyl ethers, with the stipulation that $R_1$ and $R_5$ are chemically stable under these reaction conditions. Among the agents which may be used for demethylating aryl methyl ethers are trimethylsilyl iodide, Lewis acids such as aluminum chloride, or more preferably boron tribromide. These reactions are typically conducted in aprotic solvents such as chloroform or dichloromethane and at temperatures from −78° to 100° C., preferably from −78° C. to ambient temperature. For example, ketone 69 (Scheme IX) is allowed to react with an excess of boron tribromide in dichloromethane at −78° C. to afford phenol 70.

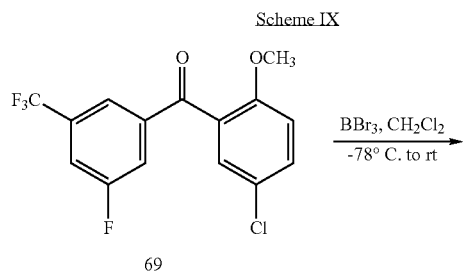

Alternatively, compounds of formula VI, in which $R_1$ and $R_5$ are as hereinbefore defined, and $R_7$ is hydrogen, can be prepared by reaction of compounds of formula IX, in which $R_5$ is as hereinbefore defined, $R_9$ is hydrogen and $R_7$ is methyl, with compounds of formula X, in which $R_1$ is as hereinbefore defined, and $R_{10}$ is a halogen, preferably chlorine, with the further stipulation that $R_1$ and $R_5$ are chemically compatible with the reaction conditions. These reactions, typically called Friedel-Craft acylations, are performed in an aprotic solvent such as nitrobenzene, 1,2-dichloroethane, sulfolane, or more preferably dichloromethane, at temperatures ranging from 0° C. to 150° C., preferably 35-60° C. In addition, the use of a compound which is capable of acting as a Lewis acid, such as titanium (IV) chloride, tin (IV) chloride, or more preferably aluminum chloride is required. For example, 4-chloroanisole (Scheme X) is allowed to react with 3,5difluorobenzoyl chloride in refluxing dichloromethane in the presence of aluminum chloride to afford ketone 47.

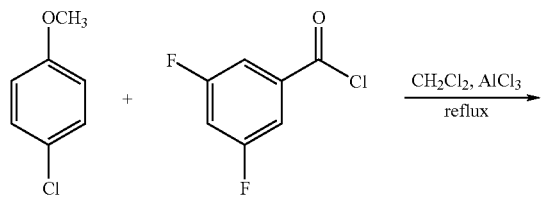

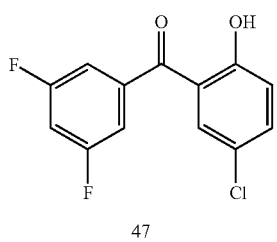

Compounds of formula X, in which $R_1$ is as hereinbefore defined, and $R_{10}$ is a halogen, are either commercially available or can be prepared by literature methods. Alternatively, compounds of formula VI, in which $R_1$ and $R_5$ are as hereinbefore described and $R_7$ is hydrogen, can prepared from the reaction of compounds of formula IX, in which $R_5$ is as hereinbefore defined, and $R_7$ and $R_9$ are hydrogen, with compounds of formula X, in which $R_1$ in as hereinbefore defined and $R_{10}$ is a halogen, preferably chlorine. These reactions, typically called Fries rearrangements, are performed in an aprotic solvent, such as nitrobenzene, sulfolane or chloroform and at temperatures ranging from 0° C. to 150° C. In addition, the reaction typically requires the presence of a compound capable of acting as a Lewis acid, such as aluminum chloride. Compounds of formula IX, in which $R_5$ is as hereinbefore defined, and $R_9$ and $R_7$ are hydrogen, are either commercially available or can be prepared by literature methods which are familiar to those skilled in the art.

Compounds of formula VI in which $R_1$ is $C_{6-14}$ aryl or $C_{6-14}$heterocycle, substituted with $C_{2-8}$ alkenyl, can be prepared from compounds of formula XIV, wherein $R_5$ is as hereinbefore defined, $R_7$ is hydrogen, methyl or methylene carboxyl ester and $R_{12}$ is a group capable of undergoing a palladium-catalyzed reaction, such as bromine, iodine, or trifluoromethanesulfonate ester, by reaction with $C_{2-8}$ alkenes.

These reactions are typically conducted in the presence of a palladium catalyst such as tetrakis(triphenylphosphine) palladium, palladium dichloride bis(acetonitrile), or more preferably palladium acetate. The solvents for these reactions are typically aprotic solvents such as acetonitrile, or more preferably DMF. The reactions are usually performed at temperatures ranging from ambient temperature to 130° C., preferably 50-90° C. In addition, the presence of a base such as potassium or sodium carbonate, or triethylamine, is usually required. Lastly, reactions of some substrates may require the addition of a compound which is capable of stabilizing any intermediate palladium species. These compounds are most often triaryl arsine or phosphine derivatives, such as triphenylphosphine, or tri-ortho-tolylphosphine.

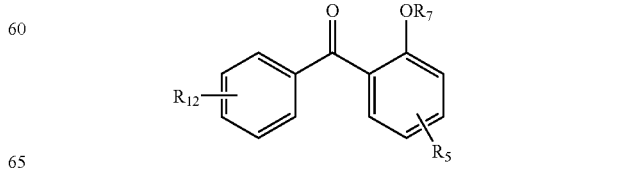

The $C_{2-8}$ alkenes used in these reactions are either commercially available or can be prepared using literature methods which are familiar to those skilled in the art.

Compounds of formula XIV in which $R_7$, and $R_5$ are as hereinbefore defined and $R_{12}$ is a group capable of undergoing a palladium-catalyzed reaction, such as bromine, iodine, or trifluoromethanesulfonate ester, are either commercially available or can be prepared by literature methods.

Compounds of formula VI in which $R_1$ is $C_{6-14}$ aryl or $C_{6-14}$heterocycle, substituted with $C_{2-8}$ alkyl, can be prepared from compounds of formula VI in which $R_1$ is $C_{6-14}$ aryl, substituted with $C_{2-8}$ alkenyl, by reaction with agents capable of selectively reducing the alkene bond. Among the agents that may be used to effect the desired reduction are palladium on carbon and Raney nickel. In addition, the presence of a reducing agent such as ammonium formate or pressurized hydrogen gas is required. These reactions are typically performed in a solvent capable of dissolving the olefinic substrate such as ethyl acetate, acetone, methyl alcohol or ethyl alcohol.

Compounds of formula VI in which $R_1$ is $C_{6-4}$ aryl or $C_{6-14}$heterocycle, substituted with $C_{2-8}$ alkynyl groups, can be prepared from compounds of formula XIV, in which $R_5$ is as hereinbefore described, $R_7$ is hydrogen, methyl or methylene carboxyl ester and $R_{12}$ is a group capable of undergoing a palladium-catalyzed reaction, preferably iodine or bromine, by reaction with $C_{2-8}$ alkynes. These reactions are typically performed in the presence of a palladium catalyst such as tetrakis(triphenylphosphine)palladium, palladium dichloride bis(acetonitrile), or palladium acetate. The solvents for these reactions are typically aprotic solvents such as acetonitrile, or more preferably DMF. The reactions are usually performed at temperatures ranging from ambient temperature to 130° C., preferably 50-90° C. In addition, the presence of a base such as potassium or sodium carbonate, or triethylamine, is usually required. Furthermore, reactions of some substrates may require the addition of a compound which is capable of stabilizing any intermediate palladium species. These compounds are most often triaryl arsine or phosphine derivatives, such as triphenylphosphine, or tri-ortho-tolylphosphine. Lastly, these reactions require the presence of a catalytic amount of copper (I) iodide. For example, ester 223 (Scheme XI) is allowed to react with trimethylsilylacetylene, in the presence of tertakis(triphenylphosphine)palladium, triethylamine and copper (I) iodide, to afford the intermediate trimethylsilyl-protected product. Treatment of the intermediate with tetrabutylammonium fluoride in THF provides compound 224

Scheme XI

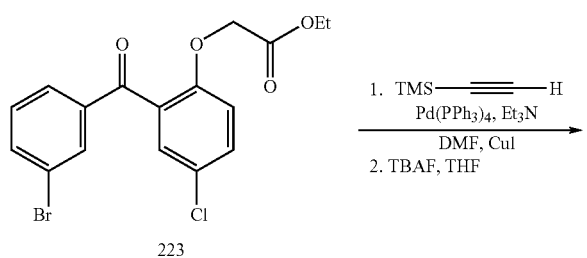

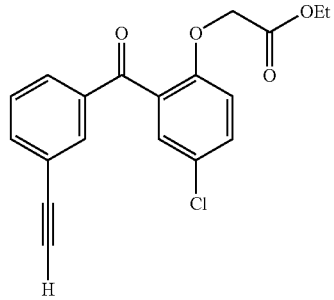

The $C_{2-8}$ alkynes used in these reactions are either commercially available or can be prepared by literature methods familiar to those skilled in the art.

Compounds of formula VI in which $R_1$ is $C_{6-14}$ aryl or $C_{6-14}$ arylheterocycle substituted with an amino group, $R_5$ is as hereinbefore described, and $R_7$ is hydrogen, methyl or methylene carboxy ester can be prepared from compounds of formula VI, in which $R_1$ is $C_{6-14}$ aryl or $C_{6-14}$ arylheterocycle substituted with nitro, by reaction with a combination of agents which are capable of reducing a nitro functionality to an amino group. Among these combination of agents are a metal containing compound, such as elemental iron, palladium or Raney nickel and a reducing agent, such as ammonium formate, formic acid, hydrochloric acid or pressurized hydrogen gas. These reactions are typically performed in a solvent such as ethyl acetate, acetone, methyl alcohol or ethyl alcohol and at temperatures ranging from 20° C. to 100° C., preferably ambient temperature.

Compounds of formula VI, in which $R_1$ is $C_{6-14}$ aryl or $C_{6-14}$ arylheterocycle, substituted with a nitro functionality, $R_5$ is as hereinbefore described and $R_7$ is hydrogen or methyl, can be prepared by methods previously described herein or by literature methods known in the art.

Compounds of formula VI, in which $R_1$ is $C_{6-14}$ aryl or $C_{6-14}$ arylheterocycle substituted with $-SO_2R_{13}$, where $R_5$ is as previously defined, $R_7$ is hydrogen, methyl or methylene carboxy ester and $R_{13}$ is $C_{1-8}$ alkyl, which is optionally substituted with hydroxy, alkylamino, or halogen, can be prepared from compounds of formula VI in which $R_1$ is $C_{6-14}$ aryl or $C_{6-14}$ arylheterocycle substituted with $SR_{13}$, by reaction with agents which are capable of oxidizing a sulfide to a sulfone. Among the agents which are capable of effecting the desired, selective oxidation are meta-chloroperbenzoic acid (m-CPBA), hydrogen peroxide in acetic acid and oxone. These reactions are typically conducted in solvents such as dichloromethane, chloroform, ethyl alcohol, water or a mixture of these solvents and in the temperature range from 0° C. to 100° C.

Compounds of formula VI, in which $R_1$ is $C_{6-14}$ aryl or $C_{6-14}$ arylheterocycle substituted with $-SR_{13}$, wherein $R_{13}$ is as previously described herein, can be prepared from commercially available material or by literature methods familiar to those skilled in the art.

Compounds of formula VI, in which $R_1$ is $C_{6-14}$ aryl or $C_{6-14}$ arylheterocycle substituted with nitrile, can be prepared from compounds of formula VI, in which $R_1$ is $C_{6-14}$ aryl or $C_{6-14}$ arylheterocycle substituted with a halogen, preferably bromine or iodine, by reaction with an agent or a combination of agents capable of replacing the halogen with a nitrile functional group. Among these agents are copper (I)

cyanide or a palladium catalyst in combination with an appropriate cyanide source such as potassium cyanide, sodium cyanide, or zinc cyanide. Among the palladium agents that can be employed for this transformation are tertrakis(triphenylphosphine)palladium, palladium acetate, or palladium dichloride bis(acetonitrile). These reactions are typically conducted in aprotic solvents such as acetonitrile, or more preferably DMF, and in the presence of phosphine ligand, such as triphenylphosphine, and at temperatures from 20° C. to 150° C., preferably 80-85° C.

Compounds of formula VI, in which $R_1$ is as hereinbefore described, $R_7$ is hydrogen, methyl or methylene carboxy ester and $R_5$ is hydrogen, halogen, nitro, trifluoromethyl, $C_{1-8}$ alkyl or alkoxy can be prepared from commercially available material using processes described herein or by literature methods familiar to those skilled in the art.

Compounds of formula VI, in which $R_1$ is as previously described, $R_7$ is hydrogen, methyl or methylene carboxy ester, and $R_5$ is amino, can be prepared from compounds of formula VI in which $R_5$ is nitro by reaction with agents or a combination of agents capable of reducing a nitro group to an amino functionality. Among these combination of agents are a metal containing compound, such as elemental iron, palladium or Raney nickel and a reducing agent, such as ammonium formate, formic acid, hydrochloric acid or pressurized hydrogen gas. These reactions are typically performed in a solvent such as ethyl acetate, acetone, methyl alcohol or ethyl alcohol and at temperatures ranging from 20° C. to 100° C., preferably ambient temperature.

Compounds of formula VI in which $R_1$ is as hereinbefore defined, $R_7$ is hydrogen, methyl or methylene carboxy ester, and $R_5$ is $C_{1-8}$ alkylamino can be prepared from compounds of formula VI in which $R_5$ is amino, by reaction with agents capable of selectively alkylating the amino group. Among these agents are alkyl halides, such as methyl iodide, alkylsulfonate esters or alkylaryl sulfonate esters. These reactions are typically performed in polar, aprotic solvents such as N-methylpyrrolidine or DMF and at temperatures ranging from ambient to 150° C.

Compounds of formula V, in which $R_3$ and $R_4$, which may be the same or different, are hydrogen, hydroxy, $C_{1-8}$alkyl, heterocycle, $C_{6-14}$arylheterocycle or $C_{6-14}$aryl are commercially available or can be prepared by literature methods familiar to those skilled in the art.

Compounds of formula V, in which $R_3$ is hydrogen and $R_4$ is $C_{6-14}$aryl substituted with —$SO_2NR_6R_7$, wherein $R_6$ and $R_7$ are as hereinbefore defined, are either commercially available or can be prepared from compounds of formula XV, in which $R_{14}$ is a nitrogen protecting group, such as trifluoromethyl acetyl, or more preferably acetyl, $R_{15}$ is hydrogen, halogen, $C_{1-8}$alkyl, $C_{1-8}$alkoxy, nitro, nitrile, trifluoromethyl, and $R_{16}$ is —$SO_2NR_6R_7$, by reaction with either aqueous base or aqueous acid. These reactions are typically performed in a protic solvent such as water, methyl alcohol, ethyl alcohol or a mixture thereof, and at temperatures ranging from 25° C. to 100° C., preferably 60-70° C. For example, compound 465 (Scheme XII) is allowed to react with 1N aqueous hydrochloric acid solution in ethanol at reflux temperature to afford 466.

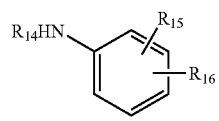

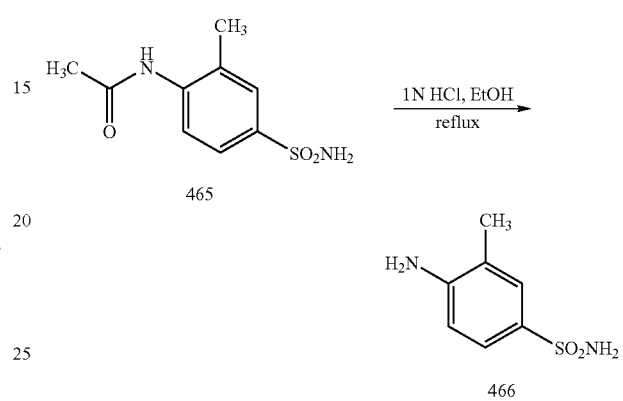

Compounds of formula V, in which $R_3$ is hydrogen and $R_4$ is $C_{6-14}$aryl substituted with —$SO_2NR_6R_7$, wherein $R_6$ and $R_7$ are as hereinbefore defined, can be prepared from compounds of formula XV, in which $R_{14}$ is a nitrogen protecting group, such as trifluoromethyl acetyl, or more preferably acetyl, $R_{15}$ is hydrogen, halogen, $C_{1-8}$alkyl, $C_{1-8}$alkoxy, nitro, nitrile, trifluoromethyl, and $R_{16}$ is —$SO_2Cl$, by reaction with an appropriate amine. These reactions are typically conducted in a solvent such as ethyl alcohol, THF or acetone and at temperatures from –10° C. to 50° C., preferably 20-25° C. For example, sulfonyl chloride 464 (Scheme XIII) is allowed to react with ammonium hydroxide in THF at ambient temperature to afford sulfonamide 465.

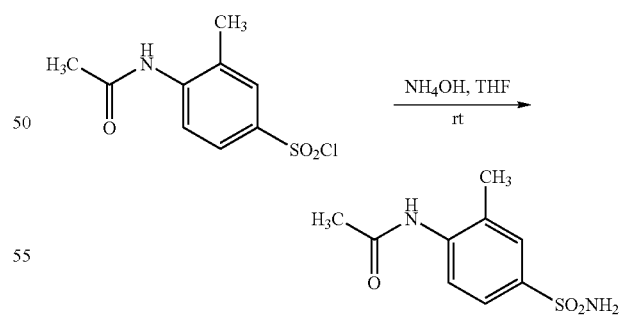

Compounds of formula XV, in which $R_{14}$ is a nitrogen protecting group, such as trifluoromethyl acetyl, or more preferably acetyl, $R_{15}$ is hydrogen, halogen, $C_{1-8}$alkyl, $C_{1-8}$alkoxy, nitro, nitrile, trifluoromethyl, and $R_{16}$ is —$SO_2Cl$, can be prepared from compounds of formula XV, in which $R_{16}$ is —$SO_3H$ or a salt thereof, by reaction with an agent capable of converting a sulfonic acid or a salt thereof to a sulfonyl chloride. Among the agents that are capable of affecting this transformation are phosphorous oxychloride (POCl$_3$), or thionyl chloride. These reactions are conducted in an aprotic solvent such as DMF, and at temperatures from −10° C. to 100° C., preferably 0° C. For example, compound 463 (Scheme XIV) is allowed to react with thionyl chloride in DMF at 0° C. to provide sulfonyl chloride 464.

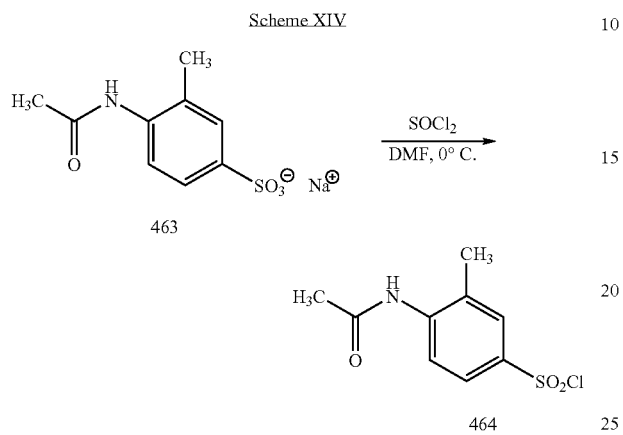

Compounds of formula XV, in which $R_{14}$ is a nitrogen protecting group, such as trifluoromethyl acetyl, or more preferably acetyl, $R_{15}$ is hydrogen, halogen, $C_{1-8}$alkyl, $C_{1-8}$alkoxy, nitro, nitrile, trifluoromethyl, and $R_{16}$ is —SO$_3$H or a salt thereof, can be prepared from compounds of formula XV, in which $R_{14}$ is hydrogen, by reaction with an agent capable of selectively protecting the amino group. Among the reagents that are capable of affecting this transformation are trifluoroacetic anhydride, acetyl chloride, or more preferably acetic anhydride. These reactions are conducted in an aprotic solvent, such as acetonitrile, dichloromethane, chloroform, or more preferably pyridine, and at temperatures from 0° C. to 100° C., preferably ambient temperatures. For example, 2-aminotoluene-5-sulfonic acid (Scheme XV) is allowed to react with acetic anhydride in pyridine at ambient temperature to provide compound 462.

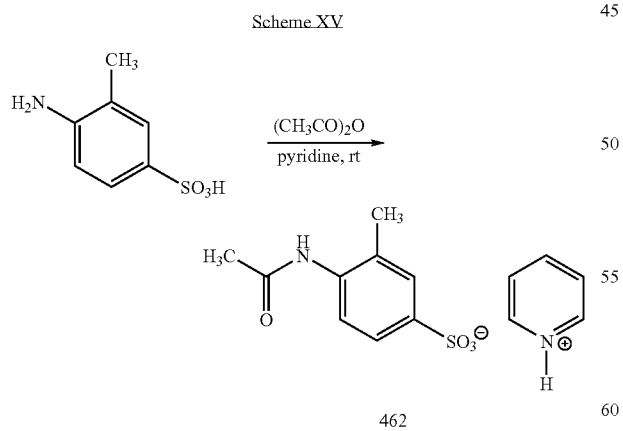

Compounds of formula XV, in which $R_{14}$ is hydrogen, $R_{15}$ is hydrogen, halogen, $C_{1-8}$alkyl, $C_{1-8}$alkoxy, nitro, nitrile, trifluoromethyl, and $R_{16}$ is —SO$_3$H or a salt thereof, are commercially available or can be prepared by literature methods familiar to those skilled in the art.

Compounds of formula V in which $R_3$ is hydrogen and $R_4$ is $C_{6-14}$arylheterocycle substituted with —SO$_2$, —S(O), or C(O), can be prepared from compounds of formula XVI, in which $R_{15}$ is hydrogen, halogen, $C_{1-8}$alkyl, $C_{1-8}$alkoxy, nitro, nitrile, trifluoromethyl, and $R_{17}$ is a heterocycle substituted with —SO$_2$, —S(O), or C(O), by reaction with an agent or a combination of agents capable of selectively reducing the nitro group to an amino group. Among the agents capable of affecting this transformation are palladium on carbon in combination with hydrogen gas, Raney nickel in combination with hydrogen gas, iron in combination with hydrochloric acid, or tin (II) chloride in combination with hydrochloric acid. These reactions are typically performed in a protic solvent such as water, methyl alcohol, ethyl alcohol or a mixture thereof, and at temperatures ranging from ambient to 100° C., preferably 40-85° C. For example, compound 397 (Scheme XVI) is allowed to react with palladium on carbon in combination with hydrogen gas in ethyl alcohol at ambient temperature to afford compound 399.

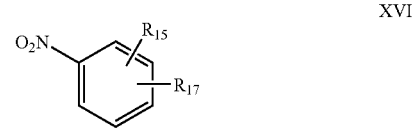

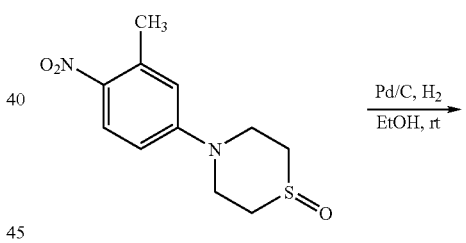

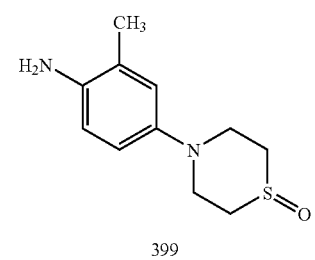

Compounds of formula XVI, in which $R_{15}$ is hydrogen, halogen, $C_{1-8}$alkyl, $C_{1-8}$alkoxy, nitro, nitrile, trifluoromethyl, and $R_{17}$ is a heterocycle substituted with —SO$_2$, or —S(O), can be prepared from compounds of formula XVI in which $R_{17}$ is a heterocycle substituted with —S, by reaction with an agent capable of oxidizing a sulfide to a sulfoxide or a sulfone. Among the agents capable of affecting this transformation are meta-chloroperbenzoic acid (mCPBA), hydrogen peroxide, or oxone. These reactions are typically performed in solvents such as water, THF, acetonitrile, dichloromethane, methyl alcohol, ethyl alcohol, or a mixture thereof and at temperatures from 0° C. to 100° C. For example, compound 394 (Scheme XVII) is allowed to react with MCPBA in chloroform at room temperature to provide both the sulfoxide 397 and the sulfone 398.

first example, 5-fluoro-2-nitrotoluene is allowed to react with thiomorpholine in pyridine and water and in the presence of potassium carbonate to afford compound X. In the second example, 5-fluoro-2-nitrotoluene is allowed to react with imidazole in dimethylsulfoxide, in the presence of potassium carbonate, at 70° C. to provide compound 394.

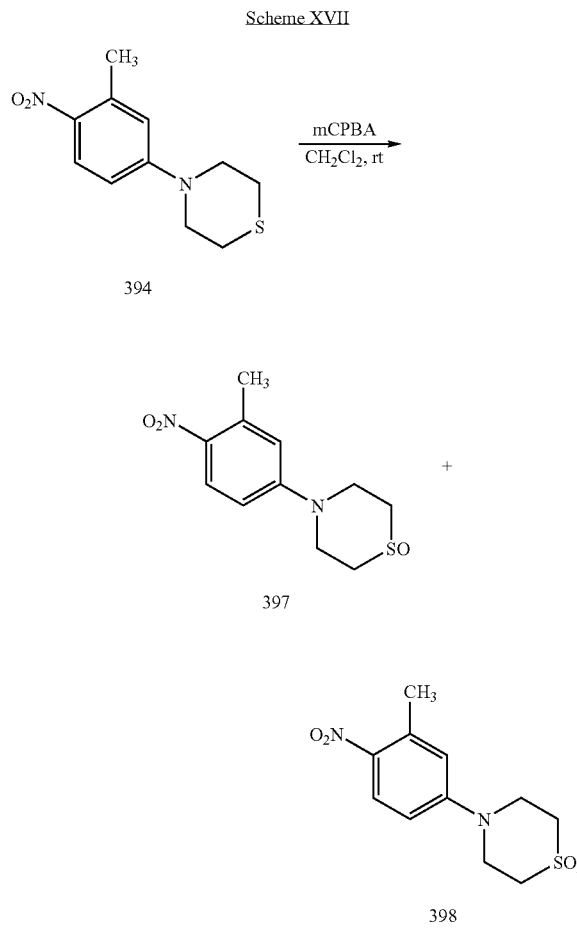

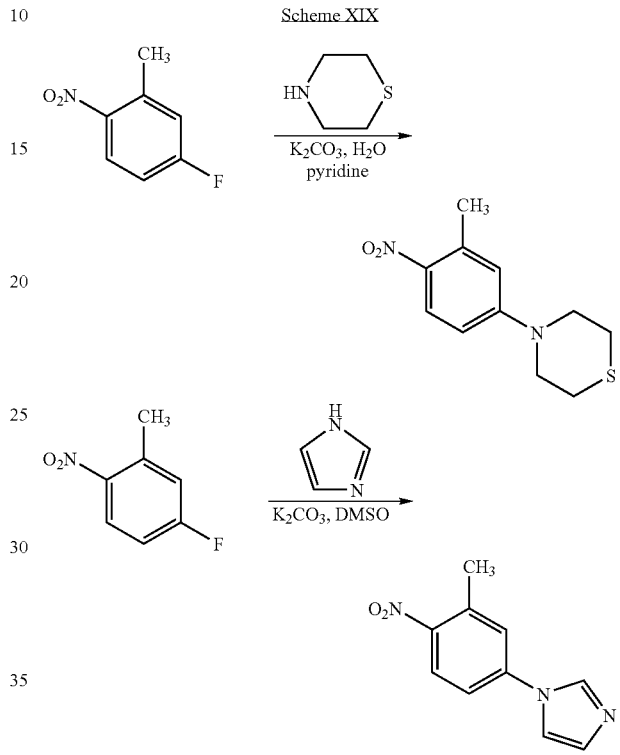

Compounds of formula XVI, in which $R_{15}$ is hydrogen, halogen, $C_{1-8}$alkyl, $C_{1-8}$alkoxy, nitro, nitrile, trifluoromethyl, and $R_{17}$ is a heterocycle substituted with —S, or —O can be prepared from compounds of formula XVI, in which $R_{17}$ is or contains a suitable leaving group, such as a halide, preferably fluorine, chlorine, or bromine, by reaction with heterocyclic compounds capable of displacing the leaving group. Among the heterocycles that can affect this transformation are imidazole, 1,2,3-triazole, 1,2,4-triazole, morpholine, thiomorpholine, N-methylpiperazine, piperazine, and piperidine. These reactions are typically performed in an aprotic solvent such as dioxane, THF, dimethylsulfoxide or pyridine, and in the presence of a base such as triethylamine, or more preferably sodium or potassium carbonate, and at temperatures from 0° C. to 150° C., preferably 50-100° C. Two such examples are shown below in Scheme XIX. In the The desired heterocycles, such as those used in the schemes above, are either commercially available or can be prepared using literature methods familiar to those skilled in the art.

Compounds of formula XV, in which $R_{14}$ is hydrogen, $R_{15}$ is hydrogen, halogen, $C_{1-8}$ alkyl, $C_{1-8}$alkoxy, nitro, nitrile, or trifluoromethyl, and $R_{16}$ is —$OR_8$, wherein $R_8$ is $C_{1-8}$alkyl, optionally substituted with $C_{1-8}$alkoxide, alkylamine, —$SO_2NR_6R_7$, wherein $R_6$ and $R_7$ are as hereinbefore defined, or heterocycle can be prepared from compounds of formula XVI in which $R_{15}$ is hydrogen, halogen, $C_{1-8}$alkyl, $C_{1-8}$alkoxy, nitro, nitrile, or trifluoromethyl, and $R_{17}$ is —$OR_8$, by reaction with agents or a combination of agents which are capable of selectively reducing the nitro group to an amino group. Among the agents capable of affecting this transformation are palladium on carbon in combination with hydrogen gas, Raney nickel in combination with hydrogen gas, iron in combination with hydrochloric acid, or tin (II) chloride in combination with hydrochloric acid. These reactions are typically performed in a protic solvent such as water, methyl alcohol, ethyl alcohol or a mixture thereof, and at temperatures ranging from ambient to 100° C., preferably 40-85° C. For example, compound 139 (Scheme XX) is allowed to react with palladium on carbon in ethyl alcohol and in the presence of pressurized hydrogen gas to afford amine 140.

Scheme XX

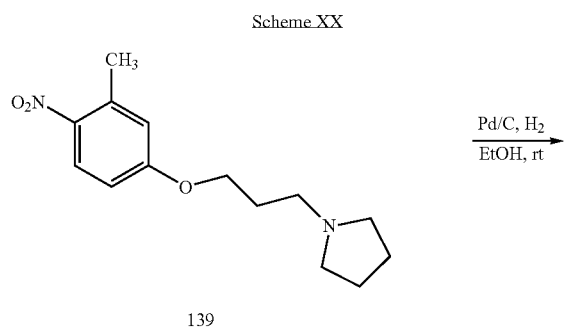

Compounds of formula XVI, in which $R_{15}$ is hydrogen, halogen, $C_{1-8}$alkyl, $C_{1-8}$alkoxy, nitro, nitrile, or trifluoromethyl, and $R_{17}$ is —$OR_8$, wherein $R_8$ is $R_8$ is $C_{1-8}$alkyl, optionally substituted with $C_{1-8}$alkoxide, alkylamine, —$SO_2NR_6R_7$, wherein $R_6$ and $R_7$ are as hereinbefore defined, or heterocycle can be prepared from compounds of formula XVI, in which $R_{17}$ is hydroxy, by reaction with compounds of formula XVII in which $R_{18}$ is $C_{1-8}$alkyl optionally substituted with $C_{1-8}$alkoxide, —$SO_2NR_6R_7$, wherein $R_6$ and $R_7$ are as hereinbefore defined, or heterocycle, and $R_{19}$ is a leaving group, preferably bromine or chlorine. These reactions are usually conducted in an aprotic solvent such as DMF, N-methylpyrrolidine, acetonitrile, or pyridine. In addition, the presence of a base such as triethylamine, or more preferably sodium or potassium carbonate is usually required. For example, 4-nitro-3-methylphenol (Scheme XXI) is allowed to react with 1,3-dibromopropane in DMF and in the presence of potassium carbonate to afford compound 249.

$R_{19}$-$R_{18}$     XVII

Scheme XXI

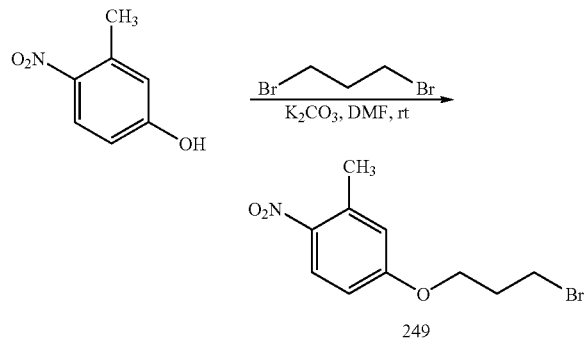

Compounds of formula XVI, in which $R_{15}$ is hydrogen, halogen, $C_{1-8}$alkyl, $C_{1-8}$alkoxy, nitro, nitrile, or trifluoromethyl, and $R_{17}$ is —$OR_8$, wherein $R_8$ is $C_{1-8}$alkyl substituted with —$SO_2NR_6R_7$, can be prepared from compounds of formula XVI, in which $R_8$ is $C_{1-8}$alkyl substituted with —$SO_2Cl$, by reaction with ammonia or an appropriate amine. These reactions are typically performed in aprotic solvents such as acetonitrile, or more preferably dichloromethane or chloroform. For example, sulfonyl chloride 260 (Scheme XXII) is allowed to react with dimethylamine in dichloromethane at 0° C. to provide sulfonamide 264.

Scheme XXII

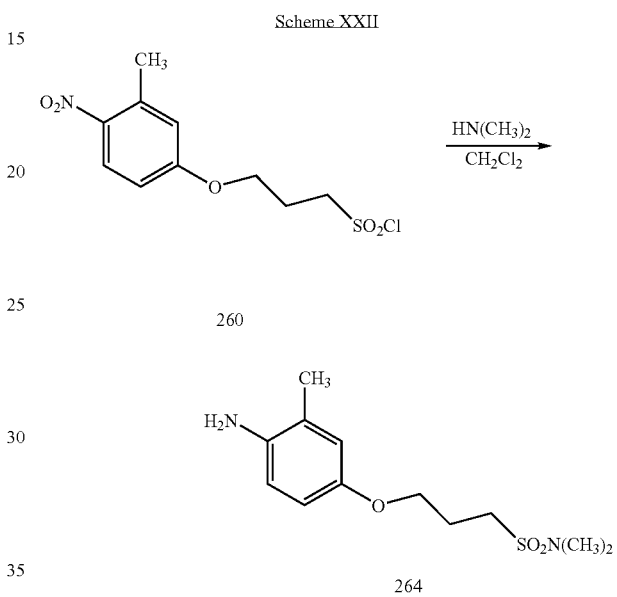

Compounds of formula XVI in which $R_{15}$ is hydrogen, halogen, $C_{1-8}$alkyl, $C_{1-8}$alkoxy, nitro, nitrile, or trifluoromethyl, and $R_{17}$ is —$OR_8$, wherein $R_8$ is $C_{1-8}$alkyl substituted with —$SO_2Cl$, can be prepared from compounds of formula XVI in which $R_{17}$ is —$OR_8$ and $R_8$ is $C_{1-8}$alkyl substituted with —$SO_3H$ or a salt thereof, by reaction with an agent capable of converting a sulfonic acid or a salt thereof to a sulfonyl chloride. Among the agents capable of affecting this transformation are $POCl_3$, or more preferably thionyl chloride. These reactions are typically performed in an aprotic solvent such as dichloromethane, chloroform, or DMF. For example, compound 253 (Scheme XXII) is allowed to react with thionyl chloride in DMF at 0° C. to afford sulfonyl chloride 254.

Scheme XXIII

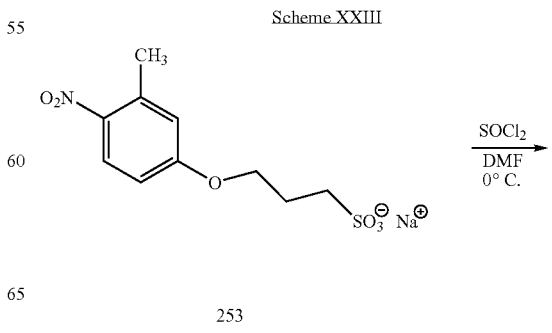

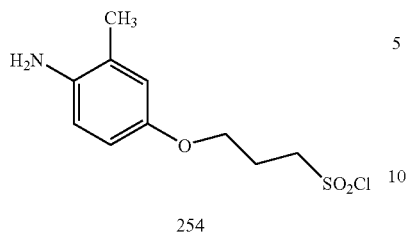

254

Compounds of formula XVI, in which $R_{15}$ is hydrogen, halogen, $C_{1-8}$alkyl, $C_{1-8}$alkoxy, nitro, nitrile, or trifluoromethyl, and $R_{17}$ is —$OR_8$, wherein $R_8$ is $C_{1-8}$alkyl substituted with —$SO_3H$ or a salt thereof, can be prepared from compounds of formula XVI, in which $R_{17}$ is —$OR_8$, wherein $R_8$ is hydrogen, by reaction with a cyclic sulfonate ester, more commonly known as a sultone. These reactions are conducted in an aprotic solvent, such as DMF, acetonitrile, acetone, or more preferably THF and in the presence of a base such as potassium carbonate, or more preferably sodium hydride. For example, 3-methyl-4-nitrophenol (Scheme XXIV) is allowed to react with 1,3-propane sultone in THF and in the presence of sodium hydride to afford sulfonic acid salt 253.

Scheme XXIV

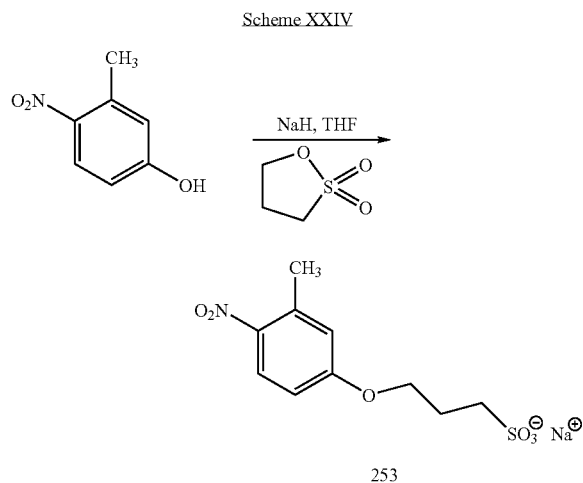

253

The desired sultones, such as 1,3-propane sultone, are either commercially available or can be prepared by literature methods familiar to those skilled in the art.

Compounds of formula XVI, wherein $R_{15}$ is hydrogen, halogen, $C_{1-8}$alkyl, $C_{1-8}$alkoxy, nitro, nitrite, or trifluoromethyl, and $R_{17}$ is —$NR_6R_7$, can be prepared from compounds of formula XVI, in which $R_{17}$ is a suitable leaving group such as a halide, preferably chlorine or fluorine, by reaction with an appropriate amine. These reactions are conducted in solvents such as DMF, acetonitrile, dioxane, water, pyridine, or a mixture thereof, and in the presence of a base such as sodium or potassium carbonate, or more preferably sodium bicarbonate. For example, 5-fluoro-2-nitrotoluene (Scheme XXV) is allowed to react with 4-(3-aminopropyl)morpholine in pyridine and water and in the presence of sodium bicarbonate to provide compound 308.

Scheme XXV

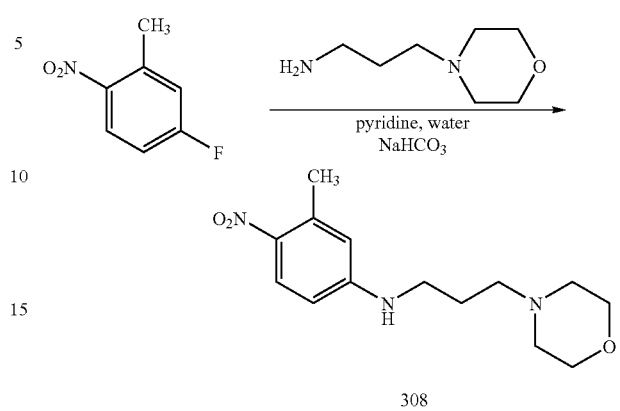

308

The desired amines of formula $HNR_6R_7$ are either commercially available or can be prepared using literature methods known in the art.

Compounds of formula V, in which $R_3$ is hydrogen and $R_4$ is an aromatic heterocycle, are either commercially available or can be prepared using literature-methods familiar to those skilled in the art.

Compounds of formula (V) in which $R_3$ is hydrogen and $R_4$ is heterocycle, pyridine for example, substituted with —$SO_2NR_6R_7$, wherein $R_6$ and $R_7$ are as hereinbefore defined, can be prepared by the methods shown below or by methods known to those skilled in the art. For example, 5-amino-4-methyl-2-pyridinesulfonamide can be prepared from 2-chloro-4-methyl-5-nitropyridine as shown in scheme XXVI. Commercially available 2-chloro-4-methyl-5-nitropyridine is allowed to react with an agent capable of displacing the 2-chloro group with a sulfur atom to provide 4-methyl-5-nitro-2-pyridinethiol, for example, thiourea. These reactions are typically performed in a polar, protic solvent, acetic acid, for example and in the presence of a base, potassium and sodium hydroxide for example, and at temperatures from 20° C. to 150° C. The resulting thiol is then allowed to react with a reagent capable of oxidizing the thiol to the sulfonic acid derivative, for example hydrogen peroxide, oxone or chlorine gas. The oxidation can be advantageously performed using chlorine gas as the oxidizing agent in an acidic solvent, 1N hydrochloric acid for example, with the concomitant formation of the corresponding, desired sulfonyl chloride. The resulting sulfonyl chloride is then allowed to react with an agent capable of converting it to the corresponding sulfonamide, ammonia gas or a solution of ammonia in an appropriate solvent such as dichloromethane, to provide 4-methyl-5-nitro-2-pyridinesulfonamide. The nitro group can then be reduced using methods known to those skilled in the art, palladium on carbon in the presence of hydrogen gas as the reducing agent for example, to produce the desired 5-amino-4-methyl-2-pyridinesulfonamide. The reduction reactions are typically performed in a polar, protic solvent, methanol for example, and at temperatures from 20° C. to 100° C., preferably at ambient temperature.

Scheme XXVI

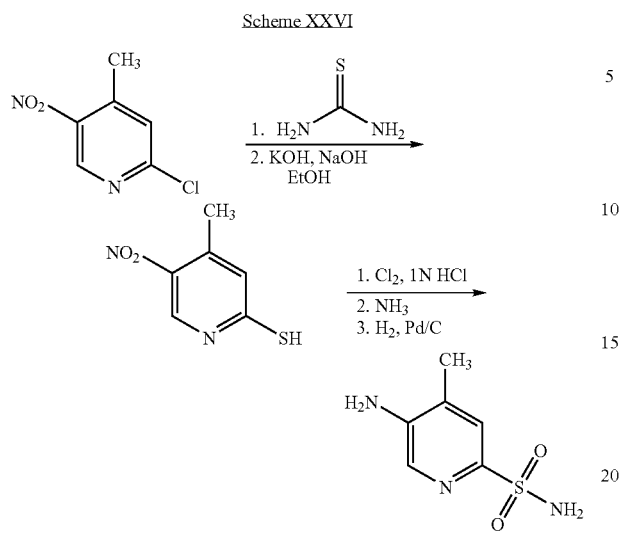

Alternatively, compounds of formula (V), in which $R_3$ is hydrogen and $R_4$ is heterocycle, pyridine for example, substituted with —$SO_2NR_6R_7$, wherein $R_6$ and $R_7$ are as hereinbefore defined, can be prepared by the methods shown below or by methods known to those skilled in the art. For example, 5-amino-6-methyl-2-pyridinesulfonamide can be prepared as shown in scheme XXVII. Commercially available 2-amino-5-methylpyridine is allowed to react with an agent capable of nitrating the pyridine ring, for example a mixture of nitric and sulfuric acids. These reactions are typically performed in concentrated sulfuric acid as solvent, and at temperatures from −10° C. to 25° C., preferably at 0° C., to produce the desired 5-amino-2-methyl-3-nitropyridine. The amino group is then allowed to react with a combination of agents capable of converting the amino group to a chlorine substituent. For example, 5-amino-2-methyl-3-nitropyridine was allowed to react with tert-butylnitrite, to produce the corresponding diazonium salt, followed by reaction with trimethylsilyl chloride in an aprotic solvent, dichloromethane for example, to afford 5-chloro-2-methyl-3-nitropyridine. The chloro group is then allowed to react with an agent capable of effecting a substitution on the pyridine ring to produce the corresponding thiol derivative. For example, 5-chloro-2-methyl-3-nitropyridine was allowed to react with thiourea in a mixture of acetic acid, potassium hydroxide and sodium hydroxide to afford the desired 6-methyl-5-nitro-2-pyridinethiol. The resulting thiol is then allowed to react with a reagent capable of oxidizing the thiol to the sulfonic acid derivative, for example hydrogen peroxide, oxone or chlorine gas. The oxidation can be advantageously performed using chlorine gas as the oxidizing agent in an acidic solvent, 1N hydrochloric acid for example, with the concomitant formation of the corresponding, desired sulfonyl chloride. The resulting sulfonyl chloride is then allowed to react with an agent capable of converting it to the corresponding sulfonamide, ammonia gas or a solution of ammonia in an appropriate solvent such as dichloromethane, to provide 6-methyl-5-nitro-2-pyridinesulfonamide. The nitro group can then be reduced using methods known to those skilled in the art, palladium on carbon in the presence of hydrogen gas as the reducing agent for example, to produce the desired 5-amino-6-methyl-2-pyridinesulfonamide. The reduction reactions are typically performed in a polar, protic solvent, methanol for example, and at temperatures from 20° C. to 100° C., preferably at ambient temperature.

Scheme XXVII

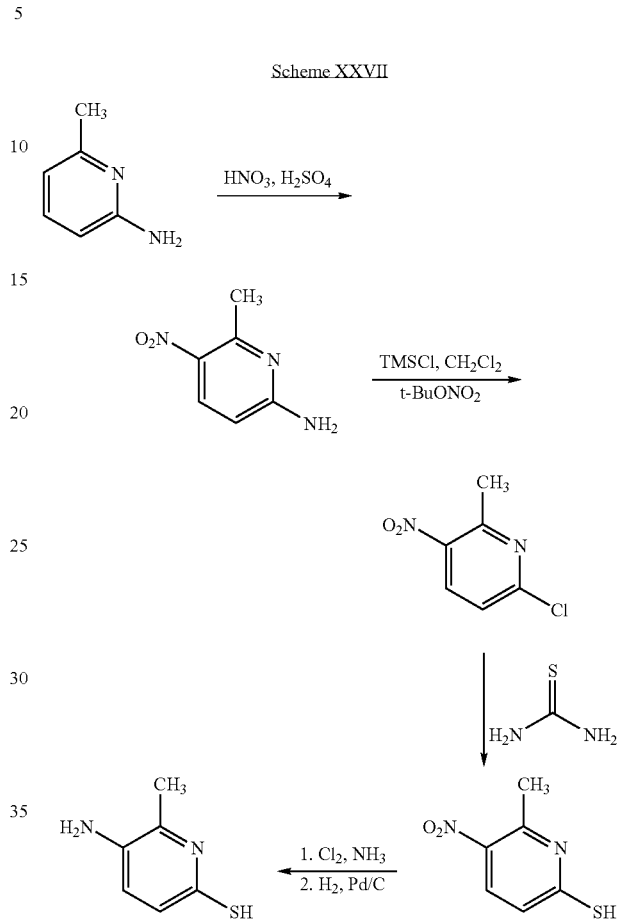

Alternatively, compounds of formula (V) in which $R_3$ is hydrogen and $R_4$ is heterocycle, pyridine for example, substituted with —$SO_2NR_6R_7$, wherein $R_6$ and $R_7$ are as hereinbefore defined, can be prepared by the methods shown below or by methods known to those skilled in the art. For example, 6-amino-5-methyl-3-pyridinesulfonamide can be prepared as shown in scheme XXVIII. Commercially available 2-amino-3-methylpyridine is allowed to react with an agent capable of sulfonylating the pyridine ring, for example oleum. These reactions are typically performed in a mixture of 20% SO3/H2SO4, at temperatures ranging from 75° C. to 200° C., preferably 160° C., to produce 6-amino-5-methyl-3-pyridinesulfonic acid. The amino group is then allowed to react with a combination of agents capable of effecting protection of the amino group from oxidation in subsequent steps. For example, 6-amino-5-methyl-3-pyridinesulfonic acid was allowed to react with a mixture of N,N-dimethylformamide (DMF) and thionyl chloride, so-called Vilsmier reagents, to produce the desired 6-[(dimethylamino)methylidene]amino-5-methyl-3-pyridinesulfonic acid intermediate. This compound is then allowed to react with a combination of agents capable of converting the sulfonic acid to the corresponding sulfonyl chloride, followed by reaction with an agent capable of converting the sulfonyl chloride to the corresponding sulfonamide derivative. For example, desired 6-[(dimethylamino)methylidene]amino-5-methyl-3- pyridinesulfonic acid is allowed to react with phosphorous oxychloride to produce the intermediate sulfonyl chloride, followed by reaction with ammonium hydroxide, to afford the desired 6-amino-5-methyl-3-pyridinesulfonamide.

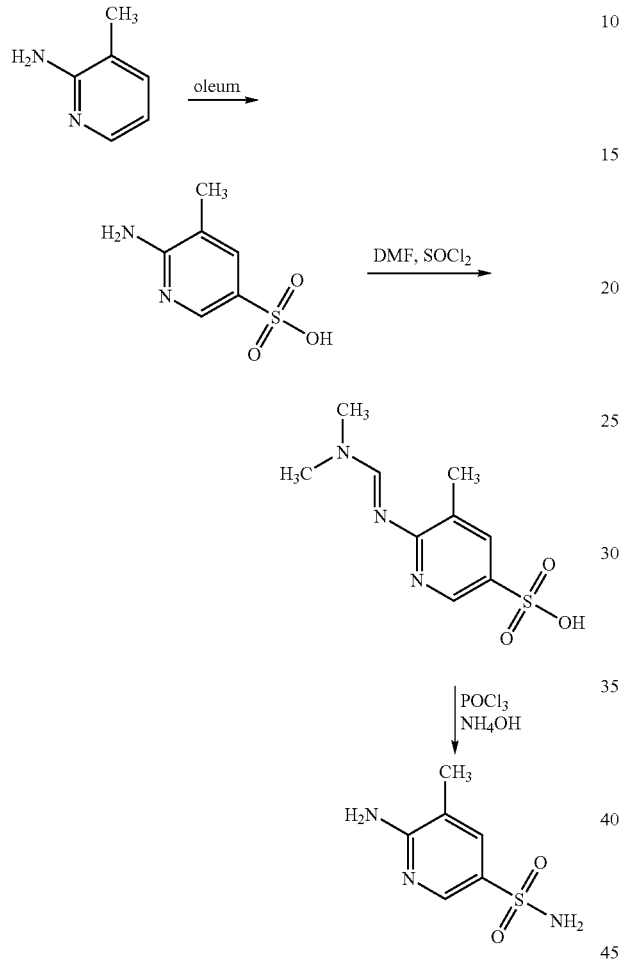

Scheme XXVIII

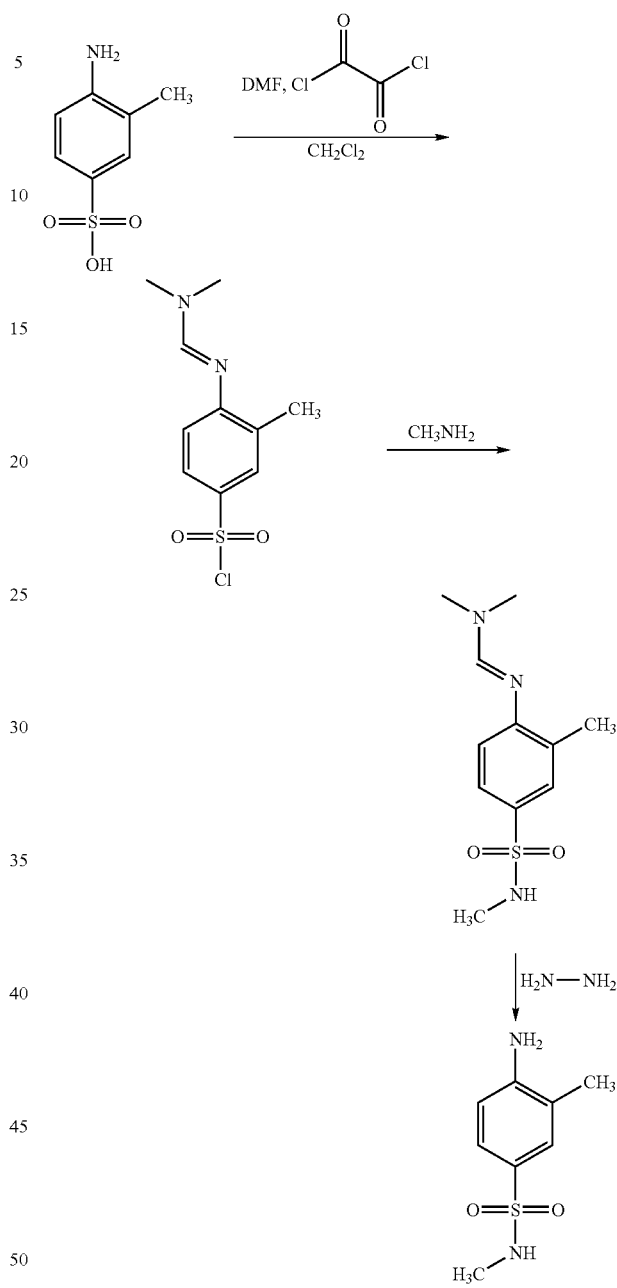

Scheme XXIX

Compounds of formula (XV) wherein $R_{14}$ is hydrogen, $R_{15}$ is hydrogen halogen, $C_{1-8}$alkyl, $C_{1-8}$alkoxy, nitro, nitrile, trifluoromethyl, and $R_{16}$ is —$SO_2NR_6R_7$, wherein $R_6$ and $R_7$ are as hereinbefore defined, can be prepared by methods known in the art or by the method shown in Scheme XXIX. For example, 4-amino-N,3-dimethylbenzenesulfonamide can be prepared from commercially available 4-amino-3-methylbenzenesulfonic acid by reaction with a combination of reagents capable of effecting protection of the amino group from oxidation in later chemical steps. For example, 4-amino-3-methylbenzenesulfonic acid was allowed to react with N,N-dimethylformamide (DMF) and oxalyl chloride in dichloromethane to effect the concomitant protection of the amino group as the corresponding amidine as well as converting the sulfonic acid to the desired sulfonyl chloride. The sulfonyl chloride was then allowed to react with an amine, methyl amine for example, to produce 4-[(dimethylamino)methylidene]amino-N,3-dimethylbenzenesulfonamide. The amidine-protecting group was then removed using hydrazine hydrochloride.

Alternatively, compounds of formula (XV), wherein $R_{14}$ is hydrogen, $R_{15}$ is hydrogen halogen, $C_{1-8}$alkyl, $C_8$alkoxy, nitro, nitrile, trifluoromethyl, and $R_{16}$ is —$SO—_2NR_6R_7$, wherein $R_6$ and $R_7$ are as hereinbefore defined, can be prepared by methods known in the art or by the method shown in Scheme XXX. For example, 4-amino-N,N,3-trimethylbenzenesulfonamide can be prepared by methods known in the art or as shown in Scheme XXX. Commercially available 4-amino-3-methylbenzenesulfonic acid is allowed to react with an agent capable of effecting protection of the amino group from oxidation in further synthetic steps. For example, 4-amino-3-methylbenzenesulfonic acid was allowed to react with benzyl bromide in the presence of a base, sodium or potassium carbonate for example, to afford sodium 4-(dibenzylamino)-3-methylbenzenesulfonate. These reactions are typically performed a polar, aprotic solvent, N,N-dimethylformamide for example, at temperature ranges from 25° C. to 125° C., preferably 75-100° C. The sodium salt is then allowed to react with an agent capable of converting the salt to the corresponding sulfonyl chloride. For example, afford sodium 4-(dibenzylamino)-3-methylbenzenesulfonate was allowed to react with thionyl chloride in N,N-dimethylformamide (DMF) to afford the desired 4-(dibenzylamino)-3-methylbenzenesulfonyl chloride. These reactions are typically performed in an aprotic solvent, dichloromethane for example, and at temperatures from 0° C. to 75° C., preferably 0 CC. The sulfonyl chloride is then allowed to react with an appropriate amine to afford the desired sulfonamide. For example, 4-(dibenzylamino)-3-methylbenzenesulfonyl chloride was allowed to react with dimethylamine to afford the desired 4-(dibenzylamino)-N,N,3-trimethylbenzenesulfonamide. The sulfonamide is then allowed to react with a combination of agent capable of effecting the deprotection of the amine to produce the desired aniline derivative. For example, desired 4-(dibenzylamino)-N,N,3-trimethylbenzenesulfonamide was allowed to react with hydrogen gas in the presence of a palladium on carbon catalyst to effect cleavage of the benzyl protecting groups and afford the desired 4-amino-N,N,3-trimethylbenzenesulfonamide.

Compounds of formula XVIII where $R_2$ is either a hydroxy or methoxy group and $R_1$ and $R_3$ are as hereinbefore defined, and X is a heteroatom, preferably oxygen or sulfur, can be prepared from compounds of formula XIX with compounds of formula X where $R_1$ is hereinbefore defined and $R_{10}$ is a halogen, preferably chlorine, with the stipulation that $R_1$ and $R_3$ are chemically compatible with the reaction conditions and that $R_2$, $R_3$ and $R_1CO$ are regiochemically compatible in such reactions. These reactions, typically called Friedel-Craft acylations, are performed according to processes previously described (see, for example, Scheme X). For example, 3-methoxythiophene (Scheme XXXI) is allowed to react with benzoyl chloride in refluxing dichloromethane in the presence of aluminum chloride to afford ketone 664.

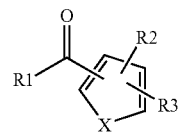

XVIII

Scheme XXX

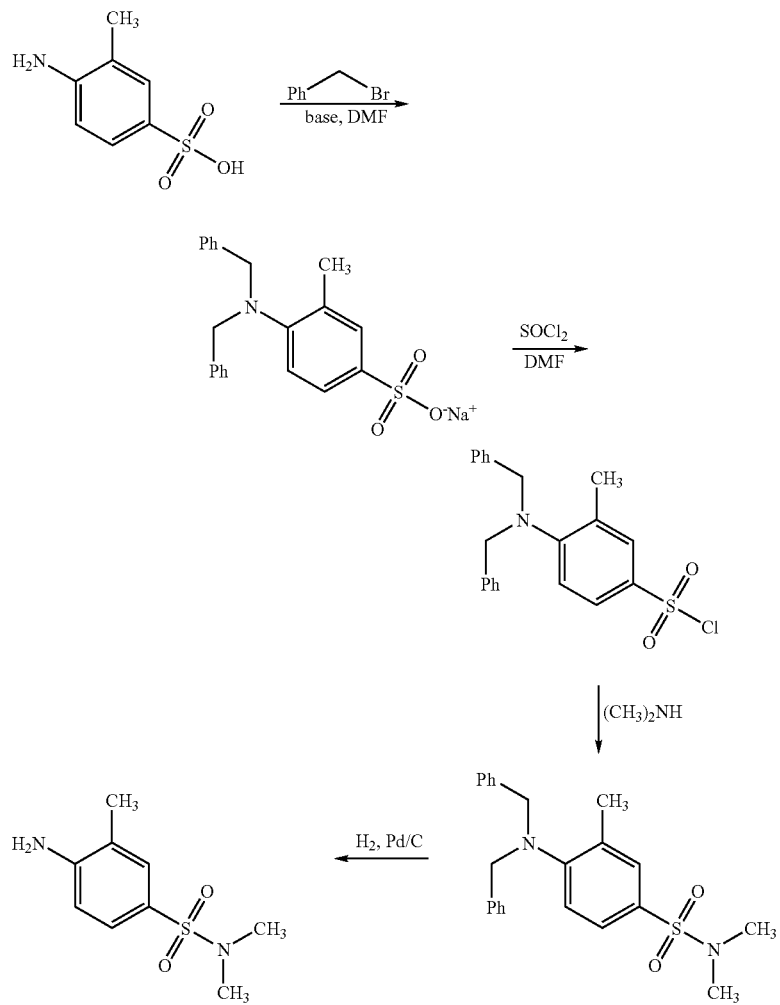

-continued

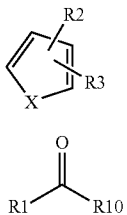
XIX

X

Scheme XXXI

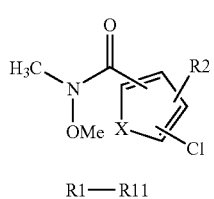

664

Compounds of formula XVIII where $R_1$ and $R_3$ are as hereinbefore defined and $R_2$ is methoxy and X is a heteroatom, preferably sulfur or oxygen, can be prepared from the reaction of compounds of formula XX in which $R_2$ and $R_3$ are as hereinbefore defined with compounds of XIII in which $R_1$ is as hereinbefore defined, and $R_{11}$ is a halogen, preferably bromine or iodine, with the stipulation that $R_1$ and $R_5$ are chemically compatible with subsequent chemical steps and that the N,O-dimethylhydroxyacetamide, $R_2$ and $R_3$ groups are regiochemically compatible in such a reaction. Typically, conditions for such reactions are similar to those described for the synthesis of compounds of formula XII.

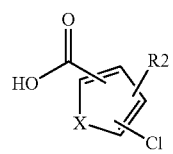
XX

XIII

R1—R11

For example, 3,5-dibromotoluene in diethyl ether was treated with n-butyllithium at −78° C. After 15 minutes at −78° C., the resulting lithium species is allowed to react with 675 to afford the desired ketone 676 (see Scheme XXXIII).

Scheme XXXIII

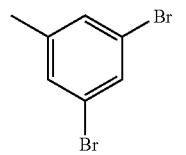

-continued

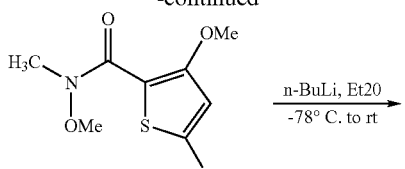

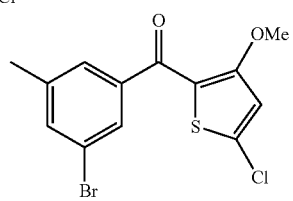

676

Finally, compounds of formula XX can be prepared from compounds of formula XXI where $R_2$ and $R_3$ are as hereinbefore defined using procedures previously described for the synthesis of compounds of formula X (See Scheme VII).

XXI

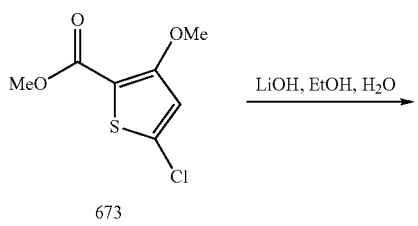

Compounds of formula XXI can, in turn, be prepared according to procedures described in the literature. See for example *Synthesis*, 1984, 847 for the synthesis of 673 which after hydrolysis provided compound 674 (Scheme XXXIV).

Scheme XXXIV

673

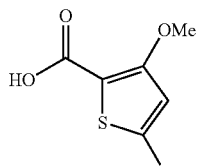

674

A further object of the present invention features intermediates 7, 32, 33, 36, 38, 44, 45, 49, 51, 52, 61, 65, 66, 71, 75, 76, 111, 112, 115, 118, 119, 128, 129, 171, 172, 191, 192, 199, 200, 206, 207, 224, 225, 232, 233, 235, 236, 246, 247, 253, 254, 255, 256, 259, 260, 261, 262, 264, 265, 267, 268, 288, 289, 290, 409, 412, 428, 430, 431, 433, 477, 490, 495, 496, 507, 511, 514, 515, 518, 519, 522, 523, 526, 527, 529, 530, 532, 533, 537, 538, 540, 541, 543, 544, 546, 553, 556, 558, 559, 561, 562, 567, 568, 572, 573, 576, 577, 582, 584, 585, 588, 589, 595, 602, 603, 608, 611, 612, 616, 620, 621, 638, 639, 648, 653, 661, 662, 671, 676, 677 useful in the manufacture of the compounds of the present invention.

The compounds according to the invention, also referred to herein as the active ingredient, may be administered for therapy by any suitable route including oral, rectal, nasal, topical (including transdermal, buccal and sublingual), vaginal and parenteral (including subcutaneous, intramuscular, intravenous, intradermal, and intravitreal). It will be appreciated that the preferred route will vary with the condition and age of the recipient, the nature of the infection and the chosen active ingredient.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 100 to 400 mg of active ingredient per unit dosage form.

While it is possible for the active ingredient to be administered alone it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal or parenteral (including subcutaneous, intramuscular, intravenous, intradermal, and intravitreal) administration. The formulations may conveniently be presented in unit dosage form and may be prepared by any methods well known in the art of pharmacy. Such methods represent a further feature of the present invention and include the step of bringing into association the active ingredients with the carrier which constitutes one or more accessory ingredients. In general, the formulations are prepared by uniformly and intimately bringing into association the active ingredients with liquid carriers or finely divided solid carriers or both, and then if necessary shaping the product.

The present invention further includes a pharmaceutical formulation as hereinbefore defined wherein a compound of formula (I) or a pharmaceutically acceptable derivative thereof and at least one further therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3 (6), 318 (1986).

Formulations of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in molds.

Formulations suitable for parenteral administration include aqueous and nonaqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents; and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Preferred unit dosage formulations are those containing a daily dose or daily subdose of the active ingredients, as hereinbefore recited, or an appropriate fraction thereof.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The following examples are intended for illustration only and are not intended to limit the scope of the invention in any way. "Active ingredient" denotes a compound according to the invention or multiples thereof or a physiologically functional derivative of any of the aforementioned compounds.

General Procedures:

General Procedure I: Friedel-Crafts Reaction of Acid Chlorides with 4-chloroanisole Into a round-bottom flask equipped with a stir bar, a reflux condenser, and nitrogen on demand, were placed 4-chloroanisole (1-1.25 mmol/mmol of acid chloride), aluminum chloride ($AlCl_3$, 1-1.75 mmol/mmol of acid chloride) and $CH_2Cl_2$. To the resulting mixture was added the appropriate acid chloride at rt. When the addition was complete, the orange mixture was heated to reflux and was allowed to stir for 2-24 h. The mixture was allowed to cool to rt and was carefully poured onto ice water, giving a two-phase mixture which was stirred at rt for 30 min to 2 h. It was then poured into a separatory funnel containing water. The organic layer was collected, washed with water, brine, dried over $MgSO_4$, filtered and the solvents were removed under reduced pressure. See specific examples for details regarding additional purification.

General Procedure II: Alkylation of Phenols with Ethyl Bromoacetate

Into a round-bottom flask equipped with a stir bar, reflux condenser, and nitrogen on demand were placed the appropriate phenol, potassium carbonate (2-10 mmol/mmol of phenol), ethyl bromoacetate (1-1.5 mmol/mmol of phenol) and acetone (1-10 mL/mmol of phenol). The resulting mixture was heated to reflux for 1-20 h, after which time it was allowed to cool to rt and was poured into a separatory funnel containing ethyl acetate and water. The organic layer was collected and was washed with water, brine, dried over $MgSO_4$, filtered and the solvents were removed under reduced pressure to leave an oil. See specific examples for details regarding additional purification.

General Procedure III: Saponification of Ethyl Esters to the Carboxylic Acids A round-bottom flask was equipped with a stir bar, nitrogen on demand and was flushed with nitrogen. To the flask were added tetrahydrofuran (THF, 1-5 mL/mmol of ester), ethyl alcohol (EtOH, 1-5 mL/mmol of ester), water (1-5 mL/mmol of ester) and lithium hydroxide monohydrate (1-5 mmol/mmol of ester). The resulting suspension was stirred vigorously and the ester was added in one portion. The mixture was allowed to stir at rt for 1-20 h, after which time the pH was adjusted to approximately pH 5 by the slow addition of 1 N aqueous hydrochloric acid. The mixture was then poured into a separatory funnel containing ethyl acetate and water. The organic layer was collected and was washed with water, brine, dried over $MgSO_4$, filtered and the solvents were removed under reduced pressure to leave a white solid. See specific examples to determine if further purification of the product was required.

General Procedure IV: Coupling of the Acid to Aromatic Amines Using 1-(3-dimethylaminopropyl)-3-ethylcarbodiimide hydrochloride (EDAC)

A round-bottom flask was equipped with a stir bar, nitrogen on demand and was flushed with nitrogen. To the flask were added the appropriate carboxylic acid, N,N-dimethylformamide (DMF, 5-20 mL/mmol acid), 1-hydroxybenztriazole (HOBt, 1-2 mmol/mmol acid), 1-(3-dimethylaminopropyl)-3-ethylcarbodiimide hydrochloride (EDAC, 1-5 mmol/mmol acid), and the appropriate aromatic amine (1-2 mmol/mmol acid). In some cases, triethylamine ($Et_3N$, 2-5-mmol/mmol of acid) was used. The resulting mixture was allowed to stir at rt for 2-24 h, after which time it was poured into a separatory funnel containing ethyl acetate and water. The organic layer was collected and was washed with water, brine, dried over $MgSO_4$, filtered and the solvents were removed under reduced pressure. See specific examples for details regarding further purification of the products.

General Procedure V: Synthesis of Acid Chlorides from Carboxylic Acids Using Oxalyl Chloride Into a round-bottom flask were placed the appropriate carboxylic acid, methylene chloride ($CH_2Cl_2$, 1-10 mL/mmol acid), and N,N-dimethylformamide (1-10 drops). The mixture was cooled to 0° C. and oxalyl chloride (1-2 mmol/mmol acid) was added dropwise, after which time the mixture was allowed to warm to rt and stir for 1-24 h. The solvents were then removed under reduced pressure and the remaining residue was dried in vacuo. In most cases, the acid chlorides were used immediately used in subsequent reactions with no further purification.

General Procedure VI: Coupling of Acid Chlorides to Aromatic Amines Using Sodium Bicarbonate Into a round-bottom flask were placed the appropriate aromatic amine, acetone (1-10 mL/mmol amine), sodium bicarbonate (2-10 mmol/mmol amine), and water (0.25-10 mL). The acid chloride was added as a solution in acetone (1-10 mL/mmol of acid chloride) in a dropwise manner and the reaction mixture was allowed to stir at rt for 1-24 h. When judged to be complete, the mixture was poured into a separatory funnel containing ethyl acetate and water. The organic layer was collected and was washed with water, brine, dried over $MgSO_4$, filtered and the solvents were removed under reduced pressure. See specific examples for details regarding further purification of the products.

General Procedure VII: Synthesis of Weinreb Amides from Acid Chlorides Using N,O-dimethylhydroxylamine hydrochloride Into a round bottom flask equipped with a stir bar and nitrogen on demand were placed the N,O-dimethylhydroxylamine (1-2 mmol/mmol acid chloride) and chloroform ($CHCl_3$, 1-10 mL/mmol acid chloride). The mixture was cooled to 0° C. and triethylamine (Et₃N, 1-5 mmol/mmol acid chloride) was added in one portion. The acid chloride was added and the reaction mixture was allowed to stir at 0° C. for 0.5-5 h, after which time was poured into a separatory funnel containing chloroform and water. The organics were collected, washed with water and brine, dried over MgSO₄, filtered and the solvents were removed under reduced pressure. See specific examples to determine if further purification of the product was required.

General Procedure VIII: Halogen-Metal Exchange of 2-bromo-4-chloroanisole, Followed by Addition of Weinreb Amides Into a round-bottom flask equipped with a stir bar, nitrogen on demand, and an addition funnel, were added 2-bromo-4-chloroanisole (1 mmol/mmol of amide) and diethyl ether (1-10 mL/mmol of anisole) and the mixture was cooled to −78° C. by means of a dry ice/acetone bath. N-Butyl lithium (1-2 mmol/mmol of anisole of a 2.5M soln. in hexanes) was added dropwise, followed by addition of the Weinreb amide. The reaction was allowed to stir at −78° C. for 0.5 h-1 h, at which time the reaction was allowed to warm to rt. When judged to be complete, the reaction was poured into a separatory funnel containing ether and water. The organics were collected, washed with water, dried over MgSO₄, filtered, and the solvents were removed under reduced pressure. See specific examples to determine if further purification was required.

General Procedure IX: Deprotection of Anisole Derivatives Using Boron Tribromide To a round-bottom flask equipped with a stir bar, nitrogen on demand, and an addition funnel was added the appropriate anisole derivative and methylene chloride ($CH_2Cl_2$, 1-15 mL/mmol of anisole). The mixture was cooled to −78° C. and boron tribromide was added dropwise at −78° C. The resulting mixture was allowed to stir at −78° C. for 30-120 minutes, after which time it was allowed to warm to rt and stir for an additional 15-120 minutes. When judged to be complete, the reaction was poured over ice and extracted with $CH_2Cl_2$. The organics were collected, washed with water, dried over MgSO₄, filtered, and the solvents were removed. See specific examples to determine if further purification was required.

General Procedure X. The appropriate acid chloride in acetonitrile was added dropwise via an addition funnel to a stirred solution of triethylamine (0-2.5 mmol/mmol acid chloride), acetonitrile (1-20 ml/mmol acid chloride), and the appropriate aniline (0.5-2.5 mmol/mmol acid chloride). The reaction was refluxed for 0-12 h. The heat was removed and the reaction mixture was stirred for 12-336 h. The mixture was concentrated, dissolved, and washed with water. The resulting organics were dried over MgSO₄ and concentrated in vacuo and purified as descried in the individual cases.

General Procedure XI. An amine (1-2.5 mmol/mmol benzene) was added dropwise via an addition funnel to a stirred suspension of a para-nitro halogenated benzene or toluene in pyridine (20-40 mmol/mmol benzene), sodium bicarbonate (1.54 mmol/mmol benzene), and water (0.2-5 mL/mmol benzene). The resulting suspension was refluxed (150° C.) for 1-7 days. The mixture was filtered and acetone (10-200 mL/mmol benzene) was added to the filtrate and brought to reflux. Water was added to the cloud point and the solution was cooled to rt. The precipitate was filtered and the resulting solid was washed with water and ether to afford the substituted product.

General Procedure XII. The appropriate nitro-benzene was added to a suspension of palladium on carbon (0.1-0.8 mmol/ mmol benzene, 10% w/w), ethanol, THF, and methanol and the reaction vessel was evacuated and charged with nitrogen several times. After evacuating the reaction vessel under reduced pressure, it was charged with hydrogen (14-100 psi). The resulting suspension was stirred at rt for 0-72 h, filtered through a celite pad, and concentrated in vacuo to afford the appropriate aniline.

General procedure XIII. Into a round-bottom flask equipped with a stir bar, cooling bath, and nitrogen on demand were placed the appropriate carboxylic acid, hexachloroacetone (HCA, 0.5 mmol/mmol acid), and THF (1-10 mL/mmol acid) and the mixture was cooled −78° C. Triphenylphosphine ($PPh_3$, 1 mmol/mmol acid) in THF (1-10 mL/mmol acid) was added to the mixture and stirred for 5-120 min. The appropriate aniline (1 mmol/mmol acid) in THF (1-10 mL/mmol-acid) and pyridine (5-20 mmol/ mmol acid) were added dropwise and the mixture was stirred −78° C. for 5-60 min. The cooling bath was removed and the mixture was stirred at rt for 1 h to 14 d. The reaction mixture was concentrated in vacuo and purified as described in the individual cases.

General procedure XIV. Thionyl chloride (1-100 mmol/ mmol acid) was added to a solution of the appropriate carboxylic acid in methylene chloride (1-100 ml/mmol acid) and the resulting solution was refluxed for 1-12 h under nitrogen. The mixture was concentrated in vacuo and placed under nitrogen to afford the appropriate acid chloride.

General Procedure XV: Palladium-Mediated Cyanation of Benzophenone Derivatives

The appropriate bromobenzophenone was treated according to the procedures outlined by Anderson et al. in *J. Org. Chem.* 1998, 63, 8224-8228. Into a heat-dried flask, fitted with a reflux condenser, was placed the bromo- or trifluoromethylsulfonyl- benzophenone (1 eq), tetrakis(triphenylphosphine) palladium (10-20%), copper iodide (2 eq relative to palladium), sodium cyanide (2 eq), and propionitrile (0.5-1.0 M in bromobenzophenone). The mixture was purged with $N_2$ for 30 min prior to use. The mixture was heated to 120° C. and stirred until TLC analysis showed complete disappearance of the starting material (1-16 h). The mixture was then cooled to rt, diluted with ethyl acetate, and filtered through silica gel, and the filtrate was concentrated in vacuo. The corresponding products were purified as described in each example.

General Procedure XVI: Synthesis of N-[4-(aminosulfonyl)-2-methylphenyl]acetamide and N-[4-(alkyl and dialkyaminosulfonyl)-2-methylphenyl]acetamides Sulfonyl chloride 464 (1-100 mmol) was added to a solution of the appropriate amine in pyridine (1-10 mL/mmol amine) and the resulting solution was stirred for 1-48 h under nitrogen. Water was added and the resulting mixture was extracted with methylene chloride and the organics were concentrated in vacuo. The resulting products were then purified by flash chromatography to afford the appropriate acetyl protected sulfonamide.

General Procedure XVII: De-Acetylation of N-[4-(aminosulfonyl)-2-methylphenyl]acetamide and N-[4-(alkyl and dialkyaminosulfonyl)-2-methylphenyl]acetamides The appropriate sulfonamide (1-100 mmol) was added to a solution of ethanol (1-50 mL), water (0-5mL), and hydrochloric acid (1-28.9 M, 1-50 mL) in a large test tube. The mixture was then heated, with stirring, to 60° C. for 1-36 h.

The mixture was allowed to cool to rt and concentrated in vacuo. The resulting products were dissolved in ethyl acetate and washed with saturated NaHCO$_3$, then purified by flash chromatography using 95:5 CH$_2$Cl$_2$:CH$_3$OH as eluant to afford the desired aniline.

EXAMPLES

Example 1

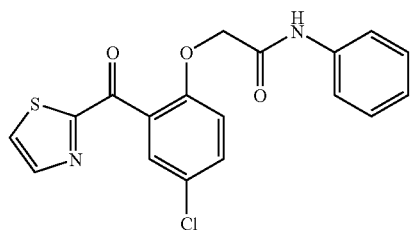

Step A:

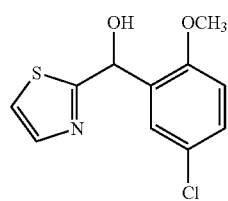

A solution of 2-Bromo-4-Chloroanisole (8.98 g, 40.54 mmol) in diethyl ether (65 mL) was cooled to −78° C. and n-butyl lithium (26 mL of a 1.6 M solution in hexanes, 41.6 mmol) was added from a syringe. The resulting orange solution was allowed to stir at −78° C. for 30 min, after which time 2-thiazolecarboxaldehyde (4.53 g, 40.04 mmol) was added neat, resulting in a purple solution. The mixture was allowed to stir at −78° C. for 15 min, after which time water (50 mL) was added and the mixture was allowed to warm to RT. The mixture was poured into a separatory funnel containing ether and water. The organic layer was collected and was washed with water, brine, dried over MgSO$_4$, filtered and the solvents were removed under reduced pressure to afford a white solid. The solid was washed with hexanes and was dried in vacuo; affording white needles (5.21 g, 51$). $^1$H NMR (CDCl$_3$, 400 MHz) δ 7.70 (d, J=4 Hz, 1H), 7.38 (d, J=4 Hz, 1H), 7.28 (d, J=4 Hz, 1H), 7.23 (m, 1H), 6.83 (d, J=8 Hz, 1H), 6.23 (d, J=8 Hz, 1H), 3.99 (d, J=8 Hz, 1H), 3.83 (s, 3H).

Step B:

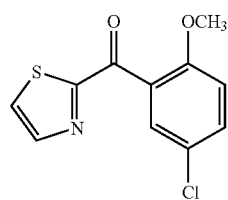

2 (5.21 g, 20.6 mmol), manganese dioxide (17.66 g, 203.1 mmol) and methylene chloride (CH$_2$Cl$_2$, 75 mL) were combined under nitrogen and were allowed to stir at RT for 2.5 h. The mixture was filtered through a pad of celite, which was washed with several portions of CH$_2$Cl$_2$, and the solvent was removed under reduced pressure to provide a tan solid (4.96 g, 95%) which was used in subsequent reactions without any further purification. $^1$H NMR (CDCl$_3$, 300 MHz) δ 8.06 (d, J=3 Hz, 1H), 7.76 (d, J=3 Hz, 1H), 7.63 (d, J=3 Hz, 1H), 7.49 (dd, J=9, 3 Hz, 1H), 7.00 (d, J=9 Hz, 1H), 3.82 (s, 3H).

Step C:

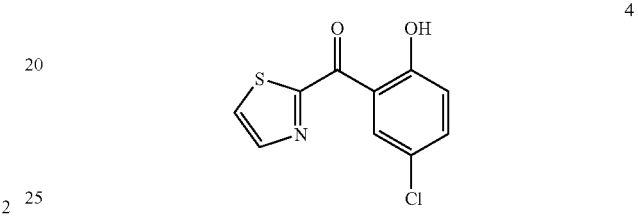

3 (4.96 g, 19.6 mmol), in CH$_2$Cl$_2$ (60 mL) was cooled to −78° C. and boron tribromide (100 mL of a 1.0 M solution in CH$_2$Cl$_2$, 100 mmol) was added via syringe over 30 min. The resulting purple solution was allowed to stir at −78° C. for 15 min, after which time it was allowed to slowly warm to RT. After 30 min at RT, the mixture was slowly poured over ice water and the resulting two-phase mixture was allowed to stir for 30 min. The mixture was then poured into a separatory funnel containing water and CH$_2$Cl$_2$. The organic layer was collected and was washed with water, brine, dried over MgSO$_4$, and the solvents were removed under reduced pressure. The product was isolated by flash chromatography using 7:3 hexane/CH$_2$Cl$_2$ to provide a yellow solid (3.59 g, 76%). $^1$H NMR (CDCl$_3$, 300 MHz) δ 12.25 (s, 1H), 9.29 (d, J=3 Hz, 1H), 8.19 (d, J=3 Hz, 1H), 7.83 (d, J=3 Hz, 1H), 7.53 (dd, J=9, 3 Hz, H), 7.05 (d, J=9 Hz, 1H).

Step D:

4 (0.12 g, 0.49 mmol), 2'-chloroacetanilide (0.09 g, 0.52 mmol), sodium carbonate (Na$_2$CO$_3$, 0.54 g, 5.1 mmol), potassium iodide (0.47 g, 3.1 mmol) and acetone (8 mL) were combined under nitrogen and the resulting mixture was heated to reflux. After 18 h at reflux, the mixture was allowed to cool to RT and was poured into a separatory funnel containing ethyl acetate and water. The organic layer was collected and was washed with water, brine, dried over MgSO$_4$, filtered and the solvents were removed under reduced pressure, leaving orange oil. The product was isolated by flash chromatography using 4:1 hexane/ethyl acetate as eluant to provide 1 as a white solid (0.09 g, 49%). $^1$H NMR (CDCl$_3$, 300 MHz) d 9.66 (s, 1H), 9.04 (d, J=3 Hz, 1H), 7.93 (d, J=2.7 Hz, 1H), 7.78 (d, J=3 Hz, 1H), 7.72 (d, J=8 Hz, 2H), 7.51 (dd, J=3 Hz, 1H), 7.35 (m, 2H), 7.15 (m, 1H), 6.97 (d, J=9 Hz, 1H), 4.67 (s, 2H).

Example 2

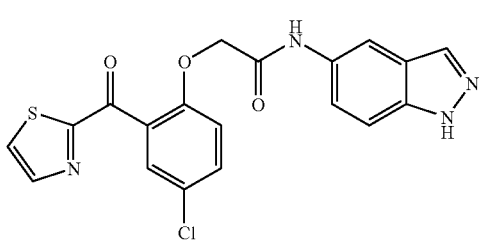

5

Step A:

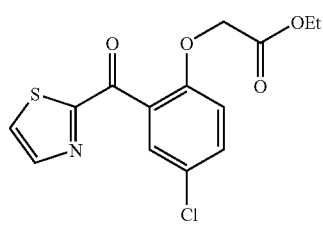

6

Phenol 4 (2.31 g, 9.64 mmol), K₂CO₃ (6.95 g, 50.3 mmol), ethyl bromoacetate (1.1 mL, 1.7 g, 9.9 mmol) and acetone (150 mL) were used according to general procedure II. The product was used in the next reaction without any further purification. ¹H NMR (CDCl₃, 300 MHz) δ 8.05 (d, J=3 Hz, 1H), 7.76 (d, J=3 Hz, 1H), 7.66 (d, J=3 Hz, 1H), 7.48 (dd, J=9, 3 Hz, 1H), 6.93 (d, J=9 Hz, 1H), 4.61 (s, 2H), 4.21 (q, J=6 Hz, 2H), 1.26 (t, J=6 Hz, 3H).

Step B:

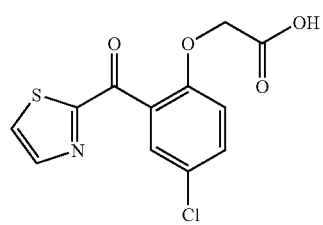

7

Ester 6 (3.1 g, 9.6 mmol), THF (30 mL), water (10 mL), EtOH (10 mL) and LiOH (1.0 g, 23.8 mmol) were used according to general procedure III. The product was used in the next reaction without any further purification. ¹H NMR (DMSO-d₆, 300 MHz) δ 8.30 (d, J=3 Hz, 1H), 8.15 (d, J=3 Hz, 1H), 7.63 (d, J=3 Hz, 1H), 7.57 (dd, J=9, 3 Hz, 1H), 7.05 (d, J=9 Hz, 1H), 4.45 (s, 2H).

Step C:

Carboxylic acid 7 (0.1 g, 0.33 mmol), HOBt (0.05 g, 0.4 mmol), EDAC (0.09 g, 0.46 mmol), Et₃N (0.1 mL, 0.07 g, 0.72 mmol), DMF (6 mL) and 5-aminoindazole (0.05 g, 0.35 mmol) were used according to general procedure IV. The product was purified by flash chromatography using 95:5 CH₂Cl₂:CH₃OH as eluant to provide 5 as a tan solid (0.03 g, 25%). ¹H NMR (CDCl₃, 400 MHz) δ 9.55 (s, 1H), 8.46 (s, 1H), 8.21 (s, 1H), 8.05 (m, 2H), 7.77 (m, 3H), 7.54 (m, 1H), 6.99 (d, J=8 Hz, 2H), 4.74 (s, 2H).

Example 3

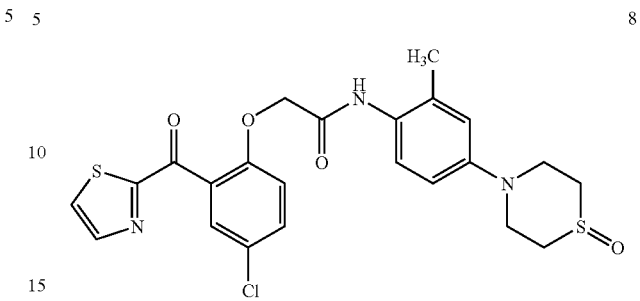

8

Carboxylic acid 7, HOBt (0.10 g, 0.75 mmol), EDAC (0.15 g, 0.79 mmol), Et₃N (0.16 mL, 0.12 g, 1.15 mmol), DMF (5 mL) and sulfoxide 399 (0.15 g, 0.68 mmol) were used according to general procedure IV. The product was purified by flash chromatography using 95:5 CH₂Cl₂:CH₃OH as eluant to afford a tan solid (0.09 g, 34%). ¹H NMR (CDCl₃, 300 MHz) δ 9.14 (s, 1H), 8.00 (m, 2H), 7.80 (d, J=3 Hz, 1H), 7.56 (m, 2H), 7.05 (d, J=9 Hz, 2H), 6.87 (br s, 1H), 4.77 (s, 2H), 4.04 (m, 1H), 3.54 (m, 1H), 3.0 (m, 2H), 2.21 (s, 3H).

Example 4

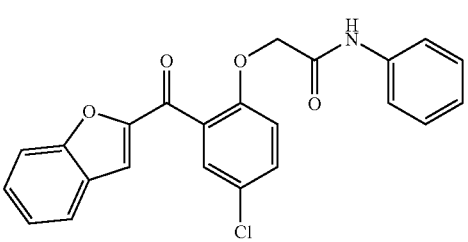

9

Step A:

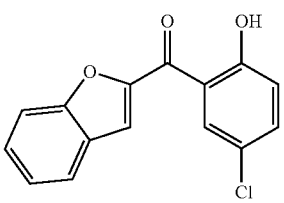

10

2-Benzofurancarboxylic acid (2.51 g, 15.48 mmol), CH₂Cl₂ (50 mL), DMF (4 drops), and oxalyl chloride (1.5 mL, 2.18 g, 17.19 mmol) were used to prepare the corresponding acid chloride according to general procedure V. The acid chloride was used immediately in combination with 4-chloroanisole (2.16 g, 15.15 mmol), AlCl₃ (3.01 g, 22.57 mmol) and CH₂Cl₂ (50 mL) according to general procedure I. Compound 10 was purified by flash chromatography using 7:3 hexane/CH₂Cl₂ as eluant to provide 10 as a yellow solid (2.39 g, 57%). ¹H NMR (CDCl₃, 300 MHz) δ 12.05 (s, 1H), 8.48 (d, J=3 Hz, 1H), 7.82 (d, J=9 Hz, 1H), 7.79 (s, 1H), 7.73 (d, J=9 Hz, 1H), 7.56 (m, 2H), 7.42 (t, J=7.5 Hz, 1H), 7.09 (d, J=9 Hz, 1H).

Step B:

Into a round-bottom flask equipped with a stir bar, a reflux condenser and nitrogen on demand were placed phenol 10 (0.14 g, 0.51 mmol), 2'-chloroacetanilide (0.10 g, 0.59 mmol), K$_2$CO$_3$ (0.50 g, 3.62 mmol) and acetone (10 mL). The mixture was heated to reflux for 16 h, after which time it was allowed to cool to rt and was poured into a separatory funnel containing ethyl acetate and water. The organic layer was collected and was washed with water, brine, dried over MgSO$_4$, filtered and the solvents were removed under reduced pressure to leave orange oil. The product was purified by flash chromatography using 4:1 hexane/ethyl acetate as eluant to provide 9 as a white solid (0.12 g, 58%). $^1$H NMR (CDCl$_3$, 300 MHz) δ 9.33 (s, 1H), 7.75 (m, 5H), 7.61 (m, 3H), 7.39 (m, 3H), 7.15 (m, 2H), 4.77 (s, 2H).

Example 5

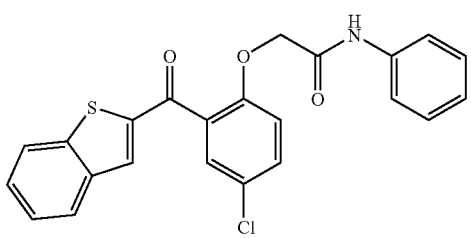

11

Step A:

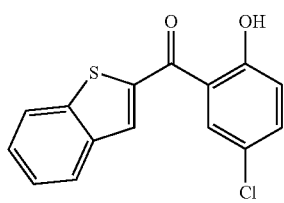

12

2-Benzothiophenecarboxylic acid (2.51 g, 14.08 mmol), CH$_2$Cl$_2$ (35 mL), DMF (4 drops), and oxalyl chloride (1.3 mL, 1.89 g, 14.9 mmol) were used to prepare the corresponding acid chloride according to general procedure V. The acid chloride was used immediately in combination with 4-chloroanisole (2.08 g, 14.59 mmol), AlCl$_3$ (3.15 g, 23.62 mmol) and —CH$_2$Cl$_2$ (35 mL) according to general procedure I. Compound 12 was purified by flash chromatography using 7:3 hexane/CH$_2$Cl$_2$ as eluant to provide a yellow solid (2.25 g, 55%). $^1$H NMR-(CDCl$_3$, 300 MHz) δ 11.45 (s, 1H), 8.02 (m, 3H), 7.55 (m, 4H), 7.10 (d, J=9 Hz, 1H).

Step B:

Into a round-bottom flask equipped with a stir bar, a reflux condenser and nitrogen on demand were placed phenol 12 (0.22 g, 1.23 mmol), 2'-chloroacetanilide (0.22 g, 1.30 mmol), K$_2$CO$_3$ (1.46 g, 10.6 mmol) and acetone (25 mL). The mixture was heated to reflux for 16 h, after which time it was allowed to cool to rt and was poured into a separatory funnel containing ethyl acetate and water. The organic layer was collected and was washed with water, brine, dried over MgSO$_4$, filtered and the solvents were removed under reduced pressure to leave orange oil. The product was purified by flash chromatography using 4:1 hexane/ethyl acetate as eluant to afford a white solid (0.27 g, 52%). $^1$H NMR (CDCl$_3$, 400 MHz) δ 9.16 (s, 1H), 7.90 (t, J=10 Hz, 2H), 7.82 (s, 1H), 7.64 (m, 2H), 7.53 (m, 2H), 7.42 (t, J=8 Hz, 1H), 7.30 (t, J=8 Hz, 2H), 7.10 (t, J=8 Hz, 1H), 7.04 (d, J=8 Hz, 1H), 4.70 (s, 2H).

Example 6

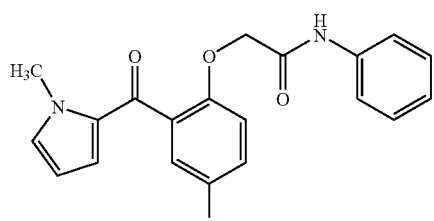

13

Step A:

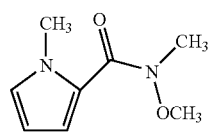

14

1-Methyl-2-pyrrolecarboxylic acid (4.75 g, 37.96 mmol), CH$_2$Cl$_2$ (100 mL), DMF (0.5 mL) and oxalyl chloride (3.6 mL, 5.24 g, 41.27 mmol) were used according to general procedure V. Into a separate flask were placed N,O-dimethylhydroxylamine hydrochloride (4.45 g, 45.62 mmol), Et$_3$N (26 mL, 19 g, 187 mmol) and chloroform (100 mL). The resulting solution was cooled to 0° C. and the acid chloride (in 20 mL of chloroform) was added dropwise. The resulting mixture was allowed to stir at 0° C. for an additional 1 h, after which time it was allowed to warm to RT. The mixture was then poured into a separatory funnel containing chloroform and water. The organic layer was collected and was washed with water, brine, dried over MgSO$_4$, filtered and the solvents were removed under reduced pressure to afford a brown oil which was used in subsequent reactions with no further purification. $^1$H NMR (CDCl$_3$, 300 MHz) δ 6.95 (m, 1H), 6.78 (m, 1H), 6.15 (m, 1H), 3.94 (s, 3H), 3.73 (s, 3H), 3.36 (s, 3H).

Step B:

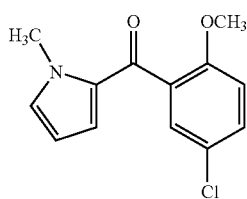

15

To a round-bottom flask equipped with a stir bar and nitrogen on demand were placed 2-bromo-4-chloroanisole (5.97 g, 26.95 mmol) and THF (75 mL). The resulting solution was cooled to −78° C. and n-butyl lithium (19.5 mL of a 1.6 M solution in hexane, 31.2 mmol) was added via syringe. The resulting solution was allowed to stir at −78° C. for 30 min and amide 14 (4.2 g, 24.97 mmol in 15 mL THF), was added via syringe. The mixture was allowed to stir at −78° C. for 30 min, after which time it was allowed to warm to RT and stir for an additional 30 min. The mixture was then poured into a separatory funnel containing ethyl acetate and water. The organic layer was collected and was washed with water, brine, dried over MgSO$_4$, filtered and the solvents were removed under reduced pressure to afford a viscous, clear oil which was used in subsequent reactions without any further purification.

Step C:

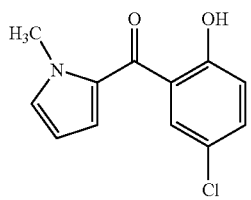

16

To a round-bottom flask equipped with a stir bar and nitrogen on demand were placed 15 (2.19 g, 8.77 mmol) and CH$_2$Cl$_2$ (80 mL). The solution was cooled to −78° C. and boron tribromide (43 mL of a 1.0 M solution in CH$_2$Cl$_2$, 43 mmol) was added via syringe. The resulting dark red mixture was allowed to warm to rt and stir for 2 h. The mixture was then carefully poured over ice water, giving a two-phase mixture, which was allowed to stir for 30 min. It was then poured into a separatory funnel containing water. The organic layer was collected and was washed with water, brine, dried over MgSO$_4$, filtered and the solvents were removed under reduced pressure to afford a yellow solid (1.56 g, 75%) which was used in subsequent reactions without any further purification. $^1$H NMR (CDCl$_3$, 300 MHz) δ 11.65 (s, 1H), 7.90 (d, J=3 Hz, 1H), 7.43 (dd, J=9, 3 Hz, 1H), 7.02 (m, 2H), 6.91 (m, 1H), 6.28 (m, 1H), 4.01 (s, 3H).

Step D:

Into a round-bottom flask equipped with a stir bar, a reflux condenser and nitrogen on demand were placed phenol 16 (0.15 g, 0.64 mmol), 2'-chloroacetanilide (0.13 g, 0.78 μmmol), K$_2$CO$_3$ (0.47 g, 3.39 mmol) and acetone (10 mL). The resulting mixture was heated to reflux for 18 h, after which time it was allowed to cool to rt and was poured into a separatory funnel containing ethyl acetate and water. The organic layer was collected and was washed with water, brine, dried over MgSO$_4$, filtered and the solvents were removed under reduced pressure. The product was purified by flash chromatography using 4:1 hexane/ethyl acetate to afford 13 as a white solid (0.18 g, 77%). $^1$H NMR (CDCl$_3$, 300 MHz) δ 9.69 (s, 1H), 7.81 (d, J=9 Hz, 2H), 7.54 (d, J=3 Hz, 1H), 7.47 (dd, J=6, 3 Hz, 1H), 7.38 (t, J=6 Hz, 2H), 7.16 (t, J=6 Hz, 1H), 7.03 (m, 2H), 6.75 (m, 1H), 6.23 (m, 1H), 4.75 (s, 2H), 4.17 (s, 3H).

Example 7

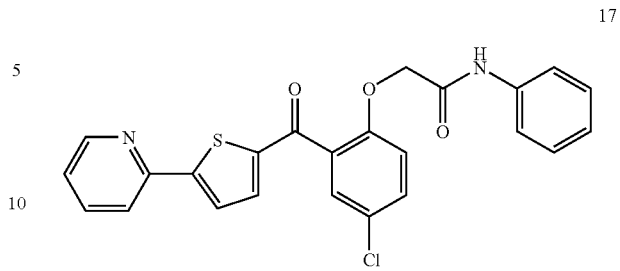

17

Step A:

18

5-(2-pyridyl)thiophene-2-carboxylic acid (2.62 g, 12.77 mmol), oxalyl chloride (1.4 mL, 2.04 g, 16.05 mmol), DMF (0.25 mL) and CH$_2$Cl$_2$ (25 mL) were used according to general procedure V. The acid chloride was used immediately in the next step without any further purification. Into a separate flask equipped with a stir bar and nitrogen on demand were placed N,O-dimethylhydroxylamine hydrochloride (1.63 g, 16.71 mmol), Et$_3$N (9 mL, 6.53 g, 64.57 mmol) and CH$_2$Cl$_2$ (25 mL). The resulting solution was cooled to 0° C., and the acid chloride (in 10 mL of CH$_2$Cl$_2$) was added dropwise. When the addition was complete, the mixture was allowed to stir at 0° C. for an additional 30 min, and then was allowed to warm to rt and stir for an additional 1 h. The mixture was then poured into a separatory funnel containing ethyl acetate and water. The organic layer was collected and was washed with water, brine, dried over MgSO$_4$, filtered and the solvents were removed under reduced pressure leaving a white solid (2.69 g, 85%). The product was used in subsequent steps without any further purification. $^1$H NMR (CDCl$_3$, 300 MHz) δ 8.64 (d, J=3 Hz, 1H), 8.00 (d, J=3 Hz, 1H), 7.75 (m, 2H), 7.60 (d, J=6 Hz, 1H), 7.26 (m, 1H), 3.88 (s, 3H), 3.43 (s, 3H).

Step B:

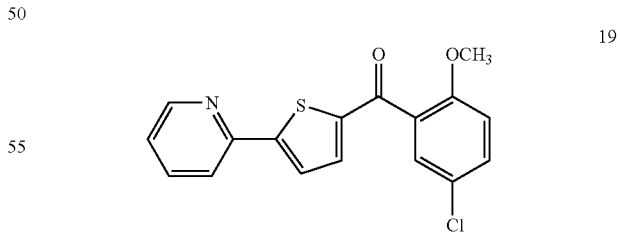

19

Into a round-bottom flask equipped with a stir bar and nitrogen on demand were placed 2-bromo-4-chloroanisole (2.42 g, 10.93 mmol) and THF (35 mL). The solution was cooled to −78° C. and n-butyl lithium (7.5 mL of a 1.6 M solution in hexane, 12 mmol) was added via syringe. The resulting yellowish mixture was allowed to stir at −78° C. for 30 min, after which time amide 18 (2.25 g, 9.06 mmol)

in THF (10 mL) was added slowly. The resulting mixture was allowed to stir at −78° C. for 30 min and it was then allowed to warm to rt and stir for an additional 1 h. The mixture was then poured into a separatory funnel containing ethyl acetate and water. The organic layer was collected and was washed with water, brine, dried over MgSO$_4$, filtered and the solvents were removed under reduced pressure. The product was further purified by flash chromatography using 7:3 hexane/ethyl acetate to afford a yellow solid (1.42 g, 48%). $^1$H NMR (CDCl$_3$, 300 MHz) δ 8.66 (d, J=6 Hz, 1H), 7.79 (m, 2H), 7.64 (d, J=6 Hz, 1H), 7.56 (d, J=6 Hz, 1H), 7.45 (m, 2H), 7.30 (m, 2H), 6.18 (d, J=6 Hz, 1H), 3.84(s, 3H).

Step C:

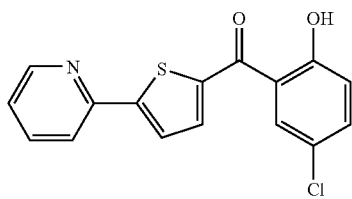

20

Into a round-bottom flask equipped with a stir bar, and nitrogen on demand were placed ketone 19 (1.42 g, 4.31 mmol) and CH$_2$Cl$_2$ (70 mL). The mixture was cooled to −78° C. and boron tribromide (20 mL of a 1.0 M solution in CH$_2$Cl$_2$, 20 mmol) was added via syringe. The resulting dark red mixture was allowed to stir at −78° C. for 1 h and it was then allowed to warm to rt and stir for an additional 1 h. The mixture was carefully poured over ice water and the resulting two-phase mixture was allowed to stir for 30 min. It was then poured into a separatory funnel containing CH$_2$Cl$_2$ and water. The organic layer was collected and was washed with water, brine, dried over MgSO$_4$, filtered and the solvents were removed under reduced pressure to afford a tan solid (1.32 g, 97%). $^1$H NMR (CDCl$_3$, 300 MHz) δ 11.55 (s, 1H), 8.70 (d, J=6 Hz, 1H), 8.00 (d, J=3 Hz, 1H), 7.82 (m, 3H), 7.75 (d, J=3 Hz, 1H), 7.51 (dd, J=9, 3 Hz, 1H), 7.34 (m, 1H), 7.08 (d, J=9 Hz, 1H).

Step D:

Into a round-bottom flask equipped with a stir bar and nitrogen on demand were placed phenol 20 (0.13 g, 0.42 mmol), 2'-chloroacetanilide (0.10 g, 0.57 mmol), K$_2$CO$_3$ (0.29 g, 2.09 mmol) and acetone (10 mL). The resulting mixture was heated to reflux for 18 h, after which time it was allowed to cool to RT and was poured into a separatory funnel containing ethyl acetate and water. The organic layer was collected and was washed with water, brine, dried over MgSO$_4$, filtered and the solvents were removed under reduced pressure. The product was purified by flash chromatography using 65:35 hexane/ethyl acetate as eluant to afford 17 as a white solid (0.16 g, 85%). $^1$H NMR (CDCl$_3$, 300 MHz) δ 9.34(s, 1H), 8.70 (d, J=6 Hz, 1H), 7.80 (m, 3H), 7.68 (m, 3H), 7.55 (dd, J=9, 3 Hz, 1H), 7.35 (m, 4H), 7.14 (t, J=6 Hz, 1H), 7.07 (d, J=9 Hz, 1H), 4.75 (s, 2H).

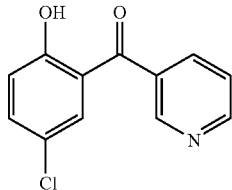

Step A:

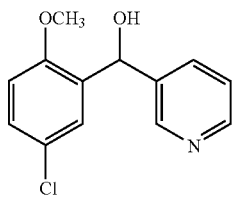

Into a round-bottom flask equipped with a stir bar and nitrogen on demand were placed 2-bromo-4-chloroanisole (7.02 g, 31.69 mmol) and diethyl ether (Et$_2$O, 75 mL). The resulting solution was cooled to −78° C. and n-butyl lithium (21 mL of a 1.6 M solution in hexane, 33.6 mmol) was added via syringe. The resulting mixture was allowed to stir at −78° C. for 15 min, after which time 3-pyridinecarboxaldehyde (3.73 g, 34.82 mmol) was added slowly. The resulting solution was allowed to stir at −78° C. for 30 min after which time it was allowed to warm to RT and stir for an additional 30 min. The mixture was poured into a separatory funnel containing Et$_2$O and water. The organic layer was collected and was washed with water, brine, dried over MgSO$_4$, filtered and the solvents were removed under reduced pressure to afford a clear, viscous oil (6.97 g, 88%) which was used without any further purification. $^1$H NMR (CDCl$_3$, 300 MHz) δ 8.65 (s, 1H), 8.53 (d, J=3 Hz, 1H), 7.80 (d, J=9 Hz, 1H), 7.40 (d, J=3 Hz, 1H), 7.31 (m, 3H), 6.84 (d, J=9 Hz, 1H), 6.10 (s, 1H), 3.82 (s, 3H).

Step B:

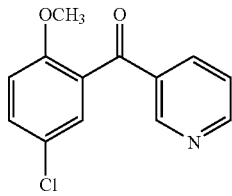

Into a round-bottom flask equipped with a stir bar and nitrogen on demand were placed alcohol 22 (6.97 g, 28 mmol), manganese dioxide (MnO$_2$, 20.27 g, 233 mmol) and CHCl$_3$ (200 mL). The resulting suspension was heated to reflux for 1 h, after which time it was allowed to cool to rt. The suspension was then filtered through a pad of celite, which was washed with several portions of CH$_2$Cl$_2$. The solvents were removed under reduced pressure to afford a tan solid (6.55 g, 95%). The solid was used in subsequent reactions without any further purification. $^1$H NMR (CDCl$_3$, 300 MHz) δ 8.94 (d, J=3 Hz, 1H), 8.81 (dd, J=6, 3 Hz, 1H), 8.19 (m, 1H), 7.49 (m, 2H), 6.98 (d, J=9 Hz, 1H), 3.74 (s, 3H).

Step C:

Into a round-bottom flask equipped with a stir bar and nitrogen on demand were placed ketone 23 (6.55 g, 26.45 mmol) and CH$_2$Cl$_2$ (200 mL). The resulting solution was cooled to −78° C. and boron tribromide (50 mL of a 1.0 M solution in CH$_2$Cl$_2$, 50 mmol) was added via syringe. The resulting solution was allowed to stir at −78° C. for 1 h, after which time it was allowed to warm to rt and stir for an additional 30 min. The mixture was carefully poured over ice water and the resulting two-phase system was stirred for 30 min. It was then poured into a separatory funnel containing water and CH$_2$Cl$_2$. The organic layer was collected and was washed with water, brine, dried over MgSO$_4$, filtered and the solvents were removed under reduced pressure to afford 21 as a yellow solid (5.25 g, 85%). $^1$H NMR (CDCl$_3$, 300 MHz) δ 11.77 (s, 1H), =3 Hz, 1H), 8.90 (dd, J=3, 1.5 Hz, 1H), 8.07 (m, 1H), 7.55 (m, 3H), 7.11 (m, 1H).

Example 9

24

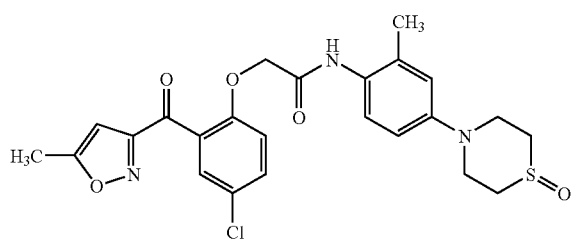

Step A:

25

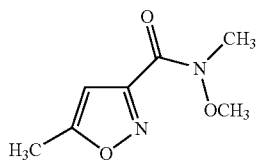

Into a round-bottom flask equipped with a stir bar and nitrogen on demand were placed N,O-dimethylhydroxylamine hydrochloride (7.79 g, 79.86 mmol), Et$_3$N (24 mL, 172.2 mmol) and CHCl$_3$ (150 mL). The resulting solution was cooled to 0° C. and 5-Methyl-3-isoxazolecarbonyl chloride (10.0 g, 68.70 mmol) in CHCl$_3$ (15 mL) was added dropwise, after which the resulting solution was allowed to stir at 0° C. for 1 h. The mixture was poured into a separatory funnel containing ethyl acetate and water. The organic layer was collected and was washed with water, brine, dried over MgSO$_4$, filtered and the solvents were removed under reduced pressure to afford a clear oil (10.53 g, 90%). $^1$H NMR (CDCl$_3$, 400 MHz) δ 6.92 (s, 1H), 3.75 (br s, 6H), 2.44 (s, 3H).

Step B:

26

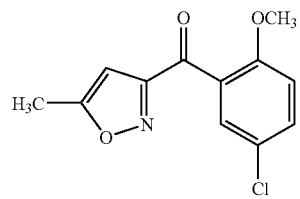

Into a round-bottom flask equipped with a stir bar and nitrogen on demand were placed 2-bromo-4-chloroanisole (5.02 g, 22.66 mmol) and Et$_2$O (150 mL). The solution was cooled to −78° C. and n-butyl lithium (15.6 mL of a 1.6 M solution in hexane, 24.96 mmol) was added via syringe. The resulting solution was allowed to stir at −78° C. for 15 min and then amide 25 (4.03 g, 23.68 mmol) in Et$_2$O (20 mL) was added slowly, after which time the solution was allowed to stir at −78° C. for 30 min. It was then allowed to warm to rt and stir for an additional 2 h. The mixture was then poured over ice water and the two-phase system was stirred for 30 min. It was then poured into a separatory funnel containing Et$_2$O and water. The organic layer was collected and was washed with water, brine, dried over MgSO$_4$, filtered and the solvents were removed under reduced pressure to provide a white solid (5.37 g, 94%). $^1$H NMR (CDCl$_3$, 400 MHz) δ 7.51 (d, J=3 Hz, 1H), 7.42 (dd J=6, 3 Hz, 1H), 6.92 (d, J=6 Hz, 1H), 6.45 (s, 1H), 3.76 (s, 3H), 2.49 (s, 3H).

Step C:

27

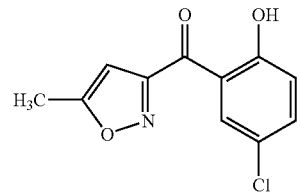

Into a round-bottom flask equipped with a stir bar and nitrogen on demand were placed ketone 26 (5.36 g, 21.30 mmol) and CH$_2$Cl$_2$ (100 mL). The solution was cooled to −78° C. and boron tribromide (40 mL of a 1.0 M solution in CH$_2$Cl$_2$) was added via syringe. The resulting dark red solution was allowed to stir at −78° C. for 1 h, after which time it was allowed to warm to RT and stir for an additional 2 h. The mixture was then carefully poured over ice water and the resulting two-phase system was stirred for 30 min. The mixture was then poured into a separatory funnel containing Et$_2$O and water. The organic layer was collected and was washed with water, brine, dried over MgSO$_4$, filtered and the solvents were removed under reduced pressure to afford a tan solid (5.44 g) which wag used in subsequent reactions without any further purification.

Step D:

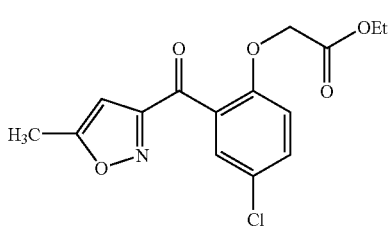
28

Phenol 27 (5.44 g crude weight, 21- mmol), ethyl bromoacetate (2.3 mL, 20.74 mmol), K$_2$CO$_3$ (12.32 g, 89.14 mmol) and acetone (150 mL) were used according to general procedure II. The product was used in subsequent reactions without any further purification.

Step E:

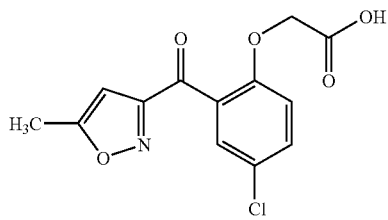
29

Ester 28 (21 mmol), THF (35 mL), EtOH (15 mL), water (15 mL) and LiOH (2.04 g, 48.62 mmol) were used according to general procedure III. Trituration with hexane provided 29 as a white foam, which was used in subsequent reactions without any further purification.

Step F:
Acid 29 (0.215 g, 0.727 mmol), HOBt (0.112 g, 0.829 mmol), EDAC (0.198 g, 1.03 mmol), Et$_3$N (0.25 mL, 1.79 mmol), DMF (5 mL) and sulfoxide 399 (0.198 g, 0.884 mmol) were used according to general procedure IV. The product was purified by flash chromatography using 95:5 CH$_2$Cl$_2$/CH$_3$OH as eluant to afford 24 as a tan solid (0.124 g, 34%). $^1$H NMR (CDCl$_3$, 400 MHz) δ 8.78 (s, 1H), 7.77 (d, J=4 Hz, 1H), 7.53-7.47 (m, 2H), 6.97 (d, J=8 Hz, 1H), 6.80 (m, 2H), 6.49 (s, 1H), 4.69 (s, 2H), 3.98-3.92 (m, 2H), 3.53 (m, 2H), 2.94-2.84 (m, 4H), 2.18 (s, 3H), 1.55 (s, 3H).

Example 10

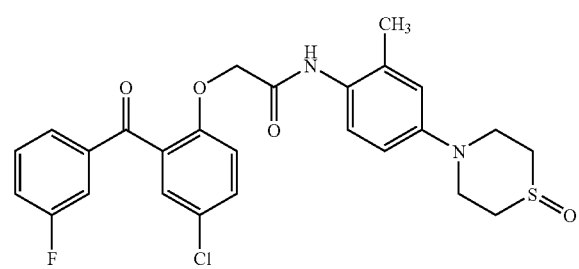
30

Step A:

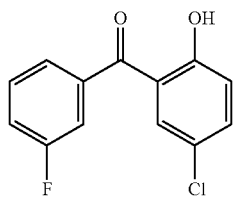
5

4-Chloroanisole (4.06 g, 28.47 mmol), 3-fluorobenzoyl chloride (4.53 g, 28.57 mmol), AlCl$_3$ (6.23 g, 46.72 mmol) and CH$_2$Cl$_2$ (100 mL) were used according to general procedure I. The product was purified by flash chromatography using 7:3 hexane/CH$_2$Cl$_2$ as eluant to provide the 31 as a yellow solid (2.60 g, 36%). $^1$H NMR (CDCl$_3$, 300 MHz) δ 11.80 (s, 1H), 7.50 (m, 6H), 7.09 (d, J=9 Hz, 1H).

Step B:

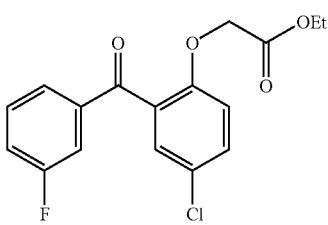
32

Phenol 31 (2.60 g, 10.37 mmol), ethyl bromoacetate (1.3 mL, 11.72 mmol), K$_2$CO$_3$ (7.15 g, 51.73 mmol), and acetone (80 mL) were used according to general procedure II. The product was used in subsequent reactions without any further purification.

Step C:

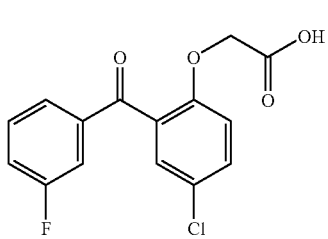
33

Ester 32 (10 mmol), THF (30 mL), EtOH (10 mL), water (10 mL) and LiOH (1.02 g, 24.31 mmol) were used according to general procedure III to afford 33 as a white solid (3.01 g, 98%). $^1$H NMR (DMSO-d$_6$, 300 MHz) δ 7.71-7.38 (m, 6H), 6.91 (d, J=9 Hz, 1H), 4.26 (s, 2H).

Step D:
Acid 33 (0.22 g, 0.71 mmol), HOBt (0.115 g, 0.851 mmol), EDAC (0.205 g, 1.07 mmol) Et$_3$N (0.25 mL, 1.79 mmol), DMF (5 mL) and sulfoxide 399 (0.185 g, 0.826 mmol) were used according to general procedure IV. The product was purified by flash chromatography using 95:5 CH$_2$Cl$_2$/CH$_3$OH as eluant to provide 30 as a white solid (0.05 g, 14%). $^1$H NMR (CDCl$_3$, 400 MHz) δ 8.21 (s, 1H), 7.58-7.38 (m, 6H), 7.28 (m, 1H), 7.01 (d, J=8 Hz, 1H), 6.76 (m, 2H), 4.66 (s, 2H), 3.98-3.91 (m, 2H), 3.53 (m, 2H), 2.91-2.83 (m, 4H), 1.54 (s, 3H).

Example 11

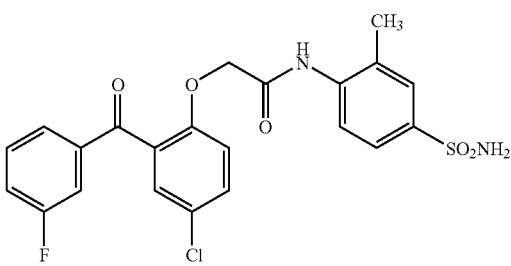

34

Carboxylic acid 33 (0.224 g, 0.726 mmol), oxalyl chloride (0.2 mL, 2.29 mmol), and CH$_2$Cl$_2$ (4 mL) were used according to general procedure V. Into a separate flask were placed sulfonamide 466 (0.158 g, 0.848 mmol), Et$_3$N (0.25 mL, 1.79 mmol) and acetonitrile (CH$_3$CN, 8 mL). The mixture was cooled to 0° C. and the acid chloride (in 2 mL CH$_3$CN) was added dropwise over several minutes. The resulting mixture was allowed to stir at 0° C. for 30 min, after which time it was allowed to warm to RT and stir for an additional 5 h. The mixture was then poured into a separatory funnel containing ethyl acetate and water. The organic layer was collected and was washed with water, brine, dried over MgSO$_4$, filtered and the solvents were removed under reduced pressure. The product was purified by flash chromatography using 95:5 CH$_2$Cl$_2$/CH$_3$OH as eluant to provide 34 as a white solid (0.117 g, 34%). $^1$H NMR (DMSO-d$_6$, 300 MHz) δ 9.39 (s, 1H), 7.71-7.52 (m, 9H), 7.31-7.27 (m, 3H), 4.85 (s, 2H), 2.21 (s, 3H).

Example 12

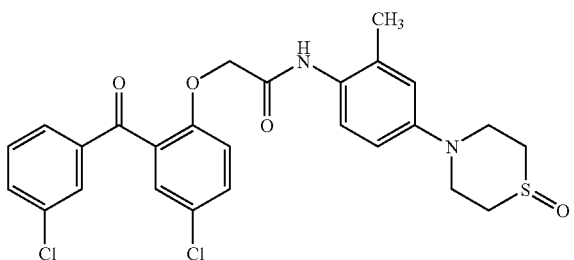

35

Step A:

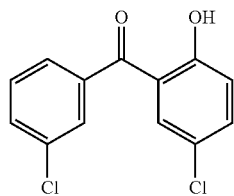

36

4-Chloroanisole (4.02 g, 28.19 mmol), 3-chlorobenzoyl chloride (3.8 mL, 4.94 g, 28.22 mmol), AlCl$_3$ (5.62 g, 42.15 mmol) and CH$_2$Cl$_2$ (75 mL) were used according to general procedure I. The product was purified by flash chromatography using 7:3 hexane/CH$_2$Cl$_2$ as eluant to provide 36 as a yellow solid (5.35 g, 71%). $^1$H NMR (CDCl$_3$, 400 MHz) δ 1.72 (s, 1H), 7.64 (s, 1H), 7.58 (d, J=8 Hz, 1H), 7.53-7.44 (m, 4H), 7.03 (d, J=12 Hz, 1H).

Step B:

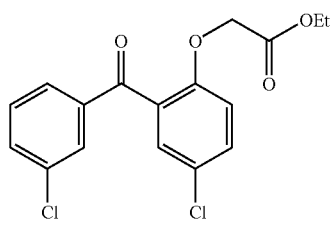

37

Phenol 36 (5.35 g, 20.03 mmol), ethyl bromoacetate (2.5 mL, 22.54 mmol), K$_2$CO$_3$ (12.91 g, 93.41 mmol), and acetone (125 mL) were used according to general procedure II. The product was used in subsequent reactions without any further purification.

Step C:

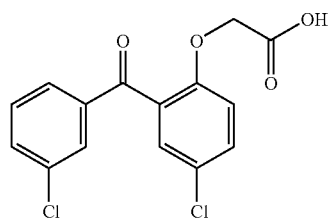

38

Ester 37 (20 mmol), THF (60 mL), EtOH (15 mL), water (15 ml) and LiOH (2.09 g, 49.81 mmol) were used according to general procedure III. The product was used in subsequent reactions without any further purification.

Step D:

Carboxylic acid 38 (0.29 g, 0.892 mmol), sulfoxide 399 (0.24 g, 1.07 μmmol), EDAC (0.261 g, 1.36 mmol), HOBt (0.142 g, 1.05 mmol) and DMF (7 mL) were used according to general procedure IV, with the exception that no Et$_3$N was used. The product was purified by flash chromatography using 97:3 CH$_2$Cl$_2$/CH$_3$OH as eluant to provide 35 as a tan solid (0.34 g, 72%). $^1$H NMR (CDCl$_3$, 300 MHz) δ 8.21 (s, 1H), 7.86 (d, J=3 Hz, 1H), 7.72 (d, J=6 Hz, 1H), 7.60-7.43 (m, 4H), 7.07 (d, J=9 Hz, 2H), 6.85-6.82 (m, 3H), 4.72 (s, 2H), 4.06-3.98 (m, 2H), 3.62-3.55 (m, 2H), 3.00-2.90 (m, 4H), 2.18 (s 3H).

Example 13

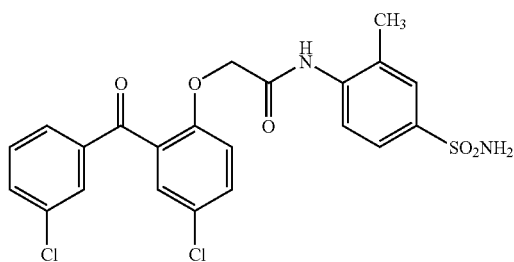

39

Carboxylic acid 38 (0.229 g, 0.704 mmol), oxalyl chloride (0.2 mL, 2.29 mmol) and $CH_2Cl_2$ (4 mL) were used according to general procedure V. Into a separate flask were placed sulfonamide 466 (0.156 g, 0.838 mmol), $Et_3N$ (0.25 mL, 1.79 mmol) and $CH_3CN$ (8 mL). The acid chloride (in 2 mL of $CH_3CN$) was added dropwise over several minutes. The resulting solution was allowed to stir at 0° C. for 30 min, after which time it was allowed to warm to rt and stir for an additional 5 h. The mixture was then poured into a separatory funnel containing ethyl acetate and water. The organic layer was collected and was washed with water, brine, dried over $MgSO_4$, filtered and the solvents were removed under reduced pressure. The product was purified by flash chromatography using 95:5 $CH_2Cl_2/CH_3OH$ as eluant to provide 39 as a white solid (0.110 g, 32%). $^1H$ NMR (DMSO-$d_6$, 300 MHz) δ 9.39 (s, 1H), 7.82-7.53 (m, 9H), 7.30 (m, 3H), 4.84 (s, 2H), 2.20 (s, 3H).

Example 14

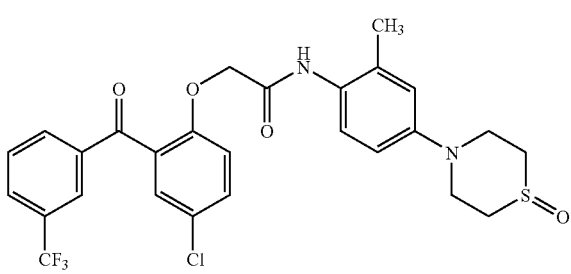

40

Step A:

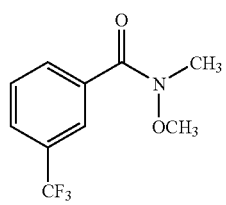

41

Into a round-bottom flask equipped with a stir bar and nitrogen on demand were placed N,O-dimethylhydroxylamine hydrochloride (3.16 g, 32.40 mmol), $Et_3N$ (9 mL, 64.57 mmol) and $CHCl_3$ (85 mL). The solution was cooled to 0° C. and 3-trifluoromethylbenzoyl chloride (4 mL, 5.53 g, 26.52 mmol) was added dropwise over several minutes. The resulting solution was allowed to stir at 0° C. for 30 min, after which time it was allowed to warm to RT and stir for an additional 30 min. The mixture was then poured into a separatory funnel containing ethyl acetate and water. The organic layer was collected and was washed with water, brine, dried over $MgSO_4$, filtered and the solvents were removed under reduced pressure to provide a clear oil which was used without any further purification.

Step B:

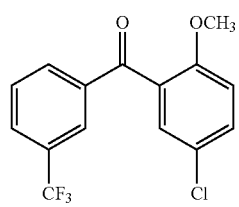

42

Into a round-bottom flask equipped with a stir bar and nitrogen on demand were placed 2-bromo-4-chloroanisole (5.23 g, 23.61 mmol) and $Et_2O$ (100 mL). The solution was cooled to -78° C. and n-butyl lithium (17 mL of a 1.6 M solution in hexane, 27.2 mmol) was added dropwise. The resulting mixture was allowed to stir at -78° C. for 15 min, after which time amide 41 (5.56 g, 23.84 mmol) was added dropwise. The mixture was allowed to stir at -78° C. for 30 min, after which time it was allowed to warm to RT and stir for an additional 2 h. The mixture was then poured into a separatory funnel containing ethyl acetate and water. The organic layer was collected and was washed with water, brine, dried over $MgSO_4$, filtered and the solvents were removed under reduced pressure to leave a yellow oil, which was used in subsequent reactions without any further purification

Step C:

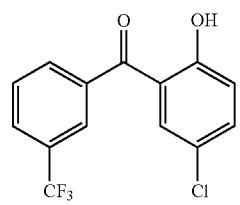

43

Into a round-bottom flask equipped with a stir bar and nitrogen on demand were placed 42 (23 mmol) and $CH_2Cl_2$ (150 mL). The solution was cooled to -78° C. and boron tribromide (35 mL of a 1.0 M solution in $CH_2C_2$, 35 mmol) was added dropwise over several minutes. The resulting dark mixture was allowed to stir at -78° C. for 30 min, after which time it was allowed to warm to rt and stir for an additional 1 h. The mixture was carefully poured over ice and the two-phase mixture was stirred for 30 min. It was then poured into a separatory funnel containing $CH_2Cl_2$ and water. The organic layer was collected, washed with water, brine, dried over $MgSO_4$, filtered and the solvents were removed under reduced pressure to afford a yellow solid (5.04 g, 73%). $^1H$ NMR ($CDCl_3$, 300 MHz)δ 11.76 (s, 1H), 8.25-7.84 (m, 3H), 7.73 (t, J=9 Hz, 1H), 7.56-7.52(m, 2H), 7.12 (d, J=9 Hz, 1H).

Step D:

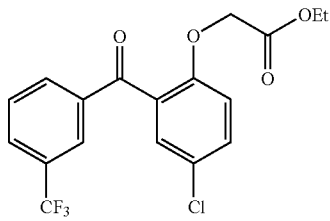

Phenol 43 (5.04 g, 16.76 mmol), ethyl bromoacetate (2.1 mL, 18.94 mmol), K$_2$CO$_3$ (9.01 g, 65.19 mmol) and acetone (100 mL) were used according to general procedure II. Removal of the solvents under reduced pressure afforded 44 as an oil (6.28 g, crude weight), which was used in subsequent reactions without any further purification.

Step E:

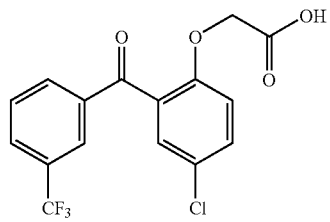

Ester 44 (6.28 g, crude weight, 16.24 mmol), THF (50 mL), water (25 mL) and EtOH (25 mL) were used according to general procedure IV. Removal of the solvents under reduced pressure provided acid 45 as a white solid (2.81 g, 48%) which was used without any further purification.

Step F:

Carboxylic acid 45 (0.208 g, 0.58 mmol), sulfoxide 399 (0.152 g, 0.679 mmol), EDAC (0.19 g, 0.991 mmol), HOBt (0.103 g, 0.76 mmol) and DMF (5 ML) were used according to general procedure IV. The product was purified by flash chromatography using 95:5 CH$_2$Cl$_2$/CH$_3$OH to provide 40 as an off-white solid (0.23 g, 70%). $^1$H NMR (CDCl$_3$, 300 MHz) δ 8.19 (d, J=9 Hz, 2H), 8.01 (d, J=9 Hz, 1H), 7.88 (d, J=9 Hz, 1H), 7.66 (t, J=6 Hz, 1H), 7.60 (dd, J=9, 3 Hz, 1H), 7.50 (d, J=9 Hz, 1H), 7.44 (d, J=3 Hz, 1H), 7.09 (d, J=9 Hz, 1H), 6.83 (m, 3H), 4.72 (s, 2H), 4.05-3.96 (m, 2H), 3.62-3.54 (m, 2H), 3.0-2.89 (m, 4H), 2.16 (s, 3H).

Example 15

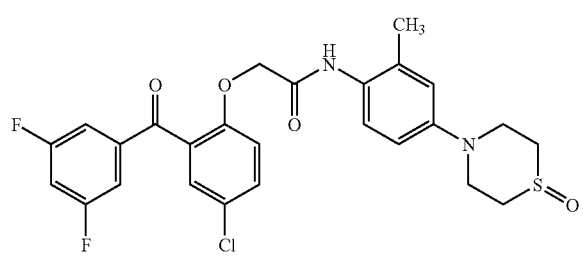

Step A:

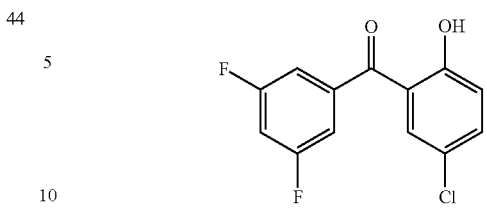

4-Chloroanisole (4.12 g, 28.89 mmol), 3,5-difluorobenzoyl chloride (5.0 g, 28.3 mmol), AlCl$_3$ (5.65 g, 42.37 mmol) and CH$_2$Cl$_2$ (75 mL) were used according to general procedure I. The product was purified by flash chromatography using 7:3 hexane/CH$_2$Cl$_2$ as eluant to provide a yellow solid (2.72 g, 36%). $^1$H NMR (CDCl$_3$, 300 MHz) δ 11.64 (s, 1H), 7.54 (m, 2H), 7.23 (m, 2H), 7.11 (m, 2H).

Step B:

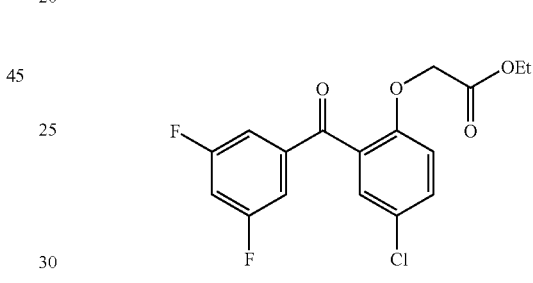

Phenol 47 (2.72 g, 10.13 mmol), ethyl bromoacetate (1.3 mL, 11.7 mmol), K$_2$CO$_3$ (5.28 g, 38.2 mmol) and acetone (100 mL) were used according to general procedure II. Removal of the solvents under reduced pressure afforded 48 as a clear oil (3.8 g, crude weight) that was used without any further purification. Step C:

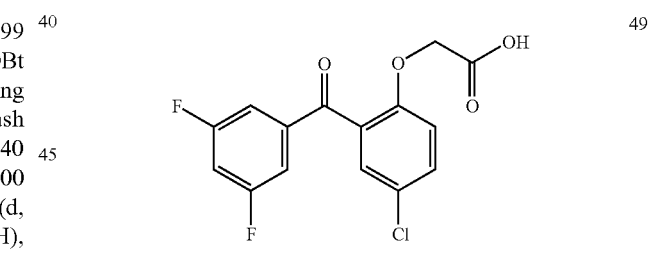

Ester 48 (10 mmol), THF (50 mL), water (25 mL) and EtOH (25 mL) were used according to general procedure III. Removal of the solvents under reduced pressure afforded 49 as a white solid, which was used in subsequent reactions without any further purification.

Step D:

Carboxylic acid 49 (0.20 g, 0.612 mmol), sulfoxide 399 (0.167 g, 1.22 mmol), EDAC (0.23 g, 1.2 mmol), HOBt (0.106 g, 0.784 mmol) and DMF (5 mL) were used according to general procedure IV, with the exception that no Et$_3$N was used. The product was purified by flash chromatography using 95:5 CH$_2$Cl$_2$/CH$_3$OH as eluant, followed by trituration with Et$_2$O, afforded 46 as an off-white solid (0.24 g, 74%). $^1$H NMR (CDCl$_3$, 300 MHz) δ 8.29 (s, 1H), 7.61-7.54 (m, 2H), 7.42 (d, J=3 Hz, 1H), 7.38 (m, 1H), 7.08 (m, 2H), 6.85 (m, 2H), 4.73 (s, 2H), 4.73 (m, 2H), 4.05-3.96 (m, 2H), 3.62-3.55 (m, 2H), 2.94-2.89 (m, 4H), 2.21 (s, 3H).

Example 16

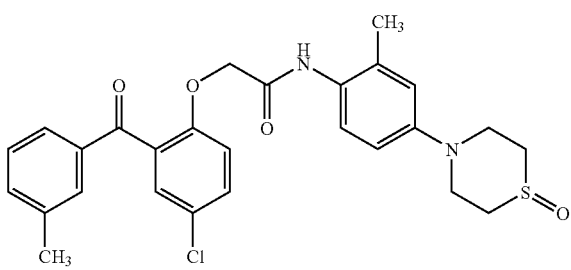

50

Step A:

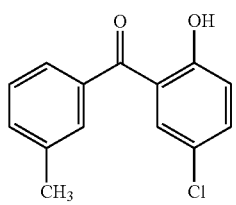

4-Chloroanisole (4.16 g, 29.17 mmol), 3-methylbenzoyl chloride (4.42 g, 28.59 mmol), AlCl₃ (6.12 g, 45.9 mmol) and CH₂Cl₂ (150 mL) were used according to general procedure I. The product was purified by flash chromatography using 7:3 hexane/CH₂Cl₂ as eluant to provide 50 as yellow solid (1.54 g, 22%). $^1$H NMR (CDCl₃, 400 MHz) δ 11.91 (s, 1H), 7.54 (d, J=4 Hz, 1H), 7.47-7.39 (m, 5H), 7.02 (d, J=8 Hz, 1H), 2.44 (s, 3H).

Step B:

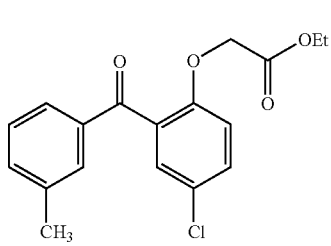

51

Phenol 50 (1.54 g, 6.24 mmol), ethyl bromoacetate (0.8 mL, 7.21 mmol), K₂CO₃ (3.15 g, 22.79 mmol) and acetone (35 mL) were used according to general procedure II. Removal of the solvents under reduced pressure afforded 51 as a clear oil that was used without any further purification.

Step C:

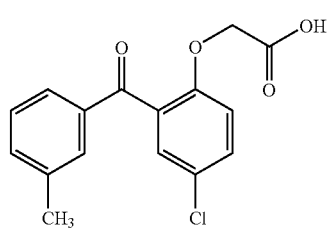

52

Ester 51 (6.3 mmol), lithium hydroxide (0.700 g, 16.68 mmol), THF (20 mL), water (10 mL) and EtOH (10 mL) were used according to general procedure III. Removal of the solvents under reduced pressure afforded 52 as a white solid (1.82 g, 96%) which was used without any further purification.

Step D:

Carboxylic acid 52 (0.21 g, 0.70 mmol), sulfoxide 399 (0.19 g, 0.853 mmol), EDAC (0.212 g, 1.11 mmol), HOBt (0.121 g, 0.895 mmol) and DMF (5 mL) were used according to general procedure IV, with the exception that no Et₃N was used. The product was purified by flash chromatography using 95:5 CH₂Cl₂/CH₃OH as eluant to provide 50 as an off-white solid (0.09 g, 25%). $^1$H NMR (CDCl₃, 300 MHz) δ 8.13 (s, 1H), 7.69-7.30 (m, 8H), 7.04 (d, J=9 Hz, 1H), 6.81 (m, 3H), 4.69 (s, 2H), 4.05-3.96 (m, 2H), 3.60-3.51 (m, 2H), 2.93-2.85 (m, 4H), 2.38 (s, 3H), 2.14 (s, 3H).

Example 17

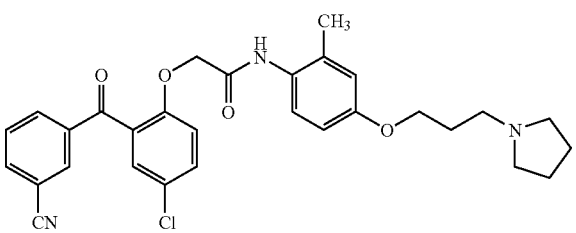

53

Carboxylic acid 129 (0.316 g, 1.00 mmol), amine 143 (0.241 g, 1.03 mmol), EDAC (0.251 g, 1.31 mmol), HOBt (0.167 g, 1.24 mmol) and DMF (5 mL) were used according to general procedure IV, with the exception that no Et₃N was used. The product was purified by flash chromatography using 9:1 CHCl₃/CH₃OH as eluant to provide 53 as a tan powder (0.082 g, 15%).

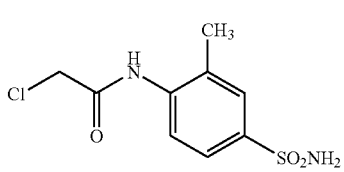

54

Into a round-bottom flask were placed aniline 466 (0.246 g, 1.32 mmol), Et₃N (0.9 mL, 0.65 g, 6.5 mmol), CHCl₃ (5 mL) and CH₃CN (5 mL). The resulting mixture was cooled to 0° C. and 2'-chloroacetyl chloride (0.2 mL, 2.51 mmol) was added dropwise over several minutes. The mixture was allowed to stir at 0° C. for 30 minutes and was then allowed to warm to rt and stir for an additional 30 minutes. The mixture was then poured into a separatory funnel containing H₂O and ethyl acetate. The organic layer was collected, washed with water, brine, dried over MgSO₄, filtered and the solvents were removed under reduced pressure to afford a dark, green oil. Several portions of hexane were added and subsequently removed under reduced pressure to afford 54 as a green solid, which was used without any further purification. $^1$H NMR (DMSO-d₆, 300 MHz) δ 9.84 (s, D 1H), 7.69 (m, 3H), 7.31 (s, 2H), 4.38 (s, 2H), 2.31 (s, 3H).

Example 18

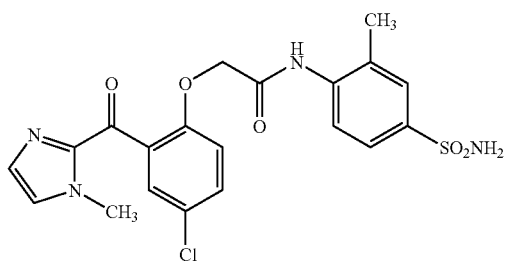

Into a round-bottom flask were placed amine 54 (0.16 g, 0.61 mmol), phenol 185 (0.14 g, 0.60 mmol), K$_2$CO$_3$ (0.66 g, 4.8 mmol) and acetone (10 mL). The resulting mixture was allowed to heat to reflux and stir overnight. The mixture was then allowed to cool to rt and was poured into a separatory funnel containing ethyl acetate and water. The organic layer was collected, washed with water, brine, dried over MgSO$_4$, filtered and the solvents were removed under reduced pressure. The product was purified by flash chromatography using 95:5 CH$_2$Cl$_2$/CH$_3$OH to provide 55 as an off-white solid (0.02 g, 7%). $^1$H NMR (DMSO-d$_6$, 400 MHz) δ 9.74 (s, 1H), 7.63-7.53 (m, 4H), 7.26-7.19 (m, 4H), 6.97 (s, 2H), 4.81 (s, 2H), 3.99 (s, 3H), 2.08 (s, 3H).

Example 19

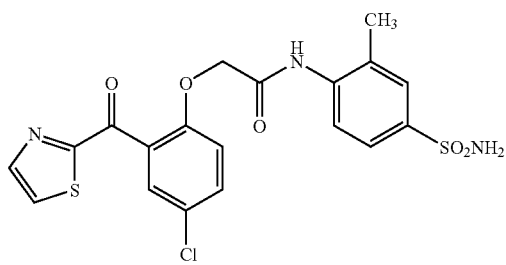

Into a round-bottom flask were placed amine 54 (0.16 g, 0.62 mmol), K$_2$CO$_3$ (0.51 g, 3.7 mmol), phenol 4 (0.22 g, 0.90 mmol) and acetone (5 mL). The same procedure was followed as in example 55. The product was purified by flash chromatography using 97:3 CHCl$_3$/CH$_3$OH to provide 56 as a tan solid (0.03 g, 10%). $^1$H NMR (DMSO-d$_6$, 300 MHz) δ 9.39 (s, 1H), 8.33 (d, J=3 Hz, 1H), 8.16 (d, J=3 Hz, 1H), 7.83-7.64 (m, 5H), 7.39-7.30 (m, 3H), 4.86 (s, 2H), 2.23 (s, 3H).

Example 20

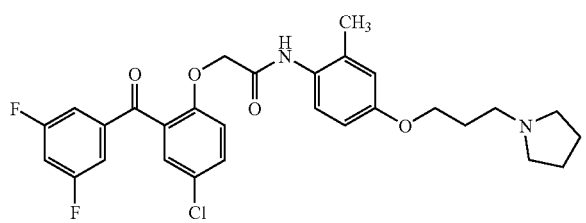

Acid 49 (0.351 g, 1.07 mmol), amine 143 (0.253 g, 1.08 mmol), EDAC (0.341 g, 1.78 mmol), HOBt (0.193 g, 1.43 mmol) and DMF (7 mL) were used according to general procedure IV, with the exception that no Et$_3$N was used. The product was purified by flash chromatography using 9:1 CHCl$_3$/CH$_3$OH to provide a tan solid (0.09 g, 15%). $^1$H NMR (CDCl$_3$, 300 MHz) δ 8.19 (s, 1H), 7.49 (dd, J=9, 3 Hz, 1H), 7.42 (d, J=9 Hz, 1H), 7.33 (d, J=3 Hz, H), 7.27 (d, J=3 Hz, 1H), 7.19 (m, 1H), 7.01-6.96 (m, 2H), 6.65-6.63 (m, 2H), 4.62 (s, 2H), 4.00-3.96 (t, J=6 Hz, 2H), 3.76 (m, 2H), 3.23-3.15 (m, 2h), 2.75 (m, 2H), 2.39-2.12 (m, 6H), 2.09 (s, 3H).

Example 21

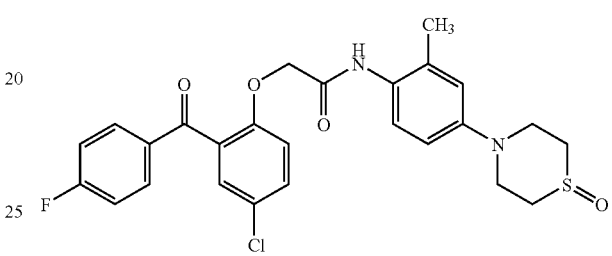

Step A:

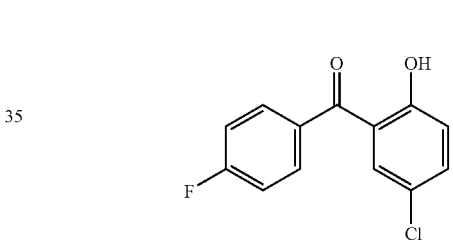

4-Fluorobenzoyl chloride (3.2 mL, 27.08 mmol), 4-chloroanisole (3.98 g, 27.91 mmol), aluminum chloride (5.78 g, 43.34 mmol) and dichloromethane (120 mL) were used according to general procedure I. The product was purified by flash chromatography using 7:3 hexane/ethyl acetate to provide 59 as a yellow solid (3.48 g, 51%).

Step B:

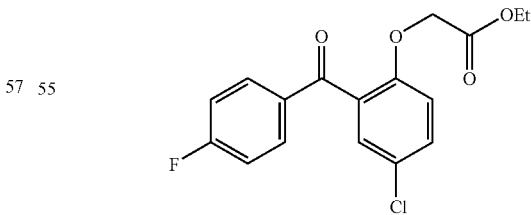

Phenol 59 (3.48 g, 13.88 mmol), ethyl bromoacetate (1.7 mL, 15.32 mmol), K$_2$CO$_3$ (7.74 g, 56.0 mmol) and acetone were used according to general procedure II to provide 60 as a white solid, which was washed with several portions of ether, dried in vacuo and used in subsequent reactions without any further purification.

83

Step C:

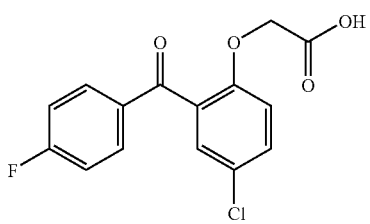
61

Ester 60 (4.7 g, 13.9 mmol), lithium hydroxide (1.45 g, 34.56 mmol), water (20 mL), THF (40 mL) and EtOH (20 mL) were used according to general procedure III to afford 61 as a viscous, clear oil. Ether was added to the oil causing a white solid to form, which was filtered and dried to provide 61 as a white solid, which was used without any further purification.

Step D:

Carboxylic acid 61 (0.237 g, 0.786 mmol), sulfoxide 399 (0.198 g, 0.88 mmol), EDAC (0.285 g, 1.49 mmol), HOBt (0.131 g, 0.97 mmol) and DMF (5 mL) were used according to general procedure IV. The product was purified by flash chromatography using 95:5 $CH_2Cl_2/CH_3OH$ as eluant to provide 58 as a tan solid (0.280 g, 71%). $^1$H NMR (DMSO-$d_6$, 300 MHz) δ 8.95 (s, 1H), 7.90 (m, 2H), 7.66 (dd, J=9, 3 Hz, 1H), 7.49 (d, J=3 Hz, 1H), 7.36 (t, J=6 Hz, 2H), 7.26 (d, J=9 Hz, 1H), 7.14 (d, J=9 Hz, 1H), 6.84 (m, 2H), 4.73 (s, 2H), 3.75 (m, 2H), 3.58 (m, 2H), 2.91 (m, 2H), 2.71 (m, 2H), 2.03 (s, 3H).

Example 22

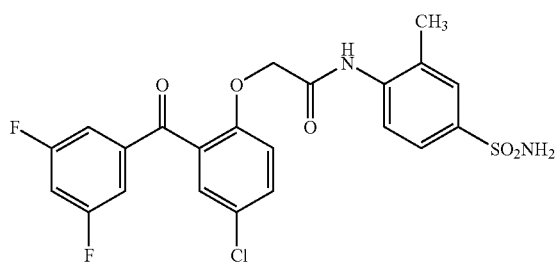
62

Carboxylic acid 49 (0.123 g, 0.377 mmol), oxalyl chloride (0.1 mL, 1.15 mmol), DMF (2 drops) and chloroform (5 mL) were used to prepare the acid chloride according to general procedure V. The acid chloride, sulfonamide 466 (0.07 g, 0.37 mmol), $NaHCO_3$ (0.13 g, 1.55 mmol), water (1 mL) and acetone (5 mL) were used according to general procedure VI to afford 62 as a tan solid (0.07 g, 40%). $^1$H NMR (DMSO-$d_6$, 300 MHz) δ 9.46 (s, 1H), 7.68-7.45 (m, 8H), 7.28 (m, 3H), 4.85 (s, 2H), 2.21 (s, 3H).

Example 23

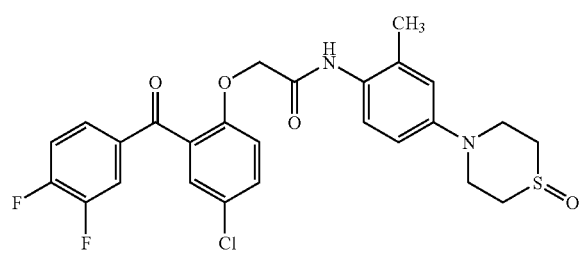
63

84

Step A:

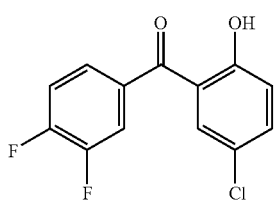
64

3,4-Difluorobenzoyl chloride (5.01 g, 28.37 mmol), 4-chloroanisole (4.04 g, 28.33 mmol), aluminum chloride (5.61 g, 42.07 mmol) and dichloromethane (100 mL) were used according to general procedure I. The product was purified by flash chromatography using 7:3 hexane/ethyl acetate as eluant to provide 64 as a yellow solid (2.65 g, 35%). $^1$H NMR ($CDCl_3$, 300 MHz) δ 11.64 (s, 1H), 7.64-7.30 (m, 5H), 7.09 (d, J=9 Hz, 1H).

Step B:

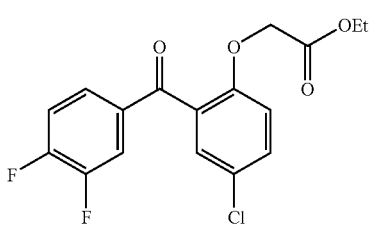
65

Phenol 64 (2.65 g, 9.86 mmol), ethyl bromoacetate (1.20 mL, 10.82 mmol), $K_2CO_3$ (5.37 g, 38.85 mmol) and acetone (35 mL) were used according to general procedure II to provide 65 as white solid (3.39 g, 96%) that was used without any further purification.

Step C:

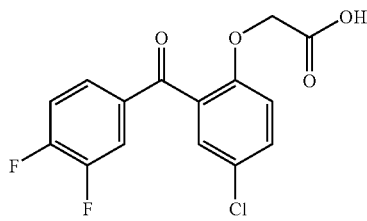
66

Ester 65 (3.39 g, 9.56 mmol), lithium hydroxide (0.80 g, 19.07 mmol), water (20 mL), THF (40 mL) and EtOH (20 mL) were used according to general procedure III to provide 66 as a white solid which was used without any further purification.

Step D:

Carboxylic acid 66 (0.146 g, 0.447 mmol), sulfoxide 399 (0.096 g, 0.429 mmol), EDAC (0.183 g, 0.955 mmol), HOBt (0.077 g, 0.569 mmol) and DMF (5 mL) were used according to general procedure IV. The product was purified by flash chromatography using 95:5 $CH_2Cl_2/CH_3OH$ as eluant to provide 63 as a tan solid (0.150 g, 63%). $^1$H NMR ($CDCl_3$, 300 MHz) δ 8.35 (s, 1H), 7.79-7.56 (m, 3H), 7.41

(d, J=3 Hz, 1H), 7.32 (m, 2H), 7.09 (d, J=9 Hz, 1H), 6.87 (br s, 1H), 4.73 (s, 2H), 4.04 (m, 2H), 3.58 (m, 2H), 3.02 (m, 4H), 1.62 (s, 3H).

Example 24

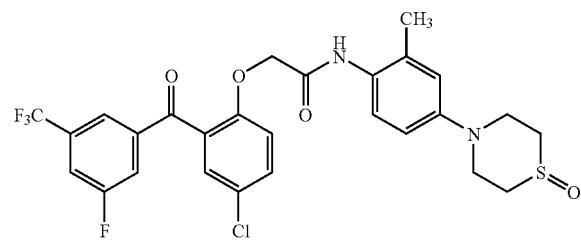

Step A:

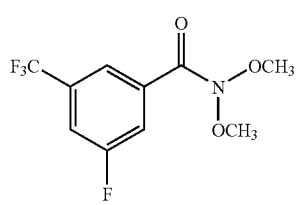

Into a round-bottom flask equipped with a stir bar and nitrogen on demand were placed N,O-dimethylhydroxy-lamine hydrochloride (2.80 g, 28.7 mmol), Et$_3$N (9.0 mL, 64.57 mmol) and CHCl$_3$ (50 mL). The solution was cooled to 0° C. and 3-trifluoromethyl-5-fluorobenzoyl chloride (5.0 g, 22.07 mmol) was added dropwise over several minutes. The resulting solution was allowed to stir at 0° C. for 30 min, after which time it was allowed to warm to rt and stir for an additional 30 min. The mixture was then poured into a separatory funnel containing ethyl acetate and water. The organic layer was collected and was washed with water, brine, dried over MgSO$_4$, filtered and the solvents were removed under reduced pressure to provide 68 as a clear oil which was used without any further purification. $^1$H NMR (CDCl$_3$, 300 MHz) δ 7.83 (s, 1H), 7.65 (d, J=9 Hz, 1H), 7.46 (d, J=9 Hz, 1H), 3.59 (s, 3H), 3.42 (s, 3H).

Step B:

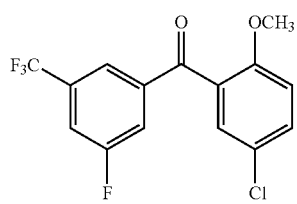

Into a round-bottom flask equipped with a stir bar and nitrogen on demand were placed 2-bromo-4-chloroanisole (4.05 g, 18.29 mmol) and Et$_2$O (75 mL). The solution was cooled to −78° C. and n-butyl lithium (13 mL of a 1.6 M solution in hexane, 20.8 mmol) was added dropwise. The resulting mixture was allowed to stir at −78° C. for 15 min, after which time amide 68 (5.04 g, 20.07 mmol) was added dropwise. The mixture was allowed to stir at −78° C. for 30 min, after which time it was allowed to warm to rt and stir for an additional 2 h. The mixture was then poured into a separatory funnel containing ethyl acetate and water. The organic layer was collected and was washed with water, brine, dried over MgSO$_4$, filtered and the solvents were removed under reduced pressure afford 69 as a yellow solid (6.14 g, 92%), which was used in subsequent reactions without any further purification. $^1$H NMR (CDCl$_3$, 300 MHz) δ 7.84 (s, 1H), 7.68 (d, J=9 Hz, 1H), 7.58-7.51 (m, 2H), 7.44 (d, J=3 Hz, 1H), 7.00 (d, J=9 Hz, 1H), 3.74 (s, 3H).

Step C:

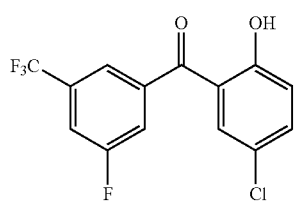

Into a round-bottom flask equipped with a stir bar and nitrogen on demand were placed 69 (6.14 g, 18.46 mmol) and CH$_2$Cl$_2$ (100 mL). The solution was cooled to −78° C. and boron tribromide (50 mL of a 1.0 M solution in CH$_2$Cl$_2$, 50 mmol) was added dropwise over several minutes. The resulting dark mixture was allowed to stir at −78° C. for 30 min, after which time it was allowed to warm to rt and stir for an additional 1 h. The mixture was carefully poured over ice and the two-phase mixture was stirred for 30 min. It was then poured into a separatory funnel containing CH$_2$Cl$_2$ and water. The organic layer was collected, washed with water, brine, dried over MgSO$_4$, filtered and the solvents were removed under reduced pressure to afford 70 as a yellow solid (5.68 g, 96%), which was used without any further purification. $^1$H NMR (CDCl$_3$, 300 MHz) δ 11.61 (s, 1H), 7.77 (s, 1H), 7.65-7.54 (m, 3H), 7.47 (d, J=3 Hz, 1H), 7.12 (d, J=9 Hz, 1H).

Step D:

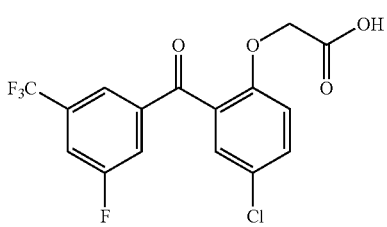

Phenol 70 (5.68 g, 17.83 mmol), ethyl bromoacetate (2 mL, 18.03 mmol), K$_2$CO$_3$ (9.61 g, 69.53 mmol) and acetone (35 mL) were used according to general procedure II to provide the ester as a yellow, viscous oil which was used without any further purification. The ester (6.83 g, 16.88 mmol), lithium hydroxide (1.42 g, 33.84 mmol), water (20 mL), THF (50 mL) and EtOH (20 mL) were used according to general procedure III. The product was washed with several portions of ether to provide 71 as a white solid that was used without any further purification.

Step E:

Carboxylic acid 71 (0.168 g, 0.445 mmol), sulfoxide 399 (0.098 g, 0.438 mmol), EDAC (0.211 g, 1.10 mmol), HOBt (0.076 g, 0.562 mmol) and DMF (5 mL) were used according to general procedure IV. The product was purified by flash chromatography using 95:5 $CH_2Cl_2/CH_3OH$ as eluant to provide 67 as a white solid (0.18 g, 69%). $^1H$ NMR ($CDCl_3$, 300 MHz) δ 8.26 (s, 1H), 7.92 (s, 1H), 7.73 (d, J=6 Hz, 1H), 7.64-7.59 (m, 3H), 7.44 (d, J=3 Hz, 1H), 7.10 (d, J=9 Hz, 1H), 6.90 (m, 1H), 4.74 (s, 2H), 4.03 (m, 2H), 3.58 (m, 2H), 3.02 (m, 4H), 2.21 (s, 3H).

Example 25

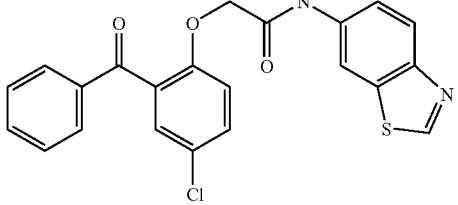

Carboxylic acid 105 (0.195 g, 0.65 mmol), 6-aminobenzthiazole (Lancaster, 0.105 g, 0.70 mmol), EDAC (0.23 g, 1.20 mmol), HOBt (0.105 g, 0.78 mmol) and DMF (5 mL) were used according to general procedure IV, with the exception that no $Et_3N$ was used. The product was purified by flash chromatograph using 1: hexane/ethyl acetate as eluant to provide 72 as a white solid (0.24 g, 87%). $^1H$ NMR ($CDCl_3$, 400 MHz) δ 9.51 (s, 1H), 8.92 (s, 1H), 8.64 (s, 1H), 8.08 (d, J=8 Hz, 1H), 7.92 (d, J=8 Hz, 1H), 7.67-7.63 (m, 2H), 7.55-7.50 (m, 3H), 7.42 (s, 1H), 7.04 (d, J=8 Hz, 1H), 4.73 (s, 2H).

Example 26

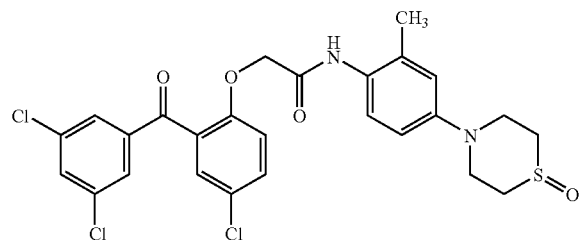

Step A:

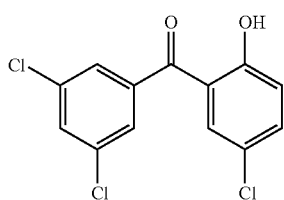

3,5-Dichlorobenzoyl chloride (5.0 g, 23.87 mmol), 4-chloroanisole (3.40 g, 23.84 mmol), aluminum chloride (5.56 g, 41.70 mmol) and dichloromethane (100 mL) were used according to general procedure I. The product was purified by flash chromatography using 7:3 hexane/dichloromethane to provide 74 as a yellow solid (1.18 g, 16%). $^1H$ NMR ($CDCl_3$, 300 MHz) δ 11.62 (s, 1H), 7.65 (s, 1H), 7.56-7.49 (m, 4H), 7.09 (d, J=9 Hz, 1H).

Step B:

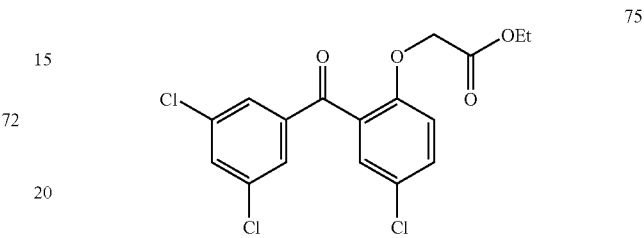

Phenol 74 (1.18 g, 3.91 mmol), ethyl bromoacetate (0.6 mL, 5.41 mmol), $K_2CO_3$ (2.66 g, 19.25 mmol) and acetone (15 mL) were used according to general procedure II to afford 75 as a viscous, yellow oil, which was used without any further purification.

Step C:

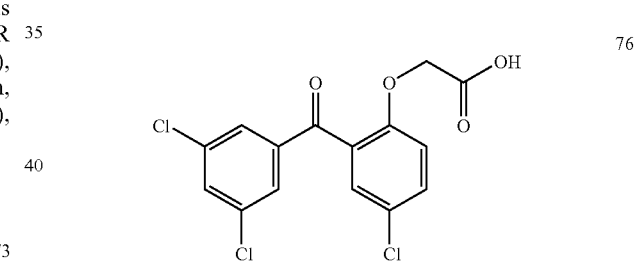

Ester 75 (3.9 mmol), lithium hydroxide (0.396 g, 9.44 mmol), water (10 mL), THF (40 mL) and EtOH (10 mL) were used according to general procedure III to afford 76 as a white solid, which was washed with hexane and dried in vacuo (1.32 g, 94%).

Step D:

Carboxylic acid 76 (0.128 g, 0.356 mmol), sulfoxide 399 (0.076 g, 0.339 mmol), EDAC (0.114 g, 0.595 mmol), HOBt (0.057 g, 0.422 mmol) and DMF (5 ML) were used according to general procedure IV. The product was purified by flash chromatography using 95:5 chloroform/methanol as eluant to afford 73 as a white solid (0.125 g, 65%). $^1H$ NMR ($CDCl_3$, 300 MHz) δ 8.20 (s, 1H), 7.70 (s, 1H), 7.62-7.59 (m, 2H), 7.42 (d, J=3 Hz, 1H), 7.08 (d, J=9 Hz, 1H), 6.86 (br s, 2H), 4.72 (s, 2H), 4.04 (m, 2H), 3.62-3.55 (m, 2H), 3.06-2.92 (m, 4H), 2.21 (s, 3H).

Example 27

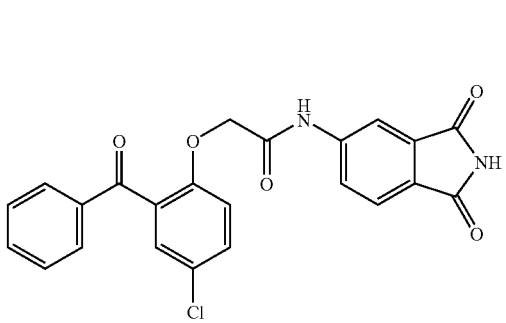

Carboxylic acid 105 (0.125 g, 0.417 mmol), 3-aminophthalimide (TCI, 0.062 g, 0.382 mmol), EDAC (0.132 g, 0.689 mmol), HOBt (0.063 g, 0.467 mmol) and DMF (5 mL) were used according to general procedure IV. The product was purified by flash chromatography using 95:5 chloroform/methanol to afford 77 as a white solid (0.038 g, 22%). $^1$H NMR (CDCl$_3$, 300 MHz) δ 10.10 (s, 1H), 8.39 (s, 1H), 8.25 (dd, J=9,3 Hz, 1H), 7.97 (d, J=9 Hz, 2H), 7.80 (d, J=9 Hz, 1H), 7.73 (t, J=6 Hz, 1H), 7.63-7.56 (m, 4H), 7.48 (d, J=3 Hz, 1H), 7.10 (d, J=9 Hz, 1H), 4.82 (s, 2H).

Example 28

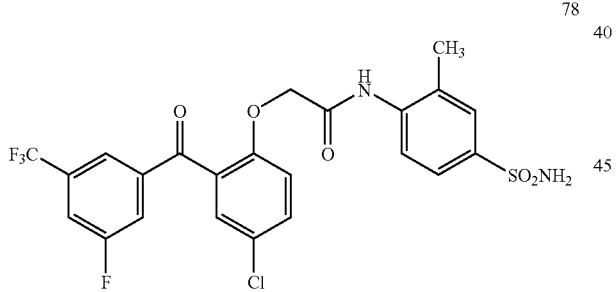

Carboxylic acid 71 (11.24 g, 29.84 mmol), oxalyl chloride (3.9 mL, 44.71 mmol), DMF (5 mL) and chloroform (250 mL) were used according to general procedure V to prepare the acid chloride, which was used without further purification. The acid chloride, sulfonamide 466 (5.12 g, 27.49 mmol), NaHCO$_3$ (11.12 g, 132 mmol), acetone (300 mL) and water (10 mL) were used according to general procedure VI. The product was purified by crystallization from a mixture of acetonitrile/water to provide 78 as a white solid (9.01 g, 60%). $^1$H NMR (DMSO-d$_6$, 300 MHz) δ 9.47 (s, 1H), 8.05 (d, J=9 Hz, 1H), 7.93-7.90 (m, 2H), 7.73-7.50 (m, 5H), 7.30-7.26 (m, 3H), 4.84 (s, 2H), 2.19 (s, 3H). Anal Calcd. for C$_{23}$H$_{17}$ClF$_4$N$_2$O$_5$S: C, 50.70; H, 3.14; N, 5.14. Found: C, 50.75; H, 3.10; N, 5.21.

Example 29

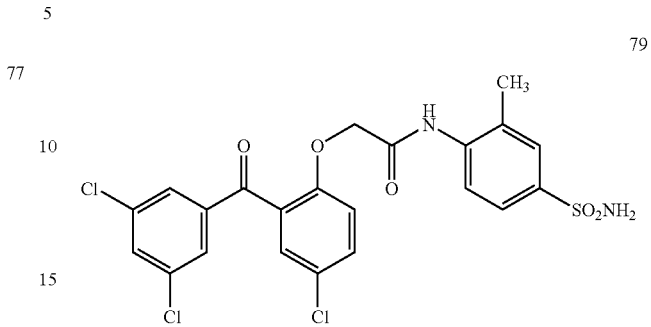

Carboxylic acid 76 (0.157 g, 0.437 mmol), oxalyl chloride (0.1 mL, 1.15 mmol), DMF (3 drops) and dichloromethane (5 mL) were used according to general procedure V to prepare the acid chloride, which was used without any further purification. The acid chloride, sulfonamide 466 (0.072 g, 0.387 mmol), NaHCO$_3$ (0.210 g, 2.5 mmol), acetone (5 mL) and water (0.5 mL) were used according to general procedure VI. The product was purified by flash chromatography using 95:5 chloroform/methanol to afford 79 as a white solid (0.117 g, 57%). $^1$H NMR (DMSO-d$_6$, 300 MHz) δ 9.45 (s, 1H), 7.94 (s, 1H), 7.76 (s, 2H), 7.75-7.55 (m, 5H), 7.30-7.25 (m, 3H), 4.85 (s, 2H), 2.22 (s, 3H).

Example 30

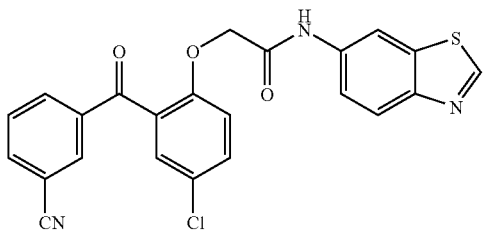

Carboxylic acid 131 (0.109 g, 0.345 mmol), 6-aminobenzthiazole (Lancaster, 0.056 g, 0.373 mmol), EDAC (0.164 g, 0.855 mmol), HOBt (0.064 g, 0.474 mmol) and DMF (5 mL) were used according to general procedure IV. The product was purified by flash chromatography using 95:5 chloroform/methanol to afford 80 as a white solid (0.120 g, 77%). $^1$H NMR (DMSO-d$_6$, 300 MHz) δ 10.18 (s, 1H), 9.30 (s, 1H), 8.50 (s, 1H), 8.26 (s, 1H), 8.13 (d, J=9 Hz, 1H), 8.05 (t, J=9 Hz, 2H), 7.75-7.66 (m, 2H), 7.56 (m, 2H), 7.26 (d, J=9 Hz, 1H), 4.81 (s, 2H).

Example 31

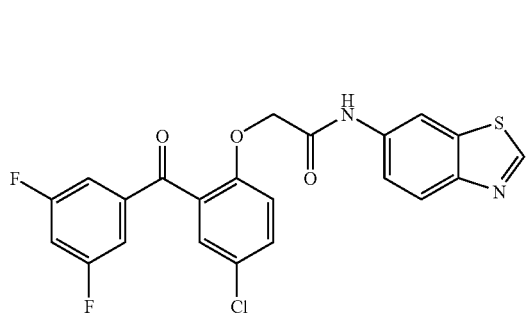

81

Carboxylic acid 49 (0.106 g, 0.324 mmol), 6-aminobenzthiazole (Lancaster, 0.051 g, 0.3393 mmol), EDAC (0.158 g, 0.824 mmol), HOBt (0.0584 g, 0.429 mmol) and DMF (5 mL) were used according to general procedure IV. The product was purified by flash chromatography using 95:5 chloroform/methanol to afford 81 as a white solid (0.105 g, 70%). $^1$H NMR (DMSO-$d_6$, 300 MHz) δ 10.22 (s, 1H), 9.31 (s, 1H), 8.48 (d, J=3 Hz, 1H), 8.04 (d, J=9 Hz, 1H), 7.67 (dd, J=9, 3 Hz, 1H), 7.59-7.48 (m, 5H), 7.25 (d, J=9 Hz, 1H), 4.82 (s, 2H).

Example 32

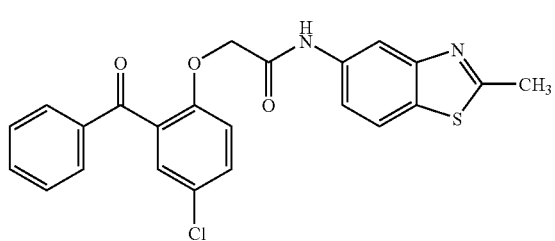

82

Carboxylic acid 105 (0.129 g, 0.43 mmol), oxalyl chloride (0.1 mL, 1.15 mmol), DMF (4 drops) and dichloromethane (3 mL) were used to prepare the acid chloride according to general procedure V. The acid chloride, 5-amino-2-methylbenzthiazole dihydrochloride (0.087 g, 0.367 mmol), NaHCO$_3$ (0.324 g, 3.86 mmol), water (0.5 mL) and acetone (5 mL) were used according to general procedure VI. The product was purified by flash chromatography using 95:5 chloroform/methanol to afford 82 as a white solid (0.118 g, 74%). $^1$H NMR (DMSO-$d_6$, 300 MHz) δ 10.02 (s, 1H), 8.20 (d, J=3 Hz, 1H), 7.95 (d, J=9 Hz, 1H), 7.85 (d, J=9 Hz, 2H), 7.66-7.47 (m, 6H), 7.26 (d, J=9 Hz, 1H), 4.78 (s, 2H), 2.80 (s, 3H).

Example 33

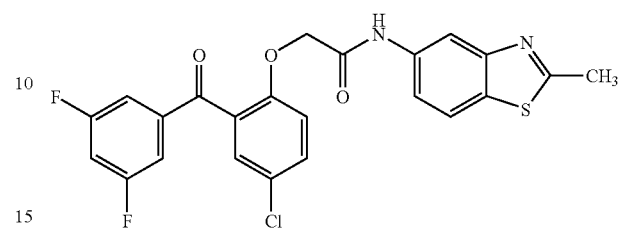

83

Carboxylic acid 49 (0.110 g, 0.337 mmol), oxalyl chloride (0.1 mL, 1.15 mmol), DMF (4 drops) and dichloromethane (5 mL) were used to prepare the acid chloride according to general procedure V. The acid chloride, 5-amino-2-methylbenzthiazole dihydrochloride (0.078 g, 0.329 mmol), NaHCO$_3$ (0.293 g, 3.49 mmol), water (0.5 mL) and acetone (5 L) were used according to general procedure VI. The product was purified by flash chromatography using 95:5 chloroform/methanol to afford 83 as a white solid (0.079 g, 49%). $^1$H NMR (DMSO-$d_6$, 300 MHz) δ 10.12 (s, 1H), 8.22 (s, 1H), 7.95 (d, J=9 Hz, 1H), 7.67 (dd, J=9,3 Hz, 1H), 7.58-7.48 (m, 5H), 7.25 (d, J=9 Hz, 1H), 4.81 (s, 2H), 2.80 (s, 3H).

Example 34

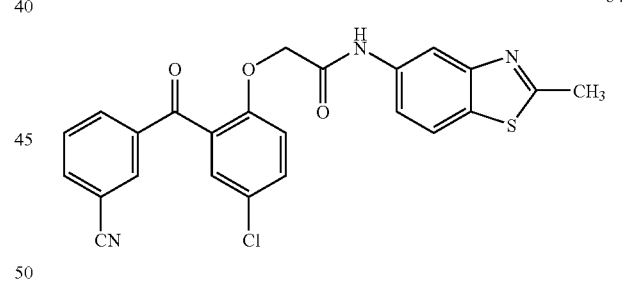

84

Carboxylic acid 129 (0.094 g, 0.298 mmol), oxalyl chloride (0.1 mL, 1.15 mmol), DMF (4 drops) and dichloromethane (5 mL) were used to prepared the acid chloride according to general procedure V. The acid chloride, 5-amino-2-methylbenzthiazole dihydrochloride (0.068 g, 0.287 mmol), NaHCO$_3$ (0.310 g, 3.69 mmol), water (0.5 mL) and acetone (5 mL) were used according to general procedure VI. The product was purified by flash chromatography using 95:5 chloroform/methanol to afford 84 as a tan solid (0.042 g, 31%). $^1$H NMR (DMSO-$d_6$, 300 MHz) δ 10.09 (s, 1H), 8.22 (d, J=9 Hz, 2H), 8.13 (d, J=6 Hz, 1H), 8.06 (d, J=9 Hz, 1H), 7.94 (d, J=9 Hz, 1H), 7.75-7.66 (m, 2H), 7.55 (d, J=3 Hz, 1H), 7.49 (d, J=3 Hz, 1H), 7.25 (d, J=6 Hz, 1H), 4.78 (s, 2H), 2.80 (s, 3H).

Example 35

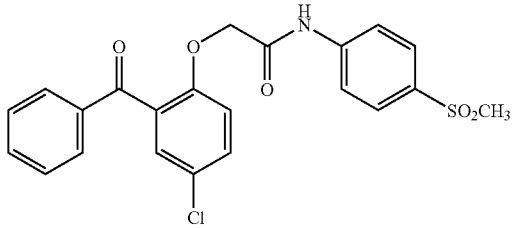
85

Carboxylic acid 105 (0.104 g, 0.347 mmol), oxalyl chloride (0.1 mL, 1.15 mmol), DMF (4 drops) and dichloromethane (4 mL) were used to prepare the acid chloride according to general procedure V. The acid chloride, 4-methylsulfonlylaniline (0.06 g, 0.350 mmol), NaHCO$_3$ (0.214 g, 2.55 mmol), water (0.5 mL) and acetone (6 mL) were used according to general procedure VI. The product was purified by flash chromatography using 3:2 ethyl acetate/hexane to afford 85 as a white solid (0.061 g, 40%). $^1$H NMR (DMSO-d$_6$, 300 MHz) δ 10.34 (s, 1H), 7.90-7.76 (m, 6H), 7.66-7.47 (m, 5H), 7.22 (d, J=9 Hz, 1H), 3.18 (s, 3H).

Example 36

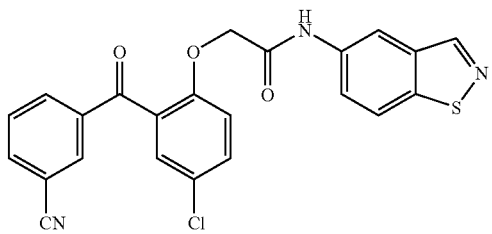
86

Step A:

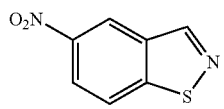
87

Into a stirred Parr bomb were placed 2-chloro-5-nitrobenzaldehyde (1.84 g, 9.92 mmol), sulfur (0.360 g, 11.23 mmol), ammonia (5 mL) and methanol (30 mL). The bomb was sealed and was heated, with stirring, to 85-90° C. for 16 h. The mixture was allowed to cool to rt and was poured into a separatory funnel containing dichloromethane and water. The organic layer was collected, washed with water, brine, dried over MgSO$_4$, filtered and the solvents were removed to afford 87 as an orange solid (1.26 g, 70%). $^1$H NMR (DMSO-d$_6$, 400 MHz) δ 9.33 (s, 1H), 9.13 (d, J=4 Hz, 1H), 8.47 (d, J=12 Hz, 1H), 8.36 (dd, J=12, 4 Hz, 1H).

Step B:

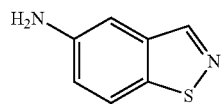
88

Compound 87 (1.26 g, 6.97 mmol), iron powder (1.89 g, 33.84 mmol), concentrated hydrochloric acid (7 mL) and ethanol (35 mL) were added to a round-bottom flask. The mixture was heated to reflux and stirred for 2 h, after which time it was allowed to cool to rt. The mixture was then poured into water and was made basic by the slow addition of solid NaHCO$_3$. It was then poured into a separatory funnel containing ethyl acetate and water. The organic layer was collected, washed with water, brine, dried over MgSO$_4$, filtered and the solvents were removed under reduced pressure to afford 88 as a tan solid (0.470 g, 45%). $^1$H NMR (DMSO-d$_6$, 400 MHz) δ 8.82 (s, 1H), 7.81 (d, J=9 Hz, 1H), 7.20 (d, J=3 Hz, 1H), 6.99 (dd, J=9, 3 Hz, 1H), 5.40 (s, 2H).

Step C:

Carboxylic acid 129 (0.125 g, 0.396 mmol), oxalyl chloride (0.1 mL, 1.15 mmol), DMF (4 drops) and dichloromethane (5 mL) were used to prepare the acid chloride according to general procedure V. The acid chloride, amine 88 (0.063 g, 0.419 mmol), NaHCO$_3$ (0.173 g, 2.06 mmol), water (0.5 mL) and acetone (5 mL) were used according to general procedure VI to afford a yellow solid. The solid was washed with several portions of ether and was dried in vacuo to provide 86 as a yellow solid (0.083 g, 47%).

Example 37

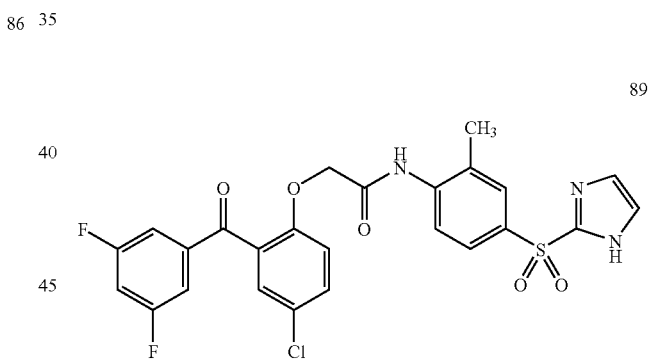
89

Step A:

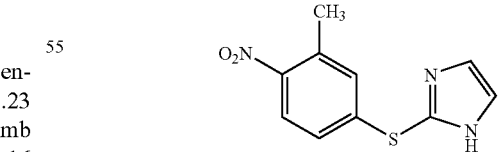
90

Into a round-bottom flask were placed 5-fluoro-2-nitrotoluene (Lancaster, 2.03 g, 13.09 mmol), 2-thioimidazole (1.54 g, 15.38 mmol), K$_2$CO$_3$ (6.31 g, 45.66 mmol) and DMF (25 mL). The resulting mixture was heated to 80-90° C. for 3 h and was then allowed to cool to 50° C. and stir overnight. The mixture was allowed to cool to rt and was poured into a separatory funnel containing ethyl acetate and water. The organic layer was collected and was washed with water, brine, dried over MgSO$_4$, filtered and the solvents were removed under reduced pressure to afford 90 as an orange oil which was used without purification. $^1$H NMR (CDCl$_3$, 300 MHz) δ 7.85 (d, J=9 Hz, 1H), 7.80-7.30 (br m, 2H), 7.08 (s, 1H), 7.03 (d, J=6 Hz, 1H), 2.53 (s, 3H).

Step B:

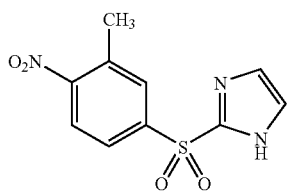

91

Into a round-bottom flask were placed compound 90 (0.121 g, 0.51 mmol), glacial acetic acid (3 mL) and hydrogen peroxide (0.491 g of a 30% W/w solution, 4.33 mmol). The resulting mixture was heated to 85-90° C. for 2 h, after which time it was allowed to cool to rt and was poured into a flask containing a saturated solution of sodium bisulfite. The pH of the mixture was adjusted to pH 7 by the slow addition of solid NaHCO$_3$ and was then poured into a separatory funnel containing ethyl acetate. The organic layer was collected, washed with water, brine, dried over MgSO$_4$, filtered and the solvents were removed under reduced pressure to afford 91 as a white solid (0.092 g, 67%). $^1$H NMR (DMSO-d$_6$, 400 MHz) δ 8.16 (d, J=8 Hz, 1H), 8.04 (s, 1H), 7.93 (d, J=8 Hz, 1H), 7.35-7.32 (br m, 2H), 2.47 (s, 3H).

Step C:

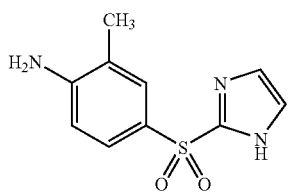

92

Into a Parr bottle were placed compound 91 (0.092 g, 0.34 mmol), Pd/C (0.01 g, 10% w/w), and ethanol. The bottle was purged with hydrogen (3×) and was finally pressurized to 40 psig. The mixture was allowed to stir at rt for 30 min, after which time the bottle was depressurized and the mixture was filtered through a pad of celite and the solvents were removed under reduced pressure to afford 92 as a yellowish solid (0.083 g, >100% yield), which was used without any further purification. $^1$H NMR (DMSO-d$_6$, 400 MHz) δ 13.54 (br s, 1H), 8.77 (s, 1H), 8.74 (s, 1H), 7.60 (dd, J=8, 4 Hz, 1H), 7.45 (d, J=4 Hz, 1H), 7.18 (br s, 2H), 7.09 (d, J=8 Hz, 1H), 2.05 (s, 3H).

Step D:

Carboxylic acid 49 (0.100 g, 0.31 mmol), oxalyl chloride (0.1 mL, 1.15 mmol), DMF (4 drops) and chloroform (3 mL) were used to prepared the acid chloride according to general procedure V. The acid chloride, amine 92 (0.065 g, 0.273 mmol), NaHCO$_3$ (0.134 g, 1.59 mmol), water (0.5 mL) and acetone (4 mL) were used according to general procedure VI to afford a tan solid. The solid was washed with several portions of ether and dried to afford 89 as a tan solid (0.105 g, 62%). $^1$H NMR (DMSO-d$_6$, 300 MHz) δ 13.74 (s, 1H), 10.26 (s, 1H), 7.70-7.27 (m, 10H), 6.95 (d, J=9 Hz, 1H), 5.19 (s, 2H), 2.20 (s, 3H).

Example 38

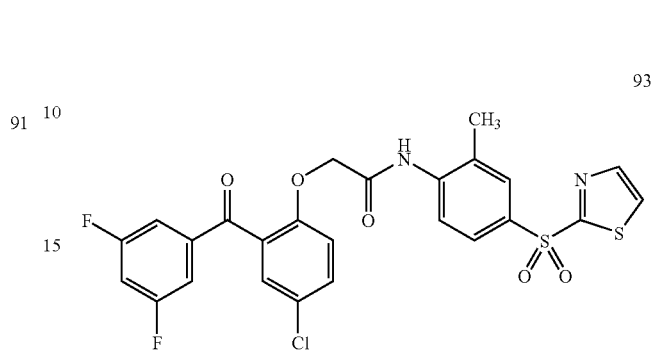

93

Step A:

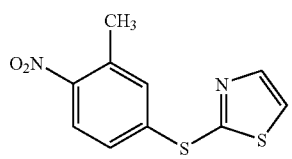

94

Into a round-bottom flask were placed 5-fluoro-2-nitrotoluene (Lancaster, 1.65 g, 13.09 mmol), 2-thiothiazole (1.46 g, 12.46 mmol), K$_2$CO$_3$ (5.04 g, 36.47 mmol) and DMF (25 mL). The resulting mixture was heated to 80-90° C. for 3 h and was then allowed to cool to 50° C. and stir overnight. The mixture was allowed to cool to rt and was poured into a separatory funnel containing ethyl acetate and water. The organic layer was collected and was washed with water, brine, dried over MgSO$_4$, filtered and the solvents were removed under reduced pressure to afford 94 (2.51 g, 93%) as an orange solid which was used without purification. $^1$H NMR (CDCl$_3$, 400 MHz) δ 7.94 (d, J=8 Hz, 1H), 7.87 (d, J=4 Hz, 1H), 7.44 (d, J=4 Hz, 1H), 7.38-7.34 (m, 2H), 2.57 (s, 3H).

Step B:

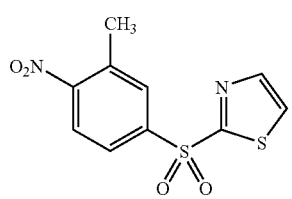

95

Into a round-bottom flask were placed compound 94 (0.103 g, 0.41 mmol), glacial acetic acid (3 mL) and hydrogen peroxide (0.210 g of a 30% w/w solution, 1.85 mmol). The resulting mixture was heated to 85-90° C. for 2 h, after which time it was allowed to cool to rt and was poured into a flask containing a saturated solution of sodium bisulfite. The pH of the mixture was adjusted to pH 7 by the slow addition of solid NaHCO$_3$ and was then poured into a separatory funnel containing ethyl acetate. The organic layer was collected, washed with water, brine, dried over MgSO$_4$, filtered and the solvents were removed under reduced pressure to afford 95 as a white solid (0.103 g, 89%). $^1$H NMR (CDCl$_3$, 400 MHz) δ 8.10-8.00 (m, 4H), 7.73 (d, J=4 Hz, 1H), 2.64 (s, 3H).

Step C:

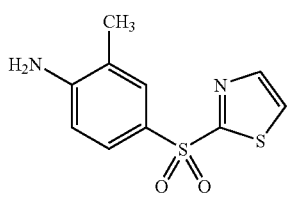

Into a Parr bottle were placed compound 95 (0.074 g, 0.34 mmol), Pd/C (0.018 g, 10% w/w), and ethanol (2 mL). The bottle was purged with hydrogen (3×) and was finally pressurized to 45 psig. The mixture was allowed to stir at rt for 30 min, after which time the bottle was depressurized and the mixture was filtered through a pad of celite and the solvents were removed under reduced pressure to afford 96 as a yellow oil, which was used without any further purification. $^1$H NMR (CDCl$_3$, 300 MHz) δ 7.94 (d, J=3 Hz, 1H), 7.87 (d, J=9 Hz, 1H), 7.74 (s, 1H), 7.65 (d, J=3 Hz, 1H), 7.31 (d, J=9 Hz, 1H), 5.81 (br s, 2H), 2.13 (s, 3H).

Step D:

Carboxylic acid 49 (0.104 g, 0.31 mmol), oxalyl chloride (0.6 mL of a 2.0 M solution in dichloromethane, 1.2 mmol), DMF (4 drops) and chloroform (4 mL) were used to prepared the acid chloride according to general procedure V. The acid chloride, amine 96 (0.071 g, 0.2793 mmol), NaHCO$_3$ (0.1434 g, 1.70 mmol), water (0.5 mL) and acetone (4 mL) were used according to general procedure VI to afford a tan solid. The solid was washed with several portions of ether and dried to afford 93 as a tan solid (0.129 g, 82%). $^1$H NMR (DMSO-d$_6$, 300 MHz) δ 10.35 (s, 1H), 8.25 (d, J=3 Hz, 1H), 8.09 (d, J=3 Hz, 1H), 7.75-7.39 (m, 7H), 7.28 (d, J=9 Hz, 1H), 6.97 (d, J=9 Hz, 1H), 5.20 (s, 2H), 2.22 (s, 3H).

Example 39

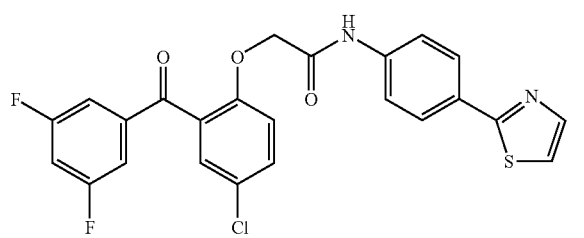

Carboxylic acid 49 (0.108 g, 0.331 mmol), oxalyl chloride (0.1 mL, 1.15 mmol), DMF (4 drops) and chloroform (3 mL) were used to prepare the acid chloride according to general procedure V. The acid chloride, the aniline (prepared according to the method of Erlenmeyer, *Helv. Chim. Acta*, 30, 2058-2060, 1947), 0.056 g, 0.318 mmol), NaHCb$_3$ (0.146 g, 1.74 mmol), water (0.5 mL) and acetone (6 mL) were used according to general procedure VI to provide 97 as a yellow solid (0.05 g, 32%). $^1$H NMR (DMSO-d$_6$, 300 MHz) δ 10.19 (s, 1H), 7.95-7.90 (m, 3H), 7.76 (d, J=3 Hz, 1H), 7.70-7.48 (m, 7H), 7.23 (d, J=9 Hz, 1H), 4.80 (s, 2H).

Example 40

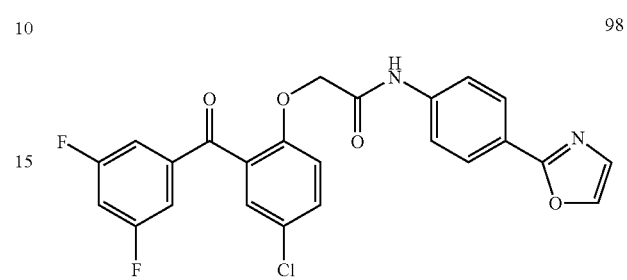

Carboxylic acid 49 (0.112 g, 0.343 mmol), oxalyl chloride (0.1 mL, 1.15 mmol), DMF (4 drops) and chloroform (3 mL) were used to prepare the acid chloride according to general procedure V. The acid chloride, the aniline (prepared according to the method of Brown, E. V., *Journal of Organic Chemistry*, 42(19), 3208-3209, 1977), 0.050 g, 0.312 mmol), NaHCO$_3$ (0.137 g, 1.63 mmol), water (0.5 mL) and acetone (6 mL) were used according to general procedure VI to provide 98 as a yellow solid (0.064 g, 44%). $^1$H NMR (DMSO-d$_6$, 300 MHz) δ 10.22 (s, 1H), 8.20 (s, 1H), 7.95 (d, J=9 Hz, 1H), 7.72 (d, J=9 Hz, 1H), 7.69-7.47 (m, 7H), 7.37 (s, 1H), 7.23 (d, J=9 Hz, 1H), 4.81 (s, 2H).

Example 41

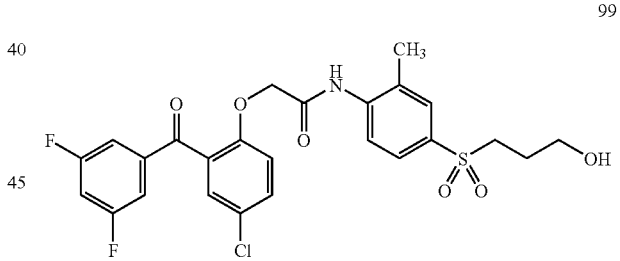

Step A:

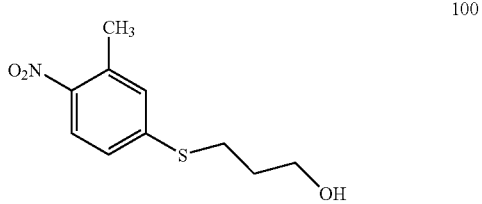

Into a round-bottom flask were placed 5-fluoro-2-nitrotoluene (5.0 g, 32.2 mmol), K$_2$CO$_3$ (15.34 g, 111 mmol), 3-mercaptoethanol (3.2 mL, 37 mmol) and DMF (30 mL). The resulting mixture was allowed to stir at rt for 16 h, after which time it was poured into a separatory funnel containing ethyl acetate and water. The organic layer was collected and washed with water, brine, dried over MgSO₄, filtered and the solvents were removed under reduced pressure to afford 100 as thick, yellow oil, which was used without any further purification.

Step B:

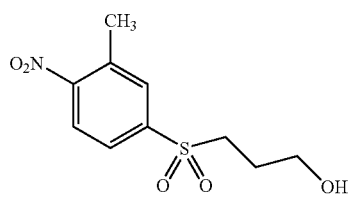

101

Into a round-bottom flask were placed compound 100 (~32 mmol), and methanol (100 mL). Into a separate flask were placed oxone (Aldrich, 29.43 g, 47.9 mmol) and water (125 mL). The oxone solution was added dropwise over several minutes to the solution of compound 100 at rt. The resulting solution was allowed to stir at rt for 1 h. It was then poured into a separatory funnel containing ethyl acetate and water. The organic layer was collected and washed with water, brine, dried over MgSO₄, filtered and the solvents were removed under reduced pressure to afford a yellow oil, which was dried in vacuo to provide 101 as a yellow solid (7.91 g, 95%).

Step C:

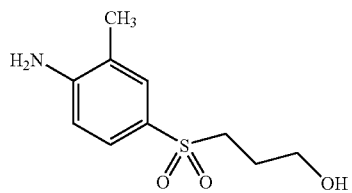

102

Into a Parr bottle were placed compound 101 (0.522 g, 2.01 mmol), Pd/C (0.04 g, 10% w/w) and EtOH (5 mL). The bottle was purged with hydrogen (3×) and was finally pressurized with hydrogen to 40 psig. The resulting mixture was allowed to stir at rt for 1 h, after which time it was filtered through a pad of celite, and the solvents were removed under reduced pressure to afford a green oil which solidified in vacuo to afford 102 as a yellowish solid (0.44 g, 95%).

Step D:

Carboxylic acid 49 (0.302 g, 0.924 mmol), oxalyl chloride (0.15 mL, 1.72 mmol), DMF (4 drops) and chloroform (10 mL) were used to prepare the acid chloride according to general procedure V. The acid chloride, amine 102 (0.190 g, 0.86 mmol), NaHCO₃ (0.323 g, 4.16 mmol), water (0.5 mL) and acetone (10 mL) were used according to general procedure X to provide 99 as a tan solid (0.326 g, 70%).

Example 43

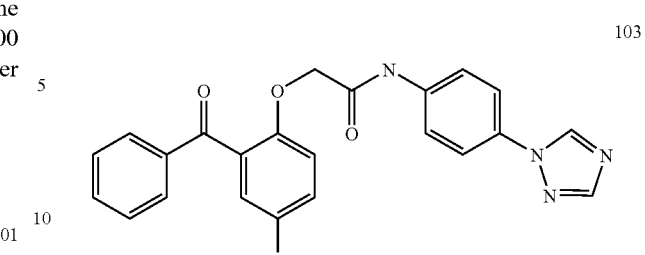

103

Step A:

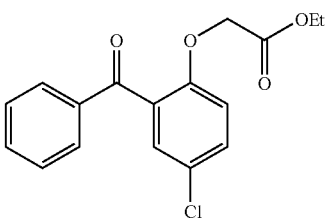

104

This reaction was run according to general procedure II using 5-chloro-2-hydroxybenzophenone (15 g, 64 mmol), ethyl bromoacetate (7.7 mL, 71 mmol) and potassium carbonate and (44 g, 320 mmol). A 96% yield of 104 was obtained as a white solid. ¹H NMR (DMSO-d₆, 300 MHz) δ 1.8 (t, 3H), 4.1 (q, 2H), 4.8 (s, 2H), 7-7.8 (m, 8H).

Step B:

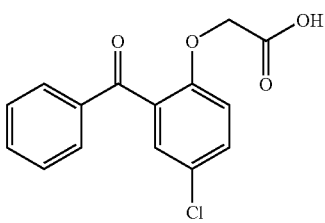

105

This reaction was run according to general procedure III using 104 (19.6 g, 62 mmol) and LiOH.H₂O (3.18 g, 76 mmol) in ethanol (250 mL) and water (70 mL) stirred for 1 h at rt. After extraction with methylene chloride, drying (MgSO₄) and solvent removal, an 86% yield of 105 was obtained as white foam. ¹H NMR (DMSO-d₆, 300 MHz) δ4.6 (s, 2H), 7-7.8 (m, 8H), 13 (s, 1H).

Step C:

A mixture of 105 (1 g, 3.4 mmol) and 18 mL of thionyl chloride was refluxed for 1 h. Concentration of the reaction mixture resulted in a crude product that was dissolved in acetonitrile. This was added dropwise to a stirred mixture of 1-(4'-aminophenyl)-1,2,4-triazole (0.54 g, 3.4 mmol) and triethylamine (0.73 mL, 5.25 mmol) in acetonitrile (10 mL). The mixture was refluxed for 6 h and stirred at rt for 24 h. Ethyl acetate was added to the reaction mixture. After washing with water, drying (MgSO₄) and solvent removal, the crude product was purified by flash column chromatography on silica with 4% methanol in methylene chloride as the eluent. This gave 0.039 g (3%) of 103 as a white solid.

¹H NMR (DMSO-d₆, 300 MHz) δ 4.7 (s, 2H), 7.2-7.8 (m, 12H), 8.2 (s, 1H), 9.2 (s, 1H), 10.0 (s, 1H).

Example 44

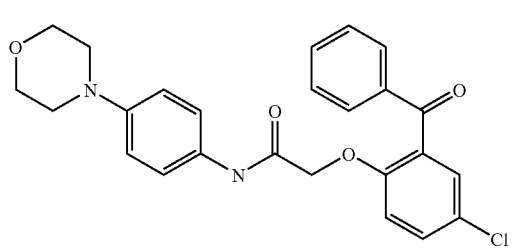

106

Following the procedure described for the synthesis of 103 and using 4-morpholinoaniline, a 38% yield of 106 was obtained as a gray solid. ¹H NMR (DMSO-d₆, 300 MHz) δ 3 (s, 4H), 3.7 (s, 4H), 4.6 (s, 2H), 6.82 (m, 2H), 7.1-7.8 (m, 10H), 9.4 (s, 1H).

Example 45

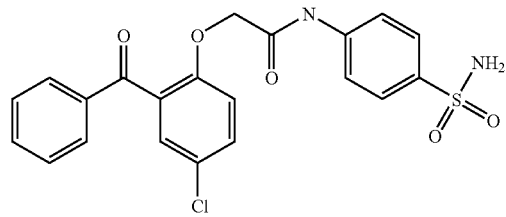

107

Following the procedure described for the synthesis of 103 and using sulfanilamide, a 6% yield of 107 was obtained as a white solid after purification by flash column chromatography on silica gel with 20% acetone in methylene chloride. ¹H NMR (DMSO-d₆, 300 MHz) δ 4.7 (s, 2H), 6.82 (m, 2H), 7.1-7.8 (m, 12H), 10.1 (s, 1H).

Example 46

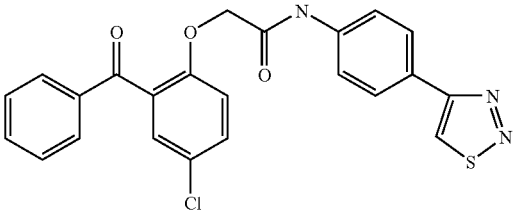

108

Following the procedure described for the synthesis of 103 and using 4-(4-aminophenyl)-1,2,3-thiadizole as the aniline, a 20% yield of 108 was obtained as a gray solid. ¹H NMR (DMSO-d₆, 300 MHz) δ 4.7 (s, 2H), 7.2 (d, 1H), 7.4-8.1 (m, 112H), 9.41 (s, 1H), 10.0 (s, 1H).

Example 47

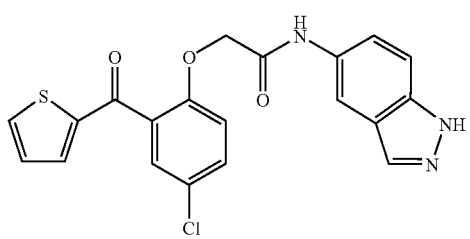

109

Step A:

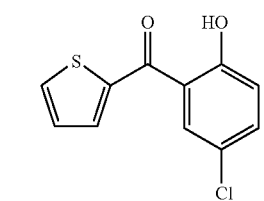

110

This reaction was run according to general procedure I with 2-thiophenecarbonyl chloride (1.5 mL, 14 mmol), p-chloroanisole (1.7 mL, 14 mmol) and aluminum chloride (1.9 g, 14 mmol) were refluxed in methylene chloride (200 mL) for 24 h. A 39% yield of 110 was obtained after purification by flash column chromatography on silica gel with methylene chloride/hexane (1:1). ¹H NMR (DMSO-d₆, 300 MHz) δ 6.95 (d, 1H), 7.19 (t, 1H), 7.32 (d, 1H), 7.38 (dd, 1H), 7.51 (d, 1H), 8.06 (d, 1H), 10.3 (s, 1H).

Step B:

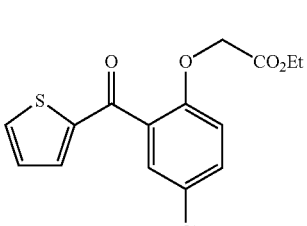

111

This reaction was run according to general procedure II using 110 (0.5 g, 2.17 mmol), ethyl bromoacetate (0.24 mL, 2.17 mmol) and potassium carbonate (1.53 g, 10.85 mmol), in acetone (25 mL) for 3 h. A 97% yield of 111 was obtained as oil after workup. ¹H NMR (DMSO-d₆, 300 MHz) δ 1.1 (t, 3H), 4.1 (q, 2H), 4.8 (s, 2H), 7.07 (d, 1H), 7.19 (t, 1H), 7.43 (d, 1H), 7.49-7.52 (m, 2H), 8.07 (d, 1H).

Step C:

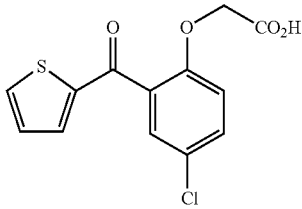

Following the procedure described in general procedure III, a 22% yield of 112 was obtained as a solid. $^1$H NMR (DMSO-d$_6$, 300 MHz) δ 4.7 (s, 2H), 7.05 (d, 1H), 7.18 (t, 1H), 7.41 (d, 1H), 7.42-7.6 (m, 2H), 8.06 (d, 1H).

Step D:

This reaction was run according to general procedure IV using 112 (0.14 g, 0.43 mmol), HOBT (0.06 g, 0.43 mmol), 5-aminoindazole(0.06 g, 0.43 mmol), EDAC (0.08 g, 0.43 mmol) and triethylamine (0.12 mL, 0.86 mmol). A 23% yield of 109 was obtained after purification by flash column chromatography on silica gel with 5% methanol in methylene chloride. $^1$H NMR (DMSQ-d$_6$, 300 MHz) δ 4.8 (s, 2H), 7.1-7.3 (m, 2H), 7.32 (d, 1H), 7.46 (d, 1H), 7.48 (s, 1H), 7.56 (d, 1H), 7.7 (d, 1H), 7.98 (s, 1H), 8.04 (s, 1H), 8.1 (d, 1H), 9.8 (s, 1H), 13 (s, 1H).

Example 48

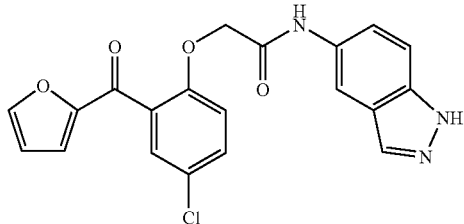

Step A:

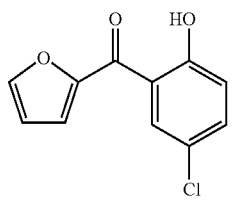

Following the procedure described in general procedure I using 2-furoyl chloride and p-chloroanisole, a 73% yield of 114 was obtained as a yellow solid. $^1$H NMR (DMSO-d$_6$, 300 MHz) δ 6.7 (m, 1H), 6.93 (d, 1H), 7.2 (2, 1H), 7.4 (m, 2H), 8.04 (s, 1H), 10.4 (1H).

Step B:

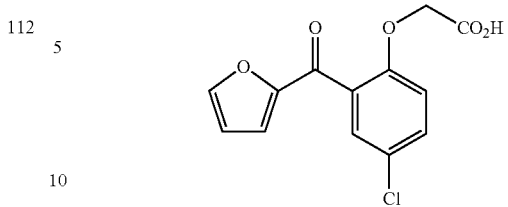

A mixture of 114 (1 g, 4.49 mmol), ethyl bromoacetate (0.5 mL, 4.49 mmol) and potassium carbonate (3.17 g, 22.45 μmmol) was stirred in acetone (50 mL) for 24 h. To this was added 1N NaOH until the solid dissolved. This NaOH solution was extracted once with ethyl acetate and was then acidified with 1N HCl. This was followed by extraction with ethyl acetate. After drying (MgSO$_4$) and solvent removal in vacuo, the crude product was re-crystallized with hexane/ethyl acetate. Compound 115 (1 g, 79%) was collected as a white solid. $^1$H NMR (DMSO-d$_6$, 300 MHz) δ 4.8 (s, 2H), 6.7 (m, 1H), 7.1 (d, 1H), 7.2 (d, 1H), 7.5 (m, 1H), 7.6 (d, 1H), 8.1 (s 1H), 13.1 (br s, 1H).

Step C:

Following the procedure described in general procedure IV using 5-indazole, a 61% yield of 113 was obtained as a solid. $^1$H NMR (DMSO-d$_6$, 300 MHz) δ 4.8 (s, 2H), 6.8 (m, 1H), 7.21 (d, 1H), 7.3-7.7 (m, 5H), 8.06 (s, 1H), 8.1 (s, 2H), 10 (s, 1H), 13 (s, 1H).

Example 49

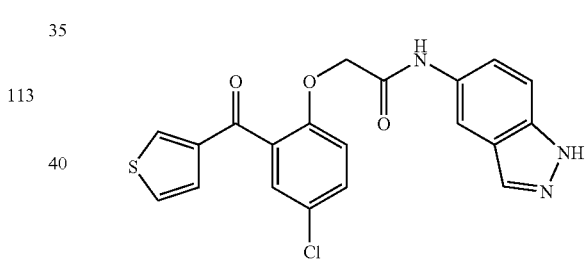

Step A:

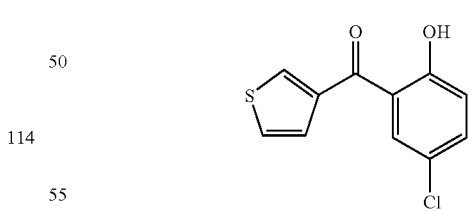

A mixture of 3-thiophenecarboxyl in acid (3.58 g, 28 mmol) and thionyl chloride (15 mL) was refluxed for 3 h. The reaction mixture was concentrated and further dried in vacuo. The resultant concentrate was added to a suspension of aluminum chloride (7.61 g, 56 mmol) and p-chloroanisole (3.41 mL, 28 mmol). The suspension was heated to reflux for 24 h. Water was slowly added to the reaction mixture and this aqueous mixture was extracted with first methylene chloride, then ethyl acetate. The organic solutions were combined and dried over MgSO$_4$. After solvent removal, the crude product was purified by flash column chromatography on silica gel with methylene chloride/hexane (1:1). This gave 0.13 g (2%) of 117 as oil. $^1$H NMR (DMSO-$d_6$, 300 MHz) δ 7 (d, 1H), 7.3-7.5 (m, 3H), 7.6-7.7 (m, 1H), 8.2 (m, 1H), 10.4 (s, 1H).

Step B:

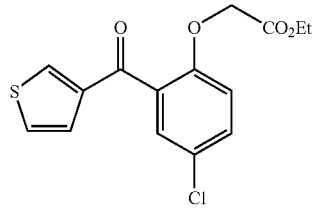

118

Following general procedure II, a 45% yield of 118 was obtained as oil. $^1$H NMR (DMSO-$d_6$, 300 MHz) δ 1.1 (t, 3H), 4.08 (q, 2H), 4.8 (s, 2H), 7.07 (d, 1H), 7.38 (d, 1H), 7.44 (d, 1H), 7.49 (dd, 1H), 7.6 (dd, 1H), 8.11 (d, 1H).

Step C:

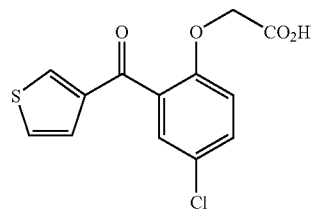

119

Following general procedure III, a 67% yield of 119 was obtained as oil. $^1$H NMR (DMSO-$d_6$, 300 MHz) δ 4.7 (s, 2H), 7.1 (d, 1H), 7.38 (d, 1H), 7.5-7.6 (m, 2H), 7.6-7.7 (m, 1H), 8.2 (m 1H).

Step D:

Following general procedure IV using 5-indazole, a 36% yield of 116 was obtained as a white solid. $^1$H NMR (DMSO-$d_6$, 300 MHz) δ 4.8 (s, 2H), 7.2 (d, 1H), 7.35 (d with fine splittings, 1H), 7.42 (d, 1H), 7.45 (d, 1H), 7.5-7.6 (m, 2H), 7.6-7.65 (m, 1H), 8 (s, 1H), 8.05 (s, 1H), 8.3 (m, 1H), 9.8 (s, 1H), 13 (s, 1H).

Example 50

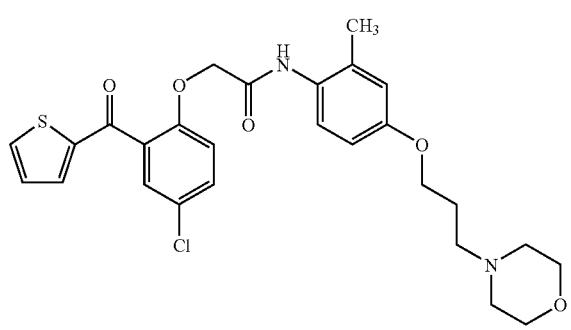

120

Following general procedure IV using 4-(3-morpholino) propyloxy-2-methylaniline, a 7% yield of 120 was obtained as a white solid after flash column chromatography on silica gel with 20% methanol in methylene chloride. $^1$H NMR (DMSO-$d_6$, 300 MHz) δ 1.7-1.9 (m, 2H), 2 (s, 3H), 2.2-2.4 (m, 6H), 3.5-3.6 (m, 4H), 3.9 (t, 2H), 4.75 (s, 2H), 6.7 (d, 1H), 6.74 (s, 1H), 7.1-7.3 (m, 3H), 7.5 (s, 1H), 7.6 (dd, 1H), 7.63 (d, 1H), 8.08 (d, 1H), 9 (s, 1H).

Example 51

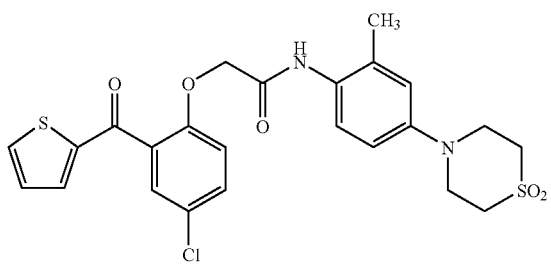

121

Following general procedure IV using 4-morpholine-sulfonyl-2-methylaniline, a 26% yield of 121 was obtained as a white solid after flash column chromatography on silica gel with 20% methanol in methylene chloride. $^1$H NMR (DMSO-$d_6$, 300 MHz) δ 3.1 (br s, 4H), 3.7 (s, 4H), 4.8 (s, 2H), 7 (d, 2H), 7.2-7.3 (m, 2H), 7.43 (d, 2H), 7.54 (d, 1H), 7.6 (dd, 1H), 7.7 (d, 1H), 8.2 (d, 1H), 9.8 (s, 1H).

Example 52

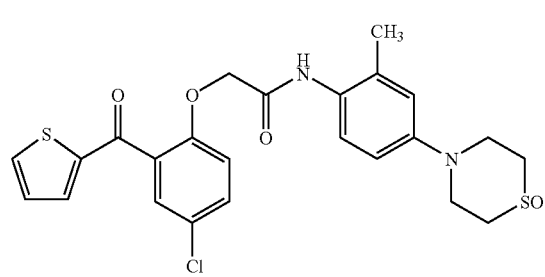

122

Following general procedure IV using 4-morpholine-sulfonyl-2-methylaniline, a 24% yield of 122 was obtained as a white solid after flash column chromatography on silica gel with 5% methanol in methylene chloride. $^1$H NMR (DMSO-$d_6$, 300 MHz) δ 2.6-2.8 (m, 2H), 2.9 (t, 2H), 3.5-3.6 (m, 2H), 3.7 (t, 2H), 4.8 (s, 2H), 7 (d, 2H), 7.2-7.3 (m, 2H), 7.43 (d, 2H), 7.54 (d, 1H), 7.6 (dd, 1H), 7.7 (d, 1H), 8.2 (d, 1H), 9.8 (s, 1H).

Example 53

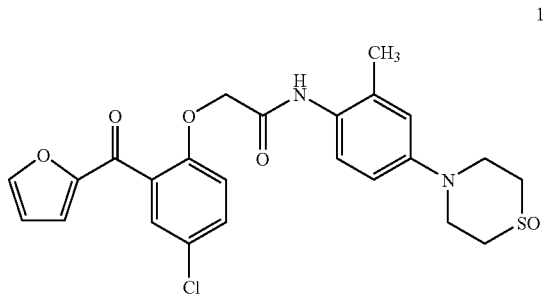

123

Following general procedure IV, a 35% yield of 123 was obtained as a white solid after flash column chromatography on silica gel with 3% methanol in methylene chloride. $^1$H NMR (DMSO-d$_6$, 300 MHz) δ 2.0 (s, 3H), 2.5-2.7 (m, 2H), 2.9 (t, 2H), 3.5-3.6 (m, 2H), 3.7 (t, 2H), 4.8 (s, 2H), 6.7 (s, 1H), 6.78 (d, 1H), 6.8 (s, 1H), 7.1-7.3 (m, 2H), 7.3 (d, 1H), 7.5 (d, 1H), 7.6 (dd, 1H), 8.05 (s, 1H), 9 (s, 1H).

Example 54

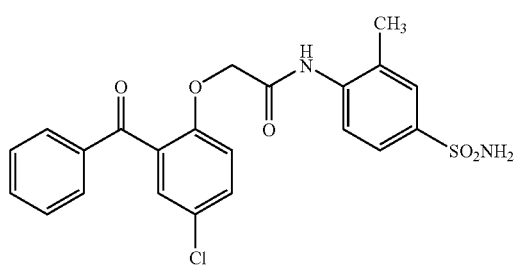

124

Following general procedure IV, a 32% yield of 124 was obtained as a white solid after flash column chromatography on silica gel with 5% methanol in methylene chloride. $^1$H NMR (DMSO-d$_6$, 300 MHz) δ 2.1 (s, 3H), 4.8 (s, 2H), 71.-7.3 (m, 3H), 7.4 (s with fine splittings, 1H), 7.42-7.5 (m, 2H), 7.5-7.7 (m, 5H), 7.8 (d, 2H), 9.2 (s, 1H).

Example 55

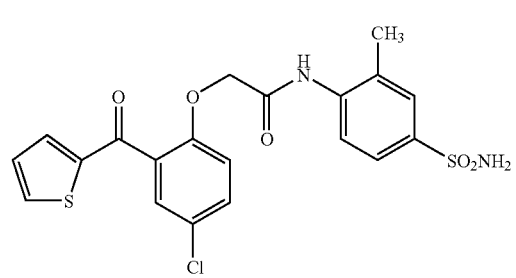

125

Following the procedure described for the synthesis of compound 103, a 42% yield 125 was obtained as a white solid after flash column chromatography on silica gel with 3% methanol in methylene chloride. $^1$H NMR (DMSO-d$_6$, 300 MHz) δ 2.2 (s, 3H), 4.8 (s, 2H), 7.1-7.3 (m, 3H), 7.5 (d, 1H), 7.5-7.7 (m, 5H), 7.73 (d, 1H), 8.1 (d, 1H), 9.3 (s, 1H).

Example 56

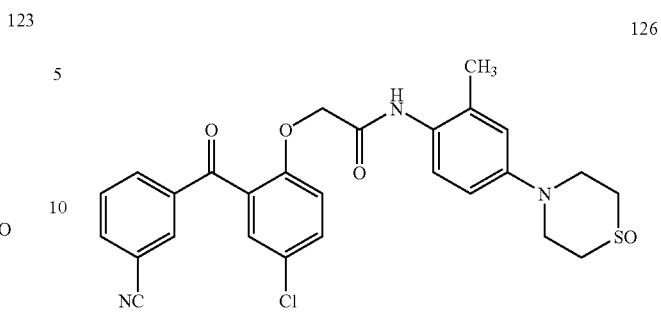

126

Step A:

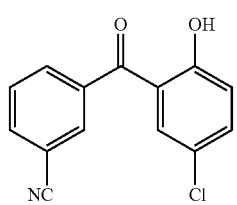

127

Following general procedure I, a 9% yield of 127 was obtained after flash column chromatography on gel with 30% hexane in methylene chloride. $^1$H NMR (DMSO-d$_6$, 300 MHz) δ 6.97 (d, 1H), 7.38 (s, 1H), 7.42 (d, 1H), 7.7 (t, 1H), 7.98 (d, 1H), 8-8.1 (m, 2H), 10.4 (s, 1H).

Step B:

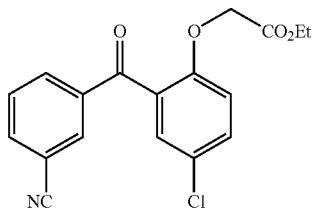

128

Following general procedure II, a quantitative yield of 128 was obtained as oil that was used in the following reaction without any additional purification.

Step C:

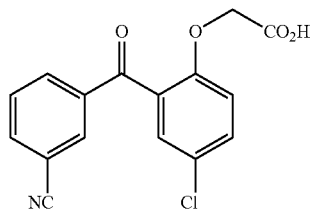

129

Following general procedure III, a quantitative yield of 129 was obtained as a white solid. $^1$H NMR (DMSO-d$_6$, 300

MHz) δ 4.6 (s, 2H), 7.1 (d, 1H), 7.5 (s, 1H), 7.5-7.6 (m, 1H), 7.6-7.7 (m, 1H), 8-8.1 (m, 2H), 12 (br s, 1H).

Step D:

Following general procedure IV, an 11% yield of 126 was obtained as a yellow solid after flash column chromatography on silica gel with 4% methanol in methylene chloride. $^1$H NMR (DMSO-$d_6$, 300 MHz) δ 2.0 (s, 3H), 2.5-2.7 (m, 2H), 2.9 (t, 2H), 3.5-3.6 (m, 2H), 3.7 (t, 2H), 4.7 (s, 2H), 6.7 (d, 1H), 6.8 (s, 1H), 7.1 (d, 1H), 7.2 (d, 1H), 7.5 (d, 1H), 7.6-7.7 (m, 2H), 8-8.1 (m, 2H), 8.2 (s, 1H), 9 (s, 1H).

Example 57

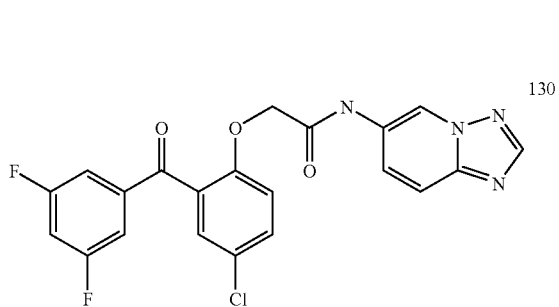

Acid 49 (0.1 g, 0.3 mmole), was converted to the acid chloride by reaction with oxalyl chloride (0.1 mL, 0.8 mmol) in dichloromethane (5 mL) and 1 drop of DMF (Aldrich, Sure Seal). The reaction was stirred at rt for 1 h. The solvent was removed in vacuo. The title compound was prepared by addition of the acid chloride to 6-amino-s-triazolo(1,5-a) pyridine (0.04 g, 0.3 mmol; prepared by the method of Potts, K. T. and Surapaneni, C. R., J. Heterocyclic Chem., 1970, 7, 1019) and sodium bicarbonate (0.2 g, 2.2 mmol) in acetone (10 mL) and water (1 mL) by general procedure VI. The product was isolated by chromatography on silica gel eluted with chloroform/methanol (95:5, v/v) in 15% yield. MS (ES(+)): m+1/z 443. $^1$H NMR (CDCl$_3$, 300 MHz) δ 9.85 (s, 1H), 9.66 (s, 1H), 8.32 (s, 1H), 7.79 (m, 2H), 7.57 (dd, 1H), 7.4 (m, 3H), 7.15-7.05 (m, 2H), 4.79 (s, 2H).

Example 58

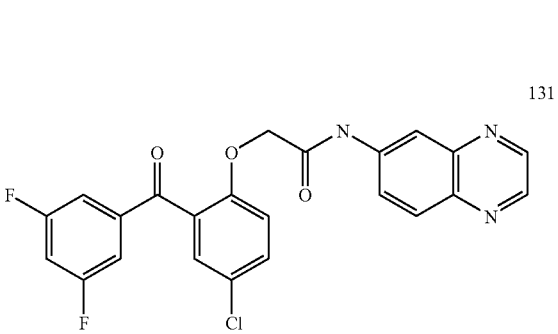

Acid 49 (0.1 g, 0.3 mmol), was converted to the acid chloride by reaction with oxalyl chloride (0.1 ml, 0.8 mmol) in dichloromethane (5 mL) and 1 drop of DMF (Aldrich, Sure Seal). The reaction was stirred at rt for 1 h. The solvent was removed in vacuo. The title compound was prepared by addition of the acid chloride to 6-aminoquinoxaline (0.045 g, 0.3 mmol; prepared by the method of Case, F. H. and Brennan, J. A., JACS, 1959, 81, 6297) and sodium bicarbonate (0.2 g, 2.2 mmol) in acetone (10 mL) and water (1 mL) by general procedure VI. The product was isolated by chromatography on silica gel eluted with chloroform/methanol (95:5, v/v) in 15% yield. MS (ES(+)): m+1/z 454. $^1$H NMR (CDCl$_3$, 300 MHz) δ 9.78 (s, 1H), 8.82 (s, 1H), 8.76 (s, 1H), 8.64 (s, 1H), 8.18 (dd, 1H), 8.09 (d, 1H), 7.56 (dd, 1H), 7.6 (m, 3H), 7.15-7.05 (m, 2H), 4.79 (s, 2H).

Example 59

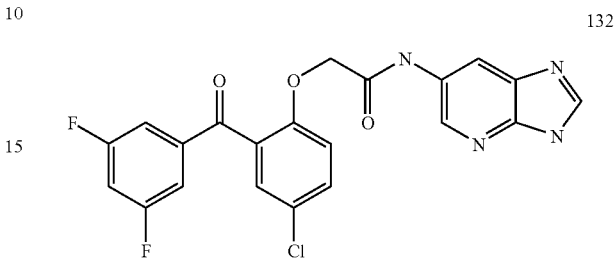

Acid 49 (0.1 g, 0.3 mmol), was converted to the acid chloride by reaction with oxalyl chloride (0.1 mL, 0.8 mmol) in dichloromethane (5 mL) and 1 drop of DMF (Aldrich, Sure Seal). The reaction was stirred at rt for 1 h. The solvent was removed in vacuo. The title compound was prepared by addition of the acid chloride to 6-amino-1H-imidazo[4,5-b] pyridine (0.04 g, 0.3 mmol; which can be prepared by the method of Brooks, W. and Day, A. R., J. Heterocyclic Chem., 1969, 6(5), 759) and sodium bicarbonate (0.2 g, 2.2 mmol) in acetone (10 mL) and water (1 mL) by general procedure VI. The product was isolated by chromatography on silica gel eluted with chloroform/methanol (9:1, v/v) in 10% yield. MS (ES(+)): m+1/z 443. $^1$H NMR (CDCl$_3$, 300 MHz) δ 9.66 (s, 1H), 8.83 (s, 1H), 8.66 (s, 1H), 8.28 (s, 1H), 7.58 (dd, 1H), 7.4 (m, 3H), 7.15-7.05 (m, 2H), 4.79 (s, 2H).

Example 60

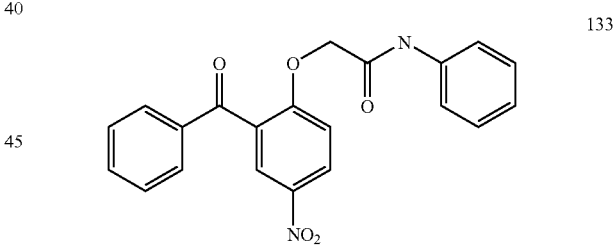

2-Hydroxy-5-nitrobenzophenone (1.09 g, 4.50 mmol, which can be prepared by the method of Hayashi, I. et. al., Bull. Chem. Soc. Jpn., 1983, 56(8), 2432-7), 2-bromo-N-phenyl acetamide (1.01 g, 4.74 mmol, which can be prepared by the method of Vloon, W. et. al., J. Med. Chem., 1987, 30, 20-24), and potassium carbonate (656 mg, 4.74 mmol) were added to DMF (20 mL). The reaction was stirred for 16 h at rt. The reaction was poured onto ice water and a precipitate formed. The precipitate was filtered and rinsed with water. The product was purified by chromatography on silica gel using a Biotage flash chromatography system, eluting with hexane/ethyl acetate (3:1) to obtain 1 g (2.66 mmol, 59% yield). MS (ES(+)): m+1/z 377, MS (ES(−)): m−1/z 375. $^1$H NMR (CDCl$_3$, 300 MHz) δ 8.96 (s, 1H), 8.46 (dd, 1H), 8.36 (d, 1H), 7.90 (d, 2H), 7.66 (m, 3H), 7.55 (m, 2H), 7.34 (t, 2H), 7.19 (d, 1H), 7.13 (t, 1H), 4.79 (s, 2H).

Example 61

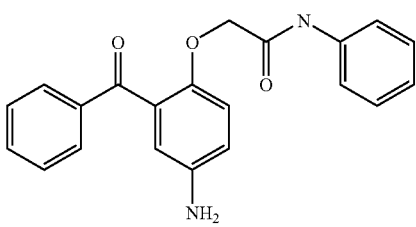

134

Compound 133 (50 mg, 133 mmol) and Raney-Nickel catalyst (Aldrich, 45 mg, 90% by weight) were added to ethanol (30 mL) and placed on a Parr hydrogenator at 50 psig hydrogen pressure. Additional catalyst (100 mg) was added at 1 h intervals. After 3 h, the catalyst was filtered and the solvents removed in vacuo. The product was purified by chromatography on silica gel eluted with chloroform/methanol (98:2) to obtain 38.6 mg (112 mmol, 84% yield). MS (ES(+)): m+1/z 347. $^1$H NMR (CDCl$_3$, 300 MHz) δ 9.06 (s, 1H), 7.90 (d, 2H), 7.60 (m, 3H), 7.48 (m, 2H), 7.30 (t, 2H), 7.09 (t, 1H), 6.90 (d, 1H), 6.84 (dd, 1H), 6.74 (d, 1H), 4.59 (s, 2H), 3.62 (br s, 2H).

Example 62

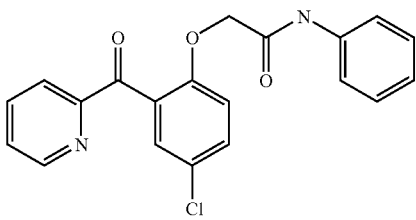

135

Step A:

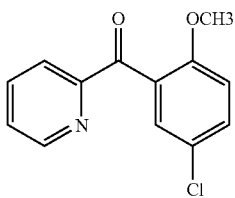

136

2-Bromo-4-chloroanisole (24.4 g, 0.11 mol) was added dropwise to a stirred suspension of magnesium (2.7 g, 0.11 mol) in diethyl ether (150 mL) containing a crystal of iodine. The mixture was heated to reflux for 2 h. A solution of 2-cyanopyridine (11.4 g, 0.11 mol) in diethyl ether (100 mL) was added dropwise and the resulting suspension (yellowish-tan precipitate formed) was refluxed for 2 h, cooled to rt and poured into cold 2N HCl (300 mL). The diethyl ether layer was separated and discarded. The aqueous layer was made basic by addition of 50% aq NaOH and extracted with ether (4×300 mL). The combined ether extracts were washed with water, dried over sodium sulfate, and evaporated to give a brown solid. The product was purified by chromatography on silica gel eluted with ethyl acetate/hexane (1:3) to give 10.9 g, in 40% yield. MS (ES$^+$) m/z: 248.0 (M+1, 85%), 270 (M+23, 45%); $^1$H NMR (CDCl$_3$, 300 MHz) δ 8.64 (d, 1H), 8.02 (d, 1H), 7.85 (t, 1H), 7.41-7.47 (m, 3H), 6.91 (d, 1H), 3.64 (s, 3H).

Step B:

1-(5-Chloro-2-methoxyphenyl)-1-(2-pyridinyl)methanone (125 mg, 0.505 mmol) was dissolved in dichloromethane (5 mL) and chilled to −78° C. in a dry ice/acetone bath. A nitrogen atmosphere was provided. Boron tribromide (1M in CH$_2$Cl$_2$, 2 mL, 2 mmol) was added dropwise and the flask warmed to rt overnight. Water (5 mL) was added dropwise, and the contents of the flask were washed once with water, once with brine, dried over sodium sulfate, and solvents removed in vacuo. The crude sample was dissolved in DMF (5 mL). 2-Bromo-N-phenyl acetamide (113 mg, 0.532 mmol, which can be prepared by the method of Vloon, W. et. al., J. Med. Chem., 1987, 30, 20-24) and potassium carbonate (73.5 mg, 0.532 mmol) were added. After 64 h the contents of the flask were poured onto ice water (50 mL) and the precipitate was filtered. The product was purified by chromatography on silica gel using a Biotage flash chromatography system, eluting with hexane/ethyl acetate (3:1) to obtain 15.5 mg (42.3 mmol, 8.4% yield over two steps). MS (ES(+)): m+1/z 367. $^1$H NMR (CDCl$_3$, 300 MHz) δ 9.38 (s, 1H), 8.60 (d, 1H), 8.20 (d, 1H), 7.93 (td, 1H), 7.60 (m, 3H), 7.47 (m, 2H), 7.33 (t, 2H), 7.12 (t, 1H), 6.94 (d, 1H), 4.63 (s, 2H).

Example 63

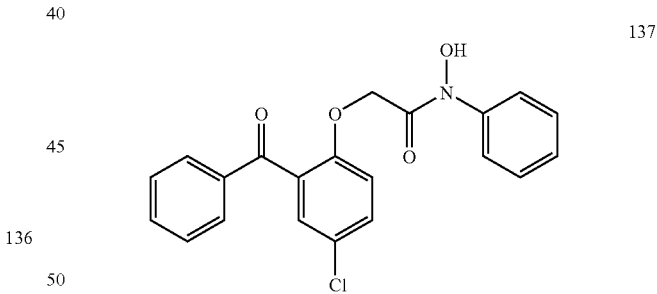

137

2-(2-Benzoyl-4-chlorophenoxy)acetyl chloride (0.1 g, 0.32 mmol was dissolved in dry acetonitrile (2 mL). 2-Phenylhydroxylamine (which was prepared by the method outlined in Org. Syn. Col. Vol. I, p. 445, 0.35 g) was dissolved in ether and dried with MgSO$_4$. The mixture was filtered and the ether removed in vacuo. The residue was dissolved in acetonitrile (2 mL) and added to the acid chloride solution. The reaction was stirred at rt for 3 h. A precipitate formed and was filtered. The reaction solvent was removed in vacuo. The product was purified by chromatography on silica gel eluted with hexane/ethyl acetate (3:1, v/v). The product containing fractions were combined and the solvents removed in vacuo to provide a 50% yield. MS (APCI(+)): m+Na/z 404. $^1$H NMR (CDCl$_3$, 300 MHz) δ 9.85 (s, 1H), 7.85-7.0(m, 13H), 4.95 (s, 2H).

Example 64

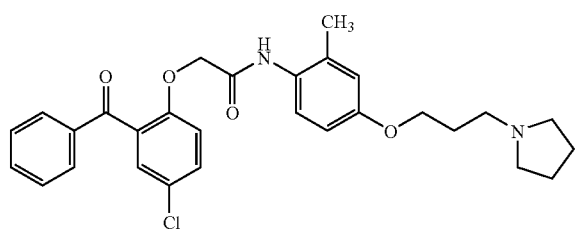

138

Step A:

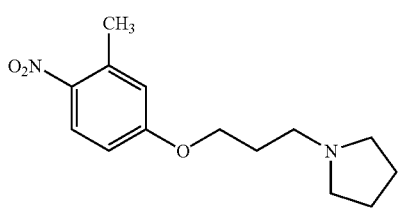

139

4-(3-bromopropoxy)-2-methyl-1-nitrobenzene (8.0 g, 29.2 mmol, which can be prepared according to the method found in Patent; Wellcome Foundation; GB 982572; 1960; Chem. Abstr.; EN; 63; 2928b; 1965), pyrrolidine (92.5 mL, 29.2 mmol) and $K_2CO_3$ (5.0 g, 35 mmol) were mixed together in DMF (30 mL) at rt for 16 h. The reaction mixture was filtered and the solvents were removed under reduced pressure to leave an oil and was dissovled in $CH_2Cl_2$, washed with aqueous NaOH (1N), water, dried and the solvents were removed under reduced pressure. The product was purified by flash chromatography using 95:5 dichloromethane/methanol as eluant to afford 139 as an orange oil (7.5 g, 97%). $^1$H NMR (CDCl$_3$, 300 MHz) δ 1.84 (m, 4H), 2.06 (ddd, 2H), 2.57 (m, 6H), 2.58 (s, 3H), 4.14 (t, 2H), 6.84 (m, 3H), 8.10 (d, 1H).

Step B:

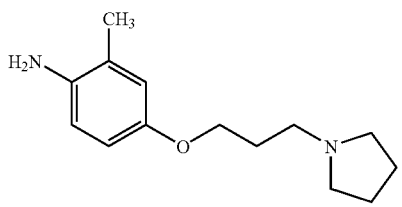

140

Into a stirred Parr bottle were placed compound 139 (7.5 g, 28.4 mmol), Pd/C (0.75 g, 10%), and EtOH (300 mL). The bottle was pressurized to 5 atm. with hydrogen gas and was allowed to stir at rt for 3 h. The mixture was then filtered through a pad of celite and the solvents were removed under reduced pressure to give 140 as an orange oil (6.0 g, 98%). $^1$H NMR (CDCl$_3$, 300 MHz) δ 1.84 (m, 4H), 1.98 (ddd, 2H), 2.19 (s, 3H), 2.42 (m, 6H), 3.28 (br s, 1H), 3.98 (t, 2H), 6.84 (m, 3H).

Step C:

Carboxylic acid 105 (1.0 g, 3.9 mmol), amine 140 (1.22 g, 3.9 mmol), HOBt (5.25 g, 3.9 mmol), EDAC (0.9 g, 4.7 mmol), triethylamine (1.3 mL, 3.9 mmol) and DMF (50 mL) were used according to general procedure IV. The product was purified by flash chromatography using 95:5 dichloromethane/methanol as eluant to provide 138 as an orange oil (0.84 g, 36%). $^1$H NMR (CDCl$_3$, 300 MHz) δ 2.07 (s, 3H), 2.11 (m, 6H), 2.30 (ddd, 2H), 3.22 (m, 4H), 4.01 (t, 2H), 4.63 (s, 2H), 6.65 (m, 2H), 7.01-7.55 (m, 6H), 7.79 (dd, 2H), 7.98 (s, 1H), 8.13 (s, 1H).

Example 65

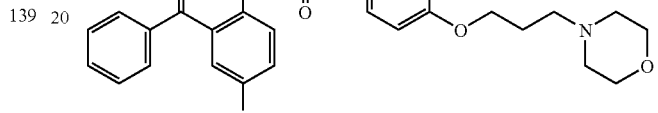

141

Step A:

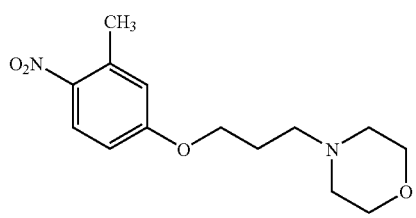

142

4-(3-bromopropoxy)-2-methyl-1-nitrobenzene, and morpholine (5.0 g, 18.2 mmol) were used in the same manner as to prepare compound 139. Compound 142 was obtained as an oil (5.1 g, 100%). $^1$H NMR (CDCl$_3$, 300 MHz) δ 2.02 (ddd, 2H), 2.38-2.56 (m, 6H), 2.64 (s, 3H), 3.73 (m, 4H), 4.11 (t, 2H), 6.81 (m, 2H), 8.09 (d, 1H).

Step B:

143

Compound 142 (5.1 g, 18.2 mmol) was used in the same manner as that to prepare compound 140. Amine 143 was obtained as an oil (4.3 g, 95%). $^1$H-NMR (CDCl$_3$, 300 MHz) δ 1.94 (ddd, 2H), 2.19 (s, 3H), 2.49-2.54 (m, 6H), 3.39 (br s, 1H), 3.75 (m, 4H), 3.96 (t, 2H), 6.64-6.70 (m, 3H).

Step C:

Carboxylic acid 105, amine 143, HOBt, EDAC, triethylamine, and DMF were used according to general procedure IV. The product was purified by flash chromatography using 95:5 dichloromethane/methanol to afford 141 as an oil (1.3 g, 67%). ¹H NMR (CDCl₃, 300 MHz) δ 1.98 (ddd, 2H), 2.11 (s, 3H), 2.48-2.56 (m, 6H), 3.75 (m, 4H), 4.02 (t, 2H), 4.68 (s, 2H), 6.6-7.37 (m, 9H), 7.86 (d, 2H), 8.11 (s, 1H).

Example 66

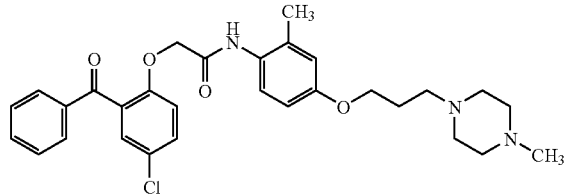

144

Step A:

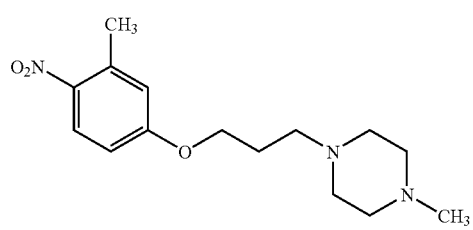

144

4-(3-bromo-propoxy)-2-methyl-1-nitro-benzene, and 1-methylpiperazine (5.0 g, 18.2 mmol) were used in the same manner as to prepare compound 139. Compound 144 was obtained as an oil (3.4 g, 63%). ¹H NMR (CDCl₃, 300 MHz) δ 1.98 (ddd, 2H), 2.26 (s, 3H), 2.38-2.60 (m, 10H), 2.65 (s, 3H), 4.11 (t, 2H), 6.80 (m, 2H), 8.10 (d, 1H).

Step B:

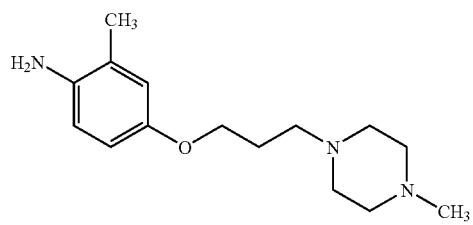

145

Compound 144 (3.4 g, 12.5 mmol) was used in the same manner as that to prepare compound 140. Amine 145 was obtained as an oil (3.1 g, 95%). ¹H NMR (CDCl₃, 300 MHz)δ 1.88 (ddd, 2H), 2.10 (s, 3H), 2.25 (s, 3H), 2.26-2.65 (m, 10H), 3.35 (br s, 1H), 3.89 (t, 2H), 6.50-6.70 (m, 3H).

Step C:

Carboxylic acid 105, amine 145, HOBt, EDAC, triethylamine, and DMF were used according to general procedure IV. The product was purified by flash chromatography using 95:5 dichloromethane/methanol to afford 144 as an oil (0.95 g, 47%). ¹H NMR (CDCl₃, 300 MHz) δ 1.92 (m, 2H), 2.05 (s, 3H), 2.29 (s, 3H), 2.40-2.70 (m, 10H), 3.39 (s, 1H), 3.95 (t, 2H), 4.62 (s, 2H), 6.70 (s, 2H), 6.90 (d, 1H), 6.72-7.60 (m, 5H), 7.81 (d, 2H), 8.06 (s, 1H).

Example 67

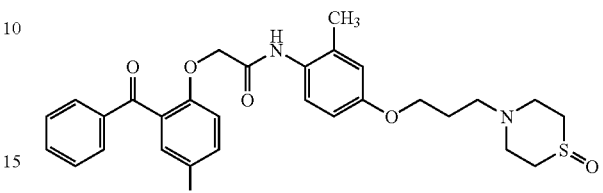

146

Step A:

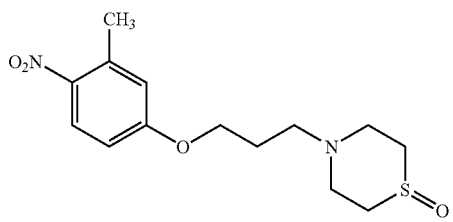

147

4-(3-bromo-propoxy)-2-methyl-1-nitro-benzene, and thiomorpholine-1-oxide (5.0 g, 18.2 mmol, which can be prepared according to Nachtergaele, Willy A.; Anteunis, Marc J. O.; Bull. Soc. Chim. Belg.; EN; 89; 7; 1980; 525-536) were used in the same manner as to prepare compound 139. Compound 147 was obtained as an oil (2.1 g, 37%). ¹H NMR (CDCl₃, 300 MHz) δ 2.05 (ddd, 2H), 2.65 (s, 3H), 2.63 (t, 2H), 2.65-3.20 (m, 8H), 4.12 (t, 2H), 6.82 (m, 2H), 8.10 (s, 1H).

Step B:

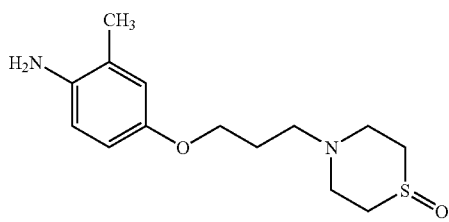

148

Compound 147 (2.1 g, 6.7 mmol) was used in the same manner as that to prepare compound 140. Amine 148 was obtained as an oil (2.1 g, 98%). ¹H NMR (CDCl₃, 300 MHz) δ 1.84 (ddd, 2H), 2.15 (s, 3H), 2.58 (t, 2H), 2.65-3.25 (m, 10H), 3.84 (t, 2H), 6.28 (m, 3H).

Step C:

Carboxylic acid 105, amine 148, HOBt, EDAC, triethylamine, and DMF were used according to general procedure IV. The product was purified by flash chromatography using 95:5 dichloromethane/methanol to afford 146 as an oil (0.7 g, 32%). ¹H NMR (CDCl₃, 300 MHz) δ 1.95 (ddd, 2H), 2.71

(s, 3H), 2.63 (t, 2H), 2.65-3.20 (m, 8H), 4.00 (t, 2H), 4.67 (s, 2H), 6.72 (s, 2H), 7.03 (d, 2H), 7.38-7.85 (m, 6H), 7.85 (m, 2H), 8.15 (s, 1H).

Example 68

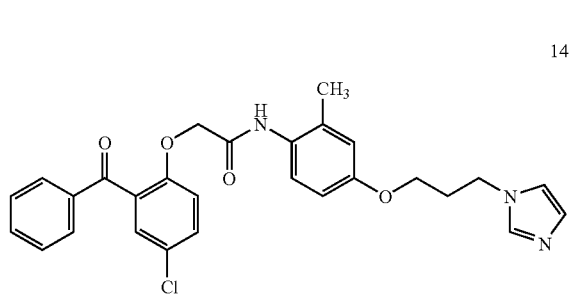

Step A:

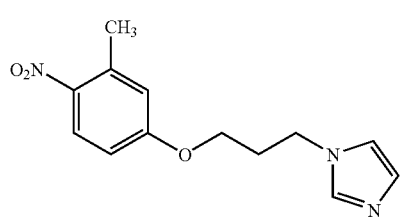

4-(3-bromo-propoxy)-2-methyl-1-nitro-benzene, and imidazole (5.0 g, 18.2 mmol) were used in the same manner as to prepare compound 139. Compound 150 was obtained as an oil (3.1 g, 61%). $^1$H NMR (CDCl$_3$, 300 MHz) δ 2.35 (ddd, 2H), 2.66 (s, 3H), 3.64 (d, 2H), 4.00 (d, 2H), 6.8 (s, 2H), 6.95 (d, 2H), 7.11 (d, 2H), 7.53 (s, 1H), 8.10 (d, 1H).

Step B:

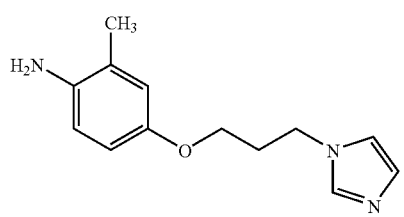

Compound 150 (3.1 g) was used in the same manner as that to prepare compound 140. Amine 148 Was obtained as an oil (0.71 g, 26%). $^1$H NMR (CDCl$_3$, 300 MHz) δ 1.27 (ddd, 2H), 2.18 (s, 3H), 3.88 (t, 2H), 4.06 (br s, 1H), 4.25 (t, 2H), 6.60 (m, 3H), 6.98 (d, 2H), 7.13 (d, 2H), 7.13 (d, 2H), 7.82 (s, 1H).

Step C:

Carboxylic acid 105, amine 151, HOBt, EDAC, triethylamine, and DMF were used according to general procedure IV. The product was purified by flash chromatography using 95:5 dichloromethane/methanol to afford 149 as an oil (1.1 g, 51%). $^1$H NMR (CDCl$_3$, 300 MHz) δ 1.27 (ddd, 2H), 2.18

(s, 3H), 3.80 (t, 2H), 4.18 (t, 2H), 4.63 (s, 2H), 6.60-7.62 (m, 8H), 7.82 (d, 2H), 8.18 (s, 1H).

Example 69

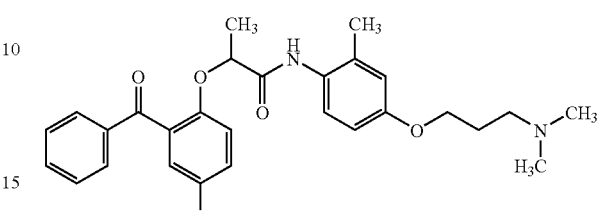

Step A:

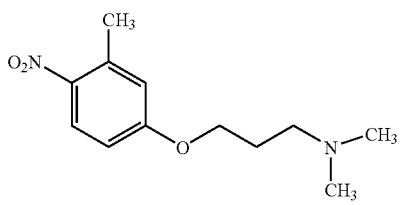

Step B:

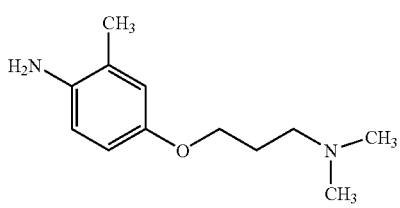

Step C:

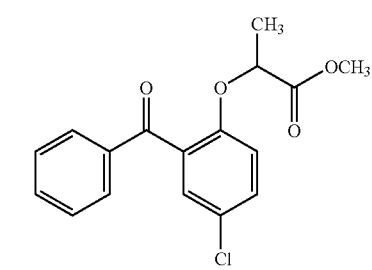

A mixture of 5-chloro-2-hydroxybenzophenone (25 g, 107.4 mmol), methyl 2-bromopropionate, K$_2$CO$_3$ (23.0 g, 161 mmol) and acetone (250 mL) were used according to general procedure II to afford 155 as a yellow oil (32.0 g, 94%). $^1$H NMR (CDCl$_3$, 300 MHz) δ 1.22 (d, 3H), 3.64 (s, 3H), 4.62 (q, 1H), 6.78 (d, 1H), 7.22-7.61 (m, 5H).

Step D:

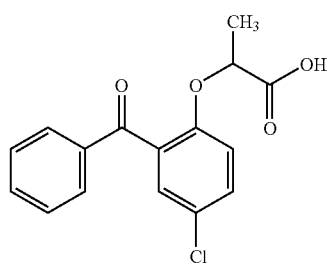

156

Ester 155 (11 g, 34.5 mmol), water (5 mL) and ethanol (150 mL) were used according to general procedure III, except that sodium hydroxide (5 mL of a 5N solution, 25 mol) was used in place of lithium hydroxide. Acid 156 was obtained as a brown oil (4.5 g, 43%). $^1$H NMR (CDCl$_3$, 300 MHz) δ 1.65 (d, 3H), 4.96 (q, 1H), 7.10-7.98 (m, 8H).

Step E:

Carboxylic acid 156, amine 154 (0.68 g, 3.3 mmol), EDAC, HOBt and DMF were used according to general procedure IV to afford compound 152 as an orange oil (1.1 g, 61%). $^1$H NMR (CDCl$_3$, 300 MHz) δ 1.6 (d, 3H), 1.95 (ddd, 2H), 2.05 (s, 3H), 2.26 (s, 6H), 2.45 (t, 2H), 3.88 (t, 2H), 4.92 (q, 1H), 6.64 (m, 9H), 7.84 (d, 2H), 8.22 (s, 1H).

Example 70

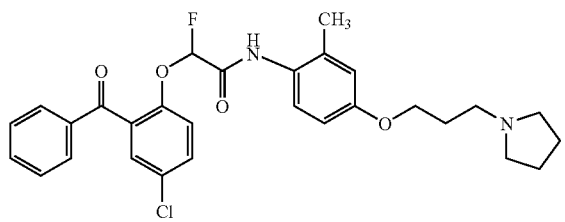

157

Step A:

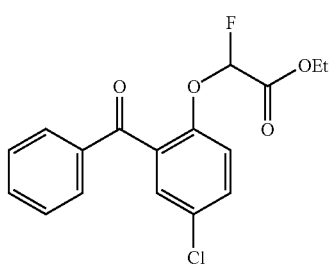

158

A mixture of 5-chloro-2-hydroxybenzophenone (6.3 g, 27 mmol), ethyl bromofluoroacetate, K$_2$CO$_3$ (4.5 g, 32 mmol) and DMF (50 mL) were combined and the reaction mixture was allowed to stir at 80° C. for 24 h. The mixture was then filtered, and poured into a separatory funnel containing ethyl acetate and water. The organic layer was collected, washed with water, brine, dried over MgSO$_4$, filtered and the solvents were removed under reduced pressure to afford 158 as an oil (7.0 g, 77%). $^1$H NMR (CDCl$_3$, 300 MHz) δ 1.22 (t, 3H), 4.17 (q, 2H), 5.66 (d, 1H), 5.87 (d, 1H), 7.19-8.82 (m, 8H).

Step B:

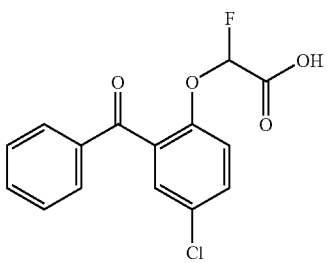

159

Ester 158, water, and ethanol (150 mL) were used according to general procedure III, except that sodium hydroxide (5 mL of a 5N aqueous solution) was used in place of lithium hydroxide. The solvents were removed under reduced pressure to afford 159 as white crystals (5.4 g, 84%). $^1$H NMR (CDCl$_3$, 300 MHz) δ 5.85 (d, 1H), 6.05 (d, 1H), 7.89 (m, 8H).

Step C:

Carboxylic acid 159, amine 140, EDAC, HOBt and DMF were used according to general procedure IV to afford 157 as a yellow foam (0.28 g, 17%). $^1$H NMR (CDCl$_3$, 300 MHz) δ 1.92 (m, 4H), 2.08 (ddd, 2H), 2.22 (s, 3H), 2.62-2.85 (m, 6H), 4.03 (t, 2H), 5.96 (d, 1H), 6.16 (d, 1H), 6.73 (br s, 2H), 7.30-7.85 (m, 7H), 7.85 (m, 7H), 8.2 (s, 1H).

Example 71

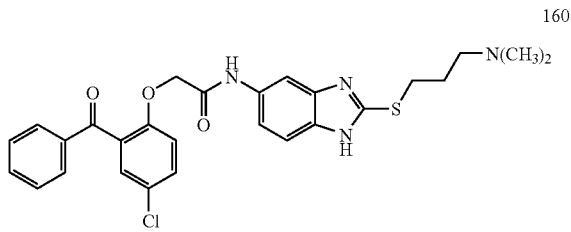

160

Step A:

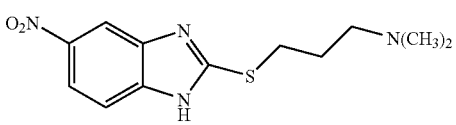

161

Into a round-bottom flask were placed 2-mercapto-5-nitrobenzimidazole (2.0 g, 10.2 mmol), K$_2$CO$_3$ (2.8 g, 20.4 mmol) and 3-(N,N-dimethylamino)-1-chloropropane hydrochloride (1.6 g, 10.2 mmol) and DMF (50 mL). The resulting mixture was allowed to stir at rt for 24 h, after which time the DMF was removed under reduced pressure to afford a brown oil. The product was purified by flash chromatography using 9:1 dichloromethane/methanol as eluant to afford 161 (1.5 g, 54%). $^1$H NMR (CDCl$_3$, 300 MHz) δ 2.12 (ddd, 2H), 2.24 (s, 6H), 3.68 (t, 2H), 3.28 (t, 2H), 5.28 (s, 1H), 7.24 (dd, H), 8.18 (dd, 1H), 8.28 (s, 1H).

Step B:

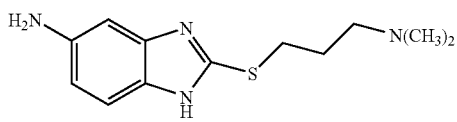

Into a stirred Parr bottle were placed compound 161 (1.50 g, 5.36 mmol), Pd/C (0.15 g, 10% w/w), and ethanol (300 mL). The bottle was pressurized to 5 atm. with hydrogen gas and the mixture was allowed to stir at rt for 3 h. The mixture was then filtered through a pad of celite and the solvents were removed under reduced pressure to afford 162 as an orange oil (0.80 g, 58%). $^1$H NMR (CDCl$_3$, 300 MHz) δ 1.91 (ddd, 2H), 2.27 (s, 6H), 3.18 (t, 2H), 3.47 (br s, 2H), 3.68 (br s, 2H), 6.54 (dd, 1H), 6.71 (s, 1H), 7.26 (dd, 1H), 8.27 (s, 1H).

Step C:

Carboxylic acid 105, amine 162, EDAC, HOBt, and DMF were used according to general procedure IV. The product was purified by flash chromatography using 95:5 dichloromethane/methanol as eluant to afford 160 as white crystals (0.24 g, 14%). $^1$H NMR (CDCl$_3$, 300 MHz) δ 2.05 (ddd, 2H), 2.48 (s, 6H), 2.96 (t, 2H), 3.20 (br s, 2H), 4.62 (s, 2H), 5.22 (s, 1H), 6.86-8.20 (m, 11H), 9.00 (s, 1H).

Example 72

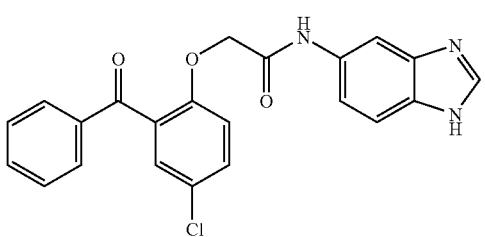

163

Carboxylic acid 105, 5-aminobenzimidazole, HOBt, EDAC and DMF were used according to general procedure IV. The product was purified by flash chromatography using 95:5 dichloromethane/methanol to afford 163 as white crystals (0.28 g, 35%). $^1$H NMR (CDCl$_3$, 300 MHz) δ 4.66 (s, 2H), 6.97-8.16 (m, 11H), 9.11 (s, 1H), 10.1 (br s, 1H).

Example 73

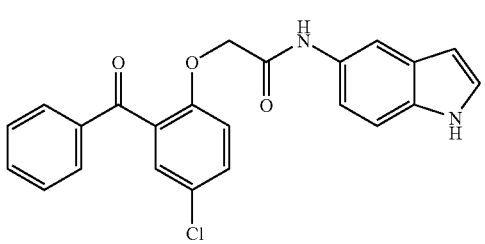

164

Carboxylic acid 105, 5-aminoindole, HOBt, EDAC, and DMF were used according to general procedure IV. The product was purified by flash chromatography using 95:5 dichloromethane/methanol to afford 164 as white crystals (0.25 g, 32%). $^1$H NMR (CDCl$_3$, 300 MHz) δ 4.71 (s, 2H), 6.58 (s, 1H), 7.06-8.72 (m, 14H).

Example 74

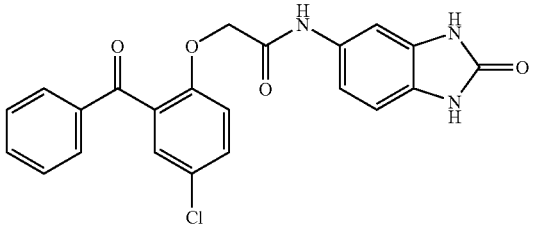

165

Carboxylic acid 105, 5-aminobenzimidazolone, HOBt, EDAC, and DMF were used according to general procedure IV. The product was purified by flash chromatography using 95:5 dichloromethane/methanol to afford 165 as white crystals (0.44 g, 27%). $^1$H NMR (CDCl$_3$, 300 MHz) δ 4.71 (s, 2H), 6.83-7.86 (m, 11H), 9.62 (s, 1H), 10.55 (s, 1H), 10.59 (s, 1H).

Example 75

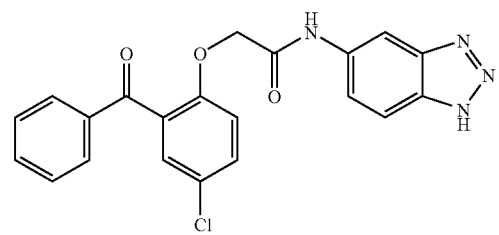

166

Carboxylic acid 105, 5-aminobenztriazole, HOBt, EDAC, and DMF were used according to general procedure IV. The product was purified by flash chromatography using 95:5 dichloromethane/methanol to afford 166 as white crystals (0.75 g, 91%). $^1$H NMR (CDCl$_3$, 300 MHz) δ 4.79 (s, 2H), 7.06-8.61 (m, 11H), 9.81 (s, 1H), 12.60 (br s, 1H).

Example 76

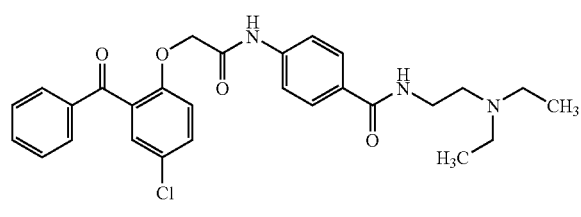

167

Carboxylic acid 105, N1-[2-(diethylamino)ethyl]-4-aminobenzamide, HOBt, EDAC, and DMF were used according to general procedure IV. The product was purified by flash chromatography using 95:5 dichloromethane/methanol to afford 167 as white crystals (0.12 g, 12%). $^1$H NMR (CDCl$_3$, 300 MHz) δ 1.21 (t, 6H), 2.83 (q, 4H), 2.90 (dd, 2H), 3.66 (dd, 2H), 4.73 (s, 2H), 7.04-7.95 (m, 13H), 9.43 (s, 1H).

Example 77

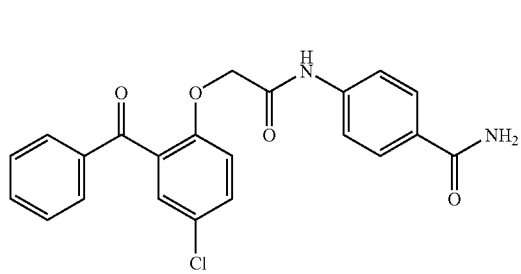

168

Carboxylic acid 105, 4-aminobenzamide, HOBt, EDAC, and DMF were used according to general procedure IV. The product was purified by flash chromatography using 95:5 dichloromethane/methanol to afford 168 as white crystals (0.13 g, 13%). $^1$H NMR (CDCl$_3$, 300 MHz) δ 4.75 (s, 2H), 5.34 (s, 2H), 7.06-7.97 (m, 12H), 9.53 (s, 1H).

Example 78

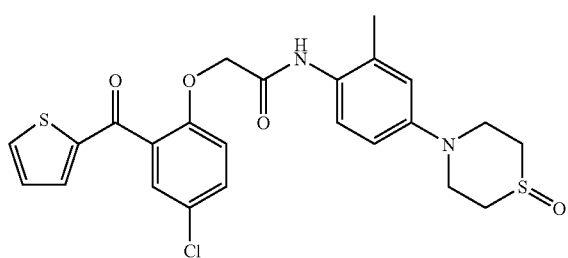

169

Carboxylic acid 112 (0.15 g, 0.51 mmol), amine 399 (0.11 g, 0.51 mmol), HOBt (0.7 g, 0.51 mmol), EDAC (0.98 g, 0.51 mmol), Et$_3$N (0.14 mL, 0.10 g, 1.0 mmol) and anhydrous DMF (7 mL) were used according to general procedure IV. Treatment of the resulting yellow oil with diethyl ether provided 169 (0.052 g, 20%) as a yellow solid: $^1$H NMR (400 MHz, DMSO-d$_6$) δ 8.99 (s, 1H), 8.08 (d, J=4.8 Hz, 1H), 7.63 (d, J=3.2 Hz, 1H), 7.58 (d, J=9.2 Hz, 1H), 7.50 (s, 1H), 7.20 (m, 3H), 6.84 (s, 1H), 6.78 (d, J=8 Hz, 1H), 4.75 (s, 2H), 3.70 (m, 2H), 3.54 (m, 2H), 2.87 (m, 2H), 2.64 (m, 2H), 2.02 (s, 3H).

Example 79

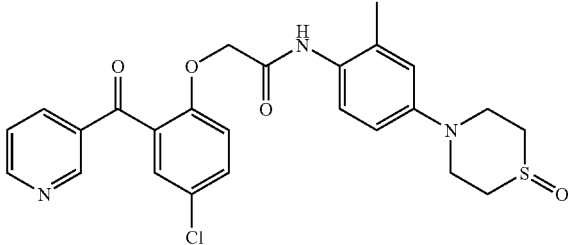

170

Step A:

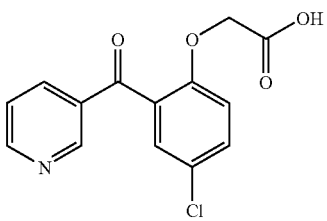

171

Phenol 21 (1.5 g, 6.4 mmol), K$_2$CO$_3$ (4.4 g, 32.2 mmol), ethyl bromoacetate (0.79 mL, 1.18 g, 7.1 mmol) and acetone (150 mL) were used according to general procedure II to provide 171 as an oil (4.0 g, >100%). The product was used in the next step without any further purification. $^1$H NMR (400 MHz, CDCl$_3$) δ 8.97 (d, J=1.6 Hz, 1H), 8.75 (d, J=4 Hz, 1H), 8.18 (d, J=7.6 Hz, 1H), 7.43 (m, 3H), 6.78 (d, J=8.8 Hz, 1H), 4.50 (s, 2H), 4.17 (m, 2H), 1.20 (m, 3H).

Step B:

172

Ester 171 (4.0 g, 12.5 mmol), THF (25 mL), water (12 mL), EtOH (12 mL) and LiOH (1.32 g, 31.5 mmol) were used according to general procedure III. Treatment of the resulting yellow gel with ether provided 172 (1.09 g, 29%) as a pale yellow solid. The product was used in the next reaction without any further purification. $^1$H NMR (400 MHz, DMSO-d$_6$) δ 8.85 (d, J=2 Hz, 1H), 8.75 (d, J=4.8 Hz, 1H), 8.10 (d, J=8 Hz, 1H), 7.56 (m, 2H), 7.47 (d, J=2.8 Hz, 1H), 7.10 (d, J=8.8 Hz, 1H), 4.82 (s, 2H).

Step C:

Carboxylic acid 172 (0.10 g, 0.34 mmol), amine 399 (0.076 g, 0.34 mmol), HOBt (0.046 g, 0.34 mmol), EDAC (0.19 g, 0.34 mmol), Et$_3$N (0.1 mL, 0.68 mmol) and anhydrous DMF (5 mL) were used according to general procedure IV. Treatment of resulting oil with diethyl ether provided 170 (0.036 g, 21%) as a pale yellow solid: $^1$H NMR (400 MHz, DMSO-d$_6$) δ 8.99 (s, 1H), 8.88 (s, 1H), 8.75 (s, 1H), 8.10 (d, J=7.6 Hz, 1H), 7.63 (d, J=8.8 Hz, 1H), 7.49 (m, 2H), 7.20 (d, J=8.8 Hz, 1H), 7.05 (d, J=8.8 Hz, 1H), 6.81 (s, 1H), 6.75 (d, J=8.8 Hz, 1H), 4.67 (s, 2H), 3.69 (m, 2H), 3.51 (m, 2H), 2.86 (m, 2H), 2.63 (m, 2H), 1.96 (s, 3H).

Example 80

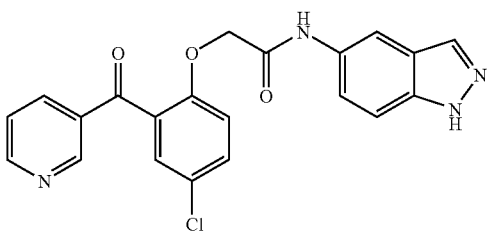

173

Carboxylic acid 172 (0.10 g, 0.34 mmol), 5-aminoindazole (0.045 g, 0.34 mmol), HOBt (0.046 g, 0.34 mmol), EDAC (0.19 g, 0.34 mmol), Et$_3$N (0.1 mL, 0.68 mmol) and anhydrous DMF (5 mL) were used according to general procedure IV. Treatment of resulting oil With diethyl ether provided 173 (0.067 g, 49%) as a brown solid: $^1$H NMR (400 MHz, DMSO-d$_6$) δ 12.97 (s, 1H), 9.82 (s, 1H), 8.91 (d, J=2 Hz, 1H), 8.71 (m, 1H), 8.14 (d, J=8 Hz, 1H), 7.99 (s, 2H), 7.61 (dd, J=2.4, 8.8 Hz, 1H), 7.50 (m, 2H), 7.44 (d, J=8.8 Hz, 1H), 7.29 (d, J=9 Hz, 1H), 7.19 (d, J=9 Hz, 1H), 4.70 (s, 2H). MS (ES): 407 (M$^+$).

Example 81

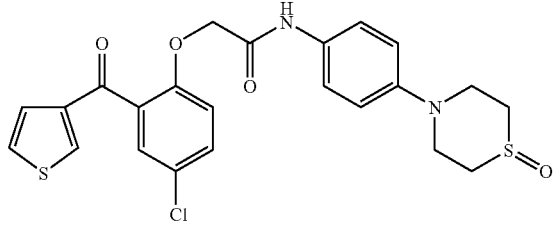

174

Carboxylic acid 119 (0.15 g, 0.51 mmol), amine 399 (0.11 g, 0.51 mmol), HOBt (0.07 g, 0.51 mmol), EDAC (0.1 g, 0.51 mmol), Et$_3$N (0.14 mL, 0.10 g, 1.0 mmol) and anhydrous DMF (5 mL) were used according to general procedure IV. The product was purified by flash chromatography using 2% MeOH:CH$_2$Cl$_2$ as eluant to provide a yellow oil. Treatment of the oil with diethyl ether provided 174 (0.065 g, 26%) as a pale yellow solid: $^1$H NMR (400 MHz, DMSO-d$_6$) δ 9.61 (s, 1H), 8.26 (s, 1H), 7.62 (m, 1H), 7.58 (m, 2H), 7.45 (m, 3H), 7.16 (d, J=9 Hz, 1H), 6.93 (m, 2H), 4.70 (s, 2H), 3.66 (m, 2H), 3.50 (m, 2H), 2.87 (m, 2H), 2.66 (m, 2H). MS (ES): 489 (M$^+$).

Example 82

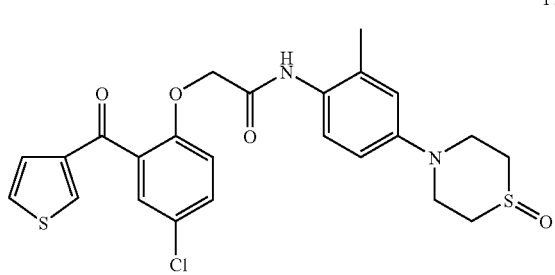

175

Carboxylic acid 119 (0.15 g, 0.51 mmol), amine 399 (0.11 g, 0.51 mmol), HOBt (0.07 g, 0.51 mmol), EDAC (0.1 g, 0.51 mmol), Et$_3$N (0.14 mL, 0.10 g, 1.0 mmol) and anhydrous DMF (5 mL) were used according to general procedure IV. The product was purified by flash chromatography using 2% MeOH:CH$_2$Cl$_2$ as eluant to provide a yellow oil. Treatment of the oil with diethyl ether provided 175 (0.046 g, 18%) as a pale yellow solid: $^1$H NMR (400 MHz, DMSO-d$_6$) δ 8.94 (s, 1H), 8.24 (s, 1H), 7.58 (m, 2H), 7.49 (s, 1H), 7.42 (s, 1H), 7.18 (m, 2H), 6.78 (m, 2H), 4.73 (s, 2H), 3.69 (m, 2H), 3.54 (m, 2H), 2.87 (m, 2H), 2.65 (m, 2H), 2.01 (s, 3H). MS (ES): 503 (M$^+$):

Example 83

176

Step A:

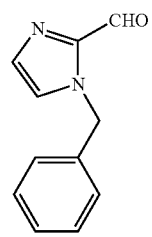

177

In a round bottom flask equipped with a stir bar, an addition funnel and nitrogen on demand, were placed 1-benzylimidazole (2.0 g, 12.6 mmol) and anhydrous THF (50 mL) and cooled to −78° C. by means of a dry ice/ acetone bath. n-Butyllitium (8.8 mL of a 1.6 M soln. in hexanes, 13.7 mmol) was added dropwise and the reaction was allowed to stir for 15-20 min at −78° C. Anhydrous N,N-dimethylformamide (1.3 mL, 0.0013 mmol) was added dropwise and reaction was allowed to stir for an additional 45 min at −78° C. When judged to be complete, the reaction was quenched by dropwise addition of water and extracted with EtOAc. The organics were dried over Na$_2$SO$_4$, filtered and concentrated under reduced pressure to provide 177 (2.1 g, 88%) as a white solid: $^1$H NMR (400 MHz, DMSO-d$_6$) δ 9.68 (s, 1H), 7.73 (s, 1H), 7.30 (m, 4H), 7.16 (d, J=7 Hz, 2H), 5.57 (s, 2H).

Step B:

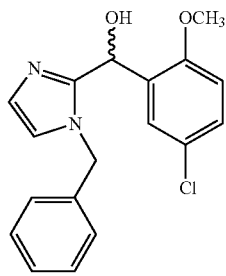
178

In a round bottom flask equipped with a stir bar, an addition funnel and nitrogen on demand, were placed 2-bromo-4-chloroanisole (1.5 mL, 2.4 g, 11.4 mmol) and diethyl ether (17 mL) and cooled to −78° C. by means of a dry ice/ acetone bath. n-Butyllithium (7.8 mL of a 1.6 M soln. in hexanes, 12.5 mmol) was added in a dropwise manner via addition funnel and the reaction was allowed to stir for 30 min at −78° C., after which time the reaction was quenched by dropwise addition of water and extracted with EtOAc. The organics were collected, dried over $Na_2SO_4$, filtered and concentrated under reduced pressure to provide 178 (1.5 g, 42%) as a white solid: $^1$H NMR (300 MHz, $CDCl_3$) δ 7.27 (m, 4H), 7.16 (m, 1H), 7.00 (m, 3H), 6.83 (d, J=2.4 Hz, 1H), 6.71 (dd, J=3, 9 Hz, 1H), 6.11 (d, J=2.4 Hz, 1H), 5.07 (m, 2H), 4.49 (bs, 1H), 3.73 (s, 3H).

Step C:

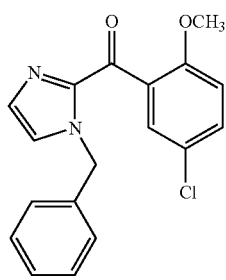
179

In a round bottom flask equipped with a stir bar and nitrogen on demand was placed alcohol 178 (1.5 g, 4.6 mmol), $CH_2Cl_2$ (55 mL) and $MnO_2$ (4.0 g, 46 mmol). The reaction was allowed to stir at RT for 30 min, after which time, the reaction was filtered through a pad of celite and the filtrate was concentrated under reduced pressure to provide 179 (1.5 g, >99%) as a clear gel: $^1$H NMR (400 MHz, $CDCl_3$) δ 7.43 (d, J=4 Hz, 1H), 7.37 (m, 4H), 7.32 (m, 3H), 7.11 (s, 1H), 6.91 (d, J=12 Hz, 1H), 5.71 (s, 2H), 3.75 (s, 3H).

Step D:

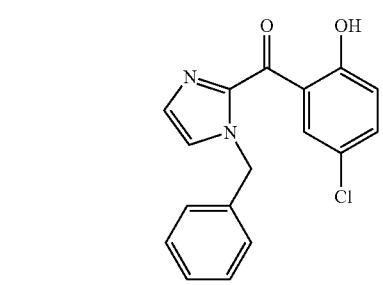
180

Anisole 179 (1.5 g, 4.6 mmol), $CH_2Cl_2$ (30 mL) and $BBr_3$ (12 mL of a 1.0 M soln. in $CH_2Cl_2$, 11.5 mmol) were used according to general procedure IX. The resulting brown oil was filtered through a pad of silica gel using $CH_2Cl_2$ as eluant and the solvents were removed under reduced pressure to provide 180 (0.9 g, 64%) as a yellow solid: $^1$H NMR (400 MHz, $CDCl_3$) δ 8.48 (s, 1H), 7.34 (m, 9H), 6.96 (d, J=9 Hz, 1H), 5.65 (s, 2H).

Step E:

In a round bottom flask equipped with a stir bar, reflux condenser and nitrogen on demand were added the phenol 180 (0.1 g, 0.32 mmol), acetone (7 mL), $K_2CO_3$ (0.22 g, 1.6 mmol) and 2'-chloroacetanilide (0.058 g, 0.34 mmol). The reaction was allowed to stir at reflux for 18-24 h, after which it was poured into a separatory funnel containing water and ethyl acetate. The organics were collected, dried over $Na_2SO_4$, filtered and concentrated under reduced pressure. The resulting product was purified by flash chromatography using 3:1 hexanes/ethyl acetate to 1:3 hexanes/ethyl acetate as a solvent gradient to provide 176 (0.077 g, 54%) as a white solid: $^1$H NMR (300 MHz, $CDCl_3$) δ 10.17 (s, 1H), 7.70 (m, 3H), 7.39 (m, 11H), 6.94 (d, J=9 Hz, 1H), 5.79 (s, 2H), 4.71 (s, 2H). MS(ES): 445($M^+$), 446 $(M+H)^+$.

Example 84

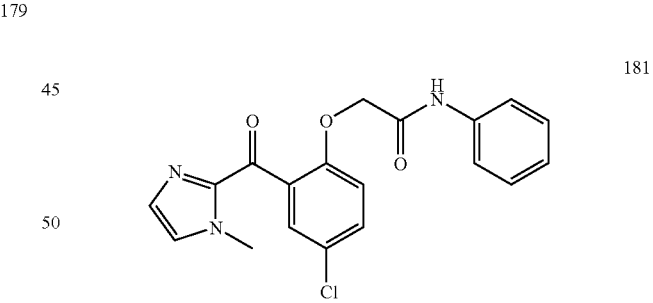
181

Step A:

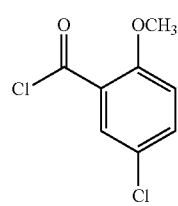
182

5-Chloro-o-anisic acid (7.5 g, 40.2 mmol), CH₂Cl₂ (75 mL), oxalyl chloride (3.7 mL, 5.3 g, 42.2 mmol), and N,N-dimethylformamide (4-5 drops) were used according to general procedure V to afford 182 (8.0 g, 97%) as a yellow oil. The product was used in the next step without further purification or characterization.

Step B:

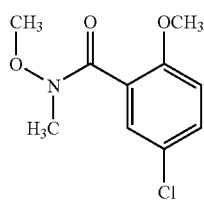

183

Acid chloride 182 (8.0 g, 39 mmol), N,O-dimethylhydroxylamine hydrochloride (7.6 g, 78.0 mmol), CHCl₃ (100 mL), and triethylamine (27 mL, 19.7 g, 195 mmol) were used according to general procedure VII. The resulting colorless oil was treated with diethyl ether to provide 183 (6.0 g, 67%) as a white solid. The product was used in the next step without further purification. ¹H NMR (400 MHz, DMSO-d₆) δ 7.40 (d, J=8.4 Hz, 1H), 7.27 (d, J=2.4 Hz, 1H), 3.75 (s, 3H), 3.42 (bs, 3H), 3.19 (bs, 3H). MS (ES): 229(M⁺).

Step C:

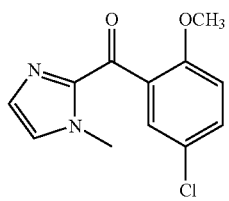

184

In a round bottom flask equipped with a stir bar, an addition funnel and nitrogen on demand, 1-methylimidazole (2.0 g, 24.4 mmol) was dissolved in diethyl ether (50 mL) and cooled to −78° C. by means of a dry ice/ acetone bath. N-Butyllithium (15 mL of a 1.6 M soln. in hexanes, 24.4 mmol) was added dropwise and the reaction was allowed to stir for 30 min at −78° C. Amide 183 (5.1 g, 22.2 mmol) was added as a solid maintaining reaction temp at −78° C. When judged to be complete, the reaction was quenched by dropwise addition of water and extracted with EtOAc. The organics were collected, dried over Na₂SO₄, filtered and concentrated under reduced pressure. The resulting product was purified by flash chromatography using 1:1 hexanes/ethyl acetate to provide 184 (3.3 g, 55%): ¹H NMR (300 MHz, DMSO-d₆) δ 7.60 (s, 1H), 7.53 (dd, J=3, 9 Hz, 1H), 7.42 (d, J=3 Hz, 1H), 7.17 (m, 1H), 7.13 (s, 1H), 4.03 (s, 3H), 3.73 (s, 3H).

Step D:

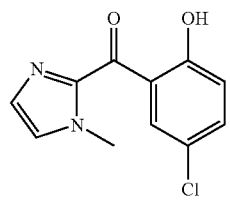

185

Anisole 184 (3.3 g, 13.2 mmol), CH₂Cl₂ (60 mL), and BBr₃ (53 mL of a 1.0 M soln. in CH₂Cl₂, 53 mmol) were used according to general procedure IX to provide 185 (2.0 g, 69%) as a yellow solid. The product was used in the next step without further purification. ¹H NMR (300 MHz, DMSO-d₆) δ 7.90 (s, 1H), 7.83 (d, J=2 Hz, 1H), 7.62 (s, 1H), 7.56 (dd, J=3, 9 Hz, 1H), 7.04 (d, J=9 Hz, 1H), 4.03 (s, 3H).

Step E:

In a round bottom flask equipped with a stir bar, reflux condenser, and nitrogen on demand were added the phenol 185 (0.15 g, 0.67 mmol), acetone (5 mL), K₂CO₃ (0.46 g, 3.3 mmol), and the amide 142 (0.12 g, 0.70 mmol). The reaction was allowed to stir at reflux for 18-24 h, after which time the reaction was poured into a separatory funnel containing water and ethyl acetate. The organics were collected, dried over Na₂SO₄, filtered and concentrated under reduced pressure. The product was purified by flash chromatography using 3:1 hexanes/EtOAc to 1:3 hexanes/EtOAc as a solvent gradient to provide 181 (0.065 g, 25%) as a white solid: ¹H NMR (400 MHz, DMSO-d₆) δ 10.06 (s, 1H), 7.55 (m, 5H), 7.29 (t, J=8 Hz, 2H), 7.10 (m, 3H), 4.74 (s, 2H), 4.02 (s, 3H).

Example 85

186

Step A:

187

In a round bottom flask equipped with a stir bar, an addition funnel and nitrogen on demand was added 2-bromo-4-chloroanisole (9.8 mL, 15.7 g, 71.3 mmol) and anhydrous THF (120 mL) and the reaction was cooled to −78° C. by means of a dry ice/ acetone bath. N-Butyllithium (45 mL of a 1.6 M soln. in hexanes, 72 mmol) was added dropwise and the reaction was allowed to stir for 30 min at −78° C. 4-Bromo-2-thiophenecarboxaldehyde (15 g, 79 mmol) was added and the reaction temperature was maintained at −78° C. When judged to be complete, the reaction was quenched by dropwise addition of water and extracted with ethyl acetate. The organics were collected, dried over Na₂SO₄, filtered and concentrated under reduced pressure to provide 187 (16.3 g, 62%). The product was used in the next step without further purification or characterization.

Step B:

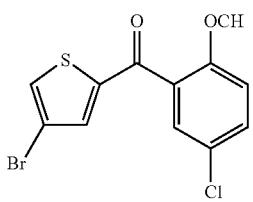

188

In a round bottom flask equipped with a stir bar and nitrogen on demand were placed the alcohol 187 (16.3 g, 49 mmol), CH₂Cl₂ (200 mL), and MnO₂ (21.1 g, 240 mmol). The reaction was allowed to stir at RT for 18-24 h, after which time the mixture was filtered through a pad of celite and the solvents were removed under reduced pressure to provide 188 (2.3 g, 14%) as an orange oil. The product was used in the next step without further purification. ¹H NMR (400 MHz, DMSO-d₆) δ 8.19 (s, 1H), 7.55 (m, 1H), 7.45 (m, 2H), 7.19 (d J=9 Hz, 1H), 3.72 (s, 3H).

Step C:

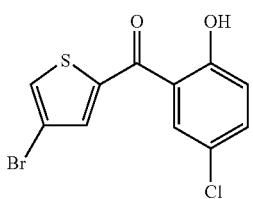

189

Anisole 188 (2.3 g, 7.0 mmol), CH₂Cl₂ (100 mL), and BBr₃ (21 mL of a 1.0 M soln. in CH₂Cl₂, 21 mmol) were used according to general procedure to provide 189 (2.1 g, 94%) as a yellow solid. The product was used without further purification in the next step. ¹H NMR (300 MHz, DMSO-d₆) δ 10.45 (s, 1H), 8.24 (s, 1H), 7.57 (d, J=1.2 Hz, 1H), 7.46 (m, 2H), 7.02 (d, J=9 Hz, 1H).

Step D:

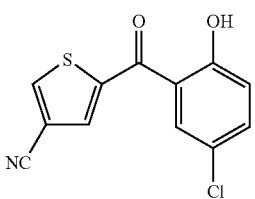

190

In a round bottom flask equipped with a stir bar and nitrogen on demand was added the phenol 189 (2.1 g, 6.6 mmol), N-methylpyrollidinone (100 mL), and CuCN (1.2 g, 13.2 mmol) and the reaction was heated to reflux for 2-5 h. When judged to be complete, the reaction was poured into a separatory funnel containing ethyl acetate and water. The organics were collected, treated with activated carbon, dried over Na₂SO₄, filtered through a pad of celite and the solvents were removed under reduced pressure. The resulting brown oil was purified by flash chromatography using 5% MeOH/CH₂Cl₂ as eluant to provide 190 (0.5 g, 29%) as a yellow solid: ¹H NMR (400 MHz, CDCl₃) δ 11.17 (s, 1H), 8.26 (s, 1H), 7.85 (s, 1H), 7.79 (s, 1H), 7.51 (d, J=9 Hz, 1H), 7.05 (d, J=9 Hz, 1H).

Step E:

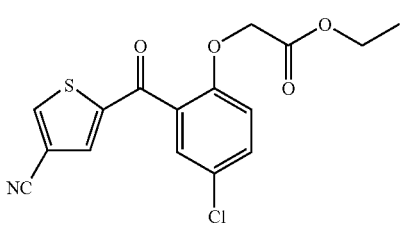

191

Phenol 190 (0.5 g, 1.9 mmol), K₂CO₃ (0.66 g, 4.7 mmol), ethyl bromoacetate (0.2 mL, 0.32 g, 1.9 mmol) and acetone (20 mL) were used according to general procedure II to provide 191 as a clear oil (0.7 g, >100%). The product was used in the next step without further purification. ¹H NMR (300 MHz, DMSO-d₆) δ 9.00 (s, 1H), 8.09 (s, 1H), 7.62 (dd, J=3, 9 Hz, 1H), 7.54 (d, J=3 Hz, 1H), 7.17 (d, J=9 Hz, 1H), 4.81 (s, 2H), 4.07 (m, 2H), 1.21 (m, 3H).

Step F:

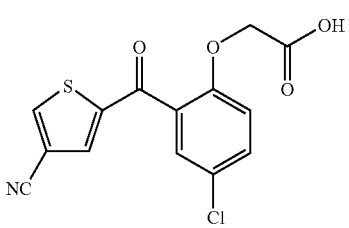

192

Ester 191 (0.7 g, 2 mmol), THF (10 mL), water (5 mL), EtOH (5 nL) and LiOH (0.2 g, 5 mmol) were used according to general procedure III to provide 192 (0.5 g, 80%) as an orange gel. The product was used in the next step without further purification or characterization.

Step G:

Carboxylic acid 192 (0.16 g, 0.49 mmol), amine 399 (0.13 g, 0.34 mmol), HOBt (0.079 g, 0.34 mmol), EDAC (0.14 g, 0.34 mmol) and anhydrous DMF (7 mL) were used according to general procedure IV. Treatment of resulting product with diethyl ether provided 186 (0.052 g, 21%) as a pale yellow solid: ¹H NMR (400 MHz, DMSO-d₆) δ 9.11 (s, 1H), 8.94 (s, 1H), 8.12 (s, 1H), 7.62 (d, J=9 Hz, 1H), 7.53 (d, J=2.4 Hz, 1H), 7.20 (d, J=9 Hz, 1H), 7.14 (d, J=9 Hz, 1H), 6.84 (s, 1H), 6.77 (d, J=8 Hz, 1H), 4.77 (s, 2H), 3.70 (m, 2H), 3.52 (m, 2H), 2.87 (m, 2H), 2.63 (m, 2H), 2.03 (s, 3H). MS(ES): 528 (M⁺).

Example 86

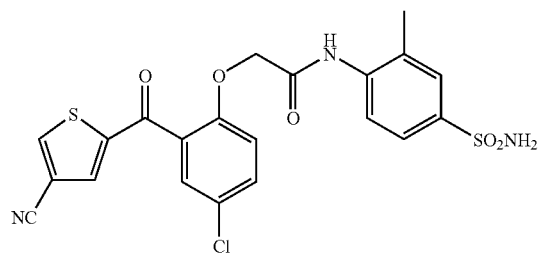

193

In a round bottom flask equipped with a stir bar and nitrogen on demand was added the acid 192 (0.36 g, 1.1 mmol), $CH_2Cl_2$ (20 mL) and oxalyl chloride (0.1 mL, 0.14 g, 1.1 mmol). The mixture was cooled to 0° C. and N,N-dimethylformamide (1-2 drops) was added. The reaction was allowed to warm to rt over a period of 30-60 min, after which time the mixture was concentrated under reduced pressure to afford the acid chloride. The acid chloride, acetonitrile (20 mL), triethylamine (0.4 mL, 0.29 g, 2.9 mmol) and the sulfonamide (0.26 g, 1.4 mmol) were combined and allowed to stir at RT for 18-24 h. When judged to be complete, the reaction was poured into a separatory funnel containing water and ethyl acetate. The organics were collected, dried over $Na_2SO_4$, filtered and the solvents were removed under reduced pressure. The resulting gel was treated with diethyl ether to provide 193 (0.11 g, 20%) as a pale yellow solid. $^1$H NMR (400 MHz, DMSO-$d_6$) δ 9.45 (s, 1H), 8.95 (s, 1H), 8.11 (s, 1H), 7.61 (m, 6H), 7.23 (s, 2H), 4.87 (s, 2H), 2.23 (s, 3H).

Example 87

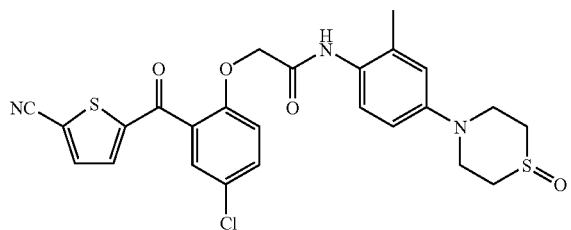

194

Step A:

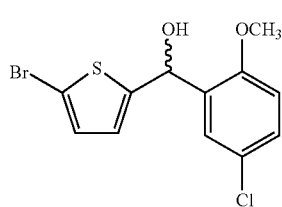

195

In a round bottom flask equipped with a stir bar, an addition funnel and nitrogen on demand was added 2-bromo-4-chloroanisole (9.8 mL, 15.7 g, 71.3 mmol) and diethyl ether (250 mL). The reaction was cooled to –78° C. by means of a dry ice/acetone bath, and n-butyllitium (45 mL of a 1.6 M soln. in hexanes, 72 mmol) was added dropwise, the reaction was allowed to stir for 30 min at –78° C., after which 5-bromo-2-thiophenecarboxaldehyde (15 g, 79 mmol) was added. When judged to be complete, the reaction was quenched by dropwise addition of water and extracted with ethyl acetate. The organics were collected, washed with brine, dried over $Na_2SO_4$, filtered and concentrated under reduced pressure to provide 195 (20 g, 77%). The product was used in the next step without further purification or characterization.

Step B:

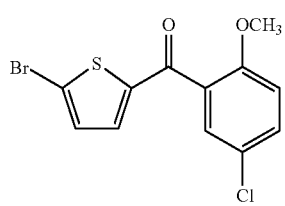

196

To a round bottom flask equipped with a stir bar and nitrogen on demand was added the alcohol 195 (20 g, 60 mmol), $CH_2Cl_2$ (300 mL), and $MnO_2$ (15.6 g, 180 mmol). The reaction was allowed to stir at RT for 90-min, after which time it was filtered through a pad of celite and the filtrate was concentrated under reduced pressure to provide 196 (15.3 g, 77%) as a pale yellow oil. The product was used in the next step without further purification. $^1$H NMR (400 MHz, DMSO-$d_6$) δ 7.55 (m, 1H), 7.42 (s, 1H), 7.33 (t, J=3, 9 Hz, 1H), 7.26 (t, J=3 Hz, 1H), 7.17 (m, 1H), 3.72 (s, 3H).

Step C:

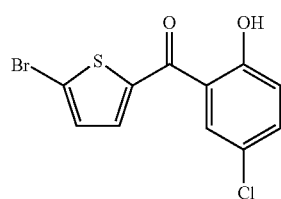

197

Anisole 196 (8.2 g, 25 mmol), $CH_2Cl_2$ (175 mL), and $BBr_3$ (74 mL of a 1.0 M soln. in $CH_2Cl_2$, 74 mmol) were used according to general procedure 1× to provide 197 (6.8 g, 87%). The product was used in the next step without further purification. $^1$H NMR (400 MHz, DMSO-$d_6$) δ 10.35 (s, 1H), 7.39 (dd, J=2.4, 6 Hz, 1H), 7.35 (m, 4H), 6.94 (dd, J=3, 9 Hz, 1H).

Step D:

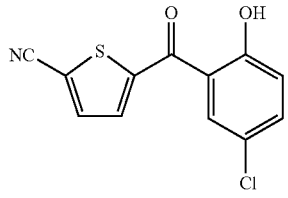

198

In a round bottom flask equipped with a stir bar and nitrogen on demand was added the phenol 197 (8.5 g, 27 mmol), N-methylpyrrolidinone (350 mL) and copper (I) cyanide (4.8 g, 54 mmol) and the reaction mixture was heated to reflux for 2-5 h. When judged to be complete, the reaction was allowed to cool to rt and poured into a beaker containing ethyl acetate and water. The organics were collected, treated with activated carbon, dried over Na$_2$SO$_4$, filtered through a pad of celite and the solvents were removed under reduced pressure. The resulting brown oil was purified by flash chromatography using 5% MeOH/CH$_2$Cl$_2$ as eluant to provide 198 (6.8 g, 21%) as a yellow solid: $^1$H NMR (300 MHz, DMSO-d$_6$) δ 10.57 (s, 1H), 8.04 (t, J=2 Hz, 1H), 7.68 (m, 1H), 7.48 (m, 2H), 7.03 (d, J=8.4 Hz, 1H). MS (ES): 262 (M−H)$^-$.

Step E:

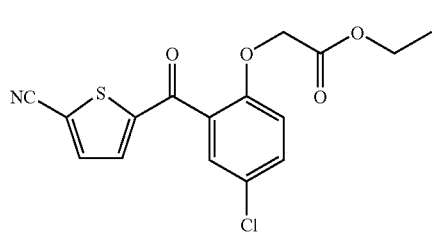

199

Phenol 198 (1.5 g, 5.7 mmol), K$_2$CO$_3$ (3.9 g, 29 mmol), ethyl bromoacetate (0.7 mL, 1.1 g, 6.3 mmol) and acetone (125 mL) were used according to general procedure II to provide 199 as a clear oil (2.0 g, >100%). The product was used in the next step without further purification or characterization.

Step F:

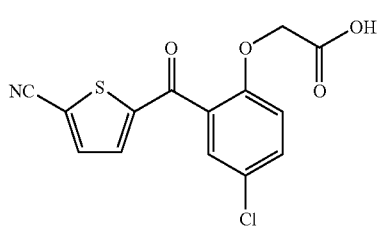

200

Ester 199 (2.0 g, 5.7 mmol), THF (20 mL), water (10 mL), EtOH (10 mL) and LiOH (1.0 g, 22.8 mmol) were used according to general procedure III to provide 200 (0.42 g, 23%) as an orange gel. The product was used in the next step without further purification or characterization.

Step G:

Carboxylic acid 200 (0.42 g, 1.3 mmol), amine 399 (0.36 g, 1.6 mmol), HOBt (0.22 g, 1.6 mmol), EDAC (0.38 g, 2.0 mmol) and anhydrous DMF (7 mL) were used according to general procedure IV. The resulting brown oil was purified by flash chromatography using 2% MeOH/CH$_2$Cl$_2$ as eluant. Treatment of the resulting product with diethyl ether provided 194 (0.071 g, 10%) as a white solid: $^1$H NMR (300 MHz, DMSO-d$_6$) δ 9.08 (s, 1H), 7.83 (d, J=4.5 Hz, 1H), 7.69 (m, 2H), 7.61 (s, 1H), 7.27 (d, J=9 Hz, 1H), 7.18 (d, J—9 Hz, 1H), 6.90 (s, 1H), 6.83 (d, J=8.4 Hz, 1H), 4.80 (s, 2H), 3.76 (m, 2H), 3.58 (m, 2H), 2.93 (m, 2H), 2.71 (m, 2H), 2.07 (s, 3H).

Example 88

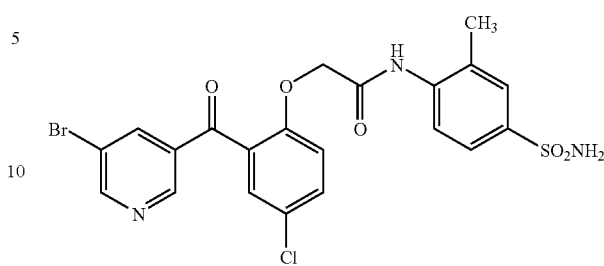

201

Step A:

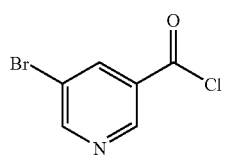

202

5-Bromonicotinic acid (5.0 g, 0.025 mol), oxalyl chloride (2.4 mL, 3.5 g, 0.027 mol), methylene chloride (125 mL), and N,N-dimethylformamide (2 drops) were used according to general procedure V to provide 202 (6.0 g, >100%) as a white solid. The product was used in the next step without further purification. $^1$H NMR (300 MHz, DMSO-d$_6$) δ 9.04 (d, J=1.5 Hz, 1H), 8.97 (d, J=2.1 Hz, 1H), 8.44 (t, J=1.8 Hz, 1H).

Step B:

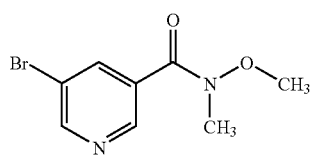

203

Acid chloride 202 (4.0 g, 0.018 mol), N,O-dimethylhydroxylamine hydrochloride (3.5 g, 0.036 mol), Et$_3$N (7.5 mL, 5.5 g, 0.054 mol), and CHCl$_3$ (150 mL) were used according to general procedure VII to provide 203 (3.2 g, 74%) as a yellow oil. The product was used in the next step without further purification. $^1$H NMR (400 MHz, DMSO-d$_6$) δ 8.79 (d, J=2 Hz, 1H), 8.72 (d, J=1.6 Hz, 1H), 8.20 (t, J=2 Hz, 1H), 3.53 (s, 3H), 3.25 (s, 3H).

Step C:

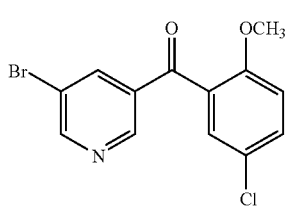

204

Amide 203 (1.8 g, 7.3 mmol), n-butyllithium (5.0 mL of a 1.6 M soln. in hexanes, 8.0 mmol), 2-bromo-4-chloroanisole (1.0 mL, 1.6 g, 7.3 mmol), and diethyl ether (20 mL) were used according to general procedure VIII. The product was purified by flash chromatography using 7:3 hexanes: ethyl acetate as eluant to afford 204 (1.5 g, 63%) as a pale yellow solid. $^1$H NMR (400 MHz, DMSO-$d_6$) δ 8.93 (d, J=2.4 Hz, 1H) 8.71 (d J=2 Hz, 1H), 8.21 (t, J=2 Hz, 1H), 7.63 (dd, J=2.8, 9.2 Hz, 1H), 7.48 (d, J=2.8 Hz, 1H), 7.22 (d, J=9.2 Hz, 1H), 3.65 (s, 3H).

Step D:

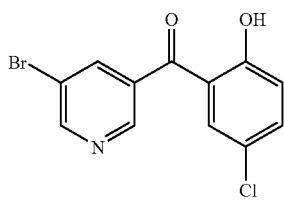

Anisole 204 (2.0 g, 6.1 mmol), BBr$_3$ (18.4 mL of a 1.0 M soln. in CH$_2$Cl$_2$, 18.4 mmol), and CH$_2$Cl$_2$ (50 mL) were used according to general procedure IX to afford 205 (3.4 g, >100%) as a yellow foam. The product was used in the next step without further purification. $^1$H NMR (400 MHz, DMSO-$d_6$) δ 10.57 (s, 1H), 8.91 (d, J=2.4 Hz, 1H), 8.75 (d, J=1.6 Hz, 1H), 8.21 (t, J=2 Hz, 1H), 7.48 (dd, J=2.8, 8.8 Hz, 1H), 7.41 (d, J=2.8 Hz, 1H), 6.97 (d, J=8.8 Hz, 1H). MS (ES): 314 (M+H)$^+$, 312 (M–H)$^-$.

Step E:

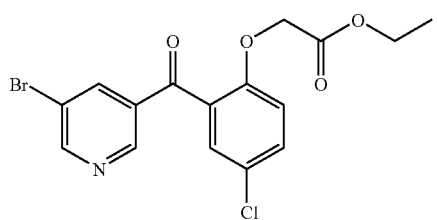

Phenol 205 (0.55 g, 1.7 mmol), ethyl bromoacetate (0.21 mL, 0.32 g, 1.9 mmol), K$_2$CO$_3$ (0.73 g, 5.3 mmol), and acetone (25 mL) were used according to general procedure II to provide 206 (0.58 g, 83%) as a red oil. The product was used in the next step without further purification. $^1$H NMR (400 MHz, DMSO-$d_6$) δ 8.97 (d, J=2.4 Hz, 1H), 8.84 (d, J=1.8 Hz, 1H), 8.30 (t, J=1.8 Hz, 1H), 7.66 (dd, J=2.7, 9 Hz, 1H), 7.57 (d, J=2.7 Hz, 1H), 7.19 (d, J=9 Hz, 1H), 4.82 (s, 2H), 4.18 (m, 2H), 1.2 (m, 3H).

Step F:

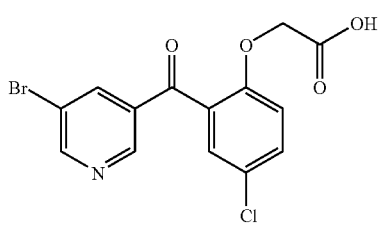

Ester 206 (0.58 g, 1.45 mmol), LiOH (0.15 g, 3.64 mmol) and a solution of THF, EtOH, and water (20 mL) were used according to general procedure III. The resulting orange residue was treated with diethyl ether to afford 207 (0.2 g, 42%) as a yellow solid. The product was used the next step without further purification or characterization.

Step G:

Acid 207 (91 mg, 0.25 mmol), oxalyl chloride (0.023 mL, 33 mg, 0.26 mmol), N,N-dimethylformamide (1 drop), and CH$_2$Cl$_2$ (10 mL) were used according to general procedure V to afford the acid chloride. The acid chloride, aniline 466 (42 mg, 0.23 mmol), NaHCO$_3$ (105 mg, 1.25 μmmol), acetone (10 mL), and water (0.5 mL) were used according to general procedure VI. The resulting yellow residue was washed with several portions of diethyl ether to afford 201 (20 mg, 15%) as a yellow solid. $^1$H NMR (400 MHz, DMSO-$d_6$) δ 9.41 (s, 1H), 8.89 (d, J=2.4 Hz, 1H), 8.83 (d, J=1.6 Hz, 1H), 8.29 (t, J=2 Hz, 1H), 7.65 (dd, J=2.8, 8.8 Hz, 1H), 7.62 (s, 1H), 7.58 (m, 2H), 7.53 (d, J=2.8 Hz, 1H), 7.22 (m, 3H), 4.79 (s, 2H), 2.15 (s, 3H). MS (ES): 538 (M–H)$^-$.

Example 89

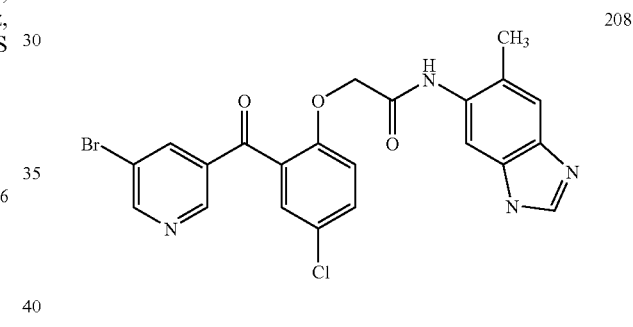

Step A:

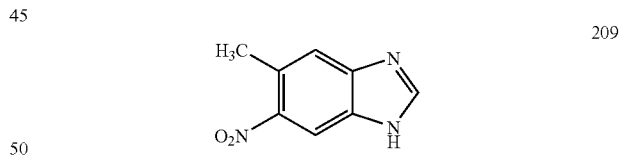

To a round-bottom flask equipped with a stir bar was added 5-methylbenzimidazole (4.0 g, 0.030 mol), and concentrated H$_2$SO$_4$ (65 mL). The reaction was cooled to 0° C. and potassium nitrate (2.75 g, 0.027 mol) was added portionwise. After stirring for 1 h, the reaction was poured over ice and solid Na$_2$CO$_3$ was added to adjust to pH>8. The aqueous layer was extracted with ethyl acetate, the organics were dried over Na$_2$SO$_4$, filtered and the solvent was removed under reduced pressure to afford a yellow solid. The solid was recrystallized using 1:1 methanol:water, making sure to filter any undissolved material while mixture was hot, to obtain 209 (1.8 g, 34%) as a pale yellow solid. $^1$H NMR (300 MHz, DMSO-$d_6$) δ 12.96 (bs, 1H), 8.48 (s, 1H), 8.34 (s, 1H), 7.65 (s, 1H), 2.64 (s, 3H). MS (ES): 222 (M–H)$^-$.

Step B:

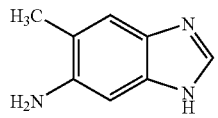
210

To a plastic-coated reaction vessel equipped with a stir bar, was added the nitro derivative 209 (2.2 g, 0.012 mol), absolute ethanol (75 mL), and palladium on charcoal (0.23 g of 10% Pd/C, 10% by weight). The vessel was placed on a hydrogenation apparatus at 50 psig for 16 h. When judged to be complete, the reaction was filtered through a celite plug and the solvents were removed under reduced pressure to provide a residue. The residue was washed several times with diethyl ether to afford 210 (1.0 g, 57%) as a pink solid. At ambient temperature, the product exists as a mixture of tautomers. $^1$H NMR (300 MHz, DMSO-$d_6$, 100° C.) δ 11.60 (bs, 1H), 7.79 (s, 1H), 7.20 (s, 1H), 6.82 (s, 1H), 4.39 (bs, 2H), 2.20 (s, 3H). MS (ES): 148 (M+H)$^+$.

Step C:

Acid 207 (0.1 g, 0.27 mmol), HOBt (40 mg, 0.27 mmol), EDAC (52 mg, 0.27 mmol), aniline 210 (40 mg, 9.27 mmol), and N,N-dimethylformamide (5 mL) were used according to general procedure IV. The product was purified by flash chromatography using 2% MeOH: 1% Et$_3$N: CHCl$_3$ as eluant to afford 208 (7.6 mg, 5%) as a pale yellow solid. $^1$H NMR (400 MHz, DMSO-$d_6$) δ 9.18 (s, 1H), 8.85 (m, 2H), 8.30 (s, 1H), 8.12 (s, 1H), 7.66 (d, J=7 Hz, 1H), 7.53 (m, 2H), 7.37 (m, 1H), 7.23 (d, J=9 Hz, 1H), 4.75 (s, 2H), 2.12 (s, 3H). MS (ES): 501 (M+H)$^+$.

Example 90

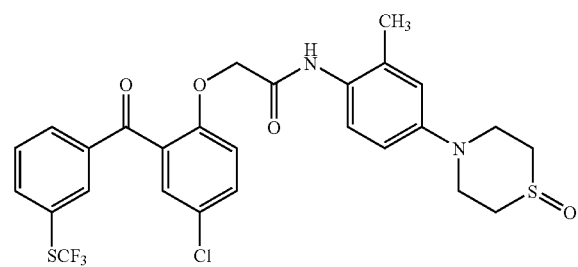
211

Step A:

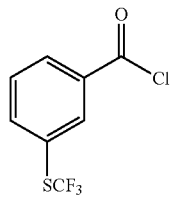
212

3-(Trifluoromethylthio)benzoic acid (2.0 g, 9.0 mmol), oxalyl chloride (0.8 mL, 1.14 g, 9.0 mmol), methylene chloride (50 mL), and N,N-dimethylformamide (4 drops) were used according to general procedure V to provide 212 (2.0 g, 94%). The product was used in the next step without further purification or characterization.

Step B:

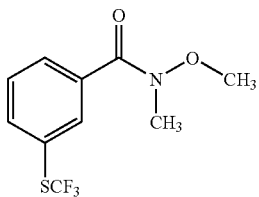
213

Acid chloride 212 (2.0 g, 8.3 mmol), N,O-dimethylhydroxylamine hydrochloride (2.0 g, 20.5 mmol), Et$_3$N (2.4 mL, 1.7 g, 16.8 mmol), and CHCl$_3$ (40 mL) were used according to general procedure VII to provide 213 (1.6 g, 70%) as a clear oil. The product was used in the next step without further purification. $^1$H NMR (400 MHz, DMSO-$d_6$) δ 7.87 (s, 1H), 7.79 (m, 2H), 7.60 (t, 1H), 3.50 (s, 3H), 3.24 (s, 3H).

Step C:

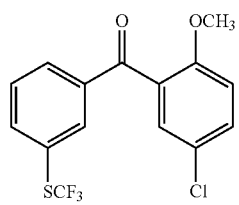
214

Amide 213 (0.8 g, 3.0 mmol), n-butyllithium (1.3 mL of a 2.5 M soln. in hexanes, 3.3 mmol), 2-bromo-4-chloroanisole (0.41 mL, 0.66 g, 3.0 mmol), and diethyl ether (10 mL) were used according to general procedure VIII. The product was purified by flash chromatography using 7:3 hexanes: ethyl acetate as eluant to afford 214 (0.56 g, 55%). $^1$H NMR (400 MHz, DMSO-$d_6$) δ 7.97 (d, J=8 Hz, 1H), 7.87 (m, 2H), 7.68 (d, J=8 Hz, 1H), 7.60 (dd, J=2.4, 8.8 Hz, 1H), 7.45 (d, J=2.8 Hz, 1H), 7.21 (d, J=8.8 Hz, 1H), 3.62 (s, 3H).

Step D:

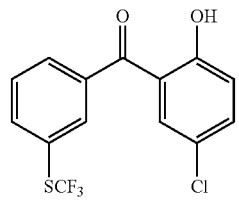
215

Anisole 214 (0.56 g, 1.6 mmol), BBr$_3$ (2.0 mL of a 1.0 M soln. in CH$_2$Cl$_2$, 2.0 mmol), and CH$_2$Cl$_2$ (10 mL) were used according to general procedure 1x to afford 215 (0.45 g, 86%). The product was used in the next step without further purification. $^1$H NMR (400 MHz, DMSO-$d_6$) δ 10.42 (s, 1H), 7.95 (m, 2H), 7.87 (d, J=8 Hz, 1H), 7.66 (t, J=8 Hz, 1H), 7.44 (dd, J=2.8, 8.8 Hz, 1H), 7.35 (d, J=2.8 Hz, 1H), 6.96 (d, J=8.8 Hz, 1H). MS (ES): 331 (M−H)$^−$ Step E:

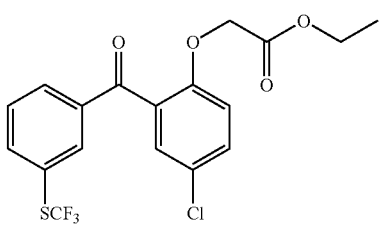

Phenol 215 (0.45 g, 1.4 mmol), ethyl bromoacetate (0.17 mL, 0.25 g, 1.5 mmol), K₂CO₃ (0.48 g, 2.5 mmol), and acetone (20 mL) were used according to general procedure II to provide 216 (0.6 g, >100%) as a yellow oil. The product was used in the next step without further purification or characterization.

Step F:

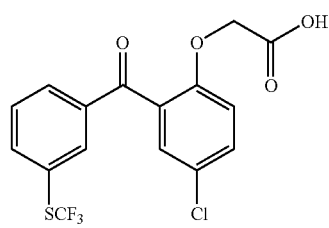

Ester 216 (0.6 g, 1.4 mmol), LiOH (0.15 g, 3.64 mmol) and a solution of THF, EtOH, and water (15 mL) were used according to general procedure III. The resulting yellow oil was treated with hexanes to afford 217 (0.2 g, 36%) as a white solid. $^1$H NMR (400 MHz, DMSO-d₆) δ 8.13 (d, J=7.6 Hz, 1H), 8.06 (s, 1H), 7.92 (d, J=7.2 Hz, 1H), 7.60 (t, J=7.6 Hz, 1H), 7.46 (dd, J=2.8, 9.2 Hz, 1H), 7.33 (d, J=2.4 Hz, 1H), 6.85 (d, J=9.2 Hz, 1H), 3.96 (s, 2H). MS (ES): 389 (M−H)⁻.

Step G:

Acid 217 (50 mg, 0.13 mmol), HOBt (18 mg, 0.13 mmol), EDAC (25 mg, 0.13 mmol), aniline 399 (29 mg, 0.13 mmol), and N,N-dimethylformamide (5 mL) were used according to general procedure IV. The product was purified by flash chromatography using 5% MeOH:CHCl₃ as eluant and treated with several portions of hexanes to afford 211 (40 mg, 51%) as a beige solid. $^1$H NMR (400 MHz, DMSO-d₆) δ 8.92 (s, 1H), 8.00 (s, 1H), 7.96 (d, J=1.6 Hz, 1H), 7.94 (d, J=1.2 Hz, 1H), 7.64 (m, 2H), 7.49 (d, J=2.4 Hz, 1H), 7.20 (d, J=8.8 Hz, 1H), 7.06 (d, J=8.8 Hz, 1H), 6.81 (d, J=2.8 Hz, 1H), 6.75 (dd, J=2.4, 8.8 Hz, 1H), 4.65 (s, 2H), 3.69 (m, 2H), 3.51 (m, 2H), 2.86 (m, 2H), 2.64 (m, 2H), 1.96 (s, 3H). MS (ES): 597 (M⁺), 596 (M−H)⁻.

Example 91

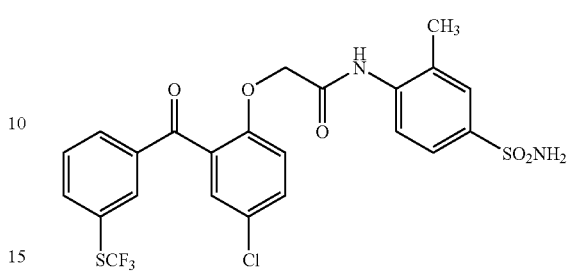

Acid 217 (70 mg, 0.18 mmol), oxalyl chloride (0.017 mL, 25 mg, 0.20 mmol), N,N-dimethylformamide (1 drop), and CH₂Cl₂ (7 mL) were used according to general procedure V to afford the acid chloride. The acid chloride, aniline 466 (39 mg, 0.21 mmol), NaHCO₃ (84 mg, 1.0 mmol), acetone (7 mL), and water (0.5 mL) were used according to general procedure VI. The resulting yellow solid was washed with minimal diethyl ether to afford 218 (50 mg, 45%) as a white solid. $^1$H NMR (300 MHz, DMSO-d₆) δ 9.44 (s, 1H), 8.38 (m, 3H), 8.01 (m, 1H), 7.70 (m, 5H), 7.31 (m, 3H), 4.80 (s, 2H), 2.16 (s, 3H). MS (ES): 559 (M⁺).

Example 92

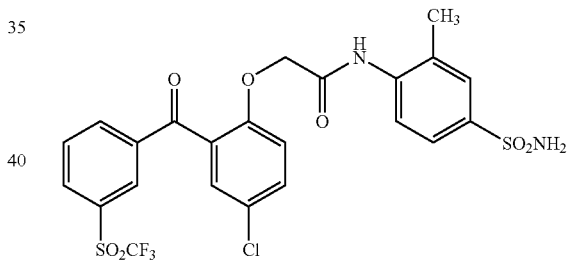

Step A:

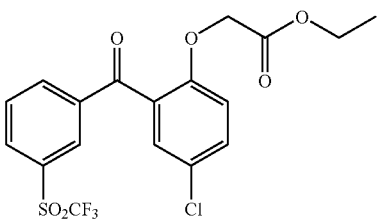

To a round-bottom flask equipped with a stir bar, nitrogen on demand, and an addition funnel; were placed the ester 216 (0.56 g, 1.34 mmol) and CH₂Cl₂ (25 mL) and the reaction mixture was cooled to 0° C. A solution of m-chloroperoxybenzoic acid in CH₂Cl₂ (10 mL) was added dropwise via addition funnel and the resulting mixture was allowed to stir at 0° C. for 0.5 h, after which time it was allowed to warm to rt and stir for an additional 16 h. When judged to be complete, the reaction was quenched with 10% sodium metabisulfite solution and extracted with CH₂Cl₂. The organics were collected, washed with saturated NaHCO₃, dried over MgSO₄, filtered and the solvent was removed under reduced pressure to afford 220 (0.56 g, 93%) as a pale yellow oil. The product was used in the next reaction without further purification. ¹H NMR (400 MHz, DMSO-d₆) δ 8.38 (d, J=8 Hz, 1H), 8.29 (d, J=8 Hz, 1H), 8.22 (s, 1H), 7.96 (t, J=7.6 Hz, 1H), 7.62 (dd, J=2.8, 9.2 Hz, 1H), 7.55 (d, J=2.8 Hz, 1H), 7.17 (d, J=8.8 Hz, 1H), 4.70 (s, 2H), 4.05 (m, 2H), 1.21 (m, 3H).

Step B:

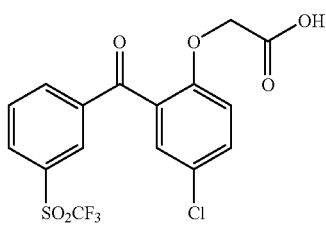

221

Ester 220 (0.56 g, 1.2 mmol), LiOH (0.13 g, 3.1 mmol) and a solution of THF, EtOH, and water (15 mL) were used according to general procedure III to afford 221 (0.1 g, 19%). The product was used in the next step without further purification or characterization.

Step C:

Acid 221 (100 mg, 0.24 mmol), oxalyl chloride (0.023 mL, 33 mg, 0.26 mmol), N,N-dimethylformamide (1 drop), and CH₂Cl₂ (10 mL) were used according to general procedure V to afford the acid chloride. The acid chloride, aniline 466 (41 mg, 0.22 mmol), NaHCO₃ (100 mg, 1.2 mmol), acetone (10 mL), and water (0.5 mL) were used according to general procedure VI. The product was purified by flash chromatography using 5% MeOH:CHCl₃ to afford 219 (72 mg, 51%) as a white solid. ¹H NMR (400 MHz, DMSO-d₆) δ 9.34 (s, 1H), 8.01 (s, 1H), 7.96 (m, 2H), 7.61 (m, 6H), 7.49 (s, 1H), 7.23 (m, 2H), 4.76 (s, 2H), 2.12 (s, 3H).

Example 93

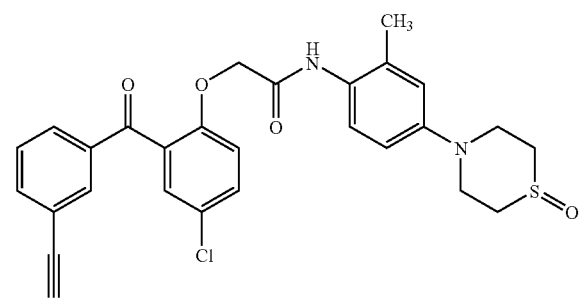

222

Step A:

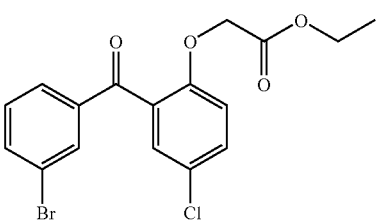

223

Phenol 432 (10 g, 0.032 mol), ethyl bromoacetate (3.5 mL, 5.3 g, 0.032 mol), K₂CO₃ (11 g, 0.080 mol), and acetone (120 mL) were used according to general procedure II to afford 223 (11.5 g, 91%) as a yellow oil. The product was used in the next step without further purification. ¹H NMR (400 MHz, DMSO-d₆) δ 7.82 (m, 2H), 7.68 (d, J=7.6 Hz, 1H), 7.53 (dd, J=2.4, 8.8 Hz, 1H), 7.44 (m, 2H), 7.09 (d, J=9.2 Hz, 1H), 4.74 (s, 2H), 4.04 (q, J=7.2 Hz, 2H), 1.13 (m, 3H).

Step B:

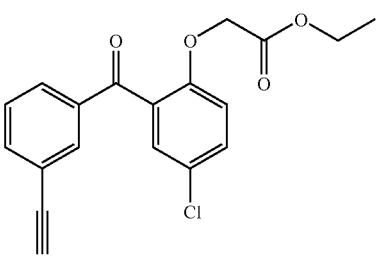

224

To a round-bottom flask equipped with a stir bar and nitrogen on demand were added the ester 223 (1.5 g, 3.8 mmol), trimethylsilylacetylene (0.6 mL, 0.4 g, 4.1 mmol), tetrakis(triphenylphosphine)palladium (0) (0.31 g, 0.27 mmol), copper(I) iodide (0.15 g, 0.80 mmol), triethylamine (1.7 mL, 1.2 g, 0.80 mmol), and N,N-dimethylformamide (15 mL) and the reaction was allowed to stir at 80° C. for 18 h. When judged to be complete, the reaction mixture was poured into ethyl acetate and water. The organics were collected, washed with water and brine, dried over Na₂SO₄, filtered through a pad of celite, and the solvents were removed under reduced pressure. To the resulting residue was added tetrahydrofuran (20 mL) and tetrabutylammonium fluoride (3 mL). The mixture was allowed to stir at RT for 10 min, after which it was poured into a separatory funnel containing ethyl acetate and water. The organics were collected, dried over Na₂SO₄, filtered, and the solvents were removed under reduced pressure. The resulting product was purified by flash chromatography using 7:3 hexanes:ethyl acetate to provide 224 (0.69 g, 53%). ¹H NMR (400 MHz, DMSO-d₆) δ 7.73 (m, 2H), 7.54 (m, 2H), 7.44 (s, 1H), 7.34 (m, 1H), 7.09 (d, J=9.2 Hz, 1H), 4.74 (s, 2H), 4.04 (m, 2H), 1.11 (m, 3H). MS (ES): 343 (M⁺).

Step C:

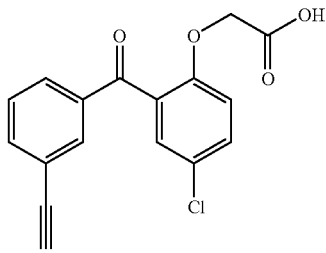
225

Ester 224 (0.69 g, 2.0 mmol), LiOH (0.2 g, 5.0 mmol) and a solution of THF, EtOH, and water (12 mL) were used according to general procedure III to afford 225 (0.37 g, 59%). $^1$H NMR (400 MHz, DMSO-d$_6$) δ 13.30 (bs, 1H), 7.86 (s, 1H), 7.73 (m, 2H), 7.54 (m, 2H), 4.62 (s, 2H), 4.25 (s, 1H).

Step D:

Acid 225 (75 mg, 0.24 mmol), HOBt (32 mg, 0.24 mmol), EDAC (46 mg, 0.24 mmol), aniline 399 (53 mg, 0.24 mmol), and N,N-dimethylformamide (5 mL) were used according to general procedure IV. The product was purified by flash chromatography using 5% MeOH:CHCl$_3$ as eluant and treated with several portions of hexanes to afford 222 (17 mg, 14%) as a pale yellow solid. $^1$H NMR-(400 MHz, DMSO-d$_6$) δ 8.86 (s, 1H), 7.75 (m, 2H), 7.70 (d, J=7.6 Hz, 1H), 7.60 (dd, J=2.8, 9.2 Hz, 1H), 7.49 (t, J=8 Hz, 1H), 7.45 (d, J=2.8 Hz, 1H), 7.21 (d, J=9.2 Hz, 1H), 7.09 (d, J=8.8 Hz, 1H), 6.81 (s, 1H), 6.75 (m, 1H), 4.66 (s; 2H), 4.28 (s, 1H), 3.69 (m, 2H), 3.52 (m, 2H), 2.86 (m,-2H), 2.63 (m, 2H), 1.96 (s, 3H). MS (ES): 521 (M$^+$).

Example 94

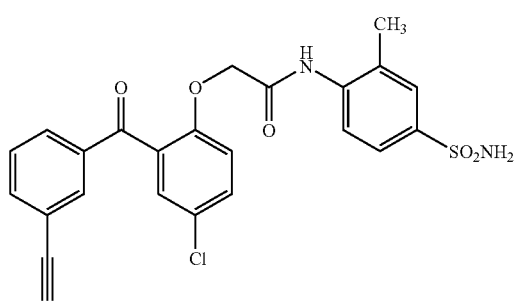
226

Step A:

Acid 225 (80 mg, 0.25 mmol), oxalyl chloride (0.024 mL, 35 mg, 0.28 mmol), N,N-dimethylformamide (1 drop), and CH$_2$Cl$_2$ (3 mL) were used according to general procedure V to afford the acid chloride. The acid chloride, aniline 466 (48 mg, 0.26 mmol), NaHCO$_3$ (105 mg, 1.3 mmol), acetone (7 mL), and water (0.5 mL) were used according to general procedure VI. The product was purified by flash chromatography using 5% MeOH:CHCl$_3$ to afford 226 (20 mg, 16%) as a white solid. $^1$H NMR (400 MHz, DMSO-d$_6$) δ 9.30 (s, 1H), 7.77 (d, J=7.6 Hz, 1H), 7.70 (d, J=7.6 Hz, 1H), 7.58 (m, 4H), 7.45 (m, 2H), 7.22 (m, 3H), 4.77 (s, 2H), 4.27 (s, 1H), 2.13 (s, 3H). MS ES): 482 (M$^+$), 481 (M–H)$^-$.

Example 95

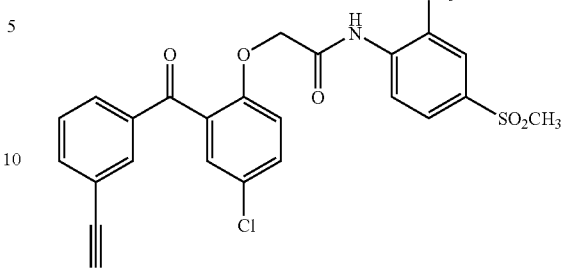
227

Step A:

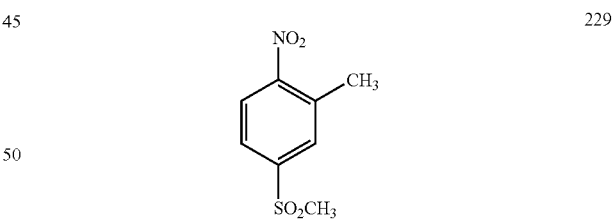
228

To a round-bottom flask equipped with a stir bar and nitrogen on demand was added 5-fluoro-2-nitrotoluene (2.4 mL, 3.0 g, 0.019 mol), sodium thiomethoxide (1.5 g, 0.021 mol), and N,N-dimethylformamide (50 mL). The reaction was allowed to stir at 85° C. for 2-4 h, after which time the reaction mixture was poured into a separatory funnel containing ethyl acetate and water. The organics were collected, washed with water, dried over Na$_2$SO$_4$, treated with activated carbon, filtered through celite and the solvents were removed under reduced pressure to afford 228 (2.95 g, 85%) as an orange oil. The product was used in the next step without further purification. $^1$H NMR (400 MHz, DMSO-d$_6$) δ 7.92 (s, 1H), 7.29 (d, J=1.6 Hz, 1H), 7.24 (dd, J=2, 8.4 Hz, 1H), 2.52 (s, 3H), 2.50 (s, 3H).

Step B:

229

To a round-bottom flask equipped with a stir bar and nitrogen on demand was added 228 (2.95 g, 0.016 mol) and CH$_2$Cl$_2$ (50 mL). The reaction was cooled to 0° C. and a solution of m-chloroperoxybenzoic acid (5.8 g, 0.033 mol) in CH$_2$Cl$_2$ (10 mL) was added dropwise via addition funnel. The resulting mixture was allowed to stir at 0° C. for 0.5 h, after which time it was allowed to warm to RT and stir for an additional 3-4 h. When judged to be complete, the reaction was quenched with 10% sodium metabisulfite solution and extracted with CH$_2$Cl$_2$. The organics were collected, washed with saturated NaHCO$_3$, dried over MgSO$_4$, filtered and the solvent was removed under reduced pressure to afford 229 (3.0 g, 88%) as yellow solid. The product was used in the next reaction without further purification. $^1$H NMR (400 MHz, CDCl$_3$)δ 8.06 (d, J=8.4 Hz, 1H), 7.92 (m, 2H), 3.08 (s, 3H), 2.65 (s, 3H).

Step C:

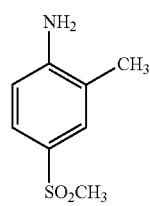
230

To a plastic-coated reaction vessel equipped with a stir bar, was added the nitro derivative 229 (1.5 g, 6.9 mmol), toluene (50 mL), and palladium on charcoal (0.15 g of 10% Pd/C, 10% by weight). The vessel was placed on a hydrogenation apparatus at 50 p.s.i. for 7 h. When judged to be complete, the reaction was filtered through a celite plug and the solvents were removed under reduced pressure to provide a crystalline material. The residue was washed several times with diethyl ether to afford 230 (1.3 g, >99%). $^1$H NMR (400 MHz, DMSO-d$_6$) δ 7.36 (m, 2H), 6.65 (d, J=8.4 Hz, 1H), 5.81 (s, 2H), 2.98 (s, 3H), 2.06 (s, 3H).

Step D:

Acid 225 (107 mg, 0.34 mmol), oxalyl chloride (0.032 mL, 47 mg, 0.37 mmol), N,N-dimethylformamide (1 drop), and CH$_2$Cl$_2$ (7 mL) were used according to general procedure V to afford the acid chloride. The acid chloride, aniline 230 (63 mg, 0.34 mmol), NaHCO$_3$ (143 mg, 1.7 mmol), acetone (7 mL), and water (0.5 mL) were used according to general procedure VI. The product was purified by flash chromatography using 5% MeOH:CHCl$_3$ to afford 227 (8 mg, 5%) as a white solid. $^1$H NMR (400 MHz, DMSO-d$_6$) δ 9.34 (s, 1H), 7.73 (m, 6H), 7.60 (dd, J=2.8, 8.8 Hz, 1H), 7.50 (t, J=8 Hz, 1H), 7.46 (d, J=2.4 Hz, 1H), 7.21 (d, J=8.8 Hz, 1H), 4.79 (s, 2H), 4.29 (s, 1H), 3.27 (s, 3H), 2.18 (s, 3H). MS ES): 481 (M-H)$^-$.

Example 96

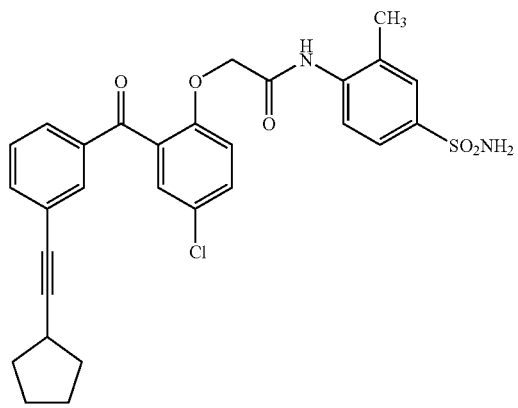
231

Step A:

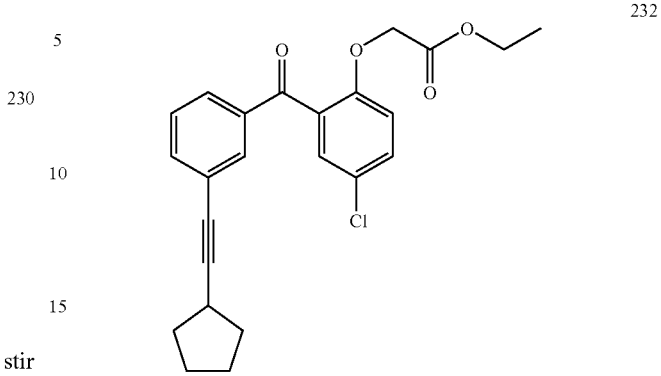
232

To a round-bottom flask equipped with a stir bar and nitrogen on demand were added the ester 223 (0.2 g, 0.5 mmol), cyclopentylacetylene (52 mg, 0.55 mmol), tetrakis(triphenylphosphine)palladium (0) (40 mg, 0.035 mmol), copper(I) iodide (20 mg, 0.11 mmol), triethylamine (0.22 mL, 0.16 g, 1.6 mmol), and N,N-dimethylformamide (5 mL) and the reaction was allowed to stir at 80° C. for 18 h. When judged to be complete, the reaction mixture was poured into ethyl acetate and water. The organics were collected, washed with water, dried over Na$_2$SO$_4$, filtered, and the solvents were removed under reduced pressure. The product was purified by flash chromatography using 8:2 hexanes:ethyl acetate to afford 232 (130 mg, 63%) as an orange oil. $^1$H NMR (300 MHz, DMSO-d$_6$) δ 7.68 (m, 3H), 7.59 (dd, J=2.7, 9 Hz, 1H), 7.48 (m, 2H), 7.13 (d, J=9 Hz, 1H), 4.79 (s, 2H), 4.10 (m, 2H), 2.88 (m, 1H), 2.00 (m, 2H), 1.63 (m, 6H), 1.17 (m, 3H).

Step B:

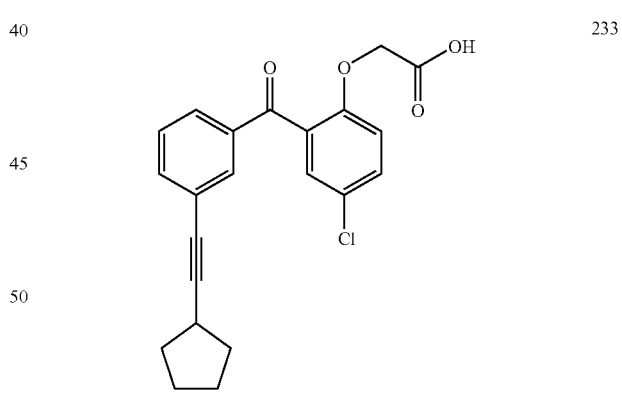
233

Ester 232 (0.13 g, 0.32 mmol), LiOH (33 mg, 0.79 mmol) and a solution of THF, EtOH, and water (8 mL) were used according to general procedure III to afford 233 (0.15 g, >99%). The product was used in the next step without further purification or characterization.

Step C:

Acid 233 (140 mg, 0.37 mmol), oxalyl chloride (0.033 mL, 48 mg, 0.38 mmol), N,N-dimethylformamide (1 drop), and CH$_2$Cl$_2$ (5 mL) were used according to general procedure V to afford the acid chloride. The acid chloride, aniline 466 (73 mg, 0.39 mmol), NaHCO$_3$ (155 mg, 1.85 mmol), acetone (7 mL), and water (0.5 mL) were used according to general procedure VI. The product was purified by flash chromatography using 5% MeOH:CHCl₃ to afford 231 (88 mg, 43%) as a white solid. ¹H NMR (400 MHz, DMSO-d₆) δ 9.28 (s, 1H), 7.61 (m, 8H), 1.44 (m, 2H), 7.21 (m, 2H), 4.77 (s, 2H), 2.81 (m, 1H), 2.14 (s, 3H), 1.93 (m, 2H), 1.58 (m, 6H).

Example 97

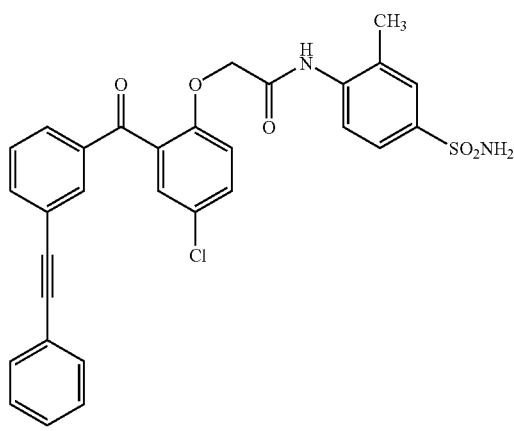

234

Step A:

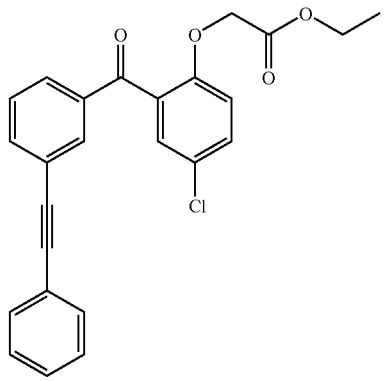

235

To a round-bottom flask equipped with a stir bar and nitrogen on demand were added the ester 223 (0.2 g, 0.5 mmol), phenylacetylene (52 mg, 0.55 mmol), tetrakis(triphenylphosphine)palladium (40 mg, 0.035 mmol), copper(I) iodide (20 mg, 0.11 mmol), triethylamine (0.22 mL, 0.16 g, 1.6 mmol), and N,N-dimethylformamide (5 mL) and the reaction was allowed to stir at 80° C. for 18 h. When judged to be complete, the reaction mixture was poured into ethyl acetate and water. The organics were collected, washed with water, dried over Na₂SO₄, filtered, and the solvents were removed under reduced pressure. The product was purified by flash chromatography using 8:2 hexanes:ethyl acetate to afford 235 (150 mg, 72%) as a green oil. ¹H NMR (300 MHz, DMSO-d₆) δ 7.87 (d, J=4.8 Hz, 1H), 7.82 (m, 2H), 7.60 (m, 4H), 7.50 (d, J=3 Hz, 1H), 7.46 (m, 3H), 7.15 (d, J=9 Hz, 1H), 4.82 (s, 2H), 4.10 (m, 2H), 1.21 (m, 3H).

Step B:

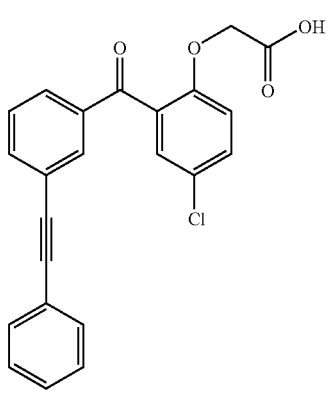

236

Ester 235 (0.15 g, 0.36 mmol), LiOH (38 mg, 0.90 mmol) and a solution of THF, EtOH, and water (8 mL) were used according to general procedure III to afford 236 (64 mg, 46%). The product was used in the next step without further purification or characterization.

Step C:

Acid 236 (64 mg, 0.16 mmol), oxalyl chloride (0.015 mL, 23 mg, 0.17 mmol), N,N-dimethylformamide (1 drop), and CH₂Cl₂ (5 mL) were used according to general procedure V to afford the acid chloride. The acid chloride, aniline 466 (31 mg, 0.17 mmol), NaHCO₃ (67 mg, 0.8 mmol), acetone (5 mL), and water (0.5 mL) were used according to general procedure VI. The product was filtered through a pad of silica gel to afford 234 (10 mg, 11%) as a white solid. ¹H NMR (400 MHz, DMSO-d₆) δ 9.34 (s, 1H), 7.90 (s, 1H), 7.79 (m, 2H), 7.62 (m, 3H), 7.54 (m, 4H), 7.47 (d, J=3 Hz, 1H), 7.38 (m, 3H), 7.22 (m, 3H), 4.80 (s, 2H), 2.15 (s, 3H).

Example 98

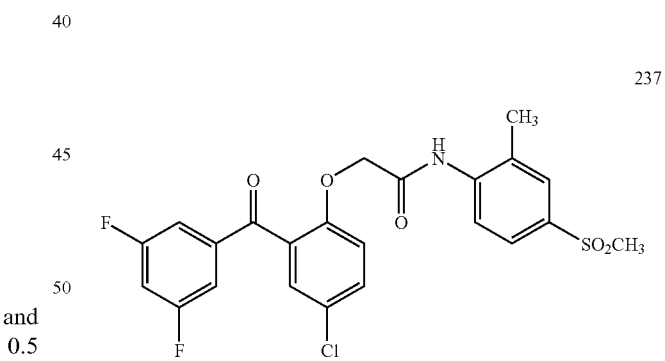

237

Step A:

Acid 49 (120 mg, 0.37 mmol), oxalyl chloride (0.035 mL, 50 mg, 0.40 mmol), N,N-dimethylformamide (1 drop), and CH₂Cl₂ (7 mL) were used according to general procedure V to afford the acid chloride. The acid chloride, aniline 230 (69 mg, 0.37 mmol), NaHCO₃ (155 mg, 1.85 mmol), acetone (7 mL), and water (0.5 mL) were used according to general procedure VI. The resulting yellow oil was treated with pentanes to afford 237 (39 mg, 21%) as a pale yellow solid. ¹H NMR (300 MHz, DMSO-d₆) δ 9.51 (s, 1H), 7.66 (m, 5H), 7.53 (d, J=2.7 Hz, 1H), 7.49 (m, 2H), 7.25 (d, J=9 Hz, 1H), 4.87 (s, 2H), 3.20 (s, 3H), 2.26 (s, 3H). MS (ES): 494 (M⁺).

Example 99

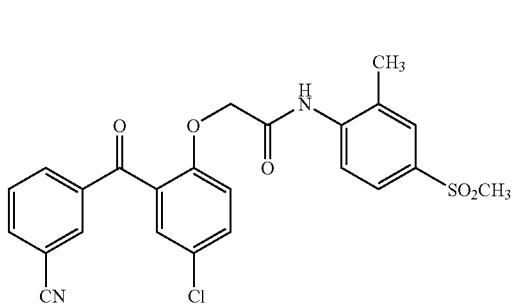

238

Acid 129 (120 mg, 0.38 mmol), oxalyl chloride (0.037 mL, 53 mg, 0.42 mmol), N,N-dimethylformamide (1 drop), and CH$_2$Cl$_2$ (7 mL) were used according to general procedure V to afford the acid chloride. The acid chloride, aniline 230 (70 mg, 0.38 mmol), NaHCO$_3$ (160 mg, 1.9 mmol), acetone (7 mL), and water (0.5 mL) were used according to general procedure VI. The product purified by flash chromatography using 5% MeOH:CHCl$_3$ to afford 238 (18 mg, 10%) as a yellow solid. $^1$H NMR (400 MHz, DMSO-d$_6$) δ 9.42 (s, 1H), 8.16 (s, 1H), 8.06 (m, 2H), 7.67 (m, 25H), 7.49 (d, J=2.8 Hz, 1H), 7.21 (d, J=9.2 Hz, 1H), 4.80 (s, 2H), 3.14 (s, 3H), 2.18 (s, 3H). MS (ES): 481 (M–H)$^-$

Example 100

239

Acid 71 (300 mg, 0.8 mmol), HOBt (108 mg, 0.8 mmol), EDAC (153 mg, 0.8 mmol), aniline 210 (118 mg, 0.8 mmol), and N,N-dimethylformamide (7 mL) were used according to general procedure IV. The product was purified by flash chromatography using 3% MeOH: 1% Et$_3$N: CH$_2$Cl$_2$ as eluant to afford 239 (60 mg, 15%) as a white solid. At ambient temp. the product exists as a mixture of tautomers. $^1$H NMR (400 MHz, DMSO-d$_6$) δ 12.27 (m, 1H), 9.15 (m, 1H), 8.00 (s, 1H), 7.99 (d, J=8 Hz, 1H), 7.87 (m, 2H), 7.66 (d, J=9 Hz, 1H), 7.45 (m, 3H), 4.74 (s, 2H), 2.12 (m, 3H). MS (ES): 506 (M$^+$), 507 (M+H)$^+$.

Example 101

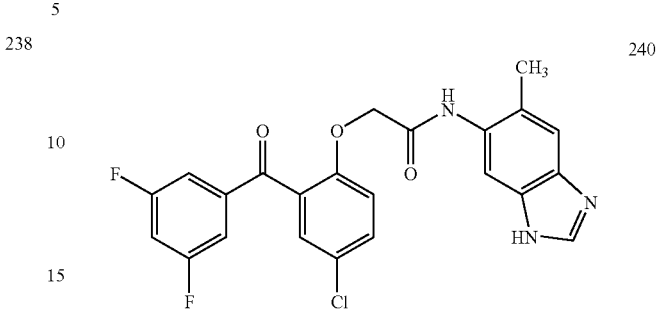

240

Acid 49 (120 mg, 0.37 mmol), oxalyl chloride (0.035 mL, 50 mg, 0.40 mmol), N,N-dimethylformamide (1 drop), and CH$_2$Cl$_2$ (10 mL) were used according to general procedure V to afford the acid chloride. The acid chloride, aniline 210 (54 mg, 0.37 mmol), NaHCO$_3$ (155 mg, 1.9 mmol), acetone (10 mL), and water (0.5 mL) were used according to general procedure VI. The product purified by flash chromatography using 5% MeOH:CHCl$_3$ to afford 240 (22 mg, 13%) as a pale yellow solid. At ambient temperature the product exists as a mixture of tautomers. $^1$H NMR (400 MHz, DMSO-d$_6$) δ 12.26 (m, 1H), 9.14 (m, 1H), 8.09 (s, 1H), 7.64 (d, J=9 Hz, 1H), 7.50 (m, 4H), 7.23 (m, 2H), 4.75 (m, 2H), 2.12 (m, 3H). MS (ES): 456 (M$^+$), 457 (M+H)$^+$, 455(M–H)$^-$.

Example 102

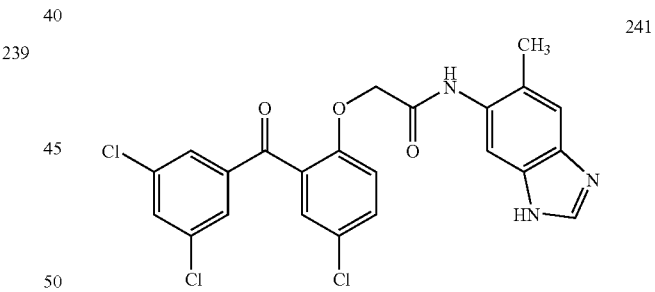

241

Acid 76 (120 mg, 0.33 mmol), oxalyl chloride (0.032 mL, 46 mg, 0.37 mmol), N,N-dimethylformamide (1 drop), and CH$_2$Cl$_2$ (10 mL) were used according to general procedure V to afford the acid chloride. The acid chloride, aniline 210 (51 mg, 0.35 mmol), NaHCO$_3$ (139 mg, 1.7 mmol), acetone (10 mL), and water (0.5 mL) were used according to general procedure VI. The product purified by flash chromatography using 2% MeOH:CH$_2$Cl$_2$ to afford 241 (11 mg, 7%) as a white solid. At ambient temperature the product exists as a mixture of tautomers. $^1$H NMR (400 MHz, DMSO-d$_6$) δ 12.26 (s, 1H), 9.15 (m, 1H), 8.09 (s, 1H), 7.87 (m, 1H), 7.70 (m, 2H), 7.64 (m, 1H), 7.55 (m, 2H), 7.21 (m, 1H), 4.75 (m, 2H), 2.12 (m, 3H). MS (ES): 490 (M+H)$^+$, 488 (M–H)$^-$.

Example 103

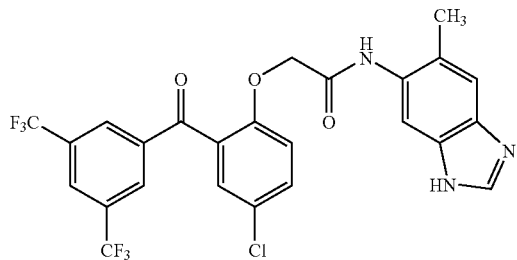

Step A:

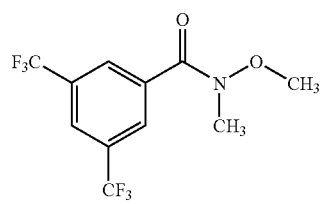

3,5-Bis(trifluoromethyl)benzoyl chloride (5.0 g, 0.018 mol), N,O-dimethylhydroxylamine hydrochloride (3.5 g, 0.036 mol), Et$_3$N (7.5 mL, 5.5 g, 0.054 mol), and CH$_2$Cl$_2$ (50 mL) were used according to general procedure VII to provide 243 (5.0 g, 92%) as a clear oil. The product was used in the next step without further purification. $^1$H NMR (400 MHz, DMSO-d$_6$) δ 8.24 (s, 1H), 8.22 (s, 2H), 3.52 (s, 3H), 3.28 (s, 3H).

Step B:

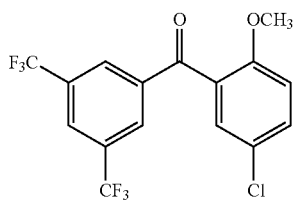

Amide 243 (5.0 g, 0.017 mol), n-butyllithium (11.4 mL of a 1.6 M solution in hexanes, 0.018 mol), 2-bromo-4-chloroanisole (2.3 mL, 3.8 g, 0.017 mol), and diethyl ether (60 mL) were used according to general procedure VIII. The product was purified by flash chromatography using 85:15 hexanes:ethyl acetate as eluant to afford 244 (3.76 g, 58%). $^1$H NMR (400 MHz, DMSO-d$_6$) 68.43 (s, 1H), 8.18 (s, 2H), 7.65 (t, J=2.8 Hz, 1H), 7.52 (d, J=2.8 Hz, 1H), 7.24 (d, J=8.8 Hz, 1H), 3.61 (s, 3H).

Step C:

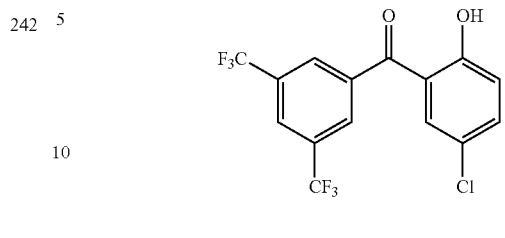

Anisole 244 (3.76 g, 9.8 mmol), BBr$_3$ (29 mL of a 1.0 M soln. in CH$_2$Cl$_2$, 29 mmol), and CH$_2$Cl$_2$ (80 mL) were used according to general procedure 1× to afford 245 (3.2 g, 89%) a pale green solid. The product was used in the next step without further purification. $^1$H NMR (400 MHz, DMSO-d$_6$) δ 10.6 (s, 1H), 8.40 (s, 1H), 8.21 (s, 2H), 7.48 (m, 2H), 6.98 (d, J=8.8 Hz, 1H).

Step D:

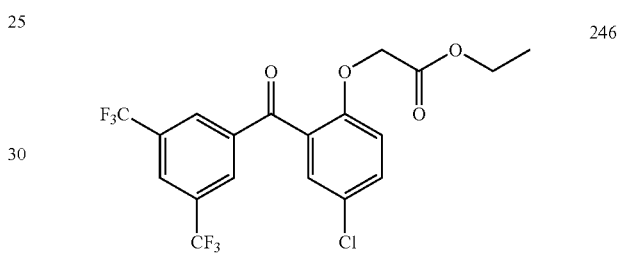

Phenol 245 (3.2 g, 8.7 mmol), ethyl bromoacetate (1.1 mL, 1.6 g, 9.5 mmol), K$_2$CO$_3$ (3.0 g, 21.7 mmol), and acetone (50 mL) were used according to general procedure II to provide 246 (3.8 g, 97%) as a pale yellow solid. The product was used in the next step without further purification. $^1$H NMR (300 MHz, DMSO-d$_6$) δ 8.47 (s, 1H), 8.31 (s, 2H), 7.68 (dd, J=3, 9 Hz, 1H), 7.61 (d, J=2.4 Hz, 1H), 7.21 (d, J=9 Hz, 1H), 4.79 (s, 2H), 4.06 (q, J=7 Hz, 2H), 1.13 (t, J=7 Hz, 3H).

Step E:

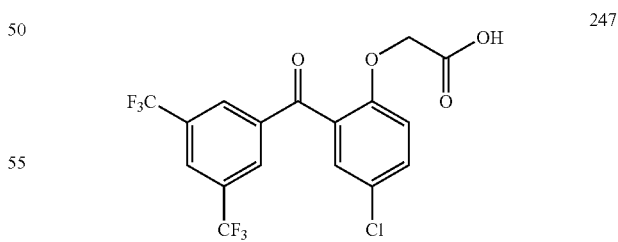

Ester 246 (3.8 g, 8.4 mmol), LiOH (0.88 g, 20.9 mmol) and a solution of THF, EtOH, and water (25 mL) were used according to general procedure III. The resulting white foam was treated with diethyl ether to afford 247 (3.1 g, 86%) as a white solid. $^1$H NMR (300 MHz, DMSO-d$_6$)δ 8.44 (s, 1H), 8.34 (s, 2H), 7.67 (dd, J=3, 9 Hz, 1H), 7.58 (d, J=3 Hz, 1H), 7.16 (d, J=9 Hz, 1H), 4.63 (s, 2H).

Step F:

Acid 247 (150 mg, 0.35 mmol), HOBt (47 mg, 0.35 mmol), EDAC (67 mg, 0.35 mmol), aniline 210 (52 mg, 0.35 mmol), and N,N-dimethylformamide (5 mL) were used according to general procedure IV. The product was purified by flash chromatography using 3% MeOH:CHCl₃ as eluant to afford 242 (9 mg, 5%) as a white solid. At ambient temperature, the product exists as a mixture of tautomers. ¹H NMR (300 MHz, DMSO-d₆) δ 12.32 (s, 1H), 9.20 (s, 1H), 8.44 (s, 1H), 8.35 (m, 2H), 8.14 (m, 1H), 7.76 (m, 1H), 7.62 (m, 1H), 7.51 (s, 1H), 7.30 (d, J=9 Hz, 1H), 4.77 (s, 2H), 2.13 (s, 3H). MS (ES): 556 (M⁺), 557 (M−H)⁻.

Example 104

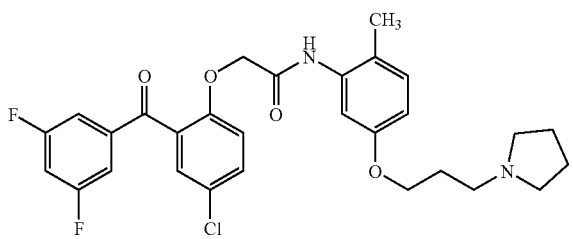

248

Step A:

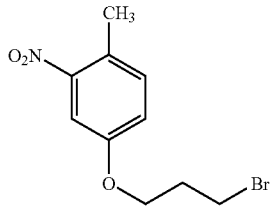

249

Into a round-bottom flask equipped with a stir bar and nitrogen on demand were placed 3-methyl-4-nitrophenol (2.0 g, 0.013 mol), dibromopropane (10.6 mL, 21.0 g, 0.10 mol), potassium carbonate (2.7 g, 0.02 mol), and N,N-dimethylformamide (50 mL) and the mixture was allowed to stir at rt for 18 h. When judged to be complete, the reaction mixture was poured into a separatory funnel containing CH₂Cl₂ and water. The organics were collected, washed with 0.5 N NaOH soln., dried over MgSO₄, filtered and the solvent was removed under reduced pressure. The resulting red oil was distilled to afford 249 (2.46 g, 69%). ¹H NMR (400 MHz, DMSO-d₆) δ 7.49 (d, J=2.4 Hz, 1H), 7.37 (d, J=8.4 Hz, 1H), 7.21 (dd, J=2.4, 8.4 Hz, 1H), 4.11 (t, J=6 Hz, 2H), 3.63 (t, J=6 Hz, 2H), 2.38 (s, 3H), 2.22 (m, 2H).

Step B:

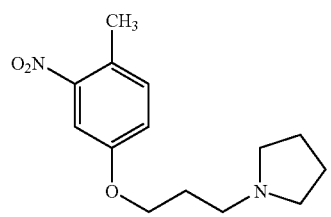

250

Into a round-bottom flask equipped with a stir bar and nitrogen on demand were placed 249 (1.5 g, 5.47 mmol), pyrrolidine (0.91 mL, 0.78 g, 10.9 mmol), potassium carbonate (1.1 g, 8.2 mmol), and N,N-dimethylformamide (30 mL) and the mixture was allowed to stir at rt for 4 h. When judged to be complete, the reaction mixture was poured into a separatory funnel containing ethyl acetate and water. The organics were collected, dried over Na₂SO₄, filtered and the solvent was removed under reduced pressure to afford 250 (1.24 g, 89%) as a brown oil. The product was used in the next step without further purification or characterization.

Step C:

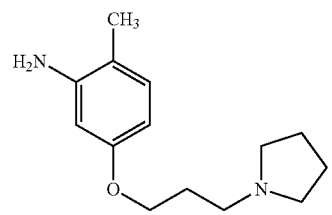

251

To a plastic-coated reaction vessel equipped with a stir bar, was added compound 250 (1.3 g, 4.9 mmol), absolute ethanol (20 µL), and palladium on charcoal (0.13 g of 10% Pd/C, 10% w/w). The vessel was placed on a hydrogenation apparatus at 60 p.s.i. for 3 h. When judged to be complete, the reaction was filtered through a celite plug and the solvents were removed under reduced pressure to provide a dark oil. The residue was treated with a small amount of ethyl acetate and hexanes and the resulting precipitate was filtered and the mother liquor was concentrated under reduced pressure to afford 251 (1.0 g, 87%), as an orange solid. ¹H NMR (400 MHz, DMSO-d₆) δ 6.72 (d, J=8.4 Hz, 1H), 6.14 (d, J=2.4 Hz, 1H), 5.98 (dd, J=2.4, 8.4 Hz, 1H), 4.73 (s, 2H), 3.82 (t, J=6.4 Hz, 2H), 2.46 (m, 2H), 2.37 (m, 4H), 1.92 (s, 3H), 1.77 (m, 2H), 1.63 (m, 4H).

Step D:

Acid 49 (120 mg, 0.37 mmol), oxalyl chloride (0.035 mL, 50 mg, 0.40 mmol), N,N-dimethylformamide (1 drop), and CH₂Cl₂ (7 mL) were used according to general procedure V to afford the acid chloride. The acid chloride, aniline 251 (87 mg, 0.37 mmol), NaHCO₃ (155 mg, 1.85 mmol), acetone (8 mL), and water (0.5 mL) were used according to general procedure VI. The resulting yellow oil was treated with pentanes to afford 248 (92 mg, 46%) as a pale yellow solid. ¹H NMR (400 MHz, DMSO-d₆) δ 9.08 (s, 1H), 7.62 (dd, J=2.8, 8.8 Hz, 1H), 7.55 (t, J=9.2 Hz, 1H), 7.47 (d, J=2.4 Hz, 1H), 7.42 (m, 2H), 7.19 (d, J=8.8 Hz, 1H), 7.01 (m, 2H), 6.63 (d, J=8.4 Hz, 1H), 4.74 (s, 2H), 3.89 (t, J=6.4 Hz, 2H), 2.45 (m, 2H), 2.39 (bs, 4H), 1.98 (s, 3H), 1.81 (t, J=6.8 Hz, 2H), 1.63 (s, 4H). MS(ES): 543 (M⁺).

Example 105

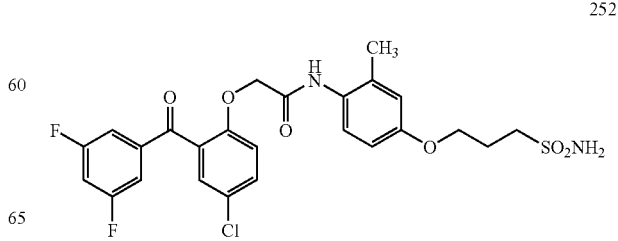

252

Step A:

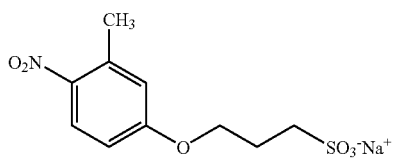

253

To a round-bottom flask equipped with an overhead stirrer, and addition funnel, and nitrogen on demand was placed sodium hydride (7.8 g of 60% by weight in mineral oil, 0.20 mol) and anhydrous tetrahydrofuran (THF, 300 mL). The mixture was cooled to 0° C. and 2-methyl-3-nitrophenol (30 g, 0.20 mol) was added dropwise as a solution in THF (100 mL). The reaction was then allowed to warm to rt, heated to 40° C. for 15 min., and then allowed to cool to rt. At this time, 1,3-propane sultone (25.6 g, 0.21 mol) in THF (100 mL) was added dropwise and the reaction was heated to reflux for 4-6 h. When judged to be complete, the reaction mixture was filtered and the resulting solid was washed with absolute ethanol and diethyl ether and dried in a vacuum oven. A solid precipitated out of the mother liquor, was filtered and washed with absolute ethanol and diethyl ether and dried in a vacuum oven to afford 253 (27 g, 46%) of a pale yellow solid. $^1$H NMR (300 MHz, DMSO-$d_6$) δ 8.06 (d, J=9 Hz, 1H), 7.05 (d, J=2.7 Hz, 1H), 6.98 (dd, J=2.7, 9.3 Hz, 1H), 4.22 (t, J=6.6 Hz, 2H), 2.58 (m, 2H), 2.52 (s, 3H), 2.04 (m, 2H).

Step B:

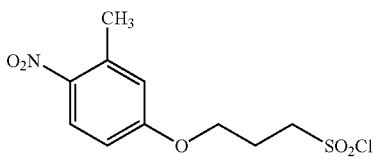

254

To a round-bottom flask equipped with a stir bar, an addition funnel, and nitrogen on demand was added the sulfonic acid salt 253 (11 g, 0.037 mol) and N,N-dimethylformamide (250 mL) and the reaction was cooled to 0° C. Thionyl chloride (8.0 mL, 13.0 g, 0.11 mol) was added dropwise and the resulting mixture was allowed to stir at 0° C. for 0.5 h, after which time it was allowed to warm to rt and stir for an additional 3 h. When judged to be complete, the reaction mixture was poured into a beaker of ice and the resulting white precipitate was filtered and placed in a vacuum oven to afford 254 (8.7 g, 80%) as a white solid. $^1$H NMR (300 MHz, DMSO-$d_6$) δ 8.06 (d, J=9 Hz, 1H), 7.05 (d, J=2.7 Hz, 1H), 6.98 (dd, J=2.7, 9.3 Hz, 1H), 4.22 (t, J=6.3 Hz, 2H), 2.61 (m, 2H), 2.57 (s, 3H), 2.04 (m, 2H).

Step C:

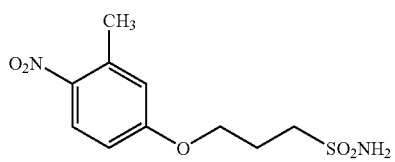

255

To a round-bottom flask equipped with a stir bar, an addition funnel, and nitrogen on demand was added ammonium hydroxide (10 mL) and THF (20 mL) and the reaction was cooled to 0° C. Sulfonyl chloride 254 (2 g, 6.8 mmol) was added dropwise and the reaction was allowed to stir at 0° C. for 15 min, after which time the reaction was poured into a beaker of ice and extracted with ethyl acetate. The organics were collected, washed with water, dried over MgSO$_4$, filtered, and the solvents were removed under reduced pressure to provide 255 (1.4 g, 77%) as a white solid. $^1$H NMR (300 MHz, DMSO-$d_6$) δ 8.07 (d J=9 Hz, 1H), 7.06 (d, J=2.7 Hz, 1H), 7.00 (dd, J=2.7, 9 Hz, 1H), 6.91 (s, 2H), 4.24 (t, J=6 Hz, 2H), 3.16 (t, J=7.5 Hz, 2H), 2.56 (s, 3H), 2.18 (m, 2H).

Step D:

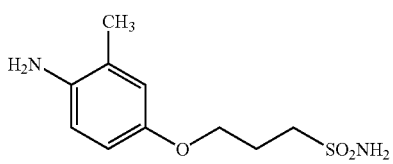

256

To a plastic-coated reaction vessel equipped with a stir bar, was added the nitro derivative 255 (0.29 g, 1.1 mmol), absolute ethanol (25 mL), and palladium on charcoal (29 mg of 10% Pd/C, 10% by weight). The vessel was placed on a hydrogenation apparatus at 60 p.s.i. for 2-4 h. When judged to be complete, the reaction was filtered through a celite plug and the solvents were removed under reduced pressure to provide 256 (0.25 g, 98%) as a pale brown solid. $^1$H NMR (400 MHz, DMSO-$d_6$) δ 6.80 (s, 2H), 6.54 (s, 1H), 6.49 (s, 2H), 4.34 (s, 2H), 3.89 (t, J=6 Hz, 2H), 2.58 (m, 2H), 3.05 (m, 2H), 1.99 (m, 5H).

Step E:

Acid 49 (120 mg, 0.37 mmol), oxalyl chloride (0.035 mL, 50 mg, 0.40 mmol), N,N-dimethylformamide (1 drop), and CH$_2$Cl$_2$ (7 mL) were used according to general procedure V to afford the acid chloride. The acid chloride, aniline 256 (81 mg, 0.33 mmol), NaHCO$_3$ (155 mg, 1.85 mmol), acetone (8 mL), and water (0.5 mL) were used according to general procedure VI to afford 252 (103 mg, 50%) as a white solid. $^1$H NMR (400 MHz, DMSO-$d_6$) δ 9.09 (s, 1H), 7.62 (dd, J=2.8, 9.2 Hz, 1H), 7.55 (m, 1H), 7.47 (d, J=2.8 Hz, 1H), 7.41 (m, 2H), 7.19 (d, J=9.2 Hz, 1H), 7.11 (d, J=8.4 Hz, 1H), 6.83 (s, 2H), 6.76 (d, J=2.8 Hz, 1H), 6.69(dd, J=2.8, 8.4 Hz), 4.70 (s, 2H), 4.01 (t, J=6.4 Hz, 2H), 3.08 (t, J=8 Hz, 2H), 2.07 (m, 2H), 2.00 (s, 3H). MS (ES): 553 (M$^+$).

Example 106

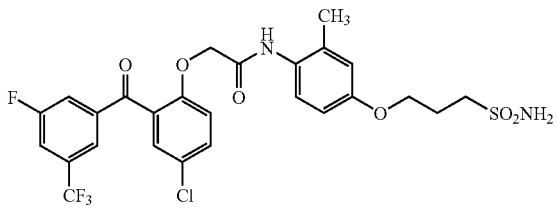

257

Acid 71 (13 g, 0.035 mol), oxalyl chloride (7.0 mL, 9.8 g, 0.077 mol), N,N-dimethylformamide (1 drop), and CH$_2$Cl$_2$ (100 mL) were used according to general procedure V to afford the acid chloride. The acid chloride, aniline 256 (7.81 g, 0.032 mol), NaHCO$_3$ (15 g, 0.18 mol), acetone (125 mL), and water (110 mL) were used according to general procedure VI. The product was crystallized from methanol to afford 257 (10.5 g, 50%) as a white solid. $^1$H NMR (300 MHz, DMSO-$d_6$) δ 9.16 (s, 1H), 8.05 (d, J=8.4 Hz, 1H), 7.90 (m, 2H), 7.71 (dd, J=2.7, 9 Hz, 1H), 7.57 (d, J=2.7 Hz, 1H), 7.25 (d, J=9 Hz, 1H), 7.13 (d, J=9 Hz, 1H), 6.88 (s, 2H), 6.80 (d, J=2.7 Hz, 1H), 6.73 (dd, J=2.7, 9 Hz, 1H), 4.74 (s, 2H), 4.07 (t, J=6 Hz, 2H), 3.13 (m, 2H), 2.13 (m, 2H), 2.03 (s, 3H). MS (ES): 602 (M−H)⁻, 603 (M⁺). Anal. Calcd for $C_{26}H_{23}N_2O_6ClF_4S$: C, 51.79; H, 3.84; N, 4.65. Found: C, 51.91; H, 3.88; N, 4.66.

Example 107

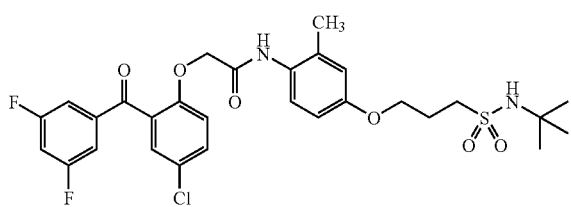

258

Step A:

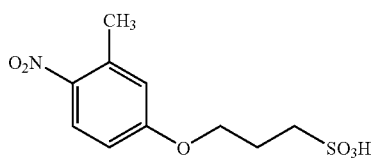

259

To a round-bottom flask equipped with a stir bar, and nitrogen on demand were placed 2-methyl-3-nitrophenol (10 g, 0.065 mol), acetone (100 mL), potassium carbonate (27 g, 0.20 mol), and 1,3-propane sultone (6.0 mL, 8.3 g, 0.068 mol). The mixture was heated to reflux for 1 h, after which time it was allowed to cool to rt and stir for an additional 72 h. When judged to be complete, the reaction mixture was concentrated under reduced pressure. The resulting yellow residue was dissolved in a minimal amount of water, acidified to pH 2 using conc. HCl, and extracted with a mixture of absolute ethanol/ethyl acetate. The organics were collected, dried over MgSO$_4$, filtered and the solvents removed under reduced pressure to afford 259 (10.2 g, 57%) of a pale yellow solid. $^1$H NMR (400 MHz, DMSO-$d_6$) δ 8.00 (d, J=9.2 Hz, 1H), 6.99 (d, J=2.4 Hz, 1H), 6.92 (dd, J=2.4, 8.8 Hz, 1H), 4.16 (t, J=6.4 Hz, 2H), 2.47 (m, 5H), 1.98 (m, 2H).

Step B:

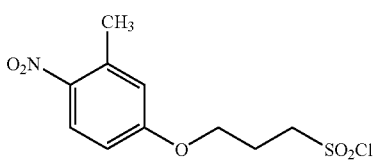

260

To a round-bottom flask equipped with a stir bar, reflux condenser, and nitrogen on demand were added the sulfonic acid 259 (3 g, 0.011 mol) and phosphorus oxychloride (POCl$_3$, 100 mL). The reaction was heated to reflux for 18 h, after which time it continued to stir at rt for 24 h. The mixture was filtered and the POCl$_3$ was removed under reduced pressure to afford 260 (3.8 g, >100%) as a brown oil. The product was used in the next step without further purification or characterization.

Step C:

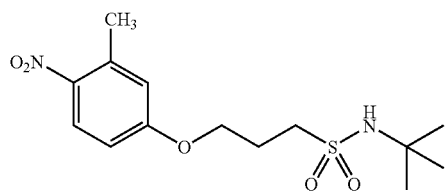

261

To a round-bottom flask equipped with a stir bar and nitrogen on demand was added t-butylamine (0.33 mL, 0.23 g, 3.1 mmol), triethylamine (0.72 mL, 0.52 g, 5.2 mmol), and chloroform (20 mL). Sulfonyl chloride 260 (0.76 g, 2.6 mmol) in chloroform (3 mL) was added dropwise and the reaction was allowed to stir at rt for 2 h. When judged to be complete, the reaction mixture was poured into a separatory funnel containing CHCl$_3$ and water, the organics were collected, washed with brine, dried over MgSO$_4$, filtered, and the solvents were removed under reduced pressure. The resulting brown residue was filtered through a pad of silica gel, eluting with hexanes to provide 261 (0.37 g, 43%) as a white solid. The product was used in the next step without further purification or characterization.

Step D:

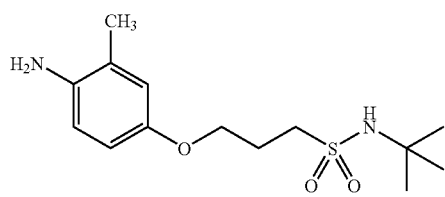

262

To a plastic-coated reaction vessel equipped with a stir bar, were added compound 261 (0.37 g, 1.1 mmol), ethanol (20 mL), and palladium on charcoal (37 mg of 10% Pd/C, 10 w/w). The vessel was placed on a hydrogenation apparatus at 60 psig for 2-4 h. When judged to be complete, the reaction was filtered through a celite plug and the solvents were removed under reduced pressure to provide 262 (0.32 g, 95%) as brown oil. $^1$H NMR (400 MHz, DMSO-$d_6$) δ 6.92 (s, 1H), 6.85 (s, 1H), 6.53 (m, 1H), 6.49 (m, 1H), 4.51 (bs, 2H), 3.90 (t, J=6 Hz, 2H), 3.09 (m, 2H), 2.08 (m, 2H), 1.99 (s, 3H), 1.22 (m, 9H).

Step E:

Acid 49 (120 mg, 0.37 mmol), oxalyl chloride (0.035 mL, 50 mg, 0.40 mmol), N,N-dimethylformamide (1 drop), and CH$_2$Cl$_2$ (10 mL) were used according to general procedure V to afford the acid chloride. The acid chloride, aniline 262 (111 mg, 0.37 mmol), NaHCO$_3$ (155 mg, 1.85 mmol), acetone (10 mL), and water (0.5 mL) were used according to general procedure VI. The product purified by flash chromatography using 5% MeOH:CH$_2$Cl$_2$ to afford 258 (28 mg, 12%) as a white solid. $^1$H NMR (400 MHz, DMSO-$d_6$) δ 9.08 (s, 1H), 7.63 (dd, J=4, 8 Hz, 1H), 7.54 (m, 1H), 7.47 (d, J=4 Hz, 1H), 7.41 (m, 2H), 7.20 (d, J=8 Hz, 1H), 7.12 (d, J=8 Hz, 1H), 6.87 (s, 1H), 6.75 (m, 1H), 6.68 (dd, J=4, 8 Hz, 1H), 4.70 (s, 2H), 4.02 (t, J=8 Hz, 2H), 3.09 (t, J=8 Hz, 2H), 2.05 (t, J=8 Hz, 2H), 2.00 (s, 3H), 1.22 (s, 9H). MS (ES): 608 (M−H)⁻.

Example 108

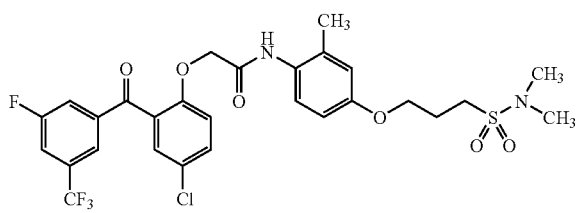

Step A:

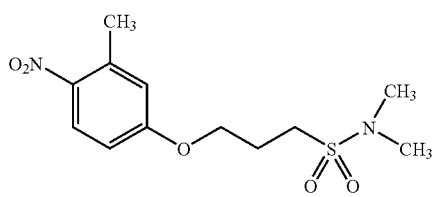

To a round-bottom flask equipped with a stir bar and a gas dispersion tube was added sulfonyl chloride 260 (3.8 g, 0.013 mol) and methylene chloride (100 mL), and the reaction was cooled to 0° C. Dimethylamine gas was bubbled through the reaction mixture for 1 h, after which time the reaction mixture was poured into $CH_2Cl_2$ and water. The organics were collected, washed with water, dried over $MgSO_4$, filtered and the solvents were removed under reduced pressure to afford 264 (2.1 g, 54%) as a pale yellow solid. The product was used in the next step without further purification or characterization.

Step B:

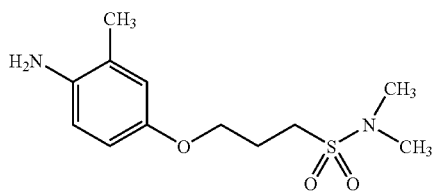

To a plastic-coated reaction vessel equipped with a stir bar, was added the nitro derivative 264 (2.1 g, 7.0 mmol), absolute ethanol (40 mL), and palladium on charcoal (0.21 g of 10% Pd/C, 10% by weight). The vessel was placed on a hydrogenation apparatus at 50 p.s.i. for 2-4 h. When judged to be complete, the reaction was filtered through a celite plug and the solvents were removed under reduced pressure to provide 265 (1.7 g, 90%) as a pale yellow solid. The product was used in the next step without further purification or characterization.

Step C:

Acid 71 (120 mg, 0.32 mmol), oxalyl chloride (0.032 mL, 44 mg, 0.35 mmol), N,N-dimethylformamide (1 drop), and $CH_2Cl_2$ (10 mL) were used according to general procedure V to afford the acid chloride. The acid chloride, aniline 265 (78 mg, 0.29 mmol), $NaHCO_3$ (134 mg, 1.6 mmol), acetone (6 mL), and water (0.5 mL) were used according to general procedure VI. The resulting residue was treated several times with pentane to afford 263 (90 mg, 45%) as a beige solid. $^1H$ NMR (400 MHz, DMSO-$d_6$) δ 9.09 (s, 1H), 7.98 (d, J=8.4 Hz, 1H), 7.84 (m, 2H), 7.65 (dd, J=2.4, 8.8 Hz, 1H), 7.51 (d, J=2.8 Hz, 1H), 7.20 (d, J=8.8 Hz, 1H), 7.08 (d, J=8.8 Hz, 1H), 6.76 (d, J=2.4 Hz, 1H), 6.68 (dd, J=2.8, 8.8 Hz, 1H), 4.69 (s, 2H), 4.00 (t, J=6 Hz, 2H), 3.13 (m, 2H), 2.75 (s, 6H), 2.05 (m, 2H), 1.98 (s, 3H). MS (ES): 631 (M$^+$)

Example 109

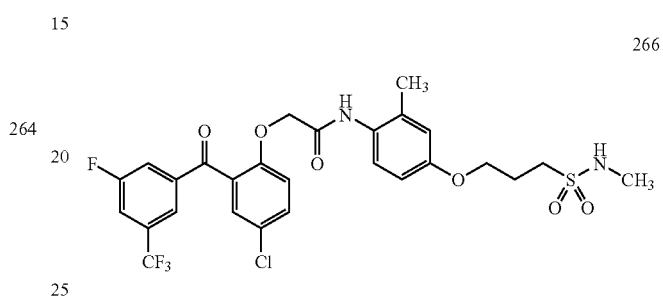

Step A:

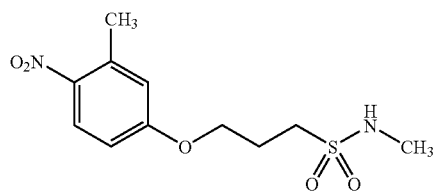

To a round-bottom flask equipped with a stir bar and a gas dispersion tube was added sulfonyl chloride 260 (3.2 g, 0.011 mol) and methylene chloride (75 mL), and the reaction was cooled to 0° C. Methylamine gas was bubbled through the reaction mixture for 1 h, after which time the reaction mixture was poured into $CH_2Cl_2$ and water. The organics were collected, washed with water, dried over $MgSO_4$, filtered and the solvents were removed under reduced pressure. The product was recrystallized from methanol to afford 267 (2.0 g, 63%) as a pale yellow solid. $^1H$ NMR (300 MHz, DMSO-$d_6$) δ 8.08 (d, J=9 Hz, 1H), 7.03 (m, 3H), 4.23 (t, J=8.4 Hz, 2H), 3.19 (m, 2H), 2.57 (m, 6H), 2.12 (m, 2H). MS (ES): 617 (M$^+$).

Step B:

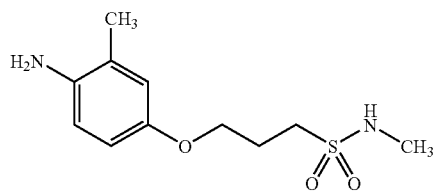

To a plastic-coated reaction vessel equipped with a stir bar, was added- the nitro derivative 267 (2.0 g, 6.9 mmol), toluene (25 mL), and palladium on charcoal (0.20 g of 10%

Pd/C, 10% by weight). The vessel was placed on a hydrogenation apparatus at 50 p.s.i. for 4 h. When judged to be complete, the reaction was filtered through a celite plug and the solvents were removed under reduced pressure. The resulting residue was treated with several portions of hexanes to provide 268 (1.1 g, 62%) as a pink solid. $^1$H NMR (400 MHz, DMSO-$d_6$) δ 6.92 (q, J=5 Hz, 1H), 6.55 (s, 1H), 6.48 (m, 2H), 4.36 (bs, 2H), 3.88 (t, J=6.4 Hz, 2H), 3.08 (m, 2H), 2.53 (d, J=5 Hz, 3H), 1.95 (m, 5H).

Step C:

Acid 71 (120 mg, 0.32 mmol), oxalyl chloride (0.032 mL, 44 mg, 0.35 mmol), N,N-dimethylformamide (1 drop), and $CH_2Cl_2$ (10 mL) were used according to general procedure V to afford the acid chloride. The acid chloride, aniline 268 (75 mg, 0.29 mmol), $NaHCO_3$ (134 mg, 1.6 mmol), acetone (6 mL), and water (0.5 mL) were used according to general procedure VI. The resulting residue was treated several times with hexanes to afford 266 (80 mg, 41%) as a beige solid. $^1$H NMR (400 MHz, DMSO-$d_6$) δ 9.09 (s, 1H), 7.98 (d, J=8.4 Hz, 1H), 7.84 (m, 2H), 7.65 (dd, J=2.4, 8.8 Hz, 1H), 7.52 (d, J=2.8 Hz, 1H), 7.20 (d, J=9.2 Hz, 1H), 7.08 (d, J=8.4 Hz, 1H), 6.94 (q, J=5 Hz, 1H), 6.74 (d, J=2.8 Hz, 1H), 6.68 (dd, J=2.8, 8.8 Hz, 1H), 4.68 (s, 3H), 4.00 (m, 2H), 3.10 (t, J=8 Hz, 2H), 2.54 (d, J=5 Hz), 2.01 (m, 5H). MS (ES): 617 (M$^+$).

Example 110

269

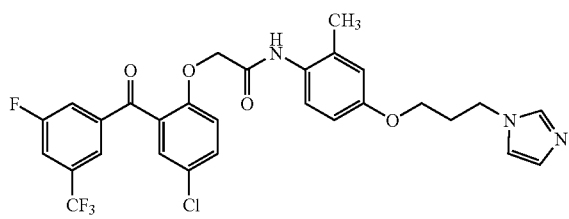

Step A:

270

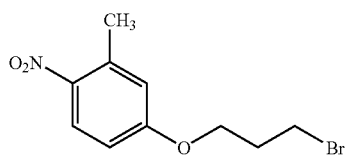

Into a round-bottom flask equipped with a stir bar and nitrogen on demand were placed 2-methyl-3-nitrophenol (5.0 g, 0.033 mol), dibromopropane (26 mL, 52.7 g, 0.26 mol), potassium carbonate (6.8 g, 0.05 mol), and N,N-dimethylformamide (100 mL) and the mixture was allowed to stir at rt for 2.5 h. When judged to be complete, the reaction mixture was poured into a separatory funnel containing ethyl acetate and water. The organics were collected, washed with water and brine, dried over $MgSO_4$, filtered and the solvent was removed under reduced pressure. The resulting oil was distilled to afford 270 (8.0 g, 89%) a brown oil. $^1$H NMR (400 MHz, DMSO-$d_6$) δ 8.01 (d, J=9.2 Hz, 1H), 7.02 (d, J=2.8 Hz, 1H), 6.96 (dd, J=2.4, 8.8 Hz, 1H), 4.16 (t, J=6 Hz, 2H), 3.63 (t, J=6 Hz, 2H), 2.51 (s, 3H), 2.24 (m, 2H).

Step B:

271

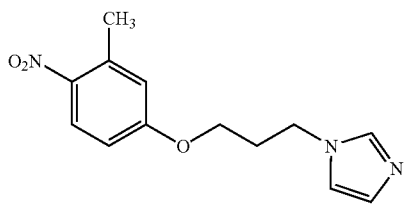

Into a round-bottom flask equipped with a stir bar and nitrogen on demand were placed 270 (0.8 g, 2.9 mmol), imidazole (0.24 g, 3.49 mmol), potassium carbonate (0.8 g, 5.83 mmol), and N,N-dimethylformamide (20 mL) and the mixture was allowed to stir at 55° C. for 18 h. When judged to be complete, the reaction mixture was poured into a separatory funnel containing ethyl acetate and water. The organics were collected, dried over MgSO-$_4$, filtered and the solvent was removed under reduced pressure. The product was purified by flash chromatography eluding with 1:1 hexanes:ethyl acetate to afford 271(0.3 g, 40%). $^1$H NMR (400 MHz, DMSO-$d_6$) δ 8.06 (d, J=9 Hz, 1H), 7.65 (s, 1H), 7.22 (s, 1H), 7.04 (d, J=2.4 Hz, 1H), 6.98 (dd, J=2.7, 9 Hz, 1H), 6.92 (s, 1H), 4.16 (t, J=7 Hz, 2H), 4.04 (t, J=6 Hz, 2H), 2.57 (s, 3H), 2.22 (m, 2H).

Step C:

272

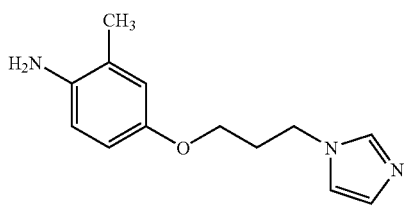

To a plastic-coated reaction vessel equipped with a stir bar, was added the nitro derivative 271 (0.3 g, 1.15 mmol), ethanol (20 mL), and palladium on-charcoal (30 mg of 10% Pd/C, 10% w/w). The vessel was placed on a hydrogenation apparatus at 55 p.s.i. for 2 h. When judged to be complete, the reaction was filtered through a celite plug and the solvents were removed under reduced pressure to provide 272 (0.23 g, 88%) a purple oil. $^1$H NMR (400 MHz, DMSO-$d_6$) δ 7.57 (s, 1H), 7.14 (s, 1H), 6.85 (s, 1H), 6.54 (s, 1H), 6.48 (s, 2H), 4.44 (bs, 2H), 4.06 (t, J=6.8 Hz, 2H), 3.70 (t, J=6 Hz, 2H), 2.03 (m, 2H), 1.99 (s, 3H).

Step D:

Acid 71 (120 mg, 0.32 mmol), oxalyl chloride (0.032 mL, 44 mg, 0.35 mmol), N,N-dimethylformamide (1 drop), and $CH_2Cl_2$ (10 mL) were used according to general procedure V to afford the acid chloride. The acid chloride, aniline 272 (67 mg, 0.29 mmol), $NaHCO_3$ (134 mg, 1.6 mmol), acetone (6 mL), and water (0.5 mL) were used according to general procedure VI. The product was purified by flash chromatography using 5% MeOH:$CHCl_3$ as eluant to afford 269 (84 mg, 45%) as a pink solid. $^1$H NMR (300 MHz, DMSO-$d_6$) δ 9.15 (s, 1H), 8.05 (d, J=9 Hz, 1H), 7.90 (m, 2H), 7.71 (dd, J=3, 9 Hz, 1H), 7.65 (s, 1H), 7.57 (d, J=3 Hz, 1H), 7.24 (m, 2H), 7.13 (d, J=6 Hz, 1H), 6.92 (s, 1H), 6.79 (d, J=3 Hz, 1H), 6.73 (dd, J=3, 9 Hz, 1H), 4.74 (s, 2H), 4.14 (t, J=6 Hz, 2H), 3.88 (t, J=6 Hz, 2H), 2.16 (m, 2H), 2.03 (s, 3H). MS (ES): 589 (M+), 590 (M+H)+.

Example 111

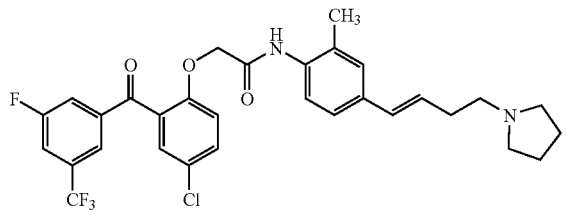
272

Step A:

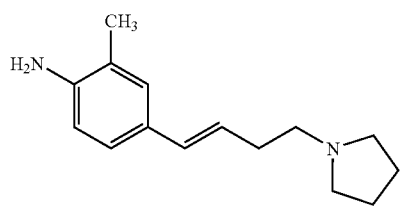
273

To a sealed-tube reaction vessel equipped with a stir bar and nitrogen on demand was added 4-bromo-2-methyl aniline (0.8 g, 4.3 mmol), palladium (II) acetate (97 mg, 0.43 mmol), tri-o-tolylphosphine (0.52 g, 1.72 mmol), N,N-dimethylformamide (15 mL), N-butylenepyrrolidine (2.7 g, 21.5 mmol), and triethylamine (4.2 mL, 3.0 g, 30.1 mmol). The tube was sealed and allowed to stir at 80° C. for 18 h. When judged to be complete, the reaction was filtered through a pad of celite and the filtrate was poured into ethyl acetate and water. The organics were collected and washed with water and brine, dried over MgSO4, filtered and the solvents were removed under reduced pressure. The product was purified by flash chromatography using 93:7 CHCl3: MeOH as eluant to provide 273 (0.2 g, 20%) as a yellow oil. The product exists as a 2.7:1 mixture of E: Z isomers. $^1$H NMR (400 MHz, DMSO-d6) δ 6.87 (m, 2H), 6.51 (m, 1H), 6.18 (m, 1H), 5.87 (m, 1H), 4.81 (m, 2H), 2.44 (m, 8H), 2.31 (m, 2H), 2.00 (m, 2H), 1.85 (s, 3H). MS (ES): 231 (M+H)+.

Step B:

Acid 71 (132 mg, 0.35 mmol), oxalyl chloride (0.034 mL, 48 mg, 0.38 mmol), N,N-dimethylformamide (1 drop), and CH2Cl2 (10 mL) were used according to general procedure V to afford the acid chloride. The acid chloride, aniline 273 (72 mg, 0.31 mmol), NaHCO3 (152 mg, 1.7 mmol), acetone (6 mL), and water (0.5 mL) were used according to general procedure VI. The product was recrystallized from absolute ethanol to afford 272 (20 mg, 10%) as a white solid. The product exists as a 2.7:1 mixture of E:Z isomers. $^1$H NMR (400 MHz, DMSO-d6) δ 9.15 (m, 1H), 7.98 (m, 1H), 7.85 (m, 2H), 7.65 (m, 1H), 7.51 (m, 1H), 7.20 (m, 4H), 6.32 (m, 1H), 6.21 (m, 1H), 4.72 (s, 2H), 2.46 (m, 8H), 2.31 (m, 2H), 2.04 (m, 2H), 1.65 (s, 3H). MS (ES): 590 (M+H)+.

Example 112

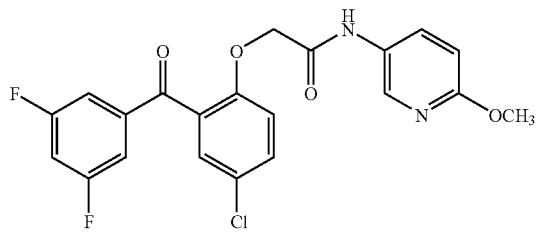
274

The title compound was prepared according to General Procedure VI from acid 49 (0.51 mmol) and 5-amino-2-methoxypyridine (0.04 mL, 0.44 mmol). Purification by flash chromatography using 25% ethyl acetate/hexane as eluant, followed by trituration with ether gave 274 (0.146 g, 77%): mp 185-187° C.; MS (ES+) m/z 433 (M+H); $^1$H NMR (400 MHz, —CDCl3) δ 9.30 (s, 1H), 8.49 (d, 1H)-8.09 (dd, 1H), 7.56 (dd, 1H), 7.41-7.38 (m, 3H), 7.13-7.09 (m, 1H), 7.05 (d, 1H), 6.76 (d, 1H), 4.72 (s, 2H), 3.94 (s, 3H).

Example 113

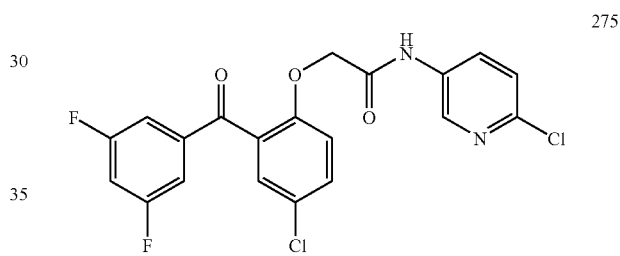
275

The title compound was prepared according to General Procedure VI from acid 49 (0.51 mmol) and 5-amino-2-methoxypyridine (0.05 mL, 0.44 mmol). Purification by flash chromatography using 25% ethyl acetate/hexane as eluant followed by trituration with ether gave 275 (0.134 g, 70%): mp 198-200° C.; MS (ES+) m/z 437 (M+H); $^1$H NMR (400 MHz, CDCl3) δ 9.79 (s, 1H), 8.80 (d, 1H), 8.30 (dd, 1H), 7.58 (dd, 1H), 7.41 (dd, 1H), 7.39-7.38 (m, 2H), 7.32 (d, 1H), 7.15-7.11 (m, 1H), 7.07 (d, 1H), 4.76 (s, 2H).

Example 114

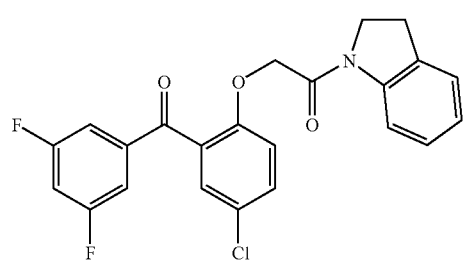
276

The title compound was prepared according to General Procedure VI from acid 49 (0.51 mmol) and indoline (0.05 mL, 0.44 mmol). Purification by flash chromatography using 25% ethyl acetate/hexane as eluant followed by crystallization from methylene chloride/hexane gave 276 (0.069 g, 37%): mp 158-160° C.; MS (ES+) m/z 428 (M+H); $^1$H NMR (400 MHz, CDCl$_3$)δ 8.14 (d, 1H), 7.44-7.39 (m, 4H), 7.22-7.18 (m, 2H), 7.07-6.97 (m, 3H), 4.70 (s, 2H), 3.98 (t, 2H), 3.18 (t, 2H) ppm.

Example 115

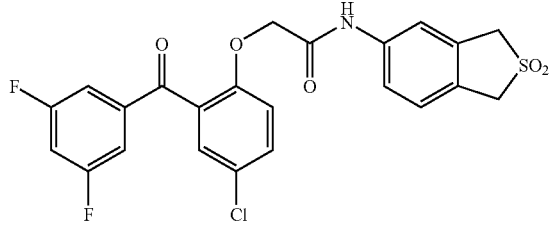

277

The title compound was prepared according to General Procedure VI from acid 49 (0.51 mmol) and 5-amino-1,3-dihydro-benzo[c]thiophene-2,2-dioxide (0.081 g, 0.44 mmol). Purification by flash chromatography using 40-60% ethyl acetate/hexane as eluant followed by crystallization from ethyl acetate gave 277 (0.080 g, 37%): mp 197-199° C.; MS (ES−) m/z 490 (M−H); $^1$H NMR (400 MHz, CDCl$_3$) δ 9.43 (s, 1H), 7.92 (s, 1H), 7.65 (dd, 1H), 7.57 (dd, 1H), 7.41-7.38 (m, 3H), 7.30 (d, 1H), 7.15-7.10 (m, 1H), 7.05 (d, 1H), 4.72 (s, 2H), 4.39 (s, 2H), 4.35 (s, 2H).

Example 116

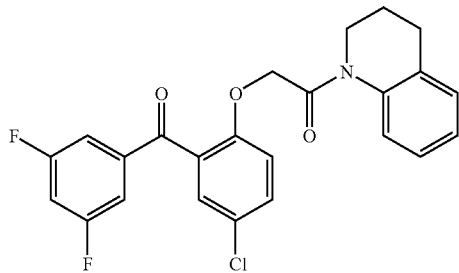

278

The title compound was prepared according to General Procedure VI from acid 49 (0.49 mmol) and 1,2,3,4-tetrahydroquinoline (0.05 mL, 0.41 mmol). Isolation by flash chromatography using 15% ethyl acetate/hexane as eluant followed by trituration with hexanes gave 278 (0.081 g, 45%) in ca. 80% purity: MS (ES+) m/z 442 (M+H), 464 (M+Na); $^1$H NMR (400 MHz, CDCl$_3$) δ 7.38 (dd, 1H), 7.33-7.31 (m, 3-H), 7.11-7.09 (m, 3H), 7.00-6.95 (m, 1H), 6.88 (br s, 1H), 4.73 (s, 2H), 3.73 (br s, 2H), 2.64 (br s, 2H), 1.93-1.86 (m, 2H).

Example 117

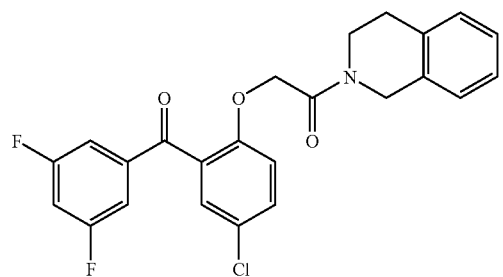

279

The title compound was prepared according to General Procedure VI from acid 49 (0.49 mmol) and 1,2,3,4-tetrahydroisoquinoline (0.035 mL, 0.41 mmol). Isolation by flash chromatography using 15% ethyl acetate/hexane as eluant followed by trituration with hexanes gave 279 (0.072 g, 40%) in ca. 80% purity: MS (ES+) m/z 442 (M+H), 464 (M+Na); $^1$H NMR (400 MHz, CDCl$_3$) δ 7.43-7.39 (m, 1H), 7.34-7.27 (m, 3H), 7.19-7.15 (m, 2H), 7.13-7.08 (m, 2H), 7.02-6.93 (m, 2H), 4.70 (s, 2H), 4.65 (s, 1H), 4.46 (s, 1H), 3.73 (t, 1H), 3.57 (t, 1H), 2.81-2.75 (m, 2H).

Example 118

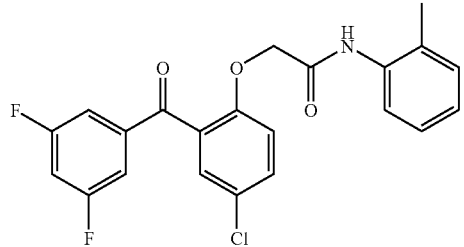

280

The title compound was prepared according to General Procedure VI from acid 49 (0.50 mmol) and o-toluidine (0.05 mL, 0.43 mmol). Isolation by flash chromatography using 10% ethyl acetate/hexane as eluant gave 280 (0.121 g, 58%): MS (ES+) m/z 416 (M+H), 438 (M+Na); MS (ES−) m/z 414 (M−H); $^1$H NMR (400 MHz, CDCl$_3$) δ 8.30 (br s, 1H), 7.71 (d, 1H), 7.53 (dd, 1H), 7.36 (d, 1H), 7.34-7.31 (m, 2H), 7.22-7.17 (m, 2H), 7.09 (app t, 1H), 7.05-7.01 (m, 2H), 4.77 (s, 2H), 2.18 (s, 3H) ppm.

Example 119

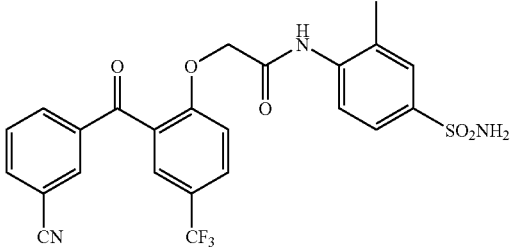

281

Step A:

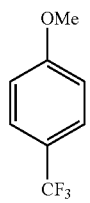
282

A mixture of trifluoro-p-cresol (18.9 g, 117 mmol), potassium carbonate (16.4 g, 119 mmol) and iodomethane (9.8 mL, 158 mmol) in 200 mL acetone was warmed to reflux for 8.5 h, then stirred at room temperature an additional 16 h. The reaction mixture was then concentrated in vacuo, and the residue was partitioned between 150 mL water and 150 mL ethyl acetate. The aqueous layer was extracted with another 150 mL of ethyl acetate, and the combined organic layers were then dried over MgSO$_4$, filtered and concentrated in vacuo to give 282 (18.97 g, 92%): $^1$H NMR (400 MHz, CDCl$_3$) δ 7.55 (d, 2H), 6.96 (d, 2H), 3.85 (s, 3H).

Step B:

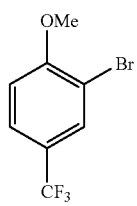
283

Bromine (4.1 mL, 79 mmol) was added dropwise to a solution of 282 (13.2 g, 75.2 mmol) and sodium acetate (6.48 g, 79 mmol) in 150 mL of glacial acetic acid over 35 min. The reaction mixture was stirred an additional 23 h at room temperature, then 10% NaHSO$_3$ (aq) was added until the orange reaction mixture became colorless. The mixture was then extracted with two 150-mL portions of CH$_2$Cl$_2$, and the combined organic layers were dried over MgSO$_4$, filtered and concentrated in vacuo to give 26.48 g of crude material. Purification by flash chromatography using 2% ethyl acetate/hexane as eluant gave 283 (2.232 g, 12%): $^1$H NMR (400 MHz, CDCl$_3$) δ 7.79 (d, 1H), 7.53 (dd, 1H), 6.94 (d, 1H), 3.93 (s, 3H) ppm.

Step C:

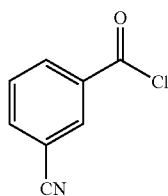
284

Oxalyl chloride (48 mL, 96.5 mmol) was added dropwise over 1 h to a solution of 3-cyanobenzoic acid (5.767 g, 38.6 mmol) in 200 mL of CH$_2$Cl$_2$ and 0.10 mL of DMF, and the resulting mixture was stirred at room temperature for 20 h. The reaction mixture was concentrated in vacuo to give 284 (8.516 g), which was used immediately without further purification or characterization.

Step D:

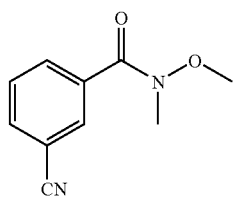
285

A solution of N,O-dimethylhydroxylamine (4.90 g, 50.2 mmol) in 20 mL of triethylamine and 100 mL of chloroform was cooled to 0° C., and 284 (8.52 g, 38.6 mmol) was added dropwise over 10 min. The resulting mixture was stirred at 0° C. for 10 min, then allowed to warm to room temperature over 1.25 h. The reaction mixture was diluted with 150 mL ethyl acetate and washed with two 100-mL portions of water and a small portion of brine. The organic layer was then dried over MgSO$_4$, filtered, and concentrated in vacuo to give 285 (6.381 g, 90%): $^1$H NMR-(400 MHz, CDCl$_3$) δ 8.02 (s, 1H), 7.95 (d, 1H), 7.75 (d, 1H), 7.55 (dd, 1H), 3.54 (s, 3H), 3.39 (s, 3H).

Step E:

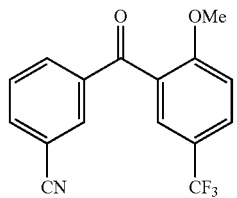
286 n-Butyl lithium (7.7 mL of 1.6 M solution in hexanes) was added dropwise to a solution of 283 (2.735 g, 10.7 mmol) in 40 mL of ether at −78° C. over 15 min. The reaction mixture was stirred at −78° C. for an additional 15 min, then absolution of 285 (2.24 g, 11.8 mmol) in 15 mL of ether was added dropwise over 20 min. The resulting mixture was stirred for 1 h at −78° C., then allowed to warm to room temperature and continue stirring for 4.67 h. The reaction mixture was quenched with the slow addition of 20 mL of water, stirred open to air for 45 minutes, and partitioned between 100 mL of ether and 100 mL of water. The organic layer was dried over MgSO$_4$, filtered and concentrated in vacuo to give 4.036 g of an orange liquid. Purification by flash chromatography using 5-10% ethyl acetate/hexane as eluant gave 286 (1.850 g, 57%) as a white solid: $^1$H NMR (400 MHz, CDCl$_3$) δ 8.01-7.99 (m, 2H), 7.83 (d, 1H), 7.78 (d, 1H), 7.67 (s, 1H), 7.59 (dd, 1H), 7.08 (d, 1H), 3.76 (s, 3H).

Step F:

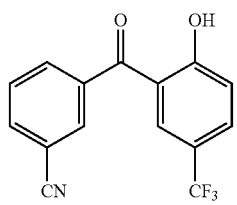
287

The title compound (1.781 g, 100%) was prepared according to General Procedure 1x from the anisole derivative 286

(1.805 g, 5.91 mmol). This intermediate was used without further purification: ¹H NMR (400 MHz, CDCl₃) δ 11.99 (s, 1H), 7.97 (s, 1H), 7.92 (d, 1H), 7.87 (d, 1H), 7.77 (dd, 1H), 7.73 (s, 1H), 7.69 (t, 1H), 7.21 (d, 1H).

Step G:

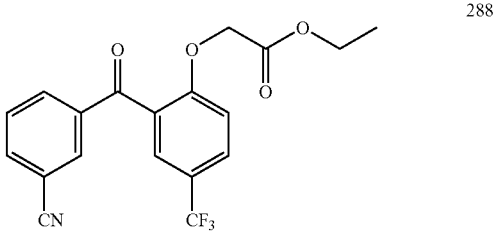

288

The title compound (2.196 g, 100%) was prepared according to General Procedure II from the phenol derivative 287 (1.78 g, 5.91 mmol). This intermediate was used without further purification: ¹H NMR (400 MHz, CDCl₃) δ 8.13 (s, 1H), 8.09 (d, 1H), 7.82 (d, 1H), 7.74 (d, 1H), 7.73 (s, 1H), 7.58 (t, 1H), 6.90 (d, 1H), 4.58 (s, 2H), 4.20 (q, 2H), 1.24 (t, 3H).

Step H:

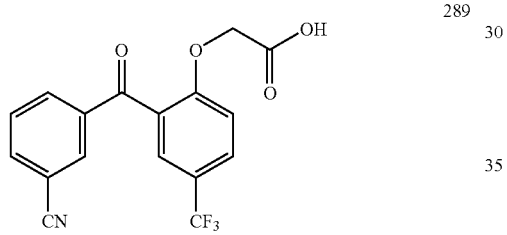

289

The title compound (1.758 g, 85%) was prepared according to General Procedure III from the ester derivative 288 (2.2 g, 5.91 mmol). This intermediate was used without further purification: ¹H NMR (400 MHz, CDCl₃) δ 8.18 (s, 1H), 8.11 (d, 1H), 7.90 (d, 1H), 7.78 (dd, 1H), 7.69 (d, 1H), 7.64 (t, 1H), 7.12 (d, 1H), 4.86 (s, 2H).

Step I:

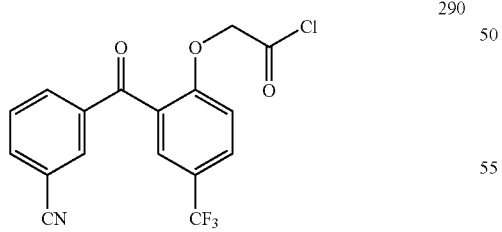

290

The title compound (0.432 g) was prepared according to General Procedure V from the acid derivative 289 (0.345 g, 0.99 mmol). This intermediate was used immediately without further purification or characterization.

Step J:

Compound 281 was prepared according to the General Procedure VI from the acid chloride 290 (0.49 mmol) and the aniline derivative 466 (0.076 g, 0.41 mmol). Purification by flash chromatography using 1% methanol/methylene chloride as eluant gave 281 (0.113 g, 53%): MS (ES+) m/z 516 (M+H); ¹H NMR (400 MHz, DMSO-d₆) δ 9.48 (s, 1H), 8.20 (s, 1H), 8.10-8.06 (m, 2H), 7.94 (dd, 1H), 7.80 (d, 1H), 7.70 (app t, 1 H), 7.65-7.62 (m, 2H), 7.57 (dd, 1H), 7.36 (d, 1H), 7.24 (s, 2H), 4.90 (s, 2H), 2.17 (s, 3H).

Example 120

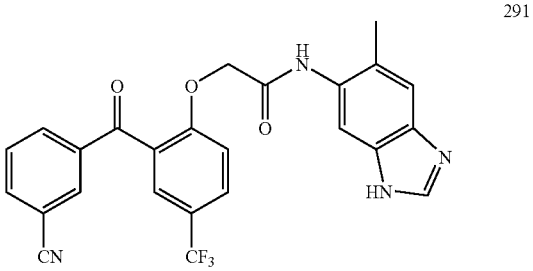

291

Compound 291 was prepared according to General Procedure VI from the acid chloride 290 (0.49 mmol) and the aniline derivative 210 (0.060 g, 0.41 mmol). Purification by flash chromatography using 1-3% methanol/methylene chloride, followed by crystallization from methylene chloride/hexane gave 291 (0.046 g, 20%): MS (ES+) m/z 479 (M+H); MS (ES−) m/z 477 (M−H); ¹H NMR (400 MHz, CD₃OD) δ 8.18-8.16 (m, 2H), 8.07 (d, 1H), 7.94-7.89 (m, 2H), 7.79 (d, 1H), 7.65 (app t, 1H), 7.62 (s, 1H), 7.44-7.41 (m, 2H), 4.85 (s, 2H), 2.20 (s, 3H).

Example 121

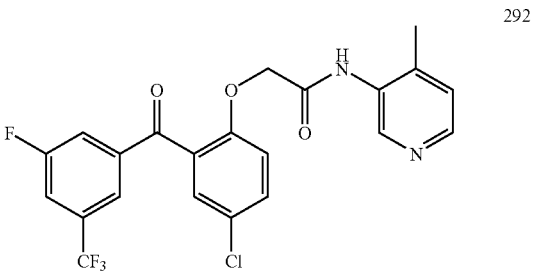

292

Step A:

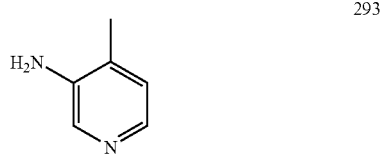

293

A mixture of 4-methyl-3-nitropyridine (1.102 g, 7.24 mmol) and 10% palladium on carbon (0.096 g) in 20 mL of methanol was stirred at room temperature under an atmosphere of 49 psi hydrogen gas for 2 h. The reaction mixture was then filtered through Celite and concentrated in vacuo to give 293 (0.849 g, quant.): ¹H NMR (400 MHz, CDCl₃) δ 8.00 (s, 1H), 7.92 (d, 1H), 6.93 (d, 1H), 3.59 (br s, 2H), 2.14 (s, 3H).

Step B:

Compound 292 was prepared according to the General Procedure IV from the acid 71 (0.188 g, 0.5 mmol) and the aminopyridyl derivative 293 (0.065 g, 0.6 mmol). Purification by flash chromatography using 0.5-2% methanol/methylene chloride as eluant gave 292 (0.071 g, 30%) as a white solid: MS (ES+) m/z 467 (M+H); MS (ES−) m/z 465 (M−H); $^1$H NMR (400 MHz, CDCl$_3$) δ 8.84 (s, 1H), 8.65 (s, 1H), 8.35 (d, 1H), 7.88 (s, 1H), 7.70 (d, 1H), 7.62-7.58 (m, 2H), 7.40 (d, 1H), 7.16 (d, 1H), 7.10 (d, 1H), 4.76 (s, 2H), 2.26 (s, 3H) ppm.

Example 122

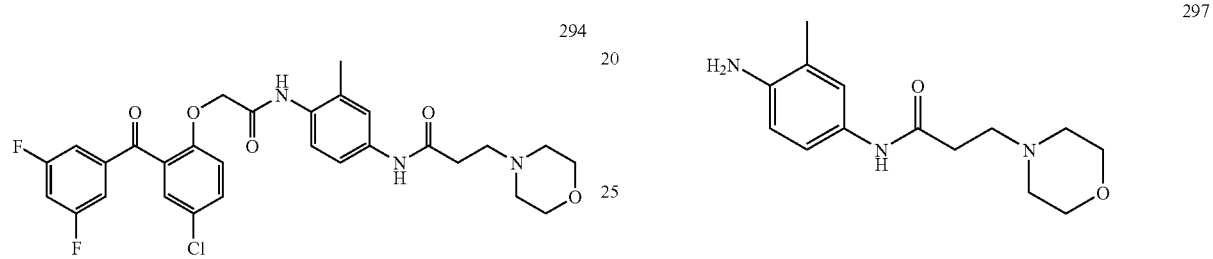

Step A:

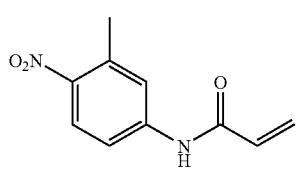

A mixture of 3-methyl-4-nitroaniline (1.052 g, 6.91 mmol) and triethylamine (1.16 mL, 8.29 mmol) in 20 mL of methylene chloride was cooled to 0° C. and acryloyl chloride (0.62 mL, 7.61 mmol) was added dropwise over 5 min. The resulting mixture was stirred an additional 1.5 h at 0° C., then diluted with 35 mL of methylene chloride, washed with brine, dried over MgSO$_4$, filtered, and concentrated in vacuo to give 295 (1.941 g) which was used without further purification: $^1$H NMR (400 MHz, CDCl$_3$) δ 8.52 (br s, 1H), 8.01 (d, 1H), 7.75 (d, 1H), 7.65 (dd, 1H), 6.49-6.40 (m, 2H), 5.78 (dd, 1H), 2.60 (s, 3H).

Step B:

A mixture of compound 295 (6.91 mmol) and morpholine (0.63 mL, 7.26 mmol) in 25 mL of ethanol was warmed to reflux for 2.3 h. The reaction mixture was then concentrated in vacuo, suspended in ethyl acetate, and filtered. The filtrate was concentrated in vacuo, dissolved in ethyl acetate, and allowed to crystallize. The crystalline impurity was removed by filtration, and the filtrate was concentrated in vacuo to give 296 (1.767 g, 87%): $^1$H NMR (400 MHz, CDCl$_3$) δ 11.24 (br s, 1H), 8.03 (d, 1H), 7.54 (d, 1H), 7.43 (dd, 1H), 3.84-3.82 (m, 4H), 2.76-2.73 (m, 2H), 2.64 (br s, 4H), 2.62 (s, 3H), 2.58-2.55 (m, 2H) ppm.

Step C:

A mixture of compound 296 (0.202 g, 0.69 mmol) and 10% palladium on carbon (0.018 g) in 10 mL of methanol was stirred at room temperature under an atmosphere of 53 psi hydrogen gas for 2.17 h. The reaction mixture was then filtered through Celite and concentrated in vacuo to give 297 (0.192 g, quant.): $^1$H NMR (400 MHz, CDCl$_3$) δ 10.44 (br s, 1H), 7.38 (s, 1H), 7.27 (dd, 1H), 6.76 (s, 1H), 3.97-3.92 (m, 4H), 2.91-2.83 (m, 2H), 2.77-2.72 (m, 4H), 2.66-2.62 (m, 2H), 2.25 (s, 3H).

Step D:

Compound 294 was prepared according to the General Procedure VI from the acid chloride 49 (0.5 mmol) and the aniline derivative 297 (0.180 g, 0.68 mmol). Purification by flash chromatography using 1-2% methanol/methylene chloride as eluant gave 294 (0.203 g, 71%): MS (ES−) m/z 570 (M−H); $^1$H NMR (400 MHz, CDCl$_3$) δ 10.64 (s, 1H), 8.27 (s, 1H), 7.57 (d, 1H), 7.52-7.48 (m, 2H), 7.35 (d, 1H), 7.31-7.30 (m, 2H), 7.22-7.20, (d, 1H), 7.04-7.00 (m, 2H), 4.64 (s, 2H), 3.77 (br s, 4H), 2.71-2.68 (m, 2H), 2.57 (br s, 4H), 2.50-2.47 (m, 2H), 2.14 (s, 3H).

Example 123

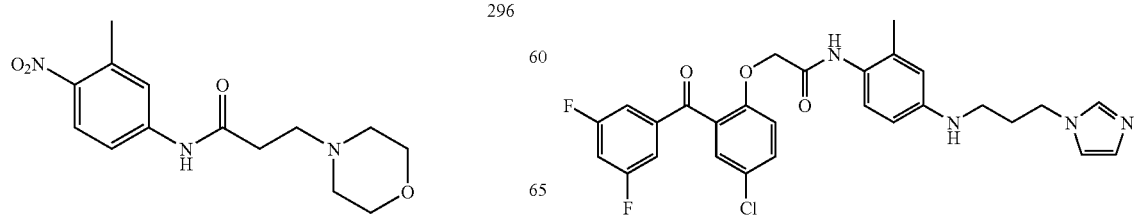

Step A:

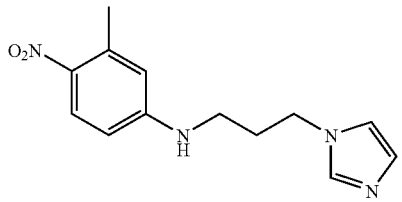

299

A mixture of 5-fluoro-2-nitrotoluene (0.24 mL, 2.0 mmol), 1-(3-aminopropyl)-imidazole (0.41 mL, 3.4 mmol), and sodium bicarbonate (0.302 g, 3.6 mmol) in 5 mL of pyridine and 0.5 mL of water was heated to reflux for 3 h. The reaction mixture was then partitioned between 50 mL of water and 50 mL of ethyl acetate. The organic layer was concentrated to give a yellow solid, which was purified by crystallization from ethyl acetate/hexane to provide 299 (0.255 g, 49%): $^1$H NMR (400 MHz, CDCl$_3$) δ 7.92 (d, 1H), 7.60 (s, 1H), 7.16 (s, 1H), 7.08 (t, 1H), 6.87 (s, 1H), 6.47 (dd, 1H), 6.40 (d, 1H), 4.04-3.98 (m, 2H), 3.06-3.01 (m, 2H), 2.47 (s, 3H), 1.98-1.91 (m, 2H).

Step B:

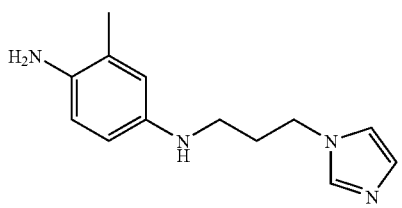

300

A mixture of compound 299 (0.233 g, 0.90 mmol) and 10% palladium on carbon (0.020 g) in 20 mL of methanol was stirred at room temperature under an atmosphere of 53 psi hydrogen gas for 1 h. The reaction mixture was then filtered through Celite and concentrated in vacuo to give 300 (0.166 g, 80%): $^1$H NMR (400 MHz, CDCl$_3$) δ 7.48 (s, 1H), 7.07 (s, 1H), 6.92 (s, 1H), 6.58 (d, 1H), 6.40 (d, 1H), 6.36 (dd, 1H), 4.08 (t, 2H), 3.49-3.48 (m, 1H), 3.26 br s, 2H), 3.08-3.05 (m, 2H), 2.13 (s, 3H), 2.08-2.02 (m, 2H).

Step C:

Compound 298 was prepared according to the General Procedure IV from the acid 49 (0.196 g, 0.6 mmol) and the aniline derivative 300 (0.155 g, 0.67 mmol). Purification by flash chromatography using 2% methanol/methylene chloride as eluant gave 298 (0.219 g, 68%): MS (ES+) m/z 539 (M+H); MS (ES−) m/z 537 (M−H); $^1$H NMR (400 MHz, CDCl$_3$) δ 8.08 (s, 1H), 7.55 (dd, 1H), 7.49 (s, 1H), 7.39 (d, 1H), 7.35-7.31 (m, 2H), 7.30 (d, 1H), 7.08 (s, 1H), 7.06-7.01 (m, 2H), 6.93 (s, 1H), 6.43-6.40 (m, 2H), 4.67 (s, 2H), 4.09-4.06(m, 2H), 3.54(br s, 1H), 3.11 (t, 2H), 2.11-2.06(m, 5H).

Example 124

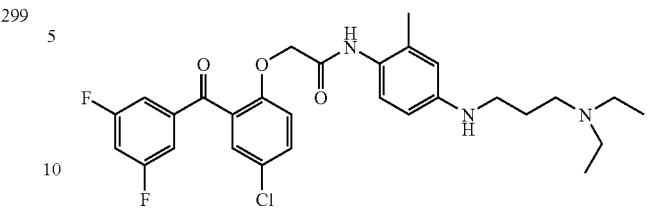

301

Step A:

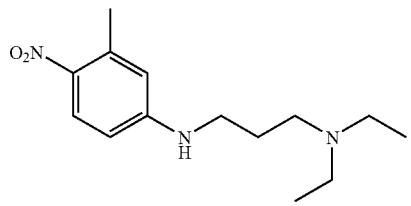

302

A mixture of 5-fluoro-2-nitrotoluene (0.37 mL, 3.0 mmol), N,N-diethyl-1,3-propanediamine (0.80 mL, 5.1 mmol), and sodium bicarbonate (0.454 g, 5.4 mmol) in 7.5 mL of pyridine and 0.75 mL of water was heated to reflux for 3 h. The reaction mixture was stirred at room temperature an additional 3 h, then partitioned between 50 mL of water and 50 mL of ethyl acetate. The aqueous layer was extracted with an additional 20 mL of ethyl acetate, and the combined organic layers were then dried over MgSO$_4$, filtered, and concentrated in vacuo to give 0.833 g of crude material. Purification by flash chromatography using 1-5% methanol/ methylene chloride as eluant gave 302 (0.742 g, 93%): $^1$H NMR (400 MHz, CDCl$_3$) δ 8.06 (d, 1H), 6.66 (br s, 1H), 6.34 (dd, 1H), 6.27 (d, 1H), 3.29-3.25 (m, 2H), 2.61 (s, 3H), 2.60-2.51 (m, 6H), 1.81-1.75 (m, 2H), 1.06 (t, 6H).

Step B:

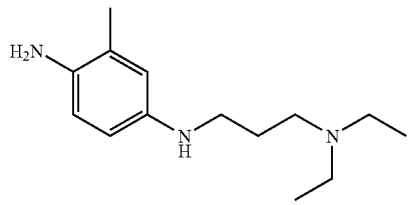

303

A mixture of compound 302 (0.730 g, 2.75 mmol) and 10% palladium on carbon (0.070 g) in 20 mL of methanol was stirred at room temperature under an atmosphere of 55 psi hydrogen gas for 1.17 h. The reaction mixture was then filtered through Celite and concentrated in vacuo to give 303 (0.581 g, 90%): $^1$H NMR (400 MHz, CDCl$_3$) δ 6.57 (d, 1H), 6.42-6.37 (m, 2H), 3.11-3.08 (m, 2H), 2.54-2.49 (m, 6H), 2.14 (s, 3H), 1.78-1.71 (m, 2H), 1.03 (t, 6H).

Step C:

Compound 301 was prepared according to the General Procedure IV from the acid 49 (0.196 g, 0.6 mmol) and the aniline derivative 303 (0.158 g, 0.67 mmol). Purification by flash chromatography using 3% methanol/0.1% triethylamine/methylene chloride as eluant, followed by crystallization from ethyl acetate/hexane gave 301 (0.113 g, 35%): MS (ES+) m/z 544 (M+H); MS (ES−) m/z 542 (M−H); ¹H NMR (400 MHz, CDCl₃) δ 7.96 (br s, 1H), 7.54 (dd, 1H), 7.39 (d, 1H), 7.34-7.31 (m, 2H), 7.25 (d, 1H), 7.05-6.99 (m, 2H), 6.43-6.41 (m, 2H), 4.65 (s, 2H), 3.15 (t, 2H), 2.57-2.52 (m, 6H), 2.07 (s, 3H), 1.80-1.73 (m, 2H), 1.05 (t, 6H).

Example 125

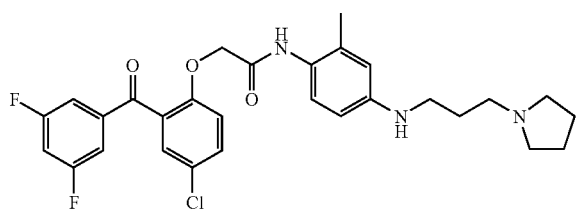

304

Step A:

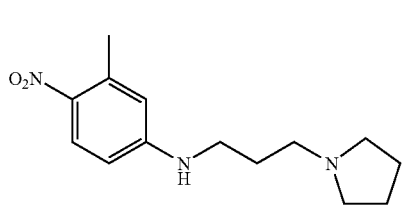

305

A mixture of 5-fluoro-2-nitrotoluene (0.37 mL, 3.0 mmol), 1-(3-aminopropyl)pyrrolidine (0.64 mL, 5.1 mmol), and sodium bicarbonate (0.454 g, 5.4 mmol) in 7.5 mL of pyridine and 0.75 mL of water was heated to reflux for 3 h. The reaction mixture was stirred at room temperature an additional 3 h, then partitioned between 50 mL of water and 50 mL of ethyl acetate. The aqueous layer was extracted with an additional 20 mL of ethyl acetate, and the combined organic layers were then dried over MgSO₄, filtered, and concentrated in vacuo to give 0.758 g of crude material. Purification by flash chromatography using 0.5-10% methanol/methylene chloride as eluant gave 305 (0.595 g, 75%): ¹H NMR (400 MHz, CDCl₃) δ 8.06 (d, 1H), 6.35 (dd, 1H), 6.29 (d, 1H), 6.09 (br s, 1H), 3.30-3.26 (m, 2H), 2.65-2.62 (m, 2H), 2.61 (s, 3H), 2.58-2.52 (m, 4H), 1.86-1.78 (m, 6H).

Step B:

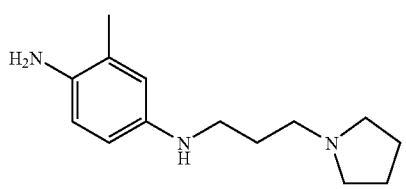

306

A mixture of compound 305 (0.590 g, 2.24 mmol) and 10% palladium on carbon (0.060 g) in 20 mL of methanol was stirred at room temperature under an atmosphere of 60 psi hydrogen gas for 1.33 h. The reaction mixture was then filtered through Celite and concentrated in vacuo to give 306 (0.520 g, 99%): ¹H NMR (400 MHz, CDCl₃) δ 6.57 (d, 1H), 6.42 (d, 1H), 6.39 (dd, 1H), 3.23 (br s, 2H), 3.12 (t, 2H), 2.56 (t, 2H), 2.53-2.48 (m, 4H), 2.13 (s, 3H), 1.84-1.75 (m, 6H) ppm.

Step C:

Compound 304 was prepared according to the General Procedure IV from the acid 49 (0.196 g, 0.6 mmol) and the aniline derivative 306 (0.156 g, 0.67 mmol). Purification by flash chromatography using 3% methanol/0.1% triethylamine/methylene chloride as eluant, followed by crystallization from ethyl acetate/hexane gave 304 (0.064 g, 20%): MS (ES+) m/z 542 (M+H); ¹H NMR (400 MHz, CDCl₃) δ 7.98 (s, 1H), 7.54 (dd, 1H), 7.39 (d, 1H), 7.36-7.31 (m, 2H), 7.26 (s, 1H), 7.05-7.00 (m, 2H), 6.44-6.42 (m, 2H), 4.65 (s, 2H), 3.18 (t, 2H), 2.65-2.59 (m, 6H), 2.07 (s, 3H), 1.87-1.79 (m, 6H).

Example 126

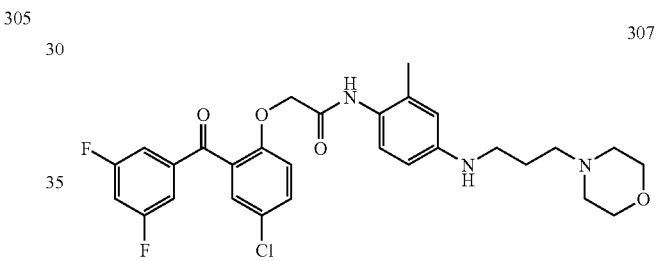

307

Step A:

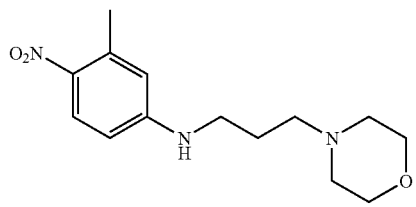

308

A mixture of 5-fluoro-2-nitrotoluene (0.24 mL, 2.0 mmol), 4-(3-aminopropyl)morpholine (0.50 mL, 3.4 mmol), and sodium bicarbonate (0.302 g, 3.6 mmol) in 5 mL of pyridine and 0.5 mL of water was heated to reflux for 1 h. The reaction mixture was then partitioned between 50 mL of water and 50 mL of ethyl acetate, and the organic layer was dried over MgSO₄, filtered, and concentrated in vacuo to give 0.493 g of crude material. Purification by flash chromatography using 1% methanol/methylene chloride as eluant gave 308 (0.279 g, 50%): ¹H NMR (400 MHz, CDCl₃) δ 8.06 (d, 1H), 6.38 (dd, 1H), 6.31 (s, 1H), 5.92 (br s, 1H), 3.77-3.75 (m, 4H), 3.31-3.27 (m, 2H), 2.6 (s, 3H), 2.54-2.50 (m, 6H), 1.85-1.79 (m, 2H).

Step B:

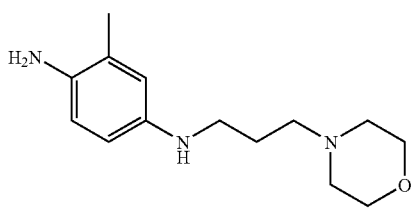

309

A mixture of compound 308 (0.266 g, 0.95 mmol) and 10% palladium on carbon (0.020 g) in 5 mL of methanol was stirred at room temperature under an atmosphere of 60 psi hydrogen gas for 2 h. The reaction mixture was then filtered through Celite and concentrated in vacuo to give 309 (0.229 g, 97%): $^1$H NMR (400 MHz, CDCl$_3$) δ 6.58 (d, 1H), 6.43 (d, 1H), 6.39 (dd, 1H), 3.74-3.72 (m, 4H), 3.14-3.11 (m, 2H), 2.48-2.45 (m, 6H), 2.14 (s, 3H), 1.81-1.75 (m, 2H).

Step C:

Compound 307 was prepared according to the General Procedure IV from the acid 49 (0.092 g, 0.28 mmol) and the aniline derivative 309 (0.070 g, 0.28 mmol). Purification by flash chromatography using 3% methanol/0.1% triethylamine/methylene chloride as eluant gave 307 (0.101 g, 65%): MS (ES+) m/z 558 (M+H); $^1$H NMR (400 MHz, CDCl$_3$) δ 8.00 (s, 1H), 7.54 (dd, 1H), 7.40-6.72 (m, 6H), 6.62 (d, 1H), 6.45-6.42 (m, 2H), 4.66 (s, 2H), 3.75-3.61 (m, 4H), 3.17 (t, 2H), 2.49-2.25 (m, 6H), 2.08 (s, 3H), 1.82-1.51 (m, 2H).

Example 127

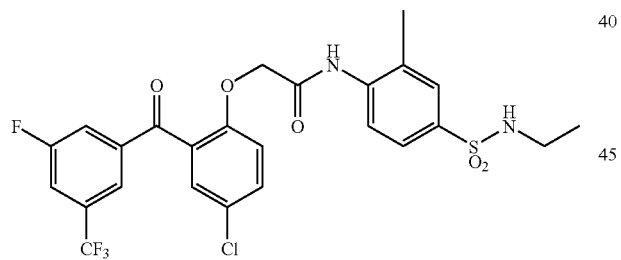

310

Step A:

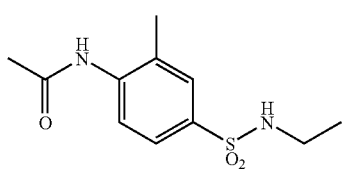

311

A mixture of sulfonyl chloride 464 (1.10 g, 4.4 mmol), ethylamine (3.3 mL of 2.0 M THF solution, 6.6 mmol), and pyridine (0.39 mL, 4.8 mmol) in 50 mL of methylene chloride was stirred at room temperature for 11 d. The reaction mixture was then diluted with 50 mL of water and filtered to give 0.605 g of crude material. Crystallization from methanol gave 311 (0.425 g, 38%): $^1$H NMR (400 MHz, CDCl$_3$) δ 9.40 (s, 1H), 7.73 (d, 1H), 7.58 (d, 1H), 7.53 (dd, 1H), 7.39 (t, 1H), 2.75-2.68 (m, 2H), 2.26 (s, 3H), 2.07 (s, 3H), 0.93 (t, 3H).

Step B:

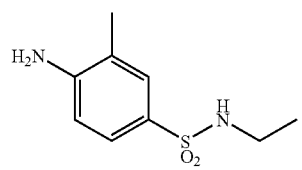

312

A mixture of compound 311 (0.308 g, 1.2 mmol), 1.5 M HCl (2.5 mL), and ethanol (12 mL) was heated to 80° C. for 18 h, then stirred at room temperature an additional 1 h. The reaction mixture was poured into 50 mL saturated NaHCO$_3$ (aq) and extracted with two 30-mL portions of methylene chloride. The combined organic layers were dried over MgSO$_4$, filtered and concentrated in vacuo to give 312 (0.337 g), which was used without further purification: $^1$H NMR (400 MHz, CDCl$_3$) δ 7.54 (m, 2H), 6.68 (d, 1H), 4.29 (t, 1H), 4.07 (br s, 2H), 3.00-2.93 (m, 2H), 2.18 (s, 3H), 1.10 (t, 3H).

Step C:

Compound 310 was prepared according to the General Procedure IV from the acid 71 (0.188 g, 0.5 mmol) and the aniline derivative 312 (0.169 g, 0.6 mmol). Purification by flash chromatography using 15-25%-ethyl acetate/hexane as eluant gave 310(0.016 g, 6%): MS (ES+) m/z 573 (M+H); MS (ES−) m/z 571 (M−H); $^1$H NMR (400 MHz, CDCl$_3$) δ 8.67 (s, 1H), 8.08 (d, 1H), 7.88 (s, 1H), 7.69 (m, 3H), 7.59 (dd, 2H), 7.38 (d, 1H), 7.09 (d, 1H), 4.74 (s, 2H), 3.03-2.95 (m, 2H), 2.31 (s, 3H), 1.11 (t, 3H).

Example 128

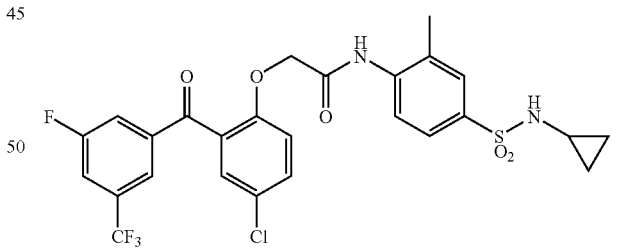

313

Step A:

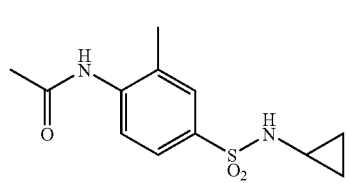

314

A mixture of sulfonyl chloride 464 (1.10 g, 4.4 mmol), cyclopropylamine (0.46 mL, 6.6 mmol), and pyridine (0.39 mL, 4.8 mmol) in 50 mL of methylene chloride was stirred at room temperature for 6 d. The reaction mixture was then filtered to give 0.800 g of crude material. Crystallization from methanol gave 314 (0.329 g, 28%): $^1$H NMR (400 MHz, CDCl$_3$) δ 9.41 (s, 1H), 7.78 (s, 1H), 7.77-7.60 (m, 2H), 7.56 (dd, 1H), 2.27 (s, 3H), 2.08 (s, 3H), 2.06-2.03 (m, 1H), 0.45-0.42 (m, 2H), 0.36-0.34 (m, 2H).

Step B:

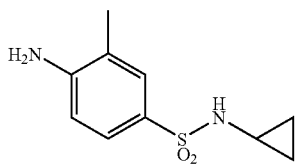

315

A mixture of compound 314 (0.324 g, 1.2 mmol), 1.5 M HCl (2.5 mL), and ethanol (12 mL) was heated to 80° C. for 18 h, then stirred at room temperature an additional 1 h. The reaction mixture was poured into 25 mL saturated NaHCO$_3$ (aq) and extracted with two 25-mL portions of methylene chloride. The combined organic layers were dried over MgSO$_4$, filtered and concentrated in vacuo to give 315 (0.256 g, 94%), which was used without further purification: $^1$H NMR (400 MHz, CDCl$_3$) δ 7.57-7.55 (m, 2H), 6.69 (d, 1H), 4.81 (br s, 2H), 2.22-2.19 (m, 4H), 0.59-0.55 (m, 4H).

Step C:

Compound 313 was prepared according to the General Procedure IV from the acid 71 (0.188 g, 0.5 mmol) and the aniline derivative 315 (0.124 g, 0.55 mmol). Purification by flash chromatography using 15-25% ethyl acetate/hexane as eluant gave 313 (0.026 µg, 9%): MS (ES+) m/z 585 (M+H); MS (ES−) m/z 583 (M−H); $^1$H NMR (400 MHz, CDCl$_3$) δ 8.68 (s, 1H), 8.12 (d, 1H), 7.88 (s, 1H), 7.75-7.71 (m, 3H), 7.59 (dd, 2H), 7.47-7.43 (m, 1H), 7.38 (d, 1H), 7.08 (d, 1H), 4.75 (s, 2H), 2.32 (s, 3H), 2.25-2.19 (m, 1H), 0.63-0.57 (m, 4H).

Example 129

316

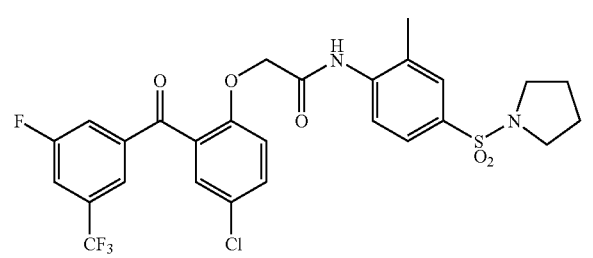

Step A:

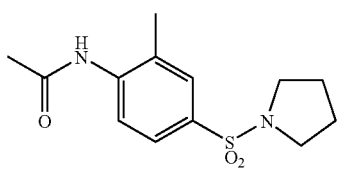

317

A mixture of sulfonyl chloride 464 (1.10 g, 4.4 mmol), pyrrolidine (0.55 mL, 6.6 mmol), and pyridine (0.39 mL, 4.8 mmol) in 50 mL of methylene chloride was stirred at room temperature for 6 d. The reaction mixture was then filtered, and the filter cake was washed with methylene chloride and methanol and dried with a vacuum pump to give 317 (0.696 g, 56%): $^1$H NMR (400 MHz, CDCl$_3$) δ 9.39 (s, 1H), 7.82 (d, 1H), 7.60 (d, 1H), 7.55 (dd, 1H), 3.10-3.07 (m, 4H), 2.28 (s, 3H), 2.09 (s, 3H), 1.64-1.58 (m, 4H).

Step B:

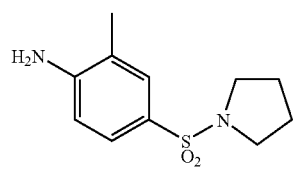

318

A mixture of compound 317 (0.690 g, 2.44 mmol), 1.5 M HCl (5.0 mL), and ethanol (25 mL) was heated to 80° C. for 18 h, then stirred at room temperature an additional 7 h. The reaction mixture was filtered to give 318 (0.369 g, 63%): $^1$H NMR (400 MHz, CDCl$_3$) δ 7.29-7.26 (m, 2H), 6.64 (d, 1H), 5.73 (br s, 2H), 3.01-2.98 (m, 4 h), 2.05 (s, 3H), 1.60-1.56 (m, 4H).

Step C:

Compound 316 was prepared according to the General Procedure IV from the acid 71 (0.188 g, 0.5 mmol) and the aniline derivative 318 (0.132 g, 0.55 mmol). Purification by flash chromatography using 15-25% ethyl acetate/hexane as eluant gave 316 (0.013 g, 4%): MS (ES+) m/z 599 (M+H); MS (ES−) m/z 597 (M−H); $^1$H NMR (400 MHz, DMSO-d$_6$) δ 9.36 (s, 1H), 7.97-7.01 (m, 9H), 4.78 (s, 2H), 3.08-3.04 (m, 4H), 2.15 (s, 3H), 1.59-1.56 (m, 4H).

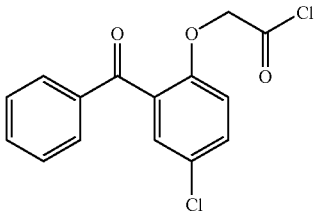

320

Carboxylic acid 105 (5 g, 17 mmol), methylene chloride (90 mL), and thionyl chloride (13.2 mL, 18 mmol) were used as described in general procedure XV to afford 320 as an orange oil (5.31 g). The crude product was used without further purification.

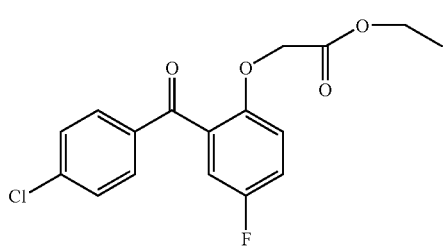

321

4'-Chloro-5-fluoro-2-hydroxybenzophenone (Lancaster, 5 g, 20 mmol), potassium carbonate (13.8 g, 100 mmol), ethyl bromoacetate (2.5 mL, 23 mmol), and acetone (200 mL) were used as in general procedure II to afford 321 as an orange/off-white solid (6.72 g, crude material). $^1$H NMR (DMSO-$d_6$, 300 MHz) δ 1.2 (t, 3H), 4.1 (m, 2H), 4.75 (s, 2H), 7.15 (dd, 1H), 7.3 (dd, 1H), 7.35-7.4 (m, 1H), 7.6 (d, 2H), 7.8 (d, 2H).

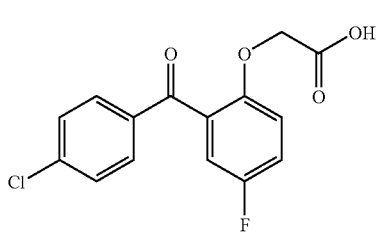

322

Ester 321 (6.72 g, 20 mmol), ethanol (80 mL), water (20 mL), and lithium hydroxide monohydrate (1 g, 24 mmol) were used as in general procedure III to afford carboxylic acid 322 as off-white solid (6.56 g, crude material). $^1$H NMR (DMSO-$d_6$, 300 MHz) δ 4.7 (s, 2H), 7.1 (d, 1H), 7.3 (d, 1H), 7.4 (m, 1H), 7.6 (d, 2H), 7.8 (d, 2H), 13 (bs, 1H); MS (ES$^-$) m/z 307 (M−H)$^-$.

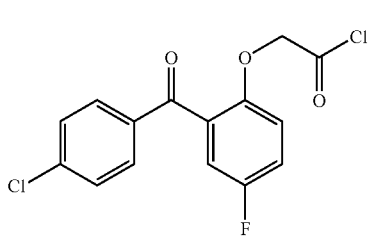

323

Into a round-bottom flask were placed acid 322 (3 g, 10 mmol) and thionyl chloride (51 mL of a 2N solution in methylene chloride, 102 mmol). After refluxing for 1½h, the mixture was concentrated in vacuo to give 323 as a dark purple oil, which was used without characterization or purification.

Example 130

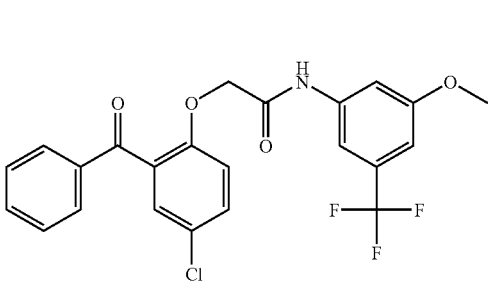

324

3-Methoxy-5-(trifluoromethyl)aniline (Aldrich, 0.309 g, 1.62 mmol), NEt$_3$ (0.23 mL, 1.65 mmol), acetonitrile (5 mL), and acid chloride 320 (0.5 g, 1.62 mmol) in acetonitrile (7 mL) were used as in general procedure X. The product was purified by flash chromatography using a gradient between 9:1 and 4:1 hexanes:ethyl acetate to afford 324 as an off-white solid (0.17 g, 23%) $^1$H NMR (DMSO-$d_6$, 300 MHz) δ 3.8 (s, 3H), 4.7 (s, 2H), 7 (s, 1H), 7.2 (d, 1H), 7.4 (s, 1H), 7.5 (m, 4H), 7.6 (m, 2H), 7.8 (d, 2H), 10 (s, 1H); MS (ES$^-$) m/z 462 (M−H)$^-$.

Example 131

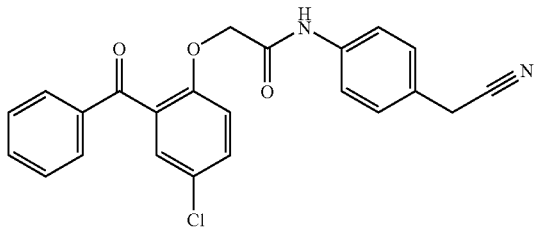

325

4-(N-Methylpiperazinyl)aniline (Biomet Research Ltd., 0.237 g, 1.24 mmol), NEt$_3$ (0.26 mL, 1.87 mmol), acetonitrile (5 mL), and acid chloride 320 (0.38 g, 1.24 mmol) in acetonitrile (2 mL) were used as in general procedure X. The product was purified by flash chromatography using a gradient between 49:1 and 24:1 methylene chloride:methanol to afford 325 as a yellow solid (0.16 g, 27%). $^1$H NMR (DMSO-$d_6$, 300 MHz) δ 2.2 (s, 3H), 2.4 (t, 4H), 3.1 (t, 4H), 4.7 (s, 2H), 6.9 (d, 2H), 7.2 (d, 2H), 7.3 (d, 2H), 7.5 (s, 1H), 7.55 (t, 2H), 7.6-7.7 (m, 2H), 7.8 (d, 2H) 9.5 (s, 1H); MS (ES$^-$) m/z 462 (M−H)$^-$.

Example 132

326

4-Aminophenyl acetonitrile (Aldrich, 0.214 g, 1.62 mmol), NEt$_3$ (0.23 mL, 1.65 mmol), acetonitrile (5 mL), and acid chloride 320 (0.5 g, 1.62 mmol) in acetonitrile (7 mL) were used as in general procedure X. The product was purified by flash chromatography using 7:3 hexanes:ethyl acetate with 0.01% NEt$_3$ to afford 326 as an orange solid (0.26 g, 40%). $^1$H NMR (DMSO-d$_6$, 300 MHz) δ 4 (s, 2H), 4.7 (s, 2H), 7.2 (d, 1H), 7.3 (d, 2H), 7.45 (s, 1H), 7.5-7.6 (m, 4H), 7.65 (m, 2H), 7.8 (d, 2H), 9.9 (s, 1H); MS (ES$^-$) m/z 403 (M−H)$^-$.

Example 133

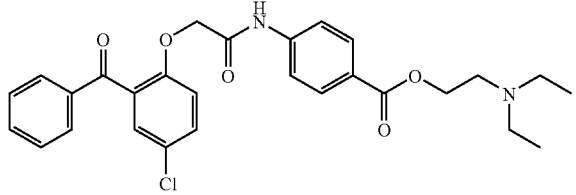

327

Procaine (ICN, 0.382 g, 1.62 mmol), NEt$_3$ (0.23 mL, 1.65 mmol), acetonitrile (5 mL), and acid chloride 320 (0.38 g, 1.24 mmol) in acetonitrile (5 mL) were used as in general procedure X. The product was purified by flash chromatography using 24:1 methylene chloride:methanol to afford 327 as an off-white solid (0.037 g, 4.5%). $^1$H NMR (DMSO-d$_6$, 300 MHz) δ 1 (t, 6H), 2.8 (bs, 2H), 4.3 (bs, 2H), 4.8 (bs, 2H), 7.2 (d, 1H), 7.5-7.7 (m, 8H), 7.8 (d, 2H), 7.9 (d, 2H), 10.2 (s, 1H); MS (AP$^+$) m/z 509 (M+H)$^+$.

Example 134

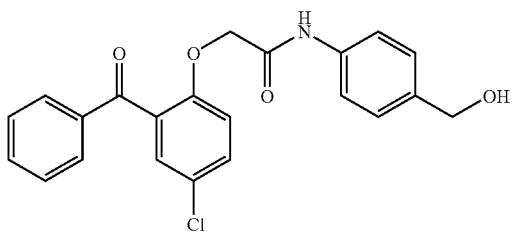

328

4-Amino benzyl alcohol (Fluka, 0.2 g, 1.62 mmol), NEt$_3$ (0.23 mL, 1.65 mmol), acetonitrile (5 mL), and acid chloride 320 (0.5 g, 1.62 mmol) in acetonitrile (5 mL) were used as in general procedure X. The product was purified by flash chromatography using 4:1 hexanes:ethyl acetate to afford 328 as a dark yellow solid (0.06 g, 10%). $^1$H NMR (DMSO-d$_6$, 300 MHz) δ 4.45 (d, 2H), 4.7 (s, 2H), 5.1 (t, 1H), 7.2 (t, 3H), 7.45 (t, 3H), 7.55 (t, 2H), 7.6 (t, 2H), 7.8 (d, 2H), 9.7 (s, 1H); MS (ES$^-$) m/z 394 (M−H)$^-$.

Example 135

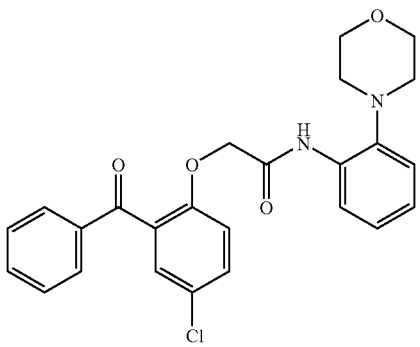

329

2-Morpholinoaniline (Lancaster, 0.288 g, 1.62 mmol), NEt$_3$ (0.23 mL, 1.65 mmol), acetonitrile (5 mL), and acid chloride 320 (0.5 g, 1.62 mmol) in acetonitrile (5 mL) were used as in general procedure X. The product was purified by flash chromatography using a gradient between 9:1 and 4:1 hexanes:ethyl acetate to afford 329 as an off-white solid (0.082 g, 11%). $^1$H NMR (DMSO-d$_6$, 400 MHz) δ 2.65 (s, 4H), 3.5 (s, 4H), 4.7 (s, 2H), 7.1 (t, 2H), 7.15 (s, 1H), 7.3 (d, 1H), 7.4 (t, 2H), 7.5 (m, 2H), 7.6 (d, 1H), 7.7 (d, 2H), 7.9 (s, 1H), 8.7 (s, 1H); MS (ES$^+$) m/z 451 (M+H)$^+$.

Example 136

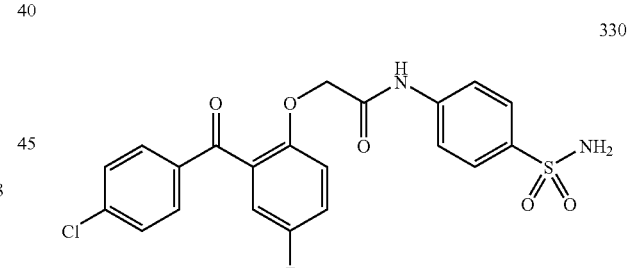

330

Sulfanilamide (Aldrich, 0.263 g, 1.53 mmol), NEt$_3$ (0.23 mL, 1.65 mmol), acetonitrile (5 mL), and acid chloride 323 (0.5 g, 1.53 mmol) in acetonitrile (5 mL) were used as in general procedure X. The reaction mixture was concentrated under reduced pressure, triturated with methylene chloride, ethyl acetate, hexanes, and methanol, and filtered. The resulting solid was washed with diethyl ether and ethyl acetate to give an off-white solid, which was triturated with water and filtered to give 330 as an off-white solid (0.078 g, 11%). $^1$H NMR (DMSO-d$_6$, 400 MHz) δ 4.7 (s, 2H), 7.15 (dd, 1H), 7.2 (s, 2H), 7.25 (d, 1H), 7.35 (t, 1H), 7.5 (d, 2H), 7.65 (d, 2H), 9.87 (bs, 2H), 10.25 (s, 1H); MS (ES$^-$) m/z 461 (M−H)$^-$.

Example 137

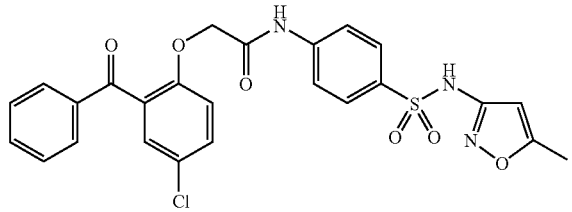
331

Sulfamethoxazole (Aldrich, 0.424 g, 1.67 mmol), NEt$_3$- (0.25 mL, 1.79 mmol), acetonitrile (5 mL), and acid chloride 320 (0.52 g, 1.68 mmol) in acetonitrile (5 mL) were used as in general procedure X. The product was purified by flash chromatography using 3:2 hexanes:ethyl acetate as elutant to afford 331 as an off-white solid (0.021 g, 2.4%). $^1$H NMR (DMSO-d$_6$, 400 MHz) δ 2.3 (s, 3H), 4.7 (s, 2H), 6.1 (s, 1H), 7.15 (d, 1H), 7.4 (s, 1H), 7.45 (d, 2H), 7.55 (m, 2H), 7.7 (d, 2H), 7.8 (d, 4H), 10.3 (s, 1H), 11.3 (s, 1H); MS (ES$^-$) m/z 524 (M−H)$^-$.

Example 138

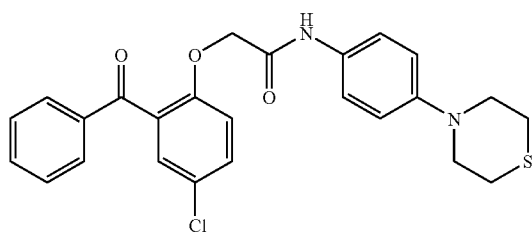
332

Step A:

333

4-Nitro-bromobenzene (Aldrich, 10.31 g, 51 mmol) in pyridine (85 mL), sodium bicarbonate (7.5 g, 89 mmol), and water (3 mL) were used as in general procedure XI to afford 333 as a yellow crystalline solid (6.5 g, 57%). $^1$H NMR (DMSO-d$_6$, 400 MHz) δ 2.6 (t, 4H), 3.8 (t, 4H), 7 (d, 2H), 8 (d, 2H); MS (ES$^+$) m/z 225 (M+H)$^+$.

Step B:

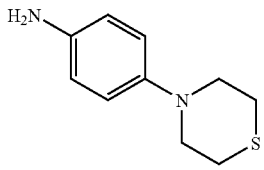
334

Compound 333 (1.04 g, 4.63 mmol), palladium on carbon (0.2 g, 10% w/w), ethanol (20 mL) and THF (20 mL) were used as in general procedure XII to afford 334 as a brown solid (0.95 g, crude material).

Step C:

Compound 334 (0.95 g, 4.9 mmol), NEt$_3$ (1 mL, 7.2 mmol), acetonitrile, and acid chloride 320 (1.51 g, 4.9 mmol) in acetonitrile (20 mL total reaction volume) were used as in general procedure X without heat. The reaction mixture was filtered and washed with acetonitrile followed by diethyl ether to afford 332 as an off-white solid (1.154 g, 51%). $^1$H NMR (DMSO-d$_6$, 400 MHz) δ 2.6 (m, 4H), 3.4 (m, 4H), 4.6 (s, 2H), 6.9 (d, 2H), 7.15 (d, 1H), 7.3 (d, 2H), 7.4 (s, 1H), 7.5 (t, 2H), 7.55-65 (m, 2H), 7.8 (d, 2H), 9.45 (s, 1H); MS (ES$^-$) m/z 465 (M−H)$^-$.

Example 139

335

Step A:

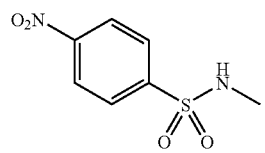
336

4-Nitrobenzenesulfonylchloride (Aldrich, 44.3 g, 200 mmol) was added portionwise to a solution of methylamine in ethanol (250 mL, 208 mmol) which was stirred at 0° C. under nitrogen. After removing the ice bath, the reaction was stirred for 45 min. Water (250 mL) was added and the resulting product was filtered to afford 336 as a crystalline solid (37.6 g, 87%). The crude material was used without purification.

Step B:

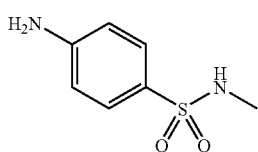
337

Palladium on carbon (2 g, 10% w/w) was added to a solution of compound 336 (17.3 g, 80 mmol), methanol (80 mL), THF (80 mL), and hydrochloric acid (concentrated, 7 mL, 84 mmol) and used as in general procedure XII to afford 337 as a white solid (14.3 g, 80%). The crude material was used without purification.

Step C:

Compound 337 (0.32 g, 1.44mmol, NEt$_3$ (0.5 mL, 3.6 mmol), acetonitrile (5 mL), and acid chloride 320 (0.444 g, 1.44 mmol) in acetonitrile (5 mL) were used as in general procedure X. After 6 d, another equivalent of acid chloride 320 (0.444 g, 1.44 mmol) was added and the solution was stirred. The reaction mixture was filtered and the resulting solid was washed with acetonitrile and water, and suspended in ethyl acetate. The suspension was filtered and the filtrate concentrated in vacuo to afford 335 as an off-white solid (0.152 g, 23%). $^1$H NMR (DMSO-d$_6$, 400 MHz) δ 2.3 (d, 3H), 4.7 (s, 2H), 7.15 (d, 1H), 7.3 (m, 1H), 7.45 (s, 1H), 7.5 (t, 2H), 7.54-7.62 (m, 2H), 7.7 (s, 4H), 7.8 (d, 2H), 10.2 (s, 1H); MS (ES$^-$) m/z 457 (M–H)$^-$.

Example 140

338
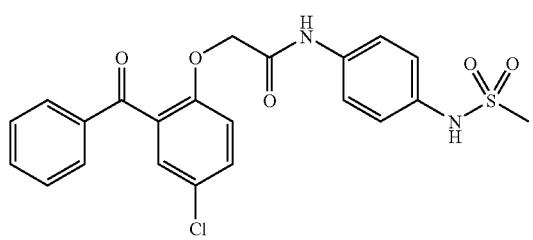

Step A:

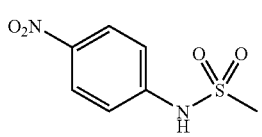
339

Methanesulfonyl chloride (5 g, 43.9 mmol) was added dropwise to a solution of 4-nitroaniline (Aldrich, 5.95 g, 43.1 mmol) in dry pyridine (100 mL) which was stirred at −15° C. under nitrogen. After storing the resulting solution at 0° C. for 2 d, the solvent was removed in vacuo. The product was triturated with ice water, filtered, and washed with ice water to afford 339 as an orange/yellow solid (8.87 g, 95%). The crude product was used without purification.

Step B:

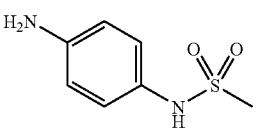
340

Palladium on carbon (0.14 g, 10% w/w) was added to a solution of compound 339 (1.0 g, 4.63 mmol), ethanol (15 mL), and THF (20 mL) and the resulting suspension was used as in general procedure XII with 50 psi of hydrogen to afford 340 as an orange oil-(0.85 g). The crude material was used without purification.

Step C:

Compound 340 (0.85 g, 4.6 mmol), NEt$_3$ (0.87 mL, 6.2 mmol), acetonitrile (8 mL), and acid chloride 320 (1.29 g, 4.2 mmol) in acetonitrile (8 mL) were used as in general procedure X. After 2 d, water was added and the resulting mixture was extracted with ethyl acetate. The organic layer was separated, washed with water, dried over MgSO$_4$, and concentrated in vacuo. The product was purified by flash chromatography using 35% ethyl acetate in hexanes to afford 338 as an off-white/pale yellow solid (0.480 g, 23%). $^1$H NMR (DMSO-d$_6$, 300 MHz) δ 2.95 (s, 3H), 4.7 (s, 2H), 7.15 (d, 2H), 7.2 (d, 1H), 7.45 (d, 3H), 7.7 (m, 7H), 7.85 (d, 2H), 9.6 (s, 1H), 9.8 (s, 1H); MS (ES$^-$) m/z 457 (M–H)$^-$.

Example 141

341
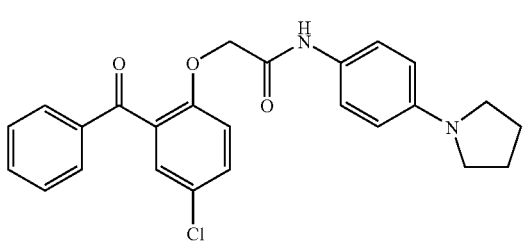

4-(N-pyrrolidine)aniline (Apin, 0.262 g, 1.61 mmol), NEt$_3$ (0.23 mL, 1.65 mmol), acetonitrile (5 mL), and acid chloride 320 (0.5 g, 1.62 mmol) in acetonitrile (5 mL) were used as in general procedure X. The product was purified by flash chromatography using a gradient between 9:1 and 4:1 hexanes:ethyl acetate to afford 341 as an off-white solid (0.112 g, 16%). $^1$H NMR (DMSO-d$_6$, 300 MHz) δ 2 (t, 4H), 3.2 (t, 4H), 4.66 (s, 2H), 6.5 (d, 2H), 7.2 (s, 1H), 7.3 (t, 2H), 7.45 (s, 1H), 7.5 (t, 2H), 7.6 (m, 2H), 7.8 (d, 2H), 9.3 (s, 1H); MS (ES$^-$) m/z 433 (M–H)$^-$.

Example 142

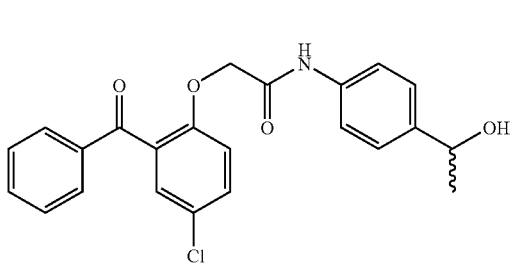

342

1-(4-Aminophenyl) ethanol (Apin, 0.25 g, 1.82 mmol), NEt$_3$ (0.25 mL, 1.79 mmol), acetonitrile (7 mL), and acid chloride 320 (0.51 g, 1.65 mmol) in acetonitrile (6 mL) were used as in general procedure X. The product was purified by flash chromatography using 45% ethyl acetate in hexanes to afford 342 as a colorless solid (0.428 g, 63%). $^1$H NMR (DMSO-d$_6$, 400 MHz) δ 1.25 (d, 3H), 4.6 (m, 1H), 4.7 (s, 2H), 5.1 (s, 1H), 7.2 (d, 1H), 7.25 (d, 2H), 7.4 (d, 3H), 7.5 (t, 2H), 7.6 (m, 2H), 7.8 (d, 2H), 9.7 (s, 1H); MS (ES$^-$) m/z 408 (M–H)$^-$.

The racemic mixture was separated to give 2 enantiomers using the following conditions: an OJ chiral column, 22% IPA, 2 mL/min., 26° C., 3000 psi on SFC. Enantiomer 1 eluted at 9.214 min. to give an off-white solid 342-A (0.092 g, 14%). Enantiomer 2 eluted at 11.118 min. to give another off-white solid 342-B (0.059 g, 9%). The enantiomeric purity was found to be >99% and the absolute stereochemistry were not determined.

Example 143

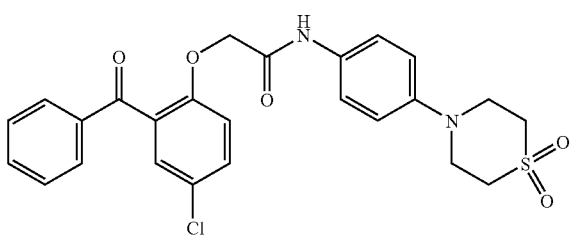

343

3-Chloroperoxybenzoic acid (~60%, 0.54 g, 1.9 mmol) was added portionwise to a solution of compound 332 (0.4 g, 0.86 mmol) in methylene chloride (30 mL) and stirred at rt. After 4 days, filtered the suspension and washed the solids with methylene chloride. The filtrate was washed with saturated sodium meta bisulfite, 10% NaOH, and water. The organics were dried over MgSO$_4$, and concentrated in vacuo. The product was purified by flash chromatography using 99:1 methylene chloride:methanol and further purified by TLC prep plate eluted with 99:1 methylene chloride:methanol to afford 343 as an off-white foam (0.062 g, 14%). $^1$H NMR (CDCl$_3$, 300 MHz), δ 3.1 (t, 4H), 3.8 (t, 4H), 4.7 (s, 2H), 6.9 (d, 2H), 7.05 (d, 1H), 7.4 (s, 1H), 7.5-7.6 (m, 5H), 7.65 (t, 1H), 7.9 (d, 2H), 9.05 (s, 1H); MS (AP$^-$) m/z 497 (M–H)$^-$.

Example 144

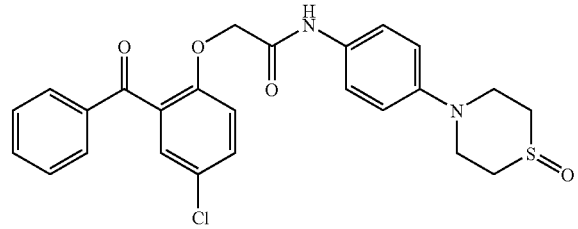

344

Step A:

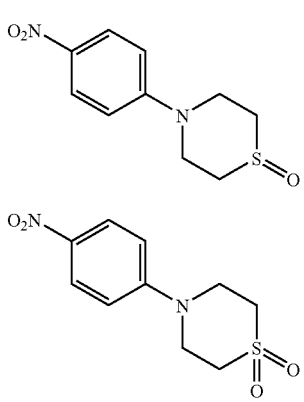

345

346

3-Chloroperoxybenzoic acid (~60%, 20.3 g, 70.6 mmol) in methylene chloride was added dropwise to a cooled solution of compound 333 (11.5 g, 51.1 mmol) in methylene chloride (250 mL total reaction volume) and stirred at –78° C. After 2 h, the reaction was warmed to rt and stirred overnight. The reaction mixture was washed with saturated sodium meta bisulfite, 2N NaOH, and water. The organics were separated, dried over MgSO$_4$, and concentrated in vacuo to give a mixture of 345 and 346 as a yellow solid (8.47 g, crude material). The crude material was used without purification.

Step B:

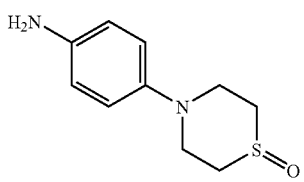

347

The mixture of 345 and 346 (8.47 g, 35.3 mmol), palladium on carbon (1.4 g, 10% w/w), ethanol (100 mL) and THF (50 mL) were used as in general procedure XII using 60 psi of hydrogen. The product was purified by flash chromatography using a gradient between 4:1 and 9:2 hexanes:ethyl acetate to afford 347 as a yellow solid (3.94 g, 53.2%). $^1$H NMR (DMSO-d$_6$, 400 MHz) δ 2.7 (dd, 2H), 2.9 (m, 2H), 3.16 (dd, 2H), 3.7 (t, 2H), 4.6 (bs, 2H), 6.46 (dd, 2H), 6.71 (dd, 2H); MS (ES$^+$) m/z 211 (M+H)$^+$.

Step C:

Carboxylic acid 105 (4.15 g, 14.3 mmol), HCA (1.08 mL, 7.1 mmol), THF (60 mL), PPh₃ (1.82 g, 6.95 mmol) in THF (15 mL), sulfoxide 347 (3 g, 14.3 mmol) in THF (125 mL), and pyridine (15 mL, 185 mmol) were used as in general procedure XIII. The product was purified by flash chromatography using a gradient between 99:1 and 9:1 methylene chloride:methanol and further purified by triturating the resulting solid with methanol and ethanol, filtering, and washing the solids with water and methanol to afford 344 as a tan solid (2.7 g, 39%). $^1$H NMR (DMSO-d$_6$, 300 MHz) δ 2.7 (d, 2H), 2.9 (t, 214), 3.5 (d, (2H), 3.7 (t, 2H), 4.7 (s, 2H), 7 (d, 2H), 7.2 (d, 1H), 7.4 (d, 2H), 7.47 (s, 1H), 7.55 (d, 2H), 7.65 (t, 2H), 7.8 (d, 2H), 9.6 (s, 1H); MS (AP$^-$) m/z 481 (M−H)$^-$.

Example 145

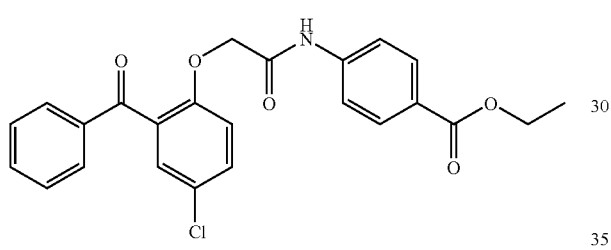

348

Glycerol-p-aminobenzoate (ICN, 0.342 g, 1.62 mmol), NEt₃ (0.25 mL, 1.79 mmol), acetonitrile (7 mL), and acid chloride 320 (0.5 g, 1.62 mmol) in acetonitrile (8 mL) were used as in general procedure X. The product was purified by flash chromatography using 9:1 hexanes:ethyl acetate then further purified by flash chromatography using 99:1 methylene chloride:methanol to afford 348 as an off-white solid (0.02 g, 3%). $^1$H NMR (DMSO-d$_6$, 300 MHz) δ 1.3 (t, 3H), 4.3 (q, 2H), 4.8 (s, 2H), 7.5 (d, 1H), 7.6 (d, 2H), 7.7 (d, 4H), 7.8 (d, 2H), 7.9 (d, 2H), 10.2 (s, 1H); MS (ES$^-$) m/z 436 (M−H)$^-$.

Example 146

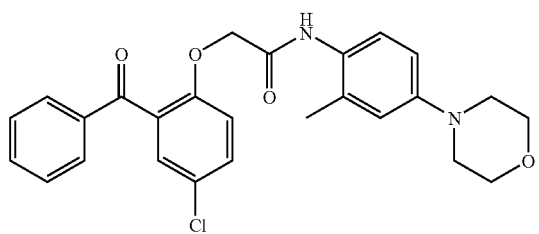

349

Step A:

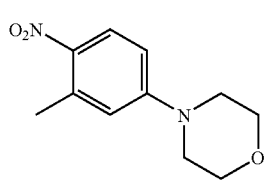

350

4-Chloro-2-nitrotoluene (SALOR, 2 g, 11.7 mmol) in pyridine (25 mL), sodium bicarbonate (2 g, 23.8 mmol), water (5 mL), and morpholine (Aldrich, 2.03 g, 23.3 mmol) were used as in general procedure XI to afford 350 as a yellow solid (0.804 g, 31%). $^1$H NMR (DMSO-d$_6$, 300 MHz) δ 2.5 (s, 3H), 3.4 (t, 4H), 3.7 (t, 4H), 6.9 (d, 2H), 8 (d, 1H). The crude material was used without purification.

Step B:

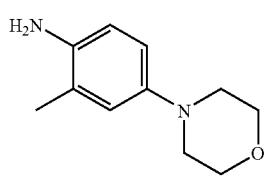

351

Compound 350 (0.72 g, 4.63 mmol), palladium on carbon (0.1 g, 10% w/w), ethanol (20 mL), and THF (20 mL) were used as in general procedure XII using 50 psi of hydrogen to afford 351 as a brown solid (0.623 g, crude material).

Step C:

Compound 351 (0.623 g, 3.2 mmol), NEt₃ (1.3 mL, 9.3 mmol) in acetonitrile (8 mL), and acid chloride 320 (1.02 g, 3.3 mmol) in acetonitrile (7 mL) were used as in general procedure X. The product was purified by flash chromatography using 99.5:0.5 methylene chloride:methanol to afford 349 as an orange foam (0.072 g, 5%). $^1$H NMR (DMSO-d$_6$, 400 MHz) δ 1.9 (s, 3H), 3 (t, 4H), 3.7 (t, 4H), 4.65 (s, 2H), 6.7 (d, 1H), 6.73 (s, 1H), 7.1 (d, 1H), 7.2 (d, 1H), 7.4 (s, 1H), 7.5 (t, 2H), 7.6 (t, 2H), 7.75 (d, 2H), 8.8 (s, 1H); MS (ES$^-$) m/z 463 (M−H)$^-$.

Example 147

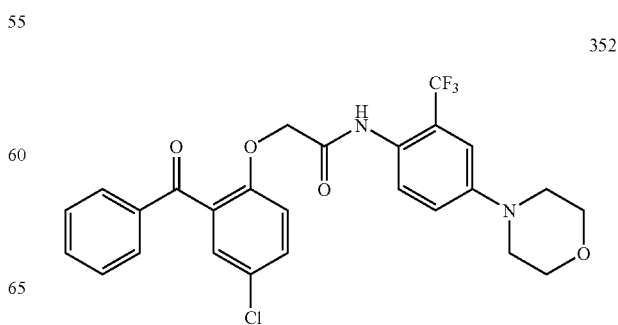

352

Step A:

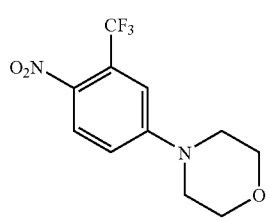

353

5-Bromo-2-nitrobenzotrifluoride (Lancaster, 2 g, 7.4 mmol) in pyridine (20 mL), sodium bicarbonate (1.25 g, 14.8 mmol), water (5 drops), and morpholine (Aldrich, 1.29 g, 14.8 mmol) were used as in general procedure XI to afford 353 as a yellow solid (1.62 g, 79%). $^1$H NMR (DMSO-$d_6$, 400 MHz) δ 3.5 (t, 4H), 3.8 (t, 4H), 7.25 (d, 1H), 7.3 (s, 1H), 8.1 (d, 1H). The crude product was used without purification.

Step B:

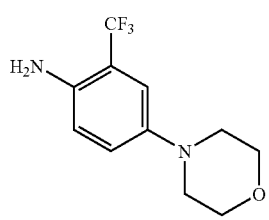

354

Compound 353 (1.62 g, 5.9 mmol), palladium on carbon (0.2 g, 10% w/w), ethanol (12 mL) and THF (12 mL) were used as in general procedure XII using 75 psi of hydrogen to afford 354 as a brown solid (1.41 g, crude material).

Step C:

Compound 354 (1.41 g, 5.73 mmol), NEt$_3$ (0.8 mL, 5.74 mmol), acetonitrile (15 mL), and acid chloride 320 (1.8 g, 5.82 mmol) in acetonitrile (15 mL) were used as in general procedure X. The product was purified by flash chromatography using 35% ethyl acetate in hexanes and further purified by flash chromatography using 1:1 ethyl acetate: hexanes to afford 352 as an off-white solid (0.426 g, 14%). $^1$H NMR (DMSO-$d_6$, 400 MHz) δ 3.2 (t, 4H), 3.75 (t, 4H), 4.7 (s, 2H), 7.15 (s, 1H), 7.2 (m, 3H), 7.45-7.55 (m, 3H), 7.6 (t, 2H), 7.8 (d, 2H), 9 (s, 1H); MS (ES$^-$) m/z 517 (M–H)$^-$.

Example 148

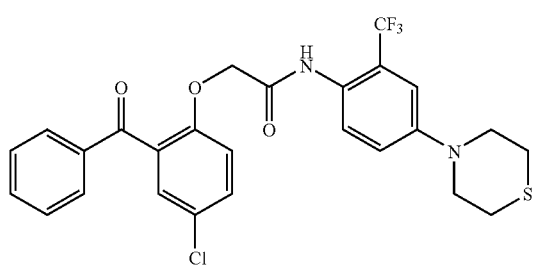

355

Step A:

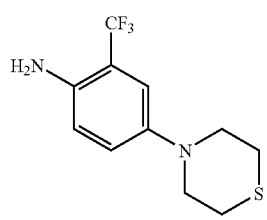

356

5-Bromo-2-nitrobenzotrifluoride (Lancaster, 2 g, 7.4 mmol) in pyridine (20 mL), sodium bicarbonate (1.25 g, 14.9 mmol), water (5 drops), and thiomorpholine (Aldrich, 1.52 g, 14.7 mmol) were used as in general procedure XI to afford 356 as a yellow solid (1.63 g, crude material). $^1$H NMR (DMSO-$d_6$, 400 MHz) δ 2.65 (t, 4H), 3.88 (t, 4H), 7.2 (d, 1H), 7.22 (s, 1H), 8 (d, 1H).

Step B:

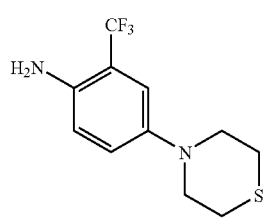

357

Compound 356 (1.63 g, 5.6 mmol), palladium on carbon (0.3 g, 10% w/w), ethanol (12 mL) and THF (12 mL) were used as described in general procedure XII using 75 psi of hydrogen to afford 357 as a brown oil (1.29 g, 88%). The crude material was used without purification.

Step C:

Compound 357 (1.29 g, 4.92 mmol), NEt$_3$ (0.7 mL, 5.02 mmol), acetonitrile (15 mL), and acid chloride 320 (1.52 g, 4.92 mmol) in acetonitrile (15 mL) were used as in general procedure X. The product was purified by flash chromatography using 35% ethyl acetate in hexanes to afford 355 as an orange oil (0.264 g, 10%). $^1$H NMR (DMSO-$d_6$, 400 MHz) δ 2.62 (m, 4H), 3.57 (m, 4H), 4.68 (s, 2H), 7.07 (d, 1H), 7.16 (q, 3H), 7.41 (d, 1H), 7.45 (m, 3H), 7.58 (m, 2H), 7.75 (d, 2H), 9 (s, 1H); MS (ES$^-$) m/z 533 (M–H)$^-$.

Example 149

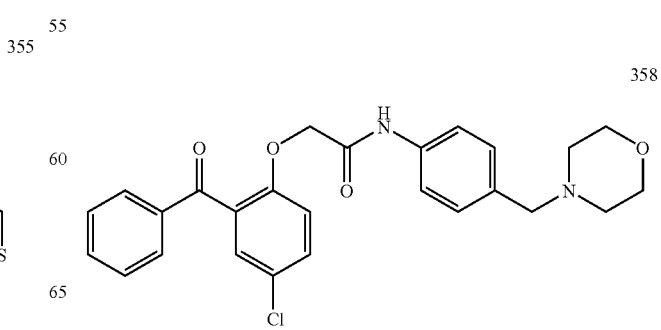

358

Step A:

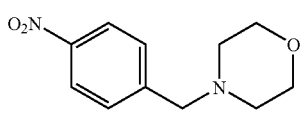
359

Morpholine (Aldrich, 0.74 mL, 8.5 mmol) was added dropwise to a solution of 4-nitro-benzylbromide (Aldrich, 2 g, 9.26 mmol), in acetone (20 mL), and potassium carbonate (2.4 g, 17.4 mmol). The resulting suspension was stirred at rt for 6 d under nitrogen. The mixture was filtered and the filtrate was concentrated in vacuo to afford 359 as a pale yellow solid (1.89 g, crude material).

Step B:

360

Compound 359 (1.89 g, 4.63 mmol), palladium on carbon (0.325 g, 10% w/w), ethanol (25 mL) and THF (25 mL) were used as in general procedure XII using 50 psi of hydrogen to afford 360 as a brown solid (1.6 g, crude material).

Step C:

Compound 360 (1.6 g, 8.3 mmol), NEt$_3$ (0.95 mL, 6.8 mmol), acetonitrile (7 mL), and acid chloride 320 (1.53 g, 4.95 mmol) in acetonitrile (7 mL) were used as in general procedure X. The product was purified by flash chromatography using a gradient between 9:1 and 4:1 hexanes:ethyl acetate 358 as an off-white solid (0.264 g, 12%). $^1$H NMR (DMSO-d$_6$, 300 MHz) δ 2.35 (d, 4H), 3.41 (s, 3H), 3.57 (t, 4H), 4.73 (s, 2H), 7.23 m, 3H), 7.47-7.67 (m, 7H), 7.83 (d, 2H), 9.78 (s, 1H); MS (ES) m/z 463 (M−H)$^−$.

Example 150 and Example 151

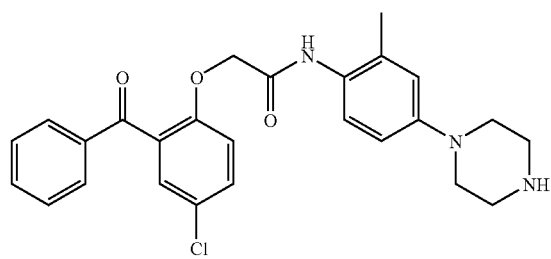
361

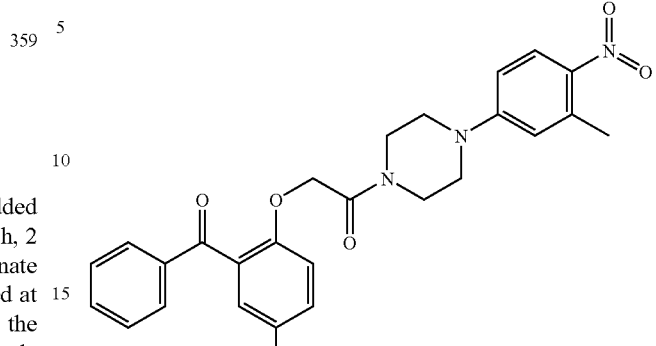
362

Step A:

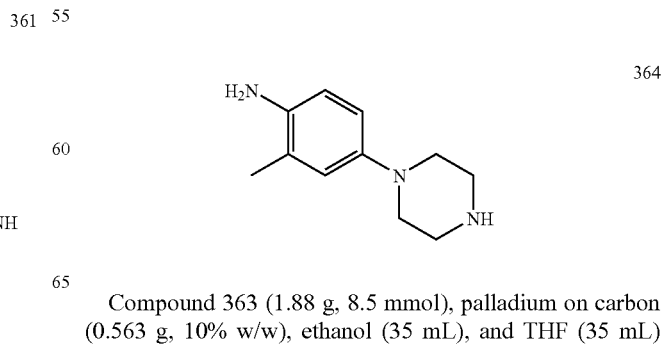
363

4-Chloro-2-nitrotoluene (SALOR, 1.46 g, 8.5 mmol) in pyridine (5 mL) was added dropwise to a solution of pyridine (22 mL), sodium bicarbonate (0.73 g, 8.7 mmol), piperazine (Aldrich, 1.5 g, 17.4 mmol), and water (3 mL) and the resulting mixture was refluxed for 2 d under nitrogen. Additional piperazine (1.5 g, 17.4 mmol) and sodium bicarbonate (0.73 g, 8.7 mmol) were added and the mixture was refluxed overnight. Acetone (200 mL) was added to the mixture and it was filtered hot. Water was added to the filtrate and the mixture was cooled to rt. Filtered the resulting suspension and concentrated the filtrate in vacuo. The concentrate was dissolved in hot methanol and ether and cooled to rt. The resulting mixture was filtered and the filtrate was concentrated in vacuo to afford 363 as a yellow solid (4.22 g). MS (ES$^+$) m/z 222 (M+H)$^+$. The crude product was used without purification.

Step B:

364

Compound 363 (1.88 g, 8.5 mmol), palladium on carbon (0.563 g, 10% w/w), ethanol (35 mL), and THF (35 mL)

were used as in general procedure XII to afford 364 as a yellow oil (1.7 g). The crude product was used without purification.

Step C:

Compound 364 (1.7 g, 8.9 mmol), NEt₃ (1.4 mL, 10 mmol), acetonitrile (12 mL), and acid chloride 320 (2.36 g, 7.6 mmol) in acetonitrile (12 mL) were used as in general procedure X. Water was added to the reaction mixture and the resulting suspension was filtered. The filtrate was partitioned between 2N NaOH and ethyl acetate. The aqueous layer was acidified with 1N sodium hydrogen sulfate to pH 1 and extracted with ethyl acetate. The product was purified by flash chromatography using a gradient between 3:2 hexanes:ethyl acetate, ethyl acetate, and methanol to afford 362 as a yellow solid (0.250 g) MS (ES⁺) m/z 494 (M+H)⁺ and 361 as an orange solid (0.005 g, 0.1%). ¹H NMR (DMSO-d₆, 400 MHz) δ 1.96 (s, 3H), 2.79 (m, 4H), 2.97 (m, 4H), 4.66 (s, 2H), 6.66 (m, 2H), 7.05 (d, 1H), 7.2 (d, 1H), 7.42 (d, 1H), 7.46 (t, 2H), 7.6 (t, 2H), 7.75 (d, 2H), 8.79 (s, 1H); MS (ES⁺) m/z 464 (M+H)⁺.

Example 152

Step A:

5-Fluoro-2-nitrotoluene (Aldrich, 2 g, 12.9 mmol) in pyridine (5 mL) was added dropwise to a solution of pyridine (15 mL), sodium bicarbonate (1.62 g, 19.3 mmol), 1-t-butoxycarbonyl piperazine (Aldrich, 3.6 g, 19.3 mmol), and water (1.2 mL) and the resulting mixture was refluxed overnight. Acetone was added to the reaction and the resulting mixture was filtered hot. Water was added and the mixture was cooled to rt. The resulting solid was filtered and washed with water and ether to afford 366 as an orange solid (4.02 g). ¹H NMR (DMSO-d₆, 400 MHz)δ 1.39 (s, 9H), 2.47 (s, 3H), 3.41 (s, 8H), 6.84 (m, 2H), 7.97 (d, 1H). The crude material was used without purification.

Step B:

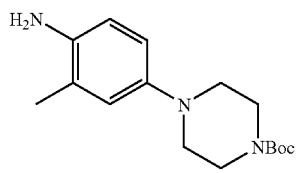

Compound 366 (4.02 g, 12.5 mmol), palladium on carbon (1.2 g, 10% w/w), ethanol (90 mL) and THF (10 mL) were used as in general procedure XII using 80 psi of hydrogen. The product was filtered through a celite pad eluted with 9:1 methylene chloride:methanol and concentrated in vacuo to afford 367 as a pink solid (2.926 g, crude material).

Step C:

Acid chloride 320 in methylene chloride was added dropwise to a solution of compound 367 (0.362 g, 1.24 mmol) in pyridine (20 mL) and stirred for 2 days. The reaction was concentrated in vacuo, ethanol and ice were added, and the resulting solid was filtered and washed with ether to afford 368 as a yellow solid (0.118 g, 20.2%). ¹H NMR (DMSO-d₆, 400 MHz) δ 1.38 (d, 9H), 1.95 (s, 3H), 3 (d, 4H), 3.4 (s, 4H), 4.67 (s, 2H), 6.7 (m, 2H), 7.1 (d, 1H), 7.42 (d, 1H), 7.48 (m, 2H), 7.6 (m, 2H), 7.75 (d, 2H), 8.8 (s, 1H).

Step D:

TFA (15 mL, 195 mmol) was added to a solution of compound 368 (0.118 g, 0.21 mmol) in acetonitrile and stirred overnight. The reaction mixture was concentrated in vacuo after carbon tetrachloride was added to azeotrope off the TFA. This procedure was repeated multiple times. The mixture was concentrated in vacuo to afford 365 as a yellow solid (0.085 g, 88%). ¹H NMR (DMSO-d₆, 400 MHz) δ 1.96 (s, 3H), 3.08 (d, 4H), 3.17 (d, 4H), 4.67 (s, 2H), 6.72 (m, 2H), 7.1 (d, 1H), 7.2 (d, 1H), 7.42 (s, 1H), 7.46 (m, 2H), 7.6 (m, 2H), 7.75 (d, 2H), 8 (bs, 1H), 8.86 (s, 1H); MS (ES⁺) m/z 464 (M+H)⁺.

Example 153

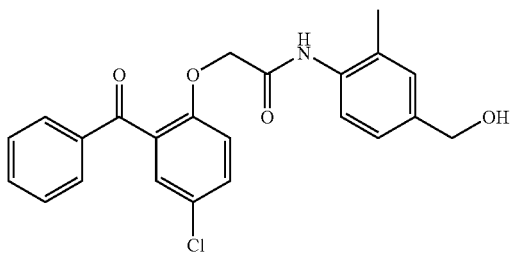

Step A:

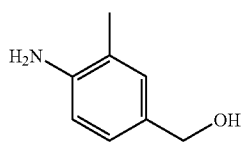

3-Methyl-4-nitrobenzyl alcohol (Aldrich, 1 g, 5.98 mmol), palladium on carbon (0.265 g, 10% w/w), ethanol (12 mL), and THF (12 mL) were used as in general procedure XII using 58 psi hydrogen to afford 370 as a yellow oil (0.65 g, 79%). The crude material was used without purification.

Step B:

Compound 370 (0.65 g, 4.74 mmol), NEt$_3$ (0.95 mL, 6.82 mmol), acetonitrile (10 mL), and acid chloride 320 (0.5 g, 1.62 mmol) in acetonitrile (10 mL) were used as in general procedure X. The product was purified by flash chromatography using 1:1 hexanes:ethyl acetate to afford 369 as a yellow solid (0.041 g, 2.1%). $^1$H NMR (DMSO-d$_6$, 400 MHz) δ 2 (s, 3H), 4.4 (s, 2H), 4.7 (s, 2H), 5.1 (bs, 1H), 7.1 (m, 2H), 7.25 (m, 2H), 7.45 (m, 3H), 7.6 (m, 2H), 7.76 (d, 2H), 8.9 (s, 1H); MS (ES$^-$) m/z 408 (M–H)$^-$.

Example 154

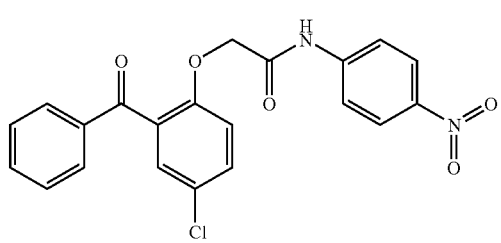

4-Nitroaniline (Sigma, 0.244 g, 1.77 mmol), NEt$_3$ (0.25 mL, 1.79 mmol), acetonitrile (5 mL), and acid chloride 320 (0.54 g, 1.75 mmol) in acetonitrile (5 mL) were used as in general procedure X. The product was purified by flash chromatography using 4:1 hexanes:ethyl acetate to afford 371 as an off-white solid (0.012 g, 2%). $^1$H NMR (CDCl$_3$, 300 MHz) δ 4.8 (s, 2H), 7.05 (d, 1H), 7.4 (d, 1H), 7.5 (m, 3H), 7.65 (t, 1H), 7.9 (d, 2H), 8 (d, 2H), 8.25 (d, 2H), 10 (s, 1H); MS (ES$^-$) m/z 409 (M–H)$^-$.

Example 155

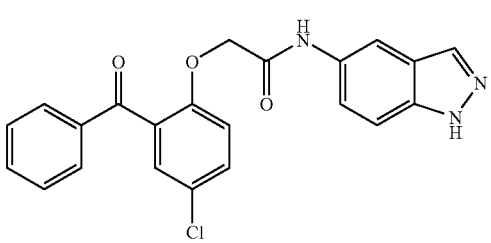

Step A:

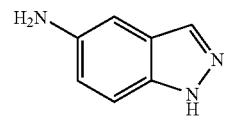

5-Nitroindazole (Aldrich, 1.2 g, 7.36 mmol), palladium on carbon (0.23 g, 10% w/w), ethanol (25 mL), and THF (5 mL) were used as in general procedure XII using 78 psi of hydrogen to afford 373 as a pink solid (0.98 g, crude material). $^1$H NMR (DMSO-d$_6$, 400 MHz) δ 4.7 (s, 2H), 6.7 (dd, 2H), 7.2 (d, 1H), 7.7 (s, 1H), 12.5 (s, 1H).

Step B:

Compound 373 (1 g, 7 mmol), NEt$_3$ (1.2 mL, 8.6 mmol), acetonitrile (20 mL), and acid chloride 320 (1.9 g, 6.2 mmol) in acetonitrile (10 mL) were used as in general procedure X. Ice water was added and the resulting suspension was filtered, washed with water, and the solid was recrystallized from ethanol and water. The resulting precipitate was filtered and washed with ether to afford 372 as a pink solid (0.679 g, 17.3%). $^1$H NMR (DMSO-d$_6$, 400 MHz) δ 4.7 (s, 2H), 7.2 (d, 1H), 7.3 (d, 1H), 7.4-7.5 (m, 4H), 7.55-7.6 (m, 2H), 7.6 (dd, 2H), 8 (s, 2H), 9.7 (s, 1H), 13 (s, 1H); MS (ES$^-$) m/z 406 (M–H)$^-$.

Example 156

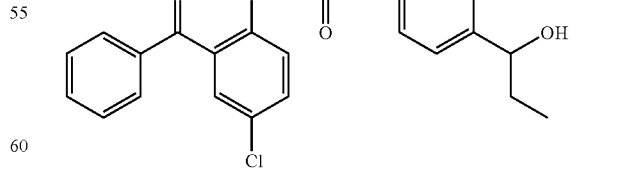

4-Aminophenyl ethyl carbinol (Apin, 0.254 g, 1.7 mmol), NEt$_3$ (0.28 mL, 2 mmol), acetonitrile (6 mL), and acid chloride 320 (0.53 g, 1.7 mmol) in acetonitrile (6 mL) were used as in general procedure X. The mixture was filtered, washed with 1M sodium hydrogen sulfate, and the filtrate was extracted with ethyl acetate. The organics were separated, dried over MgSO$_4$, and concentrated in vacuo. The product was purified by flash chromatography using 93:7 methylene chloride:methanol, flash chromatography using 95:5 methylene chloride:methanol, a TLC prep plate using 92:8 methylene chloride:methanol, and a TLC prep plate using 9:1 methylene chloride:methanol to afford 374 as an off-white solid (0.029 g, 4%). $^1$H NMR (DMSO-d$_6$, 300 MHz) δ 0.8 (t, 3H), 1.6 (m, 2H), 4.4 (m, 1H), 4.7 (s, 2H), 5.08 (d, 1H), 7.2 (t, 3H), 7.47 (d, 3H), 7.55 (m, 2H), 7.65 (m, 2H), 7.85 (d, 2H), 9.7 (s, 1H); MS (ES$^-$) m/z 422 (M–H)$^-$.

Example 157

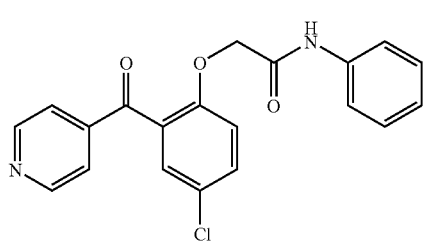

375

Compound 378 (0.143 g, 0.64 mmol) was added to a solution of compound 377 (0.15 g, 0.64 mmol), potassium carbonate (0.09 g, 0.65 mmol), and DMF (5 mL) and stirred overnight. The mixture was poured into ice water, filtered, and the resulting solid was washed with ether. The product was purified by TLC prep plate using 23:1 methylene chloride:methanol to afford 375 as an orange solid (0.021 g, 9%). $^1$H NMR (DMSO-d$_6$, 300 MHz) δ 4.7 (s, 2H), 7.06 (t, 1H), 7.25 (d, 1H), 7.3 (t, 2H), 7.55 (d, 2H), 7.58 (s, 1H), 7.67 (m, 3H), 8.77 (d, 2H) 9.86 (s, 1H); MS (ES$^-$) m/z 366 (M–H)$^-$.

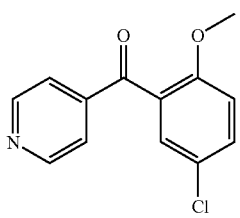

376

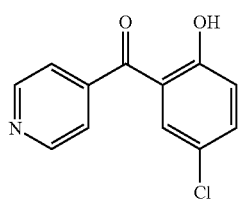

377

Compound 376 (4.2 g, 17 mmol) in methylene chloride (100 mL), THF (100 mL), and BBr$_3$ (17 g, 68 mmol) in methylene chloride (68 mL) were used as in general procedure 1× to afford, after recrystallization from methanol, 377 as a yellow solid (1.1 g, 28%). $^1$H NMR (DMSO-d$_6$, 300 MHz) δ 7 (d, 1H), 7.6 (d, 2H), 8.2 (d, 2H), 9.7 (bs, 2H), 10.95 (s, 1H); MS (ES$^-$) m/z 232 (M–H)$^-$.

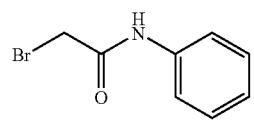

378

Example 158

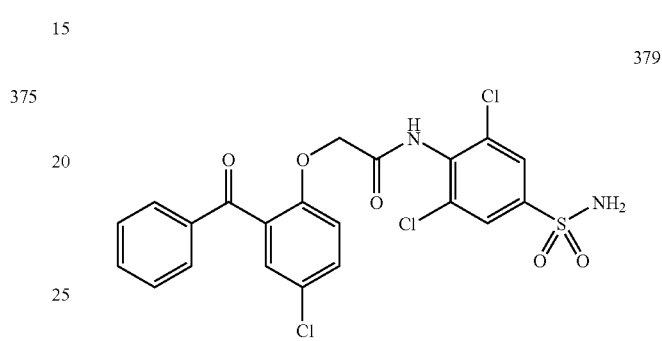

379

3,5-Dichloro sulfanilamide (Lancaster, 0.5 g, 2.1 mmol), NEt$_3$ (0.25 mL, 1.8 mmol), acetonitrile (10 mL), and acid chloride 320 (0.52 g, 1.7 mmol) in acetonitrile (6 mL) were used as in general procedure X. The reaction was heated to 40° C. and stirred for 3 d. Additional acid chloride 320 (0.52 g, 1.7 mmol) was added and the reaction was stirred for 7 d. The mixture was concentrated in vacuo, suspended in methylene chloride, filtered, and the filtrate was concentrated in vacuo. The product was purified by flash chromatography using 99:1 methylene chloride:methanol, by flash chromatography in a gradient between 1:1 and 9:1 ethyl acetate:hexanes, and by TLC prep plate using 23:1 methylene chloride:methanol, 7:3 ethyl acetate:hexanes, and 98:2 methylene chloride:methanol as elutant to afford 379 as an orange oil (0.038 g, 4.3%). $^1$H NMR (DMSO-d$_6$, 300 MHz) δ 4.56 (s, 2H), 6.57 (bs, 2H), 6.94 (d, 1H), 7.36 (s, 1H), 7.4 (m, 3H), 7.55 (m, 3H), 7.7 (d, 2H) 12.15 (bs, 1H); MS (ES$^-$) m/z 512 (M–H)$^-$.

Example 159

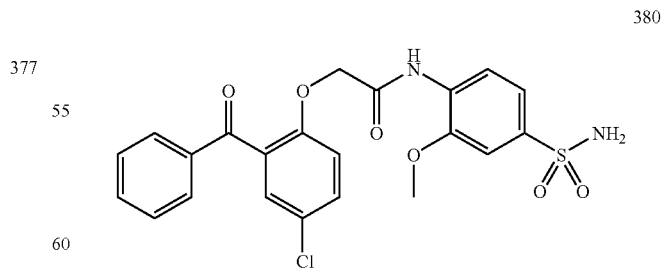

380

3-Methoxy-4-amino sulfanilamide (Pfaltz Bauer, 0.5 g, 2.5 mmol), acetonitrile (16 mL), Et$_3$N (0.41 mL, 2.9 mmol), and acid chloride 320 (0.76 g, 2.5 mmol) in acetonitrile were used as in general procedure X. The reaction mixture was filtered and the resulting solids were washed with acetonitrile and ether to afford 380 as an off-white solid (0.169 g, 14.4%). ¹H NMR (DMSO-d₆, 400 MHz) δ 3.8 (s, 3H), 4.8 (s, 2H), 7.15 (d, 1H), 7.22 (d, 3H), 7.48 (m, 4H), 7.58 (d, 2H), 7.78 (d, 2H), 8.5 (s, 1H), 8.9 (s, 1H); MS (ES⁺) m/z 575 (M+H)⁺.

Example 160

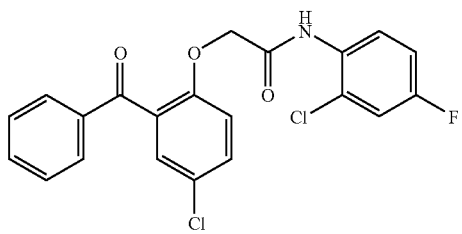

381

Acid chloride 320 (0.68 g, 2.2 mmol) in methylene chloride (5 mL) was added to a solution of 2-chloro-4-fluoroaniline (Aldrich, 0.5 g, 3.4 mmol), pyridine (12 mL) and the mixture was stirred overnight. The reaction mixture was poured over ice, ethanol (30 mL) was added, and the precipitate was filtered and washed with 1:1 ethanol:water and diethyl ether to afford 381 as a white solid (0.367 g, 40%). ¹H NMR (DMSO-d₆, 300 MHz) δ 4.8 (s, 2H), 7.25 (m, 2H), 7.5 (m, 9H), 7.65 (t, 2H), 7.75 (m, 1H), 7.8 (d, 2H), 9.2 (s, 1H); MS (ES⁺) m/z 419 (M+H)⁺.

Example 161

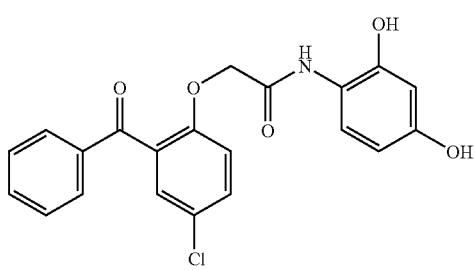

382

Resorcinol hydrochloride (Aldrich, 0.5 g, 3.4 mmol), acetonitrile (20 mL total reaction volume), Et₃N (0.75 mL, 5.4 mmol), and acid chloride 320 (0.8 g, 2.6 mmol) in acetonitrile were used as in general procedure X. The reaction mixture was poured over ice water and ethanol was added to the solution. The mixture was recrystallized from ethanol and water and the resulting solids were filtered and washed with ether to afford 382 as a pink solid (0.207 g, 20%). ¹H NMR (DMSO-d₆, 400 MHz) δ 4.6 (s, 2H), 6.1 (d, 1H), 6.28 (s, 1H), 7.19 (d, 1H), 7.4 (m, 4H), 7.56 (t, 2H), 7.75 (d, 2H), 8.5 (s, 1H), 9.1 (s, 1H), 9.6 (s, 1H); MS (ES⁺) m/z 398 (M+H)⁺.

Example 162

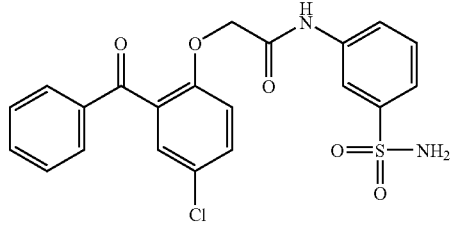

383

Step A:

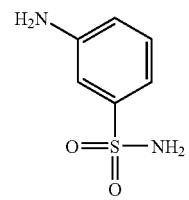

384

3-nitrobenzene sufonamide (5 g, 24.7 mmol), palladium on carbon (1 g, 10% w/w), methanol (75 mL), and THF (25 mL) were used as in general procedure XII using 67 psi of hydrogen to afford 384 as a solid (4.2 g). ¹H NMR (DMSO-d₆, 400 MHz) δ 5.48 (bs, 2H), 6.67 (dd, 1H), 6.88 (d, 1H), 6.97 (t, 1H), 7.12 (t, 3H); MS (AP⁺) m/z 173 (M+H)⁺.

Step B:
Carboxylic acid 105 (0.29 g, 1 mmol), HCA (0.132 mL, 0.5 mmol), THF, PPh₃ (0.26 g, 1 mmol) in THF, metanilamide 384 (0.17 g, 1 mmol) in THF (4.5 mL total reaction volume), and pyridine (0.5 mL, 6.2 mmol) were used as in general procedure XIII. The reaction was concentrated in vacuo and the resulting solid was recrystallized from ethanol and water, filtered, and washed with ether to afford 383 as an off-white solid (0.207 g, 47%). ¹H NMR (DMSO-d₆, 400 MHz) δ 4.7 (s, 2H), 7.15 (d, 1H), 7.36 (s, 2H), 7.4-7.5 (m, 5H), 7.58 (m, 3H), 7.77 (d, 2H), 8.1 (s, 1H), 10.1 (s, 1H); MS (ES⁺) m/z 445 (M+H)⁺.

Example 163

385

Carboxylic acid 105 (0.29 g, 1 mmol), HCA (0.08 mL, 0.53 mmol), methylene chloride (5 mL total reaction volume), and PPh₃ (0.26 g, 1 mmol) were combined in a round-bottom flask under nitrogen at −78° C. 4-Amino-3-chlorophenol (Aldrich, 0.145 g, 1 mmol) was free-based by partitioning it between methylene chloride and saturated sodium bicarbonate. The organics were separated, dried over MgSO₄, and concentrated in vacuo to give a pink solid that was dissolved in methylene chloride and Et₃N (0.26 mL, 1.9 mmol) and added dropwise to the reaction mixture at −78° C. The reaction was warmed to rt and concentrated in vacuo. The product was purified by flash chromatography using 4:1 hexanes:ethyl acetate to afford 385 as an orange solid (0.120 g, 29%). ¹H NMR (DMSO-d₆, ₄₀₀ MHz) δ 4.7 (s, 2H), 6.67 (d, 1H), 6.79 (s, 1H), 7.2 (d, 1H), 7.35 (d, 1H), 7.4 (s, 1H), 7.5 (m, 2H), 7.6 (m, 2H), 7.75 (d, 2H), 8.9 (s, 1H), 9.8 (s, 1H); MS (ES⁺) m/z 417 (M+H)⁺.

Example 164

386

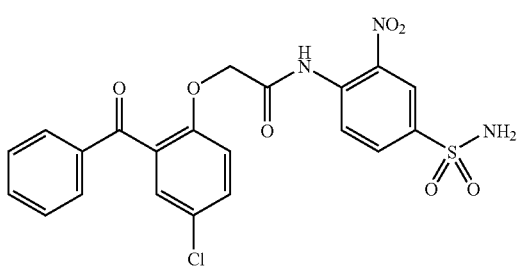

Carboxylic acid 105 (0.67 g, 2.3 mmol), HCA (0.17 mL, 1.1 mmol), THF, PPh₃ (0.61 g, 2.3 mmol) in THF, 2-nitro-4-sulfanilamide (0.5 g, 2.3 mmol) in THF (20 mL total reaction volume), and pyridine (2.25 mL, 28 mmol) were used as in general procedure XIII. The reaction mixture was concentrated in vacuo and the product was purified by flash chromatography using a gradient between 9:1 hexanes:ethyl acetate and ethyl acetate to afford 386 as, an off-white solid MS (ES⁻) m/z 488 (M−H)⁻.

Example 165

387

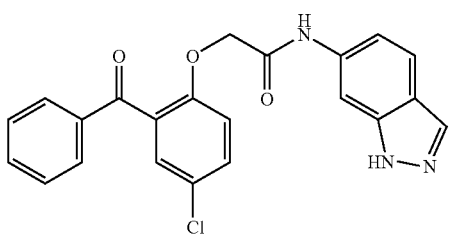

Carboxylic acid 105 (0.58 g, 2 mmol), HCA (0.152 mL, 1 mmol), THF, PPh₃ (0.52 g, 2 mmol) in THF, 6-aminoindazole (Aldrich, 0.26 g, 2 mmol) in THF (20 mL total reaction volume), and pyridine (1.94 mL) were used as in general procedure XIII. The reaction mixture was concentrated in vacuo and the resulting solid was dissolved in ethanol. Water was added to the mixture and the resulting solid was filtered and washed with ether to afford 387 as a pink solid (0.309 g, 38%). ¹H NMR (DMSO-d₆, 400 MHz) δ 4.7 (s, 2H), 6.95 (d, 1H), 7.15 (d, 1H), 7.4 (s, 1H), 7.5 (m, 2H), 7.55-7.65 (m, 3H), 7.79 (d, 2H), 7.9 (s, 1H), 8 (s, 1H), 9.89 (s, 1H), 12.85 (bs, 1H); MS (ES⁺) m/z 406 (M+H)⁺.

Example 166

388

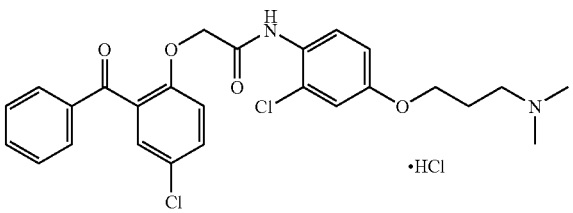

N,N-dimethyl-3-chloropropyl amine in acetone (5 mL) and water (4 drops) was added dropwise to a suspension of compound 385 (1.04 g, 2.5 mmol), acetone (10 mL), and potassium carbonate (2.82 g, 20.4 mmol) and then refluxed for 3 d under nitrogen. The suspension was cooled to rt and water and brine were added. The mixture was extracted with methylene chloride. To the organic layer was added 1N HCl in Et₂O (3 mL) and the resulting solution was concentrated in vacuo. The concentrate was purified by flash chromatography using a gradient between 9:1 and 4:1 methylene chloride:methanol as elutant to give an oil. The oil was dissolved in methylene chloride and 1N HCl in Et₂O (3 mL) was added and the mixture was stored at rt for 7 d. The precipitate was filtered and washed with ether to afford 388 as a yellow orange solid (0.125 g, 10%). ¹H NMR (DMSO-d₆, 300 MHz) δ 1.8 (m, 2H), 2.28 (s, 6H), 2.5 (m, 2), 4 (t, 2H), 4.8 (s, 2H), 6.9 (d, 1H), 7.08 (d, 1H), 7.25 (d, 1H), 7.45-7.58 (m, 4H), 7.65 (m, 2H), 7.8 (d, 2H), 9.05 (s, 1H); MS (ES⁺) m/z 502 (M+H)⁺.

Example 167

389

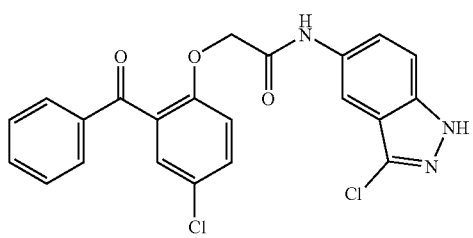

Step A:

390

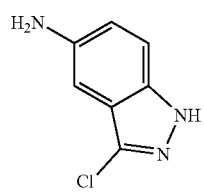

3-Chloro-5-nitroindazole (Lancaster, 5 g, 25 mmol), sodium dithionite (17.6 g, 101 mmol), ethanol (150 mL), and water (50 mL) were combined in a round-bottom flask equipped with a stir bar, reflux condenser, and nitrogen on demand and then refluxed overnight. The reaction mixture was concentrated in vacuo and the resulting solid was dissolved in ethyl acetate, washed with brine and water. The organics were separated, dried over MgSO₄, and concentrated in vacuo to give 390 as a yellow solid (1.3 g, 31%). ¹H NMR (DMSO-d₆, 400 MHz) δ 5 (s, 2H), 6.55 (s, 1H), 6.8 (d, 1H), 7.2 (s, 1H), 12.7 (s, 1H); MS (ES⁺) m/z 168 (M+H)⁺. The crude product was used without further purification.

Step B:

Carboxylic acid 105 (2.25 g, 7.74 mmol), HCA (0.59 mL, 3.88 mmol), THF, PPh₃ (2.03 g, 7.74 mmol) in THF, compound 390 (1.3 g, 7.7 mmol) in THF (45 mL total reaction volume), and pyridine (7.5 mL, 93 mmol) were used as in general procedure XIII. The reaction mixture was concentrated in vacuo and the resulting solid was suspended in ethanol, methanol, acetone, and water. The resulting solid was filtered off and recrystallized from ethyl acetate:hexanes. The precipitate was filtered and washed with ether and 7:3 ethyl acetate:hexanes to afford 389 as a tan solid (0.87 g, 26%). ¹H NMR (DMSO-d₆, 400 MHz) δ 4.7 (s, 2H), 7.2 (d, 1H), 7.35 (d, 1H), 7.415 (s, 1H), 7.43-7.52 (m, 4H), 7.55-7.6 (m, 4H), 7.78 (m, 2H), 7.9 (s, 1H), 9.88 (s, 1H), 13.2 (s, 1H).

Example 168

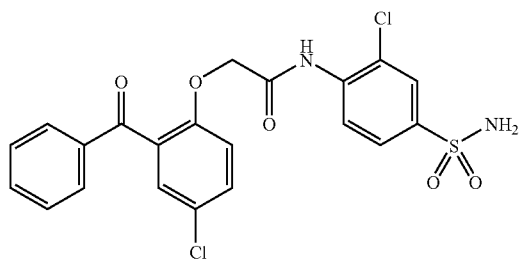

391

Step A:

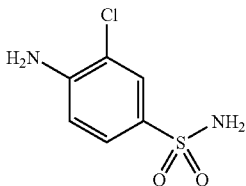

392

Ammonium hydroxide (40 mL) was added to 3-chloro-4-aminosulfonyl fluoride (Maybridge, 0.5 g, 2.4 mmol) and the mixture was heated to 62° C. for 1 h under nitrogen. The reaction was cooled to rt and the resulting mixture was extracted with ethyl acetate. The organics were dried over MgSO₄ and concentrated in vacuo to give 392 as a white solid (0.394 g, 80%). ¹H NMR (DMSO-d₆, 400 MHz) δ 6.07 (s, 2H), 6.8 (d, 1H), 7 (s, 2H), 7.39 (dd, 1H), 7.55 (d, 1H); MS (ES⁻) m/z 205 (M−H)⁻.

Step B:

Carboxylic acid 105 (0.54 g, 1.9 mmol), HCA (0.14 mL, 0.92 mmol), THF, PPh₃ (0.49 g, 1.9 mmol) in THF, compound 392 (0.384 g, 1.9 mmol), in THF (40 mL total reaction volume), and pyridine (1.8 mL) were used as in general procedure XIII. The reaction mixture was concentrated and the resulting solid was dissolved in ethanol. Water was added and the precipitate was filtered and washed with 1:1 ethanol:water and ether to afford 391 as a white solid (0.206 g, 23.1%). ¹H NMR (DMSO-d₆, 400 MHz) δ 4.8 (s, 2H), 7.2 (d, 1H), 7.43 (s, 2H), 7.47 (m, 2H), 7.6 (m, 2H), 7.75 (dd, 3H), 7.8 (d, 1H), 8.05 (d, 1H), 9.3 (s, 1H).

Example 169

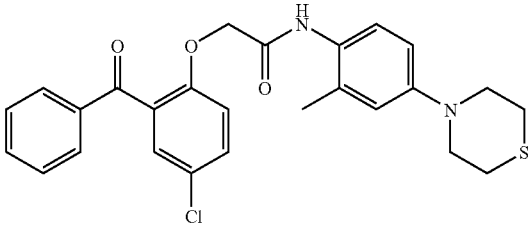

393

Step A:

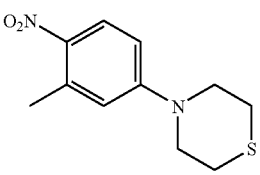

394

5-Fluoro-2-nitrotoluene (Aldrich, 50.6 g, 364 mmol), DMSO (60 mL), and thiomorpholine (37 mL, 368 mmol) were combined and heated to 75° C. for 2 h and 100° C. for 4 h under nitrogen. The reaction was cooled to rt. Ether was added to the mixture and the slurry was stirred vigorously. Water was added to the slurry and the resulting solid was filtered and washed with water and ether, then dissolved in methylene chloride. The organics were washed with water, dried over MgSO₄, and concentrated in vacuo to give 394 as a yellow solid (70 g, 81%). ¹H NMR (DMSO-d₆, 400 MHz) δ 2.5 (s, 3H), 2.6 (t, 4H), 3.8 (d, 1H), 6.85 (s, 1H), 7.95 (d, 1H). The crude product was used without further purification.

Step B:

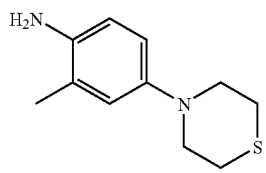

395

Compound 394 (0.29 g, 1.22 mmol), palladium on carbon (0.1 g, 10% w/w), ethanol (7 mL), and THF (7 mL) were used as in general procedure XII using 68 psi of hydrogen to afford 395 as a brown solid (0.252 g, crude material).

Step C:

Compound 395 (0.252 g, 1.2 mmol), acetonitrile (12 mL), Et₃N (0.3 mL, 2.1 mmol), and acid chloride 320 (0.38 g, 1.2 mmol) were used as in general procedure X. The product was purified by flash chromatography using 7:3 hexanes:ethyl acetate as elutant to afford 393 as an orange solid (0.084 g, 14%). ¹H NMR (DMSO-d₆, 400 MHz) δ 1.95 (d, 3H), 2.6 (d, 2H), 2.85 (t, 2H), 3.5 (d, 2H), 3.7 (t, 2H), 4.67 (s, 2H), 6.75 (dd, 1H), 6.8 (d, 1H), 7.1 (d, 1H), 7.2 (d, 1H), 7.42 (d, 1H), 7.48 (t, 2H), 7.59 (t, 2H), 7.75 (d, 2H), 8.8 (s, 1H).

Example 170

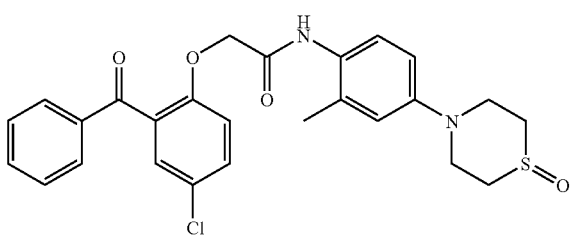

396

Step A:

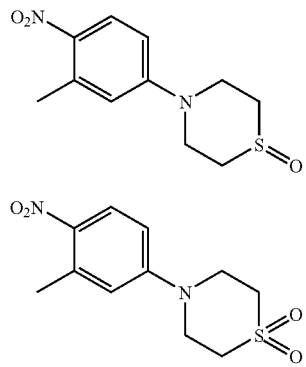

397

398

3-chloroperoxybenzoic acid (Aldrich, 0.046 g, 2.7 mmol) in methylene chloride was added dropwise to a stirred solution of compound 394 (12.5 g, 52.4 mmol) in methylene chloride (300 mL total volume for reaction) at −20° C. and the mixture was stirred for 1.5 h after which the cooling bath was removed and the reaction was stirred at rt overnight under nitrogen. The mixture was washed with saturated sodium metabisulfite, 2N NaOH, and water. The organics were separated, dried over MgSO₄, and concentrated in vacuo to give a mixture of 397 and 398 as a yellow solid (12.2 g, crude mixture).

Step B:

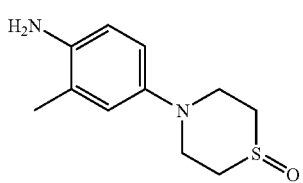

399

-continued

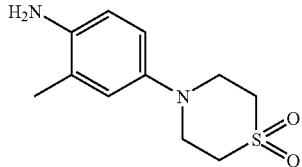

400

The mixture of 397 and 398 (12.3 g), palladium on carbon (3.7 g, 10% w/w), ethanol (100 mL), THF (30 mL), and methanol (75 mL) were used as in general procedure XII using 60 psi of hydrogen to afford an oil. The product was purified on silica gel by flash chromatography using 7:3 hexanes:ethyl acetate, 100% ethyl acetate, and 4:1 ethyl acetate:methanol as elutants to afford 399 as an orange solid (4.27 g, 39%) ¹H NMR (DMSO-d₆, 400 MHz) δ 1.99 (s, 3H), 2.68 (d, 2H), 2.87 (t, 2H), 3.15 (dd, 2H), 3.44 (t, 2H), 4.38 (bs, 2H), 6.49 (d, 1H), 6.59 (d, 1H), 6.64 (s, 1H); MS (ES⁺) m/z 225 (M+H)⁺ and 400 as a tan solid (3.57 g, 31%) ¹H NMR (DMSO-d₆, 400 MHz) δ 1.99 (s, 3H), 3.08 (m, 4H), 3.42 (m, 4H), 4.42 (bs, 2H), 6.49 (d, 1H), 6.59 (d, 1H), 6.66 (d, 1H); MS (ES⁺) m/z 241 (M+H)⁺.

Step C:

Carboxylic acid 105 (2.02 g, 6.95 mmol), HCA (0.528 mL, 3.48 mmol), THF (20 mL), PPh₃ (1.82 g, 6.95 mmol) in THF (15 mL), sulfoxide 399 (1.56 g, 6.95 mmol) in THF (125 mL total reaction volume), and pyridine (6.75 mL, 83.5 mmol) were used as in general procedure XIII. The reaction mixture was filtered and the filtrate was concentrated in vacuo. The concentrate was purified by flash chromatography using a gradient between 99:1 and 4:1 methylene chloride:methanol as elutant to afford 396 as a yellow foam (1.62 g, 47%). ¹H NMR (DMSO-d₆, 400 MHz) δ 1.95 (d, 3H), 2.62 (dd, 2H), 2.86 (t, 2H), 3.5 (dd, 2H), 3.69 (t, 2H), 4.67 (s, 2H), 6.75 (dd, 1H), 6.8 (d, 1H), 7.1 (d, 1H), 7.2 (d, 1H), 7.42 (d, 1H), 7.48 (t, 2H), 7.59 (t, 2H), 7.75 (d, 2H), 8.8 (s, 1H).

Example 171

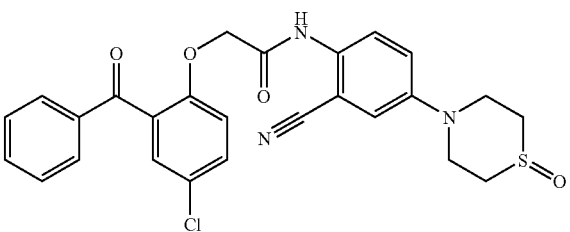

401

Step A:

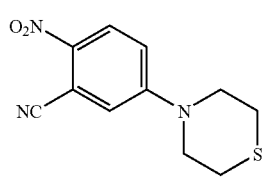

402

5-Chloro-2-nitrobenzonitrile (Aldrich, 5 g, 27.4 mmol), sodium bicarbonate (4.62 g, 55 mmol), pyridine (40 mL), water (1 mL), and thiomorpholine (5.53 mL, 55 mmol) were used as in general procedure XI to afford 402 as an orange solid (5.19 g, 76%). $^1$H NMR (DMSO-$d_6$, 400 MHz) δ 2.62 (m, 4H), 3.9 (m, 4H), 7.2 (d, 1H), 7.5 (d, 1H), 8.1 (d, 1H). The crude product was used without purification.

Step B:

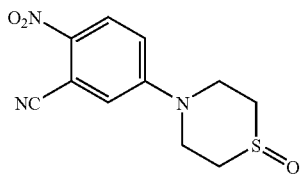

403

3-Chloroperoxybenzoic acid (Aldrich, 4.85 g, 17 mmol) in methylene chloride was added to a cooled solution of compound 402 (3 g, 12 mmol) in methylene chloride (100 mL total volume for reaction) at −20° C. and the mixture was stirred for 15 min. after which the cooling bath was removed and the mixture was stirred at rt for 4 h under nitrogen. The reaction mixture was washed with saturated sodium metabisulfite, 2N NaOH, and brine. The organics were separated, dried over MgSO$_4$, and concentrated in vacuo to afford 403 as a yellow solid (0.59 g, crude material). $^1$H NMR (DMSO-$d_6$, 400 MHz) δ 2.63 (m, 4H), 3.9 (m, 4H), 7.2 (dd, 1H), 7.5 (d, 1H), 8.1 (d, 1H).

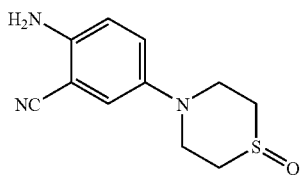

404

Palladium on carbon (0.23 g, 10% w/w), compound 403 (0.5 g, 1.9 mmol), ethanol (30 mL total reaction volume), THF (20 mL), and methanol (20 mL) were used as in general procedure XII to afford 404 as a green oil (0.41 g, 93%). $^1$H NMR (DMSO-$d_6$, 300 MHz) δ 2.68 (d, 2H), 2.9 (t, 2H); 3.3 (d, 2H), 3.55 (t, 2H), 5.6 (bs, 2H), 6.79 (d, 1H), 7.02 (d, 1H), 7.1.7 (dd, 1H).

Step C:

Compound 404 (0.41 g, 1.8 mmol), HCA (0.132 mL, 0.87 mmol), PPh$_3$ (0.46 g, 1.75 mmol), pyridine (1.7 mL, 21 mmol), THF (25 mL), and carboxylic acid 105 (0.51 g, 1.8 mmol) were used as in general procedure XIII. The concentrate was purified by flash chromatography using 95:5 methylene chloride:methanol as elutant, flash chromatography using a gradient between 7:3 hexanes:ethyl acetate and 4:1 ethyl acetate:methanol as elutant, TLC prep plate using 9:1 methylene chloride:methanol with 0.1% Et$_3$N as elutant. The concentrate was dissolved in methylene chloride and washed with 2N HCl. The organics were separated, dried over MgSO$_4$, and concentrated in vacuo to afford 401 as a tan foam (0.145 g, 16%). $^1$H NMR (DMSO-$d_6$, 300 MHz) δ 2.65 (d, 2H), 2.9 (t, 2H), 3.8 (m, 4H), 4.76 (s, 2H), 7.2-7.4 (m, 3H), 7.4-7.6 (m, 4H), 7.65 (m, 2H), 7.8 (d, 2H), 9.7 (s, 1H).

Example 172

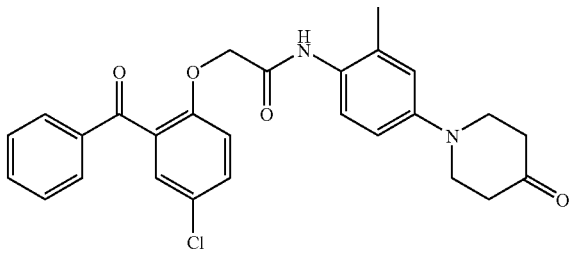

405

Step A:

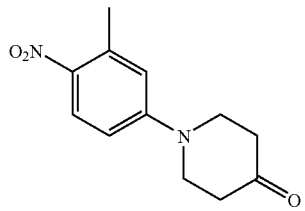

406

4-Piperidone monohydrate monohydrochloride salt (Lancaster, 2.73 g, 17.8 mmol) and saturated potassium carbonate (10 mL) were combined in a round-bottom flask and stirred for 10 min. Pyridine (45 mL) and 2-nitro-5-fluorotoluene (Aldrich, 1.41 mL, 9.35 mmol) were added and the reaction was refluxed overnight. The two-phase solution was separated and the organics were concentrated in vacuo. The concentrate was dissolved in ethyl acetate and washed with water and brine. The organics were dried over MgSO$_4$ and concentrated in vacuo to afford 406 as a red oil (0.59 g, 27). $^1$H NMR (DMSO-$d_6$, 300 MHz) δ 2.6 (t, 4H), 3.8 (t, 4H), 7 (d, 2H), 8 (d, 2H); MS (ES$^+$) m/z 235 (M+H)$^+$.

Step B:

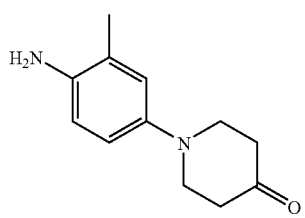

407

Compound 406 (0.57 g, 2.4 mmol), palladium on carbon (0.17 g, 10% w/w), ethanol (25 mL) and THF (25 mL) were used as in general procedure XII using 70 psi hydrogen to afford 407 as a yellow oil (0.5 g, crude material).

Step C:

Compound 407 (0.5 g, 2.1 mmol), HCA (0.16 mL, 1.05 mmol), PPh$_3$ (0.56 g, 2.1 mmol), pyridine (2 mL, 25 mmol), THF (50 mL), and carboxylic acid 105 (0.62 g, 2.1 mmol) were used as in general procedure XIII. The mixture was concentrated in vacuo and purified on by flash chromatography using a gradient between 1:1 hexanes:ethyl acetate and 100% ethyl acetate as elutant to afford 405 as a yellow solid (0.32 g, 31%). $^1$H NMR (DMSO-d$_6$, 300 MHz) δ 2 (s, 3H), 2.4 (m, 4H), 3.58 (m, 4H), 4.7 (s, 2H), 6.85 (d, 1H), 6.9 (s, 1H), 7.15 (d, 1H), 7.25 (d, 1H), 7.48 (s, 1H), 7.55 (t, 2H), 7.65 (t, 2H), 7.8 (d, 2H), 8.85 (s, 1H); MS (ES$^+$) m/z 478 (M+H)$^+$.

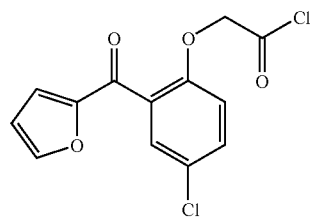
408

Carboxylic acid 115 (1 g, 3.6 mmol), methylene chloride (30 mL), and thionyl chloride (7.6 mL, 104 mmol) were used as in general procedure-XV to afford 408 as a purple oil (1.24 g, crude material).

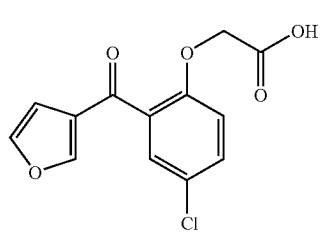
409

Ester 412 (15.92 g, 52 mmol), ethanol (EtOH, 150 mL), water (50 mL), and lithium hydroxide monohydrate (2.71 g, 65 mmol) were used as in general procedure IV to afford 409 as a tan solid (7.47 g, 51.6%). The crude material was used without purification.

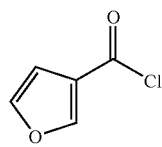
410

Thionyl chloride (60 mL, 800 mmol) was added portionwise to a solution of 3-furoic acid (11.21 g, 100 mmol) in methylene chloride (100 mL) and the mixture was refluxed for 2 h. The solution was concentrated in vacuo to afford the acid chloride 410 as an oil (13 g, crude material).

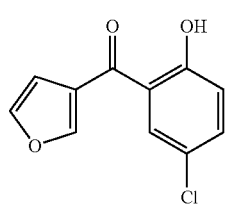
411

Acid chloride 410 (13 g, 100 mmol), aluminum chloride (AlCl$_3$, 13.6 g, 100 mmol), CH$_2$Cl$_2$ (200 mL), and 4-chloroanisole (12.25 mL, 100 mmol) were used as in general procedure III. The product was purified by flash chromatography using a 7:3 hexanes:methylene chloride and 1:1 hexanes:methylene chloride as elutant. The concentrate was triturated between ether and hexanes, filtered, and the resulting solid was washed with hexanes to afford 411 as a yellow crystalline solid (12.3 g, 55%). $^1$H NMR (DMSO-d$_6$, 400 MHz) δ 6.8 (s, 1H), 6.95 (d, 1H), 7.4 (m, 2H), 7.8 (s, 1H), 8.25 (s, 1H), 10.45 (s, 1H).

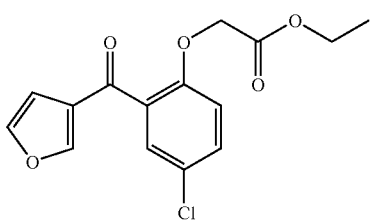
412

Phenol 411 (12.3 g, 55.3 mmol), potassium carbonate (38.21 g, 277 mmol), ethyl bromoacetate (6.4 mL, 57.7 mmol), and acetone (250 mL) were used as in general procedure II to afford 412 as a yellow/orange foam (15.9 g, 93%). MS (ES$^-$) m/z 279 (M–H)$^-$. The crude product was used without purification.

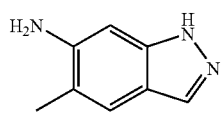
413

Compound 415 (0.4 g, 2.3 mmol), palladium on carbon (0.12 g, 10% w/w), and ethanol (50 mL) were used as in general procedure XII using 60 psi of hydrogen to afford 413 as a tan solid (0.35 g, crude material). $^1$H NMR (DMSO-d$_6$, 400 MHz) δ 2.05 (s, 3H), 4.96 (bs, 2H), 6.56 (s, 1H), 7.22 (s, 1H), 7.63 (s, 1H), 12.16 (s, 1H); MS (ES$^-$) m/z 148 (M–H)$^-$.

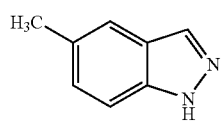
414

Potassium nitrate (10.13 mL, 100 mmol) in concentrated sulfuric acid (50 mL) was added dropwise to a stirred solution of concentrated sulfuric acid (50 mL) and 2,4-dimethylaniline (Aldrich, 4.94 g, 40.8 mmol) at 0° C. The reaction was stirred for 3 h. The mixture was poured into ice water (1800 mL) and extracted with ethyl acetate. The organics were separated and concentrated in vacuo to afford 414 as an orange solid (2.98 g, 44%). $^1$H NMR (DMSO-d$_6$, 400 MHz) δ 2.02 (s, 3H), 2.3 (s, 3H), 7 (s, 1H), 7.26 (s, 1H).

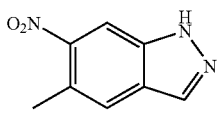

415

Sodium nitrite (0.67 g, 9.7 mmol) in water (4 mL) was added dropwise to a stirred solution of compound 414 (1.6 g, 9.6 mmol) and glacial acetic acid (250 mL) at 0° C. The reaction was stirred for 15 min. at 0° C., and rt for 3 h. The reaction was stored for 9 d. The mixture was concentrated in vacuo. The concentrate was triturated with water and the resulting slurry was stirred for 1 h. The slurry was filtered and washed with water. The solid was dissolved in methylene chloride and washed with water. The organics were separated and further purified by flash chromatography using 9:1 hexanes:ethyl acetate and 1:1 hexanes:ethyl acetate to afford 415 as a red solid (0.4 g, 19%). $^1$H NMR (DMSO-d$_6$, 400 MHz) δ 2.5 (s, 3H), 7.82 (s, 1H), 8.17 (d, 2H), 13.53 (bs, 1H).

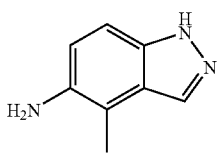

416

Compound 420 (1.07 g, 6 mmol), palladium on carbon (0.33 g, 10% w/w), ethanol (30 mL) and THF (20 mL) were used as in general procedure XII using 80 psi of hydrogen to afford 416 as a brown solid (0.53 g, 60%). $^1$H NMR (DMSO-d$_6$, 300 MHz) δ 2.25 (s, 3H), 4.5 (s, 2H), 6.8 (d, 1H), 7.1 (d, 1H), 7.85 (s, 1H), 12.55 (bs, 1H). MS (ES$^-$) m/z 148 (M–H)$^-$.

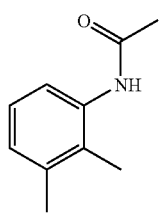

417

Acetic anhydride (25 mL, 265 mmol) was added to a stirred solution of 2,3-dimethylaniline (Aldrich, 31.2 g, 257 mmol) and toluene (50 mL) under nitrogen. The resulting solid was filtered and washed with hexanes and ether to afford 417 as a white solid (40.59 g, crude material). $^1$H NMR (DMSO-d$_6$, 300 MHz) δ 2.06 (d, 6H), 2.26 (s, 3H), 7.05 (m, 2H), 7.15 (d, 1H), 9.35 (bs, 1H).

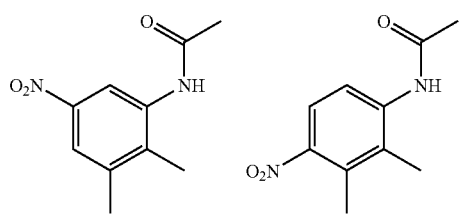

418

Potassium nitrate (6.2 g, 61 mmol) in concentrated sulfuric acid (75 mL) was added dropwise over 1 h to a cooled, stirred solution of concentrated sulfuric acid (50 mL) and compound 417 (10 g, 61 mmol) at –17° C. The cooling bath was removed and the reaction was stirred at 0° C. for 1 h. The solution was poured into ice water (2000 mL) and stirred vigorously. The solution was extracted with methylene chloride. The organics were separated, dried over MgSO$_4$, and concentrated in vacuo to afford a solid. The solid was purified by flash chromatography using a gradient between 7:3 hexanes:ethyl acetate and ethyl acetate as elutant to afford 418 as a yellow solid (4.24 g, 33%). MS (ES$^-$) m/z 201 (M–H)$^-$. Compound 418 was used as a mixture without purification.

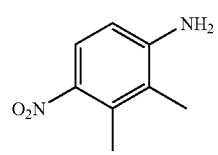

419

Compound 418 (4.24 g, 20.4 mmol) was added portionwise to a stirred solution of potassium hydroxide (1.2 g, 21 mmol), water (50 mL), and ethanol (200 mL) and the mixture was refluxed for 1 h. Water (50 mL) was added to the reaction dropwise and the resulting solution was cooled to rt. A precipitate was filtered and washed with water and ether. The filtrate was extracted with ether and the organics were combined, dried over MgSO$_4$, and concentrated in vacuo to give 419 as a yellow solid (2.02 g, 60%). $^1$H NMR (DMSO-d$_6$, 400 MHz) δ 2 (s, 3H), 2.34 (s, 3H), 6.12 (bs, 2H), 6.5 (d, 1H), 7.6 (d, 1H).

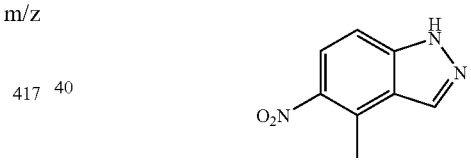

420

Sodium nitrite (0.42 g, 6 mmol) in water was added dropwise to a stirred solution of compound 419 (1 g, 6 mmol) and glacial acetic acid (50 mL) at 0° C. and stirred for 1 h. The reaction was stored for 2 d at rt. The mixture was concentrated in vacuo and the concentrate was triturated with water. The resulting solid was filtered and washed with water to afford 420 as a tan solid (2.07 g, crude material). $^1$H NMR (DMSO-d$_6$, 400 MHz) δ 2.8 (s, 3H), 7.5 (d, 1H), 7.95 (d, 1H), 8.45 (s, 1H), 13.6 (bs, 1H); MS (ES$^-$) m/z 176 (M–H)$^-$.

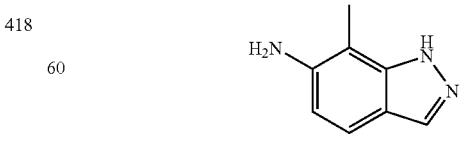

421

Compound 423 (2.69 g, 15.2 mmol), palladium on carbon (0.8 g, 10% w/w), ethanol (100 mL), and THF (20 mL) were used as in general procedure XII using 60 psi of hydrogen to afford 421 as a tan solid (1.43 g, 63.8%). The crude material was used without purification.

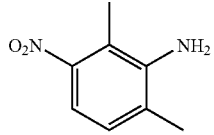

422

Potassium nitrate (10.13 mL, 100 mmol) in concentrated sulfuric acid (50 mL) was added dropwise to a stirred solution of concentrated sulfuric acid (50 mL) and 2,6-dimethylaniline (Aldrich, 12.32 g, 100 mmol) at −10° C. and stirred for 1 h. The mixture was poured into ice water and extracted with ethyl acetate. The organics were separated, dried over MgSO$_4$, and concentrated in vacuo to afford 422 as an orange solid (5.63 g, 34%). $^1$H NMR (DMSO-d$_6$, 400 MHz) δ 2.05 (d, 6H), 5.4 (bs, 2H), 6.9 (d, 1H), 6.96 (d, 2H). The crude material was used without purification.

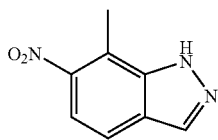

423

Sodium nitrite (2.34 g, 34 mmol) in water (10 mL) was added dropwise to a stirred solution of compound 422 (5.63 g, 34 mmol) and glacial acetic acid (500 mL) at 0° C. and stirred for 15 min. The cooling bath was removed and the reaction was stored at rt for 6 d. The mixture was concentrated in vacuo and the concentrate was triturated with water. The resulting solid was filtered and recrystallized from methanol to give 423 as a red solid (2.69 g, 45%). $^1$H NMR (DMSO-d$_6$, 400 MHz) δ 2.73 (s, 3H), 3.15 (s, 3H), 7.64 (d, 1H), 7.9 (d, 1H), 8.24 (s, 1H), 13.85 (bs, 1H). MS (ES$^-$) m/z 176 (M−H)$^-$. The crude material was used without purification.

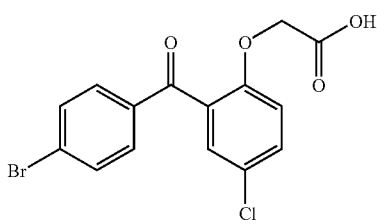

424

Ester 426 (16.72 g, 42 mmol), ethanol (EtOH, 200 mL), water (50 mL), and lithium hydroxide monohydrate (2.21 g, 52 mmol) were used as in general procedure III to afford 424 as an off-white solid (10.71 g, 69%). The crude material was used without purification.

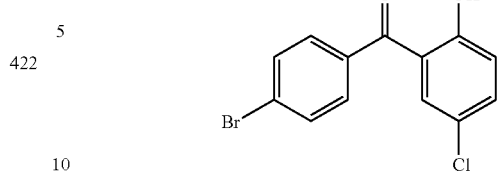

425

4-Bromobenzoyl chloride (8.73 g, 40 mmol), aluminum chloride (AlCl$_3$, 5.3 g, 40 mmol), CH$_2$Cl$_2$ (125 mL), and 4-chloroanisole (4.87 mL, 40 mmol) were used as in general procedure I to afford 425 as a yellow solid (14.27 g, crude material).

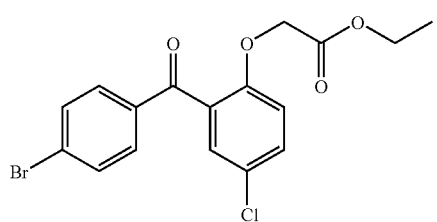

426

Compound 425 (14.27 g, 65 mmol), potassium carbonate (45 g, 325 mmol), ethyl bromoacetate (7.57 mL, 68 mmol), and acetone (250 mL) were used as in general procedure II to afford 426 as a tan solid (16.72 g, 65%). $^1$H NMR (DMSO-d$_6$, 400 MHz) δ 4.6(s, 2H), 7.07 (d, 1H), 7.4 (d, 1H), 7.54 (dd, 1H), 7.64 (m, 4H), 13.04 (bs, 1H). The crude material was used without purification.

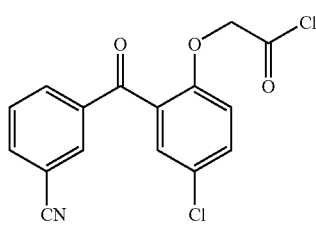

427

Carboxylic acid 129 (1.5 g, 4.8 mmol), methylene chloride (30 mL), and thionyl chloride(10 mL, 137 mmol) were used as in general procedure XV to afford 427 as an off-white, sticky solid (1.58 g, crude material).

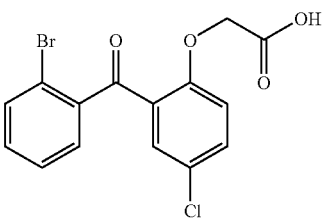

428

Ester 430 (17.24 g, 43 mmol), ethanol (200 mL), water (50 mL), and lithium hydroxide monohydrate (2.27 g, 54 mmol) were used as in general procedure III to afford 123 as a white solid (6.53 g, 41%).

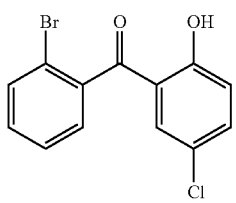

2-Bromobenzoyl chloride (10 g, 46 mmol), aluminum chloride (AlCl$_3$, 6.2 g, 46 mmol), CH$_2$Cl$_2$ (250 mL), and 4-chloroanisole (5.6 mL, 46 mmol) were used as in general procedure I to afford 429 as a tan solid (13.76 g, crude material).

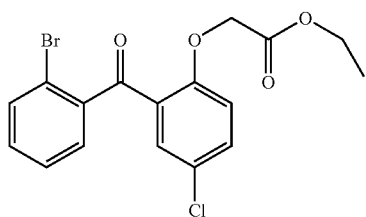

Compound 429 (13.76 g, 44 mmol), potassium carbonate (30.52 g, 221 mmol), ethyl bromoacetate (5.14 mL, 46 mmol), and acetone (250 mL) were used as in general procedure II to afford 430 as a yellow solid (17.24 g, crude material). $^1$H NMR (DMSO-d$_6$, 400 MHz) δ 4.5 (s, 2H), 7.15 (d, 1H), 7.4 (s, 4H), 7.48 (d, 1H), 7.58 (d, 1H), 7.65 (d, 1H), 12.95 (bs, 1H).

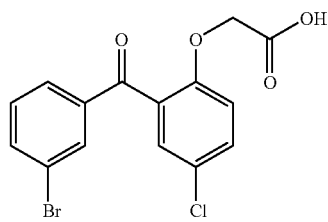

Ester 433 (17.24 g, 43 mmol), ethanol (EtOH, 200 mL), water (50 mL), and lithium hydroxide monohydrate (2.27 g, 54 mmol) were used as in general procedure III to afford 431 as a white solid (6.53 g, 41%). $^1$H NMR (DMSO-d$_6$, 400 MHz) δ 4.65 (s, 2H), 7.08 (d, 1H), 7.42 (m, 2H), 7.54 (dd, 1H), 7.71 (d, 1H), 7.83 (dd, 2H), 13.00 (bs, 1H); MS (ES$^+$) m/z 371 (M+H)$^+$. The crude material was used without purification.

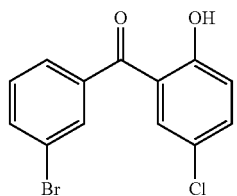

3-Bromobenzoyl chloride (24.11 g, 110 mmol), aluminum chloride (AlCl$_3$, 15 g, 113 mmol), CH$_2$Cl$_2$ (250 mL), and 4-chloroanisole (13.46 mL, 110 mmol) were used as in general procedure I to afford, after triturating the concentrate with hexanes and filtering, 432 as a green solid (25.57 g, 75%). The crude material was used without purification.

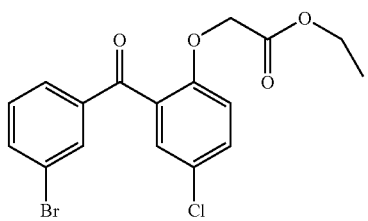

Compound 432 (9.08 g, 29 mmol), potassium carbonate (20.14 g, 146 mmol), ethyl bromoacetate (3.39 mL, 31 mmol), and acetone (200 mL) were used as in general procedure II to afford 433 as a red/brown oil (12.68 g, crude material). $^1$H NMR (DMSO-d$_6$, 400 MHz) δ 1.12 (t, 3H), 4.06 (q, 2H), 4.75 (s, 2H), 7.11 (d, 1H), 7.44 (t, 2H), 7.54 (d, 1H), 7.69 (d, 1H), 7.83 (d, 2H); MS (ES$^+$) m/z 398 (M+H)$^+$.

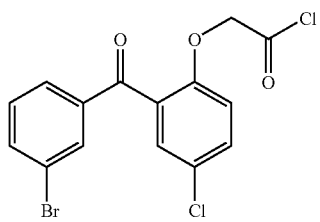

Carboxylic acid 431 (3 g, 8.1 mmol), methylene chloride (25 mL), and thionyl chloride (11.84 mL, 162 mmol) were used as in general procedure XV to afford 434 as a light brown oil (2.96 g, 94%). The crude material was used without purification.

Example 173

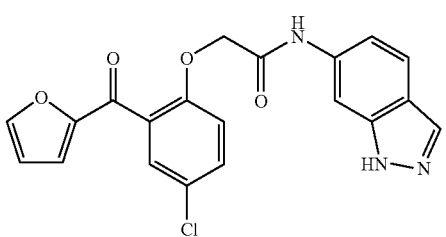

435

Compound 115 (0.28 g, 1 mmol), HCA (0.08 mL, 0.5 mmol), THF (50 mL total reaction volume), PPh₃ (0.26 g, 1 mmol) in THF, and 6-aminoindazole (0.13 g, 1 mmol) in THF were used as in general procedure XIII. The product was purified by flash chromatography using a gradient between 1:1 hexanes:ethyl acetate and 100% ethyl acetate to afford 435 as an orange oil (0.042 g, 11%). ¹H NMR (DMSO-d₆, 400 MHz) δ 4.8 (s, 2H), 6.7 (d, 1H), 7.05 (d, 1H), 7.2 (d, 2H), 7.35 (d, 1H), 7.5 (d, 1H), 7.55 (dd, 1H), 7.65 (d, 1H), 7.94 (s, 1H), 8.07 (s, 2H), 10.06 (s, 1H), 12.89 (s, 1H).

Example 174

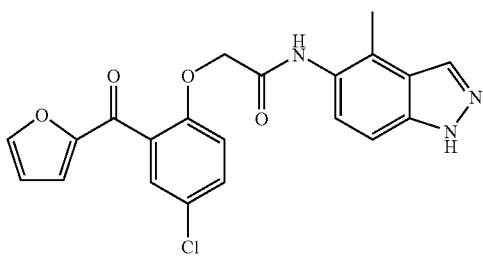

436

Compound 115 (0.19 g, 0.68 mmol), HOBt (0.09 g, 0.68 mmol), DMF (1 mL), 416 (0.1 g, 0.68 mmol) in DMF, EDAC (0.13 g, 0.69 mmol) in DMF (5 mL total reaction volume), and Et₃N (0.19 mL, 1.36 mmol) were used as in general procedure IV. The product was purified by flash chromatography using 1:1 and 7:3 ethyl acetate:hexanes to afford 436 as an off-white solid (0.126 g, 11%). ¹H NMR (DMSO-d₆, 400 MHz) δ 2.25 (s, 3H), 4.8 (s, 2H), 6.7 (s, 1H), 7.18-7.35 (m, 4H), 7.5 (s, 1H), 7.6 (d, 1H), 8.05 (dd, 2H), 9.35 (s, 1H), 13 (s, 1H).

Example 175

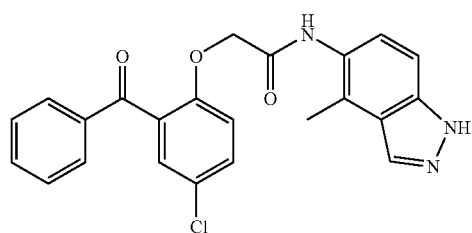

437

Compound 416 (0.1 g, 0.68 mmol), NEt₃ (0.14 mL, 0.71 mmol), acetonitrile (5 mL total reaction volume), and acid chloride 1 (0.53 g, 1.7 mmol) in acetonitrile were used as in general procedure X. The product was purified by flash chromatography using 1:1 hexanes:ethyl acetate to afford 437 as an off-white solid (0.095 g, 0.33%). ¹H NMR (DMSO-d₆, 300 MHz) δ 2.28 (s, 3H), 4.78 (s, 2H), 7.15 (d, 1H), 7.3 (t, 2H), 7.55 (dd, 3H), 7.65 (t, 2H), 7.82 (d, 2H), 8.13 (s, 1H), 9.18 (s, 1H), 13.04 (bs, 1H); MS (ES⁺) m/z 420 (M+H)⁺.

Example 176

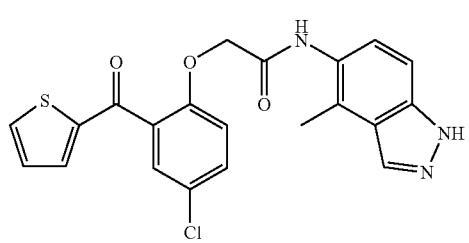

438

Compound 112 (0.20 g, 0.67 mmol), HOBt (0.09 g, 0.68 mmol), DMF (2 mL), compound 416 (0.1 g, 0.68 mmol) in DMF (3 mL), EDAC (0.13 g, 0.69 mmol), and Et₃N (0.19 mL, 1.36 mmol) were used as in general procedure IV. The product was purified by flash chromatography using 7:3 ethyl acetate:hexanes and 100% ethyl acetate to afford 438 as an off-white solid (0.192 g, 67%). ¹H NMR (DMSO-d₆, 300 MHz) δ 2.3 (s, 3H), 4.85 (s, 2H), 7.2-7.35 (m, 4H), 7.55 (s, 1H), 7.65 (d, 1H), 7.7 (s, 1H), 8.15 (s, 2H), 9.38 (s, 1H), 13.05 (s, 1H); MS (ES⁻) m/z 424 (M−H)⁻.

Example 177

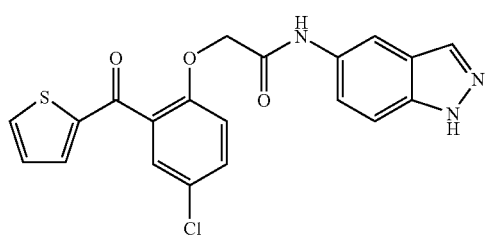

439

Compound 112 (0.20 g, 0.67 mmol), HOBt (0.09 g, 0.68 mmol), DMF (2 mL), 5-aminoindazole (Aldrich, 0.09 g, 0.68 mmol) in DMF (3 mL), EDAC (0.13 g, 0.69 mmol), and Et₃N (0.19 mL, 1.36 mmol) were used as in general procedure IV. The product was purified by flash chromatography using 1:1 ethyl acetate:hexanes as elutant and further purified by dissolving in ethyl acetate, washing with water, drying organics over MgSO₄ and concentrating in vacuo to afford 439 as an off-white solid (0.071 g, 26%). ¹H NMR (DMSO-d₆, 400 MHz) δ 4.8 (s, 2H), 7.2 (d, 2H), 7.35 (d, 1H), 7.5 (d, 2H), 7.55 (d, 1H), 7.65 (s, 1H), 8 (t, 3H), 9.85 (s, 1H), 13 (s, 1H).

Example 178

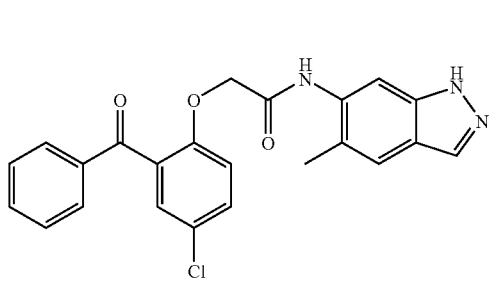

440

Compound 413 (0.1 g, 0.68 mmol), NEt$_3$ (0.19 mL, 2.6 mmol), acetonitrile (30 mL), and acid chloride 320 (0.21 g, 0.68 mmol) in acetonitrile (10 mL) were used as in general procedure X. The product was purified by flash chromatography using 7:3 hexanes:ethyl acetate then 1:1 hexanes:ethyl acetate as elutant, and a TLC prep plate eluted with 1:1 hexanes:ethyl acetate to afford 440 as an off-white solid (0.019 g, 6.7%). $^1$H NMR (DMSO-d$_6$, 300 MHz) δ 2.28 (s, 3H), 4.78 (s, 2H), 7.15 (d, 1H), 7.3 (t, 2H), 7.49 (m, 3H), 7.64 (t, 2H), 7.8 (d, 2H), 8.1 (s, 1H), 9.18 (s, 1H), 13 (bs, 1H); MS (ES$^+$) m/z 420 (M+H)$^+$.

Example 179

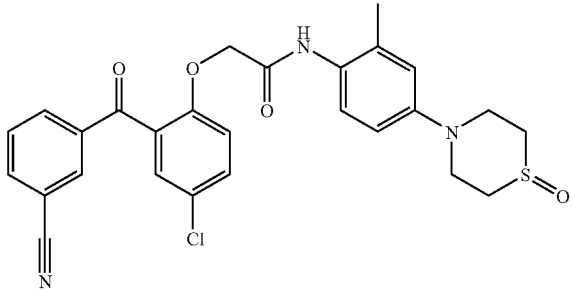

441

Compound 399 (1.2 g, 5.4 mmol) in acetonitrile (45 mL total reaction volume), acid chloride 427 (1.22 g, 3.65 mmol) in acetonitrile, and NEt$_3$ (0.7 mL, 5.1 mmol) were used as in general procedure X. The product was purified by flash chromatography using 95:5 methylene chloride:methanol as elutant to afford 441 as an off-white solid (0.59 g, 31%). $^1$H NMR (DMSO-d$_6$, 400 MHz) δ 1.97 (s, 3H), 2.6 (d, 2H), 2.85 (t, 2H), 3.5 (d, 2H), 3.7 (t, 2H), 4.67 (s, 2H), 6.75 (d, 1H), 6.82 (s, 1H), 7.06 (d, 1H), 7.2 (d, 1H), 7.48 (s, 1H), 7.65 (t, 2H), 8.05 (bs, 2H), 8.15 (s, 1H), 8.96 (s, 1H).

Example 180

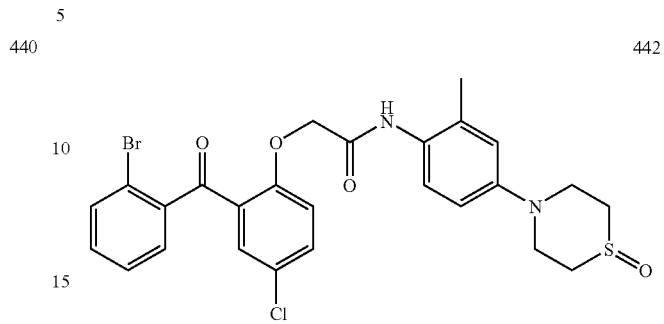

442

Compound 428 (0.443 g, 1.2 mmol), HOBt (0.16 g, 1.2 mmol), DMF, compound 399 (0.40 g, 1.8 mmol) in DMF (15 mL total reaction volume), EDAC (0.23 g, 1.2 mmol), and Et$_3$N (0.34 mL, 2.4 mmol) were used as in general procedure IV. The product was purified by flash chromatography using 98:2 methylene chloride:methanol as elutant to afford 442 as an off-white foam (0.154 g, 22%). $^1$H NMR (DMSO-d$_6$, 400 MHz) δ 2.07 (s, 3H), 2.6 (d, 2H), 2.85 (t, 2H), 3.5 (d, 2H), 3.7 (t, 2H), 4.62 (s, 2H), 6.78 (d, 1H), 6.84 (s, 1H), 7.15 (d, 1H), 7.25 (d, 1H), 7.38 (t, 1H), 7.42 (d, 2H), 7.5 (t, 1H), 7.65 (m, 2H), 8.8 (s, 1H).

Example 181

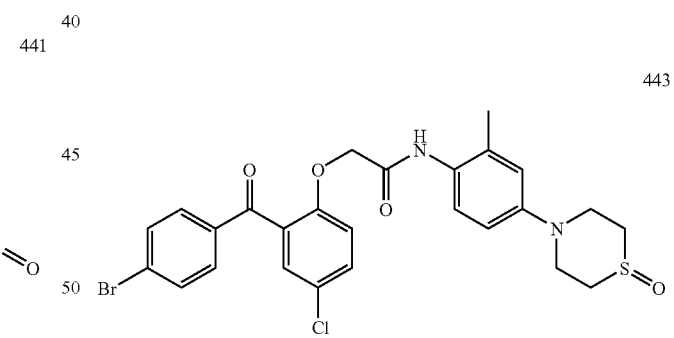

443

Compound 424 (0.443 g, 1.2 mmol), HOBt (0.16 g, 1.2 mmol), DMF, compound 399 (0.40 g, 1.8 mmol) in DMF (15 mL total reaction volume), EDAC (0.23 g, 1.2 mmol), and Et$_3$N (0.34 mL, 2.4 mmol) were used as in general procedure IV. The product was purified by flash chromatography using 98:2 methylene chloride:methanol as elutant to afford 443 as a pale yellow foam (0.105 g, 15%). $^1$H NMR (DMSO-d$_6$, 400 MHz) δ 2.06 (s, 3H), 2.75 (d, 2H), 2.95 (t, 2H), 3.6 (d, 2H), 3.8 (t, 2H), 4.77 (s, 2H), 6.88 (d, 1H), 6.92 (s, 1H), 7.15 (d, 1H), 7.3 (d, 1H), 7.55 (d, 1H), 7.72 (d, 2H), 7.78 (s, 4H), 8.97 (s, 1H); MS is (ES$^-$) m/z 574 (M−H)$^-$.

Example 182

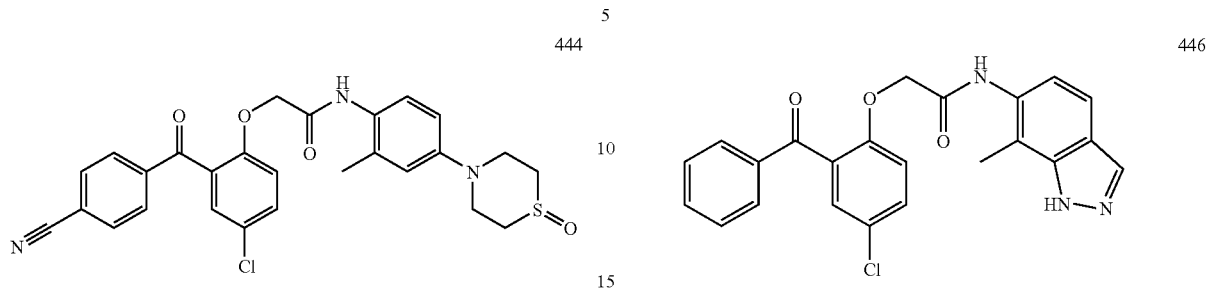

Copper cyanide (0.029 g, 0.33 mmol) was added to a solution of compound 443 (0.093 g, 0.16 mmol) in DMSO (5 mL) and the reaction was heated to 160° C. and stirred overnight. The mixture was cooled and water was added to it. The resulting solid was filtered and washed with ethyl acetate. The filtrate was separated, dried over MgSO$_4$, and concentrated in vacuo. The product was purified by flash chromatography using a gradient between 9:1 hexanes:ethyl acetate and ethyl acetate as the elutant to afford 444 as an orange foam (0.012 g, 14%). $^1$H NMR (DMSO-d$_6$, 400 MHz) δ 1.95 (s, 3H), 2.65 (d, 2H), 2.85 (t, 2H), 3.5 (d, 2H), 3.7 (t, 2H), 4.64 (s, 2H), 6.75 (dd, 1H), 6.82 (s, 1H), 7.02 (d, 1H), 7.2 (d, 1H), 7.5 (s, 1H), 7.63 (d, 2H), 7.9 (m, 4H), 8.88 (s, 1H); MS (ES$^-$) m/z 521 (M-H)$^-$.

Example 183

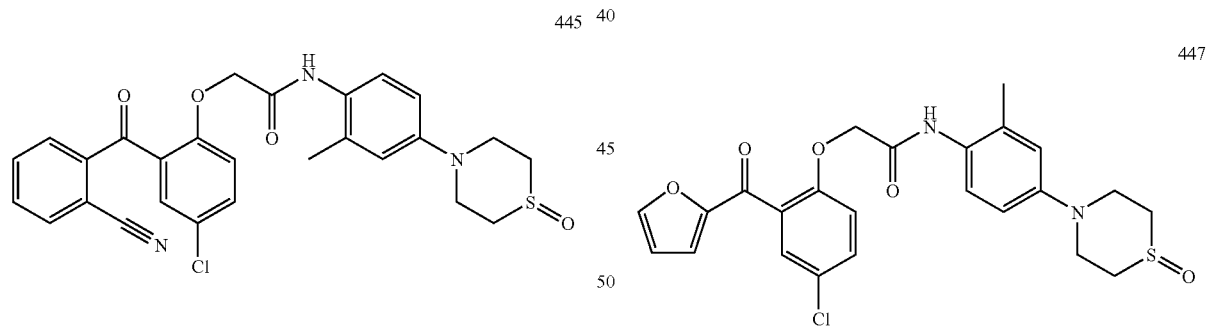

Copper cyanide (0.037 g, 0.42 mmol) was added to a solution of compound 442 (0.120 g, 0.2 mmol) in DMSO (5 mL) and the reaction was heated to 160° C. and stirred overnight. The mixture was cooled and water was added to it. The resulting solid was filtered and washed with ethyl acetate. The filtrate was separated, dried over MgSO$_4$, and concentrated in vacuo. The product was purified by flash chromatography using a gradient between 9:1 hexanes:ethyl acetate and ethyl acetate as the elutant to afford 445 as an orange foam (0.012 g, 11%. $^1$H NMR (DMSO-d$_6$, 400 MHz) δ 1.99 (s, 3H), 2.62 (d, 2H), 2.86 (t, 2H), 3.5 (d, 2H), 3.69 (t, 2H), 4.62 (s, 2H), 6.75 (d, 1H), 6.82 (s, 1H), 7.05 (d, 1H), 7.2 (d, 1H), 7.55 (d, 1H), 7.7 (m, 4H), 7.98 (d, 1H), 8.97 (s, 1H); MS (ES) m/z 521 (M-H)$^-$.

Example 184

Carboxylic acid 105 (0.296 g, 1.2 mmol), HOBt (0.136 g, 1.02 mmol), DMF, compound 421 (0.296 g, 1.02 mmol) in DMF (10 mL total reaction volume), EDAC (0.193 g, 1.02 mmol), and Et$_3$N (0.284 mL, 2.04 mmol) were used as in general procedure IV. The product was purified by flash chromatography using 1:1 ethyl acetate:hexanes as elutant. The concentrate was dissolved in methylene chloride, washed with 10% potassium carbonate. The organics were separated, dried over MgSO$_4$, and concentrated in vacuo. The resulting solid was triturated with ethyl acetate and filtered to afford 446 as an off-white solid (0.0081 g, 2%). $^1$H NMR (DMSO-d$_6$, 400 MHz) δ 2.2 (s, 3H), 4.74 (s, 2H), 6.95 (d, 1H), 7.22 (d, 1H), 7.45 (m, 4H), 7.6 (m, 2H), 7.75 (d, 2H), 7.98 (s, 1H), 9.25 (s, 1H) 13.05 (bs, 1H); MS (ES$^+$) m/z 420 (M+H)$^+$.

Example 185

Compound 399 (0.314 g, 1.4 mmol) in acetonitrile (10 mL total reaction volume), acid chloride 408 (0.3 g, 1 mmol) in acetonitrile, and NEt$_3$ (0.24 mL, 1.7 mmol) were used as in general procedure X. The product was dissolved in methylene chloride and washed with saturated potassium carbonate and water then purified by flash chromatography using 95:5 methylene chloride:methanol as elutant to afford 447 as an off-white foam (0.305 g, 63%). $^1$H NMR (DMSO-d$_6$, 400 MHz) δ 2.03 (s, 3H), 2.63 (d, 2H), 2.85 (t, 2H), 3.5 (d, 2H), 3.7 (t, 2H), 4.74 (s, 2H), 6.71 (d, 1H), 6.78 (d, 1H), 6.84 (s, 1H), 7.18 (m, 2H), 7.3 (d, 1H), 7.5 (d, 1H), 7.59 (dd, 1H), 8.06 (s, 1H), 9.02 (s, 1H); MS (ES$^+$) m/z 487 (M+H)$^+$.

Example 187

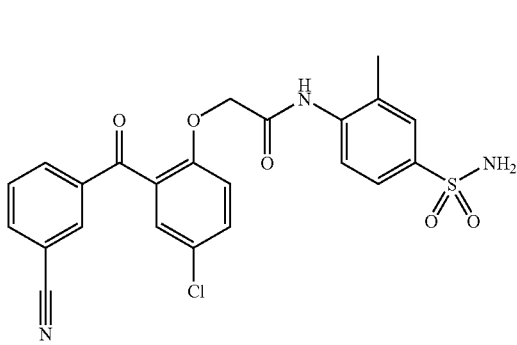
448

Compound 466 (0.15 g, 0.8 mmol) in acetonitrile (10 mL total reaction volume), acid chloride 427 (0.2 g, 0.6 mmol) in acetonitrile, and NEt₃ (0.112 mL, 0.8 mmol) were used as in general procedure X. The product was purified by flash chromatography using 95:5 methylene chloride:methanol as elutant and TLC prep plate eluted twice with 98:2 methylene chloride:methanol to afford 448 as an off-white solid (0.104 g, 36%). $^1$H NMR (DMSO-d$_6$, 400 MHz) δ 2.14 (s, 3H), 4.78 (s, 2H), 7.22 (m, 3H), 7.49 (d, 1H), 7.61 (m, 3H), 7.68 (t, 1H), 8.06 (d, 2H), 8.17 (s, 1H), 9.39 (s, 1H); MS (ES$^-$) m/z 482 (M−H)$^-$.

Example 187

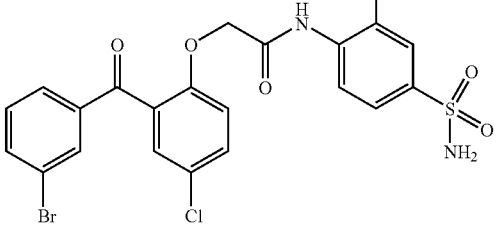
449

Compound 466 (0.141 g, 0.757 mmol), NEt₃ (0.106 mL, 0.761 mmol), acetonitrile (20 mL total reaction volume), and acid chloride 434 (0.203 g, 0.523 mmol) were used as in general procedure X. The product was purified by flash chromatography using 98:2 methylene chloride:methanol as elutant to afford 449 as an off-white solid (0.038 g, 14%). $^1$H NMR (DMSO-d$_6$, 400 MHz) δ 2.14 (s, 3H), 4.77 (s, 2H), 7.22 (m, 3H), 7.45 (dd, 2H), 7.6 (m, 4H), 7.72 (d, 1H), 7.82 (d, 1H), 7.88 (s, 1H), 9.3 (s, 1H); MS (ES$^-$) m/z 536 (M−H)$^-$.

Example 188

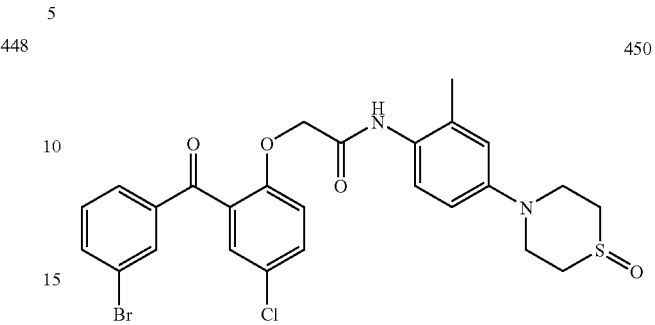
450

Compound 399 (1.43 g, 6.37 mmol), NEt₃ (0.888 mL, 6.37 mmol), acetonitrile (50 mL total reaction volume), and acid chloride 434 (1.68 g, 4.64 mmol) were used as in general procedure X. The product was purified by flash chromatography using 98:2 methylene chloride:methanol as elutant to afford 450 as an beige solid (1.3 g, 52%). $^1$H NMR (DMSO-d$_6$, 400 MHz) δ 1.98 (s, 3H), 2.62 (d, 2H), 2.85 (t, 2H), 3.5 (d, 2H), 3.69 (t, 2H), 4.67 (s, 2H), 6.75 (dd, 1H), 6.82 (d, 1H), 7.08 (d, 1H), 7.2 (d, 1H), 7.42 (d, 1H), 7.46 (d, 1H), 7.62 (dd, 1H), 7.7 (d, 1H), 7.81 (d, 1H), 7.88 (s, 1H), 8.9 (s, 1H); MS (ES$^-$) m/z 574 (M−H)$^-$.

Example 189

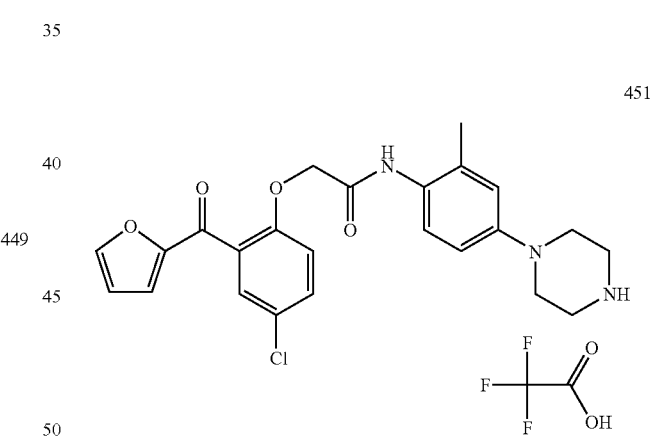
451

Trifluoroacetic acid (TFA, 5 mL, 65 mmol) was added to a solution of compound 452 (0.095 g, 0.17 mmol) in acetonitrile (10 mL) and stirred at rt under nitrogen overnight. Carbon tetrachloride was added to the reaction mixture and the resulting solution was concentrated in vacuo to azeotrope off the TFA. This procedure was repeated multiple times. The product was purified by flash chromatography using 1:1 hexanes:ethyl acetate as elutant to afford 451 as a red/orange solid (0.012 g, 16%). $^1$H NMR (DMSO-d$_6$, 400 MHz) δ 2.04 (s, 3H), 3.15 (s, 4H), 3.21 (d, 4H), 4.75 (s, 2H), 6.7 (d, 1H), 6.75 (d, 1H), 6.8 (s, 1H), 7.2 (dd, 2H), 7.3 (d, 1H), 7.5 (d, 1H), 7.58 (d, 1H), 8.06 (s, 2H), 8.19 (bs, 1H), 9.05 (s, 1H); MS (ES$^+$) m/z 454 (M+H)$^+$.

Example 190

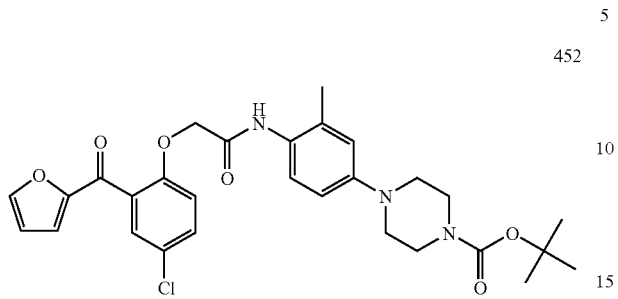

452

Compound 367 (0.409 g, 1.4 mmol) in acetonitrile (5 mL total reaction volume), acid chloride 408 (0.3 g, 1 mmol) in acetonitrile, and NEt₃ (0.24 mL, 1.7 mmol) were used as in general procedure X. The product was purified by flash chromatography using 99:1 methylene chloride:methanol as elutant to afford 452 as a brown, viscous oil (0.202 g, 36%). ¹H NMR (DMSO-d₆, 400 MHz) δ 1.38 (s, 9H), 2.02 (s, 3H), 3.01 (d, 4H), 3.4 (d, 4H), 4,74 (s, 2H), 6.72 (d, 2H), 6.77 (s, 1H), 7.19 (t, 2H), 7.3 (d, 1H), 7.5 (d, 3H), 7.57 (dd, 1H), 8.05 (s, 1H), 9.01 (s, 1H); MS (ES⁻) m/z 553 (M-H)⁻.

Example 191

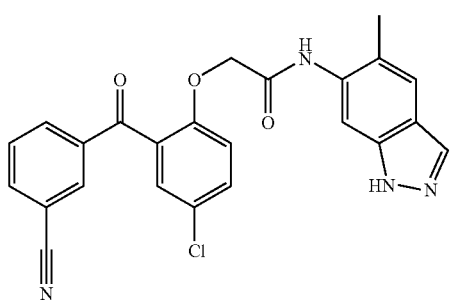

453

Compound 413 (0.072 g, 0.49 mmol) in acetonitrile (10 mL total reaction volume), acid chloride 427 (0.163 g, 0.49 mmol) in acetonitrile, and NEt₃ (0.1 mL, 0.72 mmol) were used as in general procedure X. The product was purified by flash chromatography using 98:2 methylene chloride:methanol as elutant to afford 453 as an off-white solid (0.013 g, 6%). ¹H NMR (DMSO-d₆, 400 MHz) δ 2.16 (s, 3H), 4.77 (s, 2H), 7.25 (d, 1H), 7.5 (s, 2H), 7.65 (m, 3H), 7.89 (s, 1H), 8.08 (d, 2H), 8.16 (s, 1H), 9.03 (s, 1H), 12.84 (s, 1H); MS (ES⁻) m/z 443 (M-H)⁻.

Example 192

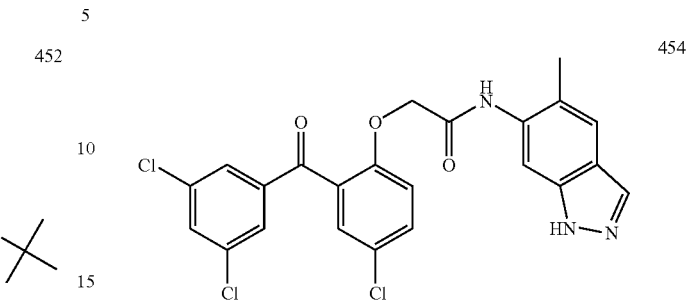

454

Carboxylic acid 76 (0.2 g, 0.55 mmol), methylene chloride (CH₂Cl₂, 3 mL), DMF (4 drops), oxalyl chloride (0.13 mL, 1.49 mmol) were used as in general procedure V. The resulting acid chloride was added to a solution of the amine 413 (0.081 g, 0.55 mmol), acetone (5 mL), sodium bicarbonate (0.42 g, 5 mmol), and water (0.5 mL) as used in general procedure VI. The solution was heated to 40° C. for 1 h, after which time water (25 mL) was added to the reaction mixture and the resulting suspension was filtered. The solids were washed with ether to afford 454 as a gray solid (0.045 g, 17%). ¹H NMR (DMSO-d₆, 300 MHz) δ 2.2 (s, 3H), 4.85 (s, 2H), 7.3 (d, 1H), 7.56 (s, 2H), 7.7 (d, 1H), 7.77 (s, 3H), 7.9 (s, 2H), 9.2 (s, 1H), 12.9 (s, 1H); MS (ES⁻) m/z 486 (M-H)⁻.

Example 193

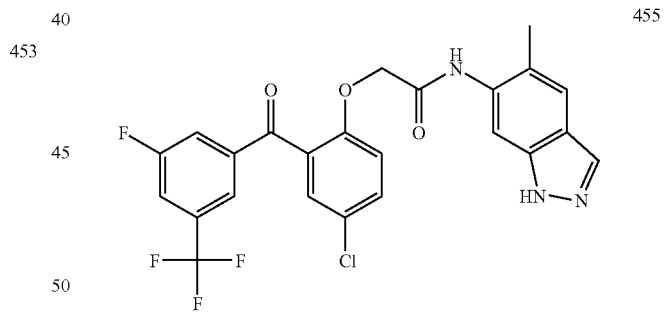

455

Carboxylic acid 71 (0.2 g, 0.53 mmol), methylene chloride (3 mL), DMF (4 drops), oxalyl chloride (0.123 mL, 1.41 mmol) were used as in general procedure V. The resulting acid chloride was then added to a solution of the amine 103 (0.078 g, 0.53 mmol), acetone (5 mL), sodium bicarbonate (0.4 g, 4.76 mmol), and water (0.5 mL) as used in general procedure VI. The reaction mixture was heated to 40° C. for 1 h, after which time water (25 mL) was added to the mixture and the resulting suspension was filtered. The solids were washed with ether to afford 455 as a gray solid (0.048 g, 18%). ¹H NMR (DMSO-d₆, 400 MHz) δ 2.13 (s, 3H), 4.78 (s, 2H), 7.2 (d, 1H), 7.5 (d, 2H), 7.65 (d, 2H), 7.88 (s, 3H), 7.98 (d, 1H), 9.15 (bs, 1H), 12.8 (bs, 1H); MS (ES⁻) m/z 504 (M-H)⁻.

Example 194

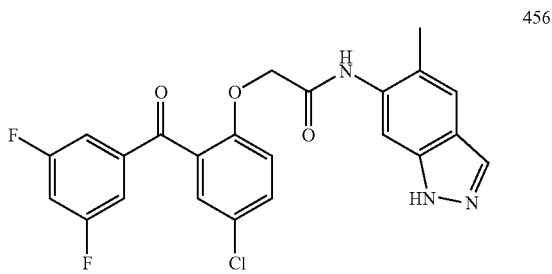

456

Carboxylic acid 49 (0.2 g, 0.6 mmol), methylene chloride (3 mL), DMF (4 drops), oxalyl chloride (0.16 mL, 1.8 mmol) were used as in general procedure V. The resulting acid chloride was then added to a solution of the amine 413 (0.09 g, 0.61 mmol), acetone (10 mL), sodium bicarbonate (0.453 g, 5.4 mmol), and water (0.5 mL) as used in general procedure VI. The reaction mixture was heated to 40° C. for 1 h, after which time water (25 mL) was added to the reaction mixture and the resulting suspension was filtered. The solids were washed with ether to give a gray solid. The product was purified by filtering through a silica gel plug eluded with 9:1 hexanes:ethyl acetate. Hexanes were added to the filtrate until a solid formed. The solid was filtered to afford 456 as a white solid (0.034 g, 12%). $^1$H NMR (DMSO-d$_6$, 300 MHz) δ 2.2 (s, 3H), 4.85 (s, 2H), 7.3 (d, 1H), 7.5 (d, 2H), 7.56 (d, 2H), 7.62(d, 1H), 7.7 (d, 1H), 7.77 (s, 1H), 7.95 (s, 1H), 9.19 (s, 1H), 12.9 (s, 1H); MS (ES$^-$) m/z 454 (M–H)$^-$.

Example 195

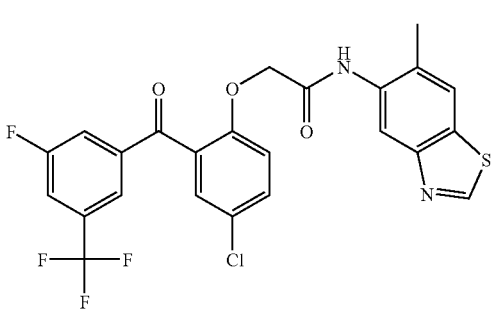

457

Step A:

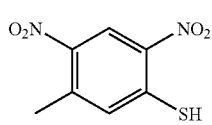

458

Sodium sulfide nonahydrate (3.19 g, 13.3 mmol) was added to a solution of 5-fluoro-2,4-dinitrotoluene (Maybridge, 2.47 g, 12.3 mmol) in DMF (20 mL) and the resulting mixture was stirred overnight under nitrogen. Water was added to the reaction and the solution was acidified to pH 2. The suspension was filtered and the solids were washed with 1N HCl to afford 458 as a yellow/orange solid (4.73 g, crude material). $^1$H NMR (DMSO-d$_6$, 400 MHz) δ 2.46 (s, 3H), 7.89 (s, 1H) 8.7 (s, 1H).

Step B:

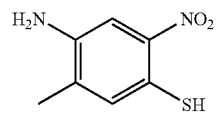

459

Compound 458 (2.64 g, 12.3 mmol), palladium on carbon (2 g, 10% w/w), ethanol (200 mL) and THF (100 mL) were used as in general procedure XII to afford 459 as a yellow solid (0.35 g, 18%). The crude material was used without purification.

Step C:

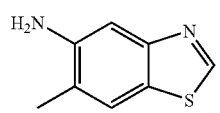

460

Formic acid (96%, 20 mL) was added to compound 459 in a round-bottom flask equipped with a stir bar, reflux condenser, and nitrogen on demand. The mixture was refluxed overnight. The mixture was poured into 2N NaOH (200 mL) and the pH was adjusted to 10. The mixture was extracted with ether, dried over MgSO$_4$, and concentrated in vacuo to give an oil. The product was purified by flash chromatography using a gradient between 1:1 hexanes:ethyl acetate and ethyl acetate as elutant to afford 460 as a white solid (0.03 g, 8%). $^1$H NMR (DMSO-d$_6$, 300 MHz) δ 2.2 (s, 3H), 5.09 (bs, 2H), 7.28 (s, 1H), 7.66 (s, 1H), 9.1 (s, 1H); MS (ES$^+$) m/z 165 (M+H)$^+$.

Step D:

Carboxylic acid 71 (0.091 g, 0.24 mmol), methylene chloride (3 mL), DMF (4 drops), oxalyl chloride (0.057 mL, 0.65 mmol) were used as in general procedure V. The resulting acid chloride was then added to a solution of the amine 460 (0.03 g, 0.18 mmol), acetone (5 mL), sodium bicarbonate (0.18 g, 2.1 mmol), and water (0.5 mL) as used in general procedure VI. The mixture was filtered and the solids were washed with water, ether, and ethyl acetate to afford 457 as an off-white solid (0.064 g, 67%). $^1$H NMR (DMSO-d$_6$, 400 MHz) δ 2.18 (s, 3H), 4.79 (s, 2H), 7.25 (d, 1H), 7.54 (d, 1H), 7.65 (dd, 1H), 7.88 (d, 2H), 7.95 (s, 1H), 7.98 (d, 1H), 8.06 (s, 1H), 9.27 (s, 1H), 9.38 (bs, 1H); MS (ES$^-$) m/z 521 (M–H)$^-$.

Example 196

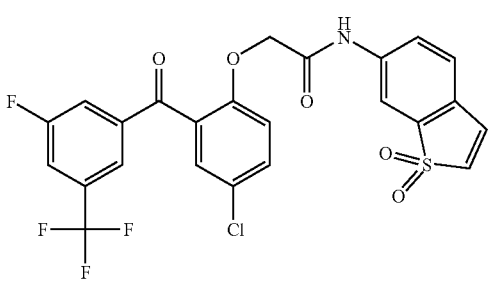

461

Carboxylic acid 71 (0.091 g, 0.24 mmol), methylene chloride (3 mL), DMF (4 drops), oxalyl chloride (0.057 mL, 0.65 mmol) were used as in general procedure V and added to a solution of 6-amino-1,1-dioxobenzo(b)thiophene (Maybridge, 0.044 g, 0.24 mmol), acetone (10 mL), sodium bicarbonate (0.184 g, 2.2 mmol), and water (1 mL) as used in general procedure VI. The product was purified by filtering through a silica pad eluted with methylene chloride. The organics were washed with saturated sodium bicarbonate, dried over MgSO$_4$, and concentrated in vacuo. The product was further purified by flash chromatography using 9:1 methylene chloride:methanol as elutant to afford 461 as a yellow solid (0.013 g, 10%). $^1$H NMR (DMSO-d$_6$, 400 MHz) δ 4.75 (s, 2H), 7.2 (d, 1H), 7.25 (d, 1H), 7.5 (d, 1H), 7.54-7.58 (m, 2H), 7.59-7.64 (m, 2H), 7.85 (d, 2H), 7.9 (d, 1H), 8 (s, 1H), 10.4 (s, 1H); MS (ES$^-$) m/z 538 (M–H)$^-$.

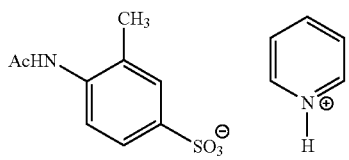

462

Into a round-bottom flask were placed 2-aminotoluene-5-sulfonic acid (50.0 g, 267 mmol), and pyridine (300 mL). Acetic anhydride (38 mL, 403 mmol) was added dropwise from an addition funnel and the resulting mixture was allowed to stir for 2 h at rt. The solvents were removed under reduced pressure, to leave a brown solid. Several portions of ethyl alcohol were added to the solid and subsequently removed under reduced pressure, to afford a brown solid which was filtered and washed with several additional portions of ethyl alcohol and dried under vacuum (67.03 g, 81%) $^1$H NMR (DMSO-d$_6$,) δ 2.08 (s, 3H), 2.22 (s, 3H), 7.39 (s, 2H), 7.45 (s, 1H), 8.02 (t, J=6 Hz, 2H), 8.53 (t, J=6 Hz, 1H), 8.92 (d, J=6 Hz, 2H), 9.31 (s, 1H).

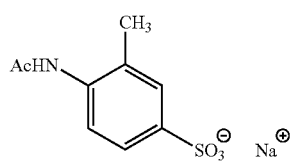

463

Compound 462 (67.03 g, 217 mmol) was added to a round-bottom flask containing 1N NaOH (225 mL) and the resulting mixture was allowed to stir at rt for 3 h. The mixture was concentrated under reduced pressure, to afford a brown solid. Several portions of ethyl alcohol were added and subsequently removed under reduced pressure. The remaining solid was filtered, washed with a final portion of ethyl alcohol and dried under vacuum (42.34 g, 77%). $^1$H NMR (DMSO-d$_6$, 300 MHz) δ 2.08 (s, 3H), 2.22 (s, 3H), 7.39 (s, 2H), 7.45 (s, 1H), 9.31 (s, 1H).

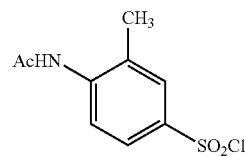

464

Sulfonic acid salt 463 (42.34 g, 169 mmol) and DMF (300 mL) were added to a flask that was equipped with a stir bar and nitrogen on demand and was cooled to 0° C. Thionyl chloride (30 mL, 411 mmol) was added dropwise from an addition funnel at a rate such that the temperature of the reaction mixture did not exceed 10° C. When the addition was complete, the mixture was allowed to warm to rt and stir for an additional 2½ h, after which time it was poured into a beaker containing crushed ice. The resulting solid was collected by filtration, washed with several portions of water and dried under vacuum (25.63 g, 61%). $^1$H NMR (DMSO, d$_6$, 400 MHz) δ 2.02 (s, 3H), 2.15 (s, 3H), 7.33 (s, 2H), 7.38 (s, 1H), 9.27 (s, 1H).

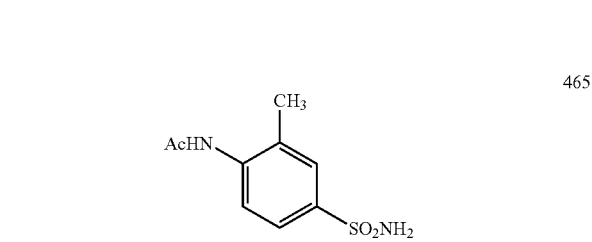

465

Into a round-bottom flask, equipped with a stir bar and nitrogen on demand, were placed sodium acetate (19.82 g, 241.6 mmol) and ethyl alcohol (200 mL) and the mixture was cooled to 0° C. Ammonia gas was bubbled through the sodium acetate solution for 5 min, then sulfonyl chloride 464 (25.63 g, 103 mmol) was added as a solid and in one portion. The resulting mixture was allowed to stir at 0° C. for 30 min, and was then allowed to warm to rt and stir for an additional 18 h. The mixture was then diluted with water and was poured into a separatory funnel containing water and ethyl acetate. The organic layer was collected, washed with water, brine, dried over MgSO$_4$, filtered and the solvents were removed under reduced pressure to provide 465 as a yellow solid (8.4 g, 36%), which was used without further purification.

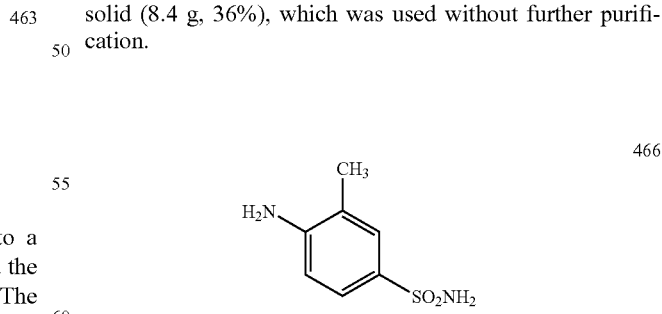

466

A round-bottom flask was equipped with a stir bar, a reflux condenser and nitrogen on demand. Into the flask were placed sulfonamide 465 (8.4 g, 36.80 mmol), ethyl alcohol (200 mL) and 2N hydrochloric acid (128 mL). The resulting mixture was allowed to heat to reflux overnight, after which time it was allowed to cool to RT and was neutralized with saturated, aqueous sodium bicarbonate. It was then poured into a separatory funnel containing water and ethyl acetate, the organic layer was collected, washed with water, brine, dried over MgSO$_4$, filtered and the solvents were removed under reduced pressure to afford a tan solid (6.35 gi 93%), which was used without further purification. $^1$H NMR (DMSO-d$_6$, 400 MHz) δ 2.06 (s, 3H), 5.54 (s, 2H), 6.58 (d, J=12 Hz, 1H), 6.82 (s, 2H), 7.30 (d, J=12 Hz, 1H), 7.33 (s, 1H).

Example 197

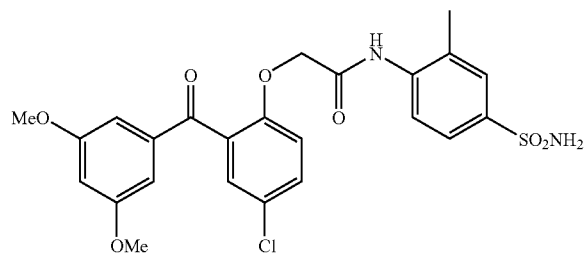

467

Step A:

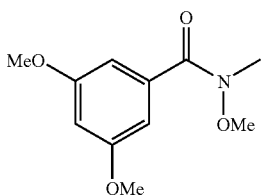

468

The title compound was prepared according to General Procedure VII from 3,5-dimethoxybenzoyl chloride (2.00 g, 10.0 mmol). The reaction gave 468 as a colorless oil (2.143 g, 95%): $^1$H NMR (CDCl$_3$, 400 MHz) δ 6.75 (d, 2H), 6.49 (t, 1H), 3.76 (s, 6H), 3.55 (s, 3H), 3.29 (s, 3H).

Step B:

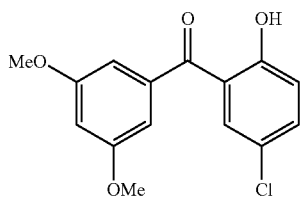

469

A solution of 2-bromo-4-chlorophenol (0.830 g, 4.0 mmol) in 20 mL of THF was cooled to –78° C. in a dry ice/acetone bath. n-Butyllithium (5.5 mL of a 1.6 M solution in hexanes, 8.8 mmol) was added dropwise over 5 min, and the resulting mixture was stirred at –78° C. for 1 h. A solution of 468 (0.901 g, 4.0 mmol) in 5 mL of THF was added dropwise over 4 min, and the resulting mixture was stirred at –78° C. for 1.25 h, then at room temperature for 14 h. The reaction mixture was poured into 50 mL of water and extracted with two 50-mL portions of EtOAc. The combined organic layers were then dried over MgSO$_4$, filtered and concentrated in vacuo to give 1.193 g of a brown oil. Purification by flash chromatography using 10% EtOAc/hexanes as an eluant followed by crystallization from hot ether gave 469 as yellow crystals (0.234 g, 20%): $^1$H NMR (CDCl$_3$, 300 MHz) δ 11.83 (s, 1H), 7.62 (d, 1H), 7.45 (dd, 1H), 7.03 (d, 1H), 6.76 (d, 2H), 6.68 (t, 1H), 3.84 (s, 6H).

Step C:

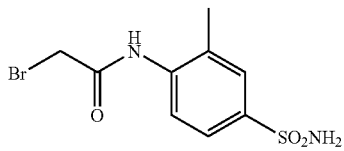

470

A solution of 466 (5.0 g, 26.85 mol) and pyridine (2.4 mL, 29.53 mmol) in 150 mL of chloroform was cooled to 0° C. in an ice bath. Bromoacetyl bromide (2.6 mL, 29.53 mmol) was added dropwise over 20 min, and the resulting mixture was allowed to slowly warm to room temperature as it was stirred for 18 h. The reaction mixture was then poured into 150 mL of water and extracted with two 100-mL portions of CH$_2$Cl$_2$. Both the organic and aqueous layers were filtered to yield a beige solid. This solid was suspended in 40 mL of 1 N HCl and stirred several minutes. The solid was then filtered and rinsed with CH$_2$Cl$_2$, MeOH, and hexanes to yield 470 (5.705 g, 69%): $^1$H NMR (CDCl$_3$, 400 MHz) δ 9.84 (s, 1H), 7.66-7.56 (m, 3H), 7.23 (br s, 2H), 4.09 (s, 2H), 2.24 (s, 3H).

Step D:

A mixture of 469 (0.144 g, 0.49 mmol), 470 (0.162 g, 0.53 mmol), and potassium carbonate (0.339 g, 2.45 mmol) in 5 mL of acetone was warmed to reflux for 6 h, then stirred at room temperature overnight. The reaction mixture went dry overnight, so another 5 mL of acetone was added, and the resulting mixture was heated to reflux for 8 h, then stirred at room temperature for 22 h. The reaction mixture was poured into 30 mL of water and extracted with two 30-mL portions of EtOAc. The combined organic layers were filtered to remove solid, washed with brine, dried over MgSO$_4$, filtered, and concentrated in vacuo to give 0.195 g of a yellow solid. Purification by suspension in hot ether followed by filtration gave 467 (0.094 g, 37%): MS (AP+) m/z 518.9 (M+H); $^1$H NMR (DMSO-d$_6$, 400 MHz) δ 9.15 (s, 1H), 7.63-7.60 (m, 3H), 7.56 (dd, 1H), 7.39 (d, 1H), 7.22 (s, 2H), 7.18 (d, 1H), 6.82 (d, 2H), 6.71 (t, 1H), 4.76 (s, 2H), 3.69 (s, 6H), 2.12 (s, 3H).

Example 198

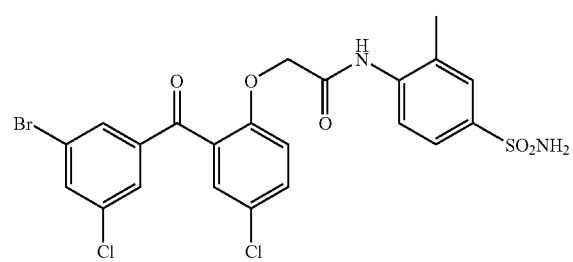

471

Step A:

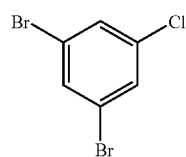
472

A solution of 1,3,5-tribromobenzene (9.44 g, 30 mmol) in 120 mL of ether was cooled to −78° C. in a dry ice/acetone bath. n-Butyllithium (13.2 mL of 2.5 M solution in hexanes, 33 mmol) was added dropwise over 10 min. The resulting mixture was stirred at −78° C. for an additional 10 min, then hexachloroethane (7.15 g, 30.2 mmol) was added in small portions over 3 min. The reaction mixture was then stirred for 15 min at −78° C., followed by 3.2 h at rt. The mixture was partitioned between 100 mL of water and 100 mL of EtOAc. The aqueous layer was separated and extracted with an additional 100 mL of EtOAc. The combined organic layers were then dried over MgSO$_4$, filtered, and concentrated in vacuo to give 472 as a pale brown solid (7.72 g, 95%): $^1$H NMR (CDCl$_3$, 300 MHz) δ 7.57 (t, 1H), 7.47 (d, 2H).

Step B:

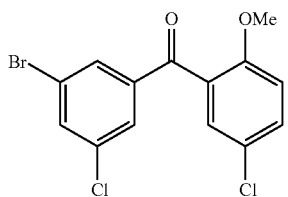
473

A solution of 472 (7.62 g, 28.2 mmol) in 100 mL of ether was cooled to −78° C. in a dry ice/acetone bath. n-Butyllithium (12.6 mL of 2.5 M solution in hexanes, 31.5 mmol) was added dropwise over 30 min. The resulting mixture was stirred at −78° C. for an additional 13 min, then 183 (6.57 g, 28.6 mmol) was added in small portions over 23 min. The reaction mixture was then stirred for 22 h as the bath was allowed to warm to room temperature. The mixture was poured into 100 mL water and extracted with two 100-mL portions of EtOAc. The combined organic layers were then dried over MgSO$_4$, filtered, and concentrated in vacuo to give 9.46 g of a beige solid. Recrystallization from hot MeOH gave 473 (6.45 g, 64%): MS (AP−) m/z 358 (M−H); $^1$H NMR (CDCl$_3$, 300 MHz) δ 7.76 (t, 1H), 7.70 (t, 1H), 7.65 (t, 1H), 7.47 (dd, 1H), 7.36(d, 1H), 6.95 (d, 1H); 3.72 (s, 3H).

Step C:

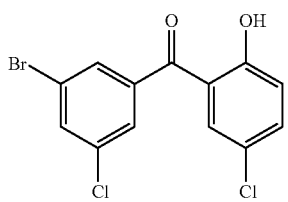
474

The title compound was prepared according to General Procedure 1x from 473 (0.338 g, 0.94 mmol). The reaction gave 474 (0.325 g, 100%): $^1$H NMR (CDCl$_3$, 400-MHz) δ 11.54 (s, 1H), 7.72 (t, 1H), 7.62 (d, 1H), 7.52 (d, 1H), 7.46 (dd, 1H), 7.41 (d, 1H), 7.02 (d, 1H).

Step D:

A mixture of 474 (0.173 g, 0.50 mmol), 470 (0.154 g, 0.50 mmol), and potassium carbonate (0.346 g, 2.5 mmol) in 10 mL of acetone was warmed to reflux for 15 h and stirred at room temperature another 4 h. The reaction mixture was then poured into 35 mL of water and extracted with two 35-mL portions of EtOAc. The aqueous layer was then filtered and extracted with another 20 mL of EtOAc. The combined organic layers were washed with brine, dried over MgSO$_4$, filtered, and concentrated in vacuo to give 0.230 g of a yellow oil. Purification by flash chromatography using 0.5-1% MeOH/CH$_2$Cl$_2$ gave 471 (0.048 g, 17%): MS (AP+) m/z 573 (M+H); $^1$H NMR (DMSO-d$_6$, 400 MHz) δ 9.36 (s, 1H), 7.97 (t, 1H), 7.79 (s, 1H), 7.71 (s, 1H), 7.68-7.47 (m, 4H), 7.45 (d, 1H), 7.21 (s, 2H), 7.20-7.18 (d, 1H), 4.77 (s, 2H), 2.13 (s, 3H).

Example 199

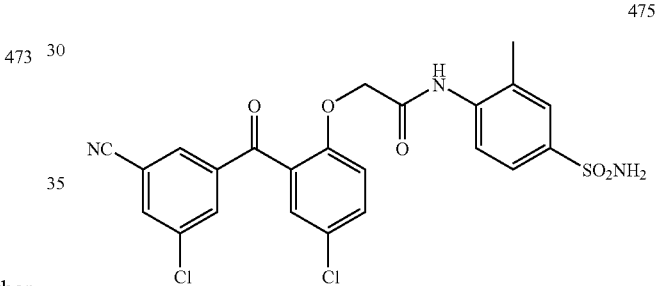
475

Step A:

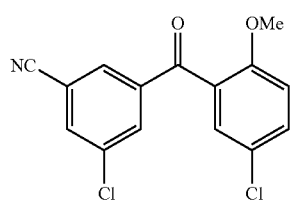
476

A solution of 473 (0.299 g, 0.83 mmol), sodium cyanide (0.086 g, 1.76 mmol), copper (I) iodide (0.028 g, 0.15 mmol), and tetrakis-(triphenylphosphine)-palladium (0.113 g, 0.10 mmol) in 8 mL of acetonitrile was heated to reflux for 40 min. The reaction mixture was then diluted with 50 mL of EtOAc and filtered through Celite. The resulting solution was washed with 25 mL of water, dried over MgSO$_4$, filtered and concentrated in vacuo to give 0.375 g of an orange gum. Purification by flash chromatography using 5% EtOAc/hexane as the eluant gave 476 (0.171 g, 56%): $^1$H NMR (CDCl$_3$, 400 MHz) δ 7.93 (t, 1H), 7.82 (t, 1H), 7.76 (t, 1H), 7.47 (dd, 1H), 7.37 (d, 1H), 6.93 (d, 1H), 3.67 (s, 3H).

Step B:

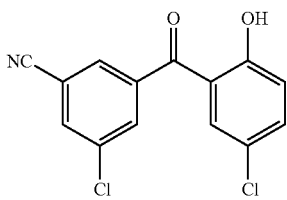
477

The title compound was prepared according to General Procedure 1× from 476 (0.165 g, 0.54 mmol). The reaction gave 477 (0.174 g, 100%): $^1$H NMR (CDCl$_3$, 400 MHz) δ 11.43 (s, 1H), 7.84-7.82 (m, 2H), 7.78 (t, 1H), 7.49 (dd, 1H), 7.34 (d, 1H), 7.05 (d, 1H).

Step C:

A mixture of 477 (0.157 g, 0.54 mmol), 470 (0.165 g, 0.54 mmol), and potassium carbonate (0.373 g, 2.7 mmol) in 10 mL of acetone was warmed to reflux for 17.5 h. The reaction mixture was then poured into 35 mL of water and extracted with two 35-mL portions of EtOAc. The combined organic layers were washed with brine, dried over MgSO$_4$, filtered, and concentrated in vacuo to give 0.276 g of a yellow oil. Purification by flash chromatography using 0.5-1% MeOH/CH$_2$Cl$_2$ gave 475 (0.033 g, 12%): MS (AP−) m/z 517 (M−H); $^1$H NMR (DMSO-d$_6$, 400 MHz) δ 9.42 (s, 1H), 8.26 (s, 1H), 8.11 (s, 1H), 8.03 (t, 1H), 7.63 (dd, 1H), 7.60-7.53 (m, 3H), 7.49 (d, 1H), 7.22 (s, 2H), 7.19 (d, 1H), 4.77 (s, 2H), 2.14 (s, 3H).

Example 200

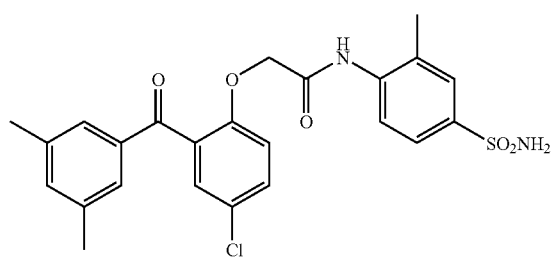
478

Step A:

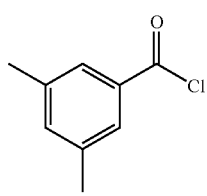
479

The title compound was prepared according to General Procedure V from 3,5-dimethylbenzoic acid (1.50 g, 10.0 mmol). The reaction work-up gave 479 (2.214 g), which was used immediately without purification.

Step B:

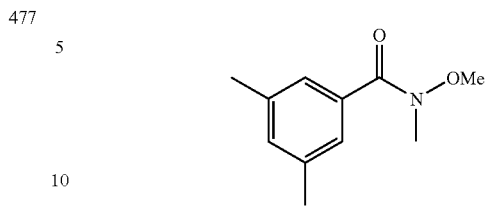
480

The title compound was prepared according to General Procedure VII from 479 (2.214 g). The reaction workup gave 480 as a yellow oil (2.073 g, 100%): $^1$H NMR (CDCl$_3$, 300 MHz) δ 7.26 (s, 2H), 7.07 (s, 1H), 3.57 (s, 3H), 3.33 (s, 3H), 2.33 (s, 6H).

Step C:

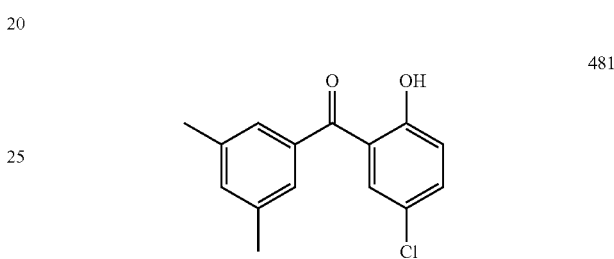
481

A solution of 2-bromo-4-chlorophenol (0.844 g, 4.07 mmol) in THF (20 mL) was cooled to −78° C. in a dry ice/acetone bath. n-Butyllithium (5.6 mL of 1.6 M solution in hexanes, 8.95 mmol) was added dropwise over 6 min, and the resulting mixture was stirred at −78° C. for 1 h. A solution of 480 (0.786 g, 4.07 mmol) in 5 mL of THF was added dropwise over 6 min, and the resulting mixture was stirred at −78° C. for 1.25 h and at room temperature for 14 h. The reaction mixture was then poured into 50 mL of water and extracted with two 50-mL portions of EtOAc. The combined organic layers were then dried over MgSO$_4$, filtered and concentrated in vacuo to give 1.014 g of a brown solid. Purification by flash chromatography using 5% EtOAc/hexanes as an eluant followed by crystallization from hot ether gave 481 as yellow crystals (0.296 g, 28%): $^1$H NMR (CDCl$_3$, 300 MHz) δ 11.94 (s, 1H), 7.57 (d, 1H), 7.44 (dd, 1H), 7.25 (s, 3H), 7.03 (d, 1H), 2.40 (s, 6H).

Step D:

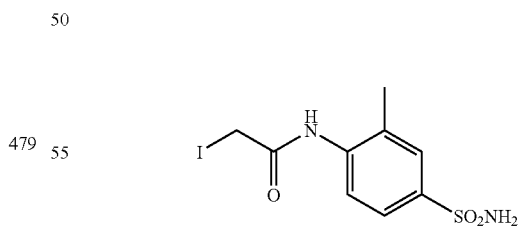
482

A mixture of 470 (1.27 g, 3.53 mmol) and sodium iodide (1.61 g, 10.7 mmol) in 10 mL of acetone was stirred at room temperature for 20.5 h. The reaction mixture was then diluted with 60 mL of water and 60 mL of CH$_2$Cl$_2$ and stirred for another 20 min. Filtration of the mixture then gave 482 as a beige solid (1.197 g, 96%): $^1$H NMR (DMSO-d$_6$, 300 MHz) δ 9.81 (s, 1H), 7.65-7.61 (m, 3H), 7.26 (s, 2H), 3.90 (s, 2H), 2.28 (s, 3H).

Step E:

A mixture of 481 (0.130 g, 0.5 mmol), 482 (0.195 g, 0.55 mmol), and potassium carbonate (0.156 g, 1.13 mmol) in 5 mL of acetone was warmed to reflux for 8 h, then stirred at room temperature an additional 12 h. The reaction mixture was then partitioned between 30 mL of water and 30 mL of EtOAc. The aqueous layer was separated and extracted with two 30-mL portions of $CH_2Cl_2$. All layers were filtered to give 0.172 g of an off-white solid. This solid was suspended in 200 mL of hot acetone and filtered again to give 0.116 g of a yellow solid. The combined organic layers were dried over $MgSO_4$, filtered, and concentrated in vacuo to give 0.117 g of a second yellow solid. The two yellow solids were combined and purified by flash chromatography using 0.5-1% MeOH/$CH_2Cl_2$ to give 478 as a white solid (0.108 g, 44%): MS (AP+) m/z 487 (M+H); $^1$H NMR (DMSO-$d_6$, 400 MHz) δ 9.08 (s, 1H), 7.63-7.54 (m, 4H), 7.36 (s, 3H), 7.22-7.18 (m, 4H), 4.75 (s, 2H), 2.22 (s, 6H), 2.10 (s, 3H).

Example 201

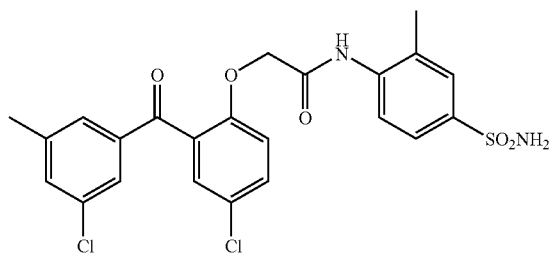
483

Step A:

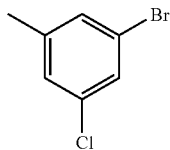
484

A solution of 3,5-dibromotoluene (1.25 g, 5.0 mmol) in 25 mL of ether was cooled to −78° C. in a dry ice/acetone bath. n-Butyllithium (2.2 mL of 2.5 M solution in hexanes, 5.5 mmol) was added dropwise over 3 min. The resulting mixture was stirred at −78° C. for an additional 11 min, then hexachloroethane (1.18 g, 5.0 mmol) was added in small portions over 4 min. The reaction mixture was then stirred for 14 min at −78° C., followed by 17 h at room temperature. The reaction mixture was poured into 50 mL of water and extracted with two 50-mL portions of EtOAc. The combined organic layers were dried over $MgSO_4$, filtered, and concentrated in vacuo to give 484 as a light brown solid (0.885 g, 86%): $^1$H NMR (CDCl$_3$, 300 MHz) δ 7.32 (s, 1H), 7.22 (s, 1H), 7.10 (s, 1H), 2.31 (s, 3H).

Step B:

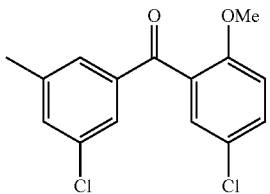
485

A solution of 484 (0.875 g, 4.26 mmol) in 24 mL of ether was cooled to −78° C. in a dry ice/acetone bath. n-Butyllithium (2.1 mL of 2.5 M solution in hexanes, 5.25 mmol) was added dropwise over 5 min. The resulting mixture was stirred at −78° C. for an additional 15 min, then 183 (0.978 g, 4.26 mmol) was added in small portions over 6 min. The reaction mixture was then stirred for 26 h as the bath was allowed to warm to room temperature. The reaction mixture was poured into 25 mL water and extracted with 50 mL of $CH_2Cl_2$. The organic layer was then dried over $MgSO_4$, filtered, and concentrated in vacuo to give 1.224 g of a brown solid. Recrystallization from hot ether gave 485 (0.536 g, 43%): $^1$H NMR (CDCl$_3$, 400 MHz) δ 7.48 (s, 1H), 7.45 (s, 1H), 7.40 (dd, 1H), 7.33 (d, 1H), 7.28 (d, 1H), 6.90 (d, 1H), 3.68 (s, 3H), 2.34 (s, 3H).

Step C:

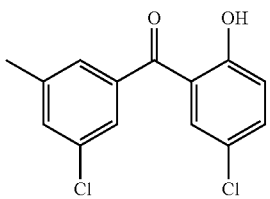
486

The title compound was prepared according to General Procedure 1× from 485 (0.295 g, 1.0 mmol). The reaction gave 486 (0.285 g, 100%): $^1$H NMR (CDCl$_3$, 400 MHz) δ 11.71 (s, 1H), 7.46 (d, 1H), 7.43 (dd, 1H), 7.39 (s, 1H), 7.38 (s, 1H), 7.29 (s, 1H), 7.00 (d, 1H), 2.40 (s, 3H).

Step D:

A mixture of 486 (0.141 g, 0.5 mmol), 482 (0.195 g, 0.55 mmol), and potassium carbonate (0.138 g, 1.0 mmol) in 10 mL of acetone was warmed to reflux for 8 h, then stirred at room temperature an additional 8 h. The reaction mixture was poured into 30 mL of water and extracted with 30 mL of EtOAc and 30 mL of $CH_2Cl_2$. The combined organic layers were dried over $MgSO_4$, filtered, and concentrated in vacuo to give 0.238 g of crude material. Purification by flash chromatography using 0.5-2% MeOH/$CH_2Cl_2$ to give 483 as a white solid (0.111 g, 44%): $^1$H NMR (DMSO-$d_6$, 400 MHz) δ 9.23 (br s, 1H), 7.62-7.54 (m, 4H), 7.51 (s, 2H), 7.49 (s, 1H), 7.42 (d, 1H), 7.21 (br s, 2H), 7.19 (d, 1H), 4.76 (s, 2H), 2.27 (s, 3H), 2.12 (s, 3H).

Example 202

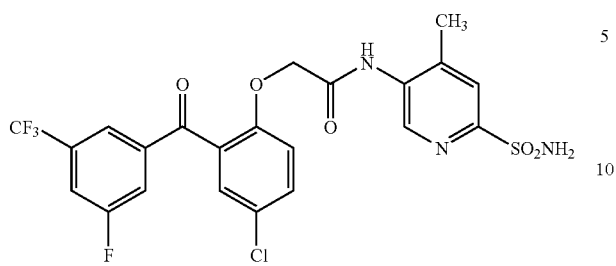

487

Step A:

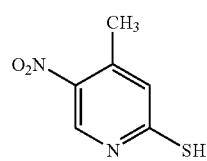

488

To a heat-dried, 3-necked, round bottom flask equipped with a nitrogen inlet and reflux condenser was added 2-chloro-4-methyl-5-nitropyridine (Aldrich Chemical Co., 4.12 g, 23.9 mmol), thiourea (1.82 g, 23.9 mmol), and ethanol (40 ml). The mixture was warmed to reflux whereupon components dissolved, and the solution stirred for 3 h at reflux. A yellow precipitate was observed after 2 h. A solution of potassium hydroxide (2.01 g, 35.9 mmol) in water (8 mL) was added and the mixture was heated for an additional 1 h. The reaction mixture was allowed to cool to rt, and was diluted with 1M sodium hydroxide (150 mL). This mixture was extracted with methylene chloride (75 mL), and the pH of the aqueous layer adjusted from 12 to 7 with glacial acetic acid. The resulting solid was filtered and dried in vacuo to yield 488 (2.36 g, 58%). $^1$H NMR (DMSO-d$_6$, 300 MHz) δ 8.47 (s, 1H), 7.25 (s, 1H), 2.39 (s, 3H).

Step B:

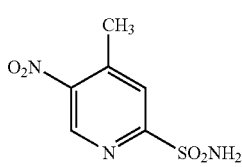

489

488 (850 mg, 5 mmol) was suspended in 1N hydrochloric acid (13 ml) and cooled to 0° C. Chlorine gas was bubbled through the suspension for 30 min, at a rate that allowed the reaction to remain near 0° C. The reaction mix was stirred for 15 min further at 0° C. after gas introduction was stopped. Chloroform (30 ml) was added to the mixture and stirred at 0° C. until the solids dissolved. The layers were partitioned, the aqueous layer extracted with chloroform (10 mL), and the organic layers were combined, placed in a 100 ml round bottom flask and cooled in an ice/water bath. Ammonia liquid (~5 mL) was added to the solution via a cold finger trap cooled to −78° C. (CO$_2$/acetone). A precipitate formed and the mixture was allowed to warm to 0° C. and for 5 min, followed by 1 h at rt. The mixture was then heated to 45° C. and concentrated in vacuo to a provide a yellow solid which was washed with ether and dried to give 489 (856 mg, 79%) as a tan solid. $^1$H NMR (DMSO-d$_6$, 300 MHz) δ 9.25 (s, 1H), 8.13 (s, 1H), 2.69 (s, 3H); MS (AP−): m/z 217 (M$^-$).

Step C:

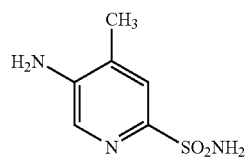

490

489 (2.36 g, 10.88 mmol) was treated according to General Procedure XII to give 490 (2.05 g, >99%), which was used without further purification.

Step D:

Acid 71 (200 mg, 0.53 mmol) was treated according to general procedure V. The product obtained was then allowed to react with 490 (0.53 mmol) according to general procedure VI. The resulting product was purified by silica gel chromatography (5% MeOH/CH$_2$Cl$_2$) followed by recrystallization from acetonitrile/water, to give 487 (27 mg, 9%). $^1$H NMR (DMSO-d$_6$, 400 MHz) δ 9.7 (s, 1H), 8.61 (s, 1H), 7.97 (d, J=8.4, 1H), 7.85 (m, 2H), 7.76 (s, 1H), 7.63 (dd, J=9, 2.8, 1H), 7.51 (d, J=2.7, 1H), 7.34 (s, 1H), 7.21 (d, J=9.2, 1H), 4.80 (s, 2H), 2.17 (s, 3H); MS (ES+): m/z 546 (M$^+$).

Example 203

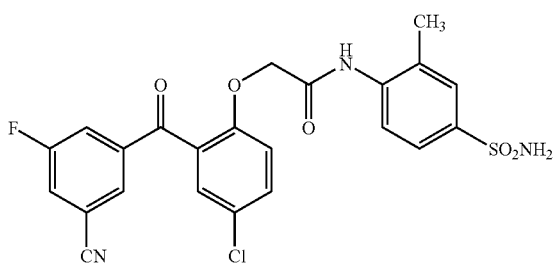

491

Step A:

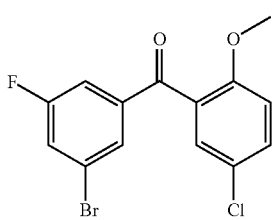

492

Into a two-neck flask equipped with a nitrogen inlet was placed 3,5-dibromofluorobenzene (1.12 g, 4.4 mmol) and anhydrous ether (8 mL). This solution was cooled to −78° C. (CO$_2$/acetone) and n-butyllithium (2.5M in hexanes, 1.92 ml, 4.8 mmol) was added dropwise. The resulting solution was stirred at −78° C. for 10 min, after which time a solution of N-methyl-N-methoxy-2-methoxy-5-chlorobenzamide (1 g, 4.37 mmol) in ether (40 mL) was added dropwise. The cooling bath was removed and the reaction was allowed to warm to rt, stir for an additional for 1 h, followed by the addition of 1M H₃PO₄ (50 mL). The mixture was stirred for 30 min, and the layers were separated. The aqueous layer was extracted with ethyl acetate, and the combined organic layers were dried (Na₂SO₄), filtered, and concentrated in vacuo. The product was then triturated with methanol to give 492 (0.63 mg, 42%) as a white solid. ¹H NMR (CDCl₃, 300 MHz) δ 7.72 (s, 1H), 7.53-7.39 (m, 4H), 6.99 (d, J=8.9, 1H), 3.76 (s, 3H).

Step B:

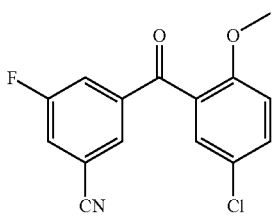

493

492 (1.3 g, 3.8 mmol) was treated according to General Procedure XV to give 493 (1.09 g, >99%). ¹H NMR (CDCl₃, 300 MHz) δ 7.83 (s, 1H), 7.78 (d, J=8.7, 1H), 7.60-7.53 (m, 2H), 7.44 (d, J=2.6, 1H), 7.00 (d, J=8.8, 1H), 3.75 (s, 3H); MS(EI+): m/z 289 (M⁺).

Step C:

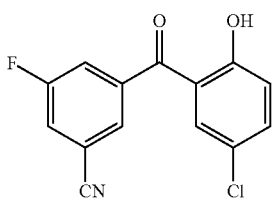

494

493 was treated according to the procedure used for the synthesis of compound 4 to give 494 (1.09 g, >99%). ¹H NMR (CDCl₃, 300 MHz)δ 11.51 (s, 1H), 7.79 (s, 1H), 7.67 (d, J=7.8, 2H), 7.57 (dd, J=9.0, 2.4, 1H), 7.44 (d, J=2.4, 1H), 7.13 (d, J=9.0, 1H); MS(ES-): m/z 274 (M-H)⁻.

Step D:

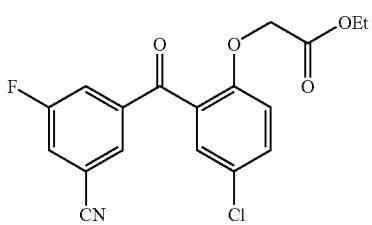

495

494 was treated according to General Procedure II. The product was purified by silica gel chromatography (20% ethyl acetate/hexanes) to afford 495 (1.27 g, 89%) as a clear oil. ¹H NMR (CDCl₃, 400 MHz) δ 7.90 (s, 1H), 7.80-7.78 (m, 1H), 7.50-7.42 (m, 3H), 6.76 (d, J=8.6, 1H), 4.49 (s, 2H), 4.18 (q, J=14.2, 7.1, 2H), 1.21 (t, J=3.5, 3H).

Step E:

496

495 was treated according to General Procedure III to give 496 (1.0 g, 85%) as a white solid which was used without further purification. ¹H NMR (DMSO-d₆, 400 MHz) δ 8.09 (d, J=7.9, 1H), 8.00 (s 1H), 7.90 (d, J=8.8, 1H), 7.55 (dd, J=8.9, 2.5, 1H), 7.43 (d, J=2.6, 1H), 7.03 (d, J=9.0 2H); MS(ES-): m/z 332 (M-H)⁻.

Step F:

496 was used according to General Procedure V, and was further allowed to react with compound 466 according to General Procedure VI, to afford 491 (290 mg, 58%) as a white solid. ¹H NMR (DMSO-d₆, 400 MHz) δ 9.43 (s, 1H), 8.1 (d, J=8.2, 1H), 8.02 (s, 1H), 7.88 (d, J=9.0, 1H), 7.64-7.48 (m, 5H), 7.22-7.17 (m, 3H), 4.77 (s, 2H), 2.14 (s, 3H); MS(ES-): m/z 500 (M-H)⁻. Anal. Calcd for C₂₃H₁₇N₃O₅ClFS: C, 55.04; H, 3.41; N, 8.37. Found: C, 55.07; H, 3.56; N, 8.35.

Example 204

497

496 was treated according to general procedure V, and was then further allowed to react with 490 according to general procedure VI. The product was purified by silica gel chromatography (5% methanol/methylene chloride), followed and by washing with ethyl acetate/hexanes to afford 497 (48 mg, 19%). ¹H NMR (DMSO-d₆, 400 MHz) δ 9.73 (s, 1H), 8.64 (s, 1H), 8.10 (d, J=8.1, 1H), 8.02 (s, 1H), 7.88 (d, J=8.8, 1H), 7.76 (s, 1H), 7.62 (dd, J=8.9, 2.7, 1H), 7.49 (d, J=2.5, 1H), 7.35 (s, 2H), 4.81 (s, 2H), 2.20 (s, 3H). MS(ES-): m/z 501 (M-H)⁻. Anal. Calcd for C₂₂H₁₆N₄O₅ClFS: C, 52.54; H, 3.21; N, 11.14. Found: C, 52.30; H, 3.34; N, 10.96.

Example 205

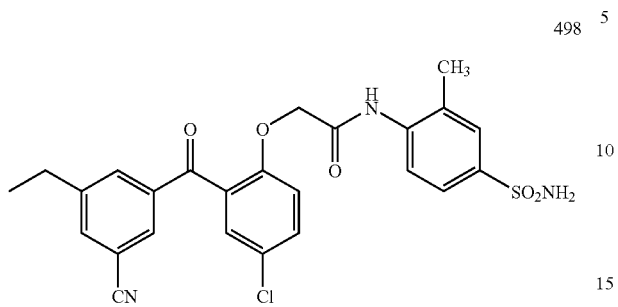

Step A:

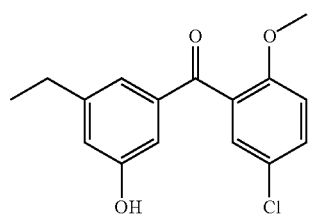

2-bromo-4-ethylphenol (prepared according to the procedure of Sargent et al. in *J. Chem. Soc. Perkin Trans.* 1, 1984, 1621), and N-methyl-N-methoxy-2-methoxy-5-chlorobenzamide were treated according to the procedures outlined by Selnick et al. in *Tetrahedron Lett.* 1993, 34, 2043-2046 to give 499 (185 mg, 11%). $^1$H NMR (CDCl$_3$, 400 MHz) δ 7.37 (dd, J=8.7, 2.5, 1H), 7.32-7.22 (m, 1H), 7.16 (s, 1H), 7.03 (s, 1H), 6.98-6.84 (m, 2H), 5.16 (bs, 1H), 3.69 (s, 3H), 2.59 (q, J=15.2, 7.5, 2H), 1.18 (t, J=7.6, 3H).

Step B:

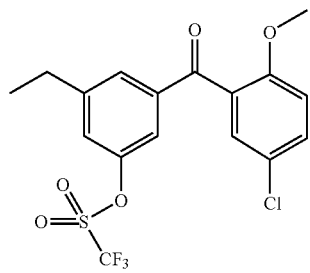

499 (185 mg, 0.64 mmol) was dissolved in DMF (2 mL) and treated with sodium hydride (31 mg 60% dispersion in oil, 0.8 mmol)and the resulting mixture was stirred for 30 min until bubbling ceased. N-phenyltriflimide (286 mg, 0.8 mmol) was added in one portion. The mixture was stirred for 3 h, then partitioned between ether and water (50 mL each). The organic layer was dried (MgSO$_4$), filtered, and concentrated in vacuo to give 500 (256 mg, 95%) which was used without purification. MS(ES+): m/z 423 (M+H$^+$).

Step C:

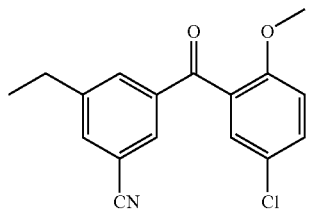

500 (256 mg, 0.61 mmol) was treated as described in General Procedure XV to give a crude product which was purified by silica gel chromatography (20% ethyl acetate/hexanes) to give 501 (158 mg, 87%). $^1$H NMR (CDCl$_3$, 400 MHz) δ 7.85 (s, 1H), 7.74 (s, 1H), 7.63 (s, 1H), 7.44 (dd, J=8.9, 2.6, 1H), 7.33 (d, J=2.7, 1H), 6.91 (d, J=8.8, 1H), 3.66 (s, 3H), 2.71 (q, J=15.2, 7.5, 2H), 1.24 (t, J=7.6, 3H).

Step D:

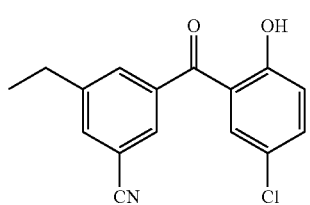

501 (158 mg, 0.53 mmol) was treated according to the procedure for the synthesis of compound 4 to give 502 (152 mg, >99%) as a yellow solid, which used without further purification. MS(ES−): m/z 284 (M−H)$^-$.

Step E:

502 (152 mg, 0.53 mmol) and 470 were treated according to the procedure for the synthesis of 467 to give a crude product which was triturated with 10% methanol/ether to give 498 (100 mg, 37%). $^1$H NMR (DMSO-d$_6$, 300 MHz) δ 9.42 (s, 1H), 8.03-7.99 (m, 2H), 7.69-7.61 (m, 4H), 7.54 (d, J=2.6, 1H), 4.84 (s, 2H), 2.72 (q, J=15.1, 7.6, 2H), 2.20 (s, 3H), 1.19 (t, J=7.5, 3H); MS(ES−): m/z 284 (M−H)$^-$.

Example 206

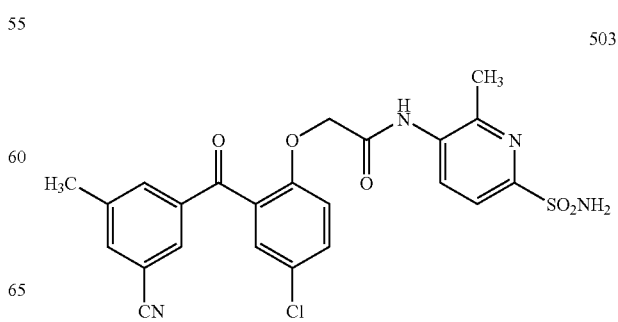

Step A:

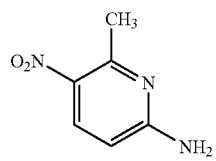
504

Concentrated sulfuric acid (200 mL) was cooled to 5° C. and 6-methyl-2-pyridinamine (50 g, 0.46 mol, Aldrich Chemical Co.) was added over 20 min. while the reaction temperature was maintained below 50° C. Fuming nitric acid (30 mL) was then added slowly over 30-40 min. and the resulting mixture was allowed to warm to rt and stand for approximately 1 h. The reaction was then heated to 55° C. for 1 h, then poured carefully into a mixture of 5N sodium hydroxide (1L) and ice. The final pH was adjusted to 10 with 5N and then 1N sodium hydroxide and the product precipitated as a mixture of the 6-methyl-4 and 5-nitro-2-pyridinamines in 75% yield. A pure sample of 504 was provided by sublimation. GCMS (EI$^+$) 153 m/z. $^1$H NMR (DMSO-d$_6$) δ 8.2 (d, 1H, Ar), 7.9 (bs, 2H, NH$_2$), 6.6 (d, 1H, Ar), 2.4 (s, 3H, CH$_3$). The structure was confirmed by a heteronuclear multiple bond coherence experiment (HMBC). A proton on the 6-methyl group exhibited a three bond coupling with the 5-carbon atom bearing the nitro group.

Step B:

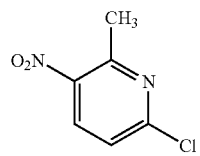
505

A mixture of 504 and 6-methyl-4-nitro-2-pyridinamines (0.5 g, 3.3 mmol) was stirred with carbon tetrachloride (15 mL). Trimethylsilyl chloride in dichloromethane (1M, 10 mL, 10 mmol) was added and the reaction heated in a 70° C. oil bath for 30 min. Trimethylsilyl chloride (0.5 mL, 4 mmol) was added the reaction was heated another 30 min. t-Butyl nitrite (4 mL, 30 mmol, 10 eq.) was added and the reaction was heated to reflux overnight. The reaction was filtered and the solvents removed in vacuo. 505 was isolated by chromatography on a 4×15 cM column of silica gel eluted with hexane/ethyl acetate (6:1, 1 L). GCMS (C$^+$) 173 m+1/z. $^1$H NMR (CDCl$_3$) δ 8.2 (d, 1H, Ar), 7.3 (d, 1H, Ar), 2.8 (s, 3H, CH$_3$). The structure was confirmed by a heteronuclear multiple-bond coherence experiment (HMBC). A proton on the 6-methyl group exhibited a three bond coupling with the 5-carbon atom bearing the nitro group.

Step C:

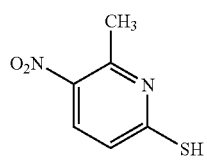
506

505 (0.4 g, 2.4 mmol) was dissolved in ethanol (30 mL). Thiourea (0.2 g, 2.6 mmol, 1.1 eq.) was added and the reaction refluxed for 7 h. Potassium hydroxide (0.2 g, 3.6 mol, 1.5 eq.) dissolved in water (1 mL) was added to the reaction and heating continued for 1 h.

The solution was diluted with 1N sodium hydroxide (25 mL). The aqueous phase was extracted with dichloromethane (25 mL, 3×). The pH was adjusted to 4 with concentrated HCl and 506 precipitated. A 30% yield was obtained. LCMS (APCI$^+$) 171 m+1/z. $^1$H NMR (DMSO-d$_6$) δ 7.9 (d, 1H, Ar), 7.1 (d, 1H, Ar), 2.7 (s, 3H, CH$_3$).

Step D:

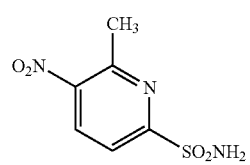
507

506 (0.115 g, 0.67 mmol) was stirred in 1N HCl (5 mL) and chilled to 5° C. Chlorine gas was passed through the mixture for 30 min. then the reaction was stirred for an additional 15 min. The product was extracted with dichloromethane (5 mL, 2×). The organic fractions were combined and chilled to 0° C. Ammonia was dripped into the solution for 15 min. by condensing ammonia gas with a −78° C. cold finger. The reaction was allowed to warm to rt and stir overnight. The solvent was removed in vacuo. The residue was dissolved in ethyl acetate (15 mL) and washed with NaHCO$_3$ solution (15 mL). The solution was dried with MgSO$_4$, filtered and the solvent removed in vacuo to give 507 in 40% yield suitable for further use. GCMS (CI$^+$) 218 m+1/z. $^1$H NMR (DMSO-d$_6$) δ 8.6 (d, 1H, Ar), 7.9 (d, 1H, Ar), 7.7 (bs, 2H, NH$_2$), 2.8 (s, 3H, CH$_3$).

Step E:

Reduction of the 5-nitro group of 507 (0.06 g, 0.27 mmol) was accomplished by catalytic reduction in ethanol (10 mL) with 10% Pd/C (0.011 g). The reaction was carried out overnight. The catalysis was removed by filtration and the amino compound was coupled with the acid chloride 589 generated by general procedure V, by the method outlined in general procedure VI to give 503 LCMS (ES$^+$) 499 m+1/z. $^1$H NMR (DMSO-d$_6$) δ 9.6 (br s, 1H, NH), 8.0 (d, 1H, Ar), 7.94 (s, 1H, Ar), 7.89 (s, 1H, Ar), 7.87 (s, 1H, Ar), 7.7 (d, 1H, Ar), 7.6 (dd, 1H, Ar), 7.45 (d, 1H, Ar), 7.32 (bs, 2H, NH$_2$), 7.2 (d, 1H, Ar), 4.8 (s, 2H, CH$_2$), 2.35 (s, 3H, CH$_3$), 2.33 (s, 3H, CH$_3$).

Example 207

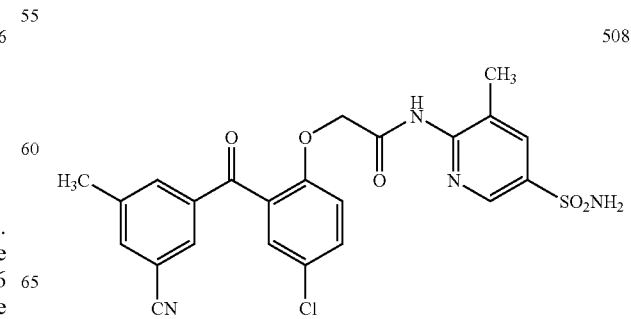
508

Step A:

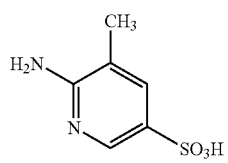
509

3-Methyl-2-pyridinamine (1 mL, 1 mmol, Aldrich Chemical Co.) was combined with 20% fuming sulfuric acid (2 mL) at rt. The reaction was heated to 160° C. for 20 h. The reaction was allowed to cool to rt and ice, ~10 mL, was added. The product precipitated and was collected by filtration. A 50% yield of 509 was obtained. LCMS (ES$^+$) 189 m+1/z. $^1$H NMR (DMSO-d$_6$) δ 13(br s, 1H, SO$_3$H), 7.88(s, 3H, 1-Ar, 2H, NH$_2$), 7.87 (s, 1H, Ar), 2.14 (s, 3H, CH$_3$).

Step B:

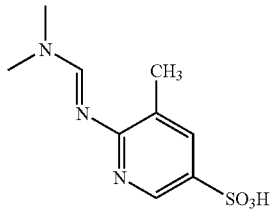
510

509 (0.9 g, 4.8 mmol) was mixed with DMF (30 mL). Thionyl chloride (0.5 mL, 6.8 mmol, 1.4 eq.) was added and reaction stirred at rt. Solution was achieved briefly. A new precipitate formed. The reaction was stirred 30-40 min and filtered. The product was washed with hexane and was suitable for further use. A 77% yield of 510 was obtained. LCMS (ES$^+$) 244 m+1/z. $^1$H NMR (DMSO-d$_6$) δ 8.4 (s, 1H, formyl-H), 7.9 (s, 2H, Ar), 3.4 (s, 3H, CH$_3$), 3.3 (s, 3H, CH$_3$), 2.35 (s, 3H, CH$_3$).

Step C:

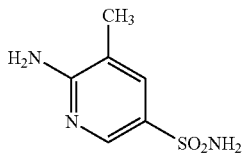
511

510 (1.0 g, 4.1 mmol) and PCl$_5$ (0.85 g, 4.1 mmol) were combined and heated in a 130° C. oil bath for 1.5 h. The resultant POCl$_3$ was removed under high vacuum. Concentrated ammonium hydroxide (25 mL) was carefully added at rt. The reaction was heated to reflux for 3 to 4 h and was then allowed to stand at rt for 60 h. The product was collected by filtration. A 45% yield of 511 was obtained. LCMS (ES$^+$) 188 m+1/z. $^1$H NMR (DMSO-d$_6$) δ 8.12 (s, 1H, Ar), 7.5 (s, 1H, Ar), 7.0 (s, 2H, NH$_2$), 6.45 (s, 1H, Ar), 2.0 (s, 3H, CH$_3$).

Step D:

511 (0.07 g, 0.37 mmol) was mixed with THF (5 mL) and (TMS)$_2$BSA (0.090 mL, 2 eq.). The reaction was refluxed for 45 min. The solution was cooled to rt and the acid chloride of acid (1 eq.) 589, prepared by general procedure V, was added. The reaction was stirred for 2 h at rt. The solvent was removed in vacuo. Partial purification of the product was accomplished by chromatography on a 4×6 cm column of silica gel eluted with chloroform/methanol (96:4) followed by chromatography on a 4×6 cm column of silica gel eluted with chloroform/methanol (95:5). Final purification was accomplished by HPLC on a Waters Symmetry C18 column, 1.9×15 cm, eluted with MeOH/H$_2$O (3:2) at 8 mL/min. A 10% yield of 508 was obtained. LCMS (APCI$^+$) 499 m+1/z. $^1$H NMR (DMSO-d$_6$) δ 10.2 (br s, 1H, NH), 8.56(s, 1H, Ar), 7.98 (s, 1H, Ar), 7.91 (s, 1H, Ar), 7.87 (s, 2H, Ar), 7.60 (dd, 1H, Ar), 7.47 (s, 2H, NH$_2$), 7.44 (s, 1H, NH$_2$), 7.12 (d, 1H, Ar), 4.8 (s, 2H, CH$_2$), 2.32 (s, 3H, CH$_3$), 2.10 (s, 3H, CH$_3$).

Example 208

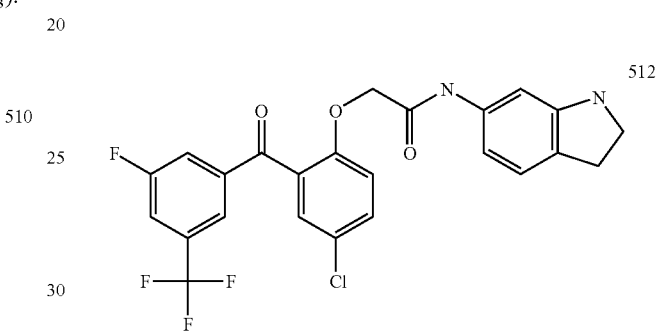
512

Carboxylic acid 71 (0.258 g, 0.68 mmol), oxalyl chloride (0.8 mL of 2.0 M solution in dichloromethane, 0.92 mmol), DMF (8 drops), and dichloromethane (5 mL), were used to prepare the acid chloride according to general procedure V. The acid chloride was then dissolved in acetone and added dropwise to 6-aminoindoline dihydrochloride (Aldrich, 0.140 g, 0.68 mmol), acetone (10 mL), sodium bicarbonate (0.501 g, 6 mmol), and water (1 mL) as in general procedure VI. Ice (5 mL) was added to the reaction mixture and the resulting suspension was filtered, washed with water and diethyl ether, then air dried. The solids were then purified by flash chromatography using 95:5 CH$_2$Cl$_2$:CH$_3$OH as eluant to afford 512 (0.06 g, 18%). $^1$H NMR (DMSO-d$_6$, 300 MHz) δ 2.92 (t, 2H), 3.94 (t, 2H), 4.93 (m, 3H), 6.21 (dd, 1H), 6.84 (d, 1H), 7.19 (d, 1H), 7.32 (m, 1H), 7.51 (d, 1H), 7.58 (dd, 1H), 8 (m, 3H); LC-MS (ES$^+$) m/z 493 (M+H)$^+$, LC-MS (ES$^-$) m/z 491 (M−H)$^-$.

Example 209

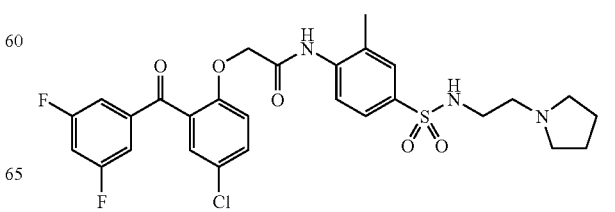
513

Step A:

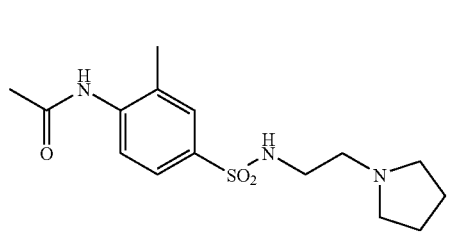

514

A mixture of 464 (1.10 g, 4.4 mmol), 1-(2-aminoethyl) pyrrolidine (0.84 mL, 6.6 mmol), and pyridine (0.39 mL, 4.8 mmol) in methylene chloride (50 mL) was stirred rt for 6 d. The reaction mixture was then diluted with 50 mL of CH$_2$Cl$_2$ and extracted with two 50-mL portions of water. The organic layer was dried over MgSO$_4$ and filtered to give 1.021 g of a brown oil. Purification by flash chromatography (elution with 3-5% MeOH/CH$_2$Cl$_2$) gave 514 as a yellow oil (0.776 g, 54%): MS (ES+) m/z 326 (M+H); $^1$H NMR (CDCl$_3$, 400 MHz) δ 8.19-8.17 (m, 1H), 7.70-7.68 (m, 2H), 7.19 (br s, 1H), 2.98 (t, 2H), 2.52 (t, 2H), 2.37-2.34 (m, 4H), 2.32 (s, 3H), 2.25 (s, 3H), 1.73-17.0 (m, 4H).

Step B:

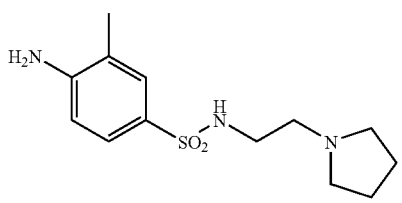

515

A mixture of 514 (0.765 g, 2.35 mmol) and 1.5 M HCl (5 mL) in 20 mL of ethanol was heated to 80° C. for 18 h. The reaction mixture was then poured into 50 mL of saturated NaHCO$_3$ (aq) and extracted with two 30-mL portions of CH$_2$Cl$_2$. The combined organic layers were dried over MgSO$_4$, filtered and concentrated in vacuo to give 515 (0.564 g, 81%): MS (ES+) m/z 284 (M+H); $^1$H NMR (CDCl$_3$, 400 MHz) δ 7.54-7.50 (m, 2H), 6.68 (d, 1H), 4.07 (br s, 2H), 2.98-2.95 (m, 2H), 2.54-2.52 (m, 2H, 2.39-2.32 (m, 4H), 2.18 (s, 3H), 1.75-1.68 (m, 4H).

Step C:

Acid 49 was converted to the acid chloride using the general procedure V. Aniline 515 (0.07 g, 0.29 mmol), acetone (4 mL), sodium bicarbonate (0.22 g, 2.6 mmol), and the acid chloride (0.1 g, 0.29 mmol) were used as in general procedure VI. Water (25 mL) was added to the reaction mixture and the resulting suspension was filtered. The solids were washed with ether to afford 513 as an off-white solid (0.015 g, 8.7%). $^1$H NMR (DMSO-d$_6$, 300 MHz) δ 1.65 (m, 4H), 2.2 (s, 3H), 2.85 (t, 2H), 3.35 (m, 6H), 4.83 (s, 2H), 7.22 (d, 1H), 7.43-7.72 (m, 8H), 9.48 (s, 1H); MS (ES$^+$) m/z 592 (M+H)$^+$.

Example 210

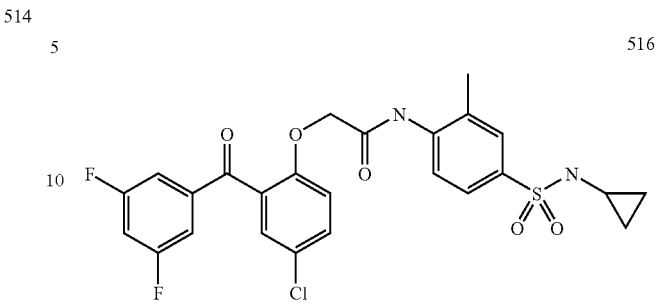

516

Acid 49 was converted to the acid chloride using the general procedure V. Aniline 315 (0.066 g, 0.29 mmol), acetone (4 mL), sodium bicarbonate (0.22 g, 2.6 mmol), and the acid chloride (0.1 g, 0.29 mmol) were used as in general procedure VI. Water (25 mL) was added to the reaction mixture and the resulting suspension was filtered. The solid was dissolved in CH$_2$Cl$_2$ then chromatographed by TLC prep plate eluded with 9:1 CH$_2$Cl$_2$:MeOH to afford 516 as an off-white solid (0.074 g, 48%). $^1$H NMR (DMSO-d$_6$, 400 MHz) δ 0.4 (m, 2H), 0.42 (m, 2H), 2 (m, 1H), 2.2 (s, 3H), 4.8 (s, 2H), 7.18 (d, 1H), 7.38 (m, 2H), 7.41 (d, 1H), 7.46-7.61 (m, 4H), 7.69 (d, 1H), 7.76 (d, 1H), 9.38 (s, 1H); MS (ES$^+$) m/z 535 (M+H)$^+$, MS (ES) m/533 (M−H)$^-$.

Example 211

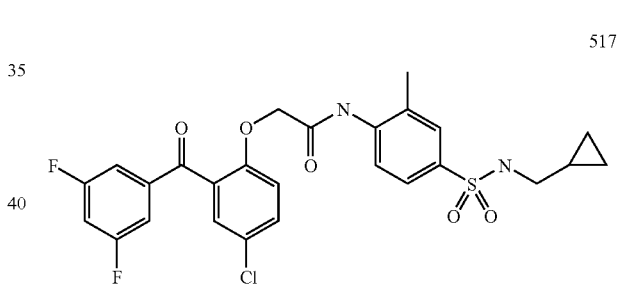

517

Step A:

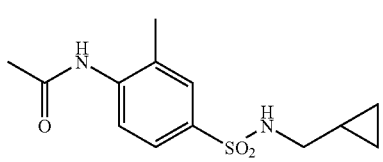

518

A mixture of 464 (1.10 g, 4.4 mmol), cyclopropanemethylamine (Aldrich, 0.57 mL, 6.6 mmol), and pyridine (0.39 mL, 4.8 mmol) in 50 mL of methylene chloride was stirred at rt for 7 d. The reaction mixture was then filtered, washed with 50 mL of CH$_2$Cl$_2$ and 50 mL of water. The organic layer was washed with an additional 50 mL of water, brine, dried over MgSO$_4$, filtered and concentrated. Crystallization of the crude material from MeOH provided 518 (0.348 g, 28%): $^1$H NMR (DMSO-d$_6$, 400 MHz) δ 9.39 (s, 1H), 7.72 (d, 1H), 7.58-7.52 (m, 3H), 2.59 (t, 2H), 2.25 (s, 3H), 2.07 (s, 3H), 0.80-0.72 (m, 1H), 0.34-0.29 (m, 2H), 0.06-0.03 (m, 2H).

Step B:

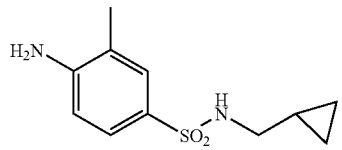

519

A mixture of 518 (0.310 g, 1.1 mmol) and 1.5 M HCl (2.5 mL) in 12 mL of ethanol was heated to 80° C. for 18 h. The reaction mixture was then poured into 50 mL of saturated NaHCO$_3$ (aq) and extracted with two 30-mL portions of CH$_2$Cl$_2$. The combined organic layers were dried over MgSO$_4$, filtered and concentrated in vacuo to afford 519, which was used without further purification (0.284 g): MS (ES+) m/z 241 (M+H); $^1$H NMR (CDCl$_3$, 400 MHz) δ 7.54-7.51 (m, 2H), 6.68 (d, 1H), 4.41 (t, 1H), 4.06 (br s, 2H), 2.78 (t, 2H), 2.18 (s, 3H), 0.92-0.83 (m, 1H), 0.48-0.43 (m, 2H), 0.11-0.07 (m, 2H).

Step C:

Acid 49 was converted to the acid chloride using the general procedure V. Aniline 519 (0.07 g, 0.29 mmol), acetone (4 mL), sodium bicarbonate (0.22 g, 2.6 mmol), and the acid chloride (0.1 g, 0.29 mmol) were used as in general procedure VI. Water (25 mL) was added to the reaction mixture and the resulting suspension was filtered. The solids were washed with ether to afford 517 as an off-white solid (0.129 g, 81%). $^1$H NMR (DMSO-d$_6$, 300 MHz) δ 0.1 (m, 2H), 0.36 (m, 2H), 0.82 (m, 1H), 2.2 (s, 3H), 2.64 (t, 2H), 4.86 (s, 2H), 7.25 (d, 1H), 7.46-7.74 (m, 9H), 9.44 (s, 1H); MS (ES$^+$) m/z 549 (M+H)$^+$, MS (ES$^-$) m/z 547 (M–H)$^-$.

Example 212

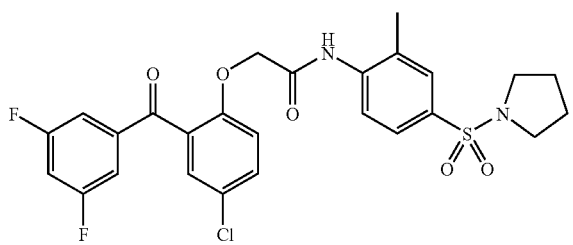

520

Acid 49 was converted to the acid chloride using the general procedure V. Aniline 318 (0.07 g, 0.29 mmol), acetone (4 mL), sodium bicarbonate (0.22 g, 2.6 mmol), and the acid chloride (0.1 g, 0.29 mmol) were used as in general procedure VI. Water (25 mL) was added to the reaction mixture and the resulting suspension was filtered. The solids were washed with ether to afford 520 as an off-white solid (0.126 g, 79%). $^1$H NMR (DMSO-d$_6$, 300 MHz) δ 1.66 (m, 4H), 2.26 (s, 3H), 3.35 (m, 4H), 4.87 (s, 2H), 7.25 (d, 1H), 7.47-7.7 (m, 7H), 7.82 (d, 1H), 9.43 (s, 1H); MS (ES$^+$) m/z 549 (M+H)$^+$, MS (ES$^-$) m/z 547 (M–H)$^-$.

Example 213

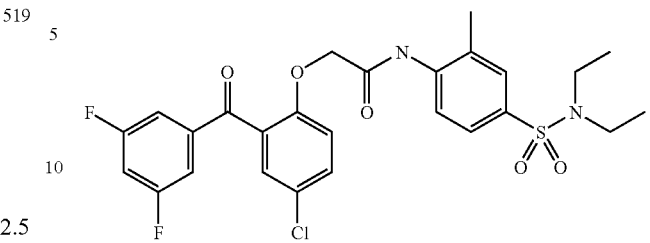

521

Step A:

522

A mixture of 464 (1.10 g, 4.4 mmol), diethylamine (0.68 mL, 6.6 mmol), and pyridine (0.39 mL, 4.8 mmol) in 50 mL of methylene chloride was stirred at rt for 5 d. The reaction mixture was then diluted with 100 mL of CH$_2$Cl$_2$ and washed with two 50-mL portions of water. The organic layer was washed with brine, dried over MgSO$_4$, and filtered to give 1.2 g of an orange oil. Crystallization from EtOAc/hexane gave 522 as orange crystals (0.446 g, 36%): MS (ES+) m/z 285 (M+H); $^1$H NMR (CDCl$_3$, 400 MHz) δ 8.08 (d, 1H), 7.61-7.58 (m, 2H), 3.21 (q, 4H), 2.29 (s, 3H), 2.24 (s, 3H), 1.13 (t, 6H).

Step B:

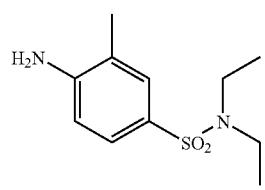

523

A mixture of 522 (0.341 g, 1.2 mmol) and 1.5 M HCl (2.5 mL) in 12 mL of ethanol was heated to 80° C. for 18 h. The reaction mixture was then poured into 50 mL of saturated NaHCO$_3$ (aq) and extracted with two 30-mL portions of CH$_2$Cl$_2$. The combined organic layers were dried over MgSO$_4$, filtered and concentrated in vacuo to give 523 as a yellow solid (0.285 g, 98%): MS (ES+) m/z 243 (M+H); $^1$H NMR (CDCl$_3$, 400 MHz) δ 7.48-7.45 (m, 2H), 6.66 (d, 1H), 4.02 (br s, 2H), 3.19 (q, 4H), 2.18 (s, 3H), 1.12 (t, 6H).

Step C:

Acid 49 was converted to the acid chloride using the general procedure V. Aniline 523 (0.07 g, 0.29 mmol), acetone (4 mL), sodium bicarbonate (0.22 g, 2.6 mmol), and the acid chloride (0.1 g, 0.29 mmol) were used as in general procedure VI. Water (25 mL) was added to the reaction mixture and the resulting suspension was filtered. The solids were washed with ether to afford 521 as an off-white solid

Example 214

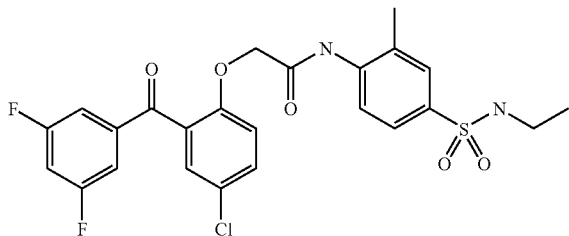

524

Acid 49 was converted to the acid chloride using the general procedure V. Aniline 312 (0.062 g, 0.29 mmol), acetone (4 mL), sodium bicarbonate (0.22 g, 2.6 mmol), and the acid chloride (0.1 g, 0.29 mmol) were used as in general procedure VI. Water (25 mL) was added to the reaction mixture and the resulting suspension was filtered. The solid was washed with ether to afford 524 as an off-white solid (0.109 g, 70%). $^1$H NMR (DMSO-d$_6$, 400 MHz) δ 0.99 (t, 3H), 2.23 (s, 3H), 2.77 (m, 2H), 4.86 (s, 2H), 7.25 (d, 1H), 7.46-7.75 (m, 9H), 9.45 (s, 1H); MS (ES$^+$) m/z 523 (M+H)$^+$, MS (ES$^-$) m/z 521 (M−H)$^-$.

Example 215

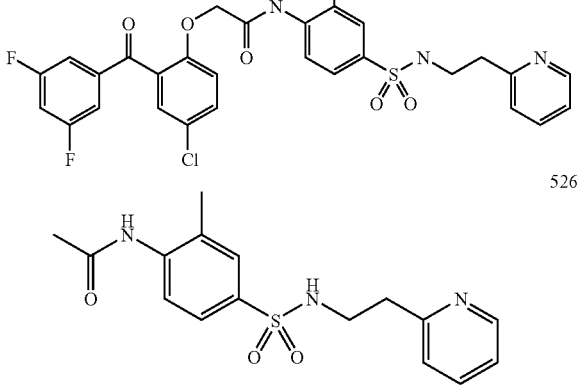

525

526

Step A:

Sulfonyl chloride 464 (0.27 g, 1.09 mmol) was added portionwise to a large test tube with a stir bar, pyridine (5 mL), and 2-(2-aminoethyl)pyridine (Aldrich, 0.28 g, 2.3 mmol). The mixture was allowed to stir for 2 d. Water was added and the mixture was extracted with dichloromethane, concentrated, and purified by flash chromatography using 95:5 CH$_2$Cl$_2$:CH$_3$OH as eluant to afford 526 (0.70 g, 51%). $^1$H NMR (DMSO-d$_6$, 400 MHz) δ 2.05 (s, 3H), 2.22 (s, 3H), 2.77 (t, 2H), 3.03 (t, 2H), 7.13 (dd, 2H), 7.48-7.71 (m, 5H), 8.38 (dd, 1H), 9.37 (s, 1H).

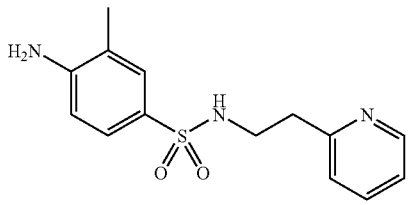

527

Step B:

Sulfonamide 526 (0.7 g, 2.09 mmol), 1.5 N HCl (10 mL), and ethanol (10 mL) were used according to general procedure XVII to afford 527 (0.11 g, 18%). The crude product was used without further purification.

Step C:

Acid 49 was converted to the acid chloride using the general procedure V. Aniline 527 (0.05 g, 0.17 mmol), the acid chloride (0.19 mmol), acetone (5 mL), sodium bicarbonate (0.3 g, 3.57 mmol), and water (4 drops) were used as in general procedure VI. Ice (5 mL) was added to the reaction mixture and the resulting suspension was filtered. The solids were purified by flash chromatography using 95:5 CH$_2$Cl$_2$:CH$_3$OH as eluant to afford 525 (0.03 g, 33%). $^1$H NMR (DMSO-d$_6$, 400 MHz) δ 2.18 (s, 3H), 2.81 (t, 2H), 3.08 (m, 2H), 4.83 (s, 2H), 7.16-7.23 (m, 3H), 7.43-7.7 (m, 10H), 8.42 (m, 1H), 9.41 (s, 1H); MS (ES$^+$) m/z 600 (M+H)$^+$, MS (ES$^-$) m/z 598 (M−H)$^-$.

Example 216

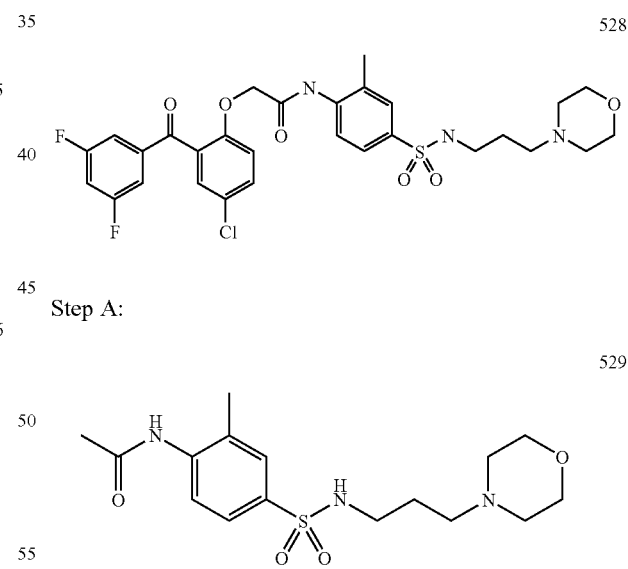

528

529

Step A:

Sulfonyl chloride 464 (0.27 g, 1.09 mmol) was added portionwise to a large test tube with a stir bar, pyridine (5 mL), and aminopropylmorpholine (Aldrich, 0.33 g, 2.3 mmol). The mixture was allowed to stir for 2 d, followed by the addition of water and extraction with dichloromethane. The organic layer was concentrated, and the product purified by flash chromatography using 95:5 CH$_2$Cl$_2$:CH$_3$OH as eluant to afford 529 (0.7 g, 49%). $^1$H NMR (DMSO-d$_6$, 400 MHz) δ 1.44 (m, 2H), 2.05 (s, 3H), 2.12 (m, 4H), 2.23 (s, 2H), 2.7 (m, 2H), 3.45 (m, 4H), 7.41 (t, 1H), 7.5 (dd, 1H), 7.55 (d, 1H), 7.71 (d, 1H), 9.38 (s, 1H).

Step B:

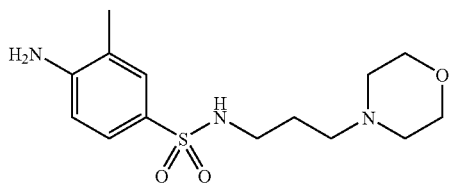
530

Sulfonamide 529 (0.7 g, 1.96 mmol), 1.5 N HCl (10 mL), and ethanol (10 mL) were used according to general procedure XVII to afford 530 (0.15 g, 24%). The crude product was used without further purification.

Step C:

Acid 49 was converted to the acid chloride using the general procedure V. Aniline 530 (0.05 g, 0.16 mmol), the acid chloride (0.19 mmol), acetone (5 mL), sodium bicarbonate (0.3 g, 3.57 mmol), and water (4 drops) were used as in general procedure VI. Ice (5 mL) was added to the reaction mixture and the resulting suspension was filtered. The product was purified by flash chromatography using 95:5 $CH_2Cl_2$:$CH_3OH$ as eluant to afford 528 (0.01 g, 6%). $^1$H NMR (DMSO-$d_6$, 400 MHz) δ 0.8 (m, 1H), 1.18 (s, 1H), 1.43 (m, 2H), 2.15 (m, 7H), 2.7 (m, 2H), 3.44 (m, 4H), 4.78 (s, 2H), 7.18 (d, 1H), 7.39-7.67 (m, 9H), 9.38 (s, 1H); LC-MS (ES$^+$) m/z 623 (M+H)$^+$, MS (ES$^-$) m/z 621 (M−H)$^-$.

Example 217

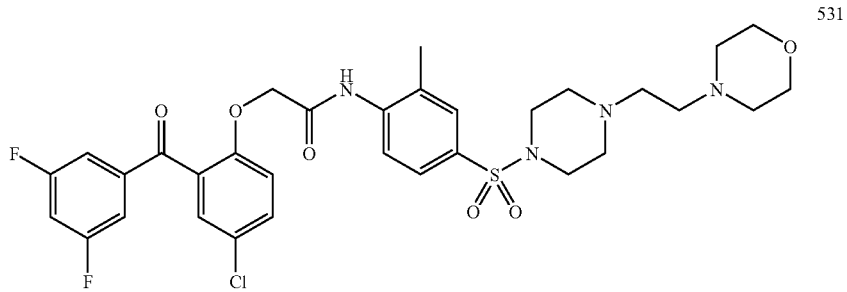

Step A:

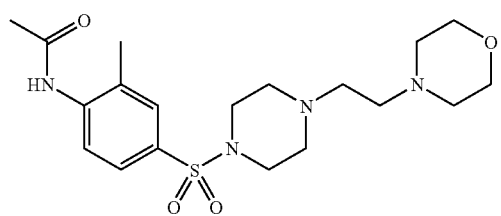
532

Sulfonyl chloride 464 (0.27 g, 1.09 mmol) was added portionwise to a large test tube with a stir bar, pyridine (5 mL), and 1-(2-morpholinoethyl)piperazine (EMKA, 0.46 g, 2.3 mmol). The mixture was allowed to stir for 2, followed by the addition of and extraction with dichloromethane. The organic layer was concentrated, and the product was purified by flash chromatography using 95:5 $CH_2Cl_2$:$CH_3OH$ as eluant to afford 532 (0.3 g, 19%). $^1$H NMR (DMSO-$d_6$, 400 MHz) δ 2.07 (s, 3H), 2.27 (m, 9H), 2.38 (m, 2H), 2.45 (m, 4H), 2.85 (m, 2H), 3.3 (m, 2H), 3.5 (m, 4H), 7.46 (m, 2H), 7.82 (d, 1H), 9.4 (s, 1H).

Step B:

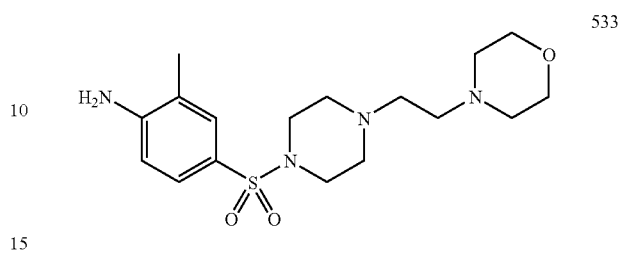

Sulfonamide 532 (0.3 g, 0.73 mmol), 1.5 N HCl (10 mL), and ethanol (10 mL) were used according to general procedure XVII to afford 533 (0.08 g, 30%). The crude product was used without further purification.

Step C:

Acid 49 was converted to the acid chloride using the general procedure V. Aniline 533 (0.05 g, 0.14 mmol), the acid chloride (0.19 mmol), acetone (5 mL), sodium bicarbonate (0.3 g, 3.57 mmol), and water (4 drops) were used as in general procedure VI. Ice (5 mL) was added to the reaction mixture and the resulting suspension was filtered. The product was purified by flash chromatography using 95:5 $CH_2Cl_2$:$CH_3OH$ as eluant to afford 531 (0.01 g, 7%). $^1$H NMR (CDCl$_3$, 400 MHz) δ 2.29 (s, 3H), 2.38-2.54 (m, 12H), 2.97 (bs, 4H), 3.63 (m, 4H), 4.69 (s, 2H), 7-7.1 (m, 2H), 7.29-7.35 (m, 3H), 7.51-7.57 (m, 3H), 8.1 (d, 1H), 8.66 (s, 1H).

Example 218

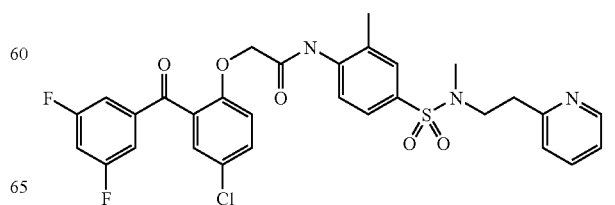

Step A:

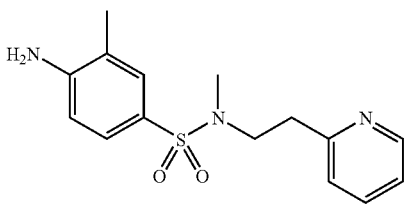
535

Sulfonyl chloride 464 (3 mmol), pyridine (5 mL), and 2-(2-methylaminoethyl)pyridine (Aldrich, 0.41 g, 3.01 mmol) were used as in general procedure XVI. The mixture was allowed to stir for 2 d. Water was added and the mixture was extracted with dichloromethane, and the organic layer was concentrated in vacuo. The resulting products were then dissolved in ethanol (10mL) and 1.5 N HCl (10 mL) and heated to 60° C. overnight. The resulting solution was concentrated in vacuo and the product was purified by flash chromatography using 95:5 $CH_2Cl_2$:$CH_3OH$ as eluant to afford 535 (0.28 g, 30%).

Step B:

Acid 49 was converted to the acid chloride using the general procedure V. Aniline 535 (0.05 g, 0.16 mmol), the acid chloride (0.15 mmol), acetone (5 mL), sodium bicarbonate (0.3 g, 3.57 mmol), and water (4 drops) were used as in general procedure VI. Ice (5 mL) was added to the reaction mixture and the resulting suspension was filtered. The solid was then purified by flash chromatography using 95:5 $CH_2Cl_2$:$CH_3OH$ as eluant to afford 534 (0.04 g, 40%). $^1$H NMR (DMSO-$d_6$, 400 MHz) δ 2.21 (s, 3H), 2.67 (s, 3H), 2.93 (m, 2H), 4.08 (m, 2H), 4.83 (s, 2H), 7.18-7.27 (m, 3H), 7.43-7.77 (m, 9H), 8.46 (m, 1H), 9.41 (s, 1H); LC-MS (ES$^+$) m/z 614 (M+H)$^+$, LC-MS (ES$^-$) m/z 612 (M-H)$^-$.

Example 219

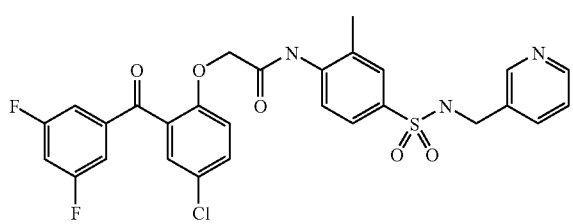
536

Step A:

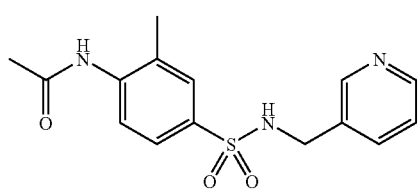
537

Sulfonyl chloride 464 (3 mmol), pyridine (5 mL), and 3-picolylamine (Aldrich, 0.25 g, 2.3 mmol) were used as in general procedure XVI. The mixture was allowed to stir for 2 d followed by the addition of water. The reaction mixture was extracted with dichloromethane, and the organic layer was separated and concentrated in vacuo. The product was purified by flash chromatography using 95:5 $CH_2Cl_2$:$CH_3OH$ as eluant to afford 537 (0.9 g, 67%). $^1$H NMR (DMSO-$d_6$, 400 MHz) δ 2.06 (s, 3H), 2.22 (s, 3H), 3.96 (d, 2H), 7.24 (dd, 1H), 7.54 (m, 3H), 7.71 (d, 1H), 8.06 (t, 1H), 8.36 (d, 2H), 9.37 (s, 1H).

Step B:

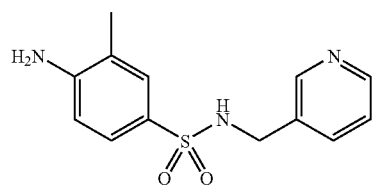
538

Sulfonamide 537 (0.9 g, 2.81 mmol), 1.5 N HCl (10 mL), and ethanol (10 mL) were used according to general procedure XVII to afford 538 (0.25 g, 32%). The crude product was used without further purification.

Step C:

Acid 49 was converted to the acid chloride using the general procedure V. Aniline 538 (0.05 g, 0.18 mmol), the acid chloride (0.15 mmol), acetone (5 mL), sodium bicarbonate (0.3 g, 3.57 mmol), and water (4 drops) as in general procedure VI. Ice (5 mL) was added to the reaction mixture and the resulting suspension was filtered. The product was purified by flash chromatography using 95:5 $CH_2Cl_2$:$CH_3OH$ as eluant to afford 536 (0.03 g, 27%). $^1$H NMR (DMSO-$d_6$, 300 MHz) δ 2.18 (s, 3H), 4 (d, 2H), 4.83 (s, 2H), 7.22 (d, 1H), 7.28 (dd, 1H), 7.45 (m, 2H), 7.51 (d, 1H), 7.57-7.72 (m, 6H), 8.13 (t, 1H), 8.41 (m, 2H), 9.42 (s, 1H); LC-MS (ES$^+$) m/z 586 (M+H)$^+$, LC-MS (ES$^-$) m/z 584 (M-H)$^-$.

Example 220

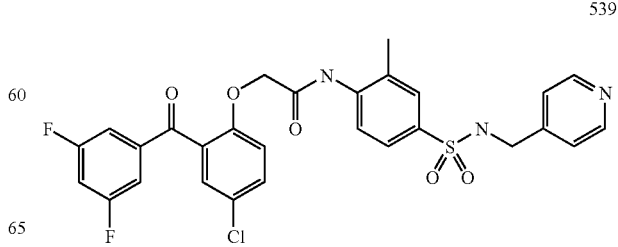
539

Step A:

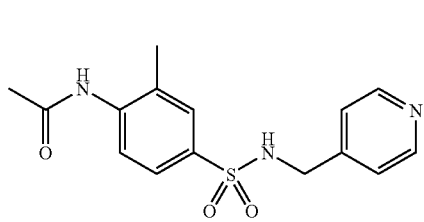

540

Sulfonyl chloride 464 (1.1 mmol), pyridine (5 mL), and 4-picolylamine (Aldrich, 0.25 g, 2.3 mmol) were used as in general procedure XVI. The mixture was allowed to stir for 2 d followed by the addition of water. The mixture was extracted with dichloromethane, the organic layer was separated and concentrated in vacuo. The product was purified by flash chromatography using 95:5 $CH_2Cl_2$:$CH_3OH$ as eluant to afford 540 (0.5 g, 37%). $^1$H NMR (DMSO-$d_6$, 400 MHz) δ 2.06 (s, 3H), 2.21 (s, 3H), 3.95 (d, 2H), 7.21 (d, 2H), 7.52 (m, 2H), 7.71 (m, 1H), 8.14 (t, 1H), 8.41 (dd, 2H), 9.38 (s, 1H).

Step B:

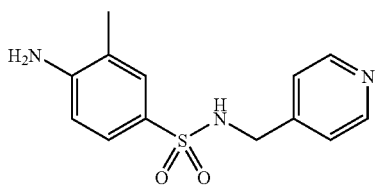

541

Sulfonamide 540 (0.5 g, 1.56 mmol), 1.5 N HCl (10 mL), and ethanol (10 mL) were used according to general procedure XVII to afford 541 (0.12 g, 28%). The crude product was used without further purification.

Step C:

Acid 49 was converted to the acid chloride using the general procedure V. Aniline 541 (0.05 g, 0.18 mmol), the acid chloride (0.15 mmol), acetone (5 mL), sodium bicarbonate (0.3 g, 3.57 mmol), and water (4 drops) as in general procedure VI. Ice (5 mL) was added to the reaction mixture and the resulting suspension was filtered. The product was purified by flash chromatography and TLC prep plate using 95:5 $CH_2Cl_2$:$CH_3OH$ as eluant to afford 539 (0.02 g, 19%). $^1$H NMR (DMSO-$d_6$, 400 MHz) δ 2.18 (s, 3H), 4.01 (m, 2H), 4.83 (s, 2H), 7.21-7.26 (m, 3H), 7.43-7.72 (m, 8H), 8.2 (t, 1H), 8.45 (m, 2H), 9.42 (s, 1H); LC-MS (ES$^+$) m/z 586 (M+H)$^+$, LC-MS (ES$^-$) m/z 584 (M-H)$^-$.

Example 221

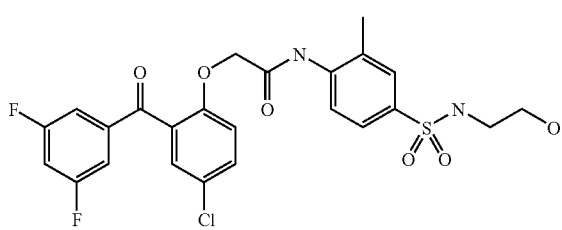

542

Step A:

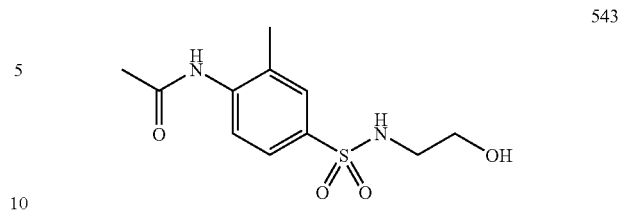

543

Sulfonyl chloride 464 (1.1 mmol), pyridine (5 mL), and ethanolamine (Aldrich, 0.14 g, 2.3 mmol) were used as in general procedure XVI. The mixture was allowed to stir for 2 d followed by the addition of water. The mixture was extracted with dichloromethane, the organic layer was separated and concentrated in vacuo. The product was purified by flash chromatography using 95:5 $CH_2Cl_2$:$CH_3OH$ as eluant to afford 543 (0.46 g, 37%). $^1$H NMR-(DMSO-$d_6$, 400 MHz) δ 2.05 (s, 3H), 2.23 (s, 3H), 2.7 (m, 2H), 3.29 (m, 2H), 4.62 (t, 1H), 7.41 (t, 1H), 7.51 (dd, 1H), 7.56 (d, 1H), 7.7 (d, 1H), 9.38 (s, 1H).

Step B;

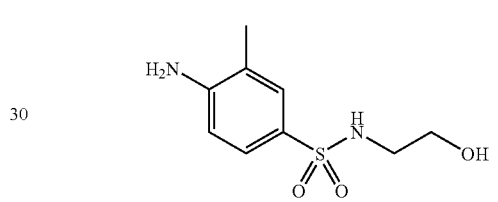

544

Sulfonamide 549 (0.46 g, 1.68 mmol), 1.5 N HCl (10 mL), and ethanol (10 mL) were used according to general procedure XVII to afford 544 (0.12 g, 31%). The crude product was used without further purification.

Step C:

Acid 49 was converted to the acid chloride using the general procedure V. Aniline 544 (0.05 g, 0.22 mmol), the acid chloride (0.15 mmol), acetone (5 mL), sodium bicarbonate (0.3 g, 3.57 mmol), and water (4 drops) as in general procedure VI. Ice (5 mL) was added to the reaction mixture and the resulting suspension was filtered. The product was purified by flash chromatography and TLC prep plate using 95:5 $CH_2Cl_2$:$CH_3OH$ as eluant to afford 542 (0.02 g, 17%). $^1$H NMR (DMSO-$d_6$, 400 MHz) δ 2.2 (s, 3H), 2.75 (q, 2H), 3.34 (m, 2H), 4.66 (t, 1H), 4.83 (s, 2H), 7.22 (d, 1H), 7.42-7.72 (m, 9H), 9.42 (s, 1H); LC-MS (ES$^+$) m/z 539 (M+H)$^+$, LC-MS (ES$^-$) m/z 537 (M-H)$^-$.

Example 222

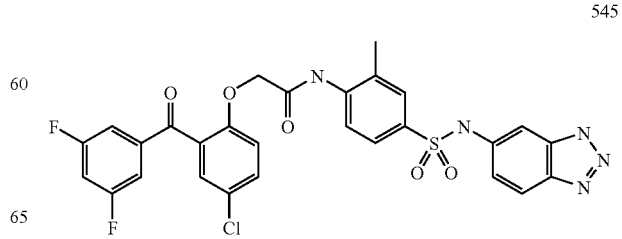

545

Step A:

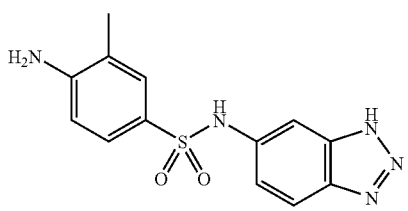

546

Sulfonyl chloride 464 (3 mmol), pyridine (5 mL), and 5-aminobenzotriazole (Lancaster, 0.41 g, 3.06 mmol) were used as in general procedure XVI. The mixture was allowed to stir for 2 days. Water was added and the mixture was extracted with dichloromethane, the organics were separated, concentrated in vacuo. The resulting products were then dissolved in ethanol (10 mL) and 1.5 N HCl (10 mL) and heated, with stirring, to 60° C. overnight. The resulting solution was concentrated in vacuo and purified by flash chromatography using 95:5 $CH_2Cl_2$:$CH_3OH$ as eluant to afford 546 (0.45 g, 48%). The crude product was used without further purification.

Step B:

Acid 49 was converted to the acid chloride using the general procedure V. Aniline 546 (0.05 g, 0.16 μmmol), the acid chloride (0.15 mmol), acetone (5 mL), sodium bicarbonate (0.3 g, 3.57 mmol), and water (4 drops) as in general procedure VI. Ice (5 mL) was added to the reaction mixture and the resulting suspension was filtered. The solids were then purified by flash chromatography and TLC prep plate using 95:5 $CH_2Cl_2$:$CH_3OH$ as eluant to afford 545 (0.01 g, 10%). $^1$H NMR (DMSO-$d_6$, 400 MHz) δ 2.13 (s, 3H), 4.78 (s, 2H), 7.16 (m, 2H), 7.39-7.85 (m, 11H), 9.34 (s, 1H) 10.5 (bs, 1H); LC-MS (ES$^+$) m/z 586 (M+H)$^+$, LC-MS (ES$^-$) m/z 584 (M−H)$^-$.

Example 223

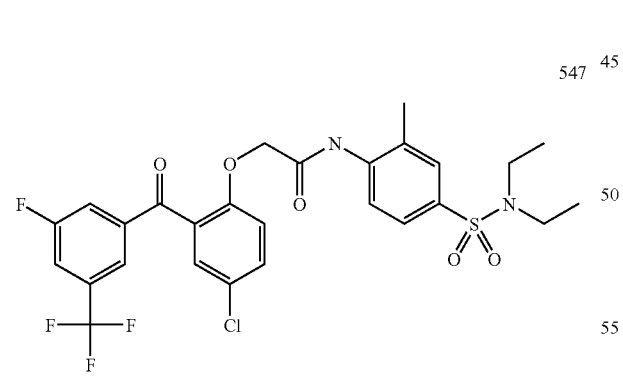

547

Acid 71 was converted to the acid chloride using the general procedure V. Aniline 523 (0.1 g, 0.41 mmol), the acid chloride (0.16 g, 0.4 mmol), acetone (4 mL), and sodium bicarbonate (0.22 g, 2.6 mmol) were used as in general procedure VI. After 2 d, the resulting solutions were concentrated, re-dissolved in dichloromethane and purified by flash chromatography using 98:2 $CH_2Cl_2$:$CH_3OH$ as eluant to afford 547 (0.085 g, 34%). $^1$H NMR (DMSO-$d_6$, 300 MHz) δ 1.02 (t, 6H), 2.18 (s, 3H), 3.12 (m, 4H), 4.81 (s, 2H), 7.22 (d, 1H), 7.54-7.71 (m, 5H), 7.87 (d, 2H), 7.98 (d, 1H), 9.38 (s, 1H); LC-MS (ES$^+$) m/z 601 (M+H)$^+$, LC-MS (ES$^-$) m/z 599 (M−H)$^-$.

Example 224

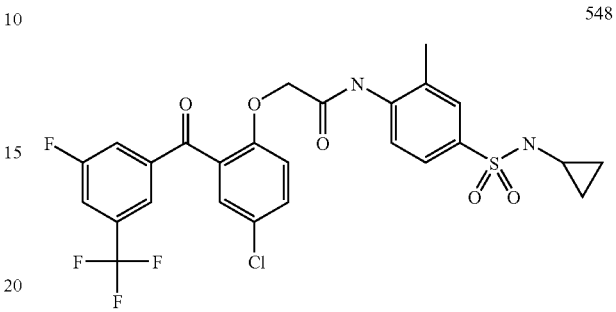

548

Acid 71 was converted to the acid chloride using the general procedure V. Aniline 315 (0.1 g, 0.44 mmol), acetone (4 mL), sodium bicarbonate (0.22 g, 2.6 mmol), and the acid chloride (0.16 g, 0.4 mmol) were used as in general procedure VI. After 2 d, the resulting solutions were concentrated, re-dissolved in dichloromethane and purified by flash chromatography and TLC prep plate using 98:2 $CH_2Cl_2$:$CH_3OH$ as eluant to afford 548 (0.074 g, 29%). $^1$H NMR (DMSO-$d_6$, 300 MHz) δ 0.3-0.5 (m, 4H), 2.04 (m, 1H), 2.18 (s, 3H), 4.81 (s, 2H), 7.24 (d, 1H), 7.54-7.88 (m, 8H), 8 (d, 1H), 9.41 (s, 1H); LC-MS (ES$^+$) m/z 585 (M+H)$^+$, LC-MS (ES$^-$) m/z 583 (M−H)$^-$.

Example 225

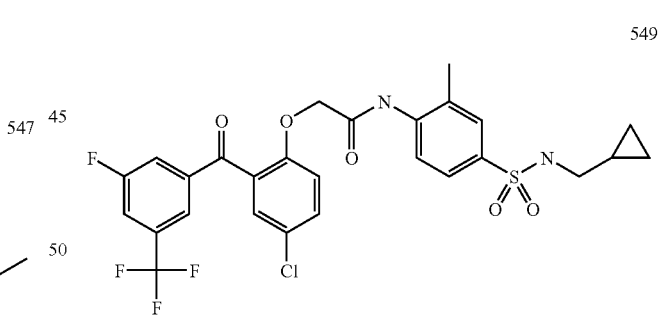

549

Acid 71 was converted to the acid chloride using the general procedure V. Aniline 518 (0.1 g, 0.42 mmol), acetone (4 mL), sodium bicarbonate (0.22 g, 2.6 mmol), and the acid chloride (0.16 g, 0.4 mmol) were used as in general procedure VI. After 2 d, the resulting solutions were concentrated, re-dissolved in dichloromethane and purified by flash chromatography using 98:2 $CH_2Cl_2$:$CH_3OH$ as eluant to afford 549 (0.095 g, 38%). $^1$H NMR (DMSO-$d_6$, 300 MHz) δ 0.05 (m, 2H), 0.33 (m, 2H), 0.77 (m, 1H), 2.16 (s, 3H), 2.6 (d, 2H), 4.8 (s, 2H), 7.22 (d, 1H), 7.54-7.67 (m, 6H), 7.86 (d, 2H), 8 (d, 1H), 9.4 (s, 1H); LC-MS (ES$^+$) m/z 599 (M+H)$^+$, LC-MS (ES$^-$) m/z 597 (M−H)$^-$.

Example 225

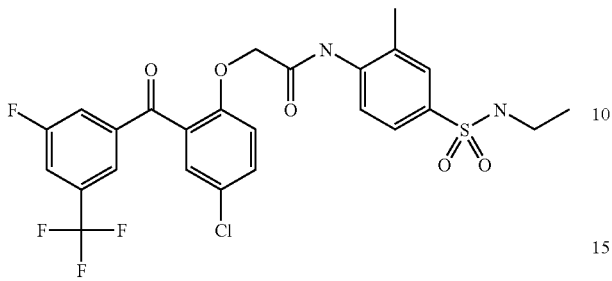

550

Acid 71 was converted to the acid chloride using the general procedure V. Aniline 312 (0.1 g, 0.42 mmol), acetone (4 mL), sodium bicarbonate (0.22 g, 2.6 mmol), and the acid chloride (0.16 g, 0.4 mmol) were used as in general procedure VI. After 2 d, the resulting solutions were concentrated, re-dissolved in dichloromethane and purified by flash chromatography using 98:2 $CH_2Cl_2$:$CH_3OH$ as eluant to afford 550 (0.125 g, 47%). $^1$H NMR (DMSO-$d_6$, 300 MHz) δ 0.94 (t, 3H), 2.17 (s, 3H), 2.72 (m, 2H), 4.81 (s, 2H), 7.22 (d, 1H), 7.43 (t, 1H), 7.53-7.68 (m, 5H), 7.87 (d, 2H), 8 (d, 1H), 9.4 (s, 1H); LC-MS (ES$^+$) m/z 573 (M+H)$^+$, LC-MS (ES$^-$) m/z 571 (M−H)$^-$.

Example 226

551

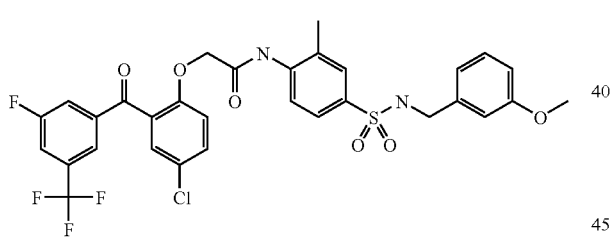

Step A:

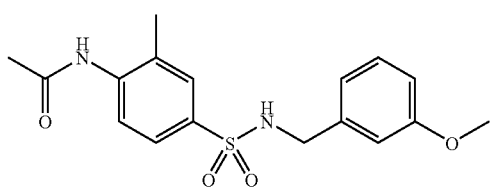

552

Sulfonyl chloride 464 (3 mmol), pyridine (5 mL), and 3-methoxybenzylamine (Aldrich, 0.41 g, 3.01 mmol) were used as in general procedure XVI. The mixture was allowed to stir for 2 d. The resulting mixture was concentrated in vacuo. Water was added and the mixture was filtered to afford 552 (0.24 g, 69%). $^1$H NMR (DMSO-$d_6$, 400 MHz) δ 2.06 (s, 3H), 2.21 (s, 3H), 3.63 (s, 3H), 3.89 (d, 2H), 6.73 (m, 3H), 7.13 (t, 1H), 7.53 (m, 2H), 7.7 (d, 1H), 7.96 (t, 1H), 9.36 (s, 1H); LC-MS (ES$^+$) m/z 349 (M+H)$^+$, LC-M (ES$^-$) m/z 347 (M−H)$^-$.

Step B:

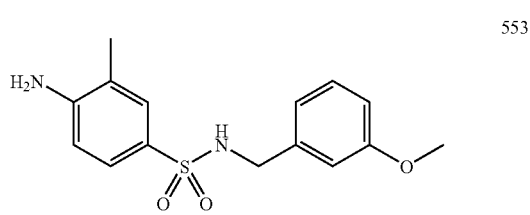

553

The sulfonamide 552 was dissolved in ethanol (10 mL) and 1.5 N HCl (10 mL). The resulting mixture was heated to 60° C. overnight. The resulting solution was concentrated in vacuo to afford 553. The product was used without further purification.

Step C:

Acid 71 was converted to the acid chloride using the general procedure V. Aniline 553 (0.1 g, 0.33 mmol), acetone (4 mL), sodium bicarbonate (0.22 g, 2.6 mmol), and the acid chloride (0.16 g, 0.40 mmol) were used as in general procedure VI. After 2 d, the resulting solutions were concentrated, re-dissolved in dichloromethane and purified by flash chromatography using 98:2 $CH_2Cl_2$:$CH_3OH$ as eluant to afford 551 (0.212 g, 98%). $^1$H NMR (DMSO-$d_6$, 300 MHz) δ 2.14 (s, 3H), 3.66 (s, 3H), 3.92 (d, 2H), 4.81 (s, 2H), 6.77 (t, 3H), 7.13-7.24 (m, 2H), 7.55 (m, 3H), 7.66 (dd, 2H), 7.87 (m, 2H), 8.02 (t, 2H), 9.4 (s, 1H); LC-MS (ES$^+$) m/z 665 (M+H)$^+$, LC-MS (ES$^-$) m/z 663 (M−H)$^-$.

Example 227

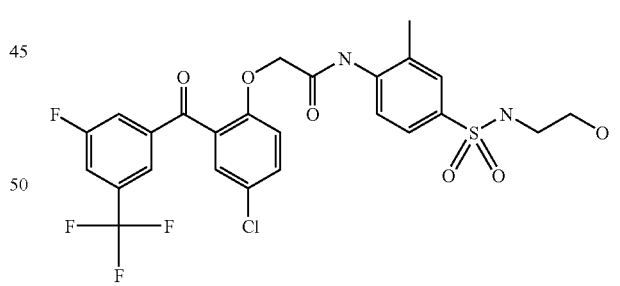

554

Acid 71 was converted to the acid chloride using the general procedure V. Aniline 544 (0.1 g, 0.43 mmol), acetone (4 mL), sodium bicarbonate (0.22 g, 2.6 mmol), and the acid chloride (0.16 g, 0.40 mmol) were used as in general procedure VI. After 2 d, the resulting solutions were concentrated, re-dissolved in dichloromethane and purified by flash chromatography using 98:2 $CH_2Cl_2$:$CH_3OH$ as eluant to afford 554 (0.073 g, 29%). $^1$H NMR (DMSO-$d_6$; 300 MHz) δ 2.17 (s, 3H), 2.74 (m, 2H), 3.35 (m, 2H), 4.65 (t, 1H), 4.81 (s, 2H), 7.22 (d, 1H), 7.45-7.68 (m, 6H), 7.87 (d, 2H), 8 (d, 1H), 9.41 (s, 1H); LC-MS (ES$^+$) m/z 589 (M+H)$^+$, LC-MS (ES$^-$) m/z 587 (M−H)$^-$.

Example 228

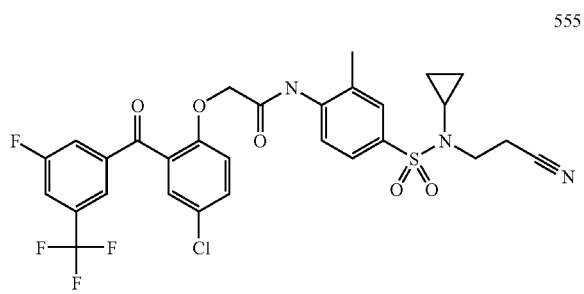
555

Step A:

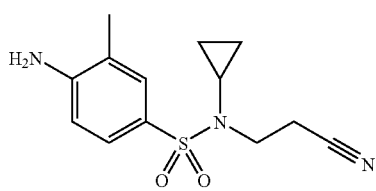
556

Sulfonyl chloride 464 (3 mmol), pyridine (5 mL), and 3-(cyclopropylamino)propionitrile (Trans World Chemical, 0.33 g, 3 mmol) were used as in general procedure XXVI. The mixture was allowed to stir for 2 d, followed by the addition of water and extraction with dichloromethane. The organic layer was separated and concentrated in vacuo. The resulting products were then dissolved in ethanol (10 mL) and 1.5 N HCl (10 mL) and heated to 60° C. overnight. The resulting solution was concentrated in vacuo and the product purified by flash chromatography using 95:5 $CH_2Cl_2$: $CH_3OH$ as eluant to afford 556 (0.22 g, 26%).

Step B:

Acid 71 was converted to the acid chloride using the general procedure V. Aniline 556 (0.1 g, 0.36 mmol), acetone (4 mL), sodium bicarbonate (0.22 g, 2.6 mmol), and the acid chloride (0.16 g, 0.40 mmol) were used as in general procedure VI. After 2 d, the resulting solution was concentrated, re-dissolved in dichloromethane and purified by flash chromatography using 98:2 $CH_2Cl_2$:$CH_3OH$ as eluant to afford 556 (0.113 g, 49%). $^1$H NMR (DMSO-$d_6$, 300 MHz) δ 0.63-0.82 (m, 4H), 2 (m, 1H), 2.21 (s, 3H), 2.78 (t, 2H), 3.36 (m, 2H), 4.82 (s, 2H), 7.22 (d, 1H), 7.54 (d, 1H), 7.63 (m, 3H), 7.79 (d, 1H), 7.87 (d, 2H), 8 (d, 1H), 9.42 (s, 1H); LC-MS (ES$^+$) m/z 638 (M+H)$^+$, LC-MS (ES$^+$) m/z 638 (M−H)$^−$

Example 229

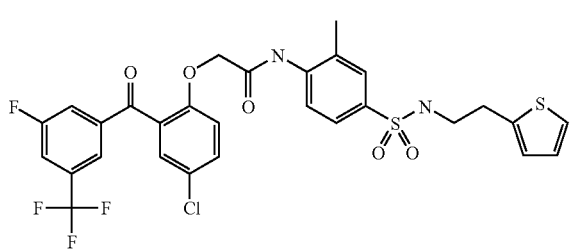
557

Step A:

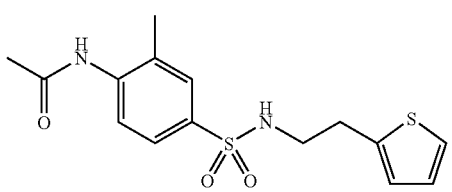
558

Sulfonyl chloride 464 (3 mmol), pyridine (5 mL), and thiophene-2-ethylamine (Aldrich, 0.41 g, 3.01 mmol) were used as in general procedure XVI. The mixture was allowed to stir at rt for 2 d, followed by concentration in vacuo. Water was added to the resulting residue and the mixture was filtered to afford the protected sulfonamide 558 (0.12 g, 35%). $^1$H NMR (DMSO-$d_6$, 400 MHz) δ 2.05 (s, 3H), 2.23 (s, 3H), 2.81-2.93 (m, 4H), 6.79 (d, 1H), 6.87 (dd, 1H), 7.26 (dd, 1H), 7.51 (dd, 1H), 7.55 (s, 1H), 7.61 (t, 1H), 7.71 (d, 1H), 9.37 (s, 1H); LC-MS (ES$^+$) m/z 339 (M+H)$^+$, LC-MS (ES$^−$) m/z 337 (M−H)$^−$.

Step B:

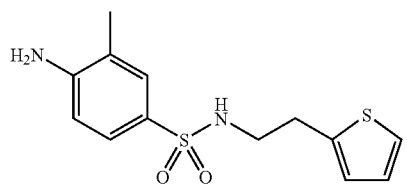
559

Sulfonamide 558 was dissolved in ethanol (10 mL) and 1.5 N HCl (10 mL) and heated to 60° C. overnight. The resulting solutions were concentrated in vacuo to afford 559. The resulting product was used without further purification.

Step C:

Acid 71 was converted to the acid chloride using the general procedure V. Aniline 559 (0.1 g, 0.34 mmol), acetone (4 mL), sodium bicarbonate (0.22 g, 2.6 mmol), and the acid chloride (0.16 g, 0.40 mmol) were used as in general procedure VI. After 2 d, the resulting solutions were concentrated, re-dissolved in dichloromethane and purified by flash chromatography using 98:2 $CH_2Cl_2$:$CH_3OH$ as eluant to afford 557 (0.206 g, 93%). $^1$H NMR (DMSO-$d_6$, 300 MHz) δ 2.16 (s, 3H), 2.87-2.95 (m, 4H), 4.8 (s, 2H), 6.83 (d, 1H), 6.91 (t, 1H), 7.22 (d, 1H), 7.3 (d, 1H), 7.54-7.68 (m, 6H), 7.87 (d, 2H), 8 (d, 1H), 9.4 (s, 1H); LC-MS (ES$^+$) m/z 654 (M+H)$^+$, LC-MS (ES$^−$) m/z 653 (M−H)$^−$.

Example 230

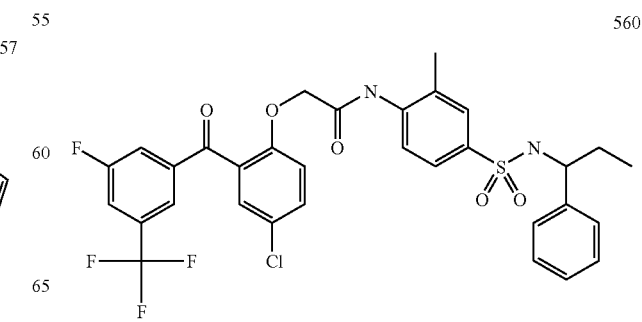
560

Step A:

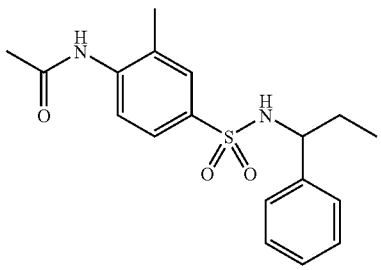

561

Sulfonyl chloride 464 (3 mmol), pyridine (5 mL), and DL-1-phenylpropylamine (Norse, 0.41 g, 3.01 mmol) were used as in general procedure XXVI. The mixture was allowed to stir at rt for 2 d, followed by concentration in vacuo. Water was added to the resulting residue and the mixture was filtered to afford the protected sulfonamide 561 (0.19 g, 55%). $^1$H NMR (DMSO-d$_6$, 400 MHz) δ 0.61 (t, 3H), 1.5 (m, 2H), 2.03 (s, 3H), 2.08 (s, 3H), 4.03 (m, 1H), 7.03-7.12 (m, 5H), 7.26 (d, 1H), 7.35 (dd, 1H), 7.56 (d, 1H), 8 (d, 1H), 9.24 (s, 1H); LC-MS (ES$^+$) m/z 347 (M+H)$^+$, LC-MS (ES$^-$) m/z 345 (M-H)$^-$.

Step B:

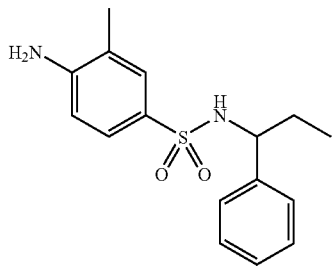

562

Sulfonamide 561 was dissolved in ethanol (10 mL) and 1.5 N HCl (10 mL) and heated to 60° C. overnight. The resulting solution was concentrated in vacuo to afford 562. The resulting product was used without further purification.

Step C:

Acid 71 was converted to the acid chloride using the general procedure V. Aniline 562 (0.1 g, 0.33 μmmol), acetone (4 mL), sodium bicarbonate (0.22 g, 2.6 mmol), and the acid chloride (0.16 g, 0.40 mmol) were used as in general procedure VI. After 2 d, the resulting solution was concentrated, re-dissolved in dichloromethane and purified by flash chromatography using 98:2 CH$_2$Cl$_2$:CH$_3$OH as eluant to afford 560 (0.185 g, 85%). $^1$H NMR (DMSO-d$_6$, 300 MHz) δ 0.63 (t, 3H), 1.55 (m, 2H), 2 (s, 3H), 4.06 (m, 1H), 4.85 (s, 2H), 7.04-7.15 (m, 5H), 7.22 (d, 1H), 7.3 (s, 1H), 7.39 (dd, 1H), 7.53 (m, 2H), 7.66 (dd, 1H), 7.87 (d, 2H), 7.99-8.07 (m, 2H), 9.29 (s, 1H); LC-MS (ES) m/z 663 (M+H)$^+$, LC-MS (ES$^-$) m/z 661 (M-H)$^-$.

Example 231

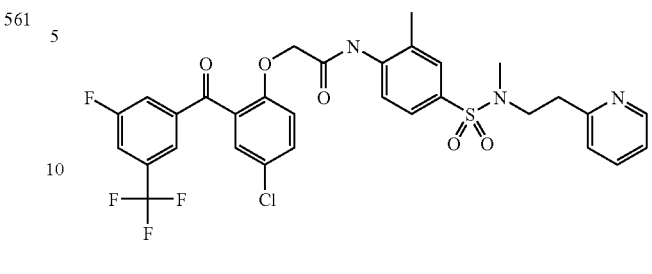

563

Acid 71 was converted to the acid chloride using the general procedure V. Aniline 535 (0.1 g, 0.33 mmol), acetone (4 mL), sodium bicarbonate (0.22 g, 2.6 mmol), and the acid chloride (0.16 g, 0.40 mmol) were used as in general procedure VI. After 2 d, the resulting solution was concentrated, re-dissolved in dichloromethane and purified by flash chromatography using 98:2 CH$_2$Cl$_2$:CH$_3$OH as eluant to afford 563 (0.193 g, 89%). $^1$H NMR (DMSO-d$_6$, 400 MHz) δ 2.21 (s, 3H), 2.67 (s, 3H), 2.92 (t, 2H), 4.09 (m, 2H), 4.83 (s, 2H), 7.18-7.27 (m, 3H), 7.42-7.78 (m, 9H), 8.46 (m, 1H), 9.41 (s, 1H); LC-MS (ES$^+$) m/z 664 (M+H)$^+$, LC-MS (ES$^-$) m/z 662 (M-H)$^-$.

Example 232

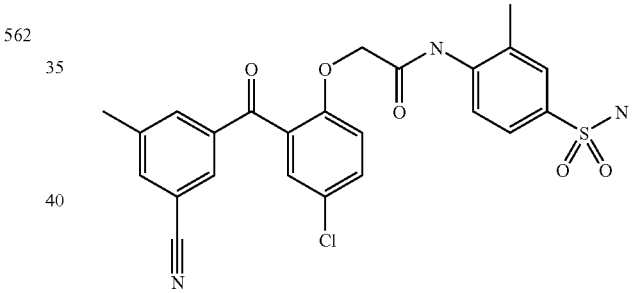

564

Step A:

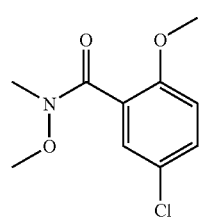

565

5-Chloro-2-methoxybenzoic acid (Aldrich, 17.1 g, 91 mmol), oxalyl chloride (50 mL of 2.0 M solution in dichloromethane, 100 mmol), DMF (1.2 mL), and dichloromethane (100 mL), were used to prepare the acid chloride according to general procedure V. The mixture was concentrated after 2 h, dissolved in chloroform (50 mL), and added dropwise to a solution of N,O-dimethylhydroxylamine (Aldrich, 13.34 g, 140 mmol), chloroform (200 mL), and triethylamine (19.06 mL, 140 mmol) at 0° C. as in general procedure VII. After 1 h, water was added to the reaction mixture and the organic layer was separated. The aqueous was further extracted with ethyl acetate. The organic layers were combined, is dried over MgSO$_4$, filtered and the solvents were removed under reduced pressure to afford 565 (18.69 g, 96%). $^1$H NMR (DMSO-d$_6$, 300 MHz) δ 3.2 (bs, 3H), 3.45 (bs, 3H), 3.77 (s, 3H), 7.1 (d, 1H), 7.3 (d, 1H), 7.42 (m, 1H).

Step B:

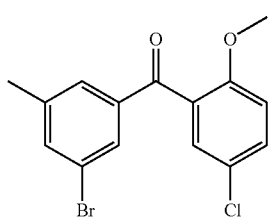

566

Into a oven dried round-bottom flask equipped with a stir bar, nitrogen on demand, and an addition funnel, were added 3,5-dibromotoluene (Avocado, 20.85 g, 83.4 mmol), and methyl t-butyl ether (500 mL) and the mixture was cooled to −50° C. by means of an acetonitrile dry ice bath. n-Butyllithium (57.4 mL of a 1.6 M solution in hexanes, 91.8 mmol) was added dropwise to the reaction and the mixture was allowed to stir for 30 min at −50° C. Weinreb amide 565 (19.16 g, 83.4 mmol) was added portionwise via a powder addition funnel. The mixture was allowed to stir at −50° C., then warm to rt overnight. When judged to be complete, the reaction was poured into saturated ammonium chloride (500 mL) and stirred vigorously for 30 min. The mixture was then added to a separatory funnel. The organics were collected, washed with water, brine, dried over MgSO$_4$, filtered, and concentrated in vacuo to give a yellow solid (28.64 g) that was pulverized, then triturated with methanol and filtered to give 566 as a pale yellow solid (19.2 g, 68%). $^1$H NMR (DMSO-d$_6$, 400 MHz) δ 2.29 (s, 3H), 3.63 (s, 3H), 7.18 (d, 1H), 7.36 (d, 1H), 7.42 (s, 1H), 7.55 (m, 2H), 7.66 (s, 1H).

Step C:

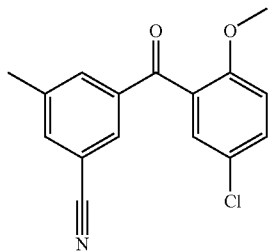

567

Into a oven dried round-bottom flask equipped with a stir bar, nitrogen on demand, and a reflux condenser, were added 566 (4.02 g, 12 mmol), sodium cyanide (1.16 g, 24 mmol), copper iodide (0.26 g, 1.4 mmol), and propionitrile (50 mL degassed with nitrogen for 30 min). To this mixture was added Pd(PPh$_3$)$_4$ (Strem, 1.37 g, 1.2 mmol) that had been triturated with methanol and filtered prior to addition. The mixture was heated to reflux and allowed to stir for 30 min. The mixture was cooled to rt and ethyl acetate (100 mL) was added. The resulting suspension was filtered through celite and the solids washed with ethyl acetate. The filtrate was washed with water, brine, dried over MgSO$_4$, filtered, and concentrated in vacuo. The resulting product was further purified by flash chromatography using 4:1 hexanes:ethyl acetate to afford 567 as an off-white solid (3.33 g, 99%). $^1$H NMR (DMSO-d$_6$, 300 MHz) δ 2.44 (s, 3H), 3.69 (s, 3H), 7.26 (d, 1H), 7.46 (d, 1H), 7.66 (dd, 1H), 7.86 (d, 2H), 7.99 (s, 1H).

Step D:

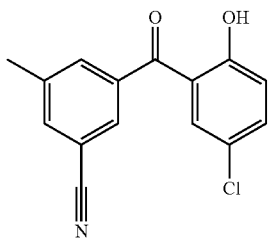

568

Anisole derivative 567 (3.27 g, 14.2 mmol), dichloromethane (45 mL), and boron tribromide (1.41 mL in 15 mL of dichloromethane) were combined as described in general procedure IX. The reaction was stirred at −78° C. for 1 h then allowed to warm to rt and stir for an additional 4 h. The reaction was then poured into ice water (500 mL) and stirred for additional 45 min, and poured into a separatory funnel. The organic layers were collected and washed with water, brine, and dried over MgSO$_4$, filtered, and concentrated in vacuo to give a yellow solid (5.62 g). The resulting solid that was recrystallized from methanol and filtered to give 568 as pale yellow crystals (2.65 g, 85%). $^1$H NMR (DMSO-d$_6$, 400 MHz) δ 2.4 (s, 3H), 6.98 (d, 1H), 7.37 (d, 1H), 7.47 (dd, 1H), 7.82 (d, 1H), 7.87 (s, 1H), 7.93 (d, 1H), 10.43 (s, 1H).

Step E:

Compound 568 (2.65 g, 9.8 mmol), potassium carbonate (6.74 g, 49 mmol), compound 470 (3.14 g, 10 mmol), and acetone (50 mL) were combined in a round-bottom flask, and heated to reflux for 4 h. The reaction was concentrated in vacuo, then water (200 mL) and dichloromethane were added and the suspension was filtered. The filtrate was poured in a separatory funnel and separated. The organic layer was collected, washed with saturated sodium bicarbonate solution, water, brine, dried over MgSO$_4$, filtered and concentrated in vacuo. The resulting solid was further purified by flash chromatography using 1:1 hexanes:ethyl acetate as eluant to afford an off-white solid. The solid was recrystallized from acetonitrile and water to afford 564 (1.61 g, 66%). $^1$H NMR (DMSO-d$_6$, 400 MHz) δ 2.17 (s, 3H), 2.37 (s, 3H), 4.81 (s, 2H), 7.24 (m, 3H), 7.5 (d, 1H), 7.58-7.66 (m, 4H), 7.92 (d, 2H), 7.98 (s, 1H), 9.39 (s, 1H).

Example 233

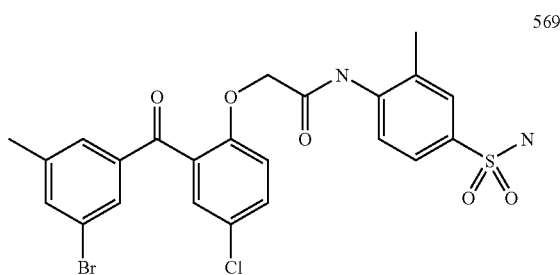

569

Step A:

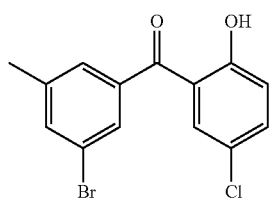

570

Anisole derivative 566 (1.02 g, 3 mmol), dichloromethane (10 mL), and boron tribromide (3 mL of a 1 M solution in dichloromethane) were combined as described in general procedure IX. The reaction was stirred at −78° C. for 90 min, and was then allowed to warm to rt and stir for an additional 1 h. Water (100 mL) was added to the reaction and the resulting mixture was stirred for 30 min. The mixture was then added to a separatory funnel, the organic layer was collected, dried over MgSO$_4$, filtered, and concentrated in vacuo to afford 570 as a pale yellow solid (0.965 g, 99%). $^1$H NMR (DMSO-d$_6$, 300 MHz) δ 2.34 (s, 3H), 6.96 (d, 1H), 7.33 (d, 1H), 7.45 (m, 2H), 7.58 (s, 1H), 7.69 (s, 1H), 10.37 (s, 1H).

Step B:

Compound 570 (0.16 g, 0.5 mmol), potassium carbonate (0.34 g, 2.5 mmol), compound 470 (0.166 g, 0.54 mmol), and acetone (5 mL) were combined in a round-bottom flask, and heated to reflux overnight. Water was added, the resulting suspension was filtered and the solids purified by flash chromatography using 9:1 CH$_2$Cl$_2$:CH$_3$OH as eluant to afford 569 as an off-white solid (0.035 g, 13%). $^1$H NMR (DMSO-d$_6$, 300 MHz) δ 2.16 (s, 3H), 2.3 (s, 3H), 4.8 (s, 2H), 7.24 (m, 3H), 7.46 (d, 1H), 7.58–7.68 (m, 6H), 9.29 (s, 1H).

Example 234

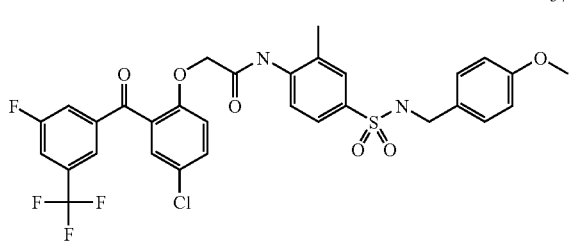

571

Step A:

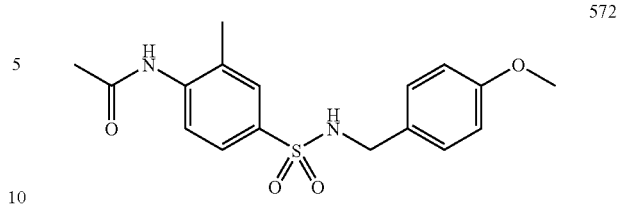

572

Sulfonyl chloride 464 (3 mmol) was added portionwise to a large test tube with a stir bar, pyridine (5 mL), and 4-methoxybenzylamine (Aldrich, 0.41 g, 3.01 mmol). The mixture was allowed to stir for 2 d and was then concentrated in vacuo. Water was added to the remaining residue and the mixture was filtered. The filtrate was extracted with dichloromethane, the organic layer was collected, dried over MgSO$_4$, filtered and concentrated in vacuo to afford the protected sulfonamide 572 (0.16 g, 46%). $^1$H NMR (DMSO-d$_6$, 400 MHz) δ 2.06 (s, 3H), 2.21 (s, 3H), 3.65 (s, 3H), 3.83 (d, 2H), 6.77 (dd, 2H), 7.08 (d, 2H), 7.52 (m, 2H), 7.7 (m, 1H), 7.87 (t, 1H), 9.36 (s, 1H); LC-MS (ES$^+$) m/z 349 (M+H)$^+$, LC-MS (ES$^−$) m/z 347 (M−H)$^−$.

Step B:

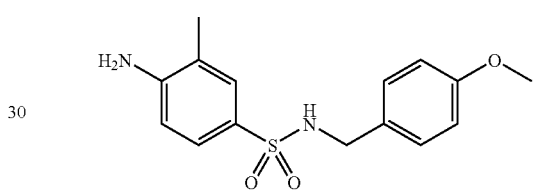

573

The sulfonamide was then dissolved in ethanol (10 mL) and 1.5 N HCl (10 mL) and heated to 60° C. overnight. The resulting solution was concentrated in vacuo to afford 573, which was used without further purification.

Step C:

Acid 71 was converted to the acid chloride using the general procedure V. Aniline 573 (0.1 g, 0.33 mmol), acetone (4 mL), sodium bicarbonate (0.22 g, 2.6 mmol), and the acid chloride (0.16 g, 0.40 mmol) were used as in general procedure VI. After 2 d, the resulting solution was concentrated, re-dissolved in dichloromethane and purified by flash chromatography using 98:2 CH$_2$Cl$_2$:CH$_3$OH as eluant to afford 571 (0.070 g, 32%). $^1$H NMR (DMSO-d$_6$, 300 MHz) δ 2.15 (s, 3H), 3.69 (s, 3H), 3.87 (d, 2H), 4.82 (s, 2H), 6.8 (m, 2H), 7:1 (d, 2H), 7.23 (d, 1H), 7.56 (dd, 3H), 7.67 (m, 2H), 7.87–8.03 (m, 4H), 9.41 (s, 1H); LC-MS (ES$^−$) m/z 663 (M−H)$^−$.

Example 235

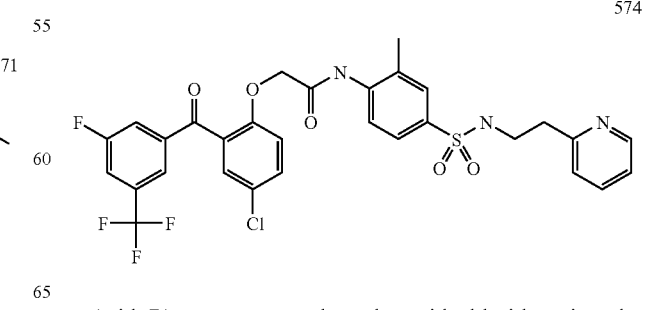

574

Acid 71 was converted to the acid chloride using the general procedure V. Aniline 521 (0.1 g, 0.34 mmol), acetone (4 mL), sodium bicarbonate (0.22 g, 2.6 mmol), and the acid chloride (0.16 g, 0.40 mmol) were used as in general procedure VI. After 2 d, the resulting solutions were concentrated, re-dissolved in dichloromethane and purified by flash chromatography using 98:2 CH$_2$Cl$_2$:CH$_3$OH as eluant to afford 574 (0.040 g, 18%). $^1$H NMR (DMSO-d$_6$, 300 MHz) δ 2.16 (s, 3H), 2.8 (dd, 2H), 3.08 (m, 2H), 4.81 (s, 2H), 7.16-7.25 (m, 3H), 7.53-7.69 (m, 7H), 7.88 (m, 2H), 8 (m, 1H), 8.42 (m, 1H), 9.4 (s, 1H); LC-MS (ES$^+$) m/z 650 (M+H)$^+$, LC-MS (ES$^-$) m/z 648 (M−H)$^-$.

Example 236 acetone (4 mL), sodium bicarbonate (0.22 g, 2.6 mmol), and the acid chloride (0.16 g, 0.40 mmol) were used as in general procedure VI. After 2 d, the resulting solutions were concentrated, re-dissolved in dichloromethane and purified by flash chromatography using 98:2 CH$_2$Cl$_2$:CH$_3$OH as eluant to afford 575 (0.067 g, 32%). $^1$H NMR (DMSO-d$_6$, 300 MHz) δ 1.47 (m, 2H), 2.04-2.21 (m, 16H), 2.73 (m, 2H), 4.82 (s, 2H), 7.23 (d, 1H), 7.45-7.7 (m, 6H), 7.87 (m, 2H), 8.01 (m, 1H), 9.41 (s, 1H); LC-MS (ES$^+$) m/z 685 (M+H)$^+$, LC-MS (ES$^-$) m/z 683 (M−H)$^-$.

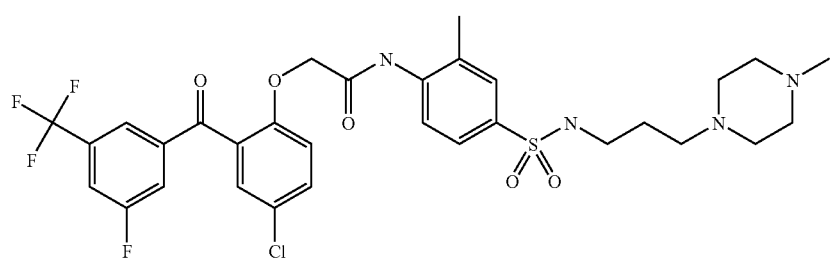

575

Step A:

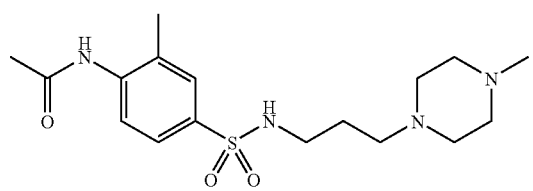

576

Sulfonyl chloride 464 (3 mmol) was added portionwise to a large test tube with a stir bar, pyridine (5 mL), and 1-(3-aminopropyl)-4-methylpiperazine (Aldrich, 0.48 g, 3.05 mmol). The mixture was allowed to stir for 2 d, followed by concentration in vacuo. Water was added to the remaining residue and the mixture was filtered. The filtrate was extracted with dichloromethane and the organic layer was collected, dried over MgSO$_4$, filtered and concentrated in vacuo to afford the protected sulfonamide 576 (0.22 g, 20%), which was used without further purification.

Step B:

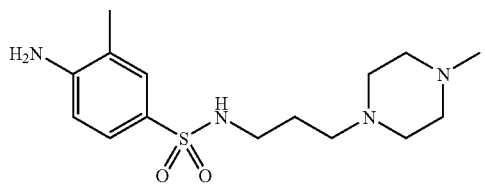

577

The sulfonamide 576 was then dissolved in ethanol (10 mL) and 1.5 N HCl (10 mL) and heated to 60° C. overnight. The resulting solutions were concentrated in vacuo to afford 577. The resulting product was used without further purification.

Step C:

Acid 71 was converted to the acid chloride using the general procedure V. Aniline 577 (0.1 g, 0.31 mmol), Example 237

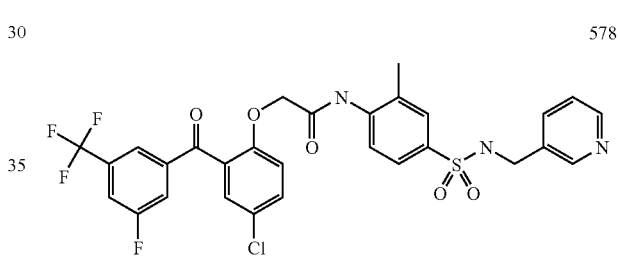

578

Acid 71 was converted to the acid chloride using the general procedure V. Aniline 538 (0.1 g, 0.36 mmol), acetone (4 mL), sodium bicarbonate (0.22 g, 2.6 mmol), and the acid chloride (0.16 g, 0.40 mmol) were used as in general procedure VI. After 2 d, the resulting solutions were concentrated, re-dissolved in dichloromethane and purified by flash chromatography using 98:2 CH$_2$Cl$_2$:CH$_3$OH as eluant to afford 77 (0.053 g, 23%). $^1$H NMR (DMSO-d$_6$, 300 MHz) δ 2.16 (s, 3H), 4 (d, 2H), 4.82 (s, 2H), 7.22-7.31 (m, 2H), 7.55-7.7 (m, 6H), 7.88 (d, 2H), 8.02 (m, 1H), 8.12 (t, 1H), 8.41 (dd, 2H), 9.42 (s, 1H); LC-MS (ES$^+$) m/z 636 (M+H)$^+$, LC-MS (ES$^-$) m/z 634 (M−H)$^-$.

Example 238

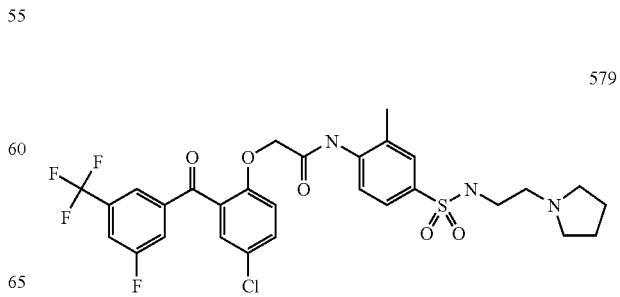

579

Acid 71 was converted to the acid chloride using the general procedure V. Aniline 515 (0.1 g, 0.35 mmol), acetone (4 mL), sodium bicarbonate (0.22 g, 2.6 mmol), and the acid chloride (0.16 g, 0.4 mmol) were used as in general procedure VI. After 2 d, the resulting solutions were concentrated, re-dissolved in dichloromethane and purified by flash chromatography using 98:2 CH$_2$Cl$_2$:CH$_3$OH as eluant to afford 579 (0.018 g, 8%). $^1$H NMR (DMSO-d$_6$, 300 MHz) δ 1.6 (m, 4H), 2.17 (s, 3H), 2.3-2.42 (m, 6H), 2.81 (t, 2H), 3.16 (m, 4H), 4.09 (m, 1H), 4.81 (s, 2H), 7.24 (d, 1H), 7.54-7.69 (m, 5H), 7.88 (d, 2H), 8 (d, 1H), 9.41 (s, 1H); LC-MS (ES$^+$) m/z 642 (M+H)$^+$, LC-MS (ES$^-$) m/z 640 (M−H)$^-$.

Step C:
Acid 71 was converted to the acid chloride using the general procedure V. Aniline 582 (0.1 g, 0.34 mmol), acetone (4 mL), sodium bicarbonate (0.22 g, 2.6 mmol), and the acid chloride (0.16 g, 0.40 mmol) were used as in general procedure VI. After 2 d, the resulting solutions were concentrated, re-dissolved in dichloromethane and purified by flash chromatography using 98:2 CH$_2$Cl$_2$:CH$_3$OH as eluant to afford 580 (0.037 g, 17%). $^1$H NMR (DMSO-d$_6$, 300 MHz) δ 1.25 (m, 2H), 1.47-1.8 (m, 4H), 1.99 (m, 2H), 2.1 (s, 3H), 2.17 (s, 3H), 2.73 (m, 2H), 2.9 (m, 1H), 4.81 (s, 2H), 7.24 (d, 1H), 7.46-7.69 (m, 6H), 7.88 (m, 2H), 8 (m, 1H), 9.41 (s, 1H); LC-MS (ES$^+$) m/z 656 (M+H)$^+$.

Example 239

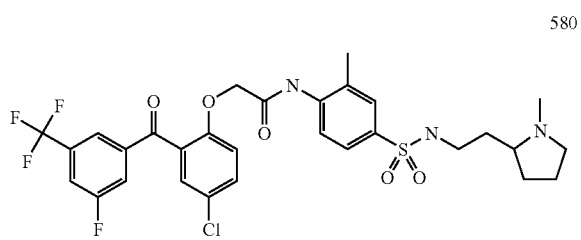

580

Example 240

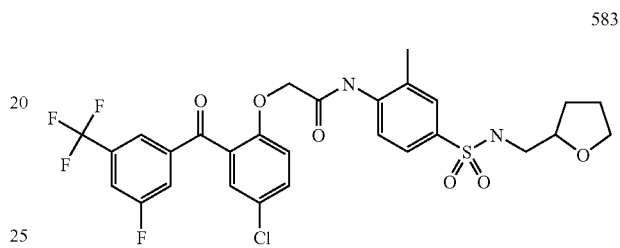

583

Step A:

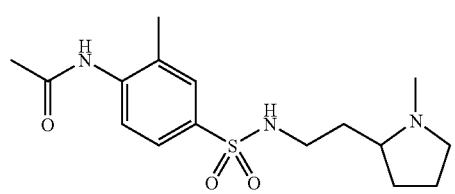

581

Step A:

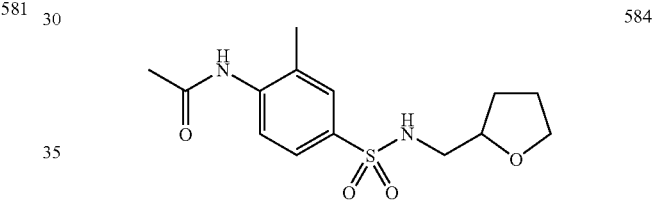

584

Sulfonyl chloride 464 (3 mmol) was added portionwise to a large test tube with a stir bar, pyridine (5 mL), and 2-(2-aminoethyl)-1-methylpyrrolidine (Aldrich, 0.29 g, 2.3 mmol). The mixture was allowed to stir at rt for 2 d, followed by concentration in vacuo. Water was added to the resulting residue and the mixture was filtered. The filtrate was extracted with dichloromethane and the organic layer was collected, dried over MgSO$_4$, filtered and concentrated in vacuo to afford the protected sulfonamide 581 (0.40 g, 51%). $^1$H NMR (DMSO-d$_6$, 400 MHz) δ 1.25 (m, 2H), 1.53 (m, 2H), 1.64 (m, 1H), 1.76 (m, 1H), 1.96 (m, 2H), 2.09 (s, 3H), 2.10 (s, 3H), 2.28 (s, 3H), 2.72 (m, 2H), 2.86 (m, 1H), 7.46 (s, 1H), 7.55 (dd, 1H), 7.59 (s, 1H), 7.76 (d, 1H), 9.42 (s, 1H); LC-MS (ES$^+$) m/z 340 (M+H)$^+$, LC-MS (ES$^-$) m/z 338 (M−H)$^-$.

Step B:

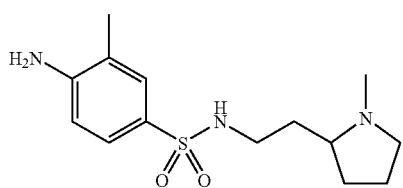

582

The sulfonamide 581 was then dissolved in ethanol (10 mL) and 1.5 N HCl (10 mL) and heated to 60° C. overnight. The resulting solutions were concentrated in vacuo to afford 582, which was used without further purification.

Sulfonyl chloride 464 (3 mmol) was added portionwise to a large test tube with a stir bar, pyridine (5 mL), and tetrahydrofurfurylamine (Aldrich, 0.41 g, 3.01 mmol). The mixture was allowed to stir at rt for 2 d, followed by concentration in vacuo. Water was added and the mixture was filtered to afford 584 (0.2 g, 64%). $^1$H NMR (DMSO-d$_6$, 400 MHz) δ 1.45 (m, 1H), 1.7 (m, 3H), 2.05 (s, 3H), 2.23 (s, 3H), 2.69 (t, 2H), 3.51 (m, 1H), 3.62 (m, 1H), 3.72 (m, 1H), 7.5-7.56 (m, 3H), 7.69 (d, 1H), 9.37 (s, 1H); LC-MS (ES$^+$) m/z 313 (M+H)$^+$, LC-MS (ES$^-$) m/z 311 (M−H)$^-$.

Step B:

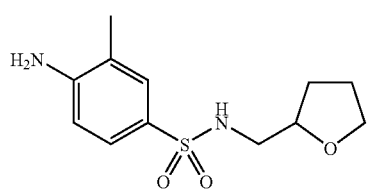

585

Sulfonamide 584 was dissolved in ethanol (10 mL) and 1.5 N HCl (10 mL) and heated to 60° C. overnight. The resulting solution was concentrated in vacuo to afford 585, which was used without further purification.

Step C:
Acid 71 was converted to the acid chloride using the general procedure V. Aniline 585 (0.1 g, 0.37 mmol), acetone (4 mL), sodium bicarbonate (0.22 g, 2.6 mmol), and the acid chloride (0.16 g, 0.40 mmol) were used as in general procedure VI. After 2 d, the resulting solutions were concentrated, re-dissolved in dichloromethane and purified by flash chromatography using 98:2 CH$_2$Cl$_2$:CH$_3$OH as eluant to afford 583 (0.038 g, 16%). $^1$H NMR (DMSO-d$_6$, 300 MHz) δ 1.69-1.88 (m, 3H), 2.17 (s, 3H), 2.73 (t, 2H), 3.51-3.81 (m, 3H), 4.81 (s, 2H), 7.24 (d, 2H), 7.54-7.69 (m, 6H), 7.88 (m, 2H), 8.01 (m, 1H), 9.41 (s, 1H); LC-MS (AP$^+$) m/z 629 (M+H)$^+$, LC-MS (AP$^-$) m/z 628 (M−H)$^-$.

Example 241

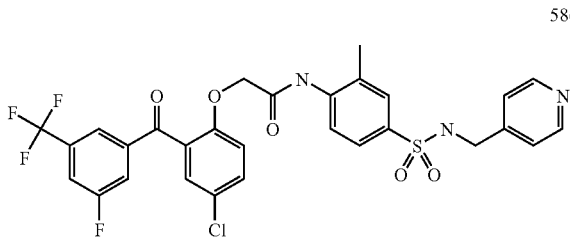

Acid 71 was converted to the acid chloride using the general procedure V. Aniline 541 (0.1 g, 0.36 mmol), acetone (4 mL), sodium bicarbonate (0.22 g, 2.6 mmol), and the acid chloride (0.16 g, 0.40 mmol) were used as in general procedure VI. After 2 d, the resulting solutions were concentrated, re-dissolved in dichloromethane and purified by flash chromatography using 98:2 CH$_2$Cl$_2$:CH$_3$OH as eluant to afford 586 (0.033 g, 14%). $^1$H NMR (DMSO-d$_6$, 300 MHz) δ 2.16 (s, 3H), 4 (d, 2H), 4.82 (s, 2H), 7.24 (m, 3H), 7.55-7.7 (m, 5H), 7.89 (m, 2H), 8.02 (m, 1H), 8.20 (t, 1H), 8.44 (dd, 2H), 9.42 (s, 1H); MS (ES$^+$) m/z 636 (M+H)$^+$.

Example 242

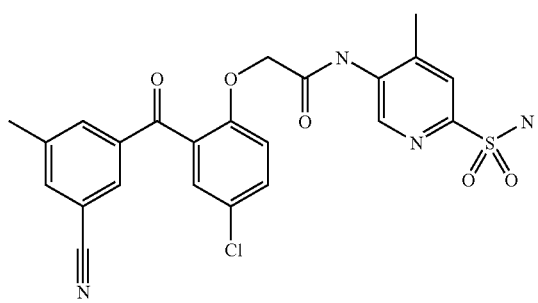

Step A:

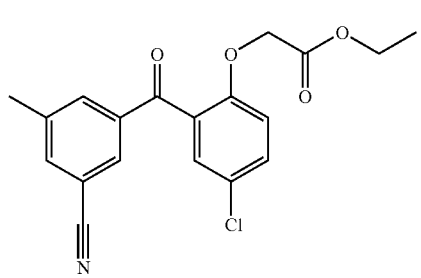

Compound 568 (2 g, 7.4 mmol), potassium carbonate (5.11 g, 37 mmol), ethyl bromoacetate (1 mL, 9 mmol), and acetone (40 mL) were used as in general procedure II to afford 588 as a yellow/off-white solid (2.73 g, crude material). $^1$H NMR (DMSO-d$_6$, 400 MHz) δ 1.14 (t, 3H), 2.39 (s, 3H), 4.08 (m, 2H), 4.78 (s, 2H), 7.14 (d, 1H), 7.47 (d, 1H), 7.58 (d, 1H), 7.9 (m, 3H).

Step B:

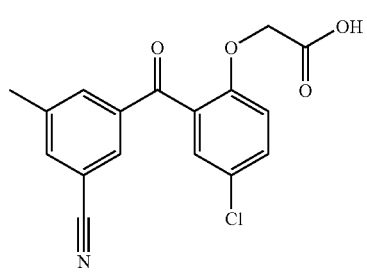

Ester 588 (2.73 g, 7.6 mmol), ethanol (EtOH, 20 mL), water (5 mL), and lithium hydroxide monohydrate (0.45 g, 10.7 mmol) were used as in general procedure III to afford 589 as an orange glass (2.45 g, 97%). $^1$H NMR (DMSO-d$_6$, 300 MHz) δ 2.3 (s, 3H), 4.67 (s, 2H), 7.1 (d, 1H), 7.44 (d, 1H), 7.58 (dd, 1H), 7.9 (m, 3H), 13.1 (bs, 1H).

Step C:

Carboxylic acid 589 (0.1 g, 0.3 mmol), oxalyl chloride (0.4 mL of 2.0 M solution in dichloromethane, 6.8 mmol), DMF (2 drops), and dichloromethane (2 mL), were used according to general procedure V. The acid chloride was dissolved in acetone and added dropwise to aniline 490 (0.086 g, 0.47 mmol), acetone (10 mL), sodium bicarbonate (0.15 g, 1.8 mmol), and water (2 drops) as in general procedure VI. After 4 d, the reaction mixture was concentrated and the product was purified by flash chromatography using 9:1 CH$_2$Cl$_2$:CH$_3$OH as eluant to afford 587 (0.046 g, 31%). $^1$H NMR (DMSO-d$_6$, 300 MHz) δ 2.24 (s, 3H), 2.38 (s, 3H), 4.85 (s, 2H), 7.24 (d, 1H), 7.39 (s, 2H), 7.49 (d, 1H), 7.65 (dd, 1H), 7.81 (s, 1H), 7.95 (m, 3H), 8.7 (s, 1H), 9.71 (s, 1H).

Example 243

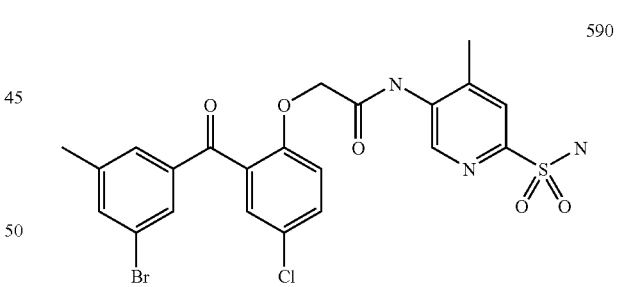

Step A:

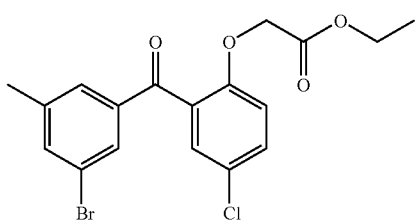

Compound 570 (0.75 g, 2.3 mmol), potassium carbonate (1.7 g, 12.3 mmol), ethyl bromoacetate (0.3 mL, 2.7 mmol), and acetone (10 mL) were used as in general procedure II to afford 591 as a clear low melting point solid (0.87 g, 92%). The crude product was used without further purification.

Step B:

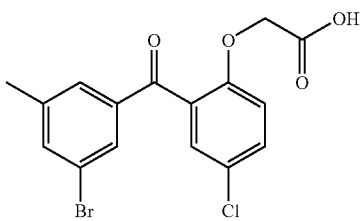

Ester 591 (0.87 g, 2.1 mmol), ethanol (EtOH, 7.5 mL), water (2.5 mL), and lithium hydroxide monohydrate (0.125 g, 2.98 mmol) were used as in general procedure III to afford 592 as an white foam (0.74 g, 91%). $^1$H NMR (DMSO-d$_6$, 300 MHz) δ 2.32 (s, 3H), 4.68 (s, 2H), 7.08 (d, 1H), 7.41 (d, 1H), 7.57 (d, 2H), 7.67 (s, 2H), 13.1 (bs, 1H).

Step C:
Carboxylic acid 592 (0.1 g, 0.26 mmol), oxalyl chloride (0.4 mL of 2.0 M solution in dichloromethane, 0.8 mmol), DMF (2 drops), and dichloromethane (2 mL), were according to general procedure V. The acid chloride was then dissolved in acetone and added dropwise to aniline 490 (0.086 g, 0.47 mmol), acetone (10 mL), sodium bicarbonate (0.15 g, 1.8 mmol), and water (2 drops) as in general procedure VI. After 5 d, the reaction mixture was concentrated, and the product was purified by flash chromatography using 9:1 CH$_2$Cl$_2$:CH$_3$OH as eluant to afford a solid. The solid was dissolved in dichloromethane, washed with saturated sodium bicarbonate, dried over MgSO$_4$, filtered, and concentrated in vacuo to give 590 (0.029 g, 20%). $^1$H NMR (DMSO-d$_6$, 300 MHz) δ 2.19 (s, 3H), 2.3 (s, 3H), 4.75 (s, 2H), 7.22 (d, 2H), 7.43 (d, 2H), 7.58-7.74 (m, 6H), 8.68 (s, 1H).

Example 244

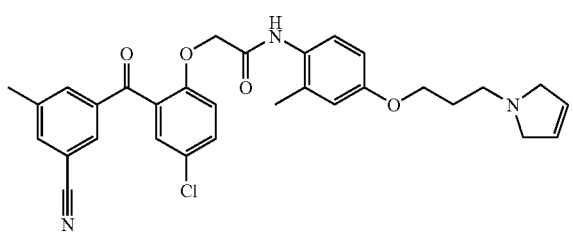

Step A:

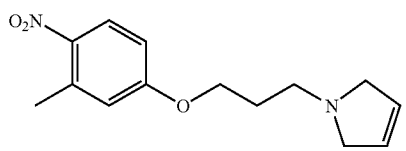

4-(3-bromo-propoxy)-2-methyl-1-nitrobenzene (3.29 g, 12 mmol), DMF (30 mL), and potassium carbonate (7.6 g, 55 mmol) were combined in a round-bottom flask. 3-Pyrroline (Aldrich, 1 g, 14.5 mmol) was added dropwise to the reaction and the resulting solution was stirred at rt overnight. Water was added to the mixture and the resulting mixture was extracted with ethyl acetate. The organic layer was collected, dried over MgSO$_4$, filtered, and concentrated in vacuo to afford 594 as an orange oil (1.22 g, 39%). $^1$H NMR (DMSO-d$_6$; 400 MHz) δ 1.88 (m, 2H), 2.54 (s, 3H), 2:69 (m, 2H), 3.4 (s, 4H), 4.14 (t, 2H), 5.78 (s, 2H), 6.96 (dd, 1H), 7.03 (d, 1H), 8.03 (d, 1H).

Step B:

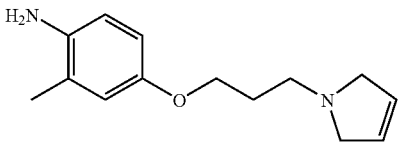

Compound 594 (0.65 g, 2.5 mmol), tin dichloride dihydrate (1.83 g, 8.1 mmol), and ethanol (10 mL) were combined and stirred overnight at rt. Sodium hydroxide (2N) was added and the mixture was extracted with ethyl acetate. The organic layer was collected, washed with water and brine, dried over MgSO$_4$, filtered, and concentrated in vacuo to afford 595 as a brown oil (0.26 g, 49%). $^1$H NMR (DMSO-d$_6$, 300 MHz) δ 1.78 (m, 2H), 2 (s, 3H), 2.65 (m, 2H), 3.37 (s, 4H), 3.83 (t, 2H), 4.34 (bs, 2H), 5.76 (m, 2H), 6.49 (s, 2H), 6.54 (d, 1H).

Step C:
Carboxylic acid 589 (0.2 g, 0.6 mmol), oxalyl chloride (1.4 mL of 2.0 M solution in dichloromethane, 2.8 mmol), DMF (1 drops), and dichloromethane (5 mL), were used to according to general procedure V. The resulting acid chloride was dissolved in acetone and added dropwise to aniline 595 (0.26 g, 1.2 mmol), acetone (10 mL), sodium bicarbonate (0.2 g, 2.4 mmol), and water (1 mL) as in general procedure VI. After 5 d, the reaction mixture was concentrated, and the product was purified by flash chromatography using 95:5 CH$_2$Cl$_2$:CH$_3$OH as eluant to afford 593 as an orange glass (0.127 g, 38%). $^1$H NMR (DMSO-d$_6$, 300 MHz) δ 1.86 (m, 4H), 2.01 (s, 3H), 2.36 (s, 3H), 2.76 (m, 2H), 3.48 (m, 2H), 3.97 (t, 2H), 4.7 (s, 2H), 5.8 (s, 2H), 6.7 (m, 2H), 7.12 (d, 1H), 7.22 (d, 1H), 7.48 (d, 1H), 7.65 (dd, 1H), 7.94 (d, 2H), 8.99 (s, 1H).

Example 245

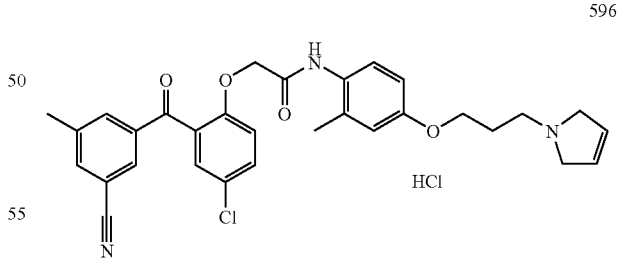

Compound 593 (0.1 g, 0.2 mmol) was dissolved in dioxane (2 mL) and hydrochloric acid (1 mL of a 4M solution in dioxane) was added dropwise. The mixture was allowed to stir for 2 d and was then concentrated in vacuo to afford 596 as a dark solid (0.071 g, 68%). $^1$H NMR (DMSO-d$_6$, 300 MHz) δ 2.02 (s, 5H), 2.36 (s, 3H), 3.68 (m, 2H), 3.95 (m, 4H), 4.2 (m, 2H), 4.71 (s, 2H), 5.93 (s, 2H), 6.75 (m, 2H), 7.2 (m, 2H), 7.49 (d, 1H), 7.65 (d, 1H), 7.95 (m, 3H), 9.06 (s, 1H), 10.95 (bs, 1H).

Example 246

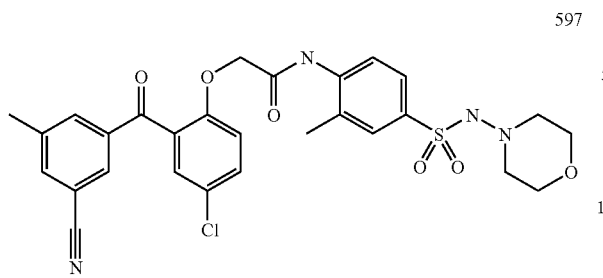

Step A:

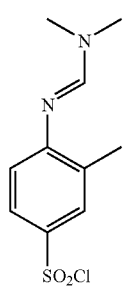

DMF (59 mL, 762 mmol) was added dropwise to stirred solution of oxalyl chloride (380 mL of a 2M solution in dichloromethane, 760 mmol) in a 1-L 3 neck round-bottom flask at 0° C. After addition was complete, the reaction was stirred for 1 h then allowed to warm to rt and stir for an additional 2 h. To the resulting white solid was added 2-aminotoluene-5-sulfonic acid (Aldrich, 50 g, 267 mmol) in one portion and the resulting reaction mixture was stirred vigorously for an 1 h. The reaction mixture was transferred to a 1-L round-bottom flask and concentrated to afford 598 as tan solid (150.24 g, crude product). The crude product was carried on without further purification or characterization.

Step B:

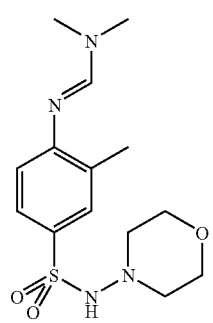

Compound 598 (10 g, 38 mmol) was added to a solution of 4-aminomorpholine (Aldrich, 5 g, 49 mmol) in THF (40 mL) and stirred at rt for 2 d. Water and saturated sodium bicarbonate solution were added and the resulting solution was extracted with ethyl acetate. The organic layer was collected, dried over MgSO$_4$, filtered, and concentrated in vacuo. The product was further purified by flash chromatography using 95:5 CH$_2$Cl$_2$:CH$_3$OH as eluant to afford 599 as an orange glass (0.53 g, crude product). The crude product was used without further purification.

Step C:

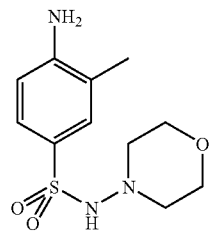

Compound 599 (0.53 g, 1.6 mmol), hydrazine dihydrochloride (0.36 g, 3.4 mmol), and methanol (30 mL) were combined and stirred overnight at rt. The reaction was concentrated in vacuo and the product was purified by flash chromatography using 1:1 hexanes:ethyl acetate as eluant to afford 600 as a white solid (0.075 g, 3.3%). $^1$H NMR (DMSO-d$_6$, 300 MHz) δ 2.06 (s, 3H), 2.5 (m, 4H), 3.42 (m, 4H), 5.7 (bs, 2H), 6.62 (d, 1H), 7.34 (m, 2H), 8.23 (s, 1H).

Step D:

Carboxylic acid 589 (0.08 g, 0.24 mmol), oxalyl chloride (0.4 mL of 2.0 M solution in dichloromethane, 0.8 mmol), DMF (1 drops), and dichloromethane (5 mL), were according to general procedure V. The resulting acid chloride was dissolved in acetone and added dropwise to amine 600 (0.07 g, 0.26 mmol), acetone (10 mL), potassium carbonate (0.1 g, 0.72 mmol), and water (1 drop) as in general procedure VI. After 1 d, the reaction mixture was concentrated, suspended in dichloromethane, filtered, then further purified by flash chromatography and TLC prep plate using 98:2 and 95:5 CH$_2$Cl$_2$:CH$_3$OH as eluant respectively to afford and off-white solid. The resulting solid was further triturated in dichloromethane and filtered to afford 597 as a white solid (0.014 g, 10%). $^1$H NMR (CDCl$_3$, 300 MHz) δ 2.34 (s, 3H), 2.50 (s, 3H), 2.66 (m, 4H), 3.64 (m, 4H), 4.74 (s, 2H), 5.26 (s, 1H), 7.08 (d, 1H), 7.35 (d, 1H), 7.59 (dd, 1H), 7.72 (s, 1H), 7.85 (m, 4H), 8.19 (d, 1H), 8.69 (s, 1H); LC-MS (AP$^+$) m/z 583 (M+H)$^+$, LC-MS (AP$^+$) m/z 581 (M−H)$^-$.

Example 247

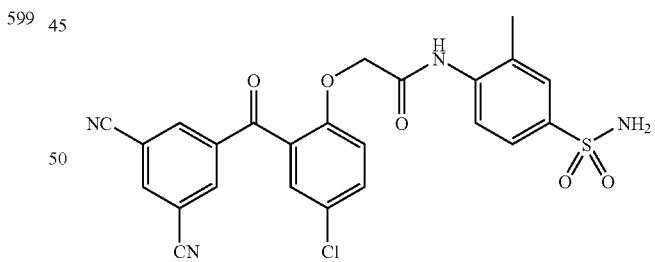

Step A:

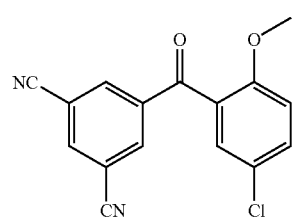

Compound 623 (0.5 g, 1.2 mmol), copper (I) cyanide (Aldrich, 0.55 g, 6.1 mmol), pyridine (4 mL, 49.5 mmol), and DMF (15 mL) were combined in a pressure tube equipped with a stir bar, nitrogen on demand, and a reflux condenser. The mixture was allowed to stir at reflux temperature for 4 d. The mixture was cooled, diethyl ether (150 mL) was added, the resulting suspension was filtered through celite and washed with diethyl ether (3×150 mL). The filtrate was washed with 2:1 water:concentrated ammonium hydroxide, saturated ammonium chloride, and saturated sodium bicarbonate. The organic layer was collected, dried over MgSO$_4$, filtered, and concentrated in vacuo. The product was further purified by flash chromatography using 4:1 hexanes:CH$_2$Cl$_2$ as eluant to afford 602 as an off-white solid (0.13 g, 35%). $^1$H NMR (DMSO-d$_6$, 300 MHz) δ 3.65 (s, 3H), 7.25 (d, 1H), 7.48 (d, 1H), 7.66 (dd, 1H), 8.4 (d, 2H), 8.71 (s, 1H); GC-MS (EI$^+$) m/z 296 (M)$^+$.

Step B:

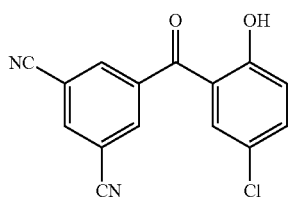

603

Anisole derivative 602 (0.125 g, 0.42 mmol), dichloromethane (10 mL), and boron tribromide (0.44 mL of a 1 M solution in dichloromethane) were combined as described in general procedure IX. The reaction was stirred at −78° C. for 1 h and was then allowed to warm to rt and stir for an additional 1 h. Water (50 mL) was added to the solution and the resulting mixture was stirred vigorously for 15 min, after which time it was added to a separatory funnel. The organic layer was collected, dried over MgSO$_4$, filtered, and concentrated in vacuo to give 603 as a yellow glass (0.12 g, 99%). $^1$H NMR (DMSO-d$_6$, 300 MHz) δ 7 (d, 1H), 7.45 (d, 1H), 7.52 (dd, 1H), 8.42 (d, 2H), 8.7 (m, 1H); GC-MS (EI$^+$) m/z 282 (M)$^+$ Step C:

Compound 603 (0.13 g, 0.46 mmol), potassium carbonate (0.12 g, 0.87 mmol), compound 470 (0.146 g, 0.42 mmol), and acetone (5 mL) were combined in a round-bottom flask and stirred at rt overnight. Water (20 mL) was added and the suspension was filtered and the resulting solids were washed with diethyl ether and air dried to afford 601 as an off-white solid (0.212 g, 98%). $^1$H NMR (DMSO-d$_6$, 300 MHz) δ 2.19 (s, 3H), 4.82 (s, 2H), 7.24 (m, 3H), 7.51-7.74 (m, 3H), 8.5 (d, 2H), 8.69 (m, 1H), 9.5 (s, 1H); LC-MS (AP$^+$) m/z 508 (M+H)$^+$, LC-MS (AP$^-$) m/z 506 (M−H)$^-$.

Example 248

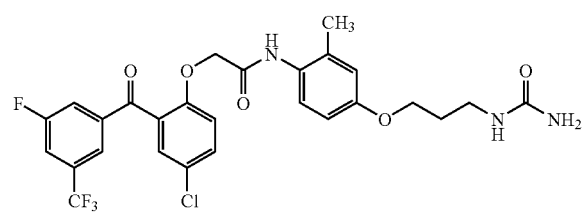

604

Step A:

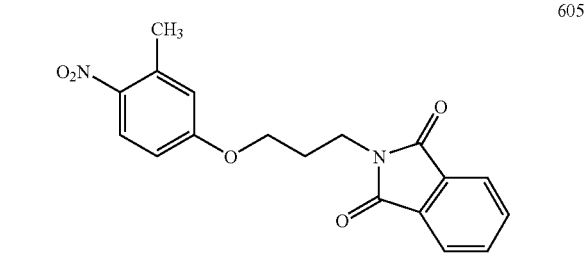

605

3-Methyl-4-nitrophenol (Aldrich, 5.0 g, 33 mmol), 3-bromopropyl phthalimide (8.8 g, 33 mmol), Cs$_2$CO$_3$ (16.1 g, 5.0 mmol), and anhydrous DMF (60 mL) were added to a round bottom flask and heated to 55° C. for 2 h. The reaction was then allowed to cool to rt and was poured into a mixture of Et$_2$O and water. The resulting solid was filtered, washed with water and Et$_2$O, and allowed to dry in a vacuum oven at 45° C. for 12-16 h to provide 605 (9.5 g, 85%) as a tan solid: $^1$H NMR (DMSO-d$_6$, 300 MHz) δ 8.03 (m, 1H), 7.87 (m, 4H), 6.87 (m, 2H), 4.16 (t, 2H), 3.79 (t, 2H), 2.51 (s, 3H), 2.11 (m, 2H).

Step B:

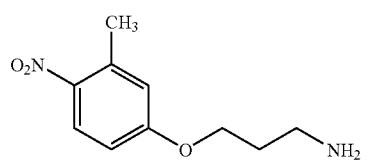

606

Into a round bottom flask equipped with a stir bar, reflux condenser, and nitrogen on demand were added 605 (3.0 g, 8.8 mmol), hydrazine hydrate (1.6 mL, 1.7 g, 53 mmol), and absolute ethanol (50 mL). The reaction was heated to reflux and allowed to stir for 4 h, after which time the reaction mixture was allowed to cool to rt and stir for an additional 48-60 h. The resulting heterogenous mixture was filtered and the filtrate was concentrated under reduced pressure. The resulting solid was washed with CH$_2$Cl$_2$, filtered and dissolved in ethyl acetate. The organic layer was washed with water, dried over MgSO$_4$, filtered and the solvents were removed under reduced pressure to provide 606 (1.1 g, 59%) as a yellow oil: $^1$H NMR (DMSO-d$_6$, 400 MHz) δ 7.99 (d, 1H), 6.97 (d, 1H), 6.91 (dd, 1H), 4.10 (t, 2H), 2.63 (t, 2H), 2.49 (s, 3H), 1.77 (m, 2H).

Step C:

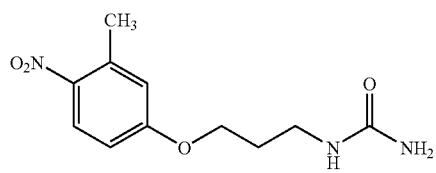

607

Into a round bottom flask equipped with a stir bar and nitrogen on demand were added 606 (0.3 g, 1.43 mmol), anhydrous THF (5 mL), and trimethylsilyl isocyanate (0.21 mL, 0.18 g, 1.57 mmol). The mixture was allowed to stir at rt for 3 h, after which time water (1 mL) was added to the heterogeneous solution. The mixture was concentrated under reduced pressure and the resulting residue was washed with a mixture of ethyl acetate and Et$_2$O, filtered, and dried to afford 607 (0.273 g, 75%) as a pale yellow solid: $^1$H NMR (DMSO-d$_6$, 400 MHz) δ 8.00 (d, 1H), 6.97 (d, 1H), 6.90 (dd, 1H), 5.97 (t, 1H), 5.35 (bs, 2H), 4.04 (t, 2H), 3.05 (m, 2H), 2.44 (s, 3H), 1.77 (m, 2H).

Step D:

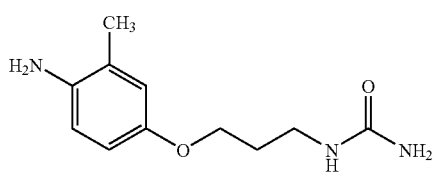

608

To a flask equipped with a stir bar were added 607 (0.055 g, 0.22 mmol), ethanol (8 mL), and palladium on carbon (0.006 g of 10% Pd/C, 10% by weight). The vessel was placed on a hydrogenation apparatus at 40 p.s.i. When judged to be complete, the reaction mixture was filtered through celite and the solvents were removed under reduced pressure to provide 608 (0.045 g, 92%) as a white solid: $^1$H NMR (DMSO-d$_6$, 400 MHz) δ 6.51 (s, 1H), 6.46 (m, 2H), 5.92 (t, 1H), 5.33 (bs, 2H), 4.30 (bs, 2H), 3.75 (t, 2H), 3.03 (m, 2H), 1.96 (s, 3H), 1.67 (m, 2H).

Step E:

Acid 71 (0.17 g, 0.45 mmol), oxalyl chloride (0.25 mL of a 2 M solution in CH$_2$Cl$_2$, 0.50 mmol), N,N-dimethylformamide (1 drop), and CH$_2$Cl$_2$ (7 mL) were used according to general procedure V. The resulting acid chloride, aniline 608 (0.95 g, 0.43 mmol), NaHCO$_3$ (0.19 g, 2.3 mmol), acetone (5 mL), and water (1 mL) were used according to general procedure VI. The resulting solid was washed with Et$_2$O, filtered, and dried in vacuo at 50° C. to afford 604 (0.115 g mg, 44%) as a white solid: MS (ES+) m/z 581 (M$^+$); $^1$H NMR (DMSO-d$_6$, 300 MHz) δ 9.10 (s, 1H), 8.01 (d, 1H), 7.86 (m, 2H), 7.67 (dd, 1H), 7.54 (d, 1H), 7.22 (d, 1H), 7.08 (d, 1H), 6.75 (d, 1H), 6.69 (dd, 1H), 5.98 (t, 1H), 5.37 (bs, 2H), 4.70 (s, 2H), 3.91 (t, 2H), 3.08 (q, 2H), 1.99 (s, 3H), 1.76 (m, 2H).

Example 249

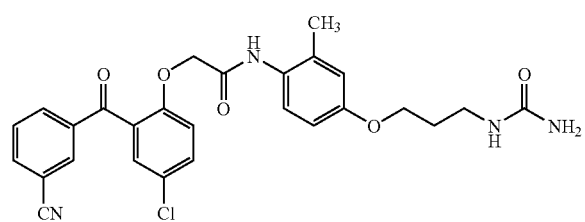

609

Step A:

Acid 129 (0.14 g, 0.45 mmol), oxalyl chloride (0.25 mL of a 2 M solution in CH$_2$Cl$_2$, 0.50 mmol), N,N-dimethylformamide (1 drop), and CH$_2$Cl$_2$ (7 mL) were used according to general procedure V. The resulting acid chloride, aniline 608 (0.095 g, 0.43 mmol), NaHCO$_3$ (0.19 g, 2.3 mmol), acetone (5 mL), and water (1 mL) were used according to general procedure VI. The resulting residue was treated with Et$_2$O and a solid precipitated. The solid was purified by flash chromatography using 5% MeOH:CH$_2$Cl$_2$ to afford 609 (0.015 g, 6%) as a white solid: $^1$H NMR (DMSO-d$_6$, 400 MHz) δ 9.01 (s, 1H), 8.13 (s, 1H), 8.03 (m, 2H), 7.63 (m, 2H), 7.47 (d, 1H), 7.18 (d, 1H), 7.07 (d, 1H), 6.72 (d, 1H), 6.65 (dd, 1H), 5.94 (I, 1H), 5.34 (bs, 2H), 4.65 (s, 2H), 3.87 (t, 2H), 3.03 (m, 2H), 1.95 (s, 3H), 1.76 (m, 2H).

Example 250

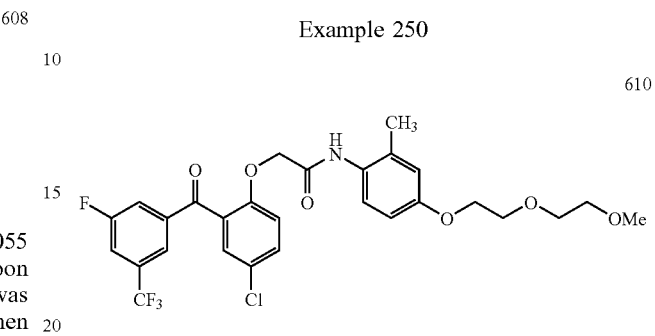

610

Step A:

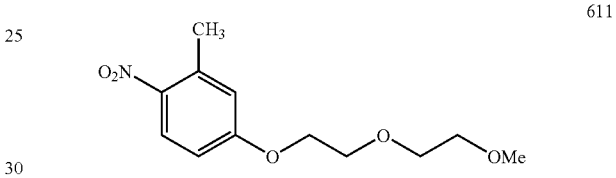

611

To a round bottom flask equipped with a stir bar and nitrogen on demand were added 5-fluoro-2-nitrotoluene (1.0 g, 6.45 mmol), di(ethylene glycol) methyl ether (0.77 mL, 0.77 g, 6.45 mmol), anhydrous DMF (20 mL), and K$_2$CO$_3$ (1.8 g, 12.9 mmol). The reaction mixture was heated to 80° C. and allowed to stir for 16-18 h, after which time additional di(ethylene glycol) methyl ether (1.15 mL, 1.16 g, 9.67 mmol) was added. The reaction was heated to 130° C. and allowed to stir for 16-18 h. When judged to be complete, the reaction was allowed to cool to rt and was poured into ethyl acetate and water. The organic layer was washed with 5% NaOH aqueous solution, dried over MgSO$_4$, filtered and the solvents were removed under reduced pressure to afford 611 (1.07 g, 65%) as a yellow oil: $^1$H NMR (DMSO-d$_6$, 300 MHz) δ 8.06 (d, 1H), 7.08 (d, 1H), 7.01 (dd, 1H), 4.24 (t, 2H), 3.78 (t, 2H), 3.60 (m, 2H), 3.48 (m, 2H), 3.27 (s, 3H), 2.57 (s, 3H).

Step B:

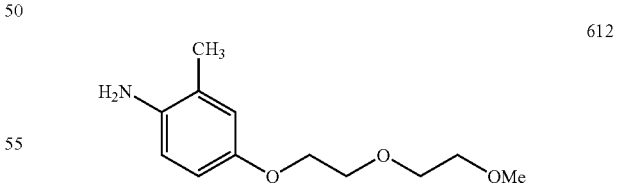

612

To a flask equipped with a stir bar were added 611 (0.36 g, 1.4 mmol), ethanol (10 mL), and palladium on charcoal (0.036 g of 10% Pd/C, 10% by weight). The vessel was placed on a hydrogenation apparatus at 43 p.s.i for 2 h, after which time the reaction mixture was filtered through celite. To the filtrate were added 1N HCl and ethyl acetate. The layers were separated and the pH of the aqueous layer was adjusted using saturated NaHCO$_3$.

The aqueous layer was extracted with ethyl acetate, dried over MgSO$_4$, filtered and the solvents were removed under reduced pressure to provide 612 (0.18 g, 57%) as a yellow oil: $^1$H NMR (DMSO-$d_6$, 400 MHz) δ 6.52 (s, 1H), 6.46 (s, 1H), 4.32 (bs, 2H), 3.86 (t, 2H), 3.60 (m, 2H), 3.50 (m, 2H), 3.39 (m, 2H), 3.19 (s, 3H), 1.96 (s, 3H).

Step C:

Acid 71 (0.16 g, 0.42 mmol), oxalyl chloride (0.04 mL, 0.058 g, 0.46 mmol), N,N-dimethylformamide (1 drop), and $CH_2Cl_2$ (7 mL) were used according to general procedure V. The resulting acid chloride, aniline 612 (0.09 g, 0.40 mmol), $NaHCO_3$ (0.176 g, 2.1 mmol), acetone (7 mL), and water (1 mL) were used according to general procedure VI. The resulting residue was treated with diethyl ether to afford 610 (0.061 g, 25%) as a white solid: MS (ES+) m/z 584 ($M^+$); $^1$H NMR (DMSO-$d_6$, 400 MHz) δ 9.06 (s, 1H), 7.97 (d, 1H), 7.82 (m, 2H), 7.63 (dd, 1H), 7.49 (d, 1H), 7.18 (d, 1H), 7.05 (d, 1H), 6.73 (s, 1H), 6.66 (dd, 1H), 4.66 (s, 2H), 3.98 (t, 2H), 3.65 (t, 2H), 3.52 (m, 2H), 3.40 (m, 2H), 3.19 (s, 3H), 1.95 (s, 3H).

Example 251

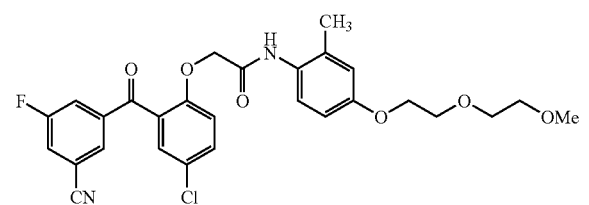

613

Step A:

Acid 496 (0.1 g, 0.3 mmol), oxalyl chloride (0.03 mL, 0.042 g, 0.33 mmol), N,N-dimethylformamide (1 drop), and $CH_2Cl_2$ (7 mL) were used according to general procedure V. The resulting acid chloride, aniline 612 (0.065 g, 0.29 mmol), $NaHCO_3$ (0.126 g, 1.5 mmol), acetone (10 mL), and water (0.5 mL) were used according to general procedure VI. The product was purified by flash chromatography using 2% MeOH:$CH_2Cl_2$ as eluant and then rechromatographed using 1:1 hexanes:ethyl acetate as eluant. Upon standing, crystals formed in the collected fractions. The crystals were collected and dried to afford 613 (0.012 g, 7%) a pink crystalline solid: $^1$H NMR (DMSO-$d_6$, 400 MHz) δ 9.08 (s, 1H), 8.09 (d, 1H), 7.99 (s, 1H), 7.87 (d, 1H), 7.63 (dd, 1H), 7.48 (d, 1H), 7.17 (d, 1H), 7.08 (d, 1H), 6.74 (d, 1H), 6.67 (dd, 1H), 4.67 (s, 2H), 3.99 (t, 2H), 3.65 (t, 2H), 3.51 (m, 2H), 3.40 (m, 2H), 3.19 (s, 3H), 1.95 (s, 3H).

Example 252

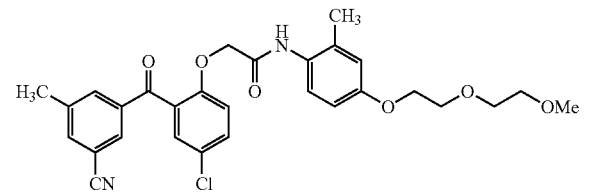

614

Acid 589 (0.138 g, 0.42 mmol), oxalyl chloride (0.04 mL, 0.058 g, 0.46 mmol), N,N-dimethylformamide (1 drop), and $CH_2Cl_2$ (7 mL) were used according to general procedure V. The resulting acid chloride, aniline 612 (0.09 g, 0.40 mmol), $NaHCO_3$ (0.176 g, 2.1 mmol), acetone (7 mL), and water (1 mL) were used according to general procedure VI. The product was purified by flash chromatography using 1:1 hexanes:ethyl acetate as eluant and subsequently treated with $Et_2O$ to afford 614 (0.048 g, 21%) as a beige solid: MS (ES+) m/z 537 ($M^+$); $^1$H NMR (DMSO-$d_6$, 400 MHz) δ 8.95 (s, 1H), 7.92 (s, 1H), 7.86 (m, 2H), 7.61 (dd, 1H), 7.45 (d, 1H), 7.18 (d, 1H), 7.08 (d, 1H), 6.74 (s, 1H), 6.67 (m, 1H), 4.66 (s, 2H), 3.99 (t, 2H), 3.65 (t, 2H), 3.51 (q, 2H), 3.40 (q, 2H), 3.19 (s, 3H), 2.31(s, 3H), 1.96 (s, 3H).

Example 253

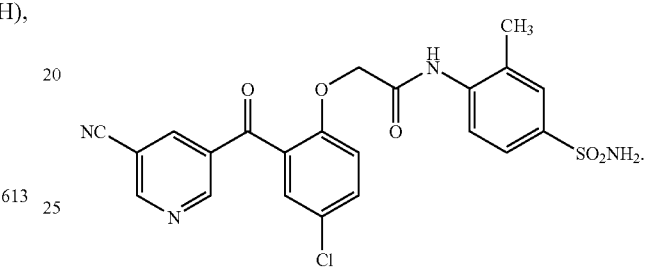

615

Step A:

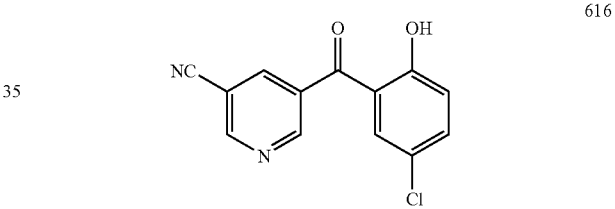

616

To a round bottom flask equipped with a reflux condenser, stir bar, and nitrogen on demand were placed 44 (0.45 g, 1.44 mmol), copper (I) cyanide (0.32 g, 3.6 mmol), and anhydrous DMF (20 mL). The reaction mixture was heated to reflux and allowed to stir for 3 h. When judged to be complete, the reaction was allowed to cool to rt and was poured into ethyl acetate and water. The resulting emulsion was filtered, the organic layer was collected, washed with brine, dried over $Na_2SO_4$, filtered and concentrated under reduced pressure to afford 616 (0.2 g, 54%) as a yellow solid: $^1$H NMR (DMSO-$d_6$, 400 MHz) δ 10.59 (s, 1H), 9.17 (d, 1H), 9.00 (d, 1H), 8.54 (m, 1H), 7.48 (dd, 1H), 7.43 (d, 1H), 6.95 (d, 1H).

Step B:

A mixture of 616 (0.20 g, 0.77 mmol), 470 (0.237 g, 0.77 mmol), potassium carbonate (0.213 g, 1.5 mmol), and sodium iodide (230 mg, 1.54 mmol) in 8 mL of acetone was warmed to reflux for 6 h. When judged to be complete, the reaction was allowed to cool to rt and was poured into EtOAc and water. The organic layer was collected, dried over $MgSO_4$, filtered, and the solvents were removed under reduced pressure. The residue was treated with $Et_2O$ and the resulting solid was filtered and recrystallized from $CH_3CN$ to provide 615 (8 mg, 3%): $^1$H NMR (DMSO-$d_6$, 300 MHz) δ 9.48 (s, 1H), 9.20 (d, 1H), 9.13 (d, 2H), 8.64 (t, 1H), 7.64 (m, 5H), 7.25 (m, 3H), 4.81 (s, 2H), 2.17 (s, 3H).

Example 254

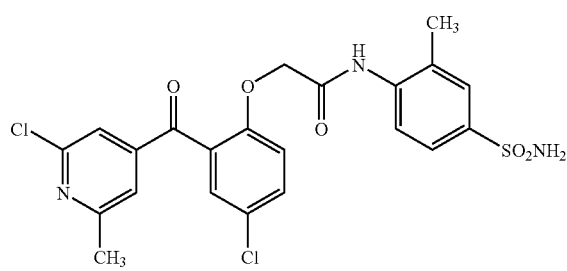

617

Step A:

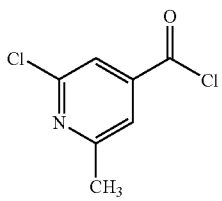

618

2-Chloro-6-methylisonicotinic acid (1 g, 5.8 mmol), CH$_2$Cl$_2$ (20 mL), oxalyl chloride (0.56 mL, 0.8 g, 6.4 mmol), and N,N-dimethylformamide (1 drop) were used according to general procedure V to afford 618 (1.1 g, >99%) as a purple oil. The product was used in the next step without further purification.

Step B:

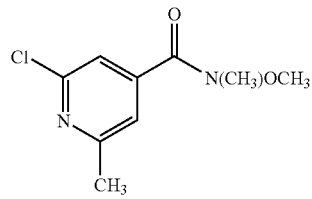

619

Acid chloride 618 (1.1 g, 5.8 mmol), N,O-dimethylhydroxylamine hydrochloride (1.1 g, 11.6 mmol), Et$_3$N (1.6 mL, 1.2 g, 11.6 mmol), and CHCl$_3$ (50 mL) were used according to general procedure VII to provide 619 (1.3 g, >99%) as a purple oil. The product was used in the next step without further purification: $^1$H NMR (DMSO-d$_6$, 300 MHz) δ 7.42 (s, 1H), 7.38 (s, 1H), 3.54 (s, 3H), 3.24 (s, 3H).

Step C:

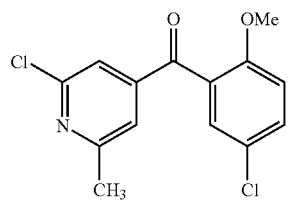

620

Amide 619 (1.3 g, 5.8 mmol), n-butyllithium (4 mL of a 1.6 M solution in hexanes, 6.4 mmol), 2-bromo-4-chloroanisole (0.8 mL, 1.3 g, 5.8 mmol), and diethyl ether (25 mL) were used according to general procedure VIII. The product was purified by flash chromatography using 3:2 hexanes: ethyl acetate as eluant to afford 620 (0.2 g, 12%) as a pale yellow solid: $^1$H NMR (DMSO-d$_6$, 300 MHz) δ 7.67 (dd, 1H), 7.50 (d, 1H), 7.42 (s, 1H), 7.38 (s, 1H), 7.24 (d, 1H), 3.65 (s, 3H), 2.51 (s, 3H).

Step D:

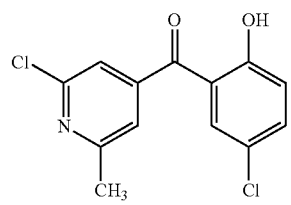

621

Anisole 620 (0.2 g, 0.68 mmol), BBr$_3$ (1.4 mL of a 1.0 M solution in CH$_2$Cl$_2$, 1.4 mmol), and CH$_2$Cl$_2$ (5 mL) were used according to general procedure 1× to afford 621 (0.163 g, 85%) as a yellow solid. The product was used without further purification: $^1$H NMR (DMSO-d$_6$, 400 MHz) δ 10.56 (s, 1H), 7.47 (dd, 1H), 7.41 (s, 1H), 7.38 (m, 2H), 6.93 (d, 1H), 2.47 (s, 3H).

Step E:

A mixture of 621 (0.08 g, 0.28 mmol), 470 (0.086 g, 0.28 mmol), and potassium carbonate (0.077 g, 0.56 mmol) in 10 mL of acetone was warmed to reflux for 1.5 h. When judged to be complete, the reaction was allowed to cool to rt and was poured into EtOAc and water. The organic layer was collected, dried over MgSO$_4$, filtered, and the solvents were removed under reduced pressure. The residue was treated with MeOH and the resulting solid was filtered to provide 617 (0.007 g, 5%): MS (ES+) m/z 508 (M$^+$); $^1$H NMR (DMSO-d$_6$, 400 MHz) δ 9.38 (s, 1H), 7.64 (m, 1H), 7.61 (s, 1H), 7.56 (s, 2H), 7.50 (m, 2H), 7.45 (s, 1H), 7.20 (m, 3H), 4.75 (s, 2H), 2.42 (s, 3H), 2.13 (s, 3H).

Example 255

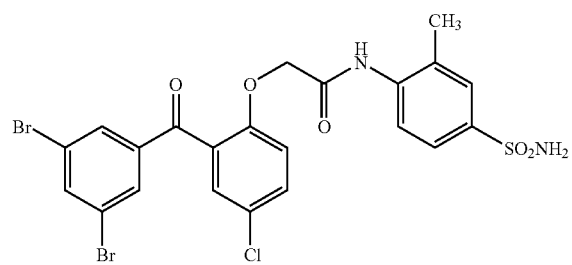

622

Step A:

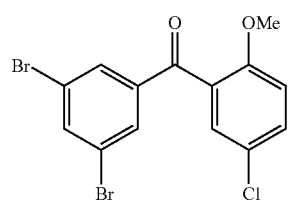

623

A solution of 1,3,5-tribromobenzene (3.0 g, 9.53 mmol) in 50 mL of ether was cooled to −78° C. in a dry ice/acetone bath. n-Butyllithium (4.2 mL of a 2.5 M solution in hexanes, 10.5 mmol) was added dropwise over 10 min. The resulting mixture was stirred at −78° C. for an additional 10 min, then 183 (2.0 g, 9.53 mmol) was added in small portions over 10 min. The reaction mixture was lifted from the cold bath, allowed to warm to rt and continue stirring for 1.5 h. The mixture was poured into water and extracted with Et$_2$O. The organic layers were collected, dried over MgSO$_4$, filtered, and concentrated in vacuo. The resulting orange residue was treated with MeOH, filtered and dried to provide 623 (2.03 g, 53%) as a yellow solid: $^1$H NMR (DMSO-d$_6$, 400 MHz) δ 8.12 (m, 1H), 7.71 (m, 2H), 7.60 (dd, 1H), 7.43 (d, 1H), 7.20 (d, 1H), 3.63 (s, 3H).

Step B:

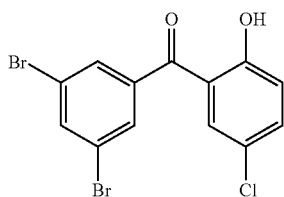

624

Anisole 623 (0.2 g, 0.49 mmol), BBr$_3$ (1 mL of a 1.0 M solution in CH$_2$Cl$_2$, 1 mmol), and CH$_2$Cl$_2$ (8 mL) were used according to general procedure 1x to afford 624-(0.176 g, 92%) as a yellow solid. The product was used without further purification: $^1$H NMR (DMSO-d$_6$, 400 MHz) δ 10.46 (s, 1H), 8.10 (m, 1H), 7.74 (m, 2H), 7.43 (dd, 1H), 7.35 (d, 1H), 6.93 (d, 1H).

Step C:

A mixture of 624 (0.12 g, 0.31 mmol), 470 (0.095 g, 0.31 mmol), potassium carbonate (0.086 g, 0.62 mmol), sodium iodide (0.093 g, 0.62 mmol) and 10 mL of acetone were warmed to reflux for 12-16 h. When judged to be complete, the reaction was allowed to cool to rt and was poured into EtOAc and water. The organic layer was collected, dried over MgSO$_4$, filtered, and the solvents were removed under reduced pressure. The residue was treated with Et$_2$O and the resulting solid was filtered and dried to provide 622 (0.04 g, 21%) as a yellow solid: $^1$H NMR (DMSO-d$_6$, 00 MHz) δ 9.35 (s, 1H), 8.07 (t, 1H), 7.83 (m, 2H), 7.60 (m, 4H), 7.47 (d, 1H), 7.20 (m, 3H), 4.77 (s, 2H), 2.14 (s, 3H).

Example 256

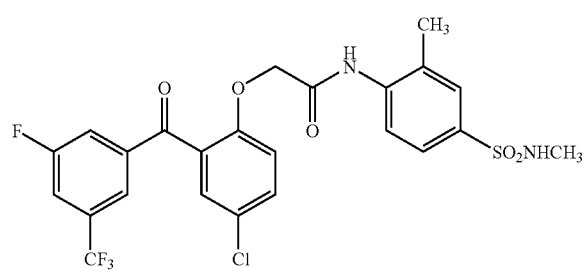

625

Step A:

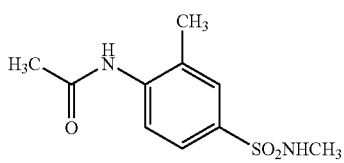

626

Into a round bottom flask equipped with a stir bar and gas dispersion tube was added sulfonyl chloride 464 (11.5 g, 0.046 mol) and THF (250 mL) and the mixture was cooled to 0° C. Methylamine gas was bubbled through the reaction mixture for 0.5 h, after which time, the mixture was poured into EtOAc and water. The pH of the aqueous layer was adjusted to 7 using concentrated HCl. The organic layer was collected, dried over MgSO$_4$, filtered and the solvents were removed under reduced pressure. The resulting orange residue was treated with Et$_2$O, filtered and dried to provide 626 (5.32 g, 48%): $^1$H NMR (DMSO-d$_6$, 300 MHz) δ 9.46 (s, 1H), 7.80 (d, 1H), 7.58 (m, 2H), 7.34 (m, 1H), 2.41 (d, 3H), 2.32 (s, 3H), 2.13 (s, 3H)

Step B:

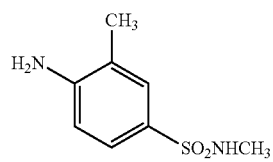

627

Into a round bottom flask equipped with a stir bar, reflux condenser, and nitrogen on demand were placed 626 (6.2 g, 0.026 mol), ethanol (250 mL), and 1.5 N (75 mL). The mixture was warmed to reflux and allowed to stir for 6 h. When judged to be complete, the reaction was allowed to cool to rt and was poured into a cold solution of saturated NaHCO$_3$. The mixture was extracted with several portions of EtOAc and the organic layer was dried over MgSO$_4$, filtered and concentrated under reduced pressure to provide 627 (3.6 g, 69%) as a yellow solid: $^1$H NMR (DMSO-d$_6$, 400 MHz). δ 7.23 (m, 2H), 6.82 (m, 1H), 6.59 (d, 1H), 5.62 (bs, 2H), 2.26 (d, 3H), 2.03 (s, 3H).

Step C:

Acid 71 (0.237 g, 0.63 mmol), oxalyl chloride (0.35 mL of a 2 M solution in CH$_2$Cl$_2$, 0.69 mmol), N,N-dimethylformamide (1 drop), and CH$_2$Cl$_2$ (7 mL) were used according to general procedure V to afford the acid chloride. The acid chloride, aniline 627 (0.12 g, 0.60 mmol), NaHCO$_3$ (0.264 g, 3.2 mmol), acetone (7 mL), and water (1 mL) were used according to general procedure VI. The resulting residue was treated with Et$_2$O and filtered to afford 625 (0.158 g, 45%) as a white solid: MS (ES+) m/z 558 (M$^+$); $^1$H NMR (DMSO-d$_6$, 400 MHz) δ 9.38 (s, 1H), 7.97 (d, 1H), 7.84 (m, 2H), 7.62 (m, 2H), 7.55 (m, 1H), 7.50 (m, 2H), 7.30 (m, 1H), 7.19 (d, 1H), 4.77 (s, 2H), 2.34 (d, 3H), 2.13 (s, 3H).

Example 257

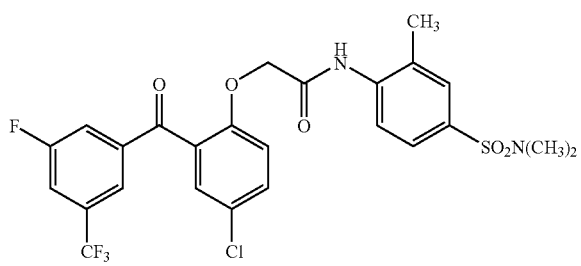
628

Step A:

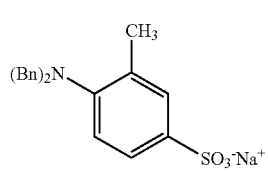
629

Into a round bottom flask equipped with a stir bar, reflux condenser and nitrogen on demand was added 2-aminotoluene-5-sulfonic acid (10 g, 0.053 mol), CH$_2$Cl$_2$ (120 mL), Na$_2$CO$_3$ (22.3 g, 0.21 mol) as a solution in water (120 mL), and the benzyl bromide (14.3 mL, 20.5 g, 0.12 mol). The reaction mixture was warmed to reflux and allowed to stir for 72 h. When judged to be complete, EtOH was added to the reaction mixture and the solvents were removed under reduced pressure to afford 629 (27.4 g, >100%) as a brown oil. The product was used in the next step without further purification.

Step B:

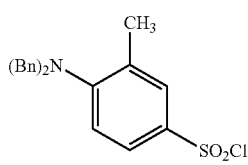
630

Into a round bottom flask equipped with a stir bar and nitrogen on demand were added 629 (20.6 g, 0.053 mol) and anhydrous DMF (200 mL). The mixture was cooled to 0° C. and thionyl chloride (11.7 mL, 19.0 g, 0.16 mol) was added dropwise over 15 min, after which time the reaction mixture was allowed to warm to rt and stir for an additional 2 h. When judged to be complete, the mixture was poured into ice water and was allowed to stir for 30 min. The aqueous mixture was extracted with EtOAc and the organic layer was dried over Na$_2$SO$_4$, filtered and concentrated under reduced pressure to afford 630 (5.0 g, 24%). The product was used without further purification.

Step C:

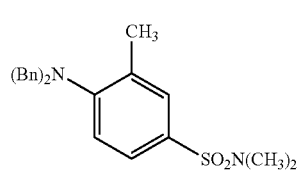
631

Dimethylamine (11.6 mL of a 5.6 M solution in EtOH, 0.065 mol) was placed in a round bottom flask equipped with a stir bar and nitrogen on demand, and cooled to 0° C. Sulfonyl chloride 630 (5.0 g, 0.013 mol) was added portion-wise over 10 min and the reaction mixture was allowed to stir at 0° C. for 30 min. When judged to be complete, the reaction mixture was poured into water and extracted with EtOAc. The organic layer was collected, dried over MgSO$_4$, filtered and concentrated under reduced pressure. The product was filtered through a pad of silica gel using CH$_2$Cl$_2$ as eluant and the filtrate concentrated under reduced pressure to afford 631 (1.0 g, 20%) as a yellow oil: $^1$H NMR (DMSO-d$_6$, 400 MHz) 7.47 (d, 1H), 7.22 (m, 11H), 7.05 (d, 1H), 4.13 (s, 4H), 2.48 (s, 6H), 2.44 (s, 3H).

Step D:

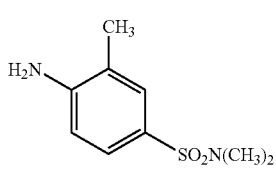
632

To a plastic-coated reaction vessel equipped with a stir bar, was added 631 (0.330 g, 0.85 mmol), toluene (10 mL), and palladium on charcoal (50 mg of 10% by weight Pd/C). The vessel was placed on a hydrogenation apparatus at 40 p.s.i. When the reaction was judged to be complete, it was filtered through celite and the filtrate was washed with saturated NaHCO$_3$ and water. The organic layer was collected, dried over MgSO$_4$, filtered and the solvents were removed under reduced pressure to provide 632 (120 mg, 67%) as a beige solid: $^1$H NMR (DMSO-d$_6$, 400 MHz) δ 7.19 (m, 2H), 6.64 (d, 1H), 5.74 (bs, 2H), 2.44 (s, 6H), 2.04 (s, 3H).

Step E:

Acid 71 (0.222 g, 0.59 mmol), oxalyl chloride (0.32 mL of a 2 M solution in CH$_2$Cl$_2$, 0.65 mmol), N,N-dimethylformamide (1 drop), and CH$_2$Cl$_2$ (7 mL) were used according to general procedure V. The resulting acid-chloride, aniline 632 (0.12 g, 0.56 mmol), NaHCO$_3$ (248 mg, 3.0 mmol), acetone (7 mL), and water (1 mL) were used according to general procedure VI. The resulting residue was treated with Et$_2$O and filtered to afford 628 (0.142 g, 42%) as a white solid: MS (ES+) m/z 572 (M$^+$); $^1$H NMR (DMSO-d$_6$, 400 MHz) δ 9.37 (s, 1H) 7.96 (d, 1H), 7.83 (m, 2H), 7.73 (d, 1H), 7.62 (dd, 1H), 7.50 (m, 3H), 7.19 (d, 1H), 4.78 (s, 2H), 2.53 (s, 6H), 2.17 (s, 3H).

Example 258

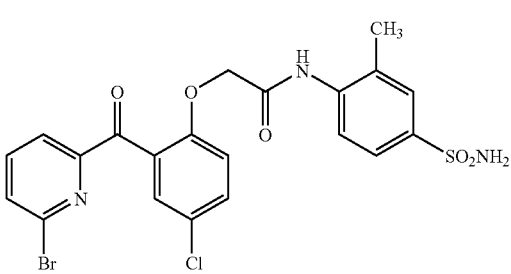
633

Step A:

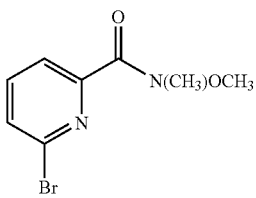

634

Picolinic acid (3 g, 0.015 mol), CH$_2$Cl$_2$ (50 mL), oxalyl chloride (1.5 mL, 2.2 g, 0.017 mol), and N,N-dimethylformamide (4-5 drops) were used according to general procedure V. The resulting acid chloride, N,O-dimethylhydroxylamine hydrochloride (2.9 g, 0.03 mol), Et$_3$N (4.2 mL, 3.0 g, 0.03 mol), and CHCl$_3$ (50 mL) were used according to general procedure VII to provide 634 (3.7 g, >99%) as a yellow oil. The product was used without further purification: $^1$H NMR (DMSO-d$_6$, 400 MHz) δ 7.83 (m, 1H), 7.72 (m, 1H), 7.59 (d, 1H), 3.61 (s, 3H), 3.21 (s, 3H).

Step B:

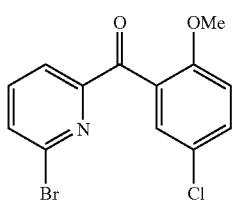

635

Amide 634 (3.7 g, 0.015 mol), n-butyllithium (6.4 mL of a 2.5 M solution in hexanes, 0.016 mol), 2-bromo-4-chloroanisole (2.1 mL, 3.3 g, 0.015 mol), and anhydrous diethyl ether (20 mL) were used according to general procedure VIII. The product was purified by flash chromatography using 9:1 hexanes:ethyl acetate as eluant and subsequently recrystallized from MeOH to afford 635 (2.25 g, 46%) as a white solid: $^1$H NMR (DMSO-d$_6$, 400 MHz) δ 7.90 (m, 3H), 7.55 (dd, 1H), 7.44 (d, 1H), 7.17 (d, 1H), 3.58 (s, 3H).

Step C:

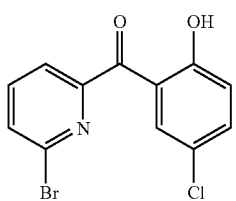

636

Anisole 635 (0.227 g, 0.85 mmol), BBr$_3$ (1.7 mL of a 1.0 M solution in CH$_2$Cl$_2$, 1.7 mmol), and CH$_2$Cl$_2$ (15 mL) were used according to general procedure 1x to afford 636 (0.069 g, 26%) as a yellow solid. The product was used in the next step without further purification: $^1$H NMR (DMSO-d$_6$, 400 MHz) δ 10.40 (s, 1H), 7.88 (m, 3H), 7.43 (m, 2H), 6.99 (d, 1H).

Step D:

A mixture of 636 (0.07 g, 0.22 mmol), 482 (0.081 g, 0.23 mmol), potassium carbonate (0.061 g, 0.44 mmol) in 10 mL of acetone was heated to reflux. When the reaction was judged to be complete, it was allowed to cool to rt and was poured into EtOAc and water. The organic layer was collected, dried over MgSO$_4$, filtered, and the solvents were removed under reduced pressure. The resulting solid was washed with warm CH$_3$CN, filtered and dried to provide 633 (0.027 g, 23%) as a white solid: MS (ES+) m/z 540 (M+H); $^1$H NMR (DMSO-d$_6$, 400 MHz) δ 9.23 (s, 1H), 7.88 (m, 3H), 7.56 (m, 5H), 7.23 (m, 3H), 4.66 (s, 2H), 2.09 (s, 3H).

Example 259

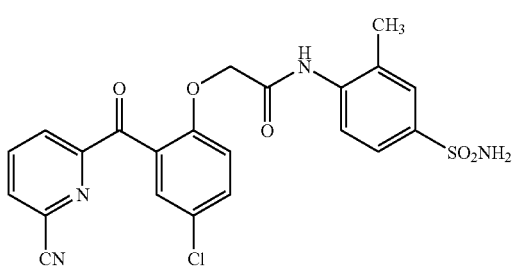

637

Step A:

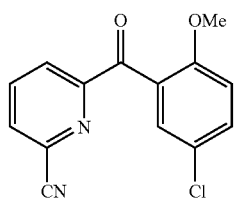

638

Into a round bottom flask equipped with a stir bar, nitrogen on demand, and a reflux condenser were added 635 (0.750 g, 2.3 mmol), sodium cyanide (0.225 g, 4.6 mmol), copper (I) iodide (0.078 g, 0.41 mmol), and acetonitrile (10 mL). A stream of nitrogen was bubbled through the reaction mixture for 5 min, after which time tetrakis-(triphenylphosphine)palladium (1.0 g, 0.89 mmol) was added and the mixture was heated to reflux for 2 h. The reaction mixture was allowed to cool to rt and poured into EtOAc and water. The organic layer was collected, dried over MgSO$_4$, filtered, and concentrated under reduced pressure. The orange residue was treated with Et$_2$O and the resulting solid was filtered and dried to provide 638 (321 mg, 51%) as a pale yellow solid: $^1$H NMR (DMSO-d$_6$, 300 MHz) δ 8.23 (m, 3H), 7.63 (dd, 1H), 7.51 (d, 1H), 7.22 (d, 1H), 3.59 (s, 3H).

Step B:

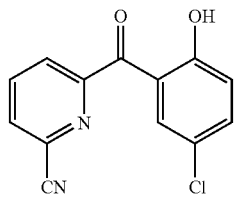

639

Anisole 638 (0.32 g, 1.17 mmol), BBr$_3$ (2.3 mL of a 1.0 M solution in CH$_2$Cl$_2$, 2.3 mmol), and CH$_2$Cl$_2$ (15 mL) were used according to general procedure IX. The resulting residue was recrystallized from MeOH to afford 639 (0.046 g, 15%) as an orange solid: $^1$H NMR (DMSO-$d_6$, 400 MHz) δ 10.39 (s, 1H), 8.20 (m, 3H), 7.45 (m, 2H), 6.90 (d, 1H).

Step C:

A mixture of 639 (0.045 g, 0.17 mmol), 482 (0.064 g, 0.18 mmol), potassium carbonate (0.047 g, 0.34 mmol) in 10 mL of acetone was heated to reflux. When the reaction was judged to be complete, the mixture was allowed to cool to rt and was poured into EtOAc and water. The organic layer was collected, dried over MgSO$_4$, filtered, and the solvents were removed under reduced pressure. The resulting solid was recrystallized from CH$_3$CN, filtered and dried to provide 637 (19 mg, 23%) as a pale yellow solid: MS (ES) m/z 484 (M$^+$), 483 (M−H)$^−$; $^1$H NMR (DMSO-$d_6$, 400 MHz) δ 9.31 (s, 1H), 8.20 (m, 3H), 7.57 (m, 5H), 7.20 (m, 3H), 4.64 (s, 2H), 2.10 (s, 3H).

Example 260

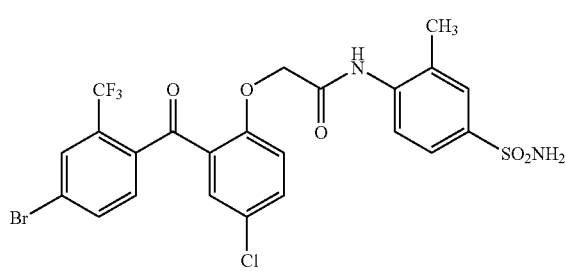

640

Step A:

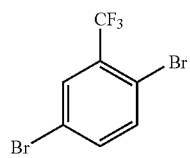

641

To a round bottom flask equipped with a stir bar and nitrogen on demand were added copper (II) bromide (5.36 g, 0.024 mol) and CH$_3$CN (100 mL). The reaction mixture was cooled to 0° C. and t-butyl nitrite (3.8 mL, 3.3 g, 0.032 mol) was added dropwise over 15 min. 2-amino-5-bromobenzotrifluoride (5 g, 0.021 mol) was added dropwise over 15 min and the resulting mixture was allowed to continue stirring at 0° C. for 1.5 The mixture was then allowed to warm to RT and stir for an additional 16-18 h. When judged to be complete, the mixture was concentrated to ½ the original volume, was poured into 1N HCl and extracted with Et$_2$O. The organic layer was collected and concentrated under reduced pressure to afford 641 (5.5 g, 86%) as a yellow oil: $^1$H NMR (400 MHz) δ 7.96 (s, 1H), 7.78 (m, 2H).

Step B:

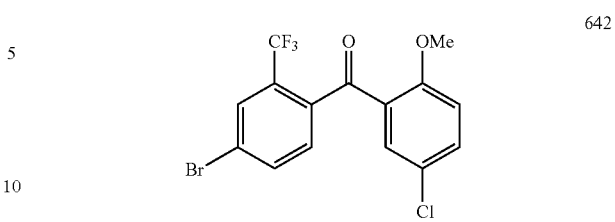

642

A solution of 641 (5.5 g, 18 mmol) in 60 mL of ether was cooled to −78° C. in a dry ice/acetone bath. n-Butyllithium (9.2 mL of 2.5 M solution in hexanes, 23 mmol) was added dropwise over 10 min. The resulting mixture was stirred at −78° C. for an additional 10 min, then 183 (3.8 g, 18 mmol) was added in small portions over 10 min. The reaction mixture was allowed to warm to rt and continue stirring for 2 h and was poured into water and extracted with EtOAc. The organic layer was collected, dried over MgSO$_4$, filtered, and concentrated under reduced pressure. The product was purified by flash chromatography using 2% EtOAc in hexanes as eluant to provide 642 (1.7 g, 24%) as a yellow oil: $^1$H NMR (DMSO-$d_6$, 400 MHz) δ 8.03 (d, 1H), 7.88 (m, 1H), 7.65 (dd, 1H), 7.60 (d, 1H), 7.36 (d, 1H), 7.16 (d, 1H), 3.47 (s, 3H).

Step C:

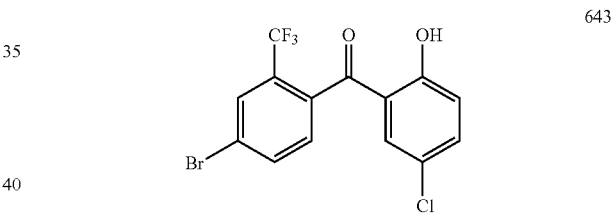

643

Anisole 642 (0.5 g, 1.27 mmol), BBr$_3$ (2.5 mL of a 1.0 M solution in CH$_2$Cl$_2$, 2.5 mmol), and CH$_2$Cl$_2$ (10 mL) were used according to general procedure 1× to afford 643 (0.4 g, 83%) as a yellow oil. $^1$H NMR (DMSO-$d_6$, 400 MHz) δ 10.71 (s, 1H), 8.03 (s, 1H), 7.92 (d, 1H), 7.50 (m, 3H), 6.90 (d, 1H).

Step D:

A mixture of 643 (0.400 g, 1.05 mmol), 470 (0.322 g, 1.05 mmol), potassium carbonate (0.290 g, 2.1 mmol) and sodium iodide (0.315 g, 2.1 mmol) in 15 mL of acetone was warmed to reflux and allowed to stir for 16 h. When the reaction was judged to be complete, the mixture was allowed to cool to rt and was poured into EtOAc and water. The organic layer was collected, dried over MgSO$_4$, filtered, and the solvents were removed under reduced pressure. The resulting residue was purified by flash chromatography using 3% MeOH/CH$_2$Cl$_2$ as eluant to provide a yellow solid. The solid was recrystallized from CH$_3$CN, filtered and dried to provide 640 (16 mg, 3%) as a white solid: $^1$H NMR (DMSO-$d_6$, 400 MHz) 69.31 (s, 1H), 8.01 (s, 1H), 7.90 (d, 2H), 7.66 (m, 5H), 7.47 (d, 1H), 7.24 (m, 3H), 4.67 (s, 2H), 2.23 (s, 3H).

Example 261

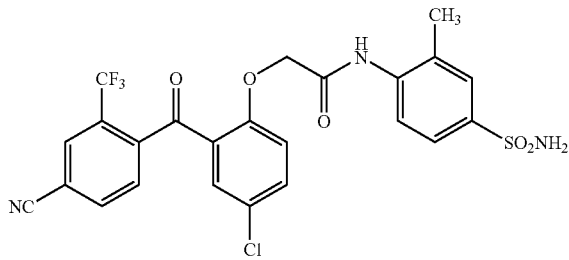

Step A:

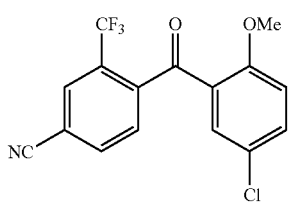

Into a round bottom flask equipped with a stir bar, nitrogen on demand, and a reflux condenser were added 642 (0.250 g, 0.64 mmol), sodium cyanide (0.063 g, 1.3 mmol), copper (I) iodide (0.023 g, 0.12 mmol), and acetonitrile (10 mL). A stream of nitrogen was bubbled through the reaction mixture for 5 min., after which time-tetrakis-(triphenylphosphine)palladium (0.086 g, 0.08 mmol) was added and the mixture was heated to reflux for 6 h. The reaction mixture was allowed to cool to rt and resulting precipitate was filtered. The precipitate was dissolved in EtOAc and washed with water. The organic layer was collected, filtered through a pad of celite, dried over $MgSO_4$, filtered, and concentrated under reduced pressure to provide an orange residue. The residue was treated with $Et_2O$, filtered and dried to afford 645 (57 mg, 26%) as a white solid: $^1$H NMR (DMSO-$d_6$, 300 MHz) δ 8.27 (s, 1H), 8.16 (d, 1H), 7.71 (dd, 1H), 7.64 (d, 1H), 7.56 (d, 1H), 7.22 (d, 1H), 3.54 (s, 3H).

Step B:

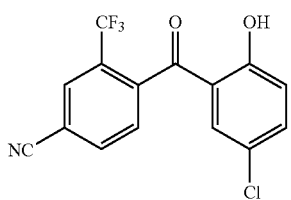

Anisole 645 (0.126 g, 0.37 mmol), $BBr_3$ (0.74 mL of a 1.0 M solution in $CH_2Cl_2$, 0.74 mmol), and $CH_2Cl_2$ (15 mL) were used according to general procedure IX. The resulting residue was treated with $Et_2O$ and filtered to afford 646 (0.077 g, 64%) as a pale yellow solid. $^1$H NMR (DMSO-$d_6$, 400 MHz) δ 10.80 (s, 1H), 8.25 (s, 1H), 8.16 (d, 1H), 7.64 (d, 1H), 7.55 (dd, 1H), 7.45 (d, 1H), 6.95 (d, 1H).

Step C:

A mixture of 646 (0.077 g, 0.24 mmol), 482 (0.089 g, 0.25 mmol), potassium carbonate (0.066 g, 0.48 mmol) in 10 mL of acetone was heated to reflux. When the reaction was judged to be complete, it was allowed to cool to rt and was poured into EtOAc and water. The organic layer was collected, dried over $MgSO_4$, filtered, and the solvents were removed under reduced pressure. The resulting residue was treated with $Et_2O$ to provide a yellow solid. The solid was recrystallized from $CH_3CN$, filtered and dried to provide 644 (11 mg, 3%) as a pale yellow solid: $^1$H NMR (DMSO-$d_6$, 400 MHz) δ 9.31 (s, 1H), 8.18 (s, 1H), 8.05 (d, 1H), 7.64 (m, 6H), 7.23 (m, 3H), 4.69(s, 2H), 2.17 (s, 3H).

Example 262

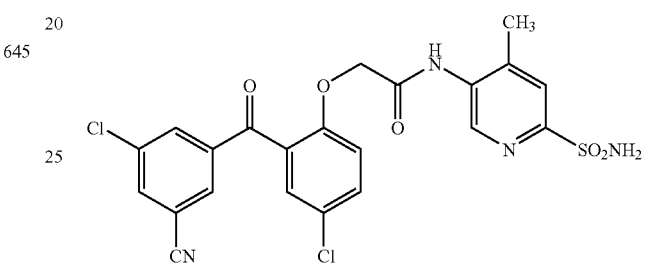

Step A:

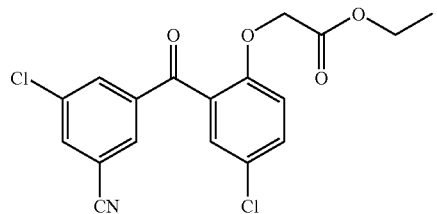

Phenol 477 (0.345 g, 1.2 mmol), $K_2CO_3$ (0.326 g, 2.4 mmol), ethyl bromoacetate (0.14 mL, 0.207 g, 1.3 mmol) and acetone (10 mL) were used according to general procedure II to provide 648 as an orange oil (0.46 g, >99%). The product was without further purification: $^1$H NMR (DMSO-$d_6$, 400 MHz) δ 8.28 (t, 1H), 8.04 (d, 1H), 7.98 (t, 1H), 7.58 (dd, 1H), 7.47 (d, 1H), 7.11(d, 1H), 4.73 (s, 2H), 4.07 (m, 2H), 1.11 (m, 3H).

Step B:

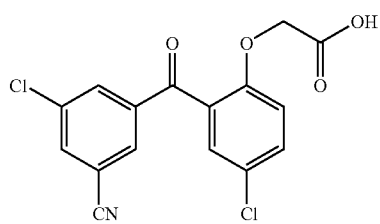

Ester 648 (0.46 g, 1.2 mmol), THF (4 mL), water (1 mL), EtOH (1 mL) and LiOH (0.128 g, 3.1 mmol) were used according to general procedure III to afford 649 (0.25 g, 60%) as a yellow foam. The product was used without further purification: ¹H NMR (DMSO-d₆, 400 MHz) δ 13.1 (bs, 1H), 8.27 (s, 1H), 8.06 (s, 1H), 8.00 (s, 1H), 7.57 (dd, 1H), 7.45 (d, 1H), 7.08 (d, 1H), 4.63 (s, 2H), 4.07 (m, 2H), 1.11 (m, 3H).

Step C:

Acid 649 (0.120 g, 0.34 mmol), oxalyl chloride (0.04 mL, 0.06 g, 0.48 mmol), N,N-dimethylformamide (1 drop), and CH₂Cl₂ (7 mL) were used according to general procedure V. The resulting acid chloride, aniline 490 (0.064 g, 0.34 mmol), NaHCO₃ (0.14 g, 1.7 mmol), acetone (7 mL), and water (1 mL) were used according to general procedure VI. The resulting residue purified by flash chromatography using 3% MeOH: CH₂Cl₂ as eluant to afford 647 (0.01 g, 6%) as a pale yellow solid: MS (ES+) m/z 519 (M⁺): ¹H NMR (400 MHz, DMSO-d₆) δ 9.72 (s, 1H), 8.66 (s, 1H), 8.26 (s, 1H), 8.12 (s, 1H), 8.04 (s, 1H), 7.75 (d, 1H), 7.62 (dd, 1H), 7.50 (d, 1H), 7.34 (s, 2H), 7.20 (d, 1H), 4.81 (s, 2H), 2.20 (s, 3H) ppm.

Example 263

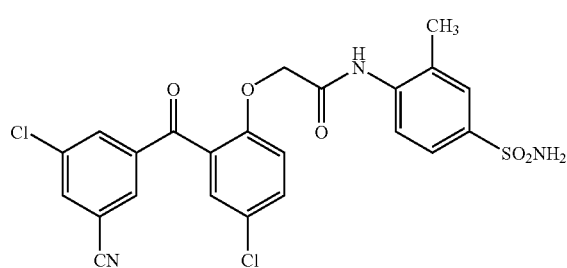

650

Acid 649 (0.1 g, 0.3 mmol) was converted to the acid chloride by general procedure V, and coupled with 5-amino-6-methyl-2-pyridinesulfonamide (0.06 g, 0.33 mmol, 1.1 eq.) as outlined in Step E for the synthesis of compound 503 in example 206 to give 650. LCMS (ES⁺) 520 m+1/z. ¹H NMR (DMSO-d₆) δ 9.65 (br s, 1H, NH), 8.3(s, 1H, Ar), 8.1 (m, 2H, Ar), 8.0 (s, 1H, Ar), 7.7 (d, 1H, Ar), 7.6 (dd, 1H, Ar), 7.5 (d, 1H, Ar), 7.32 (bs, 2H, NH₂), 7.2 (d, 1H, Ar), 4.8 (s, 2H, CH₂), 2.3 (s, 3H, CH₃).

Example 264

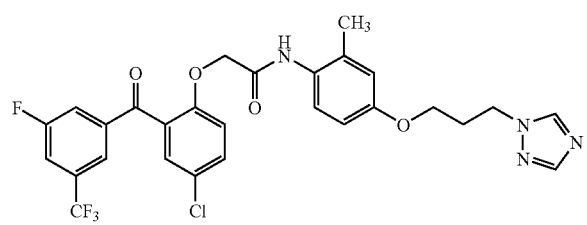

651

Step A:

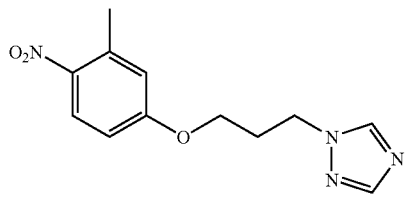

652

4-(3-Bromo-propoxy)-2-methyl-1-nitrobenzene (1 g, 3.6 mmol) and 1,2,4-triazole (Aldrich, 0.25 g, 3.6 mmol) were used in the same manner as to prepare compound 139. Compound 652 (0.45 g, 48%) was obtained as an oil. ¹H NMR (DMSO-d₆, 400 MHz) δ 2.4 (br s, 4H), 2.45 (s, 3H), 4.1 (t, 2H), 6.9 (dd, 1H), 6.92 (d, 1H), 7.9 (d, 2H), 8 (d, 1H).

Step B:

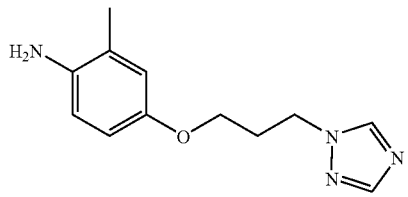

653

Compound 652 was used in the same manner as that to prepare compound 140. Aniline 653 was obtained as an oil (0.33 g, 84%). The compound was used without further purification.

Step C:

Acid 71 (0.26 g, 0.7 mmol), oxalyl chloride (0.09 mL, 1 mmol), DMF (1 drop), and CH₂Cl₂ were used according to general procedure V to afford the desired acid chloride. The acid chloride, aniline 653 (0.16 g, 0.7 mmol), NaHCO₃ (0.3 g, 3 mmol), acetone (8 mL), and water (0.3 mL) were used according to general procedure VI. Flash column chromatography of the crude product on silica gel with 2% methanol in CH₂Cl₂ afforded 651 (0.05 g, 12%) as a white solid. ¹H NMR (DMSO-d₆, 400 MHz) δ 1.9 (s, 3H), 2.1-2.2 (m, 2H), 3.8 (t, 2H), 4.3 (t, 2H), 4.66 (s, 2H), 6.6 (dd, 1H), 6.7 (d, 1H), 7.03 (d, 1H), 7.2 (d, 1H), 7.5 (d, 1H), 7.6 (dd, 1H), 7.8-7.82 (m, 2H), 7.9 (s, 1H), 8 (d, 1H), 8.5 (s, 1H), 9.02 (s, 1H).

Example 265

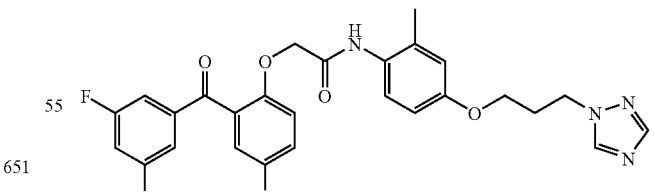

654

Acid 49 (0.14 g, 0.4 mmol), oxalyl chloride (0.2 mL, 2 mmol), DMF (1 drop), and CH₂Cl₂ were used according to general procedure V. The resulting acid chloride, aniline 653 (0.1 g, 0.4 mmol), NaHCO₃ (0.17 g, 1.7 mmol), acetone (5 mL), and water (0.1 mL) were used according to general procedure VI. Flash column chromatography of the crude product on silica gel with 2% methanol in CH₂Cl₂ resulted in 654 (0.04 g, 18%) as a white solid. $^1$H NMR (DMSO-$d_6$, 400 MHz) δ 1.9 (s, 3H), 2.1-2.2 (m, 2H), 3.8 (t, 2H), 4.3 (t, 2H), 4.7 (s, 2H), 6.6 (dd, 1H), 6.7 (d, 1H), 7.08 (d, 1H), 7.2 (d, 1H), 7.3-7.4 (m, 2H), 7.42-7.6 (m, 3H), 7.9 (s, 1H), 8.5 (s, 1H), 9 (s, 1H).

Example 266

655

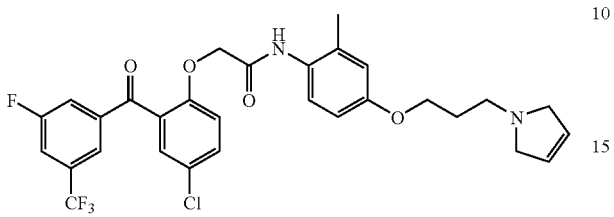

Acid 71 (1.4 g, 3.6 mmol), thionyl chloride (1.3 mL, 18 mmol), DMF (1 drop), and CH$_2$Cl$_2$ were used according to general procedure V to afford the desired acid chloride. The acid chloride, aniline 595 (0.84 g, 3.6 mmol), NaHCO$_3$ (1.36 g, 16 mmol), acetone (50 mL), and water (1 mL) were used according to general procedure VI. Flash column chromatography of the crude product on silica gel with 5% methanol in CH$_2$Cl$_2$ afforded 655 (0.53 g, 25%) as a solid. $^1$H NMR (DMSO-$d_6$, 400 MHz) δ 1.7-1.8 (m, 2H), 1.95 (s, 3H), 2.6-2.7 (m, 2H), 3.4 (br s, 4H), 3.9 (t, 2H), 4.66 (s, 2H), 5.7 (s, 2H), 6.6 (dd, 1H), 6.7 (d, 1H), 7.0 (d, 1H), 7.2 (d, 1H), 7.5 (d, 1H), 7.6 (dd, 1H), 7.8-7.82 (m, 2H), 8 (d, 1H), 9.02 (s, 1H).

Example 267

656

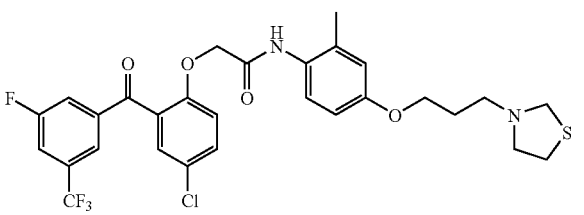

Step A:

657

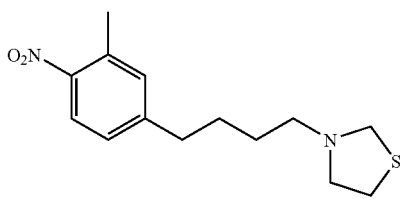

4-(3-Bromo-propoxy)-2-methyl-1-nitrobenzene (1 g, 3.6 mmol) and thiazolidine (Aldrich, 0.34 mL, 4.3 mmol) were used in the same manner as to prepare compound 139. Compound 657 (0.45 g, 48%) was obtained as an oil and was used without further purification.

Step B:

The nitro group of 657 (1 g, 3.5 mmol) was reduced under catalytic conditions (H$_2$, 10% Pd/C in EtOH). Acid 71 (1.3 g, 3.5 mmol), thionyl chloride (1.3 mL, 18 mmol), DMF (I drop), and CH$_2$Cl$_2$ were used according to general procedure V to afford the desired acid chloride. The resultant crude aniline, acid chloride, NaHCO$_3$ (1.4 g, 16 mmol), acetone (50 mL), and water (1 mL) were used according to general procedure VI. Flash column chromatography of the crude product on silica gel with EtOAc:hexane (7:3) resulted in 656 (0.14 g, 7%) as a white solid. $^1$H NMR (DMSO-$d_6$, 300 MHz) δ 1.7-1.8 (m, 2H), 2 (s, 3H), 2.4 (t, 2H), 2.8 (t, 2H), 3 (t, 2H), 3.94 (m, 5H), 4.7 (s, 1H), 6.6 (dd, 1H), 6.7 (d, 1H), 7.0 (d, 1H), 7.2 (d, 1H), 7.5 (d, 1H), 7.6 (dd, 1H), 7.8-7.82 (m, 2H), 8 (d, 1H), 9.02 (s, 1H).

Example 268

658

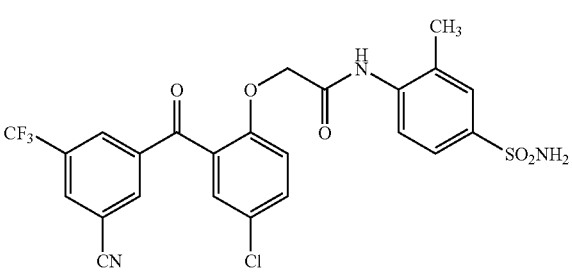

Step A:

659

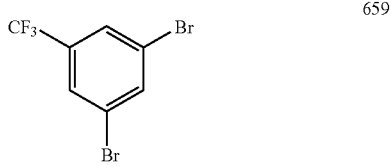

To a solution of copper (II) bromide (5.36 g, 24 mmol) in acetonitrile (100 ml) at 0° C. was added t-butyl nitrite (3.8 ml, 32 mmol) dropwise, and then 3-amino-5-bromobenzotrifluoride (5 g, 21 mmol) dropwise. The mixture was stirred at 0° C. for 1.5 h, then at room temperature for 16 h. The mixture was then concentrated to half of its original volume in vacuo, and then poured into 1N HCl (120 ml). This mixture was extracted with ether (100 mL). The organic layer was washed with 1N HCl, dried (Na$_2$SO$_4$), filtered, concentrated in vacuo (Note: product is fairly volatile, and should not be exposed to high vacuum for extended periods of time) to give 659 as a brown oil (5.12 g), which was used as is without further purification. $^1$H NMR (CDCl$_3$, 400 MHz) δ 7.82 (s, 1H), 7.67 (s, 2H).

Section B:

660

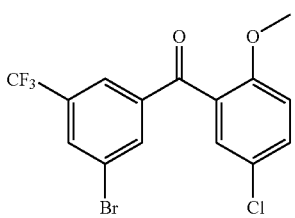

659 (5.12 g), N-methyl-N-methoxy-2-methoxy-5-chlorobenzamide (3.6 g, 16.8 mmol), and n-butyllithium (8.76 ml of 2.7M solution in heptane) were treated according to the procedure outlined in Part A of Example 2 to give 660 (3.36 g), which was used as is without further purification. $^1$H NMR (CDCl$_3$, 400 MHz) δ 8.02 (s, 1H), 7.89 (d, 2H), 7.46 (dd, 1H), 7.38 (d, 1H), 6.92 (d, 1H), 3.66 (s, 3H).

Section C:

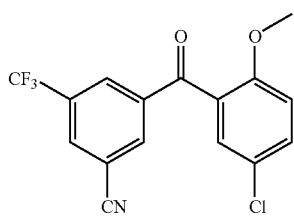
661

660 (3.36 g, 8.55 mmol), sodium cyanide (838 mg, 17 mmol), copper (I) iodide (325 mg, 1.7 mmol), and tetrakis (triphenylphospine)palladium (0) (987 mg, 0.86 mmol) were used according to General Procedure A to give 661 (1.35 g) after silica gel purification (10% ethyl acetate/hexanes). $^1$H NMR (CDCl$_3$, 400 MHz) δ 8.19 (s, 1H), 8.13 (s, 1H), 8.04 (s, 1H), 7.50 (dd, 1H), 7.43 (d, 1H), 6.94 (1H), 3.65 (s, 3H).

Section D:

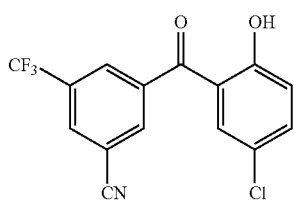
662

661 (1.35 g, 3.98 mmol) was treated according to the procedure for the synthesis of compound 4 to give 662 (1.29 g, >99%) as a yellow oil, which was used without further purification. $^1$H NMR (CDCl$_3$, 300 MHz) δ 11.49 (s, 1H), 8.20-8.16 (m, 3H), 7.59 (dd, 1H), 7.38 (d, 1H), 7.15 (d, 1H).

Step E:

662 (487 mg, 1.5 mmol) and 470 were treated according to Step D in Example 197 to give a crude product which was purified by silica gel chromatography (8:1:1 CH$_2$Cl$_2$/ethyl acetate/methanol) and triturated with ether to give 658 (315 mg) as an off-white solid. $^1$H NMR (DMSO-d$_6$, 400 MHz) δ 9.41 (s, 1H), 8.56 (s, 1H), 8.45 (s, 1H), 8.27 (s, 1H), 7.66-7.52 (m, 5H), 7.19 (m, 3H), 4.76 (s, 2H), 2.12 (s, 3H); MS(ES-): m/z 550 (M-H)$^-$.

Example 269

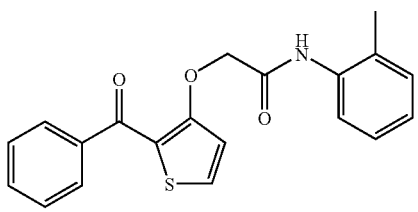
663

Step A:

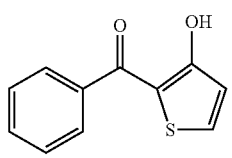
664

A mixture of 3-methoxythiophene (1.14 g, 10 mmol), aluminum chloride (2.67 g, 20 mmol), and benzoyl chloride (1.16 mL, 10 mmol) in 50 mL of methylene chloride was heated to reflux for 20 h. The reaction mixture was then poured over ice and stirred at room temperature for 5 h, after which the aqueous layer was separated and extracted with 20 mL of CH$_2$Cl$_2$. The combined organic layers were then dried over MgSO$_4$, filtered and concentrated in vacuo to give 1.897 g of orange oil. Purification by flash chromatography using 5-7% EtOAc/hexane as eluant gave 664 (0.823 g, 40%) as a yellow crystalline solid: $^1$H NMR (CDCl$_3$, 400 MHz) δ 12.35 (s, 1H), 7.92 (dd, 2H), 7.56-7.46 (m, 4H), 6.83 (d, 1H).

Step B:

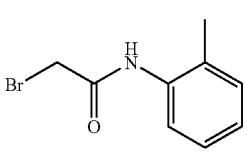
665

A solution of o-toluidine (2.67 mL, 25 mol) and pyridine (2.2 mL, 27.5 mmol) in 200 mL of chloroform was cooled to 0° C. in an ice bath. Bromoacetyl bromide (2.4 mL, 27.5 mmol) was added dropwise over 7 min, and the resulting mixture was allowed to slowly warm to rt and stirred for 24 h. The reaction mixture was then poured into 150 mL of water. The aqueous layer was separated and extracted with 100 mL of CH$_2$Cl$_2$. The combined organic layers were dried over MgSO$_4$, filtered and concentrated in vacuo to give 665 (5.86 g, quantitative): $^1$H NMR (CDCl$_3$, 400 MHz) δ 8.10 (br s, 1H), 7.81 (d, 1H), 7.20-7.17 (m, 2H), 7.10-7.06 (m, 1H), 4.04 (s, 2H), 2.27 (s, 3H).

Step C:

A mixture of 664 (0.204 g, 1.0 mmol), 665 (0.235 g, 1.03 mmol), and potassium carbonate (0.622 g, 4.5 mmol) in 10 mL of acetone was warmed to reflux for 6 h, then stirred at room temperature an additional 16 h. The reaction mixture was then poured into 30 mL of water and extracted with two 30-mL portions of EtOAc. The combined organic layers were dried over MgSO$_4$, filtered and concentrated in vacuo to yield 0.448 g of crude material. Purification by flash chromatography using 35% EtOAc/hexanes as the eluant gave 663 (0.272 g, 77%): MS (ES+) m/z 352 (M+H); $^1$H NMR (CDCl$_3$, 400 MHz) δ 8.53 (br s, 1H), 7.81-7.79 (m, 2H), 7.59 (d, 1H), 7.42-7.38 (m, 3H), 7.19-7.16 (m, 2H), 7.10-7.07 (m, 1H), 6.93 (d, 1H), 4.73 (s, 2H), 2.19 (s, 3H).

Example 270

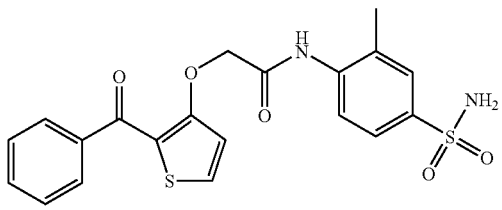

666

A mixture of 664 (0.218 g, 1.07 mmol), 470 (0.338 g, 1.1 mmol), and potassium carbonate (0.622 g, 4.5 mmol) in 10 mL of acetone was warmed to reflux for 5 h. The reaction mixture was then poured into 30 mL of water and extracted with 30 mL of EtOAc. The pH of the aqueous layer was adjusted to 7 using 3 M HCl, then extracted with 30 mL of EtOAc. The combined organic layers were filtered to remove yellow solid, dried over MgSO$_4$, filtered, and concentrated in vacuo to give 0.360 g of crude material. This material was suspended in CH$_2$Cl$_2$ and acetone and filtered, then suspended in MeOH and filtered to give 666 (0.076 g, 17%): MS (ES+) m/z 431 (M+H); $^1$H NMR (CDCl$_3$, 400 MHz) δ 9.29 (s, 1H), 7.96 (d, 1H), 7.77 (d, 2H), 7.67 (d, 1H), 7.62 (d, 1H), 7.58 (dd, 1H), 7.50 (t, 1H), 7.43-7.48 (m, 2H), 7.23 (br s, 2H), 7.15 (d, 1H), 4.83 (s, 2H), 2.16 (s, 3H).

Example 271

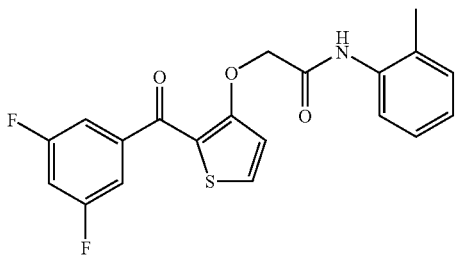

667

Step A:

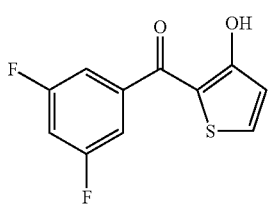

668

A mixture of 3-methoxythiophene (1.14 g, 10 mmol), aluminum chloride (2.70 g, 20.2 mmol), and 3,5-difluorobenzoyl chloride (1.18 mL, 10 mmol) in 50 mL of methylene chloride was heated to reflux for 20 h, then stirred at room temperature for 27 h. The reaction mixture was then poured over ice and stirred at room temperature for 40 min, after which the aqueous layer was separated and extracted with 20 mL of CH$_2$Cl$_2$. The combined organic layers were then dried over MgSO$_4$, filtered and concentrated in vacuo to give 1.214 g of brown solid. Purification by flash chromatography using 2% EtOAc/hexane as eluant gave 668 (0.518 g, 22%) as a yellow solid: $^1$H NMR (CDCl$_3$, 400 MHz) δ 12.04 (s, 1H), 7.57 (d, 1H), 7.43 (dd, 2H), 7.02-6.97 (m, 1H), 6.84 (d, 1H).

Step B:

A mixture of 668 (0.192 g, 0.80 mmol), 665 (0.188 g, 0.82 mmol), and potassium carbonate (0.498 g, 3.6 mmol) in 10 mL of acetone was warmed to reflux for 6 h. The reaction mixture was then poured into 30 mL of water and extracted with two 30-mL portions of EtOAc. The combined organic layers were dried over MgSO$_4$, filtered, and concentrated in vacuo to give crude material. Purification by flash chromatography using 35-40% EtOAc/hexane as eluant gave 667 as a yellow solid (0.069 g, 22%): MS (ES+) m/z 388 (M+H); $^1$H NMR (CDCl$_3$, 400 MHz) δ 8.75 (br s, 1H), 7.74 (d, 1H), 7.66 (d, 1H), 7.36-7.32 (m, 2H), 7.23-7.21 (m, 2H), 7.15-7.10 (m, 1H), 6.99 (d, 1H), 6.96-6.89 (m, 1H), 4.80 (s, 2H), 2.32 (s, 3H).

Example 272

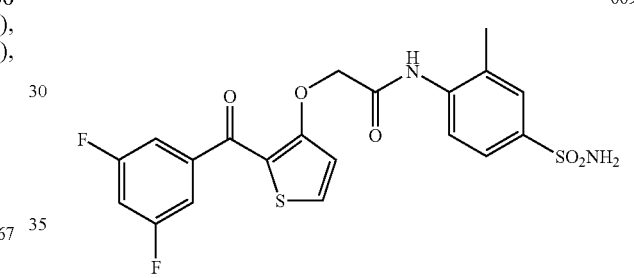

669

A mixture of 668 (0.192 g, 0.80 mmol), 470 (0.252 g, 0.82 mmol), and potassium carbonate (0.498 g, 3.6 mmol) in 10 mL of acetone was warmed to reflux for 6 h. The reaction mixture was then poured into 30 mL of water and extracted with two 30-mL portions of EtOAc. The combined organic layers were dried over MgSO$_4$, filtered, and concentrated in vacuo to give 0.272 g of crude material. Purification by flash chromatography using 35-50% EtOAc/hexane as eluant gave 669 as a yellow solid (0.103 g, 28%): MS (ES+) m/z 467 (M+H); $^1$H NMR (CDCl$_3$, 400 MHz) δ 9.47 (br s, 1H), 8.06 (d, 1H), 7.72-7.52 (m, 3H), 7.50-7.40 (m, 3H), 7.26 (br s, 2H), 7.17 (d, 1H), 4.89 (s, 2H), 2.23 (s, 3H).

Example 273

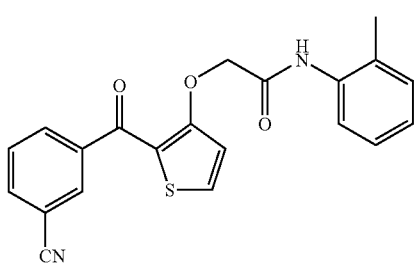

670

Step A:

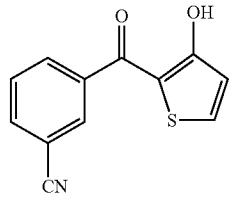

671

A mixture of 3-methoxythiophene (1.14 g, 10 mmol), aluminum chloride (2.78 g, 20.8 mmol), and 284 (10 mmol) in 50 mL of methylene chloride was heated to reflux for 24 h, then stirred at room temperature for 15 h. The reaction mixture was then poured over ice and stirred at room temperature for 1 h, after which the aqueous layer was separated and extracted with 35 mL of $CH_2Cl_2$. The combined organic layers were dried over $MgSO_4$, filtered and concentrated in vacuo to give 2.239 g of brown oil. Purification by flash chromatography using 5% EtOAc/hexane as eluant gave 671 (0.195 g, 9%): $^1$H NMR (400 MHz, $CDCl_3$) δ 12.04 (s, 1H), 8.19 (s, 1H), 8.13 (d, 1H), 7.83 (d, 1H), 7.64-7.58 (m, 2H), 6.86 (d, 1H).

Step B:

A mixture of 671 (0.164 g, 0.72 mmol), 665 (0.168 g, 0.74 mmol), and potassium carbonate (0.448 g, 3.24 mmol) in 12 mL of acetone was warmed to reflux for 15 h, then stirred at room temperature for an additional 5.5 h. Since the reaction mixture went dry overnight, another 10 mL of acetone was added, and the mixture was heated to reflux for 6 h, then stirred at room temperature overnight. The reaction mixture was poured into 50 mL of water and extracted with two 35-mL portions of EtOAc. The combined organic layers were dried over $MgSO_4$, filtered, and concentrated in vacuo to give 1.251 g of brown oil. Purification by flash chromatography using 30-40% EtOAc/hexane as eluant gave 670 as a yellow solid (0.033 g, 12%): MS (ES+) m/z 377 (M+H); $^1$H NMR ($CDCl_3$, 400 MHz) δ 8.63 (br s, 1H), 8.07 (s, 1H), 8.01 (d, 1H), 7.73-7.68 (m, 2H), 7.65 (d, 1H), 7.55 (t, 1H), 7.20-7.18 (m, 2H), 7.09 (t, 1H), 6.97 (d, 1H), 4.76 (s, 2H), 2.27 (s, 3H).

Example 274

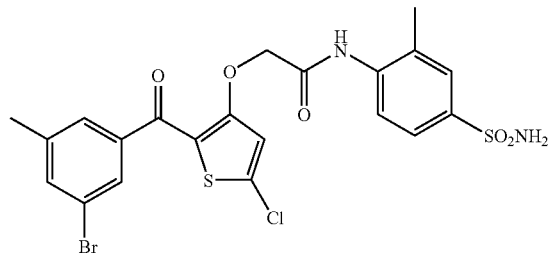

672

Step A:

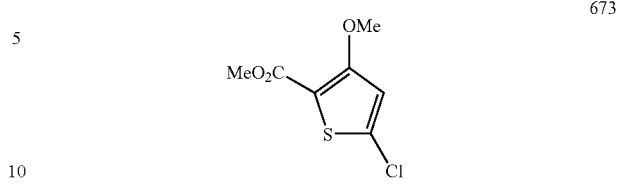

673

(Reference: *Synthesis*, 1984, 847). Sulfury chloride (2 mL, 25.5 mmol) was added to a stirred mixture of methyl 3-methoxy-2-thiophenecarboxylate (Avocado, 4 g, 23.2 mmol) in $CHCl_3$ (40 mL). The reaction mixture was gently stirred for 4-6 h after which it was concentrated. The concentrate was dissolved in glacial AcOH and HCl gas was bubbled in. The resultant mixture was left standing for 48 h. Following solvent extraction and flash column chromatography on silica with $CH_2Cl_2$, 673 (2.8 g, 58%) was obtained as a white solid. $^1$H NMR (DMSO-$d_6$, 300 MHz) δ 3.7 (s, 3H), 3.9 (s, 3H), 7.3 (s, 1H).

Step B:

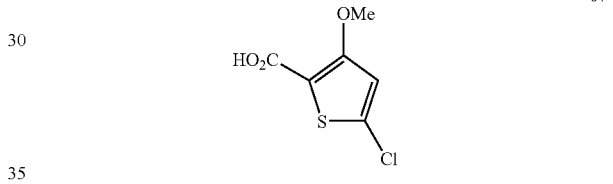

674

673 (1 g, 4.8 mmol), lithium hydroxide dihydrate (1 g), EtOH (10 mL), and water (10 mL) were used according to general procedure III. Following work-up, 674 (0.59 g, 64%) was obtained as a light brown solid. $^1$H NMR (DMSO-$d_6$, 300 MHz) δ 3.9 (s, 3H), 7.2 (s, 1H), 12.6 (br s, 1H).

Step C:

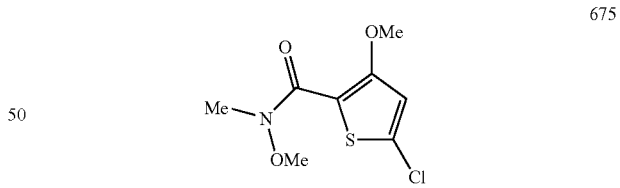

675

To a solution of 674 (0.59 g, 3.1 mmol) in THF (10 mL) was added carbonyl diimidazole (0.5 g, 3.1 mmol), N,O-dimethylhydroxylamine hydrochloride (0.45 g, 4.65 mmol), and a catalytic amount of N,N-dimethylaminopyridine. The reaction mixture was stirred at room temperature under argon for 24 h. The mixture was then diluted with EtOAc, and this was washed with water. After drying ($MgSO_4$) and solvent removal, the crude product was purified by flash column chromatography on silica gel with 5% MeOH in $CH_2Cl_2$ to give 675 (0.36 g, 49%) as an off-white solid. $^1$H NMR (DMSO-$d_6$, 300 MHz) δ 3.1 (s, 3H), 3.7 (s, 3H), 3.9 (s, 3H), 7.2 (s, 1H).

Step D:

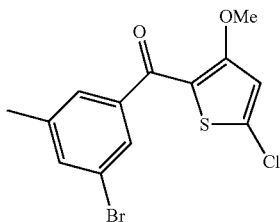
676

675 (0.36 g, 1.5 mmol), 3,5-dibromotoluene (Avocado, 0.34 g, 1.4 mmol), and n-butyllithium (1.1 mL, 1.5 mmol of 1.4 M hexane solution) in ether were used according to general procedure VIII. Following work-up and flash column chromatography on silica with $CH_2Cl_2$, 676 (0.3 g, 58%) was obtained as a white solid. $^1$H NMR (DMSO-$d_6$, 300 MHz) δ 2.3 (s, 3H), 3.8 (s; 3H), 7.4 (s, 1H), 7.5 (s, 1H), 7.6 (s, 1H), 7.62 (s, 1H).

Step E:

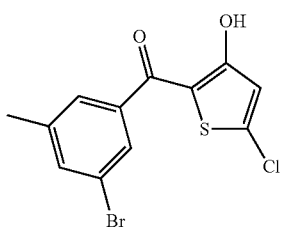
677

676 (0.3 g, 0.9 mmol), boron tribromide (1.7 mL, 1.7 mmol), and $CH_2Cl_2$ (10 mL) were used according to general procedure IX. 677 (0.26 g, 87%) was obtained as a solid. $^1$H NMR (DMSO-$d_6$, 400 MHz) δ 2.3 (s, 3H), 6.8 (s, 1H), 7.46 (s, 1H), 7.6 (s, 1H), 7.62 (s, 1H), 11.6 (s, 1H).

Step F:

A mixture of 677 (0.26 g, 0.8 mmol), 470 (0.24 g, 0.8 mmol) and potassium carbonate (0.6 g, 4 mmol) in DMF (10 mL) was stirred for 12 h. Water was added to the reaction mixture, which was in turn extracted with EtOAc. The EtOAc extract was further washed with water, brine and dried ($MgSO_4$). After solvent removal, the crude product was subjected to flash column chromatography on silica gel with 5% MeOH in $CH_2Cl_2$ to give an impure 672, which was recrystallized from EtOAc. 672 (0.016 g, 4%) was obtained as a white solid. $^1$H NMR (DMSO-$d_6$, 300 MHz) δ 2.2 (s, 3H), 2.3 (s, 3H), 4.9 (s, 2H), 7.2 (s, 1H), 7.4 (s, 1H), 7.5-7.8 (m, 7H), 9.4 (s, 1H).

Example 275

Inhibition of Viral Replication

I. HeLa Cell Assay

The HeLa cell assay was performed according to a modification of Kimpton J. and Emerman M., Detection of replication-competent and pseudotyped human immunodeficiency virus with a sensitive cell line on the basis of activation of an integrated β-galactosidase gene, *J. Virol.* 66:2232-2239 (1992), in which HIV-1 infection is detected by the activation of an HIV-LTR driven β-galactosidase reporter that is integrated into the genome of a CD4$^+$ HeLa cell line. Quantitation of β-galactosidase is achieved by measuring the activation of a chemiluminescent substrate (Tropix). The concentration of each compound required to inhibit 50% (IC$_{50}$) of the HIV-1 induced β-galactosidase signal, relative to untreated controls, was determined for each isogenic, recombinant virus.

A. Experimental Procedure

Growth and Maintenance of the CD4-HIV LTR-β-gal HeLa Cell Line.

HeLa-CD4-LTR-β-gal cells were obtained from the NIH AIDS Research and Reference Reagent Program. Cells were propagated in DMEM containing 10% fetal bovine serum, 0.2 mg/ml geneticin and 0.1 mg/ml hygromycin B. Cells were routinely split by trypsinization when confluency reached 80% (approximately every 2 to 3 days).

B. Construction of HIV-1 Reverse Transcriptase (RT) Mutants

DNA encoding the HIV-1 reverse transcriptase was subcloned from a M13 phage into a general shuttle vector, pBCSK+, as a ~1.65 kbp EcoRI/HindIII ended DNA fragment. The HIV DNA insert of the resulting plasmid, pRT2, was completely sequenced on both strands prior to use in site directed mutagenesis experiments. Specific amino acid replacements were made using Stratagene Quick Change reagents and mutagenic oligonucleotides from Oligos. Following mutagenesis, the entire mutant RT coding sequence was verified by sequencing both DNA strands.

C. Construction of Isogenic HIV-1 RT Mutant Virus

Mutant HIV-1 strains were isolated by a modified Recombinant Virus Assay (Kellam P. and Larder B., Recombinant virus assay: a rapid, phenotypic assay for assessment of drug susceptibility of human immunodeficiency virus type 1 isolates, *Antimicrobial Agents and Chemotherapy*, 38:23-30, 1994). 1×10$^7$ Jurkat T-cells (maintained in RPMI containing 10% fetal bovine serum, split 1:5 every 5 to 6 days) were co-transfected with EcoRI/HindIII digested mutant RT plasmid and Bst EII-digested HIV-1$_{HXB2\Delta RT}$ DNA in the presence of DMRIE-C transfection reagent (Gibco) according to supplier's recommended protocol. Each mutant RT coding sequence was crossed into the RT-deleted HIV-1 viral DNA backbone by in vivo homologous recombination. Transfected cell cultures were expanded and monitored until syncitia formation and CPE were extensive. Virus was harvested by clear spin of the culture supernatants and frozen at −80 C as primary stock. Recombinant progeny virus was sequenced in the RT region to confirm the mutant genotype. Virus stocks were further expanded by infection of Jurkat cells, harvested and stored as frozen aliquots. Stocks were titered in HeLa MAGI cells for assay.

D. Titering of Virus Stocks

The HIV-1$_{HXB2}$ mutants were titered in the HeLa MAGI assay system to determine the relative light units (RLU) per ml, a measure of infectivity relevant for this assay system. Virus stocks were diluted in a 2-fold series into DMEM containing 10% fetal bovine serum plus 20 ug/ml DEAE-dextran and assayed as described in the Experimental Protocol section, below.

E. Experimental Protocol 96-well microtiter plate(s) (Costar #3598) were seeded with 3×10$^3$ HeLa-CD4-LTR-β-gal in 100 µl DMEM containing 10% fetal bovine serum. Plates were placed in a 37° C., 5% $CO_2$ humidified incubator overnight. The following day, mutant virus stocks were thawed in a room temperature water bath and diluted into DMEM containing 10% fetal bovine serum and 20 μg/ml DEAE-dextran to achieve an input of 1500 to 2000 RLU/ml. All media was removed with an 8 channel manifold aspirator and 35 μl (50 to 70 total RLUs) of diluted virus was added to each well for virus adsorption. Plates were placed in a 37° C., 5% $CO_2$ humidified incubator for 1.5 to 2 hours.

Compound titration plates were prepared at 1.35× final concentration during the virus adsorption period. Compounds were titrated robotically in a five-fold stepwise manner from 2.7 μM (2 μM final) to 1.35 pM (1 pM final). This scheme allows 8 compounds to be tested per 96-well plate with 10 dilution points and 2 controls per compound (n=1). Compounds were titrated into DMEM containing 10% fetal bovine serum plus 0.135% DMSO (0.1% final). 100 μl of titrated compound was removed from every well of the titration plate and added to the virus adsorption plate. Plates were placed in a 37° C., 5% $CO_2$ humidified incubator for 72 hours.

Following incubation, supernatants were aspirated from every well as described above and 100 μl of phosphate buffered saline was added. The PBS was then aspirated as above and 15 μl of lysis buffer (Tropix) was added. Plates were maintained at room temperature for 10 minutes during which time the chemiluminescent substrate (Tropix) was diluted 1:50 into room temperature substrate dilution buffer (Tropix). 100 μl of diluted substrate was then added to each well. Plates were incubated at room temperature for 1 to 1.5 hours. Following incubation, the chemiluminescence of each well was measured with a Dynatech plate reader using the following settings:

| PARAMETER | VALUE |
|---|---|
| run | cycle |
| data | all |
| gain | low |
| cycles | 1s |
| pause | 2s |
| rows | abcdefgh |
| temp | room |
| stir | off |

The output raw data, RLUs, were analyzed by nonlinear regression to determine $IC_{50}$ values (see data analysis section below).

F. Data Analysis

Relative light units (RLU) are expressed as % control:

(RLU at compound [ ]/RLU no compound)*100=% Control

The concentration of compound that inhibits 50% of the signal produced in untreated samples ($IC_{50}$) is determined by the following nonlinear regression model available on the ROBOSAGE software package:

$Y=V_{max}*(1-(X^n/(K^n+X^n)))$

This equation describes a sigmoidal inhibition curve with a zero baseline. X is inhibitor concentration and Y is the response being inhibited. $V_{max}$ is the limiting response as X approaches zero. As X increases without bound, Y tends toward its lower limit, zero. K is the $IC_{50}$ for the inhibition curve, that is, Y is equal to 50% of $V_{max}$ when X=K.

Results in Table 1 are reported as ranges of representative $IC_{50}$ values.

II. MT4 Cell Assay

A. Experimental Procedure

Antiviral HIV activity and compound-induced cytotoxicity were measured in parallel by means of a propidium iodide based procedure in the human T-cell lymphotropic virus transformed cell line MT4. Aliquots of the test compounds were serially diluted in medium (RPMI 1640, 10% fetal calf serum (FCS), and gentamycin) in 96-well plates (Costar 3598) using a Cetus Pro/Pette. Exponentially growing MT4 cells were harvested and centrifuged at 1000 rpm for 10 min in a Jouan centrifuge (model CR 4 12). Cell pellets were resuspended in fresh medium (RPMI 1640, 20% FCS, 20% IL-2, and gentamycin) to a density of 5×105 cells/ml. Cell aliquots were infected by the addition of HIV-1 (strain IIIB) diluted to give a viral multiplicity of infection of 100×TCID50. A similar cell aliquot was diluted with medium to provide a mock-infected control. Cell infection was allowed to proceed for 1 hr at 37° C. in a tissue culture incubator with humidified 5% $CO_2$ atmosphere. After the 1 hr incubation the virus/cell suspensions were diluted 6-fold with fresh medium, and 125 μl of the cell suspension was added to each well of the plate containing pre-diluted compound. Plates were then placed in a tissue culture incubator with humidified 5% $CO_2$ for 5 days. At the end of the incubation period, 27 μl of 5% Nonidet-40 was added to each well of the incubation plate. After thorough mixing with a Costar multitip pipetter, 60 μl of the mixture was transferred to filter-bottomed 96-well plates. The plates were analyzed in an automated assay instrument (Screen Machine, Idexx Laboratories). The control and standard used was 3'-azido-3'-deoxythymidine tested over a concentration range of 0.01 to 1 μM in every assay. The expected range of $IC_{50}$ values for 3'-azido-3'-deoxythymidine is 0.04 to 0.12 μM. The assay-makes use of a propidium iodide dye to estimate the DNA content of each well.

B. Analysis

The antiviral effect of a test compound is reported as an $IC_{50}$, i.e. the inhibitory concentration that would produce a 50% decrease in the HIV-induced cytopathic effect. This effect is measured by the amount of test compound required to restore 50% of the cell growth of HIV-infected MT4 cells, compared to uninfected MT4 cell controls. $IC_{50}$ was calculated by RoboSage, Automated Curve Fitting Program, version 5.00, 10 Jul. 1995.

For each assay plate, the results (relative fluorescence units, rfU) of wells containing uninfected cells or infected cells with no compound were averaged, respectively. For measurements of compound-induced cytotoxicty, results from wells containing various compound concentrations and uninfected cells were compared to the average of uninfected cells without compound treatment. Percent of cells remaining is determined by the following formula:

Percent of cells remaining=(compound–treated uninfected cells, rfU/untreated uninfected cells)×100.

A level of percent of cells remaining of 79% or less indicates a significant level of direct compound-induced cytotoxicity for the compound at that concentration. When this condition occurs the results from the compound-treated infected wells at this concentration are not included in the calculation of $IC_{50}$.

For measurements of compound antiviral activity, results from wells containing various compound concentrations and infected cells are compared to the average of uninfected and infected cells without compound treatment. Percent inhibition of virus is determined by the following formula:

Percent inhibition of virus=(1−((ave. untreated uninfected cells−treated infected cells)/(ave. untreated uninfected cells−ave. untreated infected cells)))×100

REFERENCES

1. Averett, D. R., Anti-HIV compound assessment by two novel high capacity assays, *J. Virol. Methods* 23: 263-276, 1989.
2. Schwartz, O., et al., A rapid and simple colorimetric test for the study of anti-HIV agents, *AIDS Res. and Human Retroviruses* 4 (6): 441-447, 1988.
3. Daluge, S. M., et al., 5-chloro-2'3'-deoxy-3'fluorouridine (935U83), a selective anti-human immunodeficiency virus agent with an improved metabolic and toxicological profile. *Antimicro. Agents and Chemother.* 38 (7): 1590-1603, 1994.
4. Dornsife, R. E., et al., Anti-human immunodeficiency virus synergism by zidovudine (3'-azidothymidine) and didanosine (dideoxyinosine) contrasts with the additive inhibition of normal human marrow progenitor cells, *Antimicro. Agents and Chemother.* 35 (2): 322-328, 1991.

Results in Table 1. are expressed as representative $IC_{50}$ ranges.

TABLE 1

| Compound Number | Virus Type | IC50 (nM) Range* | Assay |
|---|---|---|---|
| 1 | HIV-1 | C | MT4 |
|  | NEV-R | D | MT4 |
| 5 | HIV-1 | B | MT4 |
|  | NEV-R | C | MT4 |
| 8 | HIV-1 | B | MT4 |
|  | NEV-R | C | MT4 |
| 9 | HIV-1 | B | MT4 |
|  | NEV-R | C | MT4 |
| 62 | HIV-1 | A | MT4 |
|  | HIV-2 | D | MT4 |
|  | NEV-R | A | MT4 |
|  | E138K | A | HeLa |
|  | G190A | A | HeLa |
|  | G190E | A | HeLa |
|  | K101E | A | HeLa |
|  | K103N | A | HeLa |
|  | K103N/G190A | B | HeLa |
|  | K103N/L1001 | A | HeLa |
|  | K103N/P225H | A | HeLa |
|  | K103N/V1081 | A | HeLa |
|  | K103N/Y181C | B | HeLa |
|  | L1001 | A | HeLa |
|  | P225H | A | HeLa |
|  | P236L | B | HeLa |
|  | V106A | B | HeLa |
|  | V106A/Y181C | B | HeLa |
|  | V1061 | A | HeLa |
|  | V1061/Y181C | B | HeLa |
|  | V1081 | A | HeLa |
|  | V1081/Y181C | A | HeLa |
|  | WTRVA | A | HeLa |
|  | Y181C | A | HeLa |
|  | Y188C | A | HeLa |
| 78 | HIV-1 | A |  |
|  | NEV-R | A |  |
|  | E138K | A | HeLa |
|  | G190A | A | HeLa |
|  | G190E | A | HeLa |
|  | K101E | A | HeLa |
|  | K103N | A | HeLa |
|  | K103N/G190A | B | HeLa |
|  | K103N/L1001 | A | HeLa |
|  | K103N/P225H | A | HeLa |
|  | K103N/V1081 | A | HeLa |
|  | K103N/Y181C | A | HeLa |
|  | L1001 | A | HeLa |
|  | P225H | A | HeLa |
|  | P236L | A | HeLa |
|  | V106A | B | HeLa |
|  | V106A/Y181C | B | HeLa |
|  | V1081 | A | HeLa |
|  | V1081/Y181C | B | HeLa |
|  | WTRVA | A | HeLa |
|  | Y181C | A | HeLa |
|  | Y188C | A | HeLa |
| 79 | HIV-1 | A | MT4 |
|  | H1V-2 | D | MT4 |
|  | NEV-R | A | MT4 |
|  | K103N | A | HeLa |
|  | K103N/Y181C | A | HeLa |
| 103 | HIV-1 | B | MT4 |
|  | NEV-R | C | MT4 |
|  | K103N | B | HeLa |
| 120 | HIV-1 | B | MT4 |
|  | NEV-R | B | MT4 |
|  | K103N | B | HeLa |
|  | K103N/Y181C | C | HeLa |
|  | WTRVA | B | HeLa |
|  | Y181C | B | HeLa |
| 122 | HIV-1 | A | MT4 |
|  | NEV-R | B | MT4 |
|  | K103N | B | HeLa |
|  | K103N/Y181C | D | HeLa |
|  | WTRVA | B | HeLa |
|  | Y181C | C | HeLa |
| 239 | HIV-1 | A | MT4 |
|  | NEV-R | A | MT4 |
|  | E138K | A | HeLa |
|  | G190A | A | HeLa |
|  | G190E | A | HeLa |
|  | K101E | A | HeLa |
|  | K103N | A | HeLa |
|  | K103N/G190A | B | HeLa |
|  | K103N/L1001 | A | HeLa |
|  | K103N/P225H | A | HeLa |
|  | K103N/V1081 | A | HeLa |
|  | K103N/Y181C | B | HeLa |
|  | L1001 | A | HeLa |
|  | P225H | A | HeLa |
|  | P236L | A | HeLa |
|  | V106A | B | HeLa |
|  | V106A/Y181C | C | HeLa |
|  | V1061 | A | HeLa |
|  | V1061/Y181C | A | HeLa |
|  | V1081 | A | HeLa |
|  | V1081/Y181C | A | HeLa |
|  | WTRVA | A | HeLa |
|  | Y181C | A | HeLa |
|  | Y188C | A | HeLa |
| 257 | HIV-1 | A | MT4 |
|  | NEV-R | A | MT4 |
|  | E138K | A | HeLa |
|  | G190A | A | HeLa |
|  | G190E | A | HeLa |
|  | K101E | A | HeLa |
|  | K103N | A | HeLa |
|  | K103N/G190A | B | HeLa |
|  | K103N/L1001 | A | HeLa |
|  | K103N/P225H | A | HeLa |
|  | K103N/V1081 | A | HeLa |
|  | K103N/Y181C | A | HeLa |
|  | L1001 | A | HeLa |
|  | P225H | A | HeLa |
|  | P236L | A | HeLa |
|  | V106A | B | HeLa |
|  | V106A/Y181C | B | HeLa |
|  | V1061 | A | HeLa |
|  | V1061/Y181C | B | HeLa |
|  | V1081 | A | HeLa |
|  | V1081/Y181C | A | HeLa |
|  | WTRVA | A | HeLa |
|  | Y181C | A | HeLa |
|  | Y188C | A | HeLa |
| 338 | HIV-1 | A | MT4 |
|  | NEV-R | B | MT4 |

TABLE 1-continued

| Compound Number | Virus Type | IC50 (nM) Range* | Assay |
|---|---|---|---|
| | K103N | B | HeLa |
| | K103N/Y181C | C | HeLa |
| | WTRVA | A | HeLa |
| | Y181C | B | HeLa |
| 387 | HIV-1 | A | MT4 |
| | NEV-R | B | MT4 |
| | K103N | A | HeLa |
| | K103N/Y181C | B | HeLa |
| | WTRVA | A | HeLa |
| | Y181C | B | HeLa |
| 435 | HIV-1 | A | MT4 |
| | NEV-R | B | MT4 |
| | K103N | A | HeLa |
| | K103N/Y181C | C | HeLa |
| | WTRVA | A | HeLa |
| | Y181C | B | HeLa |
| 448 | HIV-1 | A | MT4 |
| | HIV-2 | D | MT4 |
| | NEV-R | A | MT4 |
| | E138K | A | HeLa |
| | G190A | A | HeLa |
| | G190E | A | HeLa |
| | K101E | A | HeLa |
| | K103N | A | HeLa |
| | K103N/G190A | B | HeLa |
| | K103N/L100I | A | HeLa |
| | K103N/P225H | A | HeLa |
| | K103N/V108I | A | HeLa |
| | K103N/Y181C | B | HeLa |
| | L100I | A | HeLa |
| | P225H | A | HeLa |
| | P236L | B | HeLa |
| | V106A | B | HeLa |
| | V106A/Y181C | B | HeLa |
| | V106I | A | HeLa |
| | V106I/Y181C | B | HeLa |
| | V108I | A | HeLa |
| | V108I/Y181C | A | HeLa |
| | Y181C | A | HeLa |
| | Y188C | A | HeLa |
| 453 | HIV-1 | A | MT4 |
| | NEV-R | A | MT4 |
| | G190A | A | HeLa |
| | K101E | A | HeLa |
| | K103N | A | HeLa |
| | K103N/G190A | B | HeLa |
| | K103N/P225H | A | HeLa |
| | K103N/V108I | A | HeLa |
| | K103N/Y181C | A | HeLa |
| | L100I | A | HeLa |
| | P225H | A | HeLa |
| | P236L | B | HeLa |
| | V106A | C | HeLa |
| | V106A/Y181C | B | HeLa |
| | V106I | A | HeLa |
| | V106I/Y181C | B | HeLa |
| | V108I | C | HeLa |
| | V108I/Y181C | A | HeLa |
| | WTRVA | A | HeLa |
| | Y181C | A | HeLa |
| | Y188C | A | HeLa |
| 491 | HIV-1 | A | MT4 |
| | NEV-R | A | MT4 |
| | G190A | A | HeLa |
| | K103N | A | HeLa |
| | K103N/G190A | B | HeLa |
| | K103N/P225H | A | HeLa |
| | K103N/V108I | A | HeLa |
| | K103N/Y181C | A | HeLa |
| | L100I | A | HeLa |
| | P225H | A | HeLa |
| | P236L | A | HeLa |
| | V106A/Y181C | A | HeLa |
| | V106I | A | HeLa |
| | V106I/Y181C | B | HeLa |
| | V108I | A | HeLa |
| | V108I/Y181C | A | HeLa |
| | WTRVA | A | HeLa |
| | Y181C | A | HeLa |
| 564 | HIV-1 | A | MT4 |
| | NEV-R | A | MT4 |
| | G190A | A | HeLa |
| | K103N | A | HeLa |
| | K103N/G190A | A | HeLa |
| | K103N/P225H | A | HeLa |
| | K103N/V108I | A | HeLa |
| | K103N/Y181C | A | HeLa |
| | L100I | A | HeLa |
| | P225H | A | HeLa |
| | P236L | A | HeLa |
| | V106A/Y181C | A | HeLa |
| | V106I | A | HeLa |
| | V106I/Y181C | A | HeLa |
| | V108I/Y181C | A | HeLa |
| | WTRVA | A | HeLa |
| | Y181C | A | HeLa |
| 587 | HIV-1 | A | MT4 |
| | NEV-R | A | MT4 |
| | G190A | A | HeLa |
| | K103N | A | HeLa |
| | K103N/G190A | A | HeLa |
| | K103N/P225H | A | HeLa |
| | K103N/V108I | A | HeLa |
| | K103N/Y181C | A | HeLa |
| | L100I | A | HeLa |
| | P225H | A | HeLa |
| | P236L | A | HeLa |
| | V106A/Y181C | A | HeLa |
| | V106I | A | HeLa |
| | V106I/Y181C | B | HeLa |
| | V108I | A | HeLa |
| | V108I/Y181C | A | HeLa |
| | WTRVA | A | HeLa |
| | Y181C | A | HeLa |
| 475 | HIV-1 | A | MT4 |
| | NEV-R | A | MT4 |
| | G190A | A | HeLa |
| | K103N | A | HeLa |
| | K103N/G190A | A | HeLa |
| | K103N/P225H | A | HeLa |
| | K103N/V108I | A | HeLa |
| | K103N/Y181C | A | HeLa |
| | L100I | A | HeLa |
| | P225H | A | HeLa |
| | P236L | A | HeLa |
| | V106A/Y181C | A | HeLa |
| | V106I | A | HeLa |
| | V106I/Y181C | B | HeLa |
| | V108I | A | HeLa |
| | V108I/Y181C | A | HeLa |
| | WTRVA | A | HeLa |
| | Y181C | A | HeLa |
| 478 | HIV-1 | A | MT4 |
| | NEV-R | A | MT4 |
| | G190A | A | HeLa |
| | K103N | A | HeLa |
| | K103N/G190A | A | HeLa |
| | K103N/P225H | A | HeLa |
| | K103N/V108I | A | HeLa |
| | K103N/Y181C | A | HeLa |
| | L100I | A | HeLa |
| | P225H | A | HeLa |
| | P236L | A | HeLa |
| | V106A/Y181C | A | HeLa |
| | V106I | A | HeLa |
| | V106I/Y181C | A | HeLa |
| | V108I | A | HeLa |
| | V108I/Y181C | A | HeLa |
| | WTRVA | A | HeLa |
| | Y181C | A | HeLa |
| 498 | HIV-1 | A | MT4 |
| | NEV-R | A | MT4 |
| | G190A | A | HeLa |
| | K103N | A | HeLa |

TABLE 1-continued

| Compound Number | Virus Type | IC50 (nM) Range* | Assay |
|---|---|---|---|
| | K103N/G190A | A | HeLa |
| | K103N/P225H | A | HeLa |
| | K103N/V108I | A | HeLa |
| | K103N/Y181C | A | HeLa |
| | L100I | A | HeLa |
| | P225H | A | HeLa |
| | P236L | A | HeLa |
| | V106A/Y181C | A | HeLa |
| | V106I | A | HeLa |
| | V106I/Y181C | B | HeLa |
| | V108I | A | HeLa |
| | V108I/Y181C | A | HeLa |
| | WTRVA | A | HeLa |
| | Y181C | A | HeLa |
| 593 | HIV-1 | A | MT4 |
| | NEV-R | A | MT4 |
| | G190A | A | HeLa |
| | K103N | A | HeLa |
| | K103N/G190A | A | HeLa |
| | K103N/P225H | A | HeLa |
| | K103N/V108I | A | HeLa |
| | K103N/Y181C | A | HeLa |
| | L100I | A | HeLa |
| | P225H | A | HeLa |
| | P236L | A | HeLa |
| | V106A/Y181C | A | HeLa |
| | V106I | A | HeLa |
| | V106I/Y181C | B | HeLa |
| | V108I | A | HeLa |
| | V108I/Y181C | A | HeLa |
| | WTRVA | A | HeLa |
| | Y181C | A | HeLa |
| 483 | HIV-1 | B | MT4 |
| | NEV-R | A | MT4 |
| | K103N | C | HeLa |
| | V106A/Y181C | C | HeLa |
| | V106I | A | HeLa |
| | V106I/Y181C | B | HeLa |
| | WTRVA | B | HeLa |
| | Y181C | C | HeLa |
| 637 | HIV-1 | A | MT4 |
| | NEV-R | A | MT4 |
| | G190A | A | HeLa |
| | K103N | A | HeLa |
| | K103N/G190A | A | HeLa |
| | K103N/P225H | A | HeLa |
| | K103N/V108I | A | HeLa |
| | K103N/Y181C | A | HeLa |
| | L100I | A | HeLa |
| | P225H | A | HeLa |
| | P236L | A | HeLa |
| | V106A/Y181C | A | HeLa |
| | V106I | A | HeLa |
| | V106I/Y181C | A | HeLa |
| | V108I/Y181C | A | HeLa |
| | WTRVA | A | HeLa |
| | Y181C | A | HeLa |
| 503 | HIV-1 | A | MT4 |
| | NEV-R | A | MT4 |
| | G190A | A | HeLa |
| | K103N | A | HeLa |
| | K103N/G190A | A | HeLa |
| | K103N/P225H | A | HeLa |
| | K103N/V108I | A | HeLa |
| | K103N/Y181C | A | HeLa |
| | L100I | A | HeLa |
| | P225H | A | HeLa |
| | P236L | A | HeLa |
| | V106A/Y181C | A | HeLa |
| | V106I | A | HeLa |
| | V106I/Y181C | A | HeLa |
| | V108I | A | HeLa |
| | V108I/Y181C | A | HeLa |
| | WTRVA | A | HeLa |
| | Y181C | A | HeLa |
| 601 | HIV-1 | A | MT4 |
| | NEV-R | A | MT4 |

TABLE 1-continued

| Compound Number | Virus Type | IC50 (nM) Range* | Assay |
|---|---|---|---|
| | K103N | A | HeLa |
| | WTRVA | A | HeLa |
| | Y181C | A | HeLa |
| | V106A | A | HeLa |

*A indicates an $IC_{50}$ of 10 nM or less
B indicates an $IC_{50}$ between 11 nM and 100 nM
C indicates an $IC_{50}$ between 101 nM and 1,000 nM
D indicates an $IC_{50}$ between 1,000 nM and 3,000 nM

The invention claimed is:

1. A compound of formula (I)

wherein X is O; $R^1$ is $C_{6-14}$aryl substituted with one or more substituents selected from the group consisting of halogen, —$CF_3$, $C_{1-8}$alkyl, —CN, —$SR^6$, —$S(O)_2R^6$; or heterocycle, optionally substituted with one or more substituents selected from the group consisting of $C_{1-8}$alkyl, —CN, and $C_{6-14}$aryl$C_{1-8}$alkyl; $R^6$ is $C_{1-8}$alkyl, optionally substituted with halogen; $R^7$ is $C_{1-8}$alkyl optionally substituted with hydroxy; —$NH_2$; or heterocycle; $R^2$ is hydrogen; $R^3$ is hydrogen or $C_{1-8}$alkyl; $R^4$ is heterocycle, optionally substituted with one or more substituents selected from the group consisting of oxo, halogen, $C_{1-8}$alkyl, —$OR^{11}$ and —$SR^{10}N(R^{10})_2$, $S(O)_2NR^8R^9$; or $C_{6-14}$aryl substituted with one or more substituents selected from the group consisting of hydroxy, halogen, —$CF_3$, $C_{1-8}$alkyl, hydroxy$C_{1-8}$alkyl, —CN, —$NO_2$, —$C(O)NH_2$, —$S(O)R^7$, —$S(O)_2R^7$, —$S(O)NR^8R^9$, —$OR^{11}$, —$C(O)NR^{11}$, —$C(O)OR^{11}$, —$NR^{11}$, —$NC(O)R^{11}$, and heterocycle which may be optionally substituted with one or more substituents selected from the group consisting of oxo, $C_{1-8}$alkyl and heterocycle$C_{1-8}$alkyl; $R^8$ and $R^9$ are the same or different and are selected from the group consisting of hydrogen, $C_{1-8}$alkyl, $C_{1-8}$alkylheterocycle, heterocycle, and $C_{3-6}$cycloalkyl; $R^{10}$ is $C_{1-8}$alkyl; $R^{11}$ is $C_{1-8}$alkyl, optionally substituted with —$SO_2NR^8R^9$; and $R^5$ is halogen or —$NO_2$; or a pharmaceutically acceptable salt thereof.

2. A compound of formula (I)

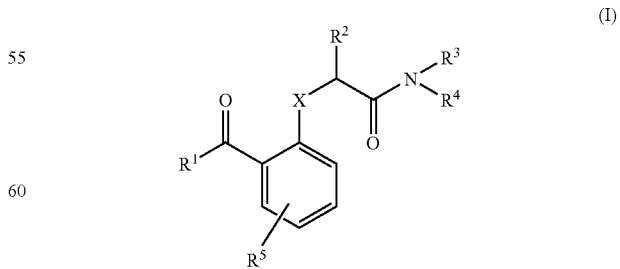

wherein X is O; $R^1$ is $C_{6-14}$ aryl substituted with one or more substituents selected from the group consisting of halogen, —$CF_3$, $C_{1-8}$alkyl, and —CN; $R^7$ and $R^3$ are hydrogen; $R^4$ is $C_{6-14}$aryl substituted with one or more substituents selected from the group consisting of halogen, $C_{1-8}$alkyl, —CN, —$NO_2$, —$S(O)R^7$, —$S(O)_2R^7$, —$NS(O)_2R^7$, wherein $R^7$ is —$NH_2$; and $R^5$ is halogen; or a pharmaceutically acceptable salt thereof.

3. A compound of formula (I)

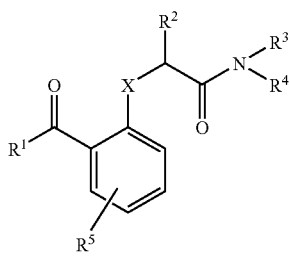

(I)

wherein X is O, $R^1$ is $C_{6-14}$aryl substituted with one or more substituents selected from the group consisting of halogen, —$CF_3$, $C_{1-8}$alkyl, and —CN; $R^2$ and $R^3$ are hydrogen; $R^4$ is $C_{6-14}$aryl substituted with one or more substituents selected from the group consisting of halogen, $C_{1-8}$alkyl, —CN, —$NO_2$, —$S(O)R^7$, —$S(O)_2R^7$, —$NS(O)_2R^7$, wherein $R^7$ is —$NH_2$; and $R^5$ is halogen; or a pharmaceutically acceptable salt thereof.

4. A compound of formula (IA)

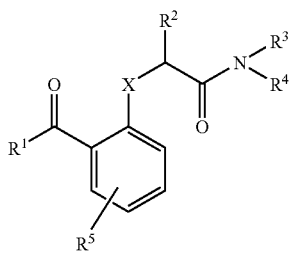

(IA)

wherein:
X is O;
$R^1$ is $C_{6-14}$aryl which may be optionally substituted with one or more substituents selected from the group consisting of halogen, —$CF_3$, $C_{1-8}$alkyl, $C_{1-8}$alkylamino, alkoxy, $C_{3-6}$cycloalkyl $C_{2-6}$alkenyl, $C_{6-14}$aryl$C_{2-6}$alkenyl, —CN, —$NO_2$, —$NH_2$, —$SR^6$, —$S(O)_2R^6$, —$S(O)R^7$, —$S(O)_2R^7$, —$C(O)R^7$, $C_{2-6}$alkenyl which may be optionally substituted with a substituent selected from the group consisting of hydroxy, halogen, aryl, and heterocycle and $C_{2-6}$alkynyl which may be optionally substituted with a substituent selected from the group consisting of hydroxy, halogen, aryl, $C_{3-6}$cycloalkyl, and heterocycle;
$R^6$ is $C_{1-8}$alkyl optionally substituted with one or more substituents selected from the group consisting of hydroxyl, halogen, —$CF_3$, aryl, and heterocycle;
$R^7$ is $C_{1-8}$alkyl, optionally substituted with one or more substituents selected from the group consisting of hydroxy, halogen, aryl, $C_{3-6}$cycloalkyl and heterocycle; —$NH_2$; or heterocycle;
$R^2$ is hydrogen, halogen, or $C_{1-8}$alkyl;
$R^3$ is hydrogen;
$R^4$ is $C_{6-14}$aryl substituted with $C_{1-8}$alkyl and at least one of hydroxy, halogen, —$CF_3$, $C_{1-8}$alkyl, hydroxy $C_{1-8}$ alkyl, —CN, —$NO_2$, $C_{1-8}$alkylamino, heterocycle$C_{1-8}$ alkyl, —$C(O)NH_2$, —$S(O)R^7$, —$S(O)_2R^7$, —$C(O)R^7$, —$NS(O)_2R^7$, —$S(O)_2NR^8R^9$, —$S(O)_2NHR^{11}$, —$S(O)_2 R^{11}$, —$S(O)_2NR^7COR^{11}$, —$S(O)_2NHCOR^{11}$, —$S(O)_2[COR^{11}]_n$ wherein n is 1, —$OR^{11}$, —$OR^{11}OR^{11}$, —$C(O)R^{11}$, —$C(O)NR^{11}$, —$C(O)OR^{11}$, —$NR^{11}$, —$NC(O)R^{11}$, heterocycle$C_{2-6}$alkenyl, heterocycle which may be optionally substituted with one or more substituents selected from the group consisting of oxo, $C_{1-8}$alkyl, and $C(O)OR^{11}$, and $C_{1-8}$alkyl which may be optionally substituted with one or more substituents selected from the group consisting of —CN and heterocycle, optionally substituted with —$C(O)R^{11}$;

$R^8$ and $R^9$ are independently selected from the group consisting of hydrogen, $C_{3-6}$cycloalkyl, $C_{1-8}$alkyl optionally substituted with one or more substituents selected from the group consisting of oxo, heterocycle, CN and $C_{6-14}$aryl optionally substituted with alkoxy, $C_{1-8}$alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloalkyl;

$R^{11}$ is $C_{1-8}$alkyl, optionally substituted with one or more substituents selected from the group consisting of hydrogen, hydroxy, halogen, $C_{1-4}$alkyl, $C_{3-6}$cycloalkyl, alkoxy, —$S(O)_2NR^8R^9$, $NCONH_2$, and heterocycle optionally substituted with one or more substituents selected from the group consisting of oxo, hydroxy, and $C_{1-8}$alkyl; heterocycle optionally substituted with heterocycle$C_{1-8}$alkyl; or $C_{6-14}$aryl optionally substituted with alkoxy;

$R^5$ is hydrogen, halogen, $C_{1-8}$alkyl, —$NO_2$, —$NH_2$, $C_{1-8}$alkylamino, $CF_3$, or alkoxy;

or a pharmaceutically acceptable salt thereof.

5. A compound of formula (IA) according to claim 4 wherein X is O; $R^1$ is $C_{6-14}$aryl substituted with one or more substituents selected from the group consisting of halogen, —$CF_3$, $C_{1-8}$alkyl, —CN, $C_{2-6}$alkenyl which may be optionally substituted with a substituent selected from the group consisting of hydroxy, halogen, aryl, and heterocycle and $C_{2-6}$alkynyl which may be optionally substituted with a substituent selected from the group consisting of hydroxy, halogen, aryl, $C_{3-6}$cycloalkyl, and heterocycle; $R^2$ and $R^3$ are hydrogen; $R^4$ is $C_{6-14}$aryl substituted with $C_{1-8}$alkyl and at least one of —$S(O)_2R^7$, —$S(O)_2NR^8R^9$, —$OR^{11}$, heterocycle$C_{2-6}$alkenyl, and heterocycle which may be optionally substituted with oxo; and $R^5$ is halogen; or a pharmaceutically acceptable salt thereof.

6. A compound of formula (IB)

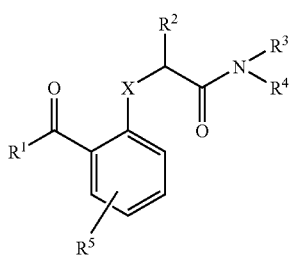

(IB)

wherein X is O; $R^1$ is $C_{6-14}$aryl substituted with one or more substituents selected from the group consisting of halogen, —$CF_3$, and —CN; $R^2$ is hydrogen; $R^3$ is hydrogen; $R^4$ is heterocycle; and $R^5$ is halogen; or a pharmaceutically acceptable salt thereof.

7. A compound of formula (ID)

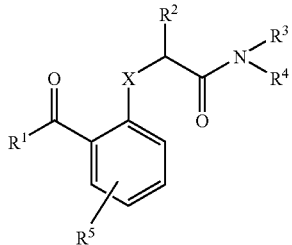

wherein X is O; $R^1$ is heterocycle; $R^2$ and $R^3$ are hydrogen; $R^4$ is heterocycle; and $R^5$ is halogen; or a pharmaceutically acceptable salt thereof.

8. A compound of formula (III)

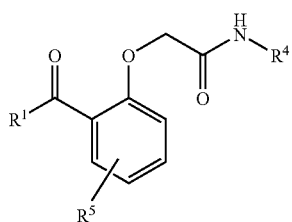

wherein $R^1$ is $C_{6-14}$aryl substituted with one or more substituents selected from the group consisting of halogen, —$CF_3$, $C_{1-8}$alkyl, —CN, —$SR^6$, —$S(O)_2R^6$; or heterocycle, optionally substituted with one or more substituents selected from the group consisting of $C_{1-8}$alkyl, —CN, and $C_{6-14}$aryl$C_{1-8}$alkyl; $R^6$ is $C_{1-8}$alkyl, optionally substituted with halogen; $R^7$ is $C_{1-8}$alkyl, optionally substituted with hydroxy; —$NH_{12}$; or heterocycle; $R^4$ is heterocycle, optionally substituted with one or more substituents selected from the group consisting of oxo, halogen, $C_{1-8}$alkyl, —$OR^{11}$ and —$SR^{10}N(R^{10})_2$; or $C_{6-14}$aryl substituted with one or more substituents selected from the group consisting of hydroxy, —$CF_3$, $C_{1-8}$alkyl, hydroxy$C_{1-8}$alkyl, —CN, —$NO_2$, —C(O)$NH_2$, —$S(O)_2R^7$, —$S(O)_2NR^8R^9$, —$OR^{11}$, —$C(O)NR^1$, —$C(O)OR^{11}$, —$NR^{11}$, —$NC(O)R^{11}$, heterocycle which may be optionally substituted with one or more substituents selected from the group consisting of oxo and $C_{1-8}$alkyl; $R^8$ and $R^9$ are the same or different and are selected from the group consisting of hydrogen, $C_{1-8}$alkyl, $C_{1-8}$alkylheterocycle, heterocycle, and $C_{3-6}$cycloalkyl; $R^{10}$ is $C_{1-8}$alkyl; $R^{11}$ is $C_{1-8}$alkyl, optionally substituted with —$S(O)_2NR^8R^9$; and $R^5$ is halogen or —$NO_2$; or a pharmaceutically acceptable salt thereof.

9. A compound of formula (III) according to claim 8 wherein $R^1$ is $C_{6-14}$aryl substituted with one or more substituents selected from the group consisting of halogen, —$CF_3$, $C_{1-8}$alkyl, and —CN; $R^4$ is $C_{6-14}$aryl substituted with one or more substituents selected from the group consisting of halogen, $C_{1-8}$alkyl, —CN, —$NO_2$, —$S(O)R^7$, —$S(O)_2R^7$, —$NS(O)_2R^7$, wherein $R^7$ is —$NH_2$; and $R^5$ is halogen; or a pharmaceutically acceptable salt thereof.

10. A compound of formula (I)

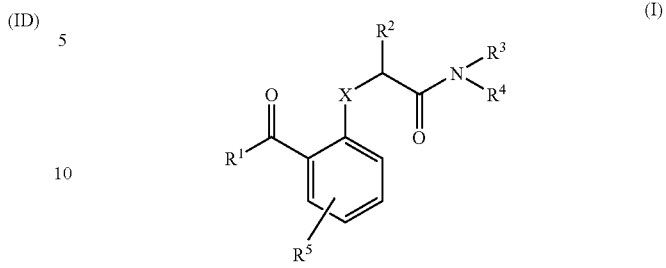

wherein:
X is O;
$R^1$ is phenyl which is substituted in the meta position with one or more substituents selected from the group consisting of halogen, —$CF_3$, $C_{1-8}$alkyl, $C_{1-8}$alkylamino, alkoxy, $C_{3-6}$cycloalkyl$C_{2-6}$alkenyl, $C_{6-14}$aryl$C_{2-6}$alkenyl, —CN, —$NO_2$, —$NH_2$, —$SR^6$, —$S(O)_2R^6$, —$S(O)R^7$, —$S(O)_2R^7$, —$C(O)R^7$, $C_{2-6}$alkenyl which may be optionally substituted with a substituent selected from the group consisting of hydroxy, halogen, aryl, and heterocycle, and $C_{2-6}$alkynyl which may be optionally substituted with a substituent selected from the group consisting of hydroxy, halogen, aryl, $C_{3-6}$cycloalkyl, and heterocycle;
$R^2$ is hydrogen;
$R^3$ is hydrogen;
$R^4$ is phenyl substituted in the ortho position with a substituent selected from the group consisting of hydroxy, halogen, —$CF_3$, or $C_{1-8}$alkyl and substituted at the para position with a substituent selected from the group consisting of hydroxy, halogen, —$CF_3$, $C_{1-8}$alkyl, hydroxy$C_{1-8}$alkyl, —CN, —$NO_2$, $C_{1-8}$alkylamino, heterocycle$C_{1-8}$alkyl, —$C(O)NH_2$, —$S(O)R^7$, —$S(O)_2R^7$, —$C(O)R^7$, —$NS(O)_2R^7$, —$S(O)_2NR^8R^9$, —$S(O)_2NHR^{11}$, —$SO_2R^{11}$, —$OR^{11}$, —$C(O)R^{11}$, —$C(O)NR^{11}$, —$C(O)OR^{11}$, —$NR^{11}$, —$NC(O)R^{11}$, heterocycle$C_{2-6}$alkenyl, heterocycle which may be optionally substituted with one or more substituents selected from the group consisting of oxo, $C_{1-8}$alkyl, and $C(O)OR^{11}$, and $C_{1-8}$alkyl which may be optionally substituted with one or more substituents selected from the group consisting of —CN and heterocycle, optionally substituted with —$C(O)R^{11}$;
$R^5$ is a substituent in the para position relative to X and is selected from the group consisting of halogen, $C_{1-8}$alkyl, —$NO_2$, —$NH_2$, $C_{1-8}$alkylamino, $CF_3$, or alkoxy;
$R^6$ is $C_{1-8}$alkyl, optionally substituted with one or more substituents selected from the group consisting of hydroxy, halogen, —$CF_3$, aryl, and heterocycle;
$R^7$ is $C_{1-8}$alkyl, optionally substituted with one or more substituents selected from the group consisting of hydroxy, halogen, aryl, $C_{3-6}$cycloalkyl and heterocycle; —$NH_2$; or heterocycle;
$R^8$ and $R^9$ are independently selected from the group consisting of hydrogen; $C_{3-6}$cycloalkyl; $C_{1-8}$alkyl optionally substituted with one or more substituents selected from the group consisting of oxo, heterocycle, CN and $C_{6-14}$aryl optionally substituted with alkoxy, $C_{1-8}$alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloakly; or —$C(O)NH_2$;

$R^{11}$ is $C_{1-8}$alkyl, optionally substituted with one or more substituents selected from the group consisting of hydrogen, $C_{1-8}$alkyl, —$S(O)_2NR^8R^9$, —$NR^8R^9$, and heterocycle, optionally substituted with one or more substituents selected from the group consisting of oxo and $C_{1-8}$alkyl; or a pharmaceutically acceptable salt thereof.

11. A compound selected from the group consisting of:
2-[2-(1-benzothiophen-2-ylcarbonyl)-4-chlorophenoxy]-N-phenylacetamide;
2-(2-benzoyl-4-chlorophenoxy)-N-[4-(1H-imidazol-1-yl)phenyl]acetamide;
2-[4-chloro-2-(2-thienylcarbonyl)phenoxy]-N-[2-methyl-4-(1-oxo-1lambda~4~,4-thiazinan-4-yl)phenyl]acetamide;
2-(2-benzoyl-4-chlorophenoxy)-N-[4-(1H-1,2,4-triazol-1-yl)phenyl]acetamide;
2-(2-benzoyl-4-chlorophenoxy)-N-[4-(4-morpholinyl)phenyl]acetamide;
N-[4-(aminosulfonyl)phenyl]-2-(2-benzoyl-4-chlorophenoxy)acetamide;
2(2-benzoyl-4-chlorophenoxy)-N-{4-[(1,3-thiazol-2-ylamino)sulfonyl]phenyl}acetamide;
2-(2-benzoyl-4-chlorophenoxy)-N-[4-(4-methyl-1-piperazinyl)phenyl]acetamide;
2-(2-benzoyl-4-chlorophenoxy)-N-[4-(hydroxymethyl)phenyl]acetamide;
2-(2-benzoyl-4-chlorophenoxy)-N-{4-[(methylamino)sulfonyl]phenyl}acetamide;
2-(2-benzoyl-4chlorophenoxy)-N-[4(1-oxo-1lambda~4~,4-thiazinan-4-yl)phenyl]acetamide;
2-(2-benzoyl-4-chlorophenoxy)-N-[4-(1,1-dioxo-1lambda~6~,4-thiazinan-4-yl)phenyl]acetamide;
2-(2-benzoyl-4-chlorophenoxy)-N-[2-methyl-4-(4-morpholinyl)phenyl]acetamide;
2-(2-benzoyl-4-chlorophenoxy)-N-{4-[3-(dimethylamino)propoxy]-2-methylphenyl}acetamide;
2-(2-benzoyl-4-chlorophenoxy)-N-[4-(1-hydroxyethyl)phenyl]acetamide;
2-(2-benzoyl-4-chlorophenoxy)-N-[4(1-hydroxyethyl)phenyl]acetamide;
2-(2-benzoyl-4-chlorophenoxy)-N-[2-methyl-4-(1-oxo-1lambda~4~,4-thiazinan-4-yl)phenyl]acetamide;
2-(2-benzoyl-4-chlorophenoxy)-N-{2-methyl-4-[3-(1-pyrrolidinyl)propoxy]phenyl}acetamide;
2-(2-benzoyl-4-chlorophenoxy)-N-(1H-indazol-5-yl)acetamide;
2-(2-benzoyl-4-chlorophenoxy)-N-{2-methyl-4-[3-(4-morpholinyl)propoxy]phenyl}acetamide;
2-(2-benzoyl-4-chlorophenoxy)-N-{4-[3-(1H-imidazol-1-yl)propoxy]-2-methylphenyl}acetamide;
2-(2-benzoyl-4-chlorophenoxy)-N-(1H-indazol-6-yl)acetamide;
2-[4-chloro-2-(2-thienylcarbonyl)phenoxy]-N-(1H-indazol-5-yl)acetamide;
2-[4-chloro-2-(2-furoyl)phenoxy]-N-(1H-indazol-5-yl)acetamide;
2-[4-chloro-2-(3-thienylcarbonyl)phenoxy]-N-(1H-indazol-5-yl)acetamide;
2-[4-chloro-2-(2-thienylcarbonyl)phenoxy]-N-{2-methyl-4-[3-(4-morpholinyl)propoxy]phenyl}acetamide;
2-[4-chloro-2-(2-thienylcarbonyl)phenoxy]-N-[4-(1-oxo-1lambda~4~,4-thiazinan-4-yl)phenyl]acetamide;
2-(2-benzoyl-4-chlorophenoxy)-N-{2-methyl-4-[3-(1-oxo-1lambda~4~,4-thiazinan-4-yl)propoxy]phenyl}acetamide;
2-[4-chloro-2-(2-furoyl)phenoxy]-N-[2-methyl(1-oxo-1lambda~4~,4-thiazinan-4-yl)phenyl]acetamide;
N-[4-(aminosulfonyl)-2-methylphenyl]-2-(2-benzoyl-4-chlorophenoxy)acetamide;
N-[4-(aminosulfonyl)-2-methylphenyl]-2-[4-chloro-2-(2-thienylcarbonyl)phenoxy]acetamide;
2-[2-(1-benzofuran-2-ylcarbonyl)-4-chlorophenoxy]-N-phenylacetamide
2-[4-chloro-2-(1,3-thiazol-2ylcarbonyl)phenoxy]-N-phenylacetamide;
N-[4-(aminosulfonyl)-2-methylphenyl]-2-[4-chloro-2-(2-furoyl)phenoxy]acetamide;
2-[4-chloro-2-(2-furoyl)phenoxy]-N-(1-indazol-6-yl)acetamide;
2-[4-chloro-2-(3-furoyl)phenoxy]-N-[2-methyl-4-(1-oxo-1lambda~4~,4-thiazinan-4-yl)phenyl]acetamide;
2-[4-chloro-2-(3-thienylcarbonyl)phenoxy]-N-[4-(1-oxo-1lambda~4~,4-thiazinan-4-yl)phenyl]acetamide;
2-[4-chloro-2-(3-thienylcarbonyl)phenoxy]-N-[2-methyl-4-(1-oxo-1lambda~4~,4-thiazinan-4-yl)phenyl]acetamide;
2-{chloro-2-[(1-methyl-1H-pyrrol-2-yl)carbonyl]phenoxy}-N-phenylacetamide;
2-(4-chloro-2-{[5-(2-pyridinyl)-2-thienyl]carbonyl}phenoxy)-N-phenylacetamide;
2-[4-chloro-2-(1,3-thiazol-2-ylcarbonyl)phenoxy]-N-(1H-indazol-5-yl)acetamide;
2-[4-chloro-2-(1,3-thiazol-2-ylcarbonyl)phenoxy]-N-[2-methyl-4-(1-oxo-1lambda~4~,4-thiazinan-4-yl)phenyl]acetamide;
2-[4-chloro-2-(3-cyanobenzoyl)phenoxy]-N-(2-methyl-4-(1-oxo-1lambda~4~,4-thiazinan-4-yl)phenyl]acetamide;
2-[4-chloro-2-(3-pyridinylcarbonyl)phenoxy]-N-[2-methyl-4-(1-oxo-1lambda~4~,4-thiazinan-4-yl)phenyl]acetamide;
2-[2-(2-bromobenzoyl)-4-chlorophenoxy]-N-[2-methyl-4-(1-oxo-1lambda~4~,4-thiazinan-4-yl)phenyl]acetamide;
2-[2-(4-bromobenzoyl)-4-chlorophenoxy]-N-[2-methyl-4-(1-oxo-1lambda~4~,4-thiazinan-4-yl)phenyl]acetamide;
N-[4-(aminosulfonyl)-2-methylphenyl]-2-[2-(2-bromobenzoyl)-4-chlorophenoxy]acetamide;
2-{4-chloro-2-[(5-methyl-3-isoxazolyl)carbonyl]phenoxy}-N-[2-methyl-4-(1-oxo-1lambda~4~,4-thiazinan-4yl)phenyl]acetamide;
2-[4-chloro-2-(3-fluorobenzoyl)phenoxy]-N-[2-methyl-4-(1-oxo-1lambda~4~,4-thiazinan-4-yl)phenyl]acetamide;
2-[4-chloro-2-(3-chlorobenzoyl)phenoxy]-N-[2-methyl-4-(1-oxo-1lambda~4~,4-thiazinan-4-yl)phenyl]acetamide;
N-[4-(aminosulfonyl)-2-methylphenyl]-2-[4-chloro-2-(3-cyanobenzoyl)phenoxy]acetamide;
N-[4-(aminosulfonyl)-2-methylphenyl]-2-[4-chloro-2-(3-fluorobenzoyl)phenoxy]acetamide;
N-[4-(aminosulfonyl)-2-methylphenyl]-2-[4-chloro-2-(3-chlorobenzoyl)phenoxy]acetamide;
2-{4-chloro-2-[(4-cyano-2-thienyl)carbonyl]phenoxy}-N-[2-methyl-4-(1-oxo-1lambda~4~,4-thiazinan-4-yl)phenyl]acetamide;
N-[4-(aminosulfonyl)-2-methylphenyl]-2-{4chloro-2-[(4-cyano-2-thienyl)carbonyl]phenoxy}acetamide;
2-{4-chloro-2-[3-(trifluoromethyl)benzoyl]phenoxy}-N-[2-methyl-4-(1-oxo-1lambda~4~,4-thiazinan-4-yl)phenyl]acetamide;

2-[2-(3-bromobenzoyl)-4-chlorophenoxy]-N-[2-methyl-4-(1-oxo-1lambda~4~,4-thiazinan-4-yl)phenyl]acetamide;
2-[4-chloro-2-(3,5-difluorobenzoyl)phenoxy]-N-(2-methyl-4-(1-oxo-1lambda~4~,4-thiazinan-4-yl)phenyl]acetamide;
N-[4-(aminosulfonyl)-2-methylphenyl]-2-[2-(3-bromobenzoyl)-4-chlorophenoxy]acetamide;
2-[4-chloro-2-(3-methylbenzoyl)phenoxy]-N-[2-methyl-4-(1-oxo-1lambda~4~,4-thiazinan-4-yl)phenyl]acetamide;
2-[4-chloro-2-(3-cyanobenzoyl)phenoxy]-N-(5-methyl-1H-indazol-6-yl)acetamide;
N-[4-(aminosulfonyl)-2-methylphenyl]-2-[4-chloro-2-(3-pyridinylcarbonyl)phenoxy]acetamide;
2-[4-chloro-2-(3-cyanobenzoyl)phenoxy]-N-{2-methyl-4-[3-(1-pyrrolidinyl)propoxy]phenyl}acetamide;
N-[4-(aminosulfonyl)-2-methylphenyl]-2-{4-chloro-2-[(1-methyl-1H-imidazol-2-yl)carbonyl]phenoxy}acetamide,
N-[4-(aminosulfonyl)-2-methylphenyl]-2-[4-chloro-2-(1,3-thiazol-2-ylcarbonyl)phenoxy]acetamide;
2-[4chloro-2-(3,5-difluorobenzoyl)phenoxy]-N-{2-methyl-4-[3-(1-pyrrolidinyl)propoxy]phenyl}acetamide;
N-[4-(aminosulfonyl)-2-methylphenyl]-2-[4-chloro-2-(3,5-difluorobenzoyl)phenoxy]acetamide;
2-{4-chloro-2-[3-fluoro-5-(trifluoromethyl)benzoyl]phenoxy}-N-[2-methyl-4(1-oxo-1lambda~4~,4-thiazinan-4-yl)phenyl]acetamide
N-(1,3-benzothiazol-6-yl)-2-(2-benzoyl-4-chlorophenoxy)acetamide
2-(4-chloro-2-{3-[(trifluoromethyl)sulfanyl]benzoyl}phenoxy)-N-[2-methyl-4-(1-oxo-1lambda~4~,4-thiazinan-4-yl)phenyl]acetamide
2-[4-chloro-2-(3-ethynylbenzoyl)phenoxy]-N-[2-methyl-4-(1-oxo-1lambda~4~,4-thiazinan-4-yl)phenyl]acetamide;
2-[4-chloro-2-(3,5-dichlorobenzoyl)phenoxy]-N-[2-methyl-4-(1-oxo-1lambda~4~,4thiazinan-4-yl)phenyl]acetamide;
N-[4-(aminosulfonyl)-2-methylphenyl]-2-[4-chloro-2-(3,5-dichlorobenzoyl)phenoxy]acetamide;
N-[4-(aminosulfonyl)-2-methylphenyl]-2-{4-chloro-2-[(3-fluoro-5-(trifluoromethyl)benzoyl]phenoxy}acetamide;
N-(1,3-benzothiazol-6-yl)-2-[4-chloro-2-(3,5-difluorobenzoyl)phenoxy]acetamide
2-[4-chloro-2-(3-cyanobenzoyl)phenoxy]-N-(2-methyl-1,3-benzothiazol-5-yl)acetamide
N-[4-(aminosulfonyl)-2-methylphenyl]-2-(4-chloro-2-{3-[(trifluoromethyl)sulfanyl]benzoyl}phenoxy)acetamide;
N-[4-(aminosulfonyl)-2-methylphenyl]-2-[4-chloro-2-(3-ethynylbenzoyl)phenoxy]acetamide;
2-(2-benzoyl-4-chlorophenoxy)-N-[4-(methylsulfonyl)phenyl]acetamide;
N-[4-(aminosulfonyl)-2-methylphenyl]-2-{4chloro-2-[3-(2-cyclopentylethynyl)benzoyl]phenoxy}acetamide;
2-{4-chloro-2-[3-fluoro-5-(trifluoromethyl)benzoyl]phenoxy}-N-(5-methyl-1H-indazol-6-yl)acetamide;
2-[4-chloro-2-(3,5-dichlorobenzoyl)phenoxy]-N-(5-methyl-1H-indazol-6-yl)acetamide;
N-[4-(aminosulfonyl)-2-methylphenyl]-2-{4-chloro-2-[3-(2-phenylethynyl)benzoyl]phenoxy}acetamide;
2-[4-chloro-2-(3,5-difluorobenzoyl)phenoxy]-N-(5-methyl-1H-indazol-6-yl)acetamide;
2-[4-chloro-2-(3,5-difluorobenzoyl)phenoxy]-N-[2-methyl-4(methylsulfonyl)phenyl]acetamide;
N-(1,2-benzisothiazol-5-yl)-2-[4chloro-2-(3-cyanobenzoyl)phenoxy]acetamide;
2-[4-chloro-2-(3,5-dichlorobenzoyl)phenoxy]-N-(5-methyl-1H-benzimidazol-6-yl)acetamide;
2-[4-chloro-2-(3,5-difluorobenzoyl)phenoxy]-N-(5-methyl-1H-benzimidazol-6-yl)acetamide;
2-{4-chloro-2-[3-fluoro-5-(trifluoromethyl)benzoyl]phenoxy}-N-(5-methyl-1H-benzimidazol-6-yl)acetamide
2-[4-chloro-2-(3,5-difluorobenzoyl)phenoxy]-1-(2,3-dihydro-1H-indol-1-yl)-1-ethanone;
2-[4-chloro-2-(3-cyanobenzoyl)phenoxy]-N-[2-methyl-4-(methylsulfonyl)phenyl]acetamide;
2-[4-chloro-2-(3-ethynylbenzoyl)phenoxy]-N-[2-methyl-4-(methylsulfonyl)phenyl]acetamide;
N-{4-[3-(aminosulfonyl)propoxy]-2-methylphenyl}-2-[4-chloro-2-(3,5-difluorobenzoyl)phenoxy]acetamide;
2-{2-[3,5-bis(trifluoromethyl)benzoyl]-4-chlorophenoxy}-N-(5-methyl-1H-benzimidazol-6-yl)acetamide;
2-{2-[(5-bromo-3-pyridinyl)carbonyl]-4-chlorophenoxy}-N-(5-methyl-1H-benzimidazol-6-yl)acetamide;
2-{4-chloro-2-[3-fluoro-5-(trifluoromethyl)benzoyl]phenoxy}-N-(6-methyl-1,3-benzothiazol-5-yl)acetamide;
N-(4-[3-(aminosulfonyl)propoxy]-2-methylphenyl}-2-{4-chloro-2-[3-fluoro-5-(trifluoromethyl)benzoyl]phenoxy}acetamide;
N-[4-(aminosulfonyl)-2-methylphenyl]-2-(4-chloro-2-{3-[(trifluoromethyl)sulfonyl]benzoyl}phenoxy)acetamide;
2-[4-chloro-2-(3,5-difluorobenzoyl)phenoxy]-N-[4-(1,3-thiazol-2-yl)phenyl]acetamide
2-[4-chloro-2-(3,5-difluorobenzoyl)phenoxy]-N-[4-(1,3-oxazol-2-yl)phenyl]acetamide
2-[4-chloro-2-(3,5-difluorobenzoyl)phenoxy]-N-{4-[(3-hydroxypropyl)sulfonyl]-2-methylphenyl}acetamide;
2-{4-chloro-2-[3-fluoro-5-(trifluoromethyl)benzoyl]phenoxy)-N-(2-methyl-4-{3-[(methylamino)sulfonyl]propoxy}phenyl)acetamide;
2-{4-chloro-2-[3-fluoro-5-(trifluoromethyl)benzoyl]phenoxy}-N-(4-3-[(dimethylamino)sulfonyl]propoxy}-2-methylphenyl)acetamide;
N-[4-(aminosulfonyl)-2-methylphenyl]-2-{2-[(5-bromo-3-pyridinyl)carbonyl]-4-chlorophenoxy}acetamide;
2-{4-chloro-2-[3-fluoro-5-(trifluoromethyl)benzoyl]phenoxy}-N-{4-[3-(1H-imidazol-1-yl)propoxy]-2-methylphenyl}acetamide;
2-{4-chloro-2-[3-fluoro-5-(trifluoromethyl)benzoyl]phenoxy}-N-{2-methyl-4-[(E)-4-(1-pyrrolidinyl)-1-butenyl]phenyl}acetamide;
N-[4-(aminosulfonyl)-2-methylphenyl]-2-[4-chloro-2-(3-cyano-5-fluorobenzoyl)phenoxy]acetamide;
N-[4-(aminosulfonyl)-2-methylphenyl]-2-[4-chloro-2-(3-cyano-5-methylbenzoyl)phenoxy]acetamide;
N-[6-(aminosulfonyl)-4-methyl-3-pyridinyl]-2-[4-chloro-2-(3-cyano-5-methylbenzoyl)phenoxy]acetamide;
N-[4-(aminosulfonyl)-2-methylphenyl]-2-[4-chloro-2-(3-chloro-5-cyanobenzoyl)phenoxy]acetamide;
N-[4-(aminosulfonyl)-2-methylphenyl]-2-[4-chloro-2-(3,5-dimethylbenzoyl)phenoxy]acetamide;
N-[4-(aminosulfonyl)-2-methylphenyl]-2-[4-chloro-2-(3-cyano-5-ethylbenzoyl)phenoxy]acetamide;
2-[4-chloro-2-(3-cyano-5-methylbenzoyl)phenoxy]-N-{4-[3-(2,5-dihydro-1H-pyrrol-1-yl)propoxy]-2-methylphenyl)acetamide hydrochloride;
N-[4-(aminosulfonyl)-2-methylphenyl]-2-[4-chloro-2-(3-chloro-5-methylbenzoyl)phenoxy]acetamide;

N-[4-(aminosulfonyl)-2-methylphenyl]-2-[4-chloro-2-(3,5dichlorobenzoyl)phenoxy]acetamide;
N-[4-(aminosulfonyl)-2-methylphenyl]-2-{4-chloro-2-[(6-cyano-2-pyridinyl)carbonyl]phenoxy}acetamide;
N-[6-(aminosulfonyl)-2-methyl-3-pyridinyl]-2-[4-chloro-2-(3-cyano-5-methylbenzoyl)phenoxy]acetamide;
N-[4-(aminosulfonyl)-2-methylphenyl]-2-[4chloro-2-(3,5-dicyanobenzoyl)phenoxy]acetamide;
N-[4-(aminosulfonyl)-2-methylphenyl]-2-{4chloro-2-[3-cyano-5-(trifluoromethyl)benzoyl]phenoxy}acetamide;
and pharmaceutically acceptable salts thereof.

12. A compound selected from the group consisting of:
N-[4(aminosulfonyl)-2-methylphenyl]-2-[4-chloro-2-(3-cyanobenzoyl)phenoxy]acetamide;
N-[4-(aminosulfonyl)-2-methylphenyl]-2-[{4-chloro-2-(3-fluoro-5-(trifluoromethyl)benzoyl]pheonoxy}acetamide;
N-{4-[3-(aminosulfonyl)propoxy]-2-methylphenyl}-2-(4-chloro-2-[3-fluoro-5-(trifluoromethyl)benzoyl]phenoxy}acetamide;
N-[4-aminosulfonyl)-2-methylphenyl]-2-[4-chloro-2-(3-cyano-5-fluorobenzoyl)phenoxy]acetamide;
N-[4-(aminosulfonyl)-2-methylphenyl]-2-[4-chloro-2-(3-cyano-5-methylbenzoyl)phenoxy]acetamide;
N-[6-(aminosulfonyl)-4-methyl-3-pyridinyl]-2-[4-chloro-2-(3-cyano-5-methylbenzoyl)phenoxy]acetamide;
N-[4-(aminosulfonyl)-2-methylphenyl]-2-[4-chloro-2-(3-chloro-5-cyanobenzoyl)phenoxy]acetamide;
N-[4-(aminosulfonyl)-2-methylphenyl]-2-[4chloro-2-(3,5-dimethylbenzoyl)phenoxy]acetamide;
N-[4-(aminosulfonyl)-2-methylphenyl]-2-[4-chloro-2-(3cyano-5-ethylbenzoyl)phenoxy]acetamide;
2-[4-chloro-2-(3-cyano-5-methylbenzoyl)phenoxy]-N-{4-[3-(2,5-dihydro-1H-pyrrol-1-yl)propoxy]-2-methylphenyl}acetamide hydrochloride;
N-[4-(aminosulfonyl)-2-methylphenyl]-2-[4-chloro-2-(3-chloro-5-methylbenzoyl)phenoxy]acetamide;
N-[4-(aminosulfonyl)-2-methylphenyl]-2-[4-chloro-2-(3,5-dichlorobenzoyl)phenoxy]acetamide;
N-[4-(aminosulfonyl)-2-methylphenyl]-2-{4chloro-2-[(6-cyano-2-pyridinyl)carbonyl]phenoxy}acetamide;
N-[6-(aminosulfonyl)-2-methyl-3-pyridinyl]-2-[4-chloro-2-(3-cyano-5-methylbenzoyl)phenoxy]acetamide;
N-[4-(aminosulfonyl)-2-methylphenyl]-2-[4-chloro-2-(3,5-dicyanobenzoyl)phenoxy]acetamide;
and pharmaceutically acceptable salts thereof.

13. A compound of formula (III)

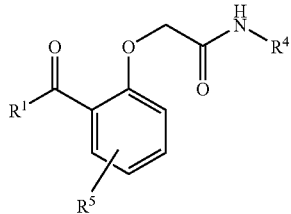

(III)

wherein
$R^1$ is phenyl which is substituted in the meta position with one or more substituents selected from the group consisting of halogen, —$CF_3$, $C_{1-8}$alkyl, $C_{1-8}$alkylamino, alkoxy, $C_{3-6}$cycloalkyl$C_{2-6}$alkenyl, $C_{6-14}$aryl$C_{2-6}$alkenyl, —CN, —$NO_2$, —$NH_2$, —$SR^6$, —$S(O)_2R^6$, —$S(O)R^7$, —$S(O)_2R^7$, —$C(O)R^7$, $C_{2-6}$alkenyl which may be optionally substituted with a substituent selected from the group consisting of hydroxy, halogen, aryl, and heterocycle, and $C_{2-6}$alkynyl which may be optionally substituted with a substituent selected from the group consisting of hydroxy, halogen, aryl, $C_{3-6}$cycloalkyl, and heterocycle;

$R^2$ is hydrogen;

$R^4$ is phenyl substituted in the ortho position with a substituent selected from the group consisting of hydroxy, halogen, —$CF_3$, or $C_{1-8}$alkyl and substituted at the para position with a substituent selected from the group consisting of hydroxy, halogen, —$CF_3$, $C_{1-8}$alkyl, hydroxy$C_{1-8}$alkyl, —CN, —$NO_2$, $C_{1-8}$alkylamino, heterocycle$C_{1-8}$alkyl, —$C(O)NH_2$, —$S(O)R^7$, —$S(O)_2R^7$, —$C(O)R^7$, —$NS(O)_2R^7$, —$S(O)_2NR^8R^9$, —$S(O)_2NHR^{11}$, —$SO_2R^{11}$, —$OR^{11}$, —$C(O)R^{11}$, —$C(O)NR^{11}$, —$C(O)OR^{11}$, —$NR^{11}$, —$NC(O)R^{11}$, heterocycle$C_{2-6}$alkenyl, heterocycle which may be optionally substituted with one or more substituents selected from the group consisting of oxo, $C_{1-8}$alkyl, and $C(O)OR^{11}$, and $C_{1-8}$alkyl which may be optionally substituted with one or more substituents selected from the group consisting of —CN and heterocycle, optionally substituted with —$C(O)R^{11}$;

$R^5$ is a substituent in the para position relative to X and is selected from the group consisting of halogen, $C_{1-8}$alkyl, —$NO_2$, —$NH_2$, $C_{1-8}$alkylamino, $CF_3$, or alkoxy;

$R^6$ is $C_{1-8}$alkyl, optionally substituted with one or more substituents selected from the group consisting of hydroxy, halogen, —$CF_3$, aryl, and heterocycle;

$R^7$ is $C_{1-8}$alkyl, optionally substituted with one or more substituents selected from the group consisting of hydroxy, halogen, aryl, $C_{3-6}$cycloalkyl and heterocycle; —$NH_2$; or heterocycle;

$R^8$ and $R^9$ are independently selected from the group consisting of hydrogen; $C_{3-6}$cycloalkyl; $C_{1-8}$alkyl optionally substituted with one or more substituents selected from the group consisting of oxo, heterocycle, CN and $C_{6-14}$aryl optionally substituted with alkoxy, $C_{1-8}$alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloaklyl; or —$C(O)NH_2$;

$R^{11}$ is $C_{1-8}$alkyl, optionally substituted with one or more substituents selected from the group consisting of hydrogen, $C_{1-8}$alkyl, —$S(O)_2NR^8R^9$, —$NR^8R^9$, and heterocycle, optionally substituted with one or more substituents selected from the group consisting of oxo and $C_{1-8}$alkyl; or a pharmaceutically acceptable salt thereof.

14. A compound according to claim 4 wherein $R^1$ is $C_{6-14}$ aryl substituted in the meta position with halogen and wherein $R^3$ is hydrogen.

15. A compound according to claim 5 wherein $R^1$ is $C_{6-14}$ aryl substituted in the meta position with halogen and wherein $R^3$ is hydrogen and $R^4$ is $C_{6-14}$aryl substituted with $C_{1-8}$alkyl.

16. A compound according to claim 1 wherein $R^1$ is $C_{6-14}$ aryl substituted in the meta position with halogen and wherein $R^3$ is hydrogen and $R^4$ is $C_{6-14}$aryl substituted with $C_{1-8}$alkyl.

17. A compound according to claim 8 wherein $R^1$ is $C_{6-14}$aryl substituted in the meta position with halogen and wherein $R^3$ is hydrogen and $R^4$ is $C_{6-14}$aryl substituted with $C_{1-8}$alkyl.

18. A compound according to claim 9 wherein $R^1$ is $C_{6-14}$ aryl substituted in the meta position with halogen and wherein $R^3$ is hydrogen and $R^4$ is $C_{6-14}$aryl substituted with $C_{1-8}$alkyl.

19. A compound of formula (I) according to claim 10 wherein $R^1$ is phenyl which is substituted in the meta position with one or more substituents selected from the group consisting of halogen, —$CF_3$, $C_{1-8}$alkyl, and —CN; $R^4$ is phenyl substituted with one or more substituents selected from the group consisting of halogen, $C_{1-8}$alkyl, —CN, —$NO_2$, —$S(O)R^7$, —$S(O)_2R^7$, —$NS(O)_2R^7$, wherein $R^7$ is —$NH_2$; and $R^5$ is halogen; or a pharmaceutically acceptable salt thereof.

20. A compound of formula (I) according to claim 10 wherein $R^1$ is phenyl which is substituted in the meta position with one or more substituents selected from the group consisting of halogen, $C_{1-8}$alkyl, $CF_3$, —CN; $R^4$ is phenyl substituted with one or more substituents selected from the group consisting of $C_{1-8}$alkyl and $S(O)_2NR^8R^9$, wherein $R^8$ and $R^9$ are independently selected from the group consisting of hydrogen, $C_{3-6}$cycloalkyl, $C_{1-8}$alkyl optionally substituted with one or more substituents selected from the group consisting of oxo, heterocycle, CN and $C_{6-14}$aryl optionally substituted with $C_{1-8}$alkoxy, $C_{1-8}$alkylamino, $C_{1-8}$alkylheterocycle, heterocycle, heterocycle$C_{1-8}$alkyl, $C_{3-6}$cycloalkyl$C_{1-8}$alkyl, and $C_{3-6}$cycloalkyl.

21. A compound of formula (I) according to claim 10 wherein $R^1$ is phenyl which is substituted in the meta position with one or more substituents selected from the group consisting of halogen, —$CF_3$, $C_{1-8}$alkyl, —CN, $C_{2-6}$alkenyl which may be optionally substituted with a substituent selected from the group consisting of hydroxy, halogen, aryl, and heterocycle and $C_{2-6}$alkynyl which may be optionally substituted with a substituent selected from the group consisting of hydroxy, halogen, aryl, $C_{3-6}$cycloalkyl, and heterocycle; $R^4$ is phenyl substituted with one or more substituents selected from the group consisting of $C_{1-8}$alkyl, —$S(O)_2R^7$, —$S(O)_2NR^8R^9$, —$OR^{11}$, heterocycle$C_{2-6}$alkenyl, and heterocycle which may be optionally substituted with oxo; and $R^5$ is halogen; or a pharmaceutically acceptable salt thereof.

22. A compound of formula (III) according to claim 13 wherein $R^1$ is phenyl which is substituted in the meta position with one or more substituents selected from the group consisting of halogen, —$CF_3$, $C_{1-8}$alkyl, —CN, —$SR^6$, —$S(O)_2R^6$; $R^6$ is $C_{1-8}$alkyl, optionally substituted with halogen; $R^7$ is $C_{1-8}$ alkyl, optionally substituted with hydroxy; —$NH_2$; or heterocycle; $R^4$ is phenyl substituted with one or more substituents selected from the group consisting of hydroxy, —$CF_3$, $C_{1-8}$alkyl, hydroxy$C_{1-8}$alkyl, —CN, —$NO_2$, —$C(O)NH_2$, —$S(O)_2R^7$, —$S(O)_2NR^8R^9$, —$OR^{11}$, —$C(O)NR^{11}$, —$C(O)OR^{11}$, —$NR^{11}$, —$NC(O)R^{11}$, heterocycle which may be optionally substituted with one or more substituents selected from the group consisting of oxo and $C_{1-8}$alkyl; $R^8$ and $R^9$ are the same or different and are selected from the group consisting of hydrogen, $C_{1-8}$alkyl, $C_{1-8}$alkylheterocycle, heterocycle, and $C_{3-6}$cycloalkyl; $R^{10}$ is $C_{1-8}$alkyl; $R^{11}$ is $C_{1-8}$alkyl, optionally substituted with —$S(O)_2NR^8R^9$; and $R^5$ is halogen or —$NO_2$; or a pharmaceutically acceptable salt thereof.

23. A compound of formula (I) according to claim 21 wherein $R^1$ is phenyl which is substituted in the meta position with one or more substituents selected from the group consisting of halogen, —$CF_3$, $C_{1-8}$alkyl, and —CN; $R^4$ is phenyl substituted with one or more substituents selected from the group consisting of halogen, $C_{1-8}$alkyl, —CN, —$NO_2$, —$S(O)R^7$, $S(O)_2R^7$, —$NS(O)_2R^7$, wherein $R^7$ is —$NH_2$; and $R^5$ is halogen; or a pharmaceutically acceptable salt thereof.

24. A pharmaceutical composition comprising an effective amount of a compound according to claim 1 together with a pharmaceutically acceptable carrier.

25. A pharmaceutical composition according to claim 24 in the form of a tablet or capsule.

26. A pharmaceutical composition according to claim 24 in the form of a liquid.

27. A pharmaceutical composition comprising an effective amount of a compound according to claim 11 together with a pharmaceutically acceptable carrier.

28. A pharmaceutical composition comprising an effective amount of a compound according to claim 4 together with a pharmaceutically acceptable carrier.

29. A pharmaceutical composition according to claim 28 in the form of a tablet or capsule.

30. A pharmaceutical composition according to claim 28 in the form of a liquid.

31. A pharmaceutical composition comprising an effective amount of a compound according to claim 8 together with a pharmaceutically acceptable carrier.

32. A method of treatment of an HIV infection in a mammal comprising administering to said mammal an anti-HIV effective amount of a compound according to claim 1.

33. A method of treatment of an HIV infection in a mammal comprising administering to said mammal an effective amount of a compound according to claim 11.

34. A method of treatment of an HIV infection in a mammal comprising administering to said mammal an effective amount of a compound according to claim 4.

35. A method of treatment of an HIV infection in a mammal comprising administering to said mammal an effective amount of a compound according to claim 8.

* * * * *